(12) United States Patent
Moussaoui et al.

(10) Patent No.: US 12,344,895 B2
(45) Date of Patent: Jul. 1, 2025

(54) LONG NON-CODING RNAS (LNCRNAS) FOR THE DIAGNOSIS AND THERAPEUTICS OF BRAIN DISORDERS, IN PARTICULAR COGNITIVE DISORDERS

(71) Applicant: AMONETA DIAGNOSTICS SAS, Huningue (FR)

(72) Inventors: Saliha Moussaoui, Bartenheim (FR); Hueseyin Firat, Huningue (FR); Eric Schordan, Wentzwiller (FR)

(73) Assignee: AMONETA DIAGNOSTICS SAS, Huningue (FR)

( * ) Notice: Subject to any disclaimer, the term of this patent is extended or adjusted under 35 U.S.C. 154(b) by 1089 days.

(21) Appl. No.: 17/274,019

(22) PCT Filed: Sep. 5, 2019

(86) PCT No.: PCT/EP2019/073775
§ 371 (c)(1),
(2) Date: Mar. 5, 2021

(87) PCT Pub. No.: WO2020/049135
PCT Pub. Date: Mar. 12, 2020

(65) Prior Publication Data
US 2021/0269881 A1 Sep. 2, 2021

Related U.S. Application Data

(60) Provisional application No. 62/727,210, filed on Sep. 5, 2018.

(51) Int. Cl.
*C12Q 1/6883* (2018.01)
(52) U.S. Cl.
CPC ..... *C12Q 1/6883* (2013.01); *C12Q 2600/158* (2013.01); *C12Q 2600/178* (2013.01)
(58) Field of Classification Search
None
See application file for complete search history.

(56) References Cited

U.S. PATENT DOCUMENTS

| 6,703,212 B1 | 3/2004 | Janoshazi et al. |
| 7,897,786 B2 | 3/2011 | Ulrich et al. |
| 9,377,472 B2 | 6/2016 | Mbebi-Liegeois et al. |

FOREIGN PATENT DOCUMENTS

| EP | 1 716 227 A2 | 11/2006 |
| WO | WO 2015/031958 | 3/2015 |

OTHER PUBLICATIONS

Zhou et al. Int J Clin Exp Med. 2015. 8(4): 4862-4883 (Year: 2015).*
Soreq et al PLoS Comput Biol. Mar. 20, 2014. 10(3): e1003517, 22 pages, and and Table S3B (Year: 2014).*
Chi et al Hindawi Parkinson's Disease. Feb. 2019. Article ID 6078251, 7 pages (Year: 2019).*
Strausberg et al. NCBI GenBank No. BI259848, Jan. 11, 2011, National Center for Biotechnology Information, National Library of Medicine, NIH, Bethesda, MD, available via url: <ncbi.nlm.nih.gov/nuccore/BI259848.1/> (Year: 2011).*
Bang et al., Lancet, vol. 386, No. 10004, Oct. 24, 2015 (Oct. 24, 2015), pp. 1672-1682.
Breiman L: "Random forests", Machine Learnin, vol. 45, No. 1, 2001, pp. 5-32, XP019213368, doi:10.1023/A:1010933404324.
C. Trapnell et al., Nat Protoc, vol. 7, No. 3, 2012, pp. 562-578.
Carlson et al., Alzheimers Dement (AMST, vol. 2, 2016, pp. 75-85.
Cummings et al., Expert Rev Clin Pharmacol, vol. 7, No. 2, 2014, pp. 161-165.
Desmarais P et al., J Neurol Neurosurg Psychiatry, vol. 90, 2019, pp. 412-423.
Dobin A. et al.: "Star: ultrafast universal RNA-seq aligner", Bioinforma. Oxf. Engl., vol. 29, 2013, pp. 15-21, XP055500895, doi:10.1093/bioinformatics/bts635.
Dubois et al., Lancet Neurol, vol. 13, No. 6, 2014, pp. 614-629.
Frisoni et al., Nat Rev Neurol, vol. 6, No. 2, 2010, pp. 67-77.
Gael Chetelat et al., NeuroImage Clinical, vol. 2, 2013, pp. 356-365.
Gotz et al., Br J Pharmacol, vol. 165, No. 5, 2012, pp. 1246-1259.
L. Wang L. et al., Nucleic Acids Res, vol. 41, No. 6, 2013, pp. e74.
Liang Feng et al: "Plasma long non-coding RNA BACE1 as a novel biomarker for diagnosis of Alzheimer disease", BMC Neurology, vol. 18, No. 1, Jan. 9, 2018 (Jan. 9, 2018), XP055636641, DOI: 10.1186/s12883-017-1008-x.
Lilach Soreq et al: "Long Non-Coding RNA and Alternative Splicing Modulations in Parkinson's Leukocytes Identified by RNA Sequencing", PLOS Computational Biology, vol. 10, No. 3, Mar. 20, 2014 (Mar. 20, 2014), pp. e1003517, XP055334570, DOI: 10.1371/journal.pcbi.1003517.
Luo et al., Clin Interv Aging, vol. 11, 2016, pp. 867-872.
Marcus et al., J Neurogenet, vol. 25, No. 4, 2011, pp. 127-133.
Pertea M. et al., Nat Biotechnol, vol. 33, No. 3, 2015, pp. 290-295.
Rama Shankar et al: "Transcriptome analysis in different rice cultivars provides novel insights into desiccation and salinity stress responses", Scientific Reports, vol. 6, No. 1, Mar. 31, 2016 (Mar. 31, 2016), XP055636000, DOI: 10.1038/srep23719.
Siemer et al., Alzheimers Dement, vol. 12, No. 2, 2016, pp. 110-120.
Slawski Mdaumer Mboulesteix al: "CMA: a comprehensive Bioconductor package for supervised classification with high dimensional data", BMC Bioinformatics, vol. 9, 2008, pp. 439, XP021047481, doi:10.1186/1471-2105-9-439.
Sun Z. et al., Scientific Reports, vol. 7, No. 1, 2017, pp. 14196.
Sunderland et al., JAMA, vol. 289, No. 16, 2003, pp. 2094-2103.
Tahmasian et al., J Nucl Med., vol. 57, No. 3, 2016, pp. 410-415.
Xing Y. et al.: "An expectation-maximization algorithm for probabilistic reconstructions of full-length isoforms from splice graphs", Nucleic Acids Res., vol. 34, 2006, pp. 3150-3160, XP002734295, doi:10.1093/nar/gk1396.

(Continued)

Primary Examiner — Carla J Myers
(74) *Attorney, Agent, or Firm* — Hoxie & Associates LLC

(57) ABSTRACT

The present invention describes a method for the therapeutic treatment and/or for the diagnosis of a brain disorder including but not limited to cognitive disorders such as mild cognitive impairment, Alzheimer disease, frontotemporal dementia, dementia with Lowy body in a subject at risk of having or developing a brain disorder such as cognitive disorder, using long non-coding RNA (lncRNA).

3 Claims, 19 Drawing Sheets
Specification includes a Sequence Listing.

(56) References Cited

OTHER PUBLICATIONS

Yanyao Deng et al: "Plasma long noncoding RNA 51A as a stable biomarker of Alzheimer's disease", Int J Clin Exp Pathol, Apr. 1, 2017 (Apr. 1, 2017), pp. 4694-4699, XP055636042, Retrieved from the Internet <URL:http://www.ijcep.com/files/ijcep0047807.pdf> [retrieved on Oct. 25, 2019].

Yaxing Gui et al: "Altered microRNA profiles in cerebrospinal fluid exosome in Parkinson disease and Alzheimer disease", Oncotarget, Nov. 10, 2015 (Nov. 10, 2015), United States, pp. 37043, XP055278437, Retrieved from the Internet <URL:https://www.ncbi.nlm.nih.gov/pmc/articles/PMC4741914/pdf/oncotarget-06-37043.pdf> DOI: 10.18632/oncotarget.6158.

Wang H.Y., et al. "Quantamatrix Multiplexed Assay Platform system for direct detection of bacteria and antibiotic resistance determinants in positive blood culture bottles," *Clin Microbiol Infect.* May 2017; 23(5):333.e1-333.e7.

Yang, et al., "Distinct Hippocampal Expression Profiles of Long Non-coding RNAs in an Alzheimer's Disease Model", *Mol. Neurobiol.*, vol. 54, No. 7, pp. 4833-4846, (2016).

Yaohui, et al., "Investigation of Long Non-coding RNA Expression Profiles in the Substantia Nigra of Parkinson's Disease", *Cell Mol. Neurobiol.*, vol. 37, No. 2, pp. 329-338, (2016).

Zhang, et al., "Preparation and application of streptavidin magnetic particles", *Sci. China Ser. B-Chem.*, vol. 50, No. 1, pp. 127-134, (2007).

\* cited by examiner

| lncRNA | Rank |
|---|---|
| lnc-TPPP-1:2 | 1 |
| LINC02345:11 | 2 |
| lnc-ZNF273-4:4 | 3 |
| lnc-TACC2-8:6 | 4 |
| LINC01206:20 | 5 |
| lnc-C5orf67-3:1 | 6 |
| HAND2-AS1:58 | 7 |
| lnc-PRDM9-20:1 | 8 |
| lnc-CLK1-1:7 | 9 |
| lnc-DNALI1-5:4 | 10 |
| RORB-AS1:6 | 11 |
| lnc-TPPP-1:3 | 12 |
| lnc-BMS1-2:1 | 13 |
| lnc-ADRB1-4:1 | 14 |
| lnc-XXYLT1-5:1 | 15 |
| MIR99AHG:104 | 16 |
| LINC01748:17 | 17 |
| lnc-AKR1E2-15:1 | 18 |

| Accuracy | 0.917 |
|---|---|
| Sensitivity | 0.833 |
| Specificity | 1.000 |
| Positive Predictive value | 1.000 |
| Negative Predictive value | 0.857 |

| lncRNA | Rank |
|---|---|
| PCBP1-AS1:302 | 1 |
| STARD7-AS1:5 | 2 |
| lnc-NID1-4:4 | 3 |
| RBM26-AS1:1 | 4 |
| LEF1-AS1:1 | 5 |
| lnc-CA6-8:1 | 6 |
| lnc-CA6-8:2 | 7 |
| lnc-OCM-3:4 | 8 |
| lnc-AFG1L-7:1 | 9 |
| lnc-LASP1-5:1 | 10 |
| lnc-GCGR-1:2 | 11 |

| Accuracy | 0,934 |
|---|---|
| Sensitivity | 0.65 |
| Specificity | 0.983 |

To achieve 100X coverage with targeted sequencing, only 8 Millions of reads are needed compared to more than 500M with regular sequencing

LONG NON-CODING RNAS (LNCRNAS) FOR THE DIAGNOSIS AND THERAPEUTICS OF BRAIN DISORDERS, IN PARTICULAR COGNITIVE DISORDERS

CROSS-REFERENCE TO RELATED APPLICATIONS

This application is a U.S. National Stage Application filed under 35 U.S.C. § 371 of International Application No. PCT/EP2019/073775, filed Sep. 5, 2019, which claims the benefit and priority of U.S. Provisional Application No. 62/727,210, filed on Sep. 5, 2018, the contents of each of which are hereby incorporated by reference in their entireties.

FIELD OF THE INVENTION

The present invention relates to the field of human medicine and specifically to the diagnostic and therapeutic of brain disorders and particularly cognitive disorders including those with mild cognitive impairment, Alzheimer disease, dementia with Lewy body and frontotemporal dementia. This invention relates to a biomarker for brain disorders, such as cognitive disorders, consisting in long non-coding RNAs (lncRNAs) in a peripheral circulating body fluid such as plasma or blood and/or expressed in brain tissue and/or whole blood and representing a therapeutic target for brain disorders, or non-invasive method for diagnosing brain disorders such as cognitive disorders, in particular Alzheimer's disease or for monitoring its development or progression using this biomarker. It further relates to associated kits, methods, protocols and transmittable forms of information for diagnosis purposes and/or for other human medicine applications including the patient stratification in clinical trials and/or monitoring the efficacy of therapeutic strategies using this biomarker and peripheral body fluids or whole blood from patients. The invention further consists in brain specific lncRNAs altered in patient with brain disease in particular cognitive disorder and representing a diagnostic or therapeutic candidate for their treatment. The present invention will thus have a strong impact on the quality of life of patients and a significant impact on the healthcare system and economy.

BACKGROUND ART

Alzheimer's disease (AD) is a chronic neurodegenerative disease characterized by progressive loss of cognitive function. Mild cognitive impairment (MCI) is a major first symptom and evolves progressively into mild, moderate and severe AD stages. Early-onset AD occurs between a 30s to mid-60s and represents less than 10% of all people with AD and is caused by a mutation in APP or PSEN1 or PSEN2 genes. Most people with AD have the late-onset form with onset of symptoms in the mid-60s and later. The causes of late-onset AD are not yet completely understood, but most documented genetic risk factor is the apolipoprotein E (APOE) gene allele ε4. All AD forms, whether early-onset familial or sporadic forms, are pathologically characterized by two typical hallmarks, extracellular deposition of amyloid-beta peptide (Aβ) (a metabolite of APP protein encoded by APP gene) in amyloid plaques and intracellular deposition of hyper-phosphorylated tau protein (encoded by MAPT gene) in neurofibrillary tangles in the brain, associated with progressive neuronal degeneration (Marcus et al. J Neurogenet. 2011; 25 (4): 127-33; Gotz et al, Br J Pharmacol. 2012; 165 (5): 1246-59).

AD is the most common form of dementia. Approximately 46.8 million people worldwide currently live with AD or other type of dementia. With an ageing population, this number is estimated to increase to 131.5 million by 2050 (World Alzheimer Report, 2015). As such, AD is becoming an increasingly important burden on the affected individuals and their families as well as economic and social costs on medical and healthcare resources in both developed and emerging countries.

Dementia with Lewy bodies (DLB) and Parkinson's disease dementia (PDD), both called Lewy body dementias, are the second most common type of degenerative dementia in patients older than 65 years and their brain pathological hallmarks are α-synuclein neuronal inclusions (Lewy bodies, and Lewy neurites), accompanied by neuronal loss (Lancet. 2015 Oct. 24; 386 (10004): 1683-97). Variants in three genes APOE, SNCA, and GBA have been associated with an increased risk of dementia with Lewy bodies, but in most cases, the cause is unknown.

Frontotemporal dementia (FTD) is the third most common dementia across all age groups and the $1^{st}$ or the $2^{nd}$ (after AD) prevalent dementia in the 45-64 years age group. The most common form is known as behavioral variant frontotemporal dementia (bvFTD), which is characterized (in its early stages) by changes in personality, behavior, and judgment. Other disorders under the "frontotemporal disorders" umbrella include Pick's disease, primary progressive aphasia, primary non-fluent aphasia, semantic dementia, corticobasal degeneration (CBD) syndrome, progressive supranuclear palsy (PSP), frontotemporal dementia (FTD) with parkinsonism, and FTD with amyotrophic lateral sclerosis (ALS).

There are overlapping clinical features between the classic clinical phenotypes of FTD spectrum disorders, thus complicating the clinical diagnostic picture. FTD spectrum disorders also share common underlying molecular pathology with findings of frontotemporal lobar degeneration, with neuronal and astrocytic inclusions of tau protein, TAR DNA-binding protein 43 (TDP-43), and rarely RNA-binding protein fused in sarcoma (FUS). bvFTD and PPA_language variants are associated with tau, TDP-43 or FUS proteinopathies, and PSP syndrome is often associated with tau proteinopathy. While CBD syndrome pathology comprises tauopathy in the form of CBD or PSP, but also beta-amyloidopathy/tauopathy (typical of AD), prionopathy, TDP-43 proteinopathy and alpha-synucleinopathy. As many as 40% of patients with FTD have a family history of the disease. 10%-20% of all cases attributed to mutations in or near the 3 genes: C9orf72 (encoding protein C9orf72), GRN (encoding progranulin) and MAPT (encoding tau). More rare, other causing genetic mutations have been identified in familial FTD: VCP, TARDBP, TIA1, TBK1 and CCNF genes for cases of FTD due to TDP proteinopathy, and in CHMP2B and FUS for cases of FTD due to tau-negative, TDP-negative, ubiquitin-positive pathology (Lancet. 2015 Oct. 24;386 (10004): 1672-82; Desmarais P, et al. J Neurol Neurosurg Psychiatry 2019; 90:412-423).

Currently, there is no cure for AD, nor for any of the other non-AD dementia types. Symptomatic treatments exist for these diseases, all trying to counterbalance neurotransmitter's disturbance. Although a number of new potential disease-modifying therapeutic candidates are currently being studied in clinical trials in AD, none has been approved yet. From 2002 to 2012, there was a failure of 99.6% of AD clinical trials that were 289 Phases 2 and 3 trials on symptomatic agents (36.6%), disease-modifying small molecules (35.1%) and disease-modifying immunotherapies (18%) (Cummings et al., Expert Rev Clin Pharmacol. 2014; 7 (2): 161-5). Among the strategies proposed by worldwide experts in the AD field and by pharmaceutical industries to improve the success rate for AD drug development, are: a) intervening earlier in the disease process before neurodegeneration begins, b) identifying and developing accurate biomarkers for early diagnosis, non-invasive and suitable for stratification of subject populations and for longitudinal monitoring of drug efficacy in clinical trials.

The AD pathological features are defined in post-mortem histopathological analysis. The presence of both types of lesions (amyloid plaques and tangles) in the brain remains an absolutely required feature for the definitive diagnosis of AD.

Current diagnosis of the disease remains uncertain (Dubois et al Lancet Neurol. 2014; 13 (6): 614-29) and it is based on combination of battery of clinical and neuropsychological tests and neuroimaging, such as structural imaging using Magnetic Resonance Imaging (MRI) and/or glucose metabolism using ositron emission tomography (PET) of fluorodeoxyglucose F18 ($^{18}$F-FDG), with an accuracy of less than 70%-85% depending on the method and the severity stage of the disease (Frisoni et al., Nat Rev Neurol. 2010; 6 (2): 67-77; Tahmasian et al., J Nucl Med. 2016; 57 (3): 410-5).

Sometimes, detection of AD-associated biomarkers Aβ42 and tau or phosphorylated-tau in cerebrospinal fluid (CSF) is additionally performed (Sunderland et al., JAMA. 2003; 289 (16): 2094-2103), but CSF tests request a lumbar puncture, which is an invasive procedure and often requires hospitalization of subjects and therefore used only in a small proportion of subjects and at a too-late-stage of AD.

Longitudinal confirmatory diagnosis test is essential for applications to early detection of the preclinical stages of AD and mild cognitive impairment (MCI; defined as an early stage during which the first subtle symptoms manifest) and thus detecting early and calculating the risk of conversion of MCI into AD. Due to its limits (invasive), a CSF test is not routinely used as a biomarker for early diagnosis in preclinical AD stages before symptoms appear, nor it is suitable as a companion biomarker repeatedly practiced at several time points in same subjects recruited in longitudinal clinical trials.

Recently, specific neuroimaging methods relevant for AD pathology are being developed, notably with radioactive ligands for in vivo amyloid-beta (Aβ) ligands for Positron Emission Tomography (PET) neuroimaging including F-18 florbetapir and F-18 flutemetamol which have been approved by FDA and/or EMA (Choi et al., 2009 and Wong et al., 2010). However, their practice is costly and very limited (available only in some hospitals of large cities, still mainly for clinical research purposes as not reimbursed by health insurances) and their diagnosis accuracy is still under studies for further understanding. Thus, the use of these AB PET neuroimaging methods remains very limited and the vast majority of patients do not profit from such tests even in rich countries.

There is a need for better definition of AD patient population to be included for the drug-development trials: PET imaging using Aβ ligands showed that up to 30% of subjects diagnosed with AD show a negative Aβ scan and that up to 35% of subjects with normal cognition status show a positive Aβ scan (Gaël Chételat et al, NeuroImage Clinical 2013; 2:356-65). Thus, PET Aβ scan is being used to guide for recruitment of subjects in the desired cohorts in some clinical trials by the large pharmaceutical companies. Anti-Aβ antibody e.g. Solanezumab tested in patients with mixed mild to moderate AD failed to show clear efficacy. In mild AD patients selected based on CSF biomarker profile, the results showed a first promising efficacy (Carlson et al., Alzheimers Dement (Amst). 2016; 2:75-85; Siemers et al., Alzheimers Dement. 2016; 12 (2): 110-20). However, the use of CSF biomarker is invasive, dramatically limiting its use as a biomarker for drug development. For example, it is not suitable for repeated use to monitor the stability and/or the progression of the disease, nor it is suitable to monitor in clinical longitudinal trials the efficacy of disease-modifying therapeutic drug candidates or preventive strategies in routine clinical practice use.

Overall, the existing tests either lack an easy accessibility and simplicity for use for diagnosis of the large AD population and/or lack accuracy (sensitivity and specificity). This represents a major impediment and bottleneck to develop reliable and rapid diagnosis test for AD. Another impediment is the identification of a biomarker that does not require invasive sample collecting, such as a spinal tap. The lack of such an accessible, sensitive and specific biomarker that could be validated by cellular, animal model, pre-clinical models, and human testing impedes the development of therapies and drugs for AD or for the studies on pathological processes triggering AD or involved in the progression of AD.

Today, clearly there is a high unmet medical need for efficient preventive or disease-modifying therapeutic treatment, as well as for an accurate and non-invasive peripheral biomarker test for early diagnosis of AD including preclinical and early MCI and for applications in drug development (patient stratification and repeated monitoring drug efficacy in clinical trials) and to monitor the efficacy and adjust the dosing novel future therapies once approved.

Likewise, for non-AD dementia, including DLB and for many FTD related neurodegenerative disorders, there is a high unmet medical need for efficient preventive or disease-modifying therapeutic treatment, and for an accurate and non-invasive peripheral biomarker test for diagnosis in particular of their early forms.

lncRNAs are typically defined as transcripts longer than 200 nucleotides and among the RNA families, lncRNAs seem to be the most tissue-specifically expressed. In the brain, lncRNAs can regulate gene expression at epigenetic, transcriptional, and posttranscriptional levels of proteins with diverse functions including neuronal transmission and synaptic plasticity. Recent studies identified a few lncRNA candidates in AD postmortem brain tissue; some lncRNA candidates have been shown in in vitro experiments or animal models to directly or indirectly regulate the formation of the neurotoxic Aβ, synaptic activity or the neuronal DNA repair (for review: Luo K and Chen Y, Clin Interv Aging 2016; 11:867-872).

We previously showed that the lncRNAs expressed or highly enriched in tissues such as cardiac tissue or brain tissue, can be released into the peripheral circulation and be easily quantifiable by classical RT-PCR in different peripheral samples (PCT/EP2018/065492). In addition of the RT-PCR, we performed also total RNA sequencing on peripheral samples and quantified significant proportion of lncRNAs in the peripheral samples such as serum, plasma and Paxgene-RNA-tube collected whole blood (PCT/EP2018/065492).

According to the invention, new lncRNA signatures specific of brain diseases, in particular mild cognitive impairment (MCI) and Alzheimer or another cognitive disorder have been identified, using a method set up combining most recent technologies and samples collected in non-invasively manner, including Paxgene whole blood tube, serum and plasma.

SUMMARY OF THE INVENTION

In the present invention, 1091 novel brain lncRNAs have been sequenced and identified for the first time in human postmortem brain tissue, in particular meditotemporal cortex of AD patients and cognitively intact healthy controls. Brain lncRNAs including novel brain lncRNAs with differential expression in the brain of AD patients when compared to the brain of healthy controls have been identified. Furthermore, new lncRNA signatures comprising the already sequenced and newly sequenced have been identified as differentially expressed in samples collected in non-invasively manner, including whole blood collected in Paxgene RNA tube and plasma derived from blood of patients suffering MCI, AD, DLB or FTD when compared to healthy controls, as well as panels that detect specifically MCI and/or one of the dementia type (AD or DLB or FTD) when compared to the other dementia types studied. Furthermore, brain-enriched lncR-NAs including novel brain-enriched lncRNAs have been identified. These brain-enriched lncRNAs include circulating lncRNAs detectable in the peripheral body fluids plasma and whole blood Paxgene RNA samples.

In an aspect, the lncRNAs including novel lncRNAs identified as having deficient expression in AD brain represent novel therapeutic candidates for development as lncRNA molecule-enhancing therapeutic approaches, and the novel brain lncRNAs identified as having an over expression in AD brain represent novel therapeutic candidates for development as lncRNA molecule-silencing therapeutic approaches, both for treatment of brain disorders in particular Alzheimer's disease and other cognitive disorders.

In another aspect, the plasma and whole blood lncRNAs panels, identified as differentially expressed in patients suffering cognitive disorders are potential therapeutic targets and/or biomarkers for the prediction and/or the diagnosis and/or the differential diagnosis of brain disorders, in particular cognitive disorders in a subject at risk to develop AD, FTD, DLB and/or another cognitive disorder or dementia type.

In another aspect, the brain-enriched lncRNAs panels identified represent therapeutic and diagnostic targets for brain disorders, including but not limited to cognitive disorders such as MCI, AD, FTD, DLB.

The novel lncRNAs, the newly identified brain-enriched lncRNAs panels we called BrainLinc, the new lncRNAs panels identified as differentially expressed in the peripheral body fluids including the common to brain and plasma (or to brain and blood) lncRNAs identified can be quantified in the peripheral samples of patients using the innovative Celemics technology with significantly higher sensitivity, precision and/or accuracy that would not have been realized using other currently existing technologies. Monitoring of large number of lncRNAs targets by Cemelics and for quantification of small number of lncRNAs by qPCR and Quantamatrix are preferred methods to other existing methods such as NGS and HTG.

Figure 1:
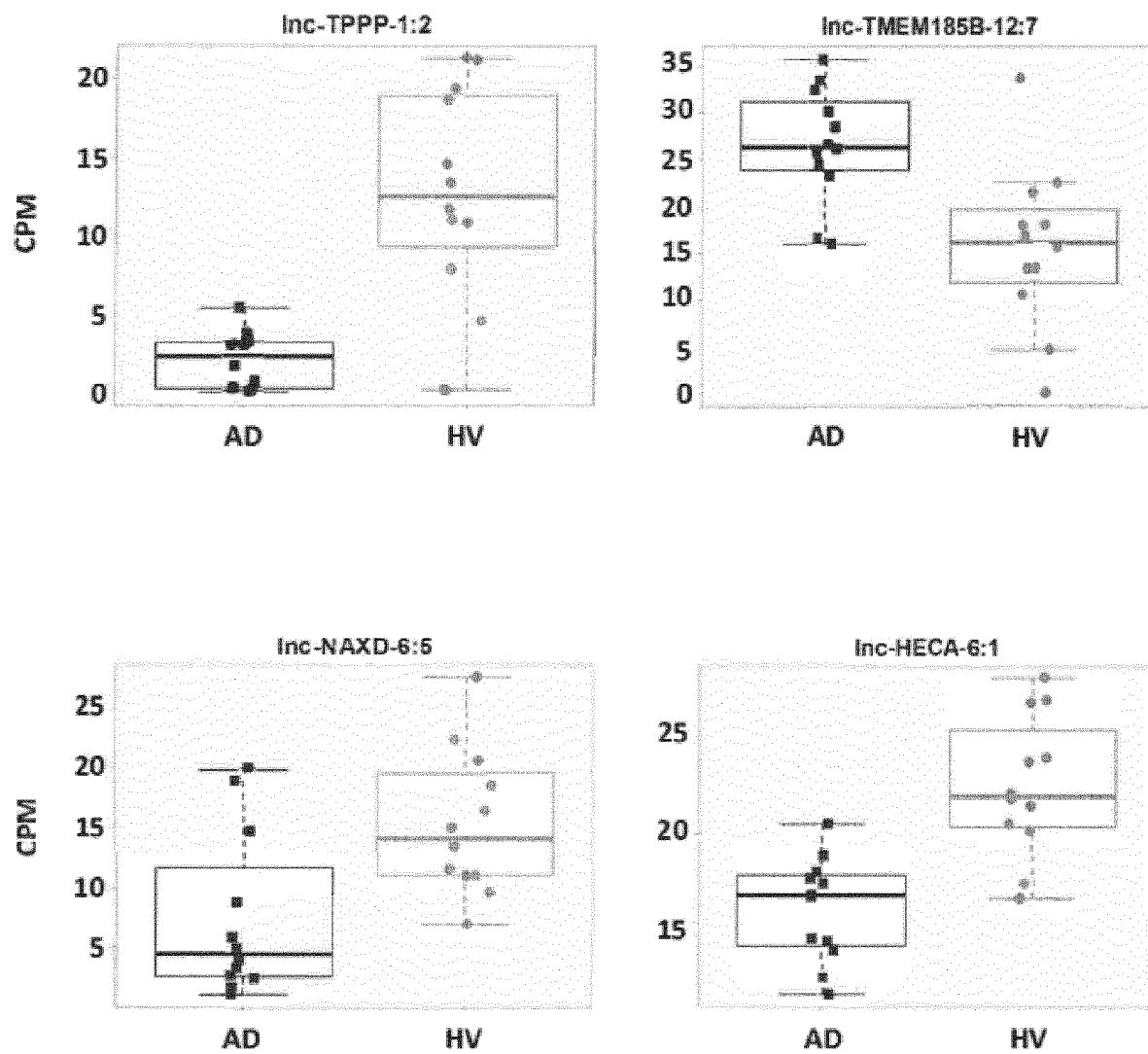
FIG. 1 shows the expression level of lncRNA candidates lnc-TPPP-1:2, lnc-TMEM185B-12:7, lnc-NAXD-6:5 and lnc-HECA-6:1 on human serum samples from patients with early to moderate Alzheimer (AD) and age-matched healthy controls. Y axis: mean+/−standard error of the mean of concentration of the lncRNAs in CPM (count per million). X axis: AD: Alzheimer patient group, HV: Healthy control group.
Figure 2:
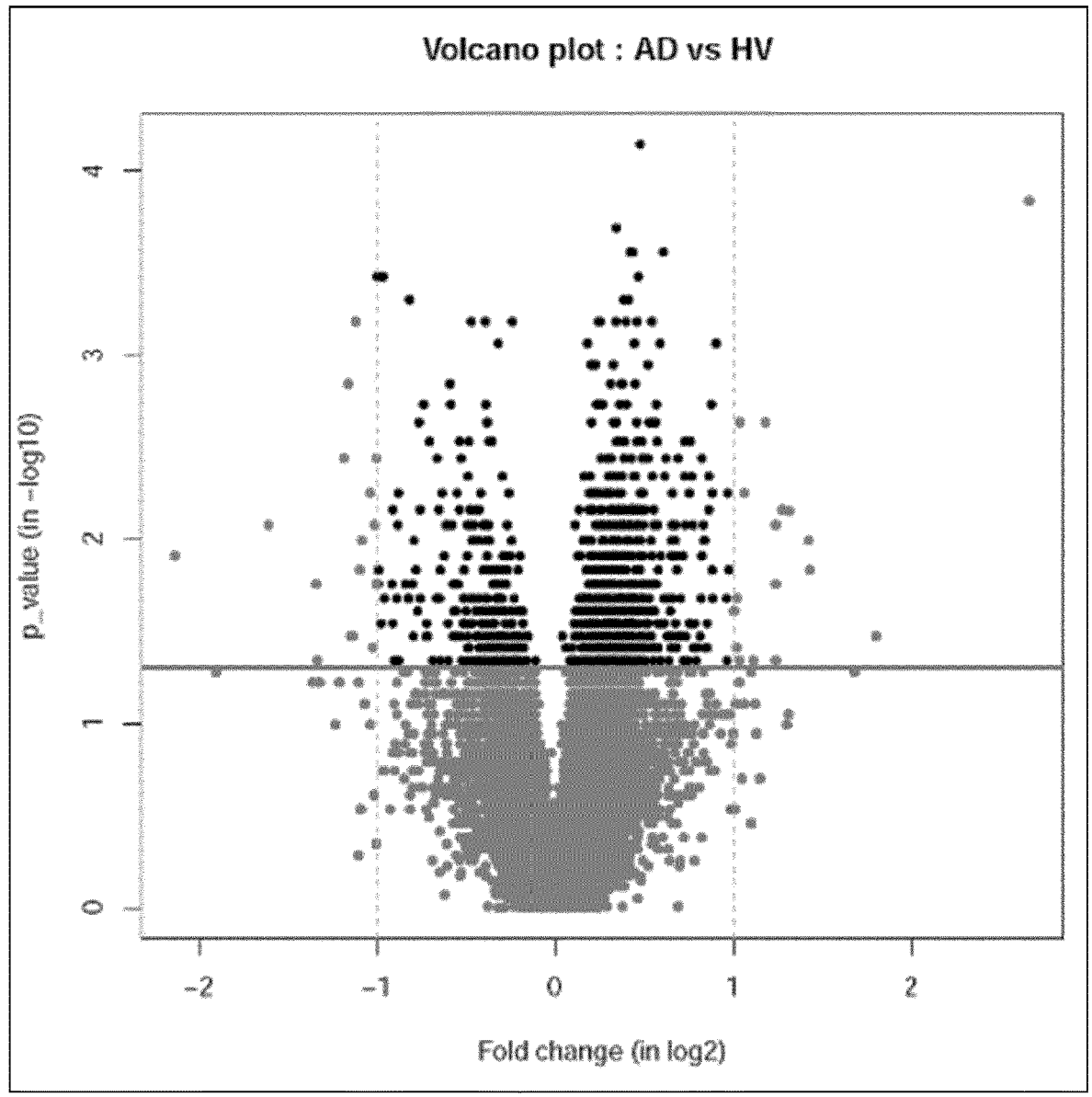
FIG. 2 shows Volcano plot of the comparison. The volcano plot shows the serum 1008 lncRNAs that are differentially expressed in AD group versus HV (healthy control) group with statistically significance (p<0.05) above the line. 33 lncRNAs show both p value of <0.05 and fold change of ≥2 or <0.5. The lncRNAs that are differentially expressed but do not reach a statistically significance are shown below the line.
Figure 3:
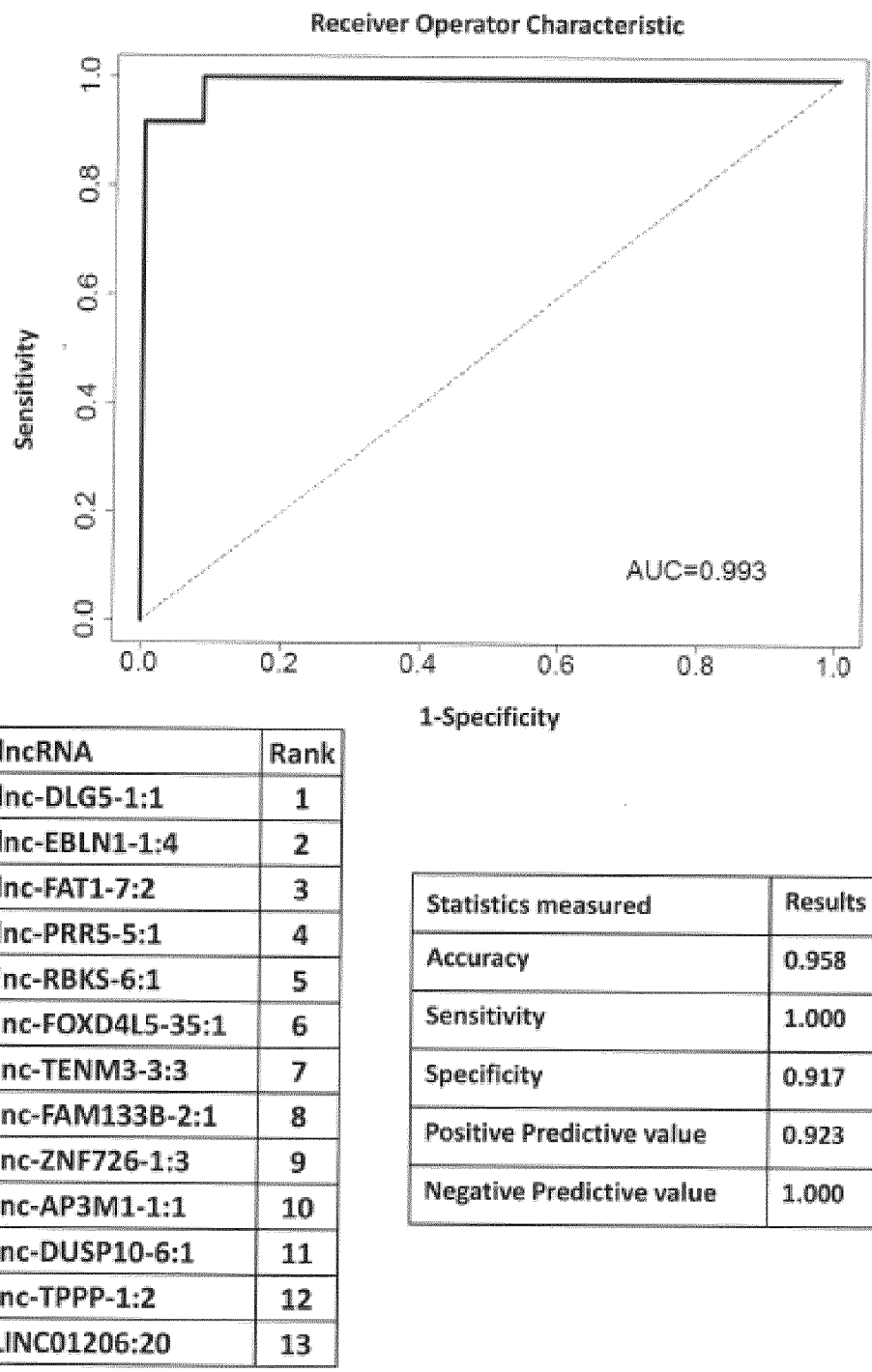
FIG. 3 shows a predictive modelling based on the random forest algorithm enabling the identification of the signature of the 13-top ranked serum lncRNAs candidates selected out of 19867 lncRNAs.
Figure 4:
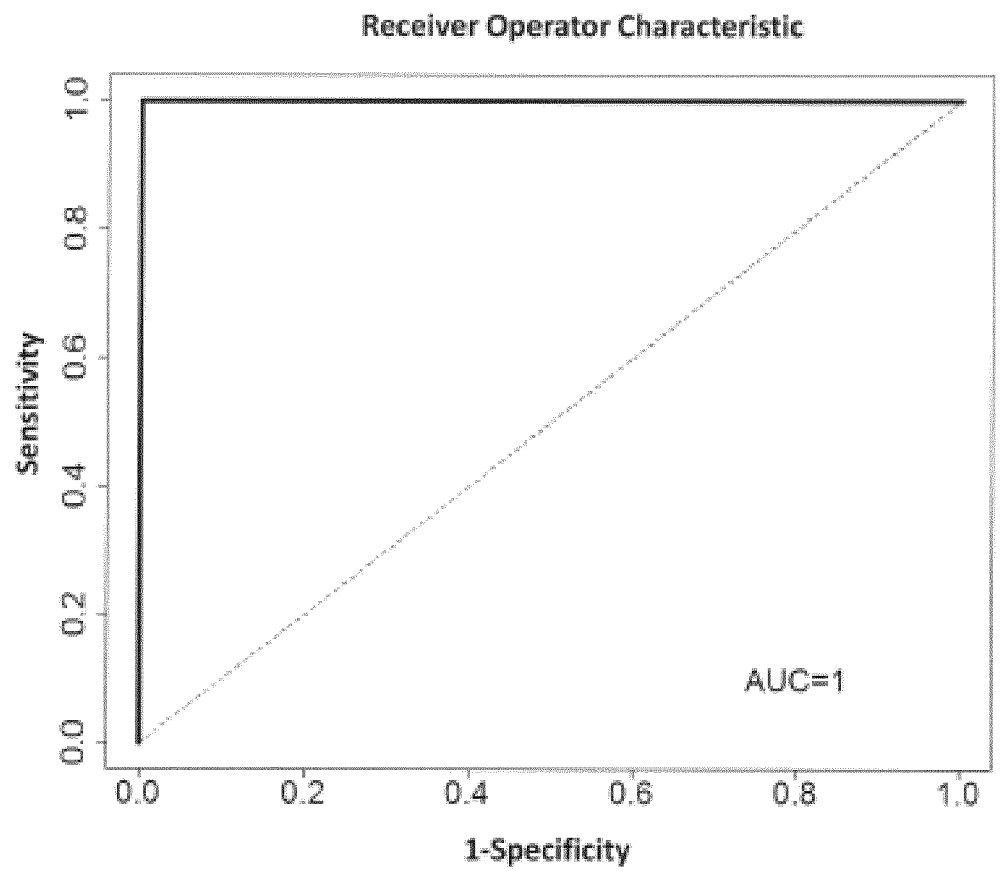
FIG. 4 shows a predictive modelling based on the random forest algorithm enabling the identification of the signature of the 7-top ranked serum lncRNAs candidates out of 90 lncRNAs with a p value of <0.05 and fold change of ≥2 or <0.5 or an AUC of ≥0.85 or ≤0.15.
Figure 5:
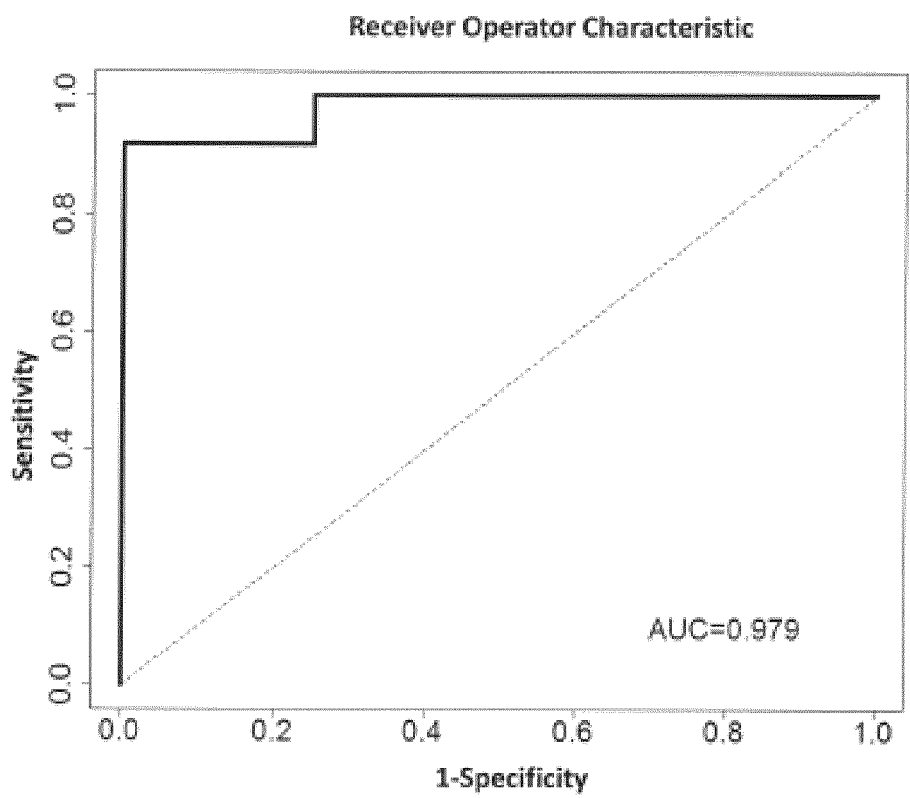
FIG. 5 shows a predictive modelling based on the random forest algorithm enabling identification of the signature of the 12 top serum lncRNAs candidates selected out of the 90 lncRNAs (with a p value of <0.05 and fold change of ≥1,6 or ≤0.6 and an AUC of ≥0.85 or ≤0.15.
Figure 6:
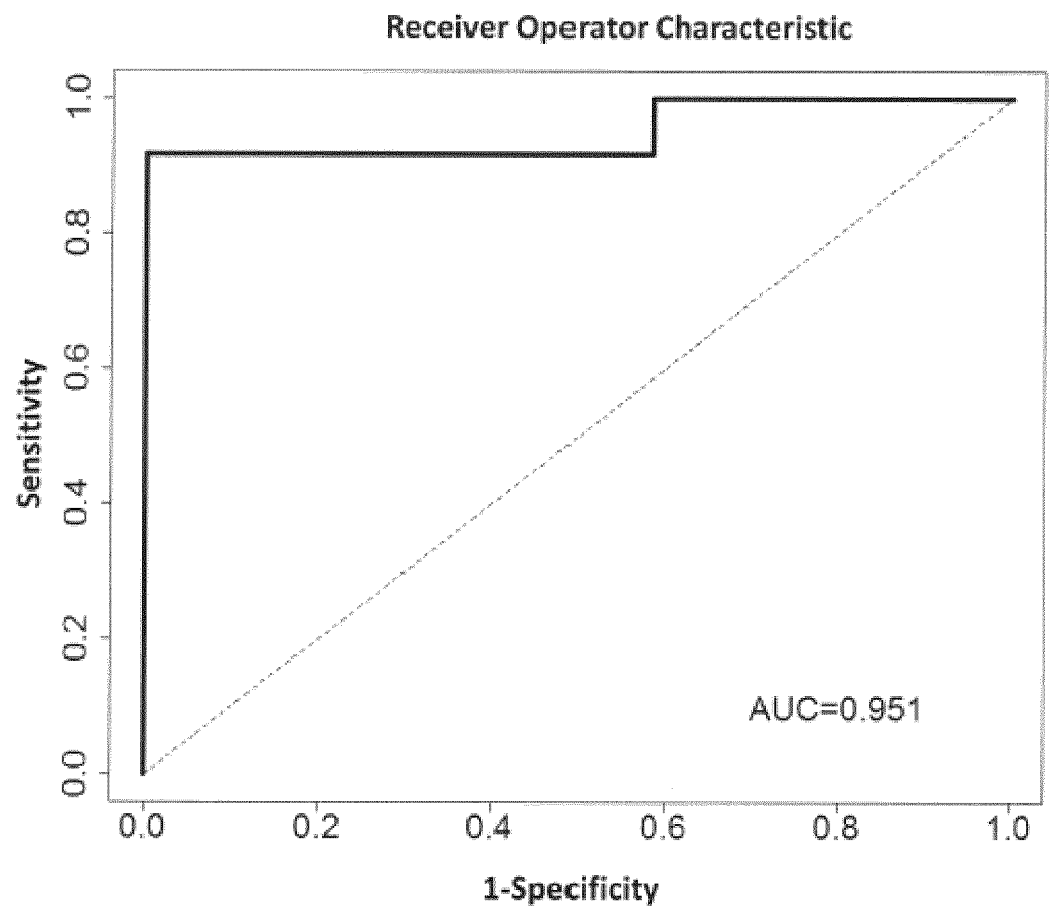
FIG. 6 shows a predictive modelling based on the random forest algorithm enabling identification of the signature of the 3 top serum lncRNA candidates selected out of the lncRNAs with a p value of <0.05 and a good correlation (Pearson) with scores of neurocognitive tests including MMSE and/or MoCA out of 7 neuropsychological tests performed.
Figure 7:
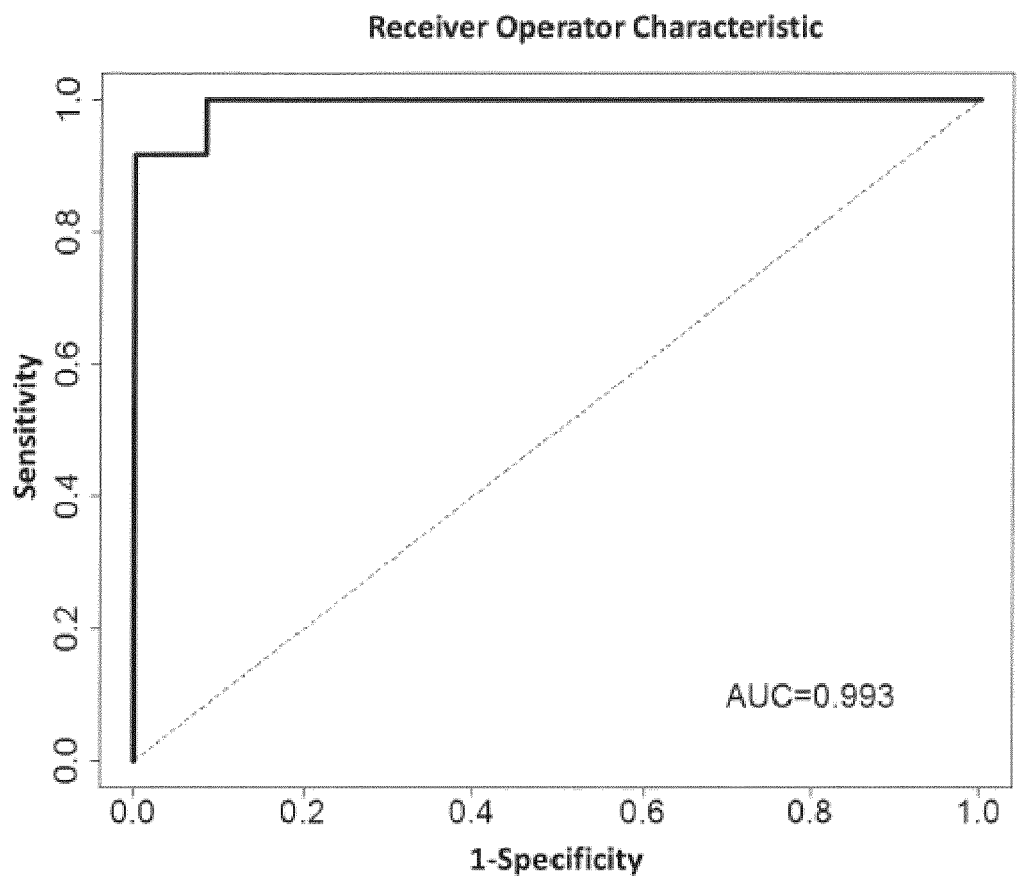
FIG. 7 shows a predictive modelling based on the random forest algorithm enabling the identification of the signature of the 7 top lncRNA candidates selected out of serum lncRNAs with a p value of <0.05 and a good correlation (Pearson) with neuroimaging scores (volume of brain structures of relevance for cognition and memory such as the meditotemporal area, left and right hippocampus, left and right amygdala, entorhinal cortex out of more than 120 structures measured.
Figure 8:
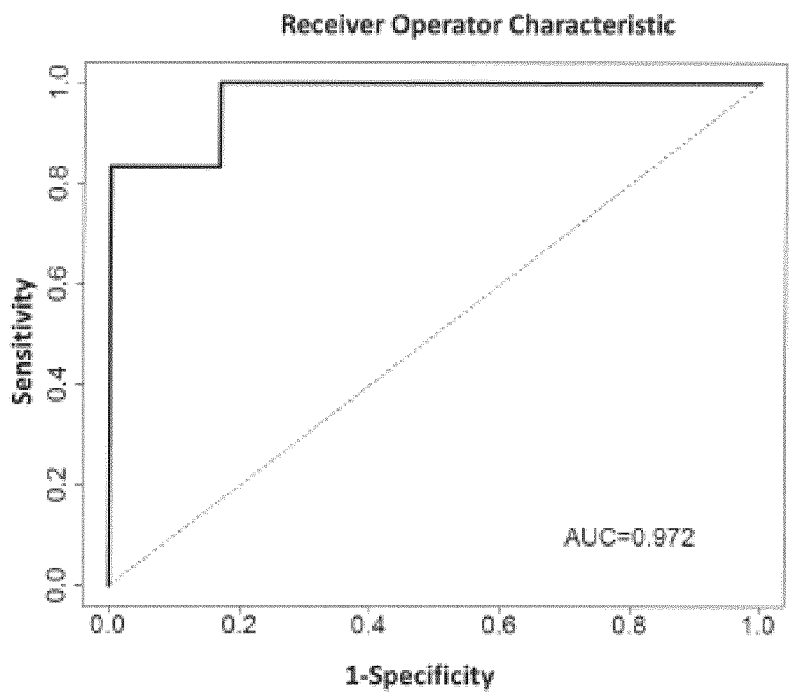
FIG. 8 shows a predictive modelling based on the random forest algorithm enabling the identification of the signature of the 18 top serum lncRNA candidates selected out of lncRNAs that show a p value of <0.05 and a good correlation (Pearson) with CSF biomarkers Aβ42 and tau (total tau or phosphorylated tau).
Figure 9:
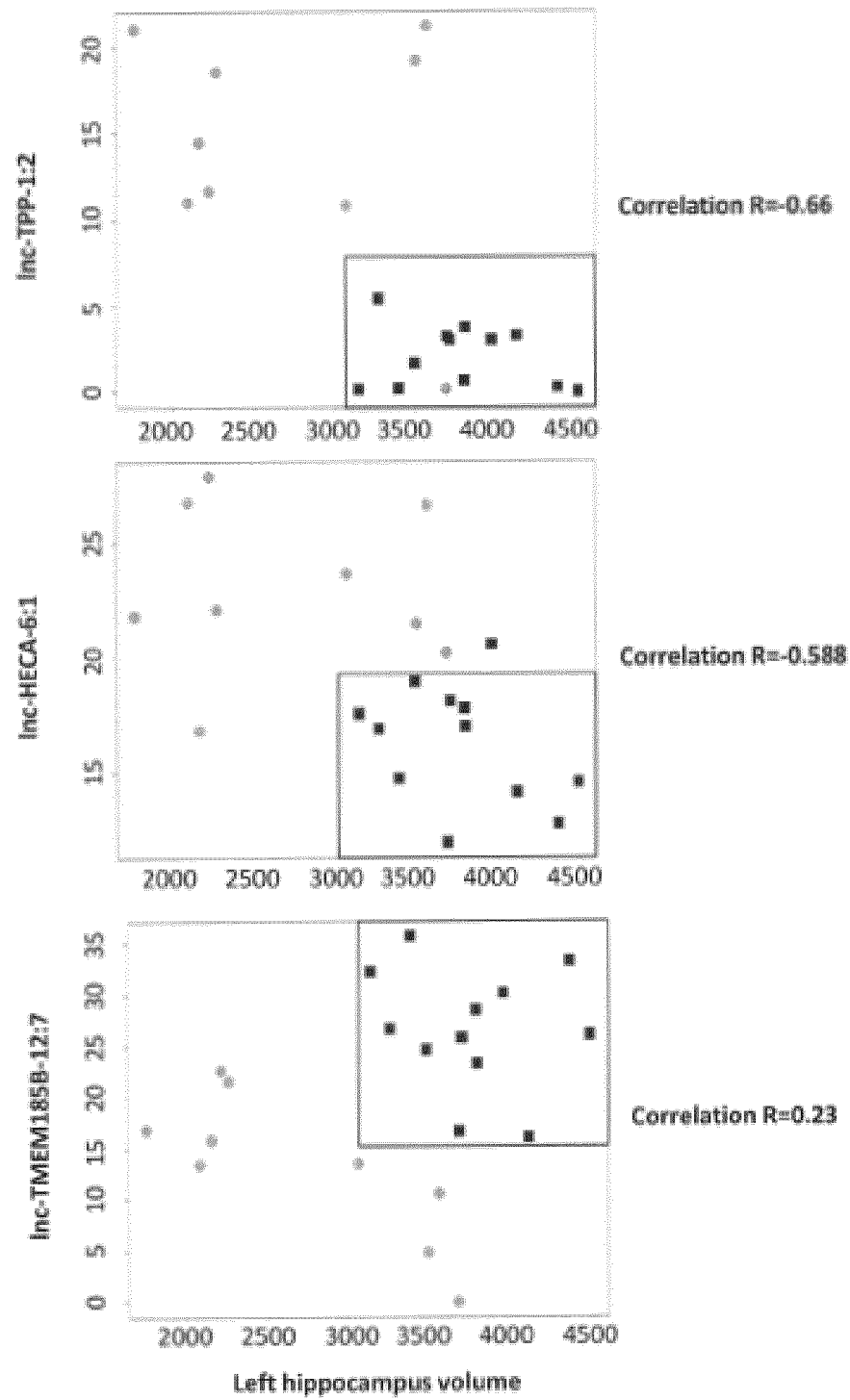
FIG. 9 shows examples of results on correlation between the level of serum lncRNAs and the volumetric neuroimaging score of brain structures implicated in cognition such as the meditotemporal area and the hippocampus.
Figure 10:
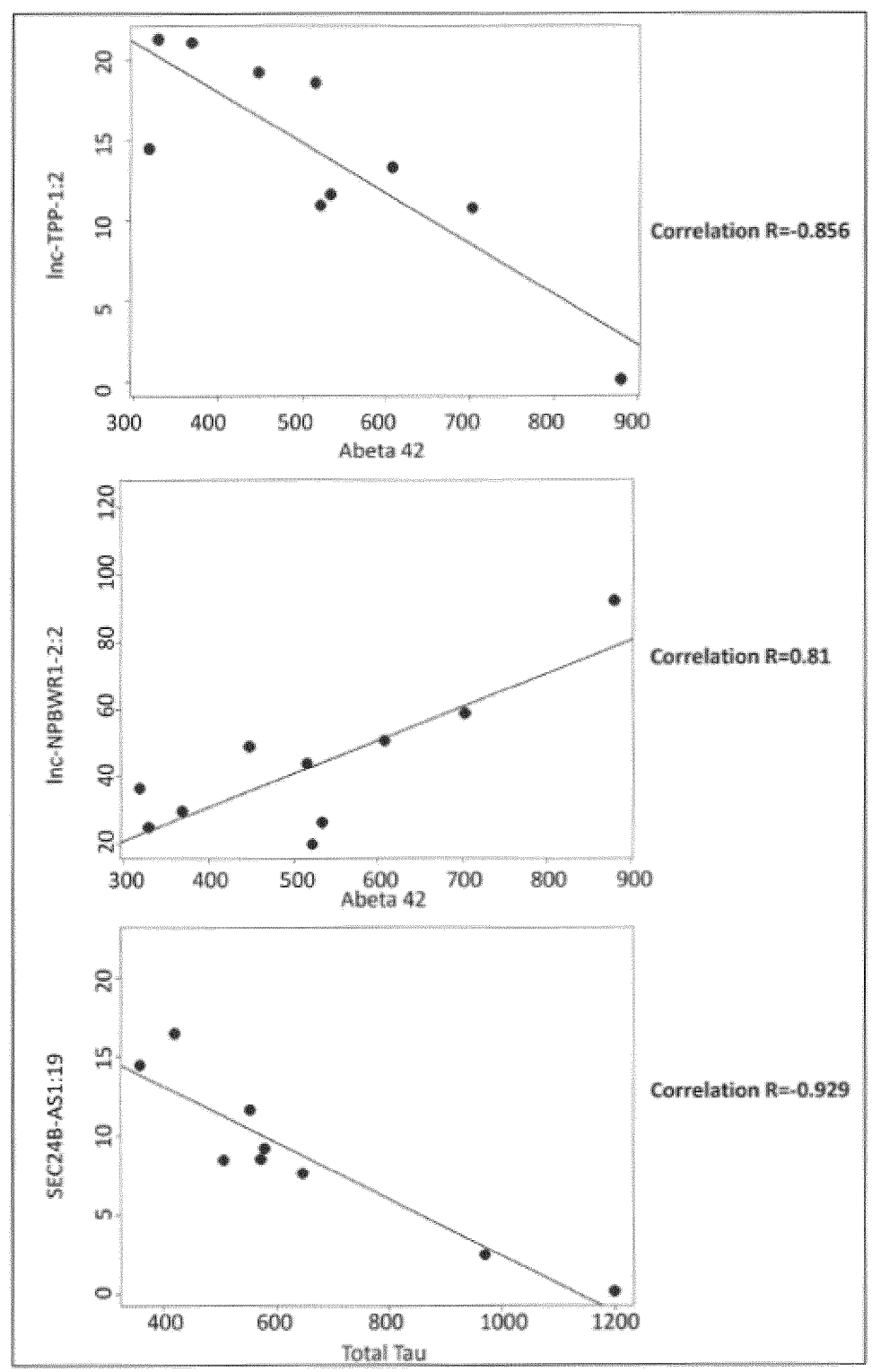
FIG. 10 shows examples of results on correlation between serum lncRNAs and CSF biomarkers Aβ42 or Tau.
Figure 11:
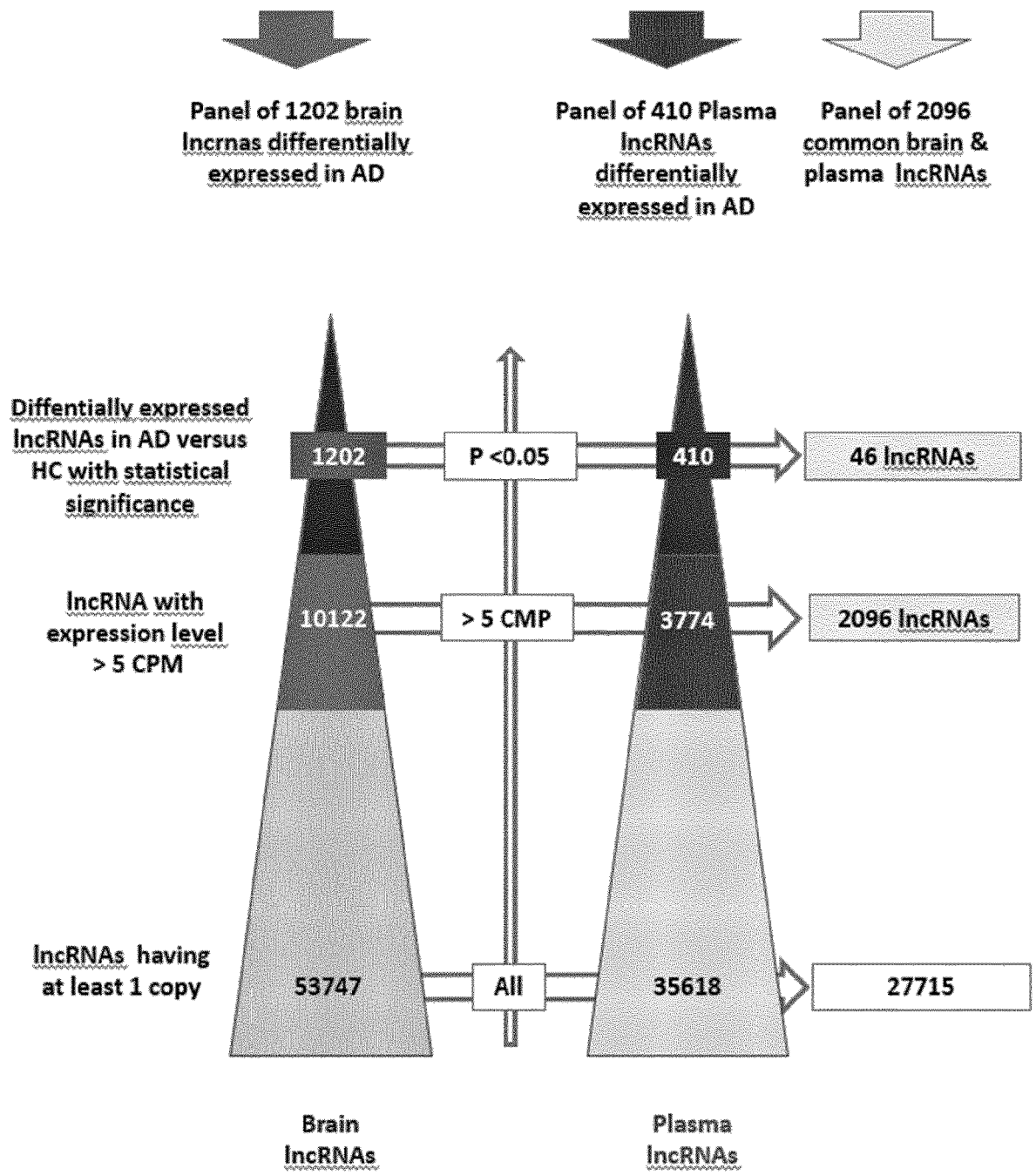
FIG. 11 shows the scheme of identifying brain and plasma lncRNAs.
Figure 12:
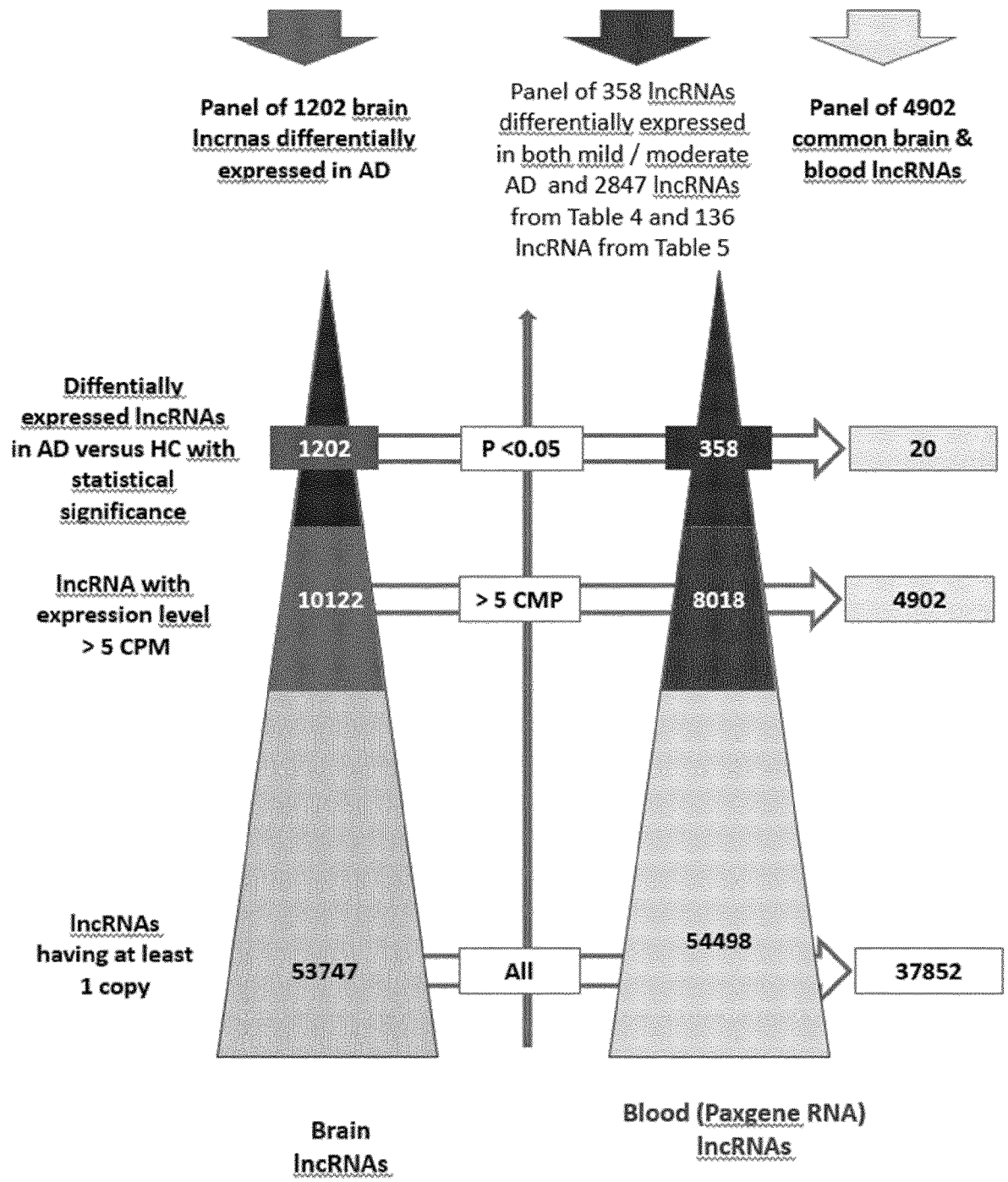
FIG. 12 shows the scheme of identifying brain and blood (Paxgene RNA) lncRNAs.
Figure 13:
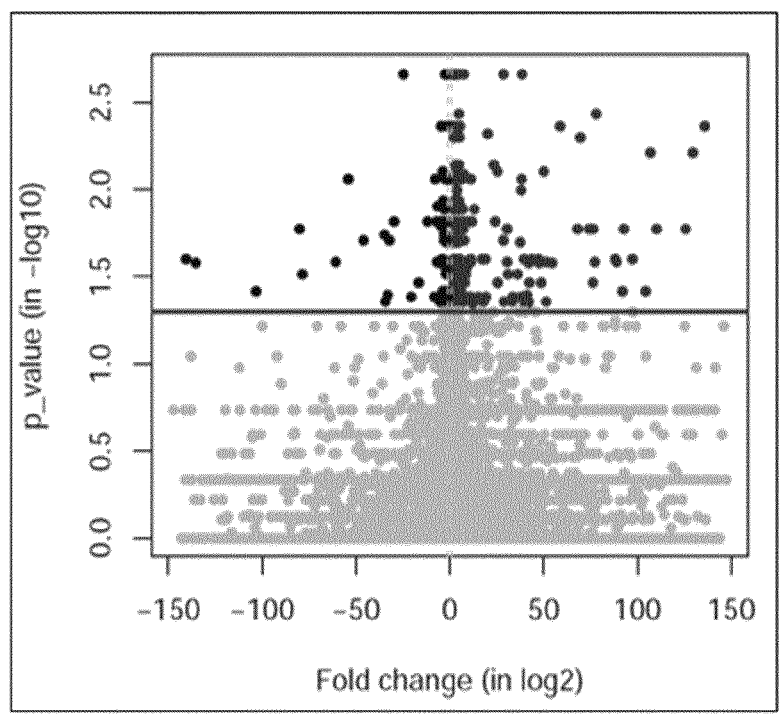
FIG. 13 shows Volcano plot of plasma lncRNAs obtained when comparing 6 Alzheimer's patients (AD) and 6 healthy control subjects (HC) and boxplot of plasma lncRNA LRRC10-1:1 and and its ROC curve showing its AUC=1. The volcano plot shows the lncRNAs that are differentially expressed with statistically significance (p<0.05, Wilcoxon test) above the line. The lncRNAs that are differentially expressed but did not reach a statistically significance, are shown below the line.
Figure 13:
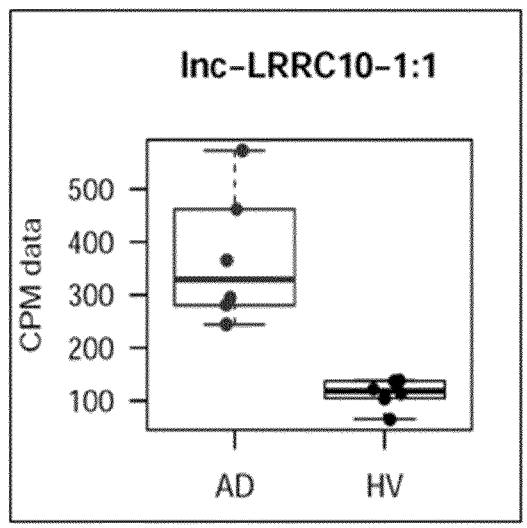
Figure 13:
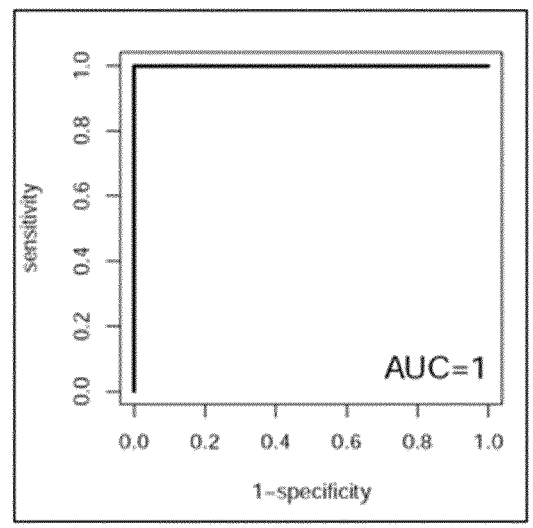
Figure 14:
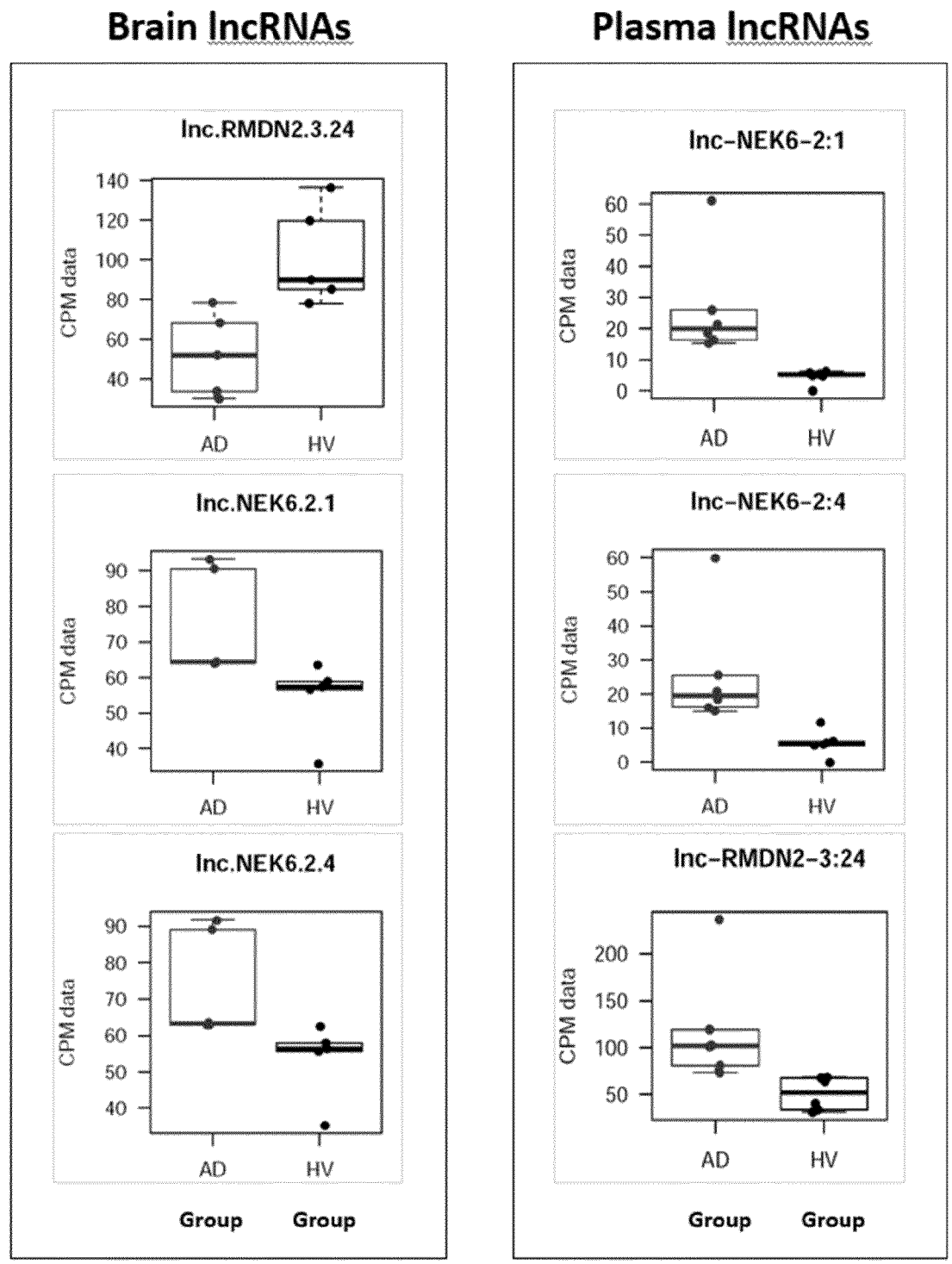
FIG. 14 shows example of 3 brain lncRNAs differentially expressed in the brain of 5 Alzheimer's patients as compared to brain of 5 healthy control subjects that are also identified as circulating plasma lncRNAs and as differentially expressed candidates in plasma of 6 Alzheimer patients as compared to 6 healthy control subjects.
Figure 15:
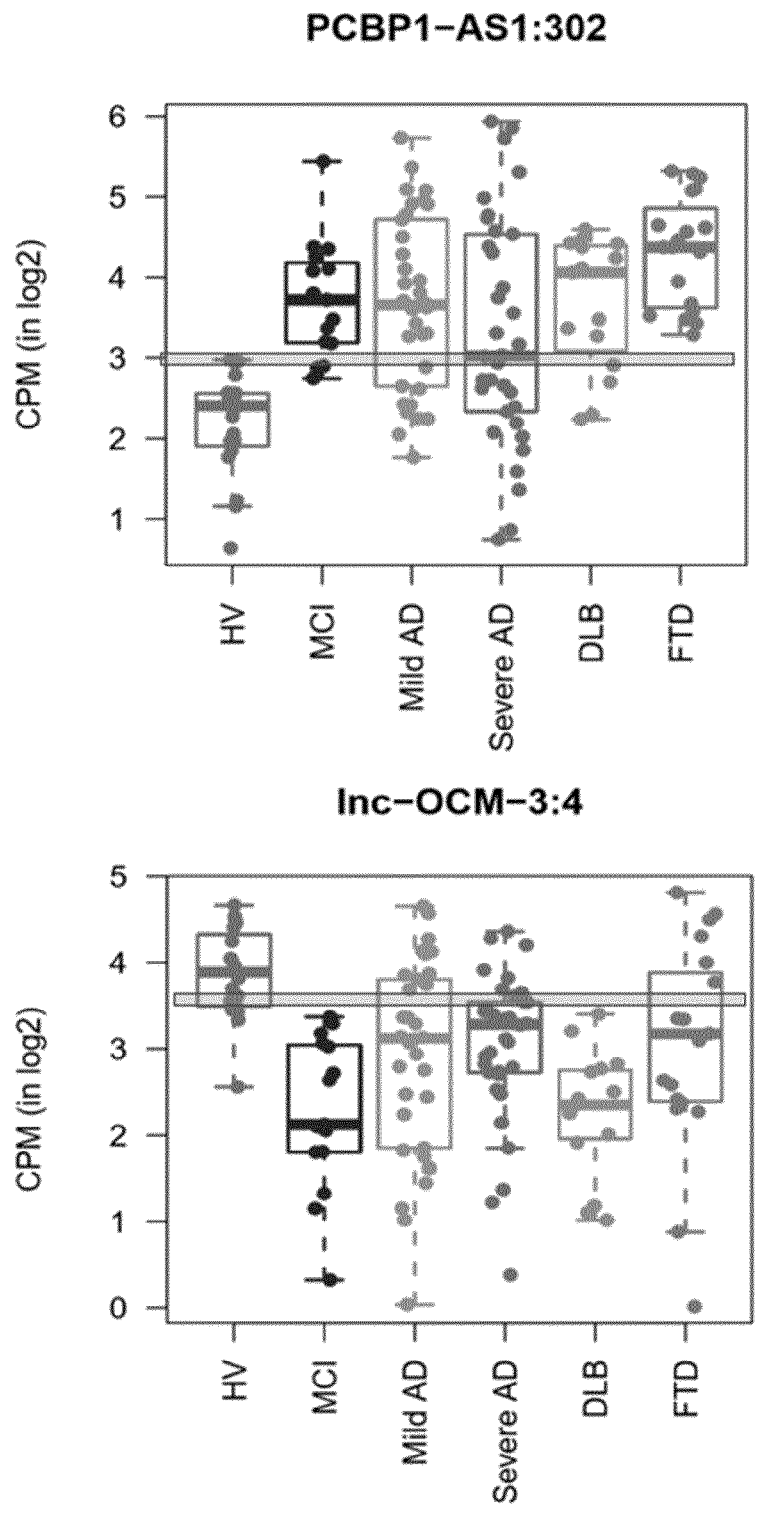
FIG. 15 shows boxplots of 2 whole blood lncRNAs: one overexpressed, the other down-expressed in MCI group and dementia groups (AD, DLB, FTD) when compared to healthy control group.
Figure 16:
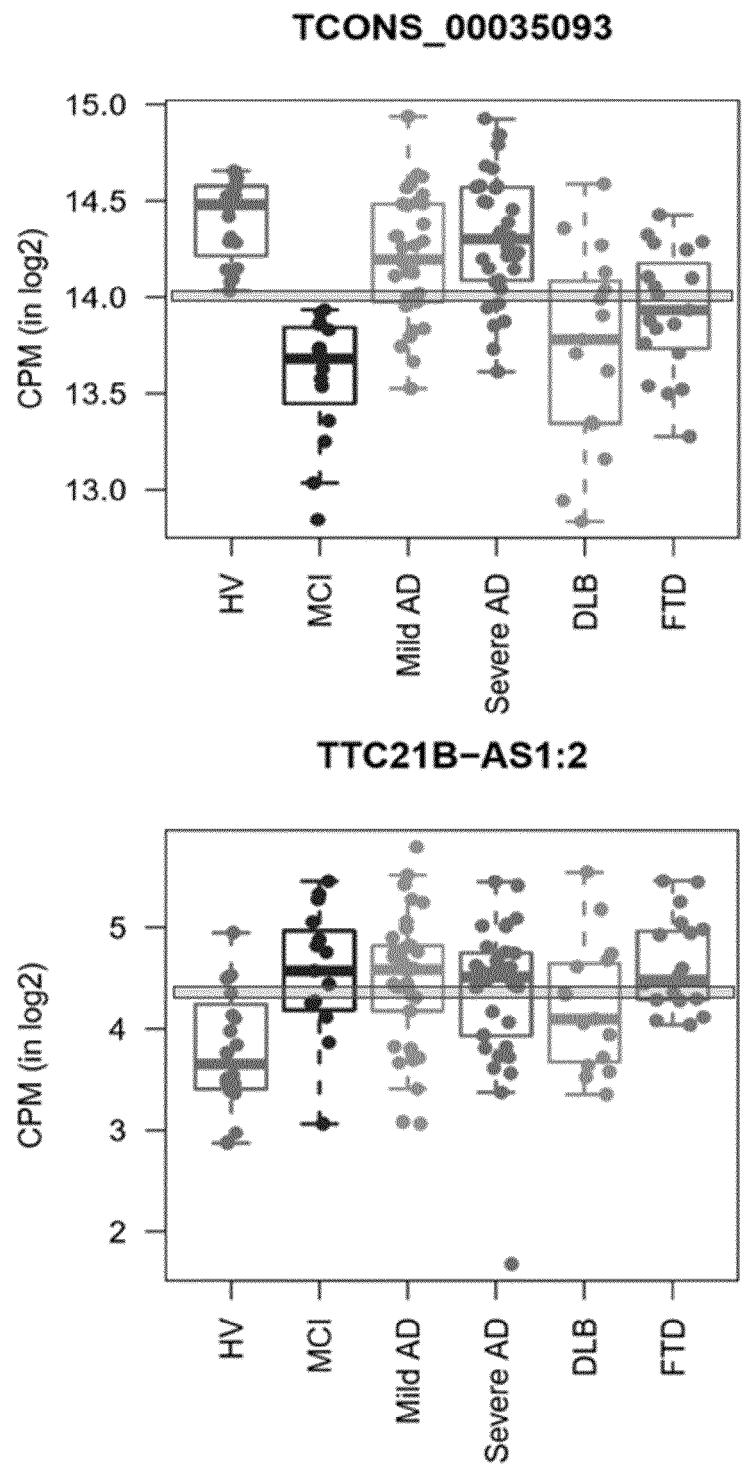
FIG. 16 shows boxplots of 2 whole blood lncRNAs differentially expressed in at least one of the patient groups as compared to healthy control group. The lncRNA TCONS_00035093 shows decreased expression in all MCI patients as compared to healthy controls. The lncRNA TTC21B-AS1:2 shows increased expression in most patients with MCI and AD patients.
Figure 17:
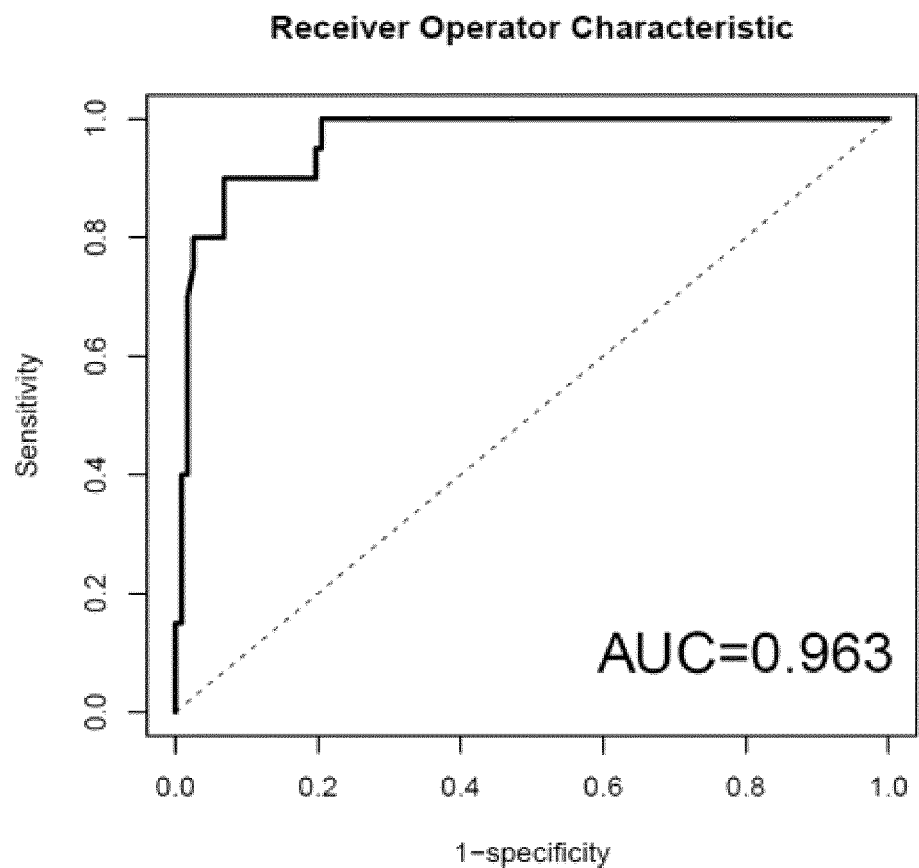
FIG. 17 shows an example of a panel of whole blood lncRNAs discriminating between HC group versus all the other groups with an accuracy 93.4%.
Figure 18:
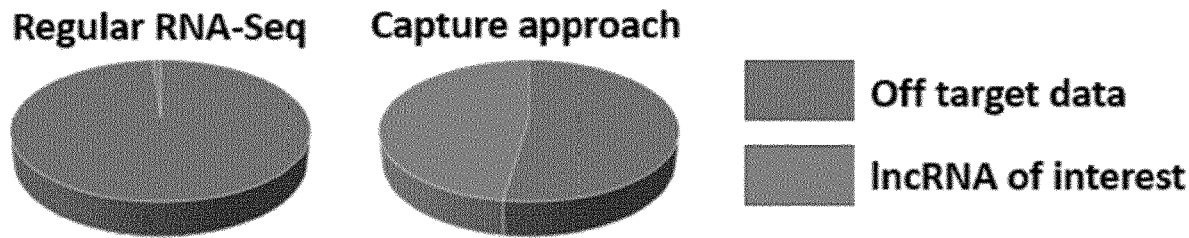
FIG. 18 shows targeted sequencing approach which shows a better efficiency to quantify precisely the selected lncRNAs. As an example, the use of FIMICS show an enrichment of 60× of the sequence of interest, representing less than 1% of the total sequences in global sequencing giving more difficult results to analyze. Only 8M of reads were needed to achieve a coverage of 100× allowing higher precision that regular RNA-Seq experiments.
Figure 18:
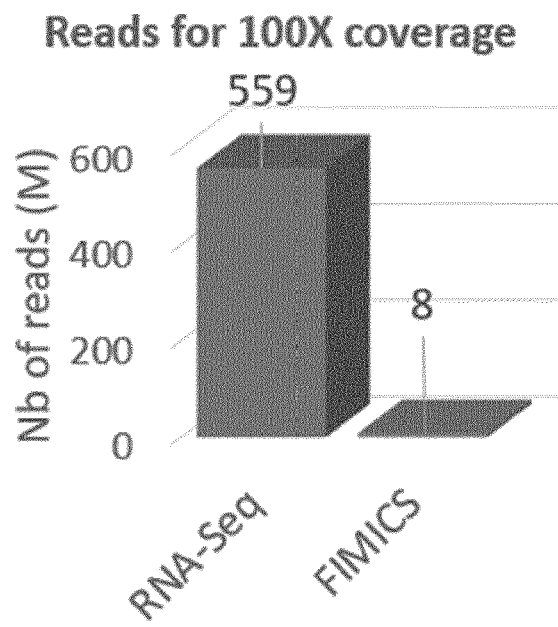
Figure 19:
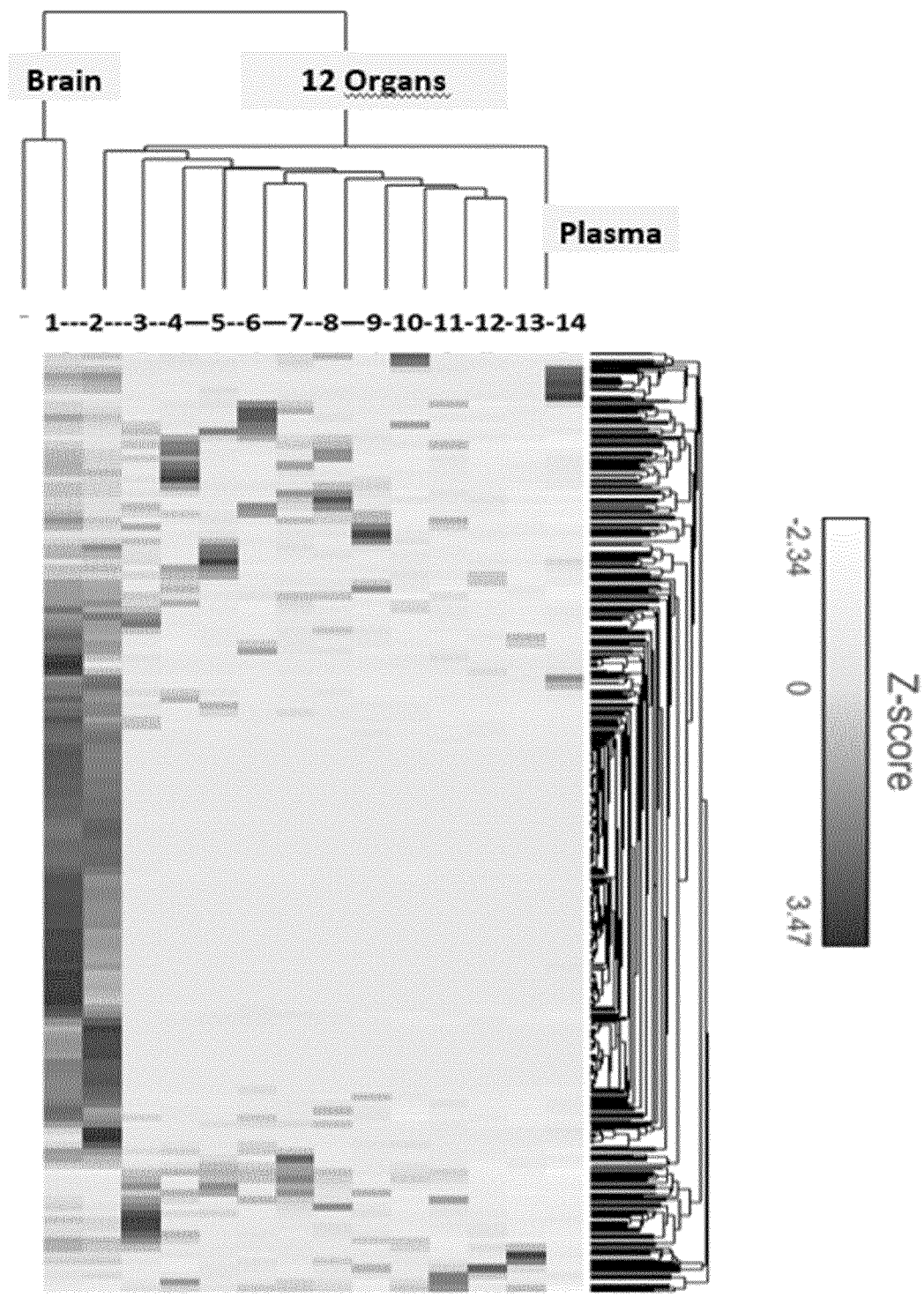
FIG. 19 shows Heat map showing that many identified brain-enriched lncRNAs that are expressed in the brain of AD and/or non-AD human subjects (columns 1,2) but not or poorly expressed in the organs tested (columns 2 to 13). Interestingly out of these brain-enriched lncRNAs, some are circulating brain-enriched lncRNAs as expressed in the plasma. 1: AD brain; 2: Non-AD brain; 3: Lung; 4: Ovary; 5: Colon; 6: Prostate; 7: Breast; 8: Liver; 9: Bladder; 10: Kidney; 11: Skin; 12: Heart; 13: Muscle; 14: Plasma.

DESCRIPTION OF THE INVENTION lncRNAs, including the 1091 novel lncRNAs identified for the first time in the present invention, that are disclosed in this disclosure may be involved in the pathogenesis of primary and secondary brain disorders including but not limited to neurodegenerative diseases, in particular Alzheimer's disease and cognitive disorders, neuropsychiatric disorders such as depression and anxiety, autism, neurological disorders such as multiple sclerosis, motoneuron disorders, stroke or implicated in systemic disorders, cardiovascular metabolic disorders indirectly involving the nervous system. Thus, these lncRNAs with altered expression represent novel targets for therapeutic and diagnostic applications. The novel brain lncRNAs identified as having an altered expression in AD brain may represent novel therapeutic candidates for development as lncRNA molecule-silencing therapeutic approaches for treatment of brain disorders in particular Alzheimer's disease and other cognitive disorders.

In addition, drug candidates or other medicinal products may induce cerebral toxicities such as autism or other syndromes. The lncRNAs identified in the present invention might be used to diagnose, predict or monitor their toxicity or efficacy.

In an aspect, the invention relates to lncRNAs for use in the treatment of brain diseases, in particular mild cognitive impairment (MCI) and Alzheimer or another cognitive disorder in a subject at risk of having or developing mild cognitive impairment or a cognitive disorder, wherein the treatment comprises administering to the subject an effective amount of a pharmaceutical agent modulating (inducing or inhibiting) the expression of the lncRNAs in the brain and/or in the periphery. The pharmaceutical agents may be specifically designed molecules such as small chemical entities or biological medicinal compounds, including but not limited to monoclonal antibodies, recombinant proteins, recombinant vector driven-therapeutics including but not limited to AV or AAV recombinant vectors, other RNA-related therapeutic means. In some embodiments, the pharmaceutical agent is administered to the subject with at least one pharmaceutically acceptable excipient. In some embodiments, the pharmaceutical agent is single or repeatedly administered to the subject as an oral, intravenous or subcutaneous or intra-cerebral treatment.

In some embodiments, the lncRNAs for use in the treatment of brain diseases are at least one novel lncRNA identified for the first time in the present invention (1091 novel lncRNAs listed in Table 7). In some embodiments, the lncRNAs are at least one novel lncRNA selected from 922 lncRNAs (430 lncRNAs with Fold change<0.9 and 492 lncRNAs with Fold change >1.1 listed in Table 7). In a preferred embodiment, the lncRNAs are at least one lncRNAs selected from the below group, which is referred as "lncRNA signature 12" in this disclosure:

| Novel lncRNA |
|---|
| TCONS_00050539 |
| TCONS_00062555 |
| TCONS_00024916 |
| TCONS_00059198 |
| TCONS_00066462 |
| TCONS_00033653 |
| TCONS_00040878 |
| TCONS_00000634 |
| TCONS_00050178 |
| TCONS_00055496 |
| TCONS_00033736 |
| TCONS_00023309 |
| TCONS_00027765 |
| TCONS_00062602 |
| TCONS_00005325 |
| TCONS_00011974 |
| TCONS_00023240 |
| TCONS_00023401 |
| TCONS_00066358 |
| TCONS_00062306 |
| TCONS_00027438 |

In some embodiments, the lncRNAs for use in the treatment of brain diseases are at least one LINCipedia-based lncRNAs that are sequenced in the brain and identified by the present invention to be differentially deficient or overexpressed in Alzheimer or dementia brain as compared to healthy control brain. In some embodiments, the lncRNAs are at least one lncRNAs selected from 681 lncRNAs with decreased level of expression in AD brain and 521 lncRNAs overexpressed in AD brain listed in Table 8. In a preferred embodiment, the lncRNAs are at least one lncRNAs selected from the below group, which is referred as "lncRNA signature 13" in this disclosure:

| lncRNA | lnc-PMM2-6:2 | |
|---|---|---|
| LINC-PINT:16 | MALAT1:23 | lnc-LTBP3-2:3 |

-continued

| | | |
|---|---|---|
| lnc-ATP6V1C1-12:1 | MALAT1:48 | MALAT1:11 |
| lnc-GABBR1-1:2 | lnc-LTBP3-2:6 | lnc-LTBP3-2:2 |

In another embodiment, the lncRNAs are at least one lncRNAs selected from the below group, which is referred as "lncRNA signature 42" in this disclosure:

| | |
|---|---|
| LncRNAs | lnc-FEM1B-4:1 |
| lnc-NEK6-2:1 | lnc-GNA14-3:1 |
| lnc-PMM2-6:4 | lnc-PINK1-2:1 |
| UGDH-AS1:10 | lnc-PRSS27-4:24 |
| lnc-RMDN2-3:24 | lnc-SLC25A3-7:1 |
| lnc-EIF1AD-1:1 | lnc-FEM1B-4:1 |
| lnc-FANCL-4:1 | NORAD:2 |
| lnc-FAAP100-2:1 | NORAD:8 |
| TCONS_00011974 | CACTIN-AS1:5 |

In some embodiments, the lncRNAs for use in the treatment of brain diseases are at least one brain-enriched lncR-NAs identified as detectable in the brain while not expressed or at least 2-fold less expressed in peripheral organ biopsies: lung, ovary, colon, prostate, breast, liver, bladder, kidney, skin, heart, muscle. In some embodiments, the lncRNAs are at least one lncRNAs selected from 860 lncRNAs listed in Table 12. In a preferred embodiment, the lncRNAs are at least one lncRNAs selected from the below group, which is referred as "lncRNA signature 14" in this disclosure:

| | | |
|---|---|---|
| TCONS_00035022 | TCONS_00035024 | lnc-ENC1-5:1 |
| TCONS_00035023 | TCONS_00035091 | lnc-SNAP25-3:1 |
| TCONS_00035094 | TCONS_00012059 | lnc-HMGA1-2:4 |
| TCONS_00035093 | TCONS_00035092 | PEG3-AS1:1 |
| TCONS_00035021 | TCONS_00012060 | lnc-UNC80-1:1 |
| TCONS_00035090 | TCONS_00050014 | |

In some embodiments, the lncRNAs for use in the treatment of brain diseases are at least one lncRNA selected from a lncRNA signature selected from lncRNA signatures 1 to 42. lncRNA signatures 1 to 42 are defined below in this disclosure.

In an aspect, the invention relates to lncRNA signatures for use in the diagnosis of brain diseases, in particular mild cognitive impairment (MCI) and Alzheimer or another cognitive disorder or for use in the diagnosis and differential diagnosis for brain disorders types, in particular dementia types, including but not limited to Alzheimer, dementia with Lewy bodies and frontotemporal dementia. lncRNA signatures comprising the already sequenced lncRNAs and newly sequenced lncRNAs that are differentially expressed in samples collected in non-invasively manner, including whole blood collected in Paxgene RNA tube and plasma derived from blood in patients suffering MCI, AD, DLB and/or FTD when compared to healthy controls, as well as panels that detect specifically MCI and one of the dementia type (AD or DLB or FTD) when compared to the other dementia types studied may be used. In some embodiments, the lncRNA signature is selected from the below group:

| lncRNA signature | lncRNAs included in the lncRNA signature |
|---|---|
| lncRNA signature 1 | 68 lncRNAs (TCONS_00050539, TCONS_00062555, TCONS_00024916, TCONS_00059198, TCONS_00066462, TCONS_00033653, LINC-PINT: 16, lnc-ATP6V1C1-12:1, lnc-GABBR1-1:2, lnc-PMM2-6:2, MALAT1:23, MALAT1:48, lnc-LTBP3-2:6, lnc-LTBP3-2:3, lnc-ANAPC11-2:8, lnc-CLLU1-2:6, lnc-KLHL36-2:2, lnc-LRRC10-1:1, lnc-RMDN2-3:24, lnc-SMN2-4:2, lnc-SPRYD3-1:17, lnc-USP47-2:1, lnc-ZC3H12B-1:5, TCONS_00019798, TSPOAP1-AS1:39, TCONS_00035093, lnc-OCM-3:4, lnc-KIF14-1:2, PCBP1-AS1:302, lnc-CA6-8:1, NEAT1:22, lnc-CA6-8:2, STARD7-AS1:5, lnc-IL31RA-1:1, lnc-ANKRD36-1:4, lnc-ATP6AP2-13:1, lnc-SOCS6-10:1, lnc-CDIPT-2:1, lnc-USP47-2:1, RBM26-AS1:1, MIR181A2HG:1, TTC21B-AS1:2, LEF1-AS1:1, lnc-SLC35E3-8:1, lnc-ZCCHC13-4:1, lnc-NEMF-1:4, TCONS_00011994, lnc-EVX1-15:1, lnc-REC8-2:1, OIP5-AS1:36, MYLK-AS1:13, lnc-PCP4L1-3:2, lnc-CGREF1-2:1, ZC3H12B-11:1, PSMB8-AS1:14, lnc-STX10-2:1, lnc-TCFL5-6:1, lnc-UQCC3-2:1, lnc-ZNF516-14:1, lnc-PDGFA-6:2, lnc-FOXD4L5-16:1, lnc-SAMD11-12:4, lnc-ADAD1-3:1, lnc-SLC35E3-8:2, lnc-NID1-4:4, FTX:19, TCONS_00017372, lnc-GRAP-1:2) |
| lncRNA signature 2 | 54 lncRNAs (lnc-ANAPC11-2:8, lnc-CLLU1-2:6, lnc-KLHL36-2:2, lnc-LRRC10-1:1, lnc-RMDN2-3:24, lnc-SMN2-4:2, lnc-SPRYD3-1:17, lnc-USP47-2:1, lnc-ZC3H12B-1:5, TCONS_00019798, TSPOAP1-AS1:39, TCONS_00035093, lnc-OCM-3:4, lnc-KIF14-1:2, PCBP1-AS1:302, lnc-CA6-8:1, NEAT1:22, lnc-CA6-8:2, STARD7-AS1:5, lnc-IL31RA-1:1, lnc-ANKRD36-1:4, lnc-ATP6AP2-13:1, lnc-SOCS6-10:1, lnc-CDIPT-2:1, lnc-USP47-2:1, RBM26-AS1:1, MIR181A2HG:1, TTC21B-AS1:2, LEF1-AS1:1, lnc-SLC35E3-8:1, lnc-ZCCHC13-4:1, lnc-NEMF-1:4, TCONS_00011994, lnc-EVX1-15:1, lnc-REC8-2:1, OIP5-AS1:36, MYLK-AS1:13, lnc-PCP4L1-3:2, lnc-CGREF1-2:1, ZC3H12B-11:1, PSMB8-AS1:14, lnc-STX10-2:1, lnc-TCFL5-6:1, lnc-UQCC3-2:1, lnc-ZNF516-14:1, lnc-PDGFA-6:2, lnc-FOXD4L5-16:1, lnc-SAMD11-12:4, lnc-ADAD1-3:1, lnc-SLC35E3-8:2, lnc-NID1-4:4, FTX: 19, TCONS_00017372, lnc-GRAP-1:2) |
| lncRNA signature 3 | 6 lncRNAs (lnc-ANAPC11-2:8, lnc-CLLU1-2:6, lnc-KLHL36-2:2, lnc-LRRC10-1:1, lnc-RMDN2-3:24, lnc-ZC3H12B-1:5) |
| lncRNA signature 4 | 11 lncRNAs (lnc-ANAPC11-2:8, lnc-CLLU1-2:6, lnc-KLHL36-2:2, lnc-LRRC10-1:1, lnc-RMDN2-3:24, lnc-SMN2-4:2, lnc-SPRYD3-1:17, lnc-USP47-2:1, lnc-ZC3H12B-1:5, TCONS_00019798, TSPOAP1-AS1:39) |
| lncRNA signature 5 | 43 lncRNAs (TCONS_00035093, lnc-OCM-3:4, lnc-KIF14-1:2, PCBP1-AS1:302, lnc-CA6-8:1, NEAT1:22, lnc-CA6-8:2, STARD7-AS1:5, lnc-IL31RA-1:1, lnc-ANKRD36-1:4, lnc-ATP6AP2-13:1, lnc-SOCS6-10:1, lnc-CDIPT-2:1, lnc-USP47-2:1, RBM26-AS1:1, MIR181A2HG:1, TTC21B-AS1:2, LEF1-AS1:1, lnc-SLC35E3-8:1, lnc-ZCCHC13-4:1, lnc-NEMF-1:4, TCONS_00011994, lnc-EVX1-15:1, lnc-REC8-2:1, OIP5-AS1:36, MYLK-AS1:13, lnc-PCP4L1-3:2, lnc-CGREF1-2:1, ZC3H12B-11:1, PSMB8-AS1:14, lnc-STX10-2:1, lnc-TCFL5-6:1, lnc-UQCC3-2:1, |

-continued

| lncRNA signature | lncRNAs included in the lncRNA signature |
|---|---|
| | lnc-ZNF516-14:1, lnc-PDGFA-6:2, lnc-FOXD4L5-16:1, lnc-SAMD11-12:4, lnc-ADAD1-3:1, lnc-SLC35E3-8:2, lnc-NID1-4:4, FTX:19, TCONS_00017372, lnc-GRAP-1:2) |
| lncRNA signature 6 | 6 lncRNAs (TCONS_00045364, TCONS_00035023, TCONS_00035091, TCONS_00035022, TCONS_00035092, TCONS_00035093) |
| lncRNA signature 7 | 14 lncRNAs (TCONS_00050539, TCONS_00062555, TCONS_00024916, TCONS_00059198, TCONS_00066462, TCONS_00033653, LINC-PINT:16, lnc-ATP6V1C1-12:1, lnc-GABBR1-1:2, lnc-PMM2-6:2, MALAT1:23, MALAT1:48, lnc-LTBP3-2:6, lnc-LTBP3-2:3) |
| lncRNA signature 8 | 2 lncRNAs (TCONS_00035093, lnc-OCM-3:4) |
| lncRNA signature 9 | 7 lncRNAs (lnc-KIF14-1:2, PCBP1-AS1:302, lnc-CA6-8:1, NEAT1:22, lnc-CA6-8:2, STARD7-AS1:5, lnc-IL31RA-1:1) |
| lncRNA signature 10 | 6 lncRNAs (lnc-CA6-8:2, lnc-ANKRD36-1:4, lnc-ATP6AP2-13:1, lnc-SOCS6-10:1, lnc-CDIPT-2:1, lnc-USP47-2:1) |
| lncRNA signature 11 | 7 lncRNAs (lnc-CA6-8:2, lnc-CA6-8:1, RBM26-AS1:1, PCBP1-AS1:302, MIR181A2HG:1, TTC21B-AS1:2, lnc-SOCS6-10:1) |
| lncRNA signature 12 | 21 lncRNAs (TCONS_00050539, TCONS_00062555, TCONS_00024916, TCONS_00059198, TCONS_00066462, TCONS_00033653, TCONS_00040878, TCONS_00000634, TCONS_00050178, TCONS_00055496, TCONS_00033736, TCONS_00023309, TCONS_00027765, TCONS_00062602, TCONS_00005325, TCONS_00011974, TCONS_00023240, TCONS_00023401, TCONS_00066358, TCONS_00062306, TCONS_00027438) |
| lncRNA signature 13 | 10 lncRNAs (LINC-PINT:16, lnc-ATP6V1C1-12:1, lnc-GABBR1-1:2, lnc-PMM2-6:2, MALAT1:23, MALAT1:48, lnc-LTBP3-2:6, lnc-LTBP3-2:3, MALAT1:11, lnc-LTBP3-2:2) |
| lncRNA signature 14 | 17 lncRNAs (TCONS_00035022, TCONS_00035023, TCONS_00035094, TCONS_00035093, TCONS_00035021, TCONS_00035090, TCONS_00035024, TCONS_00035091, TCONS_00012059, TCONS_00035092, TCONS_00012060, TCONS_00050014, lnc-ENC1-5:1, lnc-SNAP25-3:1, lnc-HMGA1-2:4, PEG3-AS1:1, lnc-UNC80-1:1) |
| lncRNA signature 15 | 2 lncRNAs (lnc-OCM-3:4, lnc-SLC35E3-8:1) |
| lncRNA signature 16 | 3 lncRNAs (lnc-ZCCHC13-4:1, PCBP1-AS1:302, lnc-NEMF-1:4) |
| lncRNA signature 17 | 6 lncRNAs (lnc-STAT3-1:2, lnc-NEMF-1:4, lnc-EPN2-3:2, lnc-SLC25A39-2:1, lnc-ARF6-1:1, lnc-CCNYL1-2:1) |
| lncRNA signature 18 | 5 lncRNAs (ANKRD44-IT1:1, APOBEC3B-AS1:2, ADAMTSL4-AS1:2, AGAP2-AS1:2, A1BG-AS1:14) |
| lncRNA signature 19 | 3 lncRNAs (LEF1-AS1:1, PCBP1-AS1:302, lnc-CA6-8:2) |
| lncRNA signature 20 | 5 lncRNAs (lnc-CGREF1-2:1, PSMB8-AS1:14, lnc-STX10-2:1, lnc-TCFL5-6:1, ZC3H12B-11:1) |
| lncRNA signature 21 | 3 lncRNAs (TCONS_00011994, lnc-EVX1-15:1, lnc-REC8-2:1) |
| lncRNA signature 22 | 3 lncRNAs (OIP5-AS1:36, MYLK-AS1:13, lnc-PCP4L1-3:2) |
| lncRNA signature 23 | 11 lncRNAs (PCBP1-AS1:302, STARD7-AS1:5, lnc-NID1-4:4, RBM26-AS1:1, LEF1-AS1:1, lnc-CA6-8:1, lnc-CA6-8:2, lnc-OCM-3:4, lnc-AFG1L-7:1, lnc-LASP1-5:1, lnc-GCGR-1:2) |
| lncRNA signature 24 | 7 lncRNAs (lnc-CA6-8:2, lnc-ANKRD36-1:4, lnc-ATP6AP2-13:1, lnc-SOCS6-10:1, lnc-CDIPT-2:1, lnc-USP47-2:1, lnc-UXS1-3:1) |
| lncRNA signature 25 | 3 lncRNAs (lnc-OCM-3:4, lnc-SLC35E3-8:1, LINC-PINT:11) |
| lncRNA signature 26 | 2 lncRNAs (lnc-ZCCHC13-4:1, PCBP1-AS1:302) |
| lncRNA signature 27 | 5 lncRNAs (lnc-JUNB-1:1, lnc-RARB-4:1, lnc-ZNF284-1:1, TCONS_00035093, lnc-TELO2-3:3) |
| lncRNA signature 28 | 5 lncRNAs (lnc-CGREF1-2:1 PSMB8-AS1:14 lnc-STX10-2:1 lnc-TCFL5-6:1 lnc-ZC3H12B-11:1) |
| lncRNA signature 29 | 13 lncRNAs (lnc-DLG5-1:1, lnc-EBLN1-1:4, lnc-FAT1-7:2, lnc-PRR5-5:1, lnc-RBKS-6:1, lnc-FOXD4L5-35:1, lnc-TENM3-3:3, lnc-FAM133B-2:1, lnc-ZNF726-1:3, lnc-AP3M1-1:1, lnc-DUSP10-6:1, lnc-TPPP-1:2, LINC01206:20) |
| lncRNA signature 30 | 7 lncRNAs (LINC02345:11, lnc-EBLN1-1:4, lnc-TPPP-1:2, lnc-TENM3-3:3, lnc-FAT1-7:2, lnc-DKK1-5:3, lnc-TACSTD2-2:4) |
| lncRNA signature 31 | 12 lnc RNAs (lnc-TPPP-1:2, ARRDC3-AS1:7, lnc-TENM3-3:5, lnc-TENM3-3:4, lnc-QRFP-5:1, lnc-CRYBB1-1:1, lnc-MGST3-1:3, lnc-FAM49B-8:1, HAND2-AS1:70, lnc-TMEM185B-12:7, lnc-CNDP1-7:1, lnc-C21orf58-1:2) |
| lncRNA signature 32 | 3 lncRNAs (lnc-TENM3-3:3, lnc-MARCH4-2:7, and lnc-LRRC1-5:2) |
| lncRNA signature 33 | 7 lncRNAs (lnc-TPPP-1:2, lnc-TENM3-3:3, lnc-TMEM185B-12:7, lnc-NAXD-6:5, lnc-HECA-6:1, lnc-COMMD6-10:1, and MIR29B2CHG:46) |
| lncRNA signature 34 | 18 lncRNAs (lnc-TPPP-1:2, LINC02345:11, lnc-ZNF273-4:4, lnc-TACC2-8:6, LINC01206:20, lnc-C5orf67-3:1, HAND2-AS1:58, lnc-PRDM9-20:1, lnc-CLK1-1:7, lnc-DNALI1-5:4, RORB-AS1:6, lnc-TPPP-1:3, lnc-BMS1-2:1, lnc-ADRB1-4:1, lnc-XXYLT1-5:1, MIR99AHG:104, LINC01748:17, lnc-AKR1E2-15:1) |

| lncRNA signature | lncRNAs included in the lncRNA signature |
|---|---|
| lncRNA signature 35 | 922 lncRNAs (430 lncRNAs with Fold change < 0.9 and 492 lncRNAs with Fold change > 1.1 listed in Table 7) |
| lncRNA signature 36 | 681 lncRNAs with decreased level of expression in AD brain and 521 lncRNAs overexpressed in AD brain listed in Table 8 |
| lncRNA signature 37 | 860 lncRNAs listed in Table 12 |
| lncRNA signature 38 | 410 lncRNAs listed in Table 9 |
| lncRNA signature 39 | 2847 lncRNAs listed in Table 10 and 136 lncRNAs listed in Table 11 |
| lncRNA signature 40 | 410 lncRNAs listed in Table 9, 2847 lncRNAs listed in Table 10 and 136 lncRNAs listed in Table 11 |
| lncRNA signature 41 | lncRNA signature 6 plus 8 lncRNAs listed in both Tables 9 and 12 or 55 lncRNAs listed in both Table 10 or 11 and Table 12 |
| lncRNA signature 42 | 17 lncRNAs (lnc-NEK6-2:1, lnc-PMM2-6:4, UGDH-AS1:10, lnc-RMDN2-3:24, lnc-EIF1AD-1:1, lnc-FANCL-4:1, lnc-FAAP100-2:1, TCONS_00011974, lnc-FEM1B-4:1, lnc-GNA14-3:1, lnc-PINK1-2:1, lnc-PRSS27-4:24, lnc-SLC25A3-7:1, lnc-FEM1B-4:1, NORAD:2, NORAD:8, CACTIN-AS1:5) |

The above 42 lncRNA signatures can be used in all methods or uses disclosed in this disclosure.

In an aspect, the invention relates to a method for the diagnosis of a brain disorder including but not limited to cognitive disorder such as mild cognitive impairment (MCI), Alzheimer disease, frontotemporal dementia and/or dementia with Lewy body in a subject at risk of having or developing mild cognitive impairment or a cognitive disorder, comprising:

(a) isolating a biological sample from the subject;
(b) detecting a level of expression in a lncRNA signature, the lncRNA signature comprising or consisting of at least one lncRNA selected from lncRNAs listed in Tables 7-12, in the biological sample from said subject;
(c) comparing the level of expression of lncRNA in the sample to a level of expression in a reference, wherein an increased or decreased level of expression in the sample compared to the level in the reference identifies the subject having a cognitive disorder or being at risk of developing a cognitive disorder.

In some embodiments, the method further comprises a step of designing the therapeutic treatment according to the said identified brain disorder such as a cognitive disorder after step (c). In some embodiments, the biological sample is whole blood, serum or plasma.

In some embodiments, the lncRNA signature comprises or consist of at least one lncRNA selected from lncRNA signature 6 plus 8 lncRNAs listed in both Tables 9 and 12 or 55 lncRNAs listed in both Table 10 or 11 and Table 12 ("lncRNA signature 41"). In some embodiments, the lncRNA signature comprises or consist of at least one lncRNA selected from brain-enriched lncRNAs circulating in plasma sample including novel brain-enriched lncRNAs circulating in plasma. In some embodiments, the lncRNA signature comprises or consist of at least one lncRNA selected from 6 lncRNAs (TCONS_00045364, TCONS_00035023, TCONS_00035091, TCONS_00035022, TCONS_00035092, TCONS_00035093) ("lncRNA signature 6"). In some embodiments, the lncRNA signature is or comprises lncRNA signature 6.

In some embodiments, the lncRNA signature comprises or consist of at least one lncRNA selected from 410 lncRNAs listed in Table 9, 2847 lncRNAs listed in Table 10 and 136 lncRNAs listed in Table 11 ("lncRNA signature 40"). In some embodiments, the lncRNA signature comprises or consist of at least one lncRNA selected from 54 lncRNAs (lnc-ANAPC11-2:8, lnc-CLLU1-2:6, lnc-KLHL36-2:2, lnc-LRRC10-1:1, lnc-RMDN2-3:24, lnc-SMN2-4:2, lnc-SPRYD3-1:17, lnc-USP47-2:1, lnc-ZC3H12B-1:5, TCONS_00019798, TSPOAP1-AS1:39, TCONS_00035093, lnc-OCM-3:4, lnc-KIF14-1:2, PCBP1-AS1:302, lnc-CA6-8:1, NEAT1:22, lnc-CA6-8:2, STARD7-AS1:5, lnc-IL31RA-1:1, lnc-ANKRD36-1:4, lnc-ATP6AP2-13:1, lnc-SOCS6-10:1, lnc-CDIPT-2:1, lnc-USP47-2:1, RBM26-AS1:1, MIR181A2HG:1, TTC21B-AS1:2, LEF1-AS1:1, lnc-SLC35E3-8:1, lnc-ZCCHC13-4:1, lnc-NEMF-1:4, TCONS_00011994, lnc-EVX1-15:1, lnc-REC8-2:1, OIP5-AS1:36, MYLK-AS1:13, lnc-PCP4L1-3:2, lnc-CGREF1-2:1, ZC3H12B-11:1, PSMB8-AS1:14, lnc-STX10-2:1, lnc-TCFL5-6:1, lnc-UQCC3-2:1, lnc-ZNF516-14:1, lnc-PDGFA-6:2, lnc-FOXD4L5-16:1, lnc-SAMD11-12:4, lnc-ADAD1-3:1, lnc-SLC35E3-8:2, lnc-NID1-4:4, FTX:19, TCONS_00017372, lnc-GRAP-1:2) ("lncRNA signature 2"). In some embodiments, the lncRNA signature is or comprises lncRNA signature 2.

In some embodiments, the lncRNA signature comprises or consist of at least one lncRNA selected from a lncRNA signature selected from lncRNA signatures 1 to 42. In some embodiments, the lncRNA signature is or comprises a lncRNA signature selected from lncRNA signatures 1 to 42.

In an aspect, the invention relates to a method for the diagnosis of a brain disorder including but not limited to cognitive disorder such as mild cognitive impairment (MCI), Alzheimer disease, frontotemporal dementia and/or dementia with Lewy body in a subject at risk of having or developing mild cognitive impairment or a cognitive disorder, comprising:

(a) isolating a biological sample from the subject, wherein the biological sample is plasma;
(b) detecting a level of expression in a lncRNA signature, the lncRNA signature comprising or consisting of at least one lncRNA selected from 410 plasma lncRNAs listed in Table 9 ("lncRNA signature 38"), in the biological sample from said subject;
(c) comparing the level of expression of lncRNA in the sample to a level of expression in a reference, wherein an increased or decreased level of expression in the sample compared to the level in the reference identifies the subject having a cognitive disorder or being at risk of developing a cognitive disorder.

In some embodiments, the method further comprises a step of designing the therapeutic treatment according to the said identified brain disorder such as a cognitive disorder after step (c).

In some embodiments, the lncRNA signature comprises or consist of at least one lncRNA selected from 6 lncRNAs (lnc-ANAPC11-2:8, lnc-CLLU1-2:6, lnc-KLHL36-2:2, lnc-LRRC10-1:1, lnc-RMDN2-3:24, lnc-ZC3H12B-1:5) "lncRNA signature 3". In a preferred embodiment, the lncRNA signature is or comprises lncRNA signature 3.

In some embodiments, the lncRNA signature comprises or consist of at least one lncRNA selected from 11 lncRNAs (lnc-ANAPC11-2:8, lnc-CLLU1-2:6, lnc-KLHL36-2:2, lnc-LRRC10-1:1, lnc-RMDN2-3:24, lnc-SMN2-4:2, lnc-SPRYD3-1:17, lnc-USP47-2:1, lnc-ZC3H12B-1:5, TCONS_00019798, TSPOAP1-AS1:39)) "lncRNA signature 4". In a preferred embodiment, the lncRNA signature is or comprises lncRNA signature 4.

In an aspect, the invention relates to a method for the diagnosis of a brain disorder including but not limited to cognitive disorder such as mild cognitive impairment (MCI), Alzheimer disease, frontotemporal dementia and/or dementia with Lewy body in a subject at risk of having or developing mild cognitive impairment or a cognitive disorder, comprising:
  (a) isolating a biological sample from the subject, wherein the biological sample is whole blood;
  (b) detecting a level of expression in a lncRNA signature, the lncRNA signature comprising or consisting of at least one lncRNA selected from 2847 lncRNAs listed in Table 10 and 136 lncRNAs listed in Table 11 ("lncRNA signature 39"), in the biological sample from said subject;
  (c) comparing the level of expression of lncRNA in the sample to a level of expression in a reference,
  wherein an increased or decreased level of expression in the sample compared to the level in the reference identifies the subject having a cognitive disorder or being at risk of developing a cognitive disorder.

In some embodiments, the method further comprises a step of designing the therapeutic treatment according to the said identified brain disorder such as a cognitive disorder after step (c).

In some embodiments, the lncRNA signature comprises or consist of at least one lncRNA selected from 43 lncRNAs (TCONS_00035093, lnc-OCM-3:4, lnc-KIF14-1:2, PCBP1-AS1:302, lnc-CA6-8:1, NEAT1:22, lnc-CA6-8:2, STARD7-AS1:5, lnc-IL31RA-1:1, lnc-ANKRD36-1:4, lnc-ATP6AP2-13:1, lnc-SOCS6-10:1, lnc-CDIPT-2:1, lnc-USP47-2:1, RBM26-AS1:1, MIR181A2HG:1, TTC21B-AS1:2, LEF1-AS1:1, lnc-SLC35E3-8:1, lnc-ZCCHC13-4:1, lnc-NEMF-1:4, TCONS_00011994, lnc-EVX1-15:1, lnc-REC8-2:1, OIP5-AS1:36, MYLK-AS1:13, lnc-PCP4L1-3:2, lnc-CGREF1-2:1, ZC3H12B-11:1, PSMB8-AS1:14, lnc-STX10-2:1, lnc-TCFL5-6:1, lnc-UQCC3-2:1, lnc-ZNF516-14:1, lnc-PDGFA-6:2, lnc-FOXD4L5-16:1, lnc-SAMD11-12:4, lnc-ADAD1-3:1, lnc-SLC35E3-8:2, lnc-NID1-4:4, FTX:19, TCONS_00017372, lnc-GRAP-1:2) ("lncRNA signature 5"). In a preferred embodiment, the lncRNA signature is or comprises lncRNA signature 5.

In an aspect, the invention relates to a method for the diagnosis of a brain disorder including but not limited to cognitive disorder such as mild cognitive impairment (MCI), Alzheimer disease, frontotemporal dementia and/or dementia with Lewy body in a subject at risk of having or developing mild cognitive impairment or a cognitive disorder, comprising:
  (a) isolating two or more biological samples (such as both plasma and whole blood) from the subject;
  (b) detecting a level of expression in a lncRNA signature, the lncRNA signature comprising or consisting of at least one lncRNA selected from 410 lncRNAs listed in Table 9, 2847 lncRNAs listed in Table 10 and 136 lncRNAs listed in Table 11 ("lncRNA signature 40"), in the biological samples from said subject;
  (c) comparing the level of expression of lncRNA in the sample to a level of expression in a reference,
  wherein an increased or decreased level of expression in the sample compared to the level in the reference identifies the subject having a cognitive disorder or being at risk of developing a cognitive disorder.

In some embodiments, the method further comprises a step of designing the therapeutic treatment according to the said identified brain disorder such as a cognitive disorder after step (c). In some embodiments, the two or more biological samples are plasma and whole blood.

In some embodiments, the lncRNA signature comprises or consist of at least one lncRNA selected from 54 lncRNAs (lnc-ANAPC11-2:8, lnc-CLLU1-2:6, lnc-KLHL36-2:2, lnc-LRRC10-1:1, lnc-RMDN2-3:24, lnc-SMN2-4:2, lnc-SPRYD3-1:17, lnc-USP47-2:1, lnc-ZC3H12B-1:5, TCONS_00019798, TSPOAP1-AS1:39, TCONS_00035093, lnc-OCM-3:4, lnc-KIF14-1:2, PCBP1-AS1:302, lnc-CA6-8:1, NEAT1:22, lnc-CA6-8:2, STARD7-AS1:5, lnc-IL31RA-1:1, lnc-ANKRD36-1:4, lnc-ATP6AP2-13:1, lnc-SOCS6-10:1, lnc-CDIPT-2:1, lnc-USP47-2:1, RBM26-AS1:1, MIR181A2HG:1, TTC21B-AS1:2, LEF1-AS1:1, lnc-SLC35E3-8:1, lnc-ZCCHC13-4:1, lnc-NEMF-1:4, TCONS_00011994, lnc-EVX1-15:1, lnc-REC8-2:1, OIP5-AS1:36, MYLK-AS1:13, lnc-PCP4L1-3:2, lnc-CGREF1-2:1, ZC3H12B-11:1, PSMB8-AS1:14, lnc-STX10-2:1, lnc-TCFL5-6:1, lnc-UQCC3-2:1, lnc-ZNF516-14:1, lnc-PDGFA-6:2, lnc-FOXD4L5-16:1, lnc-SAMD11-12:4, lnc-ADAD1-3:1, lnc-SLC35E3-8:2, lnc-NID1-4:4, FTX:19, TCONS_00017372, lnc-GRAP-1:2) ("lncRNA signature 2"). In some embodiments, the lncRNA signature is or comprises lncRNA signature 2.

In an aspect, the invention also relates to a method for diagnosis and differential diagnosis for brain disorders types, in particular dementia types, including but not limited to Alzheimer, dementia with Lewy bodies and frontotemporal dementia in a subject suffering from a brain disorder such as loss or impairment of cognitive function or dementia of subtype to be diagnosed, said method comprising:
  (a) isolating two or more biological samples (such as both plasma and whole blood) from the subject;
  (b) detecting a level of expression in a lncRNA signature, the lncRNA signature comprising or consisting of at least one lncRNA selected 410 lncRNAs listed in Table 9, 2847 lncRNAs listed in Table 10 and 136 lncRNAs listed in Table 11 ("lncRNA signature 40"), in the biological samples from said subject;
  (c) comparing the level of expression of lncRNA in the sample to a level of expression in a reference,
  wherein an increased or decreased level of expression in the sample compared to the level in the reference identifies the subject having a cognitive disorder or being at risk of developing a cognitive disorder.

In some embodiments, the method further comprises a step of designing the therapeutic treatment according to the said identified brain disorder such as a cognitive disorder after step (c). In some embodiments, the biological sample is plasma or whole blood.

In some embodiments, the lncRNA signature comprises or consist of at least one lncRNA selected from 54 lncRNAs (lnc-ANAPC11-2:8, lnc-CLLU1-2:6, lnc-KLHL36-2:2, lnc-LRRC10-1:1, lnc-RMDN2-3:24, lnc-SMN2-4:2, lnc-SPRYD3-1:17, lnc-USP47-2:1, lnc-ZC3H12B-1:5, TCONS_00019798, TSPOAP1-AS1:39, TCONS_00035093, lnc-OCM-3:4, lnc-KIF14-1:2, PCBP1-AS1:302, lnc-CA6-8:1, NEAT1:22, lnc-CA6-8:2, STARD7-AS1:5, lnc-IL31RA-1:1, lnc-ANKRD36-1:4, lnc-ATP6AP2-13:1, lnc-SOCS6-10:1, lnc-CDIPT-2:1, lnc-USP47-2:1, RBM26-AS1:1, MIR181A2HG:1, TTC21B-AS1:2, LEF1-AS1:1, lnc-SLC35E3-8:1, lnc-ZCCHC13-4:1, lnc-NEMF-1:4, TCONS_00011994, lnc-EVX1-15:1, lnc-REC8-2:1, OIP5-AS1:36, MYLK-AS1:13, lnc-PCP4L1-3:2, lnc-CGREF1-2:1, ZC3H12B-11:1, PSMB8-AS1:14, lnc-STX10-2:1, lnc-TCFL5-6:1, lnc-UQCC3-2:1, lnc-ZNF516-14:1, lnc-PDGFA-6:2, lnc-FOXD4L5-16:1, lnc-SAMD11-12:4, lnc-ADAD1-3:1, lnc-SLC35E3-8:2, lnc-NID1-4:4, FTX:19, TCONS_00017372, lnc-GRAP-1:2) ("lncRNA signature 2"). In some embodiments, the lncRNA signature is or comprises lncRNA signature 2.

In an aspect, the invention relates to a method for monitoring the development or progression of brain disorders including but not limited to cognitive disorder such as mild cognitive impairment, Alzheimer disease, dementia with Lewy bodies frontotemporal dementia in a subject suffering from a brain disorder including loss or impairment of cognitive function or dementia, said method comprising the following steps:
  (a) isolating a biological sample from the subject;
  (b) detecting a level of expression in a lncRNA signature, the lncRNA signature comprising or consisting of at least one lncRNA selected from 410 lncRNAs listed in Table 9, 2847 lncRNAs listed in Table 10 and 136 lncRNAs listed in Table 11 ("lncRNA signature 40"), in the biological sample from said subject;
  (c) comparing the level of expression of lncRNA in the sample to a level of expression in a reference, wherein an increased or decreased level of expression in the sample compared to the level in the reference identifies the subject having a cognitive disorder or being at risk of developing a cognitive disorder.

In some embodiments, the method further comprises a step of designing the therapeutic treatment according to the said identified brain disorder such as a cognitive disorder after step (c). In some embodiments, the biological sample is plasma or whole blood.

In some embodiments, the lncRNA signature comprises or consist of at least one lncRNA selected from 54 lncRNAs (lnc-ANAPC11-2:8, lnc-CLLU1-2:6, lnc-KLHL36-2:2, lnc-LRRC10-1:1, lnc-RMDN2-3:24, lnc-SMN2-4:2, lnc-SPRYD3-1:17, lnc-USP47-2:1, lnc-ZC3H12B-1:5, TCONS_00019798, TSPOAP1-AS1:39, TCONS_00035093, lnc-OCM-3:4, lnc-KIF14-1:2, PCBP1-AS1:302, lnc-CA6-8:1, NEAT1:22, lnc-CA6-8:2, STARD7-AS1:5, lnc-IL31RA-1:1, lnc-ANKRD36-1:4, lnc-ATP6AP2-13:1, lnc-SOCS6-10:1, lnc-CDIPT-2:1, lnc-USP47-2:1, RBM26-AS1:1, MIR181A2HG:1, TTC21B-AS1:2, LEF1-AS1:1, lnc-SLC35E3-8:1, lnc-ZCCHC13-4:1, lnc-NEMF-1:4, TCONS_00011994, lnc-EVX1-15:1, lnc-REC8-2:1, OIP5-AS1:36, MYLK-AS1:13, lnc-PCP4L1-3:2, lnc-CGREF1-2:1, ZC3H12B-11:1, PSMB8-AS1:14, lnc-STX10-2:1, lnc-TCFL5-6:1, lnc-UQCC3-2:1, lnc-ZNF516-14:1, lnc-PDGFA-6:2, lnc-FOXD4L5-16:1, lnc-SAMD11-12:4, lnc-ADAD1-3:1, lnc-SLC35E3-8:2, lnc-NID1-4:4, FTX:19, TCONS_00017372, lnc-GRAP-1:2) ("lncRNA signature 2"). In some embodiments, the lncRNA signature is or comprises lncRNA signature 2.

A biological sample may be a small part of a subject obtained from a body fluid, e.g. blood, plasma, serum, saliva, urine, tear or cerebrospinal fluid or organ tissue. Suitably the biological sample are plasma or serum or whole blood (Paxgene-RNA-tube).

By brain disorder is meant e.g. a cognitive disorder such as a dementia type, a neurodegenerative disease, neurological or neuropsychatric disorder or systemic disorder involving the brain from the below example of brain disease list):
  Dementia types and subtypes are numerous and include e.g.
    Alzheimer (AD) and MCI of AD type
    Frontotemporal dementia (FTD) and MCI of FTD type
    Progressive supranuclear palsy (PSP)
    Corticobasal degeneration (CBD)
    Dementia with Lewy body (DLB) and MCI of DLB type
    Parkinson's disease dementia (PDD) and MCI of PDD type
    Vascular dementia and related MCI
    Stroke-related MCI and dementia
    Other dementia types,
  Neurodegenerative and neurological and neuropsychiatric disorders with a cognitive impairment often occurring early or at later stages of the disease progression:
    Parkinson disease
    Huntington disease
    Autism
    Amyotrophic lateral sclerosis
    Motoneuron diseases
    Multiple sclerosis
    Neuropathies
    Major depressive disorder
    Anxiety
  Systemic disorders with brain involvement and negative impact on the brain health such as brain cognitive impairment, including metabolic disorders such as diabetes, cardiovascular such as stroke, autoimmune and inflammatory disorders.

For Diagnosis of Brain Disorder Including Cognitive Impairment or Dementia:

The "reference" may be suitable control sample such as for example a sample from a normal, healthy subject having no brain disorder or cognitive impairment symptoms and no abnormal neuroimaging findings and being age-matched to the patient to be diagnosed with the method of the present invention. The reference may be a sample from the same subject prior to demonstration of disorder or disease symptoms or prior to diagnosis of the brain disorder or the impairment or loss of cognitive function or dementia. The reference may be a standardized sample, e.g. a sample comprising material or data from several samples of healthy subjects who have no brain or cognitive impairment symptoms and no abnormal neuroimaging findings.

For Therapeutics, Diagnosis or Differential Diagnosis of a Specific Dementia Type or its Mild Cognitive Impairment (MCI) Versus Other Dementia Types and their MCI:

Brain disorders and subtypes are numerous and include cognitive disorders with dementia types and subtypes:
  Dementia types and subtypes are numerous and include e.g.
    Alzheimer (AD) and MCI of AD type
    Frontotemporal dementia (FTD) and MCI of FTD type Progressive supranuclear palsy (PSP)
Corticobasal degeneration (CBD)
Dementia with Lewy body (DLB) and MCI of DLB type
Parkinson's disease dementia (PDD) and MCI of PDD type
Vascular dementia and related MCI
Stroke-related MCI and dementia
Other dementia types,
Neurodegenerative and neurological and neuropsychiatric disorders with a cognitive impairment often occurring early or at later stages of the disease progression:
Parkinson disease
Huntington disease
Amyotrophic lateral sclerosis
Autism Multiple sclerosis
Motoneuron diseases
Neuropathies
Major depressive disorder
Anxiety Systemic disorders with brain involvement and negative impact on the brain health such as brain cognitive impairment, including metabolic disorders such as diabetes, cardiovascular such as stroke, autoimmune and inflammatory disorders.

For differential diagnosis of one brain disorder the reference sample may be sample(s) from patient(s) suffering another brain disorder of the same class of disorders (for example for differential diagnosis of a dementia subtype, the reference sample may be sample(s) from patient(s) suffering dementia of other type(s)). and/or to reference value obtained on samples from subject(s) who may suffer another disease but have no symptom similar to the targeted brain disorder (for example for differential diagnosis of a dementia, reference sample(s) may be from a patient having no cognitive impairment or dementia).

The invention also relates to a method of diagnosing a brain disorder including but not limited to cognitive disorder such as Alzheimer disease, frontotemporal dementia, dementia with Lewy bodies and monitoring its development or progression in a subject suffering from progressive impairment or loss of cognitive function or dementia, comprising:
(a) determining the presence of a brain disorder such as a cognitive disorder using a biological sample of the said subject using a method according to the invention, and
(b) adapting a therapeutic treatment in function of the results of step (a).

The invention also relates to a method of diagnosing a brain disorder including but not limited to cognitive disorder such early MCI and very mild Alzheimer disease in a subject with no apparent and/or no measurable symptoms when using the available methods to detect clinical symptoms (such as MMSE, MoCA and other neurocognitive tests for cognitive disorder), but with abnormal changes of biomarkers of the present invention preceding the symptoms, comprising:
(a) determining the risk of developing a cognitive disorder using a biological sample of the said subject using a method according to the invention, and
(b) adapting a therapeutic treatment in function of the results of step (a).

The invention also relates to a method of future improved diagnosing a brain disorder including but not limited to a cognitive disorder such as early MCI and very mild Alzheimer disease in a subject by measuring the biomarkers of the present invention in combination with risk factors, such as genotypes including but not limited to ApoE gene alleles, cardiovascular, metabolic, inflammatory biomarkers, comprising:
(a) determining the risk of developing a cognitive disorder using a biological sample of the said subject using a method according to the invention in combination with one of the above-mentioned risk factors, and
(b) adapting a therapeutic treatment in function of the results of step (a).

The invention further relates to a method of predictive diagnosing a brain disorder including but not limited to a cognitive disorder such as early MCI and early stages of Alzheimer disease or frontotemporal dementia or dementia with Lewy bodies in a subject with no apparent and/or no measurable abnormality by neuroimaging methods as MRI and/or CT scans, comprising:
(a) determining the risk of developing a cognitive disorder using a biological sample of the said subject using a method according to the invention, and
(b) adapting a therapeutic treatment in function of the results of step (a).

The invention further relates to a method of predictive diagnosing a cognitive disorder including but not limited to early MCI and early stages of Alzheimer disease or frontotemporal dementia or dementia with Lewy bodies in a subject with no apparent and/or no measurable abnormality by molecular neuroimaging methods, such as but not limited to amyloid or tau or dopaminergic or synucleinergic PET scan, comprising:
(a) determining the risk of developing a cognitive disorder using a biological sample of the said subject using a method according to the invention, and
(b) adapting a therapeutic treatment in function of the results of step (a).

The invention further relates to a method of diagnosing or differential diagnosing or monitoring a cognitive disorder including but not limited to early MCI and early stages of Alzheimer disease or frontotemporal dementia or dementia with Lewy bodies in a subject using combination(s) of biomarkers of the present invention with a neuroimaging method including molecular neuroimaging methods, comprising:
(a) determining the risk of developing a cognitive disorder using a biological sample of the said subject using a method according to the invention, and
(b) adapting a therapeutic treatment in function of the results of step (a).

The invention also relates to a method for treating a subject suffering from a progressive impairment or loss of cognitive function or dementia, said method comprising:
(a) diagnosing the cognitive disorder associated to the progressive impairment or loss of cognitive function or dementia in said patient using the method according to the invention, and
(b) adapting the therapeutic treatment to the results obtained in step (a).

Examples of therapeutic treatment of cognitive disorders may comprise the administration of:
a drug already approved for treatment of brain disorder for example, for a drug already approved for treatment of Alzheimer's disease, among cholinesterase inhibitors, donenepezil, rivastigmine or galantamine, or a NMDA receptor antagonist, memantine, or a combination of, e.g. donepezil and memantine, and/or
a therapeutic candidate or combination under clinical development for example as currently tested in Alzheimer patients in the anti-amyloid field, e.g. beta-secretase inhibitors and anti-beta-amyloid monoclonal antibodies, and anti-tau approaches, or as currently tested in the anti-tau field, e.g. modulators of kinases or phosphatases that regulate tau phosphorylation status and anti-tau antibodies, drug and drug candidates modulating the molecular pathways of neurodegeneration, oxidative stress, autophagy, mitochondrial dysfunction and immuno-inflammation, and/or a novel therapeutic approach derived from the present invention.

In an aspect, the invention also provides a kit for diagnosing and/or monitoring a brain disorder including but not limited to cognitive disorders such as MCI, AD, FTD, DLB, comprising at least one reagent for the determination of a lncRNA expression profile comprising or consisting of at least one lncRNA selected from 410 lncRNAs listed in Table 9, 2847 lncRNAs listed in Table 10 and 136 lncRNAs listed in Table 11 ("lncRNA signature 40"). In some embodiments, the lncRNA expression profile comprises or consist of at least one lncRNA selected from 54 lncRNAs (lnc-ANAPC11-2:8, lnc-CLLU1-2:6, lnc-KLHL36-2:2, lnc-LRRC10-1:1, lnc-RMDN2-3:24, lnc-SMN2-4:2, lnc-SPRYD3-1:17, lnc-USP47-2:1, lnc-ZC3H12B-1:5, TCONS_00019798, TSPOAP1-AS1:39, TCONS_00035093, lnc-OCM-3:4, lnc-KIF14-1:2, PCBP1-AS1:302, lnc-CA6-8:1, NEAT1:22, lnc-CA6-8:2, STARD7-AS1:5, lnc-IL31RA-1:1, lnc-ANKRD36-1:4, lnc-ATP6AP2-13:1, lnc-SOCS6-10:1, lnc-CDIPT-2:1, lnc-USP47-2:1, RBM26-AS1:1, MIR181A2HG:1, TTC21B-AS1:2, LEF1-AS1:1, lnc-SLC35E3-8:1, lnc-ZCCHC13-4:1, lnc-NEMF-1:4, TCONS_00011994, lnc-EVX1-15:1, lnc-REC8-2:1, OIP5-AS1:36, MYLK-AS1:13, lnc-PCP4L1-3:2, lnc-CGREF1-2:1, ZC3H12B-11:1, PSMB8-AS1:14, lnc-STX10-2:1, lnc-TCFL5-6:1, lnc-UQCC3-2:1, lnc-ZNF516-14:1, lnc-PDGFA-6:2, lnc-FOXD4L5-16:1, lnc-SAMD11-12:4, lnc-ADAD1-3:1, lnc-SLC35E3-8:2, lnc-NID1-4:4, FTX:19, TCONS_00017372, lnc-GRAP-1:2) ("lncRNA signature 2"). In some embodiments, the lncRNA expression profile comprises or consist of at least one lncRNA selected from a lncRNA signature selected from lncRNA signatures 1 to 42. In some embodiments, the lncRNA expression profile comprises or consists of a lncRNA signature selected from lncRNA signatures 1 to 42. In some embodiments, the lncRNA expression profile is or comprises lncRNA signature 2.

The kit of the invention allows performing the measurement of the lncRNA signature of the invention, wherein the kit comprises at least one reagent for measuring at least one lncRNA selected from the lncRNAs as indicated above.

By "reagent" is also meant a reagent which specifically allows the determination of the lncRNA expression profile, i.e. a reagent specifically intended for the specific determination of the expression level of the lncRNA present in the lncRNA expression profile. Examples include e.g. amplification primer pairs (forward and reward) and/or probes specific for the lncRNA present in the lncRNA expression profile. This definition excludes generic reagents useful for the determination of the expression level of any other lncRNA.

In some embodiments, the kit for diagnosing and/or monitoring a brain disorder including but not limited to cognitive disorders such as MCI, AD, FTD, DLB comprises one or more oligonucleotide probes specific for lncRNAs of interest and a reagent for purifying the probe-target nucleic acid complexes. The oligonucleotide probes comprise a sequence complementary to a region of the lncRNAs of interest. The oligonucleotide probes may be DNA or RNA. The oligonucleotide probes are preferably DNA. The length of oligonucleotide probes specific for lncRNAs may be from 30 to 80 nucleotides, e.g., from 40 to 70, from 40 to 60, or about 50 nucleotides. In a preferred embodiment, the oligonucleotide probes are biotinylated and the reagent for purifying the probe-target complexes is a streptavidin-coated substrate, e.g., a streptavidin-coated magnetic particle, e.g., T1 streptavidin coated magnetic bead.

A further embodiment of the invention relates to a targeted sequencing panel for next generation sequencing, comprising nucleic acids specific for at least one lncRNA selected from 68 lncRNAs (TCONS_00050539, TCONS_00062555, TCONS_00024916, TCONS_00059198, TCONS_00066462, TCONS_00033653, LINC-PINT:16, lnc-ATP6V1C1-12:1, lnc-GABBR1-1:2, lnc-PMM2-6:2, MALAT1:23, MALAT1:48, lnc-LTBP3-2:6, lnc-LTBP3-2:3, lnc-ANAPC11-2:8, lnc-CLLU1-2:6, lnc-KLHL36-2:2, lnc-LRRC10-1:1, lnc-RMDN2-3:24, lnc-SMN2-4:2, lnc-SPRYD3-1:17, lnc-USP47-2:1, lnc-ZC3H12B-1:5, TCONS_00019798, TSPOAP1-AS1:39, TCONS_00035093, lnc-OCM-3:4, lnc-KIF14-1:2, PCBP1-AS1:302, lnc-CA6-8:1, NEAT1:22, lnc-CA6-8:2, STARD7-AS1:5, lnc-IL31RA-1:1, lnc-ANKRD36-1:4, lnc-ATP6AP2-13:1, lnc-SOCS6-10:1, lnc-CDIPT-2:1, lnc-USP47-2:1, RBM26-AS1:1, MIR181A2HG:1, TTC21B-AS1:2, LEF1-AS1:1, lnc-SLC35E3-8:1, lnc-ZCCHC13-4:1, lnc-NEMF-1:4, TCONS_00011994, lnc-EVX1-15:1, lnc-REC8-2:1, OIP5-AS1:36, MYLK-AS1:13, lnc-PCP4L1-3:2, lnc-CGREF1-2:1, ZC3H12B-11:1, PSMB8-AS1:14, lnc-STX10-2:1, lnc-TCFL5-6:1, lnc-UQCC3-2:1, lnc-ZNF516-14:1, lnc-PDGFA-6:2, lnc-FOXD4L5-16:1, lnc-SAMD11-12:4, lnc-ADAD1-3:1, lnc-SLC35E3-8:2, lnc-NID1-4:4, FTX:19, TCONS_00017372, lnc-GRAP-1:2) ("lncRNA signature 1"). In some embodiments, the at least one lncRNA is selected from a lncRNA signature selected from lncRNA signatures 1 to 42. In some embodiments, the at least one lncRNA comprises or consists of a lncRNA signature selected from lncRNA signatures 1 to 42. In a preferred embodiment, the at least one lncRNA is or comprises lncRNA signature 1.

The invention also relates to the applications of the method for development of new therapeutic strategies (drug candidates) tested in clinical trials for the treatment of a brain disorder including but not limited to a cognitive disorder such as Alzheimer disease, dementia with lewy bodies, frontotemporal dementia wherein the method can be used (a) before starting the treatment for the selection of patients who would then be recruited in clinical trial; thus the test will enhance the likelihood for treating patient population that benefits from the tested therapeutic strategy (ies) while avoiding recruitment of patient subpopulation patients who do not benefit from this tested new drug candidate(s) and/or (b) for monitoring the response(s) including efficacy of the tested therapeutic strategy(ies) once treatment with the new tested drug candidate starts.

In a further aspect, the invention also relates to methods of detection. For example, the invention contemplates a method for the detection of one or more lncRNAs. In one aspect the method comprises:

(a) isolating a biological sample from the subject;
(b) detecting a level of expression in a lncRNA signature, the lncRNA signature comprising or consisting of at least one lncRNA selected from 68 lncRNAs (TCONS_00050539, TCONS_00062555, TCONS_00024916, TCONS_00059198, TCONS_00066462, TCONS_00033653, LINC-PINT:16, lnc-ATP6V1C1-12:1, lnc-GABBR1-1:2, lnc-PMM2-6:2, MALAT1:23, MALAT1:48, lnc-LTBP3-2:6, lnc-LTBP3-2:3, lnc-ANAPC11-2:8, lnc-CLLU1-2:6, lnc-KLHL36-2:2, lnc-LRRC10-1:1, lnc-RMDN2-3:24, lnc-SMN2-4:2, lnc-SPRYD3-1:17, lnc-USP47-2:1, lnc-ZC3H12B-1:5, TCONS_00019798, TSPOAP1-AS1:39, TCONS_00035093, lnc-OCM-3:4, lnc-KIF14-1:2, PCBP1-AS1:302, lnc-CA6-8:1, NEAT1:22, lnc-CA6-8:2, STARD7-AS1:5, lnc-IL31RA-1:1, lnc-ANKRD36-1:4, lnc-ATP6AP2-13:1, lnc-SOCS6-10:1, lnc-CDIPT-2:1, lnc-USP47-2:1, RBM26-AS1:1, MIR181A2HG:1, TTC21B-AS1:2, LEF1-AS1:1, lnc-SLC35E3-8:1, lnc-ZCCHC13-4:1, lnc-NEMF-1:4, TCONS_00011994, lnc-EVX1-15:1, lnc-REC8-2:1, OIP5-AS1:36, MYLK-AS1:13, lnc-PCP4L1-3:2, lnc-CGREF1-2:1, ZC3H12B-11:1, PSMB8-AS1:14, lnc-STX10-2:1, lnc-TCFL5-6:1, lnc-UQCC3-2:1, lnc-ZNF516-14:1, lnc-PDGFA-6:2, lnc-FOXD4L5-16:1, lnc-SAMD11-12:4, lnc-ADAD1-3:1, lnc-SLC35E3-8:2, lnc-NID1-4:4, FTX:19, TCONS_00017372, lnc-GRAP-1:2).

In some embodiments, the lncRNA signature comprises or consist of at least one lncRNA selected from a lncRNA signature selected from lncRNA signatures 1 to 42. In some embodiments, the lncRNA signature is or comprises a lncRNA signature selected from lncRNA signatures 1 to 42. In a preferred embodiment, the lncRNA signature is or comprises lncRNA signature 1.

The expression level of lncRNAs may be determined by any technology known by a man skilled in the art. In particular, the expression level of lncRNAs is determined by measuring the amount of nucleic acid transcripts of each lncRNAs. The amount of nucleic acid transcripts can be measured by any technology known by a man skilled in the art. The measure may be carried out directly on an extracted RNA sample or on retrotranscribed complementary DNA (cDNA) prepared from extracted RNA by technologies well-known in the art. From the RNA or cDNA sample, the amount of nucleic acid transcripts may be measured using any technology known by a man skilled in the art, including nucleic acid microarrays, quantitative PCR, sequencing (e.g., next generation sequencing), FIMAP quantification, and hybridization with a labeled probe.

In some embodiments, the expression level of lncRNAs is determined using sequencing, e.g., next generation sequencing. Sequencing may be carried out after converting extracted RNA to cDNA using reverse transcriptase or RNA molecules may be directly sequenced. In a particular embodiment, which should not be considered as limiting the scope of the invention, the measurement of the expression level using next generation sequencing may be performed as follows. Briefly, RNA is extracted from a sample (e.g., blood sample). After removing rRNA, RNA samples are then reverse transcribed into cDNA. To ensure strand specificity, single stranded cDNA is first synthetized using Super-Script II reverse transcriptase and random primers in the presence of Actinomycin D, and then converted to double stranded cDNA with the second strand marking mix that incorporates dUTP in place of dTTP. Resulting blunt ended cDNA are purified using AMPure XP magnetic beads. After a 3'end adenylation step, adaptor is attached to cDNA. So obtained cDNA (sequencing library) may be amplified by PCR. The sequencing libraries can be sequenced by any next generation sequencing technology known by a man skilled in the art.

In some embodiments, the measurement of the expression level of lncRNAs, e.g., by sequencing (e.g., next generation sequencing), is facilitated by capturing and enriching nucleic acids (RNA or cDNA) corresponding to ncRNAs of interest prior to the measurement. As used herein, enrichment refers to increasing the percentage of the nucleic acids of interest in the sample relative to the initial sample by selectively purifying the nucleic acids of interest. The enrichment of nucleic acids corresponding to lncRNAs of interest can be carried out on extracted RNA sample or cDNA sample prepared from extracted RNA. In some embodiments, nucleic acids corresponding to lncRNAs of interest are captured and enriched by hybridizing RNA or cDNA sample to oligonucleotide probes specific for lncRNAs of interest (e.g. oligonucleotide probes comprising a sequence complementary to a region of lncRNAs of interest) under conditions allowing for hybridization of the probes and target nucleic acids to form probe-target nucleic acid complexes. Probes may be DNA or RNA, preferably DNA. The length of probes specific for lncRNAs may be from 30 to 80 nucleotides, e.g., from 40 to 70, from 40 to 60, or about 50 nucleotides. The probe-target nucleic acid complexes can be purified by any technology known by a man skilled in the art. In a preferred embodiment, probes are biotinylated. The biotinylated probe-target nucleic acid complexes can be purified by using a streptavidin-coated substrate, e.g, a streptavidin-coated magnetic particle, e.g., T1 streptavidin coated magnetic bead.

In some embodiments, the expression level of lncRNAs may be determined using quantitative PCR. Quantitative, or real-time, PCR is a well known and easily available technology for those skilled in the art and does not need a precise description. In a particular embodiment, which should not be considered as limiting the scope of the invention, the determination of the expression profile using quantitative PCR may be performed as follows. Briefly, the real-time PCR reactions are carried out using the TaqMan Universal PCR Master Mix (Applied Biosystems). 6 µl cDNA is added to a 9 µl PCR mixture containing 7.5 µl TaqMan Universal PCR Master Mix, 0.75 µl of a 20× mixture of probe and primers and 0.75 µl water. The reaction consists of one initiating step of 2 min at 50 deg. C, followed by 10 min at 95 deg. C, and 40 cycles of amplification including 15 sec at 95 deg. C and 1 min at 60 deg. C. The reaction and data acquisition can be performed using the ABI 7900HT Fast Real-Time PCR System (Applied Biosystems). The number of template transcript molecules in a sample is determined by recording the amplification cycle in the exponential phase (cycle threshold or $C_Q$ or $C_T$), at which time the fluorescence signal can be detected above background fluorescence. Thus, the starting number of template transcript molecules is inversely related to $C_T$.

In some embodiments, the expression level of lncRNAs may be determined by the use of a nucleic acid microarray. A nucleic acid microarray consists of different nucleic acid probes that are attached to a substrate, which can be a microchip, a glass slide or a microsphere-sized bead. A microchip may be constituted of polymers, plastics, resins, polysaccharides, silica or silica-based materials, carbon, metals, inorganic glasses, or nitrocellulose. Probes can be nucleic acids such as cDNAs ("cDNA microarray") or oligonucleotides ("oligonucleotide microarray"). To determine the expression profile of a target nucleic acid sample, said sample is labelled, contacted with the microarray in hybridization conditions, leading to the formation of complexes between target nucleic acids that are complementary to probe sequences attached to the microarray surface. The presence of labelled hybridized complexes is then detected. Many variants of the microarray hybridization technology are available to the man skilled in the art.

In some embodiments, the expression level of lncRNAs may be determined by FIMAP quantification. Briefly, lncRNAs are amplified by PCR using primers with the same sequences as for qPCR that are chemically modified. Forward primers are phosphorylated in 5' and Reverse primers biotinylated in 5'. PCR products are digested with exonuclease to eliminate the phosphorylated strand and keep only the biotinylated ones. Biotinylated PCR products are incubated with coded silica microdisks coated with oligos complementary to the RNAs of interest (one code per target oligo), and hybridized products are revealed by addition of a fluorescent streptavidin conjugate. The expression level of lncRNAs is determined by measuring fluorescence signal.

In a still further aspect, the method of detection contemplates the use of a reagent to measure or detect the one or more lncRNA. By "reagent" is meant a reagent that specifically allows the determination of the lncRNA expression profile, i.e. a reagent specifically intended for the specific determination of the expression level of the lncRNA present in the lncRNA expression profile. Examples include e.g. amplification primer pairs (forward and reward) and/or or the lncRNA present in the lncRNA expression profile. This definition excludes generic reagents useful for the determination of the expression level of any other lncRNA.

In yet a further aspect, the method of detection comprises detecting one or more lncRNA from a biological sample, wherein the biological sample is selected from blood, plasma, serum, urine, cerebrospinal fluid, tear, saliva. In some embodiments, the biological sample is blood.

By "treating" or "treatment" of a subject being at risk to develop or having a cognitive disorder, particularly a progressive impairment or loss of cognitive function or dementia, e.g. AD, FTD, DLB, is meant administering or administration of a regimen to the subject in need thereof such that at least one symptom of the disorder or disease is cured, alleviated, remedied or improved. According to the present invention, depending on the diagnosing results, the subject is submitted to an adapted therapeutic treatment and is further monitored. The monitoring of the subject based on the lncRNA signature of the invention allows to further adapt or modify the therapeutic treatment, e.g. increasing the drug amount, administering a combination of drugs to obtain a synergy effect, or replacing the drug by an effective amount of another drug.

The invention also relates to the modification of a therapeutic strategy in subjects suffering from brain disorder such as a cognitive disorder who have been diagnosed and/or monitored using a method for (in vitro) diagnosis or monitoring of a progressive brain function such as impairment or loss of cognitive function or dementia according to the invention. According to the invention, the lncRNAs of the invention may be used in combination with one or more biomarkers currently used for diagnosing a cognitive disorder including but not limited to MCI, AD, FTD, DLB. Examples of such biomarkers include without any limitation the biomarkers as disclosed in U.S. Pat. Nos. 9,377,472, 7,897,786 and in U.S. Pat. No. 6,703,212, PCT/EP2018/073905/PCT/EP2018/073905), the contents thereof being included herein by reference. The method of the invention combining the lncRNAs of the invention with one or more known biomarkers may allow enhanced accuracy of diagnosis; or differential diagnosis; and a more efficient and successful drug development, e.g. enhanced accuracy for patient stratification before recruitment in clinical trials and monitoring of the efficacy of approved therapies or novel drugs under development.

According to the invention, the lncRNAs of the invention may be used in combination with one or more tests currently used for diagnosing a cognitive disorder including but not limited to AD, FTD, DLB and/or for differential diagnostic purposes. Examples of such tests include without any limitation the neuropsychological tests, such as MMSE, MoCA, FCSRT tests, and the neuroimaging methods, in particular volumetric MRI and molecular neuroimaging PET methods using a ligand specific to amyloid, Tau, alpha-synucelin or other molecules to visualize in the brain a proteinopathy. The method of the invention combining the lncRNAs of the invention with one or more known biomarkers may allow enhanced accuracy of diagnosis; or differential diagnosis; and a more efficient and successful drug development, e.g. enhanced accuracy for patient stratification before recruitment in clinical trials and monitoring of the efficacy of approved therapies or novel drugs under development.

According to the invention, novel therapeutic approaches consisting in normalizing the expression and/or amount of the lncRNAs identified for the first time by the invention in the brain may be used as treatment (alone or in combination with existing and novel other therapies) of brain disorders characterized by an altered expression or amount of such novel lncRNAs identified by the invention.

According to the invention, the identified brain-enriched lncRNAs, the identified circulating lncRNAs in the plasma, serum, blood or another body fluid may be used for the design and development of novel therapeutic treatment and for diagnosis applications for brain disorders characterized by an altered expression or amount of such circulating lncRNAs identified by the invention.

According to the invention, the altered lncRNAs identified by the invention as differentially expressed in a brain disorder such as a cognitive disorder (MCI, AD, DLB and/or FTD) in the brain or in peripheral body fluids may be used for the design and development of novel therapeutic treatment and for diagnosis applications for brain disorders characterized by an altered expression or amount of such lncRNAs identified by the invention as differentially expressed in the brain or peripheral body fluids.

To identify lncRNA signatures involved specifically in the pathogenesis of AD and mild cognitive impairment (MCI) of AD type, a total of 127802 lncRNAs in samples from different groups, including a group of patients with AD or MCI of AD type and group of cognitively intact healthy controls with no brain imaging abnormalities, have been screened. Subsequently lncRNA profiling in all samples, 19867 lncRNAs have been detected above the threshold. By comparison of lncRNA-expression levels measured in the samples of the different groups, the lncRNA differentially expressed in the samples of the control group as compared to the expression level in the samples of patient group diagnosed as having AD or cognitive impairment of AD type (at the Neurology department of clinical sites, based on neurocognitive and neuropsychological tests and neuroimaging tests and on cerebrospinal fluid biomarkers: beta-amyloid peptide 1-42 (Aβ42) and tau (total and/or phosphorylated) were identified as lncRNA biomarker candidates.

Expression levels were analyzed using a two-tailed Welch t test and/or Wilcoxon Mann-Whitney test between two groups. Significant differential expression was identified as $p<0.05$. Fold change and AUC (Area Under the Curve) are calculated for each lncRNA and for each tested condition.

Serum lncRNA candidates were also selected when differential expression was determined based on fold-changes ≥1.6 (or ≤0.6) and/or an AUC ≥0.80 (or <0.20), are indicated in Tables 2 and 3.

Random Forest algorithm (Breimann 2001, Breiman and Cutler 2001) was used to build the model and also used to select the top lncRNAs. A predictive model based on the combination of the top 2-20 lncRNAs enables to predict the disease with an accuracy of ≥80%.

Out of the 127802 serum lncRNAs sequenced, 19867 lncRNAs were selected based on their threshold expression level for statistical analysis. The comparison of the AD patient with healthy control populations showed that 1008 lncRNAs are differentially expressed with a statistical significance (p value <0.05, Wilcoxon test) (Table 1). The sequences of these 1008 lncRNAs are shown in the sequence listing included in this application.

TABLE 1

The Sequence number, p value, mean +/− SD, fold change and AUC of the 1008 serum lncRNAs with differential expression in AD group versus healthy control group (p value <0.05, Wilcoxon test)

| lncRNA | SEQ | p value | Fold change | AUC |
| --- | --- | --- | --- | --- |
| ADAMTS9-AS2:12 | SEQ 0397 | 0.02049 | 0.852 | 0.778 |
| ADNP-AS1:12 | SEQ 0340 | 0.01727 | 0.809 | 0.785 |
| ADPGK-AS1:7 | SEQ 0858 | 0.0449 | 1.225 | 0.257 |
| APTR:17 | SEQ 0260 | 0.01209 | 1.147 | 0.201 |
| ARF4-AS1:8 | SEQ 0859 | 0.0449 | 1.143 | 0.257 |
| ARRDC3-AS1:7 | SEQ 0050 | 0.00232 | 0.441 | 0.854 |
| BISPR:24 | SEQ 0566 | 0.02842 | 0.579 | 0.764 |
| BLACAT1:3 | SEQ 0300 | 0.01449 | 1.717 | 0.208 |
| BLACAT1:5 | SEQ 0341 | 0.01727 | 0.424 | 0.785 |
| CALML3-AS1:9 | SEQ 0136 | 0.00681 | 1.567 | 0.181 |
| CASC15:51 | SEQ 0567 | 0.02842 | 1.273 | 0.236 |
| CASC20:2 | SEQ 0860 | 0.0449 | 0.765 | 0.743 |
| CERS3-AS1:5 | SEQ 0301 | 0.01449 | 1.251 | 0.208 |
| CFAP58-AS1:4 | SEQ 0109 | 0.00556 | 1.464 | 0.174 |
| CLRN1-AS1:1 | SEQ 0475 | 0.02418 | 0.793 | 0.771 |
| CPB2-AS1:18 | SEQ 0476 | 0.02418 | 0.682 | 0.771 |
| CYTOR:18 | SEQ 0062 | 0.00291 | 1.278 | 0.153 |
| DARS-AS1:47 | SEQ 0178 | 0.00829 | 2.015 | 0.188 |
| DDX11-AS1:5 | SEQ 0861 | 0.0449 | 1.256 | 0.257 |
| DLEU2:26 | SEQ 0862 | 0.0449 | 1.076 | 0.257 |
| DLEU2:45 | SEQ 0863 | 0.0449 | 0.882 | 0.743 |
| DLGAP2-AS1:18 | SEQ 0656 | 0.03324 | 0.789 | 0.757 |
| DPH6-AS1:3 | SEQ 0342 | 0.01727 | 2.004 | 0.215 |
| EGFR-AS1:4 | SEQ 0093 | 0.00451 | 0.81 | 0.833 |
| EGOT:11 | SEQ 0110 | 0.00556 | 1.195 | 0.174 |
| EIF3J-AS1:21 | SEQ 0261 | 0.01209 | 0.87 | 0.799 |
| ERICH3-AS1:4 | SEQ 0864 | 0.0449 | 0.888 | 0.743 |
| EXTL3-AS1:16 | SEQ 0568 | 0.02842 | 0.739 | 0.764 |
| FAM66B:14 | SEQ 0063 | 0.00291 | 0.604 | 0.847 |
| FLG-AS1:14 | SEQ 0752 | 0.03872 | 1.18 | 0.25 |
| FLVCR1-AS1:13 | SEQ 0137 | 0.00681 | 0.413 | 0.819 |
| FRG1-DT:6 | SEQ 0865 | 0.0449 | 0.873 | 0.743 |
| GAS1RR:11 | SEQ 0302 | 0.01449 | 0.848 | 0.792 |
| GAS6-AS2:9 | SEQ 0303 | 0.01449 | 0.787 | 0.792 |
| GPC5-AS1:7 | SEQ 0753 | 0.03872 | 0.623 | 0.75 |
| GPR158-AS1:1 | SEQ 0398 | 0.02049 | 0.775 | 0.778 |
| GRM5-AS1:1 | SEQ 0138 | 0.00681 | 0.83 | 0.819 |
| HAND2-AS1:58 | SEQ 0094 | 0.00451 | 0.587 | 0.833 |
| HAND2-AS1:59 | SEQ 0111 | 0.00556 | 0.592 | 0.826 |
| HAND2-AS1:70 | SEQ 0039 | 0.00183 | 0.543 | 0.861 |
| HAND2-AS1:71 | SEQ 0076 | 0.00364 | 0.565 | 0.84 |
| HCG23:5 | SEQ 0754 | 0.03872 | 0.813 | 0.75 |
| KAZN-AS1:4 | SEQ 0399 | 0.02049 | 0.732 | 0.778 |
| KCNQ1-AS1:3 | SEQ 0569 | 0.02842 | 0.848 | 0.764 |
| KCNQ1OT1:8 | SEQ 0139 | 0.00681 | 0.908 | 0.819 |
| LACTB2-AS1:1 | SEQ 0755 | 0.03872 | 1.206 | 0.25 |
| LINC00158:5 | SEQ 0570 | 0.02842 | 0.748 | 0.764 |
| LINC00200:6 | SEQ 0064 | 0.00291 | 1.29 | 0.153 |
| LINC00276:2 | SEQ 0866 | 0.0449 | 0.846 | 0.743 |
| LINC00354:4 | SEQ 0867 | 0.0449 | 1.284 | 0.257 |
| LINC00458:19 | SEQ 0571 | 0.02842 | 0.789 | 0.764 |
| LINC00460:13 | SEQ 0868 | 0.0449 | 0.752 | 0.743 |
| LINC00472:21 | SEQ 0140 | 0.00681 | 1.389 | 0.181 |
| LINC00554:2 | SEQ 0756 | 0.03872 | 0.766 | 0.75 |
| LINC00554:4 | SEQ 0757 | 0.03872 | 0.766 | 0.75 |
| LINC00574:13 | SEQ 0112 | 0.00556 | 0.771 | 0.826 |
| LINC00589:3 | SEQ 0869 | 0.0449 | 0.781 | 0.743 |
| LINC00649:23 | SEQ 0077 | 0.00364 | 0.619 | 0.84 |
| LINC00698:2 | SEQ 0657 | 0.03324 | 0.85 | 0.757 |
| LINC00707:9 | SEQ 0572 | 0.02842 | 1.304 | 0.236 |
| LINC00839:18 | SEQ 0113 | 0.00556 | 0.874 | 0.826 |
| LINC00882:70 | SEQ 0028 | 0.00111 | 0.867 | 0.875 |

TABLE 1-continued

The Sequence number, p value, mean +/− SD, fold change and
AUC of the 1008 serum lncRNAs with differential expression in
AD group versus healthy control group (p value <0.05, Wilcoxon test)

| lncRNA | SEQ | p value | Fold change | AUC |
|---|---|---|---|---|
| LINC00882:71 | SEQ 0029 | 0.00111 | 0.867 | 0.875 |
| LINC00887:15 | SEQ 0870 | 0.0449 | 0.925 | 0.743 |
| LINC00895:3 | SEQ 0179 | 0.00829 | 1.491 | 0.188 |
| LINC00927:21 | SEQ 0658 | 0.03324 | 0.619 | 0.757 |
| LINC00927:22 | SEQ 0659 | 0.03324 | 0.619 | 0.757 |
| LINC00927:24 | SEQ 0343 | 0.01727 | 0.772 | 0.785 |
| LINC00938:6 | SEQ 0262 | 0.01209 | 0.811 | 0.799 |
| LINC00963:67 | SEQ 0573 | 0.02842 | 1.379 | 0.236 |
| LINC01050:6 | SEQ 0114 | 0.00556 | 0.82 | 0.826 |
| LINC01058:3 | SEQ 0871 | 0.0449 | 1.225 | 0.257 |
| LINC01087:1 | SEQ 0141 | 0.00681 | 0.764 | 0.819 |
| LINC01088:18 | SEQ 0660 | 0.03324 | 0.757 | 0.757 |
| LINC01107:1 | SEQ 0304 | 0.01449 | 0.768 | 0.792 |
| LINC01122:27 | SEQ 0574 | 0.02842 | 1.263 | 0.236 |
| LINC01146:14 | SEQ 0758 | 0.03872 | 0.774 | 0.75 |
| LINC01153:1 | SEQ 0661 | 0.03324 | 1.169 | 0.243 |
| LINC01185:7 | SEQ 0575 | 0.02842 | 0.793 | 0.764 |
| LINC01197:26 | SEQ 0759 | 0.03872 | 0.847 | 0.75 |
| LINC01206:11 | SEQ 0662 | 0.03324 | 0.612 | 0.757 |
| LINC01206:20 | SEQ 0400 | 0.02049 | 1.94 | 0.222 |
| LINC01226:8 | SEQ 0663 | 0.03324 | 0.902 | 0.757 |
| LINC01270:15 | SEQ 0477 | 0.02418 | 1.703 | 0.229 |
| LINC01320:22 | SEQ 0576 | 0.02842 | 0.785 | 0.764 |
| LINC01322:20 | SEQ 0223 | 0.01004 | 0.561 | 0.806 |
| LINC01355:9 | SEQ 0664 | 0.03324 | 0.854 | 0.757 |
| LINC01376:10 | SEQ 0760 | 0.03872 | 0.934 | 0.75 |
| LINC01394:15 | SEQ 0401 | 0.02049 | 1.238 | 0.222 |
| LINC01394:26 | SEQ 0402 | 0.02049 | 1.238 | 0.222 |
| LINC01394:50 | SEQ 0095 | 0.00451 | 0.797 | 0.833 |
| LINC01410:11 | SEQ 0023 | 0.00086 | 0.734 | 0.882 |
| LINC01419:6 | SEQ 0872 | 0.0449 | 0.663 | 0.743 |
| LINC01426:10 | SEQ 0577 | 0.02842 | 0.871 | 0.764 |
| LINC01481:8 | SEQ 0478 | 0.02418 | 0.9 | 0.771 |
| LINC01519:3 | SEQ 0305 | 0.01449 | 0.805 | 0.792 |
| LINC01527:1 | SEQ 0578 | 0.02842 | 0.781 | 0.764 |
| LINC01568:12 | SEQ 0479 | 0.02418 | 0.68 | 0.771 |
| LINC01629:11 | SEQ 0579 | 0.02842 | 0.59 | 0.764 |
| LINC01653:2 | SEQ 0580 | 0.02842 | 0.792 | 0.764 |
| LINC01684:16 | SEQ 0480 | 0.02418 | 0.907 | 0.771 |
| LINC01697:9 | SEQ 0873 | 0.0449 | 0.874 | 0.743 |
| LINC01719:19 | SEQ 0761 | 0.03872 | 0.855 | 0.75 |
| LINC01748:17 | SEQ 0481 | 0.02418 | 0.791 | 0.771 |
| LINC01762:4 | SEQ 0874 | 0.0449 | 0.941 | 0.743 |
| LINC01793:2 | SEQ 0344 | 0.01727 | 0.743 | 0.785 |
| LINC01798:4 | SEQ 0482 | 0.02418 | 0.791 | 0.771 |
| LINC01845:3 | SEQ 0115 | 0.00556 | 1.55 | 0.174 |
| LINC01856:2 | SEQ 0762 | 0.03872 | 1.176 | 0.25 |
| LINC01903:2 | SEQ 0345 | 0.01727 | 0.774 | 0.785 |
| LINC01918:13 | SEQ 0763 | 0.03872 | 1.138 | 0.25 |
| LINC02104:7 | SEQ 0306 | 0.01449 | 0.82 | 0.792 |
| LINC02177:6 | SEQ 0403 | 0.02049 | 0.768 | 0.778 |
| LINC02177:8 | SEQ 0764 | 0.03872 | 0.494 | 0.75 |
| LINC02197:6 | SEQ 0483 | 0.02418 | 0.76 | 0.771 |
| LINC02204:2 | SEQ 0142 | 0.00681 | 0.78 | 0.819 |
| LINC02204:3 | SEQ 0143 | 0.00681 | 0.78 | 0.819 |
| LINC02232:10 | SEQ 0665 | 0.03324 | 0.646 | 0.757 |
| LINC02246:11 | SEQ 0346 | 0.01727 | 0.74 | 0.785 |
| LINC02252:3 | SEQ 0765 | 0.03872 | 0.881 | 0.75 |
| LINC02323:8 | SEQ 0307 | 0.01449 | 0.622 | 0.792 |
| LINC02334:6 | SEQ 0581 | 0.02842 | 0.737 | 0.764 |
| LINC02345:11 | SEQ 0013 | 0.00066 | 1.181 | 0.111 |
| LINC02432:9 | SEQ 0180 | 0.00829 | 0.776 | 0.813 |
| LINC02473:3 | SEQ 0065 | 0.00291 | 0.786 | 0.847 |
| LINC02519:7 | SEQ 0875 | 0.0449 | 0.682 | 0.743 |
| LINC02554:5 | SEQ 0404 | 0.02049 | 0.744 | 0.778 |
| LINC02580:5 | SEQ 0484 | 0.02418 | 0.767 | 0.771 |
| lnc-AASDHPPT-3:1 | SEQ 0409 | 0.02049 | 0.715 | 0.778 |
| lnc-ABCA1-8:9 | SEQ 0589 | 0.02842 | 0.592 | 0.764 |
| lnc-ABCA5-14:2 | SEQ 0881 | 0.0449 | 1.164 | 0.257 |
| lnc-ABCA5-7:1 | SEQ 0014 | 0.00066 | 1.309 | 0.111 |
| lnc-ABCG2-3:5 | SEQ 0667 | 0.03324 | 0.758 | 0.757 |
| lnc-ACO1-1:1 | SEQ 0590 | 0.02842 | 0.759 | 0.764 |
| lnc-ACOT12-9:1 | SEQ 0053 | 0.00232 | 0.727 | 0.854 |
| lnc-ACTL7B-8:1 | SEQ 0493 | 0.02418 | 0.697 | 0.771 |

TABLE 1-continued

The Sequence number, p value, mean +/− SD, fold change and
AUC of the 1008 serum lncRNAs with differential expression in
AD group versus healthy control group (p value <0.05, Wilcoxon test)

| lncRNA | SEQ | p value | Fold change | AUC |
|---|---|---|---|---|
| lnc-ADAD1-3:1 | SEQ 0774 | 0.03872 | 0.828 | 0.75 |
| lnc-ADAMTS20-3:1 | SEQ 0494 | 0.02418 | 1.219 | 0.229 |
| lnc-ADAMTS5-1:1 | SEQ 0882 | 0.0449 | 0.851 | 0.743 |
| lnc-ADAT1-1:1 | SEQ 0495 | 0.02418 | 0.877 | 0.771 |
| lnc-ADRA2A-4:1 | SEQ 0883 | 0.0449 | 0.729 | 0.743 |
| lnc-ADRB1-4:1 | SEQ 0118 | 0.00556 | 0.858 | 0.826 |
| lnc-AFG1L-5:1 | SEQ 0263 | 0.01209 | 1.407 | 0.201 |
| lnc-AGO2-2:2 | SEQ 0119 | 0.00556 | 0.511 | 0.826 |
| lnc-AGO2-2:3 | SEQ 0668 | 0.03324 | 1.442 | 0.243 |
| lnc-AGR3-6:1 | SEQ 0884 | 0.0449 | 1.156 | 0.257 |
| lnc-AHR-5:1 | SEQ 0264 | 0.01209 | 0.792 | 0.799 |
| lnc-AIG1-5:1 | SEQ 0496 | 0.02418 | 0.862 | 0.771 |
| lnc-AKAP9-1:2 | SEQ 0775 | 0.03872 | 0.704 | 0.75 |
| lnc-AKIRIN1-1:11 | SEQ 0591 | 0.02842 | 0.553 | 0.764 |
| lnc-AKR1C2-3:17 | SEQ 0097 | 0.00451 | 0.768 | 0.833 |
| lnc-AKR1D1-5:2 | SEQ 0098 | 0.00451 | 0.891 | 0.833 |
| lnc-AKR1D1-8:3 | SEQ 0885 | 0.0449 | 0.797 | 0.743 |
| lnc-AKR1E2-15:1 | SEQ 0410 | 0.02049 | 1.303 | 0.222 |
| lnc-AKR7A2-2:1 | SEQ 0145 | 0.00681 | 1.339 | 0.181 |
| lnc-AKT1-1:15 | SEQ 0411 | 0.02049 | 0.825 | 0.778 |
| lnc-ALB-1:12 | SEQ 0146 | 0.00681 | 1.448 | 0.181 |
| lnc-ALB-1:6 | SEQ 0886 | 0.0449 | 0.881 | 0.743 |
| lnc-ALDH3B2-3:4 | SEQ 0412 | 0.02049 | 0.89 | 0.778 |
| lnc-ALG14-5:2 | SEQ 0350 | 0.01727 | 0.697 | 0.785 |
| lnc-ALS2CR12-1:2 | SEQ 0351 | 0.01727 | 0.729 | 0.785 |
| lnc-ANAPC11-2:6 | SEQ 0887 | 0.0449 | 1.836 | 0.257 |
| lnc-ANKRD1-1:6 | SEQ 0888 | 0.0449 | 0.77 | 0.743 |
| lnc-ANKRD26-1:3 | SEQ 0497 | 0.02418 | 0.852 | 0.771 |
| lnc-ANKRD30BL-2:2 | SEQ 0413 | 0.02049 | 0.747 | 0.778 |
| lnc-ANKRD46-1:3 | SEQ 0669 | 0.03324 | 0.687 | 0.757 |
| lnc-ANXA3-8:1 | SEQ 0670 | 0.03324 | 0.838 | 0.757 |
| lnc-APBA1-5:1 | SEQ 0592 | 0.02842 | 0.781 | 0.764 |
| lnc-APIP-1:13 | SEQ 0776 | 0.03872 | 0.807 | 0.75 |
| lnc-APLP2-4:1 | SEQ 0054 | 0.00232 | 0.786 | 0.854 |
| lnc-APOB-1:2 | SEQ 0777 | 0.03872 | 0.583 | 0.75 |
| lnc-APPL2-1:2 | SEQ 0498 | 0.02418 | 1.133 | 0.229 |
| lnc-AQP8-2:7 | SEQ 0352 | 0.01727 | 1.254 | 0.215 |
| lnc-ARAP2-9:1 | SEQ 0147 | 0.00681 | 0.795 | 0.819 |
| lnc-ARHGAP15-17:1 | SEQ 0353 | 0.01727 | 0.857 | 0.785 |
| lnc-ARHGAP15-22:1 | SEQ 0593 | 0.02842 | 0.846 | 0.764 |
| lnc-ARHGAP21-1:2 | SEQ 0309 | 0.01449 | 0.723 | 0.792 |
| lnc-ARHGAP26-4:11 | SEQ 0189 | 0.00829 | 0.923 | 0.813 |
| lnc-ARHGAP26-4:33 | SEQ 0778 | 0.03872 | 0.71 | 0.75 |
| lnc-ARHGAP26-4:39 | SEQ 0889 | 0.0449 | 1.383 | 0.257 |
| lnc-ARHGEF26-2:1 | SEQ 0067 | 0.00291 | 1.399 | 0.153 |
| lnc-ARHGEF5-5:1 | SEQ 0354 | 0.01727 | 0.712 | 0.785 |
| lnc-ARID2-7:1 | SEQ 0671 | 0.03324 | 0.924 | 0.757 |
| lnc-ARNTL-2:1 | SEQ 0265 | 0.01209 | 0.61 | 0.799 |
| lnc-ARRDC4-7:1 | SEQ 0779 | 0.03872 | 0.876 | 0.75 |
| lnc-ART5-2:1 | SEQ 0414 | 0.02049 | 0.787 | 0.778 |
| lnc-ATAD1-5:2 | SEQ 0148 | 0.00681 | 0.738 | 0.819 |
| lnc-ATIC-2:8 | SEQ 0780 | 0.03872 | 0.554 | 0.75 |
| lnc-ATP12A-3:1 | SEQ 0499 | 0.02418 | 0.763 | 0.771 |
| lnc-ATP13A4-2:4 | SEQ 0672 | 0.03324 | 1.64 | 0.243 |
| lnc-ATP5O-3:1 | SEQ 0224 | 0.01004 | 1.358 | 0.194 |
| lnc-ATP6V0E2-7:1 | SEQ 0500 | 0.02418 | 1.361 | 0.229 |
| lnc-ATP6V1B2-2:6 | SEQ 0594 | 0.02842 | 1.132 | 0.236 |
| lnc-ATP6V1B2-2:7 | SEQ 0595 | 0.02842 | 1.132 | 0.236 |
| lnc-ATP8A2-1:1 | SEQ 0355 | 0.01727 | 1.477 | 0.215 |
| lnc-ATXN2-1:1 | SEQ 0099 | 0.00451 | 0.792 | 0.833 |
| lnc-ATXN7-11:1 | SEQ 0501 | 0.02418 | 1.319 | 0.229 |
| lnc-ATXN7L1-1:1 | SEQ 0890 | 0.0449 | 1.32 | 0.257 |
| lnc-AUH-2:7 | SEQ 0190 | 0.00829 | 0.584 | 0.813 |
| lnc-AUH-2:9 | SEQ 0673 | 0.03324 | 1.35 | 0.243 |
| lnc-AUH-4:1 | SEQ 0596 | 0.02842 | 0.79 | 0.764 |
| lnc-BAG3-4:4 | SEQ 0891 | 0.0449 | 1.314 | 0.257 |
| lnc-BARHL2-4:4 | SEQ 0100 | 0.00451 | 0.736 | 0.833 |
| lnc-BCHE-1:1 | SEQ 0674 | 0.03324 | 0.741 | 0.757 |
| lnc-BCL6-9:1 | SEQ 0310 | 0.01449 | 0.885 | 0.792 |
| lnc-BIRC2-5:5 | SEQ 0225 | 0.01004 | 0.831 | 0.806 |
| lnc-BIRC6-1:4 | SEQ 0892 | 0.0449 | 0.829 | 0.743 |
| lnc-BMS1-2:1 | SEQ 0675 | 0.03324 | 1.124 | 0.243 |
| lnc-BNC2-5:1 | SEQ 0191 | 0.00829 | 1.299 | 0.188 |
| lnc-BORA-31:1 | SEQ 0192 | 0.00829 | 0.67 | 0.813 |

TABLE 1-continued

The Sequence number, p value, mean +/− SD, fold change and
AUC of the 1008 serum lncRNAs with differential expression in
AD group versus healthy control group (p value <0.05, Wilcoxon test)

| lncRNA | SEQ | p value | Fold change | AUC |
| --- | --- | --- | --- | --- |
| lnc-BRD1-17:1 | SEQ 0311 | 0.01449 | 0.669 | 0.792 |
| lnc-BRINP1-3:1 | SEQ 0893 | 0.0449 | 0.894 | 0.743 |
| lnc-BRINP2-3:1 | SEQ 0597 | 0.02842 | 0.878 | 0.764 |
| lnc-C10orf90-2:2 | SEQ 0415 | 0.02049 | 1.687 | 0.222 |
| lnc-C12orf40-3:3 | SEQ 0894 | 0.0449 | 1.434 | 0.257 |
| lnc-C12orf42-3:6 | SEQ 0598 | 0.02842 | 1.303 | 0.236 |
| lnc-C15orf41-18:5 | SEQ 0676 | 0.03324 | 1.649 | 0.243 |
| lnc-C15orf41-18:6 | SEQ 0895 | 0.0449 | 1.561 | 0.257 |
| lnc-C19orf57-1:1 | SEQ 0896 | 0.0449 | 1.361 | 0.257 |
| lnc-C1QTNF9-4:1 | SEQ 0781 | 0.03872 | 1.282 | 0.25 |
| lnc-C21orf58-1:2 | SEQ 0033 | 0.00143 | 2.231 | 0.132 |
| lnc-C2CD4B-6:4 | SEQ 0193 | 0.00829 | 1.39 | 0.188 |
| lnc-C2orf42-10:1 | SEQ 0502 | 0.02418 | 1.28 | 0.229 |
| lnc-C3orf58-7:1 | SEQ 0599 | 0.02842 | 0.725 | 0.764 |
| lnc-C5orf30-10:1 | SEQ 0266 | 0.01209 | 0.708 | 0.799 |
| lnc-C5orf30-10:2 | SEQ 0600 | 0.02842 | 0.891 | 0.764 |
| lnc-C5orf67-3:1 | SEQ 0149 | 0.00681 | 0.876 | 0.819 |
| lnc-C7orf57-4:1 | SEQ 0356 | 0.01727 | 1.461 | 0.215 |
| lnc-C9orf3-5:1 | SEQ 0120 | 0.00556 | 0.782 | 0.826 |
| lnc-CA7-2:2 | SEQ 0677 | 0.03324 | 0.817 | 0.757 |
| lnc-CAB39L-1:4 | SEQ 0267 | 0.01209 | 0.769 | 0.799 |
| lnc-CAB39L-4:2 | SEQ 0601 | 0.02842 | 1.181 | 0.236 |
| lnc-CACNA1I-1:1 | SEQ 0503 | 0.02418 | 0.813 | 0.771 |
| lnc-CACNA2D1-1:1 | SEQ 0897 | 0.0449 | 0.82 | 0.743 |
| lnc-CACNG1-1:1 | SEQ 0602 | 0.02842 | 0.652 | 0.764 |
| lnc-CALML6-1:10 | SEQ 0898 | 0.0449 | 0.577 | 0.743 |
| lnc-CAPS2-1:1 | SEQ 0357 | 0.01727 | 0.708 | 0.785 |
| lnc-CASC10-3:1 | SEQ 0899 | 0.0449 | 0.744 | 0.743 |
| lnc-CASP9-1:1 | SEQ 0782 | 0.03872 | 1.246 | 0.25 |
| lnc-CAVIN2-2:1 | SEQ 0416 | 0.02049 | 1.425 | 0.222 |
| lnc-CBLB-9:1 | SEQ 0900 | 0.0449 | 0.788 | 0.743 |
| lnc-CCDC102B-7:1 | SEQ 0901 | 0.0449 | 0.816 | 0.743 |
| lnc-CCDC167-5:1 | SEQ 0417 | 0.02049 | 1.25 | 0.222 |
| lnc-CCDC177-6:1 | SEQ 0783 | 0.03872 | 1.157 | 0.25 |
| lnc-CCDC192-3:1 | SEQ 0902 | 0.0449 | 0.8 | 0.743 |
| lnc-CCDC197-2:1 | SEQ 0068 | 0.00291 | 0.672 | 0.847 |
| lnc-CCDC61-4:1 | SEQ 0194 | 0.00829 | 0.561 | 0.813 |
| lnc-CCDC7-17:1 | SEQ 0226 | 0.01004 | 1.341 | 0.194 |
| lnc-CCDC93-10:2 | SEQ 0603 | 0.02842 | 0.87 | 0.764 |
| lnc-CCL1-10:1 | SEQ 0227 | 0.01004 | 1.307 | 0.194 |
| lnc-CCNB1IP1-1:2 | SEQ 0903 | 0.0449 | 0.512 | 0.743 |
| lnc-CCR8-2:1 | SEQ 0904 | 0.0449 | 1.409 | 0.257 |
| lnc-CCSER1-2:1 | SEQ 0678 | 0.03324 | 0.791 | 0.757 |
| lnc-CCT8L2-28:1 | SEQ 0418 | 0.02049 | 0.812 | 0.778 |
| lnc-CD47-11:2 | SEQ 0905 | 0.0449 | 1.317 | 0.257 |
| lnc-CD47-11:4 | SEQ 0906 | 0.0449 | 1.139 | 0.257 |
| lnc-CDADC1-1:1 | SEQ 0907 | 0.0449 | 1.18 | 0.257 |
| lnc-CDH23-2:1 | SEQ 0908 | 0.0449 | 0.757 | 0.743 |
| lnc-CDK20-14:1 | SEQ 0358 | 0.01727 | 1.274 | 0.215 |
| lnc-CDK2AP1-1:8 | SEQ 0909 | 0.0449 | 0.84 | 0.743 |
| lnc-CEACAM16-2:1 | SEQ 0195 | 0.00829 | 0.708 | 0.813 |
| lnc-CEBPD-11:2 | SEQ 0784 | 0.03872 | 0.763 | 0.75 |
| lnc-CELF4-15:1 | SEQ 0785 | 0.03872 | 0.89 | 0.75 |
| lnc-CELSR1-2:3 | SEQ 0268 | 0.01209 | 0.762 | 0.799 |
| lnc-CEP170-9:2 | SEQ 0042 | 0.00183 | 0.828 | 0.861 |
| lnc-CFAP36-3:2 | SEQ 0786 | 0.03872 | 0.69 | 0.75 |
| lnc-CHD1L-5:13 | SEQ 0312 | 0.01449 | 0.37 | 0.792 |
| lnc-CHMP2B-1:11 | SEQ 0679 | 0.03324 | 0.858 | 0.757 |
| lnc-CHN1-5:11 | SEQ 0419 | 0.02049 | 0.739 | 0.778 |
| lnc-CHRAC1-1:1 | SEQ 0680 | 0.03324 | 0.747 | 0.757 |
| lnc-CHRAC1-6:1 | SEQ 0420 | 0.02049 | 1.247 | 0.222 |
| lnc-CHRM2-1:1 | SEQ 0121 | 0.00556 | 0.833 | 0.826 |
| lnc-CHRM3-1:5 | SEQ 0681 | 0.03324 | 0.714 | 0.757 |
| lnc-CHST2-6:2 | SEQ 0196 | 0.00829 | 0.763 | 0.813 |
| lnc-CLDN10-5:1 | SEQ 0313 | 0.01449 | 0.717 | 0.792 |
| lnc-CLEC19A-3:1 | SEQ 0787 | 0.03872 | 1.284 | 0.25 |
| lnc-CLK1-1:7 | SEQ 0197 | 0.00829 | 0.602 | 0.813 |
| lnc-CLVS2-2:5 | SEQ 0359 | 0.01727 | 0.818 | 0.785 |
| lnc-CMPK2-34:4 | SEQ 0101 | 0.00451 | 0.651 | 0.833 |
| lnc-CMTM7-2:2 | SEQ 0269 | 0.01209 | 0.838 | 0.799 |
| lnc-CMTR1-10:1 | SEQ 0788 | 0.03872 | 0.868 | 0.75 |
| lnc-CNBD1-4:13 | SEQ 0682 | 0.03324 | 0.568 | 0.757 |
| lnc-CNDP1-7:1 | SEQ 0024 | 0.00086 | 0.534 | 0.882 |
| lnc-CNOT6-10:1 | SEQ 0270 | 0.01209 | 1.19 | 0.201 |

TABLE 1-continued

The Sequence number, p value, mean +/− SD, fold change and
AUC of the 1008 serum lncRNAs with differential expression in
AD group versus healthy control group (p value <0.05, Wilcoxon test)

| lncRNA | SEQ | p value | Fold change | AUC |
|---|---|---|---|---|
| lnc-COL6A6-2:1 | SEQ 0910 | 0.0449 | 0.717 | 0.743 |
| lnc-COMMD6-10:1 | SEQ 0079 | 0.00364 | 1.58 | 0.16 |
| lnc-COX10-9:2 | SEQ 0911 | 0.0449 | 0.849 | 0.743 |
| lnc-CPEB3-2:1 | SEQ 0789 | 0.03872 | 0.78 | 0.75 |
| lnc-CPM-2:11 | SEQ 0912 | 0.0449 | 0.424 | 0.743 |
| lnc-CPM-3:1 | SEQ 0228 | 0.01004 | 0.831 | 0.806 |
| lnc-CRIPT-1:3 | SEQ 0790 | 0.03872 | 0.802 | 0.75 |
| lnc-CRISP1-1:2 | SEQ 0271 | 0.01209 | 0.685 | 0.799 |
| lnc-CRYBA1-4:1 | SEQ 0421 | 0.02049 | 0.693 | 0.778 |
| lnc-CRYBB1-1:1 | SEQ 0055 | 0.00232 | 0.487 | 0.854 |
| lnc-CSGALNACT2-2:3 | SEQ 0791 | 0.03872 | 0.781 | 0.75 |
| lnc-CSNK1A1-6:1 | SEQ 0030 | 0.00111 | 0.696 | 0.875 |
| lnc-CTIF-9:2 | SEQ 0504 | 0.02418 | 1.28 | 0.229 |
| lnc-CTNNA2-3:11 | SEQ 0198 | 0.00829 | 0.812 | 0.813 |
| lnc-CTNNA3-1:2 | SEQ 0683 | 0.03324 | 0.82 | 0.757 |
| lnc-CTNND2-3:1 | SEQ 0913 | 0.0449 | 0.797 | 0.743 |
| lnc-CTR9-7:1 | SEQ 0914 | 0.0449 | 0.763 | 0.743 |
| lnc-CYB5R2-3:13 | SEQ 0199 | 0.00829 | 0.749 | 0.813 |
| lnc-CYBA-4:3 | SEQ 0150 | 0.00681 | 0.784 | 0.819 |
| lnc-CYP2E1-1:1 | SEQ 0684 | 0.03324 | 1.733 | 0.243 |
| lnc-CYTIP-2:1 | SEQ 0200 | 0.00829 | 0.727 | 0.813 |
| lnc-DAO-3:1 | SEQ 0685 | 0.03324 | 1.109 | 0.243 |
| lnc-DAPP1-2:11 | SEQ 0505 | 0.02418 | 0.822 | 0.771 |
| lnc-DAZAP2-3:1 | SEQ 0056 | 0.00232 | 0.797 | 0.854 |
| lnc-DDX1-3:1 | SEQ 0915 | 0.0449 | 1.251 | 0.257 |
| lnc-DDX18-1:1 | SEQ 0506 | 0.02418 | 0.721 | 0.771 |
| lnc-DDX18-1:7 | SEQ 0314 | 0.01449 | 0.755 | 0.792 |
| lnc-DEFB112-3:4 | SEQ 0422 | 0.02049 | 0.565 | 0.778 |
| lnc-DEK-4:1 | SEQ 0507 | 0.02418 | 0.715 | 0.771 |
| lnc-DEPTOR-5:3 | SEQ 0360 | 0.01727 | 0.846 | 0.785 |
| lnc-DGCR2-5:1 | SEQ 0423 | 0.02049 | 0.872 | 0.778 |
| lnc-DGCR6-7:26 | SEQ 0792 | 0.03872 | 0.736 | 0.75 |
| lnc-DHX37-18:1 | SEQ 0229 | 0.01004 | 0.751 | 0.806 |
| lnc-DHX38-25:1 | SEQ 0230 | 0.01004 | 0.894 | 0.806 |
| lnc-DKK1-5:3 | SEQ 0005 | 0.00027 | 0.739 | 0.91 |
| lnc-DKK1-5:4 | SEQ 0793 | 0.03872 | 0.893 | 0.75 |
| lnc-DLG5-1:1 | SEQ 0034 | 0.00143 | 0.773 | 0.868 |
| lnc-DLX2-12:1 | SEQ 0151 | 0.00681 | 0.747 | 0.819 |
| lnc-DMRTA1-17:1 | SEQ 0201 | 0.00829 | 0.79 | 0.813 |
| lnc-DNAH9-1:1 | SEQ 0508 | 0.02418 | 0.812 | 0.771 |
| lnc-DNALI1-5:4 | SEQ 0102 | 0.00451 | 0.776 | 0.833 |
| lnc-DOCK7-7:1 | SEQ 0015 | 0.00066 | 0.843 | 0.889 |
| lnc-DTWD2-14:1 | SEQ 0361 | 0.01727 | 0.811 | 0.785 |
| lnc-DUSP10-6:1 | SEQ 0057 | 0.00232 | 0.675 | 0.854 |
| lnc-DUSP26-3:2 | SEQ 0031 | 0.00111 | 0.796 | 0.875 |
| lnc-DYNAP-1:1 | SEQ 0604 | 0.02842 | 0.761 | 0.764 |
| lnc-EAF1-2:1 | SEQ 0509 | 0.02418 | 0.737 | 0.771 |
| lnc-EBF3-1:6 | SEQ 0686 | 0.03324 | 1.241 | 0.243 |
| lnc-EBLN1-1:4 | SEQ 0016 | 0.00066 | 0.725 | 0.889 |
| lnc-EDDM13-5:11 | SEQ 0231 | 0.01004 | 0.372 | 0.806 |
| lnc-EDDM13-5:3 | SEQ 0035 | 0.00143 | 1.505 | 0.132 |
| lnc-EDEM3-7:3 | SEQ 0272 | 0.01209 | 0.86 | 0.799 |
| lnc-EDRF1-1:5 | SEQ 0916 | 0.0449 | 0.728 | 0.743 |
| lnc-EEF1AKMT1-3:6 | SEQ 0202 | 0.00829 | 0.423 | 0.813 |
| lnc-EEF2-3:1 | SEQ 0687 | 0.03324 | 1.301 | 0.243 |
| lnc-EFR3B-7:2 | SEQ 0362 | 0.01727 | 0.821 | 0.785 |
| lnc-EGFR-7:1 | SEQ 0917 | 0.0449 | 1.181 | 0.257 |
| lnc-EIF2AK3-31:7 | SEQ 0918 | 0.0449 | 0.848 | 0.743 |
| lnc-EIF2AK3-4:81 | SEQ 0688 | 0.03324 | 1.466 | 0.243 |
| lnc-ELF1-5:1 | SEQ 0510 | 0.02418 | 0.799 | 0.771 |
| lnc-ELFN2-1:3 | SEQ 0080 | 0.00364 | 0.764 | 0.84 |
| lnc-EPB42-1:3 | SEQ 0689 | 0.03324 | 0.917 | 0.757 |
| lnc-EPHA7-3:1 | SEQ 0081 | 0.00364 | 0.763 | 0.84 |
| lnc-ERCC6L2-10:2 | SEQ 0605 | 0.02842 | 0.927 | 0.764 |
| lnc-ERCC6L2-6:1 | SEQ 0363 | 0.01727 | 1.784 | 0.215 |
| lnc-ERFE-1:1 | SEQ 0919 | 0.0449 | 0.489 | 0.743 |
| lnc-ERGIC2-2:2 | SEQ 0364 | 0.01727 | 0.799 | 0.785 |
| lnc-ERH-1:1 | SEQ 0424 | 0.02049 | 0.708 | 0.778 |
| lnc-ERICH1-9:1 | SEQ 0920 | 0.0449 | 0.85 | 0.743 |
| lnc-ERV3-1-9:1 | SEQ 0203 | 0.00829 | 1.32 | 0.188 |
| lnc-ESRP1-2:4 | SEQ 0315 | 0.01449 | 0.542 | 0.792 |
| lnc-ETS1-2:2 | SEQ 0082 | 0.00364 | 1.436 | 0.16 |
| lnc-EXOC2-21:6 | SEQ 0204 | 0.00829 | 1.528 | 0.188 |
| lnc-EZH2-3:1 | SEQ 0273 | 0.01209 | 0.79 | 0.799 |

TABLE 1-continued

The Sequence number, p value, mean +/− SD, fold change and
AUC of the 1008 serum lncRNAs with differential expression in
AD group versus healthy control group (p value <0.05, Wilcoxon test)

| lncRNA | SEQ | p value | Fold change | AUC |
|---|---|---|---|---|
| lnc-F11-8:1 | SEQ 0690 | 0.03324 | 0.876 | 0.757 |
| lnc-F13A1-2:7 | SEQ 0691 | 0.03324 | 1.485 | 0.243 |
| lnc-FAM133B-2:1 | SEQ 0036 | 0.00143 | 0.767 | 0.868 |
| lnc-FAM171B-1:6 | SEQ 0205 | 0.00829 | 0.851 | 0.813 |
| lnc-FAM19A3-6:3 | SEQ 0274 | 0.01209 | 0.75 | 0.799 |
| lnc-FAM217A-1:2 | SEQ 0032 | 0.00111 | 0.854 | 0.875 |
| lnc-FAM231B-2:1 | SEQ 0511 | 0.02418 | 1.252 | 0.229 |
| lnc-FAM231B-2:2 | SEQ 0512 | 0.02418 | 1.252 | 0.229 |
| lnc-FAM236D-2:1 | SEQ 0692 | 0.03324 | 0.601 | 0.757 |
| lnc-FAM46C-3:1 | SEQ 0794 | 0.03872 | 0.755 | 0.75 |
| lnc-FAM49B-8:1 | SEQ 0010 | 0.0005 | 1.758 | 0.104 |
| lnc-FAM71F2-5:1 | SEQ 0425 | 0.02049 | 0.642 | 0.778 |
| lnc-FAM72B-6:3 | SEQ 0606 | 0.02842 | 1.327 | 0.236 |
| lnc-FAM84A-5:1 | SEQ 0607 | 0.02842 | 0.697 | 0.764 |
| lnc-FAM84B-17:4 | SEQ 0608 | 0.02842 | 0.741 | 0.764 |
| lnc-FAM84B-4:3 | SEQ 0083 | 0.00364 | 0.803 | 0.84 |
| lnc-FAP-3:1 | SEQ 0206 | 0.00829 | 0.749 | 0.813 |
| lnc-FARSB-6:1 | SEQ 0232 | 0.01004 | 1.292 | 0.194 |
| lnc-FAT1-7:2 | SEQ 0017 | 0.00066 | 1.383 | 0.111 |
| lnc-FAT4-6:1 | SEQ 0609 | 0.02842 | 0.751 | 0.764 |
| lnc-FBRSL1-3:3 | SEQ 0610 | 0.02842 | 1.645 | 0.236 |
| lnc-FCGR3B-4:11 | SEQ 0513 | 0.02418 | 0.848 | 0.771 |
| lnc-FCGR3B-4:12 | SEQ 0514 | 0.02418 | 0.848 | 0.771 |
| lnc-FER1L6-2:1 | SEQ 0515 | 0.02418 | 0.779 | 0.771 |
| lnc-FGD4-8:1 | SEQ 0233 | 0.01004 | 0.688 | 0.806 |
| lnc-FGD4-9:1 | SEQ 0084 | 0.00364 | 0.711 | 0.84 |
| lnc-FILIP1L-3:1 | SEQ 0058 | 0.00232 | 0.867 | 0.854 |
| lnc-FNBP1L-1:11 | SEQ 0006 | 0.00027 | 0.743 | 0.91 |
| lnc-FOXC1-6:2 | SEQ 0516 | 0.02418 | 0.736 | 0.771 |
| lnc-FOXD4L5-35:1 | SEQ 0152 | 0.00681 | 1.878 | 0.181 |
| lnc-FOXO1-2:8 | SEQ 0611 | 0.02842 | 1.402 | 0.236 |
| lnc-FRG2-13:3 | SEQ 0275 | 0.01209 | 0.908 | 0.799 |
| lnc-FSIP1-6:4 | SEQ 0795 | 0.03872 | 1.401 | 0.25 |
| lnc-FSIP2-2:1 | SEQ 0921 | 0.0449 | 0.76 | 0.743 |
| lnc-FTCD-5:1 | SEQ 0796 | 0.03872 | 0.722 | 0.75 |
| lnc-FTMT-2:14 | SEQ 0517 | 0.02418 | 0.792 | 0.771 |
| lnc-GALC-9:8 | SEQ 0234 | 0.01004 | 0.557 | 0.806 |
| lnc-GALNT2-1:1 | SEQ 0426 | 0.02049 | 0.729 | 0.778 |
| lnc-GALNTL5-3:1 | SEQ 0693 | 0.03324 | 0.759 | 0.757 |
| lnc-GCLC-1:13 | SEQ 0922 | 0.0449 | 0.597 | 0.743 |
| lnc-GDPD5-6:1 | SEQ 0153 | 0.00681 | 0.799 | 0.819 |
| lnc-GFI1B-2:3 | SEQ 0797 | 0.03872 | 0.681 | 0.75 |
| lnc-GGH-3:1 | SEQ 0798 | 0.03872 | 0.782 | 0.75 |
| lnc-GHR-1:1 | SEQ 0003 | 0.0002 | 0.787 | 0.917 |
| lnc-GJC1-2:2 | SEQ 0799 | 0.03872 | 0.832 | 0.75 |
| lnc-GJC1-2:3 | SEQ 0800 | 0.03872 | 0.832 | 0.75 |
| lnc-GLIPR1-3:2 | SEQ 0923 | 0.0449 | 0.923 | 0.743 |
| lnc-GLIPR1L1-2:3 | SEQ 0427 | 0.02049 | 1.26 | 0.222 |
| lnc-GMDS-6:8 | SEQ 0694 | 0.03324 | 0.721 | 0.757 |
| lnc-GNG5-8:1 | SEQ 0695 | 0.03324 | 0.771 | 0.757 |
| lnc-GOLGA4-4:7 | SEQ 0365 | 0.01727 | 0.855 | 0.785 |
| lnc-GOLGA6L6-9:1 | SEQ 0069 | 0.00291 | 0.711 | 0.847 |
| lnc-GOLGA8F-2:1 | SEQ 0235 | 0.01004 | 0.756 | 0.806 |
| lnc-GOLGA80-5:6 | SEQ 0428 | 0.02049 | 0.715 | 0.778 |
| lnc-GPAT4-1:3 | SEQ 0316 | 0.01449 | 1.56 | 0.208 |
| lnc-GPATCH11-1:1 | SEQ 0612 | 0.02842 | 0.703 | 0.764 |
| lnc-GPATCH2L-2:1 | SEQ 0317 | 0.01449 | 0.85 | 0.792 |
| lnc-GPC2-2:5 | SEQ 0518 | 0.02418 | 1.355 | 0.229 |
| lnc-GPR157-6:1 | SEQ 0924 | 0.0449 | 0.827 | 0.743 |
| lnc-GPR161-4:1 | SEQ 0070 | 0.0029 | 0.726 | 0.847 |
| lnc-GPR27-18:1 | SEQ 0925 | 0.0449 | 0.774 | 0.743 |
| lnc-GPR33-14:1 | SEQ 0236 | 0.01004 | 0.828 | 0.806 |
| lnc-GPR37-1:1 | SEQ 0926 | 0.0449 | 0.793 | 0.743 |
| lnc-GPR39-10:2 | SEQ 0154 | 0.00681 | 1.393 | 0.181 |
| lnc-GPRC5A-4:1 | SEQ 0613 | 0.02842 | 0.717 | 0.764 |
| lnc-GPRC6A-2:1 | SEQ 0927 | 0.0449 | 0.865 | 0.743 |
| lnc-GPSM1-3:3 | SEQ 0928 | 0.0449 | 0.64 | 0.743 |
| lnc-GRAMD2B-4:1 | SEQ 0801 | 0.03872 | 0.879 | 0.75 |
| lnc-GRIP1-1:2 | SEQ 0429 | 0.02049 | 1.564 | 0.222 |
| lnc-GRIP1-5:2 | SEQ 0519 | 0.02418 | 0.914 | 0.771 |
| lnc-GRIP1-8:1 | SEQ 0802 | 0.03872 | 1.339 | 0.25 |
| lnc-GRM1-1:19 | SEQ 0929 | 0.0449 | 1.338 | 0.257 |
| lnc-GRM1-1:31 | SEQ 0155 | 0.00681 | 0.864 | 0.819 |
| lnc-GRM1-1:32 | SEQ 0156 | 0.00681 | 0.864 | 0.819 |

TABLE 1-continued

The Sequence number, p value, mean +/− SD, fold change and
AUC of the 1008 serum lncRNAs with differential expression in
AD group versus healthy control group (p value <0.05, Wilcoxon test)

| lncRNA | SEQ | p value | Fold change | AUC |
|---|---|---|---|---|
| lnc-GRM8-2:2 | SEQ 0430 | 0.02049 | 0.902 | 0.778 |
| lnc-GSN-2:4 | SEQ 0930 | 0.0449 | 0.94 | 0.743 |
| lnc-GSN-2:5 | SEQ 0803 | 0.03872 | 0.955 | 0.75 |
| lnc-GTDC1-28:5 | SEQ 0157 | 0.00681 | 0.725 | 0.819 |
| lnc-GUCY1A3-1:1 | SEQ 0520 | 0.02418 | 0.724 | 0.771 |
| lnc-GUSB-1:1 | SEQ 0931 | 0.0449 | 0.829 | 0.743 |
| lnc-HECA-3:13 | SEQ 0237 | 0.01004 | 0.8 | 0.806 |
| lnc-HECA-6:1 | SEQ 0007 | 0.00037 | 0.723 | 0.903 |
| lnc-HELT-6:1 | SEQ 0932 | 0.0449 | 0.784 | 0.743 |
| lnc-HHATL-2:1 | SEQ 0933 | 0.0449 | 1.127 | 0.257 |
| lnc-HHLA2-2:1 | SEQ 0696 | 0.03324 | 1.238 | 0.243 |
| lnc-HJURP-7:1 | SEQ 0431 | 0.02049 | 0.776 | 0.778 |
| lnc-HLCS-5:1 | SEQ 0238 | 0.01004 | 0.866 | 0.806 |
| lnc-HMG20A-1:2 | SEQ 0432 | 0.02049 | 0.513 | 0.778 |
| lnc-HMGA1-2:3 | SEQ 0804 | 0.03872 | 1.288 | 0.25 |
| lnc-HMGN1-2:1 | SEQ 0433 | 0.02049 | 1.424 | 0.222 |
| lnc-HOMEZ-4:1 | SEQ 0434 | 0.02049 | 0.848 | 0.778 |
| lnc-HOXC4-1:3 | SEQ 0805 | 0.03872 | 0.845 | 0.75 |
| lnc-HS3ST3A1-1:1 | SEQ 0239 | 0.01004 | 0.75 | 0.806 |
| lnc-HS6ST1-8:1 | SEQ 0697 | 0.03324 | 1.344 | 0.243 |
| lnc-HSCB-7:1 | SEQ 0614 | 0.02842 | 0.742 | 0.764 |
| lnc-HSD17B11-2:1 | SEQ 0276 | 0.01209 | 0.792 | 0.799 |
| lnc-IFRD2-6:1 | SEQ 0806 | 0.03872 | 1.31 | 0.25 |
| lnc-IFT80-8:1 | SEQ 0934 | 0.0449 | 0.916 | 0.743 |
| lnc-IL6-8:4 | SEQ 0318 | 0.01449 | 0.77 | 0.792 |
| lnc-IPO5-7:1 | SEQ 0521 | 0.02418 | 0.869 | 0.771 |
| lnc-IQCF6-2:3 | SEQ 0807 | 0.03872 | 2.026 | 0.25 |
| lnc-IRF2BP2-11:3 | SEQ 0103 | 0.00451 | 1.403 | 0.167 |
| lnc-IRF6-1:1 | SEQ 0808 | 0.03872 | 0.894 | 0.75 |
| lnc-IRS1-2:5 | SEQ 0615 | 0.02842 | 1.878 | 0.236 |
| lnc-IRS1-6:1 | SEQ 0037 | 0.00143 | 0.804 | 0.868 |
| lnc-IRS1-7:3 | SEQ 0522 | 0.02418 | 1.153 | 0.229 |
| lnc-IRX2-10:1 | SEQ 0698 | 0.03324 | 0.744 | 0.757 |
| lnc-ITGB8-2:8 | SEQ 0616 | 0.02842 | 0.805 | 0.764 |
| lnc-JMJD4-2:1 | SEQ 0435 | 0.02049 | 0.736 | 0.778 |
| lnc-JRK-2:1 | SEQ 0935 | 0.0449 | 1.162 | 0.257 |
| lnc-JRK-2:2 | SEQ 0699 | 0.03324 | 0.764 | 0.757 |
| lnc-KAT5-2:1 | SEQ 0936 | 0.0449 | 0.769 | 0.743 |
| lnc-KBTBD7-1:1 | SEQ 0523 | 0.02418 | 0.742 | 0.771 |
| lnc-KBTBD8-4:3 | SEQ 0366 | 0.01727 | 1.457 | 0.215 |
| lnc-KCNA1-1:23 | SEQ 0122 | 0.00556 | 0.633 | 0.826 |
| lnc-KCND3-1:1 | SEQ 0085 | 0.00364 | 0.808 | 0.84 |
| lnc-KCNE1B-15:1 | SEQ 0319 | 0.01449 | 0.823 | 0.792 |
| lnc-KCNS3-9:1 | SEQ 0320 | 0.01449 | 1.265 | 0.208 |
| lnc-KCTD13-3:1 | SEQ 0700 | 0.03324 | 0.709 | 0.757 |
| lnc-KCTD19-1:1 | SEQ 0701 | 0.03324 | 0.761 | 0.757 |
| lnc-KDM3A-1:4 | SEQ 0104 | 0.00451 | 0.731 | 0.833 |
| lnc-KDM8-3:1 | SEQ 0436 | 0.02049 | 0.758 | 0.778 |
| lnc-KIAA0141-3:1 | SEQ 0702 | 0.03324 | 1.15 | 0.243 |
| lnc-KIF21B-2:1 | SEQ 0937 | 0.0449 | 0.873 | 0.743 |
| lnc-KIN-5:1 | SEQ 0703 | 0.03324 | 0.835 | 0.757 |
| lnc-KLF11-1:8 | SEQ 0704 | 0.03324 | 0.286 | 0.757 |
| lnc-KLF12-4:1 | SEQ 0938 | 0.0449 | 0.806 | 0.743 |
| lnc-KLF12-7:1 | SEQ 0240 | 0.01004 | 0.88 | 0.806 |
| lnc-KLHL24-2:1 | SEQ 0321 | 0.01449 | 1.206 | 0.208 |
| lnc-KLK2-4:3 | SEQ 0524 | 0.02418 | 0.881 | 0.771 |
| lnc-KLRG1-8:1 | SEQ 0809 | 0.03872 | 1.222 | 0.25 |
| lnc-KREMEN2-1:1 | SEQ 0705 | 0.03324 | 1.279 | 0.243 |
| lnc-KRR1-4:7 | SEQ 0706 | 0.03324 | 0.801 | 0.757 |
| lnc-KY-4:1 | SEQ 0123 | 0.00556 | 0.708 | 0.826 |
| lnc-L3MBTL2-1:1 | SEQ 0367 | 0.01727 | 1.259 | 0.215 |
| lnc-LARP1B-1:15 | SEQ 0277 | 0.01209 | 0.786 | 0.799 |
| lnc-LARP1B-1:17 | SEQ 0278 | 0.01209 | 0.786 | 0.799 |
| lnc-LARP1B-1:18 | SEQ 0279 | 0.01209 | 1.214 | 0.201 |
| lnc-LARP4-6:1 | SEQ 0368 | 0.01727 | 0.803 | 0.785 |
| lnc-LBH-4:1 | SEQ 0707 | 0.03324 | 1.312 | 0.243 |
| lnc-LBX1-1:1 | SEQ 0241 | 0.01004 | 0.788 | 0.806 |
| lnc-LEPROTL1-12:1 | SEQ 0011 | 0.0005 | 0.749 | 0.896 |
| lnc-LIMS3-1:10 | SEQ 0086 | 0.00364 | 2.27 | 0.16 |
| lnc-LINC00675-1:3 | SEQ 0810 | 0.03872 | 0.669 | 0.75 |
| lnc-LINS1-2:1 | SEQ 0811 | 0.03872 | 0.81 | 0.75 |
| lnc-LMBRD1-5:17 | SEQ 0812 | 0.03872 | 0.574 | 0.75 |
| lnc-LMX1A-2:1 | SEQ 0708 | 0.03324 | 0.786 | 0.757 |
| lnc-LONP2-6:10 | SEQ 0280 | 0.01209 | 0.912 | 0.799 |

TABLE 1-continued

The Sequence number, p value, mean +/− SD, fold change and
AUC of the 1008 serum lncRNAs with differential expression in
AD group versus healthy control group (p value <0.05, Wilcoxon test)

| lncRNA | SEQ | p value | Fold change | AUC |
|---|---|---|---|---|
| lnc-LRCH1-1:1 | SEQ 0437 | 0.02049 | 0.793 | 0.778 |
| lnc-LRP12-4:3 | SEQ 0939 | 0.0449 | 1.165 | 0.257 |
| lnc-LRP5L-2:14 | SEQ 0940 | 0.0449 | 1.203 | 0.257 |
| lnc-LRR1-1:2 | SEQ 0813 | 0.03872 | 0.729 | 0.75 |
| lnc-LRR1-1:3 | SEQ 0814 | 0.03872 | 0.725 | 0.75 |
| lnc-LRRC1-5:2 | SEQ 0087 | 0.00364 | 0.649 | 0.84 |
| lnc-LRRC3B-1:3 | SEQ 0941 | 0.0449 | 0.463 | 0.743 |
| lnc-LRRC41-3:2 | SEQ 0942 | 0.0449 | 1.272 | 0.257 |
| lnc-LRRC4C-7:1 | SEQ 0815 | 0.03872 | 0.818 | 0.75 |
| lnc-LRRFIP2-3:4 | SEQ 0617 | 0.02842 | 0.74 | 0.764 |
| lnc-LRRK1-3:4 | SEQ 0242 | 0.01004 | 0.79 | 0.806 |
| lnc-LRRK2-1:10 | SEQ 0369 | 0.01727 | 0.86 | 0.785 |
| lnc-LRRK2-1:9 | SEQ 0370 | 0.01727 | 0.86 | 0.785 |
| lnc-LRRTM4-3:2 | SEQ 0618 | 0.02842 | 0.865 | 0.764 |
| lnc-LY9-3:1 | SEQ 0207 | 0.00829 | 1.317 | 0.188 |
| lnc-LYN-8:1 | SEQ 0619 | 0.02842 | 1.516 | 0.236 |
| lnc-MAFB-1:4 | SEQ 0525 | 0.02418 | 0.839 | 0.771 |
| lnc-MAMDC2-1:1 | SEQ 0526 | 0.02418 | 0.828 | 0.771 |
| lnc-MAML3-2:1 | SEQ 0438 | 0.02049 | 0.768 | 0.778 |
| lnc-MAN1A1-1:3 | SEQ 0158 | 0.00681 | 0.722 | 0.819 |
| lnc-MAP9-6:1 | SEQ 0281 | 0.01209 | 0.741 | 0.799 |
| lnc-MARCH4-2:7 | SEQ 0088 | 0.00364 | 2 | 0.16 |
| lnc-MARCKS-1:9 | SEQ 0527 | 0.02418 | 0.717 | 0.771 |
| lnc-MASTL-2:1 | SEQ 0943 | 0.0449 | 0.756 | 0.743 |
| lnc-MB-3:1 | SEQ 0944 | 0.0449 | 1.302 | 0.257 |
| lnc-MBP-16:2 | SEQ 0208 | 0.00829 | 1.204 | 0.188 |
| lnc-MC5R-5:1 | SEQ 0945 | 0.0449 | 0.742 | 0.743 |
| lnc-MC5R-6:2 | SEQ 0243 | 0.01004 | 0.626 | 0.806 |
| lnc-MDM4-8:1 | SEQ 0816 | 0.03872 | 0.791 | 0.75 |
| lnc-ME3-1:1 | SEQ 0946 | 0.0449 | 1.353 | 0.257 |
| lnc-MED10-23:1 | SEQ 0209 | 0.00829 | 1.295 | 0.188 |
| lnc-MED15-1:2 | SEQ 0620 | 0.02842 | 1.191 | 0.236 |
| lnc-MESD-6:1 | SEQ 0947 | 0.0449 | 0.762 | 0.743 |
| lnc-MEST-6:1 | SEQ 0124 | 0.00556 | 0.817 | 0.826 |
| lnc-METTL22-11:1 | SEQ 0709 | 0.03324 | 0.747 | 0.757 |
| lnc-MFSD8-6:3 | SEQ 0528 | 0.02418 | 0.845 | 0.771 |
| lnc-MFSD8-6:8 | SEQ 0371 | 0.01727 | 0.794 | 0.785 |
| lnc-MGST3-1:3 | SEQ 0043 | 0.00183 | 1.664 | 0.139 |
| lnc-MIB1-1:1 | SEQ 0159 | 0.00681 | 0.68 | 0.819 |
| lnc-MNX1-10:1 | SEQ 0322 | 0.01449 | 1.204 | 0.208 |
| lnc-MOGAT1-3:2 | SEQ 0948 | 0.0449 | 0.703 | 0.743 |
| lnc-MPLKIP-3:1 | SEQ 0710 | 0.03324 | 0.867 | 0.757 |
| lnc-MPP4-3:1 | SEQ 0817 | 0.03872 | 0.813 | 0.75 |
| lnc-MRC2-2:1 | SEQ 0818 | 0.03872 | 0.835 | 0.75 |
| lnc-MRGPRD-2:1 | SEQ 0244 | 0.01004 | 0.79 | 0.806 |
| lnc-MRGPRF-4:4 | SEQ 0105 | 0.00451 | 0.604 | 0.833 |
| lnc-MROH7-2:1 | SEQ 0529 | 0.02418 | 0.844 | 0.771 |
| lnc-MRPL57-5:8 | SEQ 0621 | 0.02842 | 0.855 | 0.764 |
| lnc-MRPS30-13:1 | SEQ 0819 | 0.03872 | 0.814 | 0.75 |
| lnc-MSH2-3:2 | SEQ 0711 | 0.03324 | 1.401 | 0.243 |
| lnc-MTRNR2L1-3:1 | SEQ 0530 | 0.02418 | 1.325 | 0.229 |
| lnc-MVB12B-6:1 | SEQ 0531 | 0.02418 | 0.811 | 0.771 |
| lnc-MYC-12:1 | SEQ 0622 | 0.02842 | 1.418 | 0.236 |
| lnc-MYO18B-2:3 | SEQ 0323 | 0.01449 | 0.833 | 0.792 |
| lnc-MYO18B-3:3 | SEQ 0160 | 0.00681 | 0.762 | 0.819 |
| lnc-MYOCOS-2:1 | SEQ 0439 | 0.02049 | 0.891 | 0.778 |
| lnc-NAA38-3:1 | SEQ 0532 | 0.02418 | 0.854 | 0.771 |
| lnc-NAALADL2-8:1 | SEQ 0324 | 0.01449 | 0.864 | 0.792 |
| lnc-NANOS1-3:1 | SEQ 0712 | 0.03324 | 1.277 | 0.243 |
| lnc-NAXD-6:5 | SEQ 0125 | 0.00556 | 0.479 | 0.826 |
| lnc-NBPF14-1:2 | SEQ 0089 | 0.00364 | 0.815 | 0.84 |
| lnc-NBPF14-3:1 | SEQ 0623 | 0.02842 | 0.889 | 0.764 |
| lnc-NCR3LG1-3:1 | SEQ 0018 | 0.00066 | 0.837 | 0.889 |
| lnc-NDFIP2-7:13 | SEQ 0820 | 0.03872 | 0.775 | 0.75 |
| lnc-NDFIP2-7:14 | SEQ 0440 | 0.02049 | 0.77 | 0.778 |
| lnc-NDRG2-5:1 | SEQ 0949 | 0.0449 | 0.773 | 0.743 |
| lnc-NDUFA10-6:1 | SEQ 0161 | 0.00681 | 0.712 | 0.819 |
| lnc-NDUFB9-2:2 | SEQ 0713 | 0.03324 | 1.345 | 0.243 |
| lnc-NDUFS6-15:1 | SEQ 0950 | 0.0449 | 0.805 | 0.743 |
| lnc-NEUROD2-4:1 | SEQ 0071 | 0.00291 | 0.772 | 0.847 |
| lnc-NKAIN2-5:1 | SEQ 0821 | 0.03872 | 0.794 | 0.75 |
| lnc-NKX6-1-2:1 | SEQ 0282 | 0.01209 | 0.773 | 0.799 |
| lnc-NOC2L-1:21 | SEQ 0245 | 0.01004 | 1.382 | 0.194 |
| lnc-NOC2L-12:1 | SEQ 0372 | 0.01727 | 1.479 | 0.215 |

TABLE 1-continued

The Sequence number, p value, mean +/− SD, fold change and
AUC of the 1008 serum lncRNAs with differential expression in
AD group versus healthy control group (p value <0.05, Wilcoxon test)

| lncRNA | SEQ | p value | Fold change | AUC |
|---|---|---|---|---|
| lnc-NOS2-7:1 | SEQ 0951 | 0.0449 | 1.203 | 0.257 |
| lnc-NPBWR1-2:2 | SEQ 0952 | 0.0449 | 1.517 | 0.257 |
| lnc-NPIPB12-1:1 | SEQ 0822 | 0.03872 | 1.13 | 0.25 |
| lnc-NPY5R-4:1 | SEQ 0823 | 0.03872 | 0.817 | 0.75 |
| lnc-NR2E1-4:4 | SEQ 0714 | 0.03324 | 0.688 | 0.757 |
| lnc-NR5A2-1:13 | SEQ 0441 | 0.02049 | 0.908 | 0.778 |
| lnc-NRP1-4:1 | SEQ 0953 | 0.0449 | 1.258 | 0.257 |
| lnc-NUB1-4:1 | SEQ 0126 | 0.00556 | 0.809 | 0.826 |
| lnc-NUP35-4:2 | SEQ 0715 | 0.03324 | 0.858 | 0.757 |
| lnc-NUTM1-14:4 | SEQ 0716 | 0.03324 | 0.638 | 0.757 |
| lnc-NUTM2B-3:1 | SEQ 0533 | 0.02418 | 0.801 | 0.771 |
| lnc-NUTM2E-1:5 | SEQ 0127 | 0.00556 | 0.849 | 0.826 |
| lnc-ODF1-5:2 | SEQ 0325 | 0.01449 | 0.847 | 0.792 |
| lnc-ODF1-9:1 | SEQ 0824 | 0.03872 | 0.806 | 0.75 |
| lnc-OPRK1-2:1 | SEQ 0717 | 0.03324 | 0.826 | 0.757 |
| lnc-OR10AD1-1:1 | SEQ 0624 | 0.02842 | 0.826 | 0.764 |
| lnc-OR13C4-8:1 | SEQ 0625 | 0.02842 | 0.806 | 0.764 |
| lnc-OR4F21-7:9 | SEQ 0283 | 0.01209 | 0.761 | 0.799 |
| lnc-OR4F29-3:11 | SEQ 0044 | 0.00183 | 0.85 | 0.861 |
| lnc-OR4F29-8:4 | SEQ 0210 | 0.00829 | 0.633 | 0.813 |
| lnc-OR5H2-1:2 | SEQ 0326 | 0.01449 | 0.768 | 0.792 |
| lnc-OR6S1-2:1 | SEQ 0373 | 0.01727 | 0.857 | 0.785 |
| lnc-OR8G5-7:2 | SEQ 0626 | 0.02842 | 0.763 | 0.764 |
| lnc-ORAOV1-3:3 | SEQ 0442 | 0.02049 | 0.895 | 0.778 |
| lnc-OSBPL6-1:1 | SEQ 0443 | 0.02049 | 1.366 | 0.222 |
| lnc-OSBPL7-3:3 | SEQ 0534 | 0.02418 | 0.855 | 0.771 |
| lnc-OSBPL7-3:4 | SEQ 0535 | 0.02418 | 0.855 | 0.771 |
| lnc-OSBPL7-3:6 | SEQ 0536 | 0.02418 | 0.855 | 0.771 |
| lnc-OSBPL7-5:1 | SEQ 0162 | 0.00681 | 1.685 | 0.181 |
| lnc-OST4-6:2 | SEQ 0954 | 0.0449 | 0.774 | 0.743 |
| lnc-OXGR1-6:2 | SEQ 0374 | 0.01727 | 1.987 | 0.215 |
| lnc-OXGR1-6:3 | SEQ 0163 | 0.00681 | 0.861 | 0.819 |
| lnc-OXR1-1:1 | SEQ 0627 | 0.02842 | 0.752 | 0.764 |
| lnc-P2RY2-11:1 | SEQ 0537 | 0.02418 | 0.86 | 0.771 |
| lnc-PABPC1-3:1 | SEQ 0444 | 0.02049 | 0.814 | 0.778 |
| lnc-PABPC4L-21:3 | SEQ 0375 | 0.01727 | 1.485 | 0.215 |
| lnc-PABPC4L-5:7 | SEQ 0284 | 0.01209 | 0.626 | 0.799 |
| lnc-PACRGL-5:1 | SEQ 0718 | 0.03324 | 0.64 | 0.757 |
| lnc-PAGR1-2:4 | SEQ 0719 | 0.03324 | 1.176 | 0.243 |
| lnc-PALLD-3:1 | SEQ 0164 | 0.00681 | 0.741 | 0.819 |
| lnc-PAN3-3:1 | SEQ 0955 | 0.0449 | 0.758 | 0.743 |
| lnc-PANK1-7:1 | SEQ 0211 | 0.00829 | 0.723 | 0.813 |
| lnc-PAPD7-2:3 | SEQ 0956 | 0.0449 | 0.786 | 0.743 |
| lnc-PAPPA-1:3 | SEQ 0720 | 0.03324 | 2.192 | 0.243 |
| lnc-PAPPA-1:4 | SEQ 0721 | 0.03324 | 0.814 | 0.757 |
| lnc-PAPPA2-1:10 | SEQ 0246 | 0.01004 | 0.753 | 0.806 |
| lnc-PAPPA2-7:1 | SEQ 0165 | 0.00681 | 0.839 | 0.819 |
| lnc-PATE2-1:1 | SEQ 0247 | 0.01004 | 0.728 | 0.806 |
| lnc-PAX8-6:2 | SEQ 0538 | 0.02418 | 1.413 | 0.229 |
| lnc-PAXIP1-8:1 | SEQ 0957 | 0.0449 | 0.731 | 0.743 |
| lnc-PCDH10-11:1 | SEQ 0958 | 0.0449 | 0.719 | 0.743 |
| lnc-PCDH8-12:1 | SEQ 0166 | 0.00681 | 0.742 | 0.819 |
| lnc-PCOLCE2-1:1 | SEQ 0959 | 0.0449 | 0.909 | 0.743 |
| lnc-PCSK9-4:6 | SEQ 0327 | 0.01449 | 1.154 | 0.208 |
| lnc-PCSK9-4:9 | SEQ 0328 | 0.01449 | 1.154 | 0.208 |
| lnc-PDLIM1-3:1 | SEQ 0960 | 0.0449 | 0.837 | 0.743 |
| lnc-PFKP-16:15 | SEQ 0628 | 0.02842 | 0.662 | 0.764 |
| lnc-PFKP-17:1 | SEQ 0445 | 0.02049 | 0.834 | 0.778 |
| lnc-PHF14-14:19 | SEQ 0825 | 0.03872 | 0.678 | 0.75 |
| lnc-PIGB-1:5 | SEQ 0539 | 0.02418 | 0.691 | 0.771 |
| lnc-PIGM-4:1 | SEQ 0248 | 0.01004 | 0.715 | 0.806 |
| lnc-PINX1-7:1 | SEQ 0329 | 0.01449 | 1.307 | 0.208 |
| lnc-PLA2G2F-1:2 | SEQ 0285 | 0.01209 | 1.224 | 0.201 |
| lnc-PLA2G4A-7:5 | SEQ 0446 | 0.02049 | 0.865 | 0.778 |
| lnc-PLA2G4A-7:8 | SEQ 0826 | 0.03872 | 0.74 | 0.75 |
| lnc-PLAT-1:3 | SEQ 0961 | 0.0449 | 0.738 | 0.743 |
| lnc-PLCB1-7:2 | SEQ 0827 | 0.03872 | 0.854 | 0.75 |
| lnc-PLEKHA8-3:5 | SEQ 0962 | 0.0449 | 0.793 | 0.743 |
| lnc-PLK1-1:6 | SEQ 0963 | 0.0449 | 0.663 | 0.743 |
| lnc-PLN-2:1 | SEQ 0722 | 0.03324 | 0.781 | 0.757 |
| lnc-PLSCR2-2:1 | SEQ 0964 | 0.0449 | 0.813 | 0.743 |
| lnc-POC5-3:1 | SEQ 0629 | 0.02842 | 0.747 | 0.764 |
| lnc-POLE4-3:1 | SEQ 0330 | 0.01449 | 0.798 | 0.792 |
| lnc-POU2AF1-1:2 | SEQ 0447 | 0.02049 | 0.874 | 0.778 |

TABLE 1-continued

The Sequence number, p value, mean +/− SD, fold change and
AUC of the 1008 serum lncRNAs with differential expression in
AD group versus healthy control group (p value <0.05, Wilcoxon test)

| lncRNA | SEQ | p value | Fold change | AUC |
| --- | --- | --- | --- | --- |
| lnc-PPIAL4F-3:2 | SEQ 0828 | 0.03872 | 1.302 | 0.25 |
| lnc-PPM1D-1:8 | SEQ 0540 | 0.02418 | 0.8 | 0.771 |
| lnc-PPP2R3C-4:1 | SEQ 0025 | 0.00086 | 0.879 | 0.882 |
| lnc-PPP5C-4:1 | SEQ 0723 | 0.03324 | 0.757 | 0.757 |
| lnc-PRDM9-19:2 | SEQ 0829 | 0.03872 | 0.709 | 0.75 |
| lnc-PRDM9-20:1 | SEQ 0376 | 0.01727 | 0.678 | 0.785 |
| lnc-PRELID2-1:2 | SEQ 0541 | 0.02418 | 1.232 | 0.229 |
| lnc-PRKACG-1:2 | SEQ 0724 | 0.03324 | 0.738 | 0.757 |
| lnc-PRKACG-2:1 | SEQ 0630 | 0.02842 | 1.186 | 0.236 |
| lnc-PRKCH-1:1 | SEQ 0286 | 0.01209 | 0.904 | 0.799 |
| lnc-PRKN-8:1 | SEQ 0212 | 0.00829 | 1.368 | 0.188 |
| lnc-PRND-2:1 | SEQ 0287 | 0.01209 | 0.798 | 0.799 |
| lnc-PRR11-1:4 | SEQ 0288 | 0.01209 | 0.862 | 0.799 |
| lnc-PRR5-5:1 | SEQ 0167 | 0.00681 | 0.703 | 0.819 |
| lnc-PRSS54-2:2 | SEQ 0168 | 0.00681 | 0.769 | 0.819 |
| lnc-PSMB1-6:4 | SEQ 0331 | 0.01449 | 2.134 | 0.208 |
| lnc-PTDSS1-1:2 | SEQ 0448 | 0.02049 | 1.246 | 0.222 |
| lnc-PTP4A2-1:2 | SEQ 0725 | 0.03324 | 1.223 | 0.243 |
| lnc-PTPN14-11:1 | SEQ 0449 | 0.02049 | 1.341 | 0.222 |
| lnc-PTPN4-1:1 | SEQ 0631 | 0.02842 | 0.755 | 0.764 |
| lnc-QRFP-5:1 | SEQ 0019 | 0.00066 | 2.17 | 0.111 |
| lnc-RAB3B-1:1 | SEQ 0965 | 0.0449 | 0.843 | 0.743 |
| lnc-RAB6C-3:1 | SEQ 0966 | 0.0449 | 0.836 | 0.743 |
| lnc-RAI14-3:1 | SEQ 0542 | 0.02418 | 0.835 | 0.771 |
| lnc-RALGAPA1-1:2 | SEQ 0726 | 0.03324 | 0.86 | 0.757 |
| lnc-RALGAPA2-2:4 | SEQ 0967 | 0.0449 | 0.805 | 0.743 |
| lnc-RARRES1-3:2 | SEQ 0632 | 0.02842 | 0.84 | 0.764 |
| lnc-RASGRP1-3:3 | SEQ 0968 | 0.0449 | 0.796 | 0.743 |
| lnc-RBFOX1-2:1 | SEQ 0377 | 0.01727 | 1.269 | 0.215 |
| lnc-RBKS-6:1 | SEQ 0128 | 0.00556 | 0.802 | 0.826 |
| lnc-RBM11-11:1 | SEQ 0450 | 0.02049 | 0.714 | 0.778 |
| lnc-RBM25-1:1 | SEQ 0969 | 0.0449 | 0.89 | 0.743 |
| lnc-RBM33-3:1 | SEQ 0727 | 0.03324 | 0.762 | 0.757 |
| lnc-RBM45-7:1 | SEQ 0830 | 0.03872 | 0.792 | 0.75 |
| lnc-RBMS1-7:1 | SEQ 0249 | 0.01004 | 0.778 | 0.806 |
| lnc-RCSD1-4:1 | SEQ 0831 | 0.03872 | 0.831 | 0.75 |
| lnc-RDH13-1:2 | SEQ 0250 | 0.01004 | 0.635 | 0.806 |
| lnc-RGMA-28:2 | SEQ 0378 | 0.01727 | 0.875 | 0.785 |
| lnc-RGS9-15:6 | SEQ 0970 | 0.0449 | 0.705 | 0.743 |
| lnc-RHNO1-1:1 | SEQ 0026 | 0.00086 | 1.248 | 0.118 |
| lnc-RHOB-1:3 | SEQ 0451 | 0.02049 | 0.612 | 0.778 |
| lnc-RHOB-21:1 | SEQ 0971 | 0.0449 | 0.817 | 0.743 |
| lnc-RHOBTB2-4:1 | SEQ 0213 | 0.00829 | 0.839 | 0.813 |
| lnc-RIPPLY3-1:3 | SEQ 0832 | 0.03872 | 0.889 | 0.75 |
| lnc-RIT2-5:1 | SEQ 0289 | 0.01209 | 1.302 | 0.201 |
| lnc-RNF6-2:1 | SEQ 0059 | 0.00232 | 0.692 | 0.854 |
| lnc-RNFT2-1:5 | SEQ 0379 | 0.01727 | 0.8 | 0.785 |
| lnc-RNLS-1:1 | SEQ 0972 | 0.0449 | 0.829 | 0.743 |
| lnc-ROBO2-16:1 | SEQ 0251 | 0.01004 | 0.799 | 0.806 |
| lnc-RPE65-4:2 | SEQ 0129 | 0.00556 | 0.857 | 0.826 |
| lnc-RPIA-25:1 | SEQ 0130 | 0.00556 | 0.866 | 0.826 |
| lnc-RPL10L-5:1 | SEQ 0452 | 0.02049 | 0.77 | 0.778 |
| lnc-RPL24-6:1 | SEQ 0728 | 0.03324 | 1.245 | 0.243 |
| lnc-RPL35-2:1 | SEQ 0543 | 0.02418 | 0.812 | 0.771 |
| lnc-RPL37-2:1 | SEQ 0214 | 0.00829 | 1.309 | 0.188 |
| lnc-RPRM-7:1 | SEQ 0380 | 0.01727 | 0.679 | 0.785 |
| lnc-RPS12-4:1 | SEQ 0633 | 0.02842 | 0.806 | 0.764 |
| lnc-RPS21-4:2 | SEQ 0027 | 0.00086 | 0.664 | 0.882 |
| lnc-RRM1-2:5 | SEQ 0973 | 0.0449 | 0.934 | 0.743 |
| lnc-RSL1D1-2:1 | SEQ 0215 | 0.00829 | 0.762 | 0.813 |
| lnc-RTL1-3:9 | SEQ 0544 | 0.02418 | 0.848 | 0.771 |
| lnc-RUBCN-1:1 | SEQ 0833 | 0.03872 | 0.788 | 0.75 |
| lnc-S1PR1-13:1 | SEQ 0381 | 0.01727 | 0.686 | 0.785 |
| lnc-SAMD11-1:1 | SEQ 0729 | 0.03324 | 1.247 | 0.243 |
| lnc-SAMD5-1:10 | SEQ 0090 | 0.00364 | 0.708 | 0.84 |
| lnc-SC5D-4:1 | SEQ 0730 | 0.03324 | 1.249 | 0.243 |
| lnc-SCD-7:1 | SEQ 0974 | 0.0449 | 0.731 | 0.743 |
| lnc-SCGB1C2-8:1 | SEQ 0975 | 0.0449 | 0.776 | 0.743 |
| lnc-SCNN1B-3:1 | SEQ 0976 | 0.0449 | 1.155 | 0.257 |
| lnc-SCTR-2:4 | SEQ 0634 | 0.02842 | 0.852 | 0.764 |
| lnc-SEPT14-6:1 | SEQ 0545 | 0.02418 | 0.878 | 0.771 |
| lnc-SERHL2-1:8 | SEQ 0546 | 0.02418 | 1.483 | 0.229 |
| lnc-SERINC1-8:3 | SEQ 0731 | 0.03324 | 0.827 | 0.757 |
| lnc-SERP1-4:6 | SEQ 0072 | 0.00291 | 0.719 | 0.847 |

TABLE 1-continued

The Sequence number, p value, mean +/− SD, fold change and AUC of the 1008 serum lncRNAs with differential expression in AD group versus healthy control group (p value <0.05, Wilcoxon test)

| lncRNA | SEQ | p value | Fold change | AUC |
|---|---|---|---|---|
| lnc-SERP1-4:8 | SEQ 0977 | 0.0449 | 0.831 | 0.743 |
| lnc-SERPINI1-14:1 | SEQ 0978 | 0.0449 | 0.85 | 0.743 |
| lnc-SERTM1-1:1 | SEQ 0290 | 0.01209 | 0.817 | 0.799 |
| lnc-SFPQ-2:1 | SEQ 0169 | 0.00681 | 0.72 | 0.819 |
| lnc-SGCG-7:2 | SEQ 0453 | 0.02049 | 0.733 | 0.778 |
| lnc-SGK1-3:14 | SEQ 0979 | 0.0449 | 1.836 | 0.257 |
| lnc-SGMS1-4:1 | SEQ 0834 | 0.03872 | 0.793 | 0.75 |
| lnc-SH3BGRL2-4:1 | SEQ 0980 | 0.0449 | 1.174 | 0.257 |
| lnc-SKIL-2:3 | SEQ 0981 | 0.0449 | 1.222 | 0.257 |
| lnc-SLC1A3-1:1 | SEQ 0547 | 0.02418 | 0.791 | 0.771 |
| lnc-SLC22A23-11:2 | SEQ 0732 | 0.03324 | 1.239 | 0.243 |
| lnc-SLC25A21-1:1 | SEQ 0733 | 0.03324 | 0.77 | 0.757 |
| lnc-SLC25A24-2:1 | SEQ 0548 | 0.02418 | 0.883 | 0.771 |
| lnc-SLC25A30-2:4 | SEQ 0291 | 0.01209 | 1.539 | 0.201 |
| lnc-SLC2A10-1:1 | SEQ 0549 | 0.02418 | 0.788 | 0.771 |
| lnc-SLC38A2-1:11 | SEQ 0252 | 0.01004 | 0.892 | 0.806 |
| lnc-SLC38A2-1:15 | SEQ 0332 | 0.01449 | 1.425 | 0.208 |
| lnc-SLC39A11-10:11 | SEQ 0292 | 0.01209 | 4.38 | 0.201 |
| lnc-SLC46A3-7:1 | SEQ 0550 | 0.02418 | 0.858 | 0.771 |
| lnc-SLCO6A1-2:1 | SEQ 0635 | 0.02842 | 0.775 | 0.764 |
| lnc-SLITRK5-17:1 | SEQ 0293 | 0.01209 | 0.636 | 0.799 |
| lnc-SLTM-1:2 | SEQ 0982 | 0.0449 | 0.9 | 0.743 |
| lnc-SMARCA5-4:18 | SEQ 0253 | 0.01004 | 0.825 | 0.806 |
| lnc-SMIM14-4:1 | SEQ 0454 | 0.02049 | 0.788 | 0.778 |
| lnc-SMIM17-5:4 | SEQ 0734 | 0.03324 | 0.715 | 0.757 |
| lnc-SNAPC3-12:5 | SEQ 0455 | 0.02049 | 1.387 | 0.222 |
| lnc-SNCA-3:1 | SEQ 0551 | 0.02418 | 0.498 | 0.771 |
| lnc-SNRPB2-2:4 | SEQ 0254 | 0.01004 | 1.727 | 0.194 |
| lnc-SNX10-6:1 | SEQ 0636 | 0.02842 | 0.764 | 0.764 |
| lnc-SNX13-2:6 | SEQ 0456 | 0.02049 | 1.576 | 0.222 |
| lnc-SNX16-6:1 | SEQ 0983 | 0.0449 | 0.83 | 0.743 |
| lnc-SNX17-1:13 | SEQ 0333 | 0.01449 | 1.985 | 0.208 |
| lnc-SNX17-1:8 | SEQ 0984 | 0.0449 | 0.754 | 0.743 |
| lnc-SNX19-6:1 | SEQ 0835 | 0.03872 | 1.249 | 0.25 |
| lnc-SNX19-9:1 | SEQ 0836 | 0.03872 | 0.837 | 0.75 |
| lnc-SNX20-8:5 | SEQ 0985 | 0.0449 | 0.933 | 0.743 |
| lnc-SOX11-5:1 | SEQ 0382 | 0.01727 | 1.216 | 0.215 |
| lnc-SOX14-2:1 | SEQ 0045 | 0.00183 | 0.837 | 0.861 |
| lnc-SPAG9-2:1 | SEQ 0383 | 0.01727 | 0.851 | 0.785 |
| lnc-SPAG9-2:2 | SEQ 0384 | 0.01727 | 0.851 | 0.785 |
| lnc-SPATA31A6-10:1 | SEQ 0837 | 0.03872 | 0.804 | 0.75 |
| lnc-SPATA31D4-1:6 | SEQ 0838 | 0.03872 | 0.718 | 0.75 |
| lnc-SPP1-1:1 | SEQ 0046 | 0.00183 | 0.846 | 0.861 |
| lnc-SPRY1-9:1 | SEQ 0839 | 0.03872 | 0.767 | 0.75 |
| lnc-SPTSSA-5:2 | SEQ 0552 | 0.02418 | 1.31 | 0.229 |
| lnc-SRCIN1-1:18 | SEQ 0553 | 0.02418 | 0.798 | 0.771 |
| lnc-SRSF2-2:5 | SEQ 0735 | 0.03324 | 0.633 | 0.757 |
| lnc-ST8SIA4-3:5 | SEQ 0457 | 0.02049 | 1.584 | 0.222 |
| lnc-STARD10-1:6 | SEQ 0840 | 0.03872 | 1.156 | 0.25 |
| lnc-STAT1-2:3 | SEQ 0986 | 0.0449 | 0.832 | 0.743 |
| lnc-STK32B-2:1 | SEQ 0170 | 0.00681 | 0.807 | 0.819 |
| lnc-STOML3-6:1 | SEQ 0038 | 0.00143 | 0.731 | 0.868 |
| lnc-STPG1-1:1 | SEQ 0637 | 0.02842 | 0.82 | 0.764 |
| lnc-STRADB-6:2 | SEQ 0987 | 0.0449 | 0.723 | 0.743 |
| lnc-SUCLA2-13:2 | SEQ 0736 | 0.03324 | 1.22 | 0.243 |
| lnc-SUCLA2-13:3 | SEQ 0737 | 0.03324 | 1.22 | 0.243 |
| lnc-SUGT1-3:1 | SEQ 0131 | 0.00556 | 2.047 | 0.174 |
| lnc-SULT1A4-1:27 | SEQ 0841 | 0.03872 | 1.274 | 0.25 |
| lnc-SULT1C2-3:1 | SEQ 0842 | 0.03872 | 1.396 | 0.25 |
| lnc-SUSD1-1:5 | SEQ 0638 | 0.02842 | 0.798 | 0.764 |
| lnc-SYCP1-4:1 | SEQ 0843 | 0.03872 | 1.204 | 0.25 |
| lnc-TAAR9-3:2 | SEQ 0738 | 0.03324 | 0.806 | 0.757 |
| lnc-TAB2-1:4 | SEQ 0988 | 0.0449 | 0.846 | 0.743 |
| lnc-TACC2-8:6 | SEQ 0171 | 0.00681 | 0.869 | 0.819 |
| lnc-TACSTD2-2:4 | SEQ 0020 | 0.00066 | 0.757 | 0.889 |
| lnc-TADA2B-6:1 | SEQ 0554 | 0.02418 | 1.467 | 0.229 |
| lnc-TAF9-10:1 | SEQ 0639 | 0.02842 | 0.825 | 0.764 |
| lnc-TASP1-11:1 | SEQ 0989 | 0.0449 | 1.217 | 0.257 |
| lnc-TBC1D22A-4:12 | SEQ 0739 | 0.03324 | 0.969 | 0.757 |
| lnc-TBC1D3H-1:1 | SEQ 0334 | 0.01449 | 0.729 | 0.792 |
| lnc-TBC1D3H-3:1 | SEQ 0294 | 0.01209 | 0.72 | 0.799 |
| lnc-TBL1XR1-7:1 | SEQ 0458 | 0.02049 | 0.754 | 0.778 |
| lnc-TCEANC2-3:1 | SEQ 0106 | 0.00451 | 0.549 | 0.833 |
| lnc-TCEANC2-3:2 | SEQ 0385 | 0.01727 | 1.882 | 0.215 |

TABLE 1-continued

The Sequence number, p value, mean +/− SD, fold change and
AUC of the 1008 serum lncRNAs with differential expression in
AD group versus healthy control group (p value <0.05, Wilcoxon test)

| lncRNA | SEQ | p value | Fold change | AUC |
| --- | --- | --- | --- | --- |
| lnc-TCF19-1:80 | SEQ 0740 | 0.03324 | 1.351 | 0.243 |
| lnc-TCF7-1:3 | SEQ 0990 | 0.0449 | 0.866 | 0.743 |
| lnc-TCP10-2:1 | SEQ 0991 | 0.0449 | 0.876 | 0.743 |
| lnc-TCP11-2:3 | SEQ 0640 | 0.02842 | 0.67 | 0.764 |
| lnc-TCP11L2-1:4 | SEQ 0741 | 0.03324 | 0.74 | 0.757 |
| lnc-TDO2-6:1 | SEQ 0641 | 0.02842 | 0.758 | 0.764 |
| lnc-TDP2-1:1 | SEQ 0335 | 0.01449 | 1.29 | 0.208 |
| lnc-TEAD4-1:1 | SEQ 0992 | 0.0449 | 1.868 | 0.257 |
| lnc-TEFM-10:2 | SEQ 0993 | 0.0449 | 0.736 | 0.743 |
| lnc-TEKT3-3:1 | SEQ 0844 | 0.03872 | 0.744 | 0.75 |
| lnc-TEKT4-4:1 | SEQ 0132 | 0.00556 | 1.332 | 0.174 |
| lnc-TENM3-3:3 | SEQ 0001 | 0.00007 | 0.717 | 0.938 |
| lnc-TENM3-3:4 | SEQ 0008 | 0.00037 | 1.947 | 0.097 |
| lnc-TENM3-3:5 | SEQ 0009 | 0.00037 | 1.993 | 0.097 |
| lnc-TENM4-4:1 | SEQ 0742 | 0.03324 | 2.209 | 0.243 |
| lnc-TEX10-1:1 | SEQ 0459 | 0.02049 | 0.814 | 0.778 |
| lnc-TEX29-3:1 | SEQ 0172 | 0.00681 | 0.767 | 0.819 |
| lnc-TEX49-4:1 | SEQ 0994 | 0.0449 | 0.789 | 0.743 |
| lnc-TF-4:1 | SEQ 0743 | 0.03324 | 0.898 | 0.757 |
| lnc-TFCP2L1-6:1 | SEQ 0460 | 0.02049 | 0.743 | 0.778 |
| lnc-TGM6-2:1 | SEQ 0216 | 0.00829 | 0.741 | 0.813 |
| lnc-THAP12-1:5 | SEQ 0642 | 0.02842 | 1.427 | 0.236 |
| lnc-THOC5-3:1 | SEQ 0133 | 0.00556 | 0.717 | 0.826 |
| lnc-THY1-3:1 | SEQ 0995 | 0.0449 | 0.788 | 0.743 |
| lnc-THYN1-1:1 | SEQ 0461 | 0.02049 | 1.173 | 0.222 |
| lnc-TLDC2-4:1 | SEQ 0555 | 0.02418 | 1.214 | 0.229 |
| lnc-TLE4-7:1 | SEQ 0255 | 0.01004 | 1.184 | 0.194 |
| lnc-TLK1-1:2 | SEQ 0556 | 0.02418 | 0.76 | 0.771 |
| lnc-TLNRD1-3:1 | SEQ 0462 | 0.02049 | 0.829 | 0.778 |
| lnc-TMEM126B-2:3 | SEQ 0336 | 0.01449 | 0.508 | 0.792 |
| lnc-TMEM126B-2:4 | SEQ 0643 | 0.02842 | 1.964 | 0.236 |
| lnc-TMEM132C-6:5 | SEQ 0996 | 0.0449 | 1.222 | 0.257 |
| lnc-TMEM168-1:1 | SEQ 0073 | 0.00291 | 0.761 | 0.847 |
| lnc-TMEM185B-12:1 | SEQ 0173 | 0.00681 | 0.549 | 0.819 |
| lnc-TMEM185B-12:7 | SEQ 0060 | 0.00232 | 1.694 | 0.146 |
| lnc-TMEM185B-2:3 | SEQ 0386 | 0.01727 | 1.212 | 0.215 |
| lnc-TMEM211-2:8 | SEQ 0644 | 0.02842 | 1.278 | 0.236 |
| lnc-TMEM242-6:1 | SEQ 0463 | 0.02049 | 0.879 | 0.778 |
| lnc-TMEM248-4:11 | SEQ 0845 | 0.03872 | 0.842 | 0.75 |
| lnc-TMEM70-7:1 | SEQ 0217 | 0.00829 | 1.404 | 0.188 |
| lnc-TMX4-3:1 | SEQ 0464 | 0.02049 | 0.776 | 0.778 |
| lnc-TNFRSF19-2:1 | SEQ 0744 | 0.03324 | 1.177 | 0.243 |
| lnc-TNFSF4-3:3 | SEQ 0337 | 0.01449 | 1.714 | 0.208 |
| lnc-TOGARAM2-1:5 | SEQ 0645 | 0.02842 | 0.81 | 0.764 |
| lnc-TOGARAM2-1:6 | SEQ 0646 | 0.02842 | 0.81 | 0.764 |
| lnc-TP53TG3-65:1 | SEQ 0465 | 0.02049 | 1.227 | 0.222 |
| lnc-TP53TG3D-2:1 | SEQ 0846 | 0.03872 | 0.9 | 0.75 |
| lnc-TP53TG3F-8:1 | SEQ 0647 | 0.02842 | 1.33 | 0.236 |
| lnc-TPPP-1:2 | SEQ 0002 | 0.00014 | 0.158 | 0.924 |
| lnc-TPPP-1:3 | SEQ 0134 | 0.00556 | 1.834 | 0.174 |
| lnc-TRAM1-1:1 | SEQ 0074 | 0.00291 | 0.59 | 0.847 |
| lnc-TRIB2-14:1 | SEQ 0021 | 0.00066 | 0.788 | 0.889 |
| lnc-TRIM13-2:1 | SEQ 0174 | 0.00681 | 0.739 | 0.819 |
| lnc-TRIM26-2:33 | SEQ 0745 | 0.03324 | 0.782 | 0.757 |
| lnc-TRIM26-2:74 | SEQ 0338 | 0.01449 | 1.231 | 0.208 |
| lnc-TRIM27-10:2 | SEQ 0107 | 0.00451 | 1.227 | 0.167 |
| lnc-TRIM37-2:1 | SEQ 0997 | 0.0449 | 1.221 | 0.257 |
| lnc-TRIM43B-1:2 | SEQ 0387 | 0.01727 | 0.8 | 0.785 |
| lnc-TRIM49D1-4:1 | SEQ 0175 | 0.00681 | 1.36 | 0.181 |
| lnc-TRIM77-7:1 | SEQ 0847 | 0.03872 | 0.741 | 0.75 |
| lnc-TRIML2-11:1 | SEQ 0557 | 0.02418 | 1.296 | 0.229 |
| lnc-TRMT11-4:1 | SEQ 0218 | 0.00829 | 0.773 | 0.813 |
| lnc-TRPM1-3:1 | SEQ 0388 | 0.01727 | 0.83 | 0.785 |
| lnc-TSC22D2-1:4 | SEQ 0466 | 0.02049 | 0.633 | 0.778 |
| lnc-TSHB-2:3 | SEQ 0295 | 0.01209 | 0.564 | 0.799 |
| lnc-TSHB-2:4 | SEQ 0467 | 0.02049 | 1.766 | 0.222 |
| lnc-TSHB-2:5 | SEQ 0468 | 0.02049 | 1.766 | 0.222 |
| lnc-TSHB-2:6 | SEQ 0296 | 0.01209 | 0.564 | 0.799 |
| lnc-TSR3-1:2 | SEQ 0339 | 0.01449 | 0.784 | 0.792 |
| lnc-TSTD2-4:3 | SEQ 0848 | 0.03872 | 1.229 | 0.25 |
| lnc-TTC26-9:1 | SEQ 0558 | 0.02418 | 0.686 | 0.771 |
| lnc-TTC38-7:1 | SEQ 0849 | 0.03872 | 1.169 | 0.25 |
| lnc-TTF2-4:1 | SEQ 0998 | 0.0449 | 0.848 | 0.743 |
| lnc-TUBA1C-1:12 | SEQ 0999 | 0.0449 | 0.731 | 0.743 |

TABLE 1-continued

The Sequence number, p value, mean +/− SD, fold change and AUC of the 1008 serum lncRNAs with differential expression in AD group versus healthy control group (p value <0.05, Wilcoxon test)

| lncRNA | SEQ | p value | Fold change | AUC |
|---|---|---|---|---|
| lnc-TUBE1-6:1 | SEQ 0850 | 0.03872 | 1.141 | 0.25 |
| lnc-TUBGCP3-11:1 | SEQ 0469 | 0.02049 | 0.885 | 0.778 |
| lnc-TUSC5-3:1 | SEQ 1000 | 0.0449 | 1.345 | 0.257 |
| lnc-TWSG1-2:1 | SEQ 0047 | 0.00183 | 0.673 | 0.861 |
| lnc-UBE2QL1-4:1 | SEQ 0648 | 0.02842 | 0.864 | 0.764 |
| lnc-UBE3C-10:1 | SEQ 0075 | 0.00291 | 1.627 | 0.153 |
| lnc-UBLCP1-2:6 | SEQ 0048 | 0.00183 | 0.755 | 0.861 |
| lnc-UCK1-2:1 | SEQ 0851 | 0.03872 | 0.774 | 0.75 |
| lnc-UGCG-1:1 | SEQ 0219 | 0.00829 | 0.802 | 0.813 |
| lnc-UGT1A8-3:1 | SEQ 0649 | 0.02842 | 1.428 | 0.236 |
| lnc-UGT2B28-1:2 | SEQ 1001 | 0.0449 | 0.818 | 0.743 |
| lnc-UGT2B28-2:1 | SEQ 0559 | 0.02418 | 0.764 | 0.771 |
| lnc-UGT3A2-3:1 | SEQ 0389 | 0.01727 | 0.855 | 0.785 |
| lnc-UNC93B1-1:5 | SEQ 1002 | 0.0449 | 0.806 | 0.743 |
| lnc-UNCX-3:26 | SEQ 0470 | 0.02049 | 0.493 | 0.778 |
| lnc-UPK3B-7:1 | SEQ 0297 | 0.01209 | 0.607 | 0.799 |
| lnc-USP16-15:1 | SEQ 0650 | 0.02842 | 0.811 | 0.764 |
| lnc-USP16-9:3 | SEQ 0091 | 0.00364 | 0.834 | 0.84 |
| lnc-USP17L7-1:1 | SEQ 0746 | 0.03324 | 1.48 | 0.243 |
| lnc-USP24-2:3 | SEQ 0747 | 0.03324 | 0.694 | 0.757 |
| lnc-USP31-2:3 | SEQ 0022 | 0.00066 | 0.685 | 0.889 |
| lnc-USP53-1:1 | SEQ 0390 | 0.01727 | 0.824 | 0.785 |
| lnc-USP6NL-13:1 | SEQ 0748 | 0.03324 | 1.209 | 0.243 |
| lnc-VGLL3-11:1 | SEQ 0220 | 0.00829 | 0.81 | 0.813 |
| lnc-VPS8-2:4 | SEQ 0852 | 0.03872 | 0.742 | 0.75 |
| lnc-VSTM2B-5:12 | SEQ 0560 | 0.02418 | 0.771 | 0.771 |
| lnc-VWA5B1-2:1 | SEQ 0391 | 0.01727 | 1.479 | 0.215 |
| lnc-WDR4-2:6 | SEQ 1003 | 0.0449 | 0.929 | 0.743 |
| lnc-WDR63-6:2 | SEQ 0471 | 0.02049 | 0.655 | 0.778 |
| lnc-WDR70-7:6 | SEQ 1004 | 0.0449 | 0.929 | 0.743 |
| lnc-WDR7-11:1 | SEQ 0749 | 0.03324 | 1.151 | 0.243 |
| lnc-WDYHV1-1:2 | SEQ 0561 | 0.02418 | 0.912 | 0.771 |
| lnc-WISP1-17:2 | SEQ 0135 | 0.00556 | 0.715 | 0.826 |
| lnc-WSB1-2:1 | SEQ 0256 | 0.01004 | 1.293 | 0.194 |
| lnc-XCL2-4:1 | SEQ 1005 | 0.0449 | 0.714 | 0.743 |
| lnc-XXYLT1-5:1 | SEQ 0221 | 0.00829 | 0.681 | 0.813 |
| lnc-YPEL5-5:1 | SEQ 0750 | 0.03324 | 1.357 | 0.243 |
| lnc-ZC3H12D-2:3 | SEQ 0392 | 0.01727 | 0.831 | 0.785 |
| lnc-ZC3H15-2:1 | SEQ 0012 | 0.0005 | 0.765 | 0.896 |
| lnc-ZFAT-1:3 | SEQ 0562 | 0.02418 | 0.907 | 0.771 |
| lnc-ZFAT-1:8 | SEQ 0393 | 0.01727 | 0.841 | 0.785 |
| lnc-ZFC3H1-16:2 | SEQ 0651 | 0.02842 | 0.789 | 0.764 |
| lnc-ZFP57-15:1 | SEQ 0177 | 0.00701 | 0.402 | 0.826 |
| lnc-ZFP90-3:6 | SEQ 0563 | 0.02418 | 0.739 | 0.771 |
| lnc-ZMYM2-7:1 | SEQ 0853 | 0.03872 | 1.335 | 0.25 |
| lnc-ZNF107-7:1 | SEQ 0652 | 0.02842 | 0.735 | 0.764 |
| lnc-ZNF124-1:2 | SEQ 0564 | 0.02418 | 0.827 | 0.771 |
| lnc-ZNF189-2:1 | SEQ 0751 | 0.03324 | 0.903 | 0.757 |
| lnc-ZNF25-7:1 | SEQ 0257 | 0.01004 | 1.37 | 0.194 |
| lnc-ZNF25-9:4 | SEQ 0298 | 0.01209 | 0.663 | 0.799 |
| lnc-ZNF273-4:4 | SEQ 0092 | 0.00364 | 0.742 | 0.84 |
| lnc-ZNF330-2:1 | SEQ 0854 | 0.03872 | 0.833 | 0.75 |
| lnc-ZNF33A-14:1 | SEQ 0049 | 0.00183 | 1.499 | 0.139 |
| lnc-ZNF33A-8:1 | SEQ 1006 | 0.0449 | 1.115 | 0.257 |
| lnc-ZNF33B-3:11 | SEQ 1007 | 0.0449 | 0.846 | 0.743 |
| lnc-ZNF33B-6:1 | SEQ 0394 | 0.01727 | 2.524 | 0.215 |
| lnc-ZNF33B-6:3 | SEQ 0299 | 0.01209 | 0.825 | 0.799 |
| lnc-ZNF385C-4:1 | SEQ 0472 | 0.02049 | 1.311 | 0.222 |
| lnc-ZNF423-3:3 | SEQ 1008 | 0.0449 | 1.258 | 0.257 |

TABLE 1-continued

The Sequence number, p value, mean +/− SD, fold change and
AUC of the 1008 serum lncRNAs with differential expression in
AD group versus healthy control group (p value <0.05, Wilcoxon test)

| lncRNA | SEQ | p value | Fold change | AUC |
|---|---|---|---|---|
| lnc-ZNF430-3:1 | SEQ 0855 | 0.03872 | 0.797 | 0.75 |
| lnc-ZNF430-3:4 | SEQ 0258 | 0.01004 | 0.788 | 0.806 |
| lnc-ZNF442-1:2 | SEQ 0061 | 0.00232 | 0.683 | 0.854 |
| lnc-ZNF460-2:1 | SEQ 0473 | 0.02049 | 0.842 | 0.778 |
| lnc-ZNF506-5:2 | SEQ 0108 | 0.00451 | 0.684 | 0.833 |
| lnc-ZNF544-2:1 | SEQ 0474 | 0.02049 | 0.805 | 0.778 |
| lnc-ZNF573-2:2 | SEQ 0856 | 0.03872 | 0.823 | 0.75 |
| lnc-ZNF624-4:3 | SEQ 0395 | 0.01727 | 1.241 | 0.215 |
| lnc-ZNF654-3:1 | SEQ 0857 | 0.03872 | 0.869 | 0.75 |
| lnc-ZNF720-5:3 | SEQ 0222 | 0.00829 | 1.313 | 0.188 |
| lnc-ZNF724-6:1 | SEQ 0176 | 0.00681 | 0.729 | 0.819 |
| lnc-ZNF726-1:3 | SEQ 0259 | 0.01004 | 2.115 | 0.194 |
| lnc-ZNF827-2:1 | SEQ 0653 | 0.02842 | 0.924 | 0.764 |
| lnc-ZNF99-3:2 | SEQ 0396 | 0.01727 | 0.751 | 0.785 |
| lnc-ZRANB2-2:1 | SEQ 0654 | 0.02842 | 0.801 | 0.764 |
| lnc-ZSWIM2-15:1 | SEQ 0655 | 0.02842 | 0.696 | 0.764 |
| lnc-ZWINT-2:4 | SEQ 0565 | 0.02418 | 0.637 | 0.771 |
| LRP4-AS1:5 | SEQ 0766 | 0.03872 | 1.288 | 0.25 |
| LYRM4-AS1:17 | SEQ 0485 | 0.02418 | 0.893 | 0.771 |
| MAPT-AS1:1 | SEQ 0767 | 0.03872 | 0.785 | 0.75 |
| MCPH1-AS1:2 | SEQ 0308 | 0.01449 | 1.321 | 0.208 |
| MDC1-AS1:5 | SEQ 0486 | 0.02418 | 1.248 | 0.229 |
| MEF2C-AS1:25 | SEQ 0582 | 0.02842 | 0.907 | 0.764 |
| MIR155HG:7 | SEQ 0876 | 0.0449 | 0.606 | 0.743 |
| MIR29B2CHG:33 | SEQ 0583 | 0.02842 | 0.624 | 0.764 |
| MIR29B2CHG:46 | SEQ 0181 | 0.00829 | 1.522 | 0.188 |
| MIR31HG:9 | SEQ 0768 | 0.03872 | 0.835 | 0.75 |
| MIR4290HG:1 | SEQ 0405 | 0.02049 | 0.773 | 0.778 |
| MIR9-3HG:29 | SEQ 0769 | 0.03872 | 0.557 | 0.75 |
| MIR99AHG:104 | SEQ 0096 | 0.00451 | 0.871 | 0.833 |
| MIR99AHG:37 | SEQ 0584 | 0.02842 | 0.879 | 0.764 |
| MIR99AHG:46 | SEQ 0877 | 0.0449 | 2.516 | 0.257 |
| NAV2-AS5:1 | SEQ 0051 | 0.00232 | 1.302 | 0.146 |
| NAV2-AS5:2 | SEQ 0052 | 0.00232 | 1.302 | 0.146 |
| NBAT1:11 | SEQ 0347 | 0.01727 | 1.738 | 0.215 |
| NIFK-AS1:25 | SEQ 0487 | 0.02418 | 0.846 | 0.771 |
| NUTM2A-AS1:49 | SEQ 0182 | 0.00829 | 0.633 | 0.813 |
| NUTM2B-AS1:40 | SEQ 0348 | 0.01727 | 0.74 | 0.785 |
| NUTM2B-AS1:53 | SEQ 0004 | 0.00027 | 0.655 | 0.91 |
| PACRG-AS3:1 | SEQ 0666 | 0.03324 | 1.162 | 0.243 |
| PCBP1-AS1:250 | SEQ 0770 | 0.03872 | 1.266 | 0.25 |
| PITRM1-AS1:10 | SEQ 0488 | 0.02418 | 1.274 | 0.229 |
| PTPRG-AS1:14 | SEQ 0183 | 0.00829 | 0.625 | 0.813 |
| PURPL:13 | SEQ 0585 | 0.02842 | 1.386 | 0.236 |
| RAPGEF4-AS1:1 | SEQ 0878 | 0.0449 | 0.824 | 0.743 |
| RFX3-AS1:22 | SEQ 0586 | 0.02842 | 0.819 | 0.764 |
| RORB-AS1:6 | SEQ 0116 | 0.00556 | 0.845 | 0.826 |
| SCHLAP1:9 | SEQ 0144 | 0.00681 | 0.8 | 0.819 |
| SEC24B-AS1:19 | SEQ 0406 | 0.02049 | 1.852 | 0.222 |
| SLC16A12-AS1:1 | SEQ 0771 | 0.03872 | 0.773 | 0.75 |
| SMILR:3 | SEQ 0040 | 0.00183 | 1.306 | 0.139 |
| SNCA-AS1:3 | SEQ 0041 | 0.00183 | 0.777 | 0.861 |
| SPATA41:13 | SEQ 0879 | 0.0449 | 1.607 | 0.257 |
| SRGAP3-AS2:10 | SEQ 0349 | 0.01727 | 0.674 | 0.785 |
| SUCLG2-AS1:14 | SEQ 0489 | 0.02418 | 0.92 | 0.771 |
| SUCLG2-AS1:9 | SEQ 0490 | 0.02418 | 0.92 | 0.771 |
| TCL6:24 | SEQ 0066 | 0.00291 | 1.448 | 0.153 |
| TM4SF19-AS1:10 | SEQ 0184 | 0.00829 | 1.84 | 0.188 |
| TM4SF19-AS1:15 | SEQ 0491 | 0.02418 | 0.853 | 0.771 |
| TMEM9B-AS1:11 | SEQ 0185 | 0.00829 | 3.049 | 0.188 |
| TPT1-AS1:26 | SEQ 0186 | 0.00829 | 0.763 | 0.813 |
| TRIM52-AS1:24 | SEQ 0492 | 0.02418 | 1.183 | 0.229 |
| TRIM52-AS1:8 | SEQ 0587 | 0.02842 | 1.272 | 0.236 |
| TTN-AS1:79 | SEQ 0187 | 0.00829 | 0.829 | 0.813 |
| TTN-AS1:80 | SEQ 0188 | 0.00829 | 0.829 | 0.813 |
| UCA1:7 | SEQ 0078 | 0.00364 | 0.697 | 0.84 |
| UGDH-AS1:10 | SEQ 0407 | 0.02049 | 0.541 | 0.778 |
| WDR86-AS1:15 | SEQ 0588 | 0.02842 | 1.212 | 0.236 |
| WEE2-AS1:23 | SEQ 0408 | 0.02049 | 0.704 | 0.778 |
| WT1-AS:9 | SEQ 0117 | 0.00556 | 0.542 | 0.826 |
| YEATS2-AS1:3 | SEQ 0772 | 0.03872 | 0.806 | 0.75 |
| ZNF528-AS1:1 | SEQ 0773 | 0.03872 | 0.636 | 0.75 |
| ZNF529-AS1:21 | SEQ 0880 | 0.0449 | 0.819 | 0.743 |

Out of the 1008 serum lncRNAs differentially expressed with a statistical significance (p value <0.05), 33 lncRNAs showed a fold change of >2 or <0.5 and are shown in the Table 2.

TABLE 2

Mean +/− SD of the 33 serum lncRNAs that shows a differential expression with both a statistically significance (p < 0.05, Wilcoxon test) and a fold change > 2 or < 0.5

| lncRNA | p value | Fold change |
|---|---|---|
| lnc-QRFP-5:1 | 0.00066 | 2.170 |
| lnc-C21orf58-1:2 | 0.00143 | 2.231 |
| ARRDC3-AS1:7 | 0.00232 | 0.441 |
| lnc-CRYBB1-1:1 | 0.00232 | 0.487 |
| lnc-LIMS3-1:10 | 0.00364 | 2.270 |
| lnc-MARCH4-2:7 | 0.00364 | 2.000 |
| lnc-SUGT1-3:1 | 0.00556 | 2.047 |
| DARS-AS1:47 | 0.00829 | 2.015 |
| TMEM9B-AS1:11 | 0.00829 | 3.049 |
| lnc-ZNF726-1:3 | 0.01004 | 2.115 |
| lnc-SLC39A11-10:11 | 0.01209 | 4.380 |
| lnc-PSMB1-6:4 | 0.01449 | 2.134 |
| DPH6-AS1:3 | 0.01727 | 2.004 |
| lnc-ZNF33B-6:1 | 0.01727 | 2.524 |
| lnc-PAPPA-1:3 | 0.03324 | 2.192 |
| lnc-TENM4-4:1 | 0.03324 | 2.209 |
| lnc-IQCF6-2:3 | 0.03872 | 2.026 |
| MIR99AHG:46 | 0.04490 | 2.516 |
| lnc-CPM-2:11 | 0.04490 | 0.424 |
| lnc-ERFE-1:1 | 0.04490 | 0.489 |
| lnc-LRRC3B-1:3 | 0.04490 | 0.463 |
| LINC02177:8 | 0.03872 | 0.494 |
| lnc-KLF11-1:8 | 0.03324 | 0.286 |
| lnc-SNCA-3:1 | 0.02418 | 0.498 |
| lnc-UNCX-3:26 | 0.02049 | 0.493 |
| BLACAT1:5 | 0.01727 | 0.424 |
| lnc-CHD1L-5:13 | 0.01449 | 0.370 |
| lnc-EDDM13-5:11 | 0.01004 | 0.372 |
| lnc-EEF1AKMT1-3:6 | 0.00829 | 0.423 |
| FLVCR1-AS1:13 | 0.00681 | 0.413 |
| lnc-NAXD-6:5 | 0.00556 | 0.479 |
| lnc-ZFP57-15:1 | 0.00701 | 0.402 |
| lnc-TPPP-1:2 | 0.00014 | 0.158 |

Out of the 1008 serum lncRNAs differentially expressed with a statistical significance (p value <0.05), 60 lncRNAs showed an AUC of ≥0.85 and are shown in Table 3.

TABLE 3

60 serum lncRNAs with a p value < 0.05 and an individual AUC value AUC ≥ 0.85

| lncRNA | AUC |
|---|---|
| ARRDC3-AS1:7 | 0.854 |
| HAND2-AS1:70 | 0.861 |
| LINC00882:70 | 0.875 |
| LINC00882:71 | 0.875 |
| LINC01410:11 | 0.882 |
| LINC02345:11 | 0.111 |
| NAV2-AS5:1 | 0.146 |
| NAV2-AS5:2 | 0.146 |
| NUTM2B-AS1:53 | 0.910 |
| SMILR:3 | 0.139 |
| SNCA-AS1:3 | 0.861 |
| lnc-ABCA5-7:1 | 0.111 |
| lnc-ACOT12-9:1 | 0.854 |
| lnc-APLP2-4:1 | 0.854 |
| lnc-C21orf58-1:2 | 0.132 |
| lnc-CEP170-9:2 | 0.861 |
| lnc-CNDP1-7:1 | 0.882 |
| lnc-CRYBB1-1:1 | 0.854 |
| lnc-CSNK1A1-6:1 | 0.875 |
| lnc-DAZAP2-3:1 | 0.854 |
| lnc-DKK1-5:3 | 0.910 |
| lnc-DLG5-1:1 | 0.868 |
| lnc-DOCK7-7:1 | 0.889 |
| lnc-DUSP10-6:1 | 0.854 |
| lnc-DUSP26-3:2 | 0.875 |
| lnc-EBLN1-1:4 | 0.889 |
| lnc-EDDM13-5:3 | 0.132 |
| lnc-FAM133B-2:1 | 0.868 |
| lnc-FAM217A-1:2 | 0.875 |
| lnc-FAM49B-8:1 | 0.104 |
| lnc-FAT1-7:2 | 0.111 |
| lnc-FILIP1L-3:1 | 0.854 |
| lnc-FNBP1L-1:11 | 0.910 |
| lnc-GHR-1:1 | 0.917 |
| lnc-HECA-6:1 | 0.903 |
| lnc-IRS1-6:1 | 0.868 |
| lnc-LEPROTL1-12:1 | 0.896 |
| lnc-MGST3-1:3 | 0.139 |
| lnc-NCR3LG1-3:1 | 0.889 |
| lnc-OR4F29-3:11 | 0.861 |
| lnc-PPP2R3C-4:1 | 0.882 |
| lnc-QRFP-5:1 | 0.111 |
| lnc-RHNO1-1:1 | 0.118 |
| lnc-RNF6-2:1 | 0.854 |
| lnc-RPS21-4:2 | 0.882 |
| lnc-SOX14-2:1 | 0.861 |
| lnc-SPP1-1:1 | 0.861 |
| lnc-STOML3-6:1 | 0.868 |
| lnc-TACSTD2-2:4 | 0.889 |
| lnc-TENM3-3:3 | 0.938 |
| lnc-TENM3-3:4 | 0.097 |
| lnc-TENM3-3:5 | 0.097 |
| lnc-TMEM185B-12:7 | 0.146 |
| lnc-TPPP-1:2 | 0.924 |
| lnc-TRIB2-14:1 | 0.889 |
| lnc-TWSG1-2:1 | 0.861 |
| lnc-UBLCP1-2:6 | 0.861 |
| lnc-USP31-2:3 | 0.889 |
| lnc-ZC3H15-2:1 | 0.896 |
| lnc-ZNF33A-14:1 | 0.139 |
| lnc-ZNF442-1:2 | 0.854 |

The predictive modelling based on the random forest algorithm to discriminate between AD patient and healthy control populations when using the total of the 19867 serum lncRNAs analyzed, enabled to show that the AUC in function of the number of lncRNA reached a plateau with the following 13 lncRNAs. These 13 lncRNAs were used to construct the model. The results show that this lncRNA signature enabled a discrimination between the 2 populations (mild AD patient and healthy control populations) with an AUC value=0.993, an accuracy=95.8%, sensitivity=100% and specificity=91.7%.

| lncRNA | Rank |
|---|---|
| lnc-DLG5-1:1 | 1 |
| lnc-EBLN1-1:4 | 2 |
| lnc-FAT1-7:2 | 3 |
| lnc-PRR5-5:1 | 4 |
| lnc-RBKS-6:1 | 5 |
| lnc-FOXD4L5-35:1 | 6 |
| lnc-TENM3-3:3 | 7 |
| lnc-FAM133B-2:1 | 8 |
| lnc-ZNF726-1:3 | 9 |
| lnc-AP3M1-1:1 | 10 |
| lnc-DUSP10-6:1 | 11 |
| lnc-TPPP-1:2 | 12 |
| LINC01206:20 | 13 |

Out of the 1008 serum lncRNAs differentially expressed with a statistical significance (p value <0.05), the 90 lncRNAs with a fold change of >2 (or <0.5) or an AUC of ≥0.85 (or ≤0.15) were used for the predictive modelling based on the random forest algorithm. The results show that with the following 7 top ranked candidates enabled a full discrimination between AD and HV groups, with an AUC value of 100% as well as 100% accuracy, 100% sensitivity and 100% specificity.

| lncRNA | Rank |
|---|---|
| LINC02345:11 | 1 |
| lnc-EBLN1-1:4 | 2 |
| lnc-TPPP-1:2 | 3 |
| lnc-TENM3-3:3 | 4 |
| lnc-FAT1-7:2 | 5 |
| lnc-DKK1-5:3 | 6 |
| lnc-TACSTD2-2:4 | 7 |

When applying another filter considering a list of the lncRNAs which have a fold change of ≥1.6 and an AUC of ≥0.85, the use of random forest algorithm enabled to select the following 12-top ranked serum lncRNAs to construct the model and this enabled to discriminate between the AD and HV populations with still an excellent AUC=0.979, excellent accuracy of 95.8% sensitivity of 91.7% and specificity of 100%.

| lncRNA | Rank |
|---|---|
| lnc-TPPP-1:2 | 1 |
| ARRDC3-AS1:7 | 2 |
| lnc-TENM3-3:5 | 3 |
| lnc-TENM3-3:4 | 4 |
| lnc-QRFP-5:1 | 5 |
| lnc-CRYBB1-1:1 | 6 |
| lnc-MGST3-1:3 | 7 |
| lnc-FAM49B-8:1 | 8 |
| HAND2-AS1:70 | 9 |
| lnc-TMEM185B-12:7 | 10 |
| lnc-CNDP1-7:1 | 11 |
| lnc-C21orf58-1:2 | 12 |

Further to select the best serum lncRNA candidates, modeling using Random Forest algorithm was applied to a specific set of lncRNA candidates having both a statistically significant differential expression in AD patients versus healthy control populations and a good correlation (Pearson R coefficient) with scores of neurocognitive tests including MMSE and/or MOCA out of 7 neuropsychological tests performed (Table 4): The results show that the signature of the following 3 top ranked lncRNAs enabled an excellent discrimination between AD patients and healthy control populations with AUC=0.953, accuracy, sensitivity and specificity of 91.7%. 91.7% and 91.7%.

| lncRNA | Rank |
|---|---|
| lnc-TENM3-3:3 | 1 |
| lnc-MARCH4-2:7 | 2 |
| lnc-LRRC1-5:2 | 3 |

TABLE 4

Serum lncRNAs of the present invention that correlate with neurocognitive tests, MoCA, MMSE.

| Cognitive test | lncRNA | R_HV + AD | R_HV | R_AD | p value | AUC |
|---|---|---|---|---|---|---|
| MoCA | LINC00839:18 | −0.80 | 0.29 | −0.78 | 0.00556 | 0.83 |
| MoCA | LINC01087:1 | −0.74 | −0.13 | −0.89 | 0.00681 | 0.82 |
| MMSE | LINC01087:1 | −0.68 | 0.05 | −0.75 | 0.00681 | 0.82 |
| MMSE | lnc-ANAPC11-2:6 | 0.65 | 0.26 | 0.77 | 0.04490 | 0.26 |
| MoCA | lnc-ANAPC11-2:6 | 0.59 | −0.46 | 0.77 | 0.04490 | 0.26 |
| MoCA | lnc-ARHGAP26-4:33 | −0.64 | −0.66 | −0.72 | 0.03872 | 0.75 |
| MoCA | lnc-CCDC197-2:1 | −0.14 | −0.42 | 0.74 | 0.00291 | 0.85 |
| MMSE | lnc-CFAP36-3:2 | −0.62 | 0.05 | −0.75 | 0.03872 | 0.75 |
| MoCA | lnc-DHX38-25:1 | −0.69 | −0.60 | −0.77 | 0.01004 | 0.81 |
| MMSE | lnc-DHX38-25:1 | −0.65 | −0.57 | −0.71 | 0.01004 | 0.81 |
| MoCA | lnc-EZH2-3:1 | −0.69 | 0.18 | −0.78 | 0.01209 | 0.80 |
| MMSE | lnc-GNG5-8:1 | −0.72 | 0.32 | −0.71 | 0.03324 | 0.76 |
| MoCA | lnc-GPRC5A-4:1 | −0.65 | −0.02 | −0.74 | 0.02842 | 0.76 |
| MMSE | lnc-GRAMD2B-4:1 | −0.59 | 0.42 | −0.72 | 0.03872 | 0.75 |
| MMSE | lnc-GRIP1-8:1 | −0.03 | 0.30 | −0.73 | 0.03872 | 0.25 |
| MoCA | lnc-LYN-8:1 | 0.13 | 0.54 | −0.71 | 0.02842 | 0.24 |
| MMSE | lnc-MAP9-6:1 | −0.73 | −0.08 | −0.74 | 0.01209 | 0.80 |
| MMSE | lnc-NRP1-4:1 | −0.11 | 0.27 | −0.72 | 0.04490 | 0.26 |
| MoCA | lnc-RBFOX1-2:1 | 0.02 | 0.13 | −0.75 | 0.01727 | 0.22 |
| MoCA | lnc-RPL37-2:1 | 0.62 | −0.16 | 0.75 | 0.00829 | 0.19 |
| MMSE | lnc-RUBCN-1:1 | 0.11 | 0.33 | 0.72 | 0.03872 | 0.75 |
| MMSE | lnc-SNCA-3:1 | 0.08 | 0.12 | 0.76 | 0.02418 | 0.77 |
| MMSE | lnc-SRSF2-2:5 | 0.10 | 0.04 | 0.75 | 0.03324 | 0.76 |
| MoCA | lnc-SRSF2-2:5 | −0.05 | −0.32 | 0.73 | 0.03324 | 0.76 |
| MMSE | lnc-TMEM185B-12:7 | 0.06 | −0.14 | −0.73 | 0.00232 | 0.15 |
| MoCA | lnc-TRIB2-14:1 | −0.76 | −0.45 | −0.71 | 0.00066 | 0.89 |
| MMSE | lnc-TRIM43B-1:2 | −0.74 | −0.11 | −0.76 | 0.01727 | 0.78 |
| MoCA | lnc-TRIM43B-1:2 | −0.72 | −0.12 | −0.74 | 0.01727 | 0.78 |
| MMSE | lnc-ZNF189-2:1 | −0.70 | −0.35 | −0.74 | 0.03324 | 0.76 |
| MoCA | lnc-ZNF189-2:1 | −0.67 | 0.03 | −0.76 | 0.03324 | 0.76 |
| MMSE | lnc-ZRANB2-2:1 | −0.65 | −0.36 | −0.82 | 0.02842 | 0.76 |
| MoCA | lnc-ZRANB2-2:1 | −0.59 | 0.16 | −0.80 | 0.02842 | 0.76 |

R: correlation coefficient (Pearson). HV: healthy control group, AD: mild to moderate AD group Modeling using Random Forest algorithm was also applied to a specific set of serum lncRNA candidates from Table 5 having both a statistically significant differential expression in AD patients versus healthy control populations and a good correlation (Pearson) with neuroimaging scores (volume of brain structures of relevance for cognition and memory such as the mediotemporal area, left and right hippocampus, left and right amygdala, entorhinal cortex out of more than 120 structures measured): The results show that the signature of the following 7 top ranked lncRNAs enabled an excellent discrimination between AD patients and healthy control population with AUC=0.993, accuracy=95.8%, sensitivity=91.7% and specificity=100%.

| lncRNA | Rank |
| --- | --- |
| lnc-TPPP-1:2 | 1 |
| lnc-TENM3-3:3 | 2 |
| lnc-TMEM185B-12:7 | 3 |
| lnc-NAXD-6:5 | 4 |
| lnc-HECA-6:1 | 5 |
| lnc-COMMD6-10:1 | 6 |
| MIR29B2CHG:46 | 7 |

TABLE 5

Serum lncRNAs of the present invention that correlate with MRI (volumes of the brain structures).

| MRI | lncRNA | R_HV + AD | R_HV | R_AD | p value | AUC |
| --- | --- | --- | --- | --- | --- | --- |
| Left.Amygdala | CYTOR:18 | 0.71 | 0.30 | 0.69 | 0.00291 | 0.15 |
| Left.Hippocampus | DLGAP2-AS1:18 | −0.71 | −0.51 | −0.76 | 0.03324 | 0.76 |
| Left.Hippocampus | LINC00458:19 | −0.79 | −0.48 | −0.78 | 0.02842 | 0.76 |
| Mediotemporal | LINC00458:19 | −0.72 | −0.48 | −0.53 | 0.02842 | 0.76 |
| Left.Hippocampus | LINC00938:6 | −0.82 | −0.48 | −0.76 | 0.01209 | 0.80 |
| Mediotemporal | LINC00938:6 | −0.76 | −0.63 | −0.46 | 0.01209 | 0.80 |
| Right.Hippocampus | LINC00938:6 | −0.75 | −0.56 | −0.48 | 0.01209 | 0.80 |
| Left.Amygdala | LINC01629:11 | −0.78 | −0.53 | −0.83 | 0.02842 | 0.76 |
| Left.Hippocampus | lnc-AIG1-5:1 | −0.78 | −0.64 | −0.73 | 0.02418 | 0.77 |
| Left.Hippocampus | lnc-AKR1D1-5:2 | −0.74 | −0.47 | −0.69 | 0.00451 | 0.83 |
| Right.Hippocampus | lnc-AKR1D1-5:2 | −0.71 | −0.27 | −0.73 | 0.00451 | 0.83 |
| Mediotemporal | lnc-AKR1D1-5:2 | −0.71 | −0.26 | −0.72 | 0.00451 | 0.83 |
| Right.Amygdala | lnc-C3orf58-7:1 | −0.73 | −0.22 | −0.69 | 0.02842 | 0.76 |
| Left.Hippocampus | lnc-C5orf30-10:2 | −0.73 | −0.58 | −0.58 | 0.02842 | 0.76 |
| Right.Amygdala | lnc-CASP9-1:1 | 0.73 | 0.26 | 0.81 | 0.03872 | 0.25 |
| Right.Hippocampus | lnc-CHN1-5:11 | −0.72 | −0.44 | −0.67 | 0.02049 | 0.78 |
| Right.Amygdala | lnc-CLVS2-2:5 | −0.74 | −0.39 | −0.75 | 0.01727 | 0.78 |
| Left.Hippocampus | lnc-DAZAP2-3:1 | −0.72 | −0.53 | −0.58 | 0.00232 | 0.85 |
| Mediotemporal | lnc-DTWD2-14:1 | −0.75 | −0.49 | −0.79 | 0.01727 | 0.78 |
| Left.Amygdala | lnc-DTWD2-14:1 | −0.74 | −0.46 | −0.82 | 0.01727 | 0.78 |
| Ih_entorhinal | lnc-DTWD2-14:1 | −0.74 | −0.59 | −0.61 | 0.01727 | 0.78 |
| Right.Hippocampus | lnc-ELFN2-1:3 | −0.77 | −0.26 | −0.76 | 0.00364 | 0.84 |
| Left.Amygdala | lnc-ELFN2-1:3 | −0.74 | −0.27 | −0.81 | 0.00364 | 0.84 |
| Mediotemporal | lnc-ELFN2-1:3 | −0.74 | −0.22 | −0.73 | 0.00364 | 0.84 |
| Right.Amygdala | lnc-ELFN2-1:3 | −0.74 | −0.37 | −0.61 | 0.00364 | 0.84 |
| Left.Hippocampus | lnc-FAM171B-1:6 | −0.72 | −0.28 | −0.62 | 0.00829 | 0.81 |
| Left.Hippocampus | lnc-FGD4-8:1 | −0.74 | −0.49 | −0.61 | 0.01004 | 0.81 |
| Left.Amygdala | lnc-FGD4-9:1 | −0.76 | −0.49 | −0.56 | 0.00364 | 0.84 |
| Right.Hippocampus | lnc-FGD4-9:1 | −0.74 | −0.19 | −0.64 | 0.00364 | 0.84 |
| Mediotemporal | lnc-FGD4-9:1 | −0.72 | −0.28 | −0.54 | 0.00364 | 0.84 |
| Left.Hippocampus | lnc-FGD4-9:1 | −0.71 | −0.33 | −0.52 | 0.00364 | 0.84 |
| Ih_entorhinal | lnc-GPR39-10:2 | 0.77 | 0.68 | 0.49 | 0.00681 | 0.18 |
| Left.Amygdala | lnc-GPR39-10:2 | 0.72 | 0.54 | 0.37 | 0.00681 | 0.18 |
| Left.Hippocampus | lnc-GRM1-1:31 | −0.76 | −0.39 | −0.72 | 0.00681 | 0.82 |
| Right.Hippocampus | lnc-GRM1-1:31 | −0.71 | −0.38 | −0.56 | 0.00681 | 0.82 |
| Left.Hippocampus | lnc-GRM1-1:32 | −0.76 | −0.39 | −0.72 | 0.00681 | 0.82 |
| Right.Hippocampus | lnc-GRM1-1:32 | −0.71 | −0.38 | −0.56 | 0.00681 | 0.82 |
| Right.Hippocampus | lnc-HECA-3:13 | −0.72 | −0.31 | −0.67 | 0.01004 | 0.81 |
| Right.Amygdala | lnc-HJURP-7:1 | −0.77 | −0.46 | −0.77 | 0.02049 | 0.78 |
| Left.Hippocampus | lnc-HJURP-7:1 | −0.73 | −0.33 | −0.73 | 0.02049 | 0.78 |
| Right.Hippocampus | lnc-HJURP-7:1 | −0.73 | −0.02 | −0.93 | 0.02049 | 0.78 |
| Mediotemporal | lnc-HJURP-7:1 | −0.72 | −0.20 | −0.82 | 0.02049 | 0.78 |
| Left.Amygdala | lnc-IRS1-6:1 | −0.75 | −0.35 | −0.72 | 0.00143 | 0.87 |
| Right.Hippocampus | lnc-IRS1-6:1 | −0.73 | −0.36 | −0.56 | 0.00143 | 0.87 |
| Mediotemporal | lnc-IRS1-6:1 | −0.71 | −0.34 | −0.51 | 0.00143 | 0.87 |
| Right.Hippocampus | lnc-KDM3A-1:4 | −0.81 | −0.35 | −0.80 | 0.00451 | 0.83 |
| Mediotemporal | lnc-KDM3A-1:4 | −0.77 | −0.36 | −0.70 | 0.00451 | 0.83 |
| Left.Hippocampus | lnc-KDM3A-1:4 | −0.72 | −0.26 | −0.61 | 0.00451 | 0.83 |
| Left.Hippocampus | lnc-LARP1B-1:15 | −0.75 | −0.56 | −0.75 | 0.01209 | 0.80 |
| Right.Amygdala | lnc-LARP1B-1:15 | −0.75 | −0.63 | −0.71 | 0.01209 | 0.80 |
| Left.Hippocampus | lnc-LARP1B-1:17 | −0.75 | −0.56 | −0.75 | 0.01209 | 0.80 |
| Right.Amygdala | lnc-LARP1B-1:17 | −0.75 | −0.63 | −0.71 | 0.01209 | 0.80 |
| Right.Amygdala | lnc-MAMDC2-1:1 | −0.75 | −0.72 | −0.70 | 0.02418 | 0.77 |
| Left.Hippocampus | lnc-MAP9-6:1 | −0.79 | −0.43 | −0.87 | 0.01209 | 0.80 |
| Right.Hippocampus | lnc-NAALADL2-8:1 | −0.71 | −0.28 | −0.72 | 0.01449 | 0.79 |
| Right.Hippocampus | lnc-NBPF14-1:2 | −0.80 | −0.38 | −0.82 | 0.00364 | 0.84 |
| Mediotemporal | lnc-NBPF14-1:2 | −0.75 | −0.37 | −0.67 | 0.00364 | 0.84 |
| Right.Amygdala | lnc-NBPF14-1:2 | −0.73 | −0.40 | −0.60 | 0.00364 | 0.84 |

TABLE 5-continued

Serum lncRNAs of the present invention that correlate with MRI (volumes of the brain structures).

| MRI | lncRNA | R_HV + AD | R_HV | R_AD | p value | AUC |
|---|---|---|---|---|---|---|
| Left.Hippocampus | lnc-NBPF14-1:2 | −0.72 | −0.48 | −0.52 | 0.00364 | 0.84 |
| Right.Hippocampus | lnc-PIGB-1:5 | −0.73 | −0.26 | −0.79 | 0.02418 | 0.77 |
| Right.Amygdala | lnc-PLN-2:1 | −0.77 | −0.66 | −0.72 | 0.03324 | 0.76 |
| Mediotemporal | lnc-PLN-2:1 | −0.76 | −0.66 | −0.67 | 0.03324 | 0.76 |
| Left.Hippocampus | lnc-PLN-2:1 | −0.75 | −0.67 | −0.64 | 0.03324 | 0.76 |
| Right.Hippocampus | lnc-PLN-2:1 | −0.73 | −0.54 | −0.68 | 0.03324 | 0.76 |
| Left.Hippocampus | lnc-PTPN4-1:1 | −0.74 | −0.59 | −0.69 | 0.02842 | 0.76 |
| Right.Amygdala | lnc-SLC38A2-1:11 | −0.76 | −0.73 | −0.57 | 0.01004 | 0.81 |
| Left.Amygdala | lnc-SLC38A2-1:11 | −0.73 | −0.57 | −0.38 | 0.01004 | 0.81 |
| Right.Amygdala | lnc-SMARCA5-4:18 | −0.72 | −0.35 | −0.78 | 0.01004 | 0.81 |
| Mediotemporal | lnc-SMARCA5-4:18 | −0.72 | −0.29 | −0.84 | 0.01004 | 0.81 |
| Left.Amygdala | lnc-SMARCA5-4:18 | −0.71 | −0.30 | −0.92 | 0.01004 | 0.81 |
| lh_entorhinal | lnc-TMEM242-6:1 | −0.77 | −0.64 | −0.78 | 0.02049 | 0.78 |
| Mediotemporal | lnc-TMEM242-6:1 | −0.72 | −0.62 | −0.63 | 0.02049 | 0.78 |
| Right.Hippocampus | lnc-TPPP-1:2 | −0.73 | −0.03 | −0.42 | 0.00014 | 0.92 |
| Left.Hippocampus | lnc-TRIM43B-1:2 | −0.75 | −0.47 | −0.72 | 0.01727 | 0.78 |
| lh_entorhinal | lnc-TRMT11-4:1 | −0.80 | −0.86 | −0.30 | 0.00829 | 0.81 |
| Mediotemporal | lnc-TRMT11-4:1 | −0.74 | −0.73 | −0.30 | 0.00829 | 0.81 |
| Left.Amygdala | lnc-TRMT11-4:1 | −0.73 | −0.58 | −0.35 | 0.00829 | 0.81 |
| Left.Hippocampus | lnc-USP53-1:1 | −0.75 | −0.24 | −0.84 | 0.01727 | 0.78 |
| Left.Hippocampus | lnc-ZNF33B-6:3 | −0.78 | −0.40 | −0.81 | 0.01209 | 0.80 |
| Right.Amygdala | lnc-ZNF33B-6:3 | −0.74 | −0.47 | −0.65 | 0.01209 | 0.80 |
| Right.Amygdala | MIR29B2CHG:46 | 0.74 | 0.35 | 0.82 | 0.00829 | 0.19 |
| rh_entorhinal | MIR29B2CHG:46 | 0.71 | 0.45 | 0.80 | 0.00829 | 0.19 |
| Right.Amygdala | PCBP1-AS1:250 | 0.73 | 0.20 | 0.71 | 0.03872 | 0.25 |
| Mediotemporal | PCBP1-AS1:250 | 0.71 | 0.19 | 0.70 | 0.03872 | 0.25 |

R: correlation coefficient (Pearson).
HV: healthy control group,
AD: mild to moderate AD group.

Modeling using Random Forest algorithm was also applied to a specific set of serum lncRNA candidates from Table 6 having both a statistically significant differential expression in AD patients versus healthy control populations and a good correlation (Pearson) with level of the CSF biomarkers of high relevance to AD pathology: Aβ42, tau or phosphorylated-tau: The results show that the signature of the following 18 top ranked lncRNAs enabled an excellent discrimination between AD patients and healthy control population with AUC=0.972 accuracy=0,917 sensitivity=0.83 and specificity=1.

| lncRNA | Rank |
|---|---|
| lnc-TPPP-1:2 | 1 |
| LINC02345:11 | 2 |
| lnc-ZNF273-4:4 | 3 |
| lnc-TACC2-8:6 | 4 |
| LINC01206:20 | 5 |
| lnc-C5orf67-3:1 | 6 |
| HAND2-AS1:58 | 7 |
| lnc-PRDM9-20:1 | 8 |
| lnc-CLK1-1:7 | 9 |
| lnc-DNALI1-5:4 | 10 |
| RORB-AS1:6 | 11 |
| lnc-TPPP-1:3 | 12 |
| lnc-BMS1-2:1 | 13 |
| lnc-ADRB1-4:1 | 14 |
| lnc-XXYLT1-5:1 | 15 |
| MIR99AHG: 104 | 16 |
| LINC01748:17 | 17 |
| lnc-AKR1E2-15:1 | 18 |

TABLE 6

Serum lncRNAs of the present invention that correlate with CSF biomarkers

| CSF BM | lncRNA | R_AD | PValue | AUC |
|---|---|---|---|---|
| AB42 | LINC01748:17 | −0.73 | 0.0242 | 0.77 |
| AB42 | lnc-C5orf67-3:1 | 0.72 | 0.0068 | 0.82 |
| Aβ42 | lnc-CYP2E1-1:1 | −0.74 | 0.0332 | 0.24 |
| AB42 | lnc-FAP-3:1 | −0.72 | 0.0083 | 0.81 |
| Aβ42 | lnc-FGD4-9:1 | −0.73 | 0.0036 | 0.84 |
| AB42 | lnc-GLIPR1L1-2:3 | 0.72 | 0.0205 | 0.22 |
| AB42 | lnc-KDM3A-1:4 | −0.77 | 0.0045 | 0.83 |
| AB42 | lnc-LRCH1-1:1 | −0.75 | 0.0205 | 0.78 |
| AB42 | lnc-NPBWR1-2:2 | 0.81 | 0.0449 | 0.26 |
| AB42 | lnc-PLA2G2F-1:2 | −0.74 | 0.0121 | 0.20 |
| AB42 | lnc-POU2AF1-1:2 | −0.84 | 0.0205 | 0.78 |
| Aβ42 | lnc-RCSD1-4:1 | −0.72 | 0.0387 | 0.75 |
| AB42 | lnc-SERPINI1-14:1 | −0.74 | 0.0449 | 0.74 |
| AB42 | lnc-TAF9-10:1 | −0.75 | 0.0284 | 0.76 |
| AB42 | lnc-TNFRSF19-2:1 | 0.71 | 0.0332 | 0.24 |
| AB42 | lnc-TPPP-1:2 | −0.86 | 0.0001 | 0.92 |
| AB42 | lnc-TPPP-1:3 | 0.8 | 0.0056 | 0.17 |
| AB42 | lnc-ZNF273-4:4 | −0.87 | 0.0036 | 0.84 |
| T-tau | HAND2-AS1:58 | 0.92 | 0.0045 | 0.83 |
| T-tau | HAND2-AS1:59 | 0.9 | 0.0056 | 0.83 |
| T-tau | HAND2-AS1:70 | 0.8 | 0.0018 | 0.86 |
| T-tau | HAND2-AS1:71 | 0.8 | 0.0036 | 0.84 |
| T-tau | LINC00200:6 | 0.71 | 0.0029 | 0.15 |
| T-tau | LINC00649:23 | −0.74 | 0.0036 | 0.84 |
| T-tau | LINC01206:11 | −0.74 | 0.0332 | 0.76 |
| T-tau | LINC01355:9 | 0.83 | 0.0332 | 0.76 |
| T-tau | lnc-ADRB1-4:1 | 0.8 | 0.0056 | 0.83 |
| T-tau | lnc-AKR1E2-15:1 | 0.75 | 0.0205 | 0.22 |
| T-tau | lnc-APBA1-5:1 | 0.8 | 0.0284 | 0.76 |
| T-tau | lnc-BMS1-2:1 | 0.76 | 0.0332 | 0.24 |
| T-tau | lnc-CA7-2:2 | −0.73 | 0.0332 | 0.76 |
| T-tau | lnc-CLK1-1:7 | −0.83 | 0.0083 | 0.81 |
| T-tau | lnc-DAPP1-2:11 | 0.8 | 0.0242 | 0.77 |
| T-tau | lnc-DNALI1-5:4 | −0.76 | 0.0045 | 0.83 |
| T-tau | lnc-ELF1-5:1 | 0.86 | 0.0242 | 0.77 |

TABLE 6-continued

Serum lncRNAs of the present invention that correlate with CSF biomarkers

| CSF BM | lncRNA | R_AD | PValue | AUC |
|---|---|---|---|---|
| T-tau | lnc-LBH-4:1 | −0.79 | 0.0332 | 0.24 |
| T-tau | lnc-MVB12B-6:1 | 0.89 | 0.0242 | 0.77 |
| T-tau | lnc-MYO18B-2:3 | −0.72 | 0.0145 | 0.79 |
| T-tau | lnc-OR8G5-7:2 | −0.81 | 0.0284 | 0.76 |
| T-tau | lnc-PAX8-6:2 | 0.71 | 0.0242 | 0.23 |
| T-tau | lnc-POLE4-3:1 | 0.71 | 0.0145 | 0.79 |
| T-tau | lnc-SERTM1-1:1 | −0.72 | 0.0121 | 0.80 |
| T-tau | lnc-SOX14-2:1 | 0.71 | 0.0018 | 0.86 |
| T-tau | lnc-SYCP1-4:1 | −0.83 | 0.0387 | 0.25 |
| T-tau | lnc-TACC2-8:6 | −0.78 | 0.0068 | 0.82 |
| T-tau | lnc-TEAD4-1:1 | −0.71 | 0.0449 | 0.26 |
| T-tau | lnc-TF-4:1 | 0.82 | 0.0332 | 0.76 |
| T-tau | lnc-TTF2-4:1 | −0.8 | 0.0449 | 0.74 |
| T-tau | lnc-XXYLT1-5:1 | −0.71 | 0.0083 | 0.81 |
| T-tau | lnc-ZC3H12D-2:3 | −0.72 | 0.0173 | 0.78 |
| T-tau | lnc-ZNF430-3:4 | −0.79 | 0.01 | 0.81 |
| T-tau | MIR99AHG:104 | 0.9 | 0.0045 | 0.83 |
| T-tau | PITRM1-AS1:10 | 0.91 | 0.0242 | 0.23 |
| T-tau | RORB-AS1:6 | 0.73 | 0.0056 | 0.83 |
| T-tau | SEC24B-AS1:19 | −0.93 | 0.0205 | 0.22 |
| T-tau | ZNF528-AS1:1 | −0.74 | 0.0387 | 0.75 |
| p-tau | BLACAT1:3 | −0.71 | 0.0145 | 0.21 |
| p-tau | HAND2-AS1:58 | 0.71 | 0.0045 | 0.83 |
| p-tau | KAZN-AS1:4 | −0.73 | 0.0205 | 0.78 |
| p-tau | LINC00649:23 | −0.71 | 0.0036 | 0.84 |
| p-tau | LINC01206:11 | −0.77 | 0.0332 | 0.76 |
| p-tau | LINC01206:20 | 0.84 | 0.0205 | 0.22 |
| p-tau | LINC01684:16 | 0.71 | 0.0242 | 0.77 |
| p-tau | LINCO2246:11 | 0.74 | 0.0173 | 0.78 |
| p-tau | LINC02345:11 | −0.75 | 0.0007 | 0.11 |
| p-tau | lnc-AQP8-2:7 | −0.82 | 0.0173 | 0.22 |
| p-tau | lnc-AUH-2:9 | −0.78 | 0.0332 | 0.24 |
| p-tau | lnc-CA7-2:2 | −0.79 | 0.0332 | 0.76 |
| p-tau | lnc-CLK1-1:7 | −0.73 | 0.0083 | 0.81 |
| p-tau | lnc-ELF1-5:1 | 0.74 | 0.0242 | 0.77 |
| p-tau | lnc-FER1L6-2:1 | 0.83 | 0.0242 | 0.77 |
| p-tau | lnc-HS3ST3A1-1:1 | 0.77 | 0.01 | 0.81 |
| p-tau | lnc-KCTD19-1:1 | 0.78 | 0.0332 | 0.76 |
| p-tau | lnc-LMBRD1-5:17 | −0.73 | 0.0387 | 0.75 |
| p-tau | lnc-MVB12B-6:1 | 0.72 | 0.0242 | 0.77 |
| p-tau | lnc-NKX6-1-2:1 | 0.79 | 0.0121 | 0.80 |
| p-tau | lnc-OR8G5-7:2 | −0.85 | 0.0284 | 0.76 |
| p-tau | lnc-PACRGL-5:1 | 0.71 | 0.0332 | 0.76 |
| p-tau | lnc-PRDM9-20:1 | 0.73 | 0.0173 | 0.78 |
| p-tau | lnc-RHOB-1:3 | −0.76 | 0.0205 | 0.78 |
| p-tau | lnc-RPE65-4:2 | −0.79 | 0.0056 | 0.83 |
| p-tau | lnc-SERTM1-1:1 | −0.82 | 0.0121 | 0.80 |
| p-tau | lnc-SOX14-2:1 | 0.76 | 0.0018 | 0.86 |
| p-tau | lnc-SPAG9-2:1 | 0.71 | 0.0173 | 0.78 |
| p-tau | lnc-SPAG9-2:2 | 0.71 | 0.0173 | 0.78 |
| p-tau | lnc-SYCP1-4:1 | −0.76 | 0.0387 | 0.25 |
| p-tau | lnc-TACC2-8:6 | −0.75 | 0.0068 | 0.82 |
| p-tau | lnc-TEKT3-3:1 | −0.84 | 0.0387 | 0.75 |
| p-tau | lnc-TF-4:1 | 0.73 | 0.0332 | 0.76 |
| p-tau | lnc-TP53TG3D-2:1 | 0.71 | 0.0387 | 0.75 |
| p-tau | MIR99AHG:104 | 0.92 | 0.0045 | 0.83 |
| p-tau | RORB-AS1:6 | 0.81 | 0.0056 | 0.83 |
| p-tau | SEC24B-AS1:19 | −0.75 | 0.0205 | 0.22 |
| p-tau | TM4SF19-AS1:10 | 0.76 | 0.0083 | 0.19 |

To identify additional brain lncRNAs implicated specifically in brain disorders, in particular in MCI, AD, for therapeutic applications, frozen tissue samples consisting of postmortem brain mediotemporal cortex from AD patients (tissue histo-pathologically showing typical AD lesions: amyloid plaques and tangles) and from non-demented healthy control (HC) subjects (tissue devoid from AD and other lesions) were used in the experiments of deep sequencing and quantification of novel lncRNAs and the 127802 lncRNAs based on LNCipedia, a database for annotated human lncRNA transcript sequences and structures.

A total of 1091 novel lncRNAs were identified in the AD and/or HC brains. These novel 1091 lncRNAs were subsequently added in the list of the sequenced 127802 lncRNAs totalizing 128,894 lncRNAs profiled in all experiments in the brain. The 1091 novel lncRNAs are shown in Table 7.

TABLE 7

The 1091 novel lncRNAs identified by the invention and fold change and p-value (differential expression in AD group versus healthy control group).

| lncRNA | SEQ | p-value | FC |
|---|---|---|---|
| TCONS_00062603 | SEQ 2031 | 0.00794 | <0.01 |
| TCONS_00045361 | SEQ 1784 | 0.00794 | 0.36 |
| TCONS_00059198 | SEQ 1931 | 0.00794 | 0.32 |
| TCONS_00055496 | SEQ 1898 | 0.00794 | 0.30 |
| TCONS_00033736 | SEQ 1544 | 0.00794 | 5.08 |
| TCONS_00027765 | SEQ 1436 | 0.00794 | 4.55 |
| TCONS_00017427 | SEQ 1285 | 0.01193 | 0.36 |
| TCONS_00012083 | SEQ 1209 | 0.01193 | 0.09 |
| TCONS_00005009 | SEQ 1130 | 0.01193 | 0.08 |
| TCONS_00036823 | SEQ 1627 | 0.01193 | 2.26 |
| TCONS_00050539 | SEQ 1828 | 0.01471 | 22.25 |
| TCONS_00005139 | SEQ 1106 | 0.01587 | 0.34 |
| TCONS_00050178 | SEQ 1833 | 0.01587 | 0.11 |
| TCONS_00050218 | SEQ 1850 | 0.01587 | 0.03 |
| TCONS_00062555 | SEQ 1991 | 0.01587 | 19.87 |
| TCONS_00000634 | SEQ 1045 | 0.01587 | 5.10 |
| TCONS_00066462 | SEQ 2061 | 0.02118 | 9.50 |
| TCONS_00055487 | SEQ 1896 | 0.03175 | 0.50 |
| TCONS_00036834 | SEQ 1628 | 0.03175 | 0.45 |
| TCONS_00017409 | SEQ 1280 | 0.03175 | 0.43 |
| TCONS_00011974 | SEQ 1218 | 0.03175 | 0.42 |
| TCONS_00026584 | SEQ 1418 | 0.03175 | 0.40 |
| TCONS_00059199 | SEQ 1932 | 0.03175 | 0.37 |
| TCONS_00040994 | SEQ 1713 | 0.03175 | 0.36 |
| TCONS_00005325 | SEQ 1141 | 0.03175 | 0.34 |

TABLE 7-continued

The 1091 novel lncRNAs identified by the invention and fold change and p-value (differential expression in AD group versus healthy control group).

| lncRNA | SEQ | p-value | FC |
| --- | --- | --- | --- |
| TCONS_00050200 | SEQ 1841 | 0.03175 | 0.31 |
| TCONS_00027438 | SEQ 1450 | 0.03175 | 0.22 |
| TCONS_00024916 | SEQ 1404 | 0.03175 | 11.52 |
| TCONS_00023309 | SEQ 1355 | 0.03175 | 4.71 |
| TCONS_00062602 | SEQ 2030 | 0.03175 | 3.75 |
| TCONS_00023240 | SEQ 1383 | 0.03175 | 3.68 |
| TCONS_00023401 | SEQ 1386 | 0.03175 | 2.81 |
| TCONS_00062306 | SEQ 1989 | 0.03175 | 2.27 |
| TCONS_00027556 | SEQ 1495 | 0.03445 | 0.32 |
| TCONS_00000570 | SEQ 1032 | 0.03615 | 0.31 |
| TCONS_00000571 | SEQ 1033 | 0.03615 | 0.25 |
| TCONS_00033653 | SEQ 1548 | 0.03615 | 7.72 |
| TCONS_00040878 | SEQ 1680 | 0.03615 | 7.58 |
| TCONS_00066358 | SEQ 2068 | 0.03615 | 2.31 |
| TCONS_00004915 | SEQ 1109 | 0.04322 | 0.15 |
| TCONS_00050234 | SEQ 1855 | 0.04587 | 0.19 |
| TCONS_00000601 | SEQ 1037 | 0.04653 | 0.44 |
| TCONS_00008841 | SEQ 1158 | 0.05556 | 0.44 |
| TCONS_00050014 | SEQ 1803 | 0.05556 | 0.44 |
| TCONS_00012062 | SEQ 1202 | 0.05556 | 0.43 |
| TCONS_00008942 | SEQ 1177 | 0.05556 | 0.43 |
| TCONS_00012009 | SEQ 1185 | 0.05556 | 0.42 |
| TCONS_00050606 | SEQ 1861 | 0.05556 | 0.32 |
| TCONS_00035031 | SEQ 1583 | 0.05556 | 0.32 |
| TCONS_00055481 | SEQ 1894 | 0.05556 | 0.31 |
| TCONS_00028007 | SEQ 1498 | 0.05556 | 0.15 |
| TCONS_00035091 | SEQ 1565 | 0.05556 | 2.67 |
| TCONS_00066501 | SEQ 2066 | 0.05556 | 2.54 |
| TCONS_00023133 | SEQ 1357 | 0.05556 | 2.54 |
| TCONS_00005141 | SEQ 1108 | 0.05556 | 2.21 |
| TCONS_00055535 | SEQ 1909 | 0.05556 | 1.88 |
| TCONS_00040949 | SEQ 1706 | 0.05556 | 1.88 |
| TCONS_00036895 | SEQ 1643 | 0.05556 | 1.57 |
| TCONS_00028131 | SEQ 1522 | 0.05556 | 0.60 |
| TCONS_00000237 | SEQ 1052 | 0.05556 | 0.57 |
| TCONS_00027683 | SEQ 1521 | 0.05556 | 0.56 |
| TCONS_00012063 | SEQ 1203 | 0.05556 | 0.56 |
| TCONS_00062422 | SEQ 2040 | 0.05556 | 0.54 |
| TCONS_00024801 | SEQ 1392 | 0.05701 | 0.15 |
| TCONS_00068994 | SEQ 2110 | 0.05701 | 6.03 |
| TCONS_00008747 | SEQ 1175 | 0.05933 | 4.40 |
| TCONS_00066312 | SEQ 2053 | 0.07201 | 1.09 |
| TCONS_00050655 | SEQ 1875 | 0.07464 | 0.19 |
| TCONS_00040935 | SEQ 1702 | 0.07491 | 6.49 |
| TCONS_00045332 | SEQ 1775 | 0.09269 | 0.31 |
| TCONS_00062739 | SEQ 2052 | 0.09269 | 2.40 |
| TCONS_00035032 | SEQ 1585 | 0.09369 | 0.46 |
| TCONS_00014419 | SEQ 1250 | 0.09369 | 0.40 |
| TCONS_00045210 | SEQ 1742 | 0.09369 | 0.19 |
| TCONS_00040809 | SEQ 1720 | 0.09369 | 6.83 |
| TCONS_00021525 | SEQ 1313 | 0.09369 | 1.77 |
| TCONS_00066459 | SEQ 2058 | 0.09369 | 1.71 |
| TCONS_00000337 | SEQ 1073 | 0.09369 | 0.59 |
| TCONS_00028030 | SEQ 1505 | 0.09369 | 0.57 |
| TCONS_00027502 | SEQ 1479 | 0.09369 | 0.56 |
| TCONS_00000744 | SEQ 1071 | 0.09524 | 0.50 |
| TCONS_00059197 | SEQ 1930 | 0.09524 | 0.49 |
| TCONS_00037029 | SEQ 1675 | 0.09524 | 0.48 |
| TCONS_00045125 | SEQ 1790 | 0.09524 | 0.47 |
| TCONS_00066422 | SEQ 2093 | 0.09524 | 0.46 |
| TCONS_00017476 | SEQ 1261 | 0.09524 | 0.46 |
| TCONS_00000765 | SEQ 1085 | 0.09524 | 0.46 |
| TCONS_00012067 | SEQ 1204 | 0.09524 | 0.41 |
| TCONS_00050090 | SEQ 1814 | 0.09524 | 0.37 |
| TCONS_00027933 | SEQ 1464 | 0.09524 | 0.37 |

TABLE 7-continued

The 1091 novel lncRNAs identified by the invention and fold change and p-value (differential expression in AD group versus healthy control group).

| lncRNA | SEQ | p-value | FC |
| --- | --- | --- | --- |
| TCONS_00019766 | SEQ 1300 | 0.09524 | 0.26 |
| TCONS_00005240 | SEQ 1115 | 0.09524 | 0.26 |
| TCONS_00005376 | SEQ 1147 | 0.09524 | 4.67 |
| TCONS_00028169 | SEQ 1538 | 0.09524 | 2.52 |
| TCONS_00055703 | SEQ 1892 | 0.09524 | 2.38 |
| TCONS_00021393 | SEQ 1318 | 0.09524 | 2.12 |
| TCONS_00028111 | SEQ 1513 | 0.09524 | 1.89 |
| TCONS_00000468 | SEQ 1014 | 0.09524 | 1.86 |
| TCONS_00027920 | SEQ 1455 | 0.09524 | 1.82 |
| TCONS_00036021 | SEQ 1604 | 0.09524 | 1.79 |
| TCONS_00036894 | SEQ 1642 | 0.09524 | 1.75 |
| TCONS_00062311 | SEQ 1996 | 0.09524 | 1.71 |
| TCONS_00027931 | SEQ 1462 | 0.09524 | 1.70 |
| TCONS_00021544 | SEQ 1320 | 0.09524 | 1.59 |
| TCONS_00021556 | SEQ 1332 | 0.09524 | 1.56 |
| TCONS_00045262 | SEQ 1758 | 0.09524 | 1.51 |
| TCONS_00019840 | SEQ 1292 | 0.09524 | 0.66 |
| TCONS_00033666 | SEQ 1553 | 0.09524 | 0.61 |
| TCONS_00026547 | SEQ 1410 | 0.09524 | 0.58 |
| TCONS_00023102 | SEQ 1346 | 0.09524 | 0.56 |
| TCONS_00014407 | SEQ 1245 | 0.09524 | 0.52 |
| TCONS_00062324 | SEQ 2004 | 0.09524 | 0.52 |
| TCONS_00044977 | SEQ 1753 | 0.11496 | 2.62 |
| TCONS_00028123 | SEQ 1519 | 0.11496 | 2.31 |
| TCONS_00055574 | SEQ 1917 | 0.11496 | 0.52 |
| TCONS_00011923 | SEQ 1208 | 0.11607 | 0.32 |
| TCONS_00026753 | SEQ 1424 | 0.11607 | 6.14 |
| TCONS_00040926 | SEQ 1698 | 0.11752 | 0.15 |
| TCONS_00008975 | SEQ 1183 | 0.13386 | 0.41 |
| TCONS_00040879 | SEQ 1681 | 0.13756 | 3.00 |
| TCONS_00026537 | SEQ 1408 | 0.13756 | 2.67 |
| TCONS_00062522 | SEQ 1976 | 0.13879 | 0.14 |
| TCONS_00005286 | SEQ 1134 | 0.13879 | 0.13 |
| TCONS_00033735 | SEQ 1543 | 0.13879 | 3.16 |
| TCONS_00000311 | SEQ 1063 | 0.13879 | 0.55 |
| TCONS_00000139 | SEQ 1035 | 0.14124 | 0.47 |
| TCONS_00037036 | SEQ 1616 | 0.14124 | 0.32 |
| TCONS_00040743 | SEQ 1715 | 0.14246 | 0.43 |
| TCONS_00037019 | SEQ 1672 | 0.14246 | 2.20 |
| TCONS_00037027 | SEQ 1674 | 0.14246 | 1.96 |
| TCONS_00040820 | SEQ 1721 | 0.14246 | 0.84 |
| TCONS_00050289 | SEQ 1866 | 0.14246 | 0.61 |
| TCONS_00045439 | SEQ 1795 | 0.14246 | 0.55 |
| TCONS_00066425 | SEQ 2096 | 0.15079 | 0.47 |
| TCONS_00024810 | SEQ 1396 | 0.15079 | 0.46 |
| TCONS_00027448 | SEQ 1451 | 0.15079 | 0.44 |
| TCONS_00035100 | SEQ 1577 | 0.15079 | 0.42 |
| TCONS_00035102 | SEQ 1579 | 0.15079 | 0.40 |
| TCONS_00059196 | SEQ 1929 | 0.15079 | 0.37 |
| TCONS_00027930 | SEQ 1461 | 0.15079 | 0.34 |
| TCONS_00000734 | SEQ 1066 | 0.15079 | 0.22 |
| TCONS_00024864 | SEQ 1388 | 0.15079 | 7.03 |
| TCONS_00023390 | SEQ 1384 | 0.15079 | 4.26 |
| TCONS_00035092 | SEQ 1569 | 0.15079 | 3.18 |
| TCONS_00059499 | SEQ 1963 | 0.15079 | 2.96 |
| TCONS_00024865 | SEQ 1389 | 0.15079 | 2.81 |
| TCONS_00066369 | SEQ 2072 | 0.15079 | 2.64 |
| TCONS_00035090 | SEQ 1564 | 0.15079 | 2.60 |
| TCONS_00050071 | SEQ 1807 | 0.15079 | 2.43 |
| TCONS_00033669 | SEQ 1555 | 0.15079 | 2.31 |
| TCONS_00004965 | SEQ 1114 | 0.15079 | 2.04 |
| TCONS_00062729 | SEQ 2050 | 0.15079 | 2.04 |
| TCONS_00035094 | SEQ 1573 | 0.15079 | 1.97 |
| TCONS_00045265 | SEQ 1761 | 0.15079 | 1.97 |
| TCONS_00005138 | SEQ 1105 | 0.15079 | 1.93 |
| TCONS_00066313 | SEQ 2054 | 0.15079 | 1.90 |
| TCONS_00027929 | SEQ 1460 | 0.15079 | 1.73 |
| TCONS_00055752 | SEQ 1906 | 0.15079 | 1.72 |
| TCONS_00062338 | SEQ 2009 | 0.15079 | 1.68 |
| TCONS_00005242 | SEQ 1118 | 0.15079 | 1.55 |
| TCONS_00027945 | SEQ 1483 | 0.15079 | 1.45 |
| TCONS_00027766 | SEQ 1437 | 0.15079 | 1.43 |
| TCONS_00026617 | SEQ 1422 | 0.15079 | 1.32 |
| TCONS_00066314 | SEQ 2055 | 0.15079 | 1.29 |
| TCONS_00062497 | SEQ 1967 | 0.15079 | 1.22 |

TABLE 7-continued

The 1091 novel lncRNAs identified by the invention and fold change and p-value
(differential expression in AD group versus healthy control group).

| lncRNA | SEQ | p-value | FC |
|---|---|---|---|
| TCONS_00019689 | SEQ 1290 | 0.15079 | 1.13 |
| TCONS_00062351 | SEQ 2026 | 0.15079 | 0.69 |
| TCONS_00066357 | SEQ 2067 | 0.15079 | 0.65 |
| TCONS_00062341 | SEQ 2012 | 0.15079 | 0.61 |
| TCONS_00037250 | SEQ 1673 | 0.15079 | 0.60 |
| TCONS_00017351 | SEQ 1265 | 0.15079 | 0.60 |
| TCONS_00019772 | SEQ 1301 | 0.15079 | 0.58 |
| TCONS_00027507 | SEQ 1484 | 0.15079 | 0.57 |
| TCONS_00000828 | SEQ 1096 | 0.15079 | 0.55 |
| TCONS_00036133 | SEQ 1607 | 0.15079 | 0.55 |
| TCONS_00050012 | SEQ 1801 | 0.15079 | 0.54 |
| TCONS_00035046 | SEQ 1588 | 0.15079 | 0.54 |
| TCONS_00044939 | SEQ 1736 | 0.15079 | 0.53 |
| TCONS_00014261 | SEQ 1249 | 0.15079 | 0.53 |
| TCONS_00055513 | SEQ 1901 | 0.15794 | 0.03 |
| TCONS_00019796 | SEQ 1303 | 0.16926 | 0.33 |
| TCONS_00008691 | SEQ 1159 | 0.17190 | 0.39 |
| TCONS_00000350 | SEQ 1084 | 0.17190 | 4.60 |
| TCONS_00000760 | SEQ 1083 | 0.17322 | 0.50 |
| TCONS_00019866 | SEQ 1295 | 0.17322 | 0.44 |
| TCONS_00055525 | SEQ 1907 | 0.17322 | 0.40 |
| TCONS_00033608 | SEQ 1541 | 0.17322 | 2.45 |
| TCONS_00036061 | SEQ 1614 | 0.17322 | 2.39 |
| TCONS_00033668 | SEQ 1554 | 0.17322 | 0.51 |
| TCONS_00021549 | SEQ 1327 | 0.17971 | >100 |
| TCONS_00050263 | SEQ 1860 | 0.17971 | >100 |
| TCONS_00068989 | SEQ 2111 | 0.17971 | >100 |
| TCONS_00037221 | SEQ 1667 | 0.20309 | 0.16 |
| TCONS_00011831 | SEQ 1191 | 0.20309 | 4.10 |
| TCONS_00044961 | SEQ 1746 | 0.20309 | 2.12 |
| TCONS_00066547 | SEQ 2099 | 0.20309 | 2.08 |
| TCONS_00045056 | SEQ 1773 | 0.20450 | 0.50 |
| TCONS_00037177 | SEQ 1657 | 0.20450 | 0.46 |
| TCONS_00066513 | SEQ 2077 | 0.20450 | 1.13 |
| TCONS_00012089 | SEQ 1210 | 0.20450 | 0.55 |
| TCONS_00027715 | SEQ 1535 | 0.20590 | 0.24 |
| TCONS_00000536 | SEQ 1021 | 0.20730 | 0.45 |
| TCONS_00027498 | SEQ 1474 | 0.20730 | 1.34 |
| TCONS_00036797 | SEQ 1621 | 0.20730 | 0.75 |
| TCONS_00062437 | SEQ 2044 | 0.20869 | 0.47 |
| TCONS_00023224 | SEQ 1381 | 0.20869 | 2.27 |
| TCONS_00036792 | SEQ 1620 | 0.20869 | 2.03 |
| TCONS_00045156 | SEQ 1796 | 0.20869 | 1.59 |
| TCONS_00036933 | SEQ 1655 | 0.20869 | 0.75 |
| TCONS_00027513 | SEQ 1487 | 0.20869 | 0.51 |
| TCONS_00050460 | SEQ 1809 | 0.22222 | 0.50 |
| TCONS_00011972 | SEQ 1217 | 0.22222 | 0.50 |
| TCONS_00059439 | SEQ 1956 | 0.22222 | 0.49 |
| TCONS_00037143 | SEQ 1649 | 0.22222 | 0.44 |
| TCONS_00045093 | SEQ 1782 | 0.22222 | 0.40 |
| TCONS_00045133 | SEQ 1792 | 0.22222 | 0.33 |
| TCONS_00035101 | SEQ 1578 | 0.22222 | 0.28 |
| TCONS_00050087 | SEQ 1811 | 0.22222 | 0.20 |
| TCONS_00036899 | SEQ 1644 | 0.22222 | 16.33 |
| TCONS_00036100 | SEQ 1600 | 0.22222 | 4.21 |
| TCONS_00044916 | SEQ 1729 | 0.22222 | 4.18 |
| TCONS_00044921 | SEQ 1734 | 0.22222 | 4.01 |
| TCONS_00035021 | SEQ 1566 | 0.22222 | 3.65 |
| TCONS_00045203 | SEQ 1731 | 0.22222 | 3.29 |
| TCONS_00017370 | SEQ 1271 | 0.22222 | 2.90 |
| TCONS_00037224 | SEQ 1668 | 0.22222 | 2.08 |
| TCONS_00000357 | SEQ 1087 | 0.22222 | 1.98 |
| TCONS_00035024 | SEQ 1571 | 0.22222 | 1.90 |
| TCONS_00000204 | SEQ 1044 | 0.22222 | 1.65 |
| TCONS_00021407 | SEQ 1326 | 0.22222 | 1.65 |
| TCONS_00050176 | SEQ 1831 | 0.22222 | 1.62 |
| TCONS_00062700 | SEQ 2045 | 0.22222 | 1.61 |
| TCONS_00045048 | SEQ 1772 | 0.22222 | 1.61 |
| TCONS_00021555 | SEQ 1331 | 0.22222 | 1.60 |
| TCONS_00000202 | SEQ 1042 | 0.22222 | 1.59 |
| TCONS_00044996 | SEQ 1755 | 0.22222 | 1.58 |
| TCONS_00021554 | SEQ 1330 | 0.22222 | 1.54 |
| TCONS_00000809 | SEQ 1090 | 0.22222 | 1.48 |
| TCONS_00045266 | SEQ 1762 | 0.22222 | 1.47 |
| TCONS_00027936 | SEQ 1469 | 0.22222 | 1.44 |

TABLE 7-continued

The 1091 novel lncRNAs identified by the invention and fold change and p-value
(differential expression in AD group versus healthy control group).

| lncRNA | SEQ | p-value | FC |
| --- | --- | --- | --- |
| TCONS_00059492 | SEQ 1962 | 0.22222 | 1.42 |
| TCONS_00037052 | SEQ 1619 | 0.22222 | 1.42 |
| TCONS_00059234 | SEQ 1942 | 0.22222 | 0.76 |
| TCONS_00023148 | SEQ 1363 | 0.22222 | 0.73 |
| TCONS_00059245 | SEQ 1946 | 0.22222 | 0.69 |
| TCONS_00017373 | SEQ 1274 | 0.22222 | 0.68 |
| TCONS_00050224 | SEQ 1854 | 0.22222 | 0.67 |
| TCONS_00014393 | SEQ 1240 | 0.22222 | 0.65 |
| TCONS_00062299 | SEQ 1977 | 0.22222 | 0.64 |
| TCONS_00005308 | SEQ 1139 | 0.22222 | 0.62 |
| TCONS_00062317 | SEQ 2002 | 0.22222 | 0.61 |
| TCONS_00040718 | SEQ 1711 | 0.22222 | 0.61 |
| TCONS_00045364 | SEQ 1785 | 0.22222 | 0.55 |
| TCONS_00044917 | SEQ 1732 | 0.22222 | 0.54 |
| TCONS_00017354 | SEQ 1268 | 0.22222 | 0.53 |
| TCONS_00066426 | SEQ 2097 | 0.22222 | 0.53 |
| TCONS_00045333 | SEQ 1776 | 0.22222 | 0.52 |
| TCONS_00000341 | SEQ 1075 | 0.22222 | 0.52 |
| TCONS_00050220 | SEQ 1852 | 0.22222 | 0.51 |
| TCONS_00045227 | SEQ 1745 | 0.22222 | 0.51 |
| TCONS_00050127 | SEQ 1820 | 0.23932 | 0.07 |
| TCONS_00000692 | SEQ 1055 | 0.24184 | 0.21 |
| TCONS_00014277 | SEQ 1254 | 0.24332 | 0.90 |
| TCONS_00066518 | SEQ 2084 | 0.24771 | 0.49 |
| TCONS_00027340 | SEQ 1435 | 0.24771 | 4.23 |
| TCONS_00050549 | SEQ 1835 | 0.24771 | 1.25 |
| TCONS_00045466 | SEQ 1798 | 0.24771 | 0.91 |
| TCONS_00027787 | SEQ 1439 | 0.24771 | 0.57 |
| TCONS_00037103 | SEQ 1635 | 0.24915 | 0.47 |
| TCONS_00023136 | SEQ 1358 | 0.24915 | 5.81 |
| TCONS_00036799 | SEQ 1622 | 0.24915 | 0.68 |
| TCONS_00045086 | SEQ 1780 | 0.24915 | 0.66 |
| TCONS_00000556 | SEQ 1026 | 0.24915 | 0.59 |
| TCONS_00024823 | SEQ 1400 | 0.24915 | 0.58 |
| TCONS_00023237 | SEQ 1382 | 0.28733 | 3.80 |
| TCONS_00050217 | SEQ 1849 | 0.29035 | 0.39 |
| TCONS_00062303 | SEQ 1986 | 0.29035 | 0.01 |
| TCONS_00050615 | SEQ 1865 | 0.29035 | 1.60 |
| TCONS_00036878 | SEQ 1636 | 0.29035 | 1.46 |
| TCONS_00062432 | SEQ 2043 | 0.29184 | 0.36 |
| TCONS_00023255 | SEQ 1385 | 0.29184 | 1.40 |
| TCONS_00040948 | SEQ 1705 | 0.29184 | 0.62 |
| TCONS_00050540 | SEQ 1829 | 0.29333 | 2.93 |
| TCONS_00019817 | SEQ 1310 | 0.29333 | 1.52 |
| TCONS_00062492 | SEQ 1965 | 0.29333 | 0.71 |
| TCONS_00027901 | SEQ 1453 | 0.29480 | 0.26 |
| TCONS_00026536 | SEQ 1407 | 0.29480 | 2.63 |
| TCONS_00000424 | SEQ 1094 | 0.29480 | 1.61 |
| TCONS_00008797 | SEQ 1182 | 0.29480 | 0.71 |
| TCONS_00066544 | SEQ 2098 | 0.29480 | 0.63 |
| TCONS_00040973 | SEQ 1709 | 0.30952 | 0.50 |
| TCONS_00035104 | SEQ 1582 | 0.30952 | 0.47 |
| TCONS_00062518 | SEQ 1972 | 0.30952 | 0.46 |
| TCONS_00033687 | SEQ 1558 | 0.30952 | 0.41 |
| TCONS_00040951 | SEQ 1708 | 0.30952 | 0.40 |
| TCONS_00036892 | SEQ 1640 | 0.30952 | 0.38 |
| TCONS_00035976 | SEQ 1596 | 0.30952 | 0.35 |
| TCONS_00066533 | SEQ 2088 | 0.30952 | 0.35 |
| TCONS_00014406 | SEQ 1244 | 0.30952 | 0.34 |
| TCONS_00040803 | SEQ 1719 | 0.30952 | 0.29 |
| TCONS_00068990 | SEQ 2112 | 0.30952 | 7.13 |
| TCONS_00044915 | SEQ 1728 | 0.30952 | 3.75 |
| TCONS_00045202 | SEQ 1730 | 0.30952 | 2.94 |
| TCONS_00035025 | SEQ 1572 | 0.30952 | 2.73 |
| TCONS_00028005 | SEQ 1496 | 0.30952 | 2.50 |
| TCONS_00068991 | SEQ 2113 | 0.30952 | 2.49 |
| TCONS_00059210 | SEQ 1935 | 0.30952 | 2.45 |
| TCONS_00027492 | SEQ 1459 | 0.30952 | 1.96 |
| TCONS_00055571 | SEQ 1915 | 0.30952 | 1.87 |
| TCONS_00045041 | SEQ 1769 | 0.30952 | 1.85 |
| TCONS_00062340 | SEQ 2011 | 0.30952 | 1.84 |
| TCONS_00062276 | SEQ 1969 | 0.30952 | 1.80 |
| TCONS_00062557 | SEQ 1993 | 0.30952 | 1.69 |
| TCONS_00045252 | SEQ 1752 | 0.30952 | 1.62 |
| TCONS_00012112 | SEQ 1214 | 0.30952 | 1.61 |

TABLE 7-continued

The 1091 novel lncRNAs identified by the invention and fold change and p-value
(differential expression in AD group versus healthy control group).

| lncRNA | SEQ | p-value | FC |
|---|---|---|---|
| TCONS_00035027 | SEQ 1575 | 0.30952 | 1.60 |
| TCONS_00026721 | SEQ 1417 | 0.30952 | 1.60 |
| TCONS_00014391 | SEQ 1237 | 0.30952 | 1.58 |
| TCONS_00023372 | SEQ 1374 | 0.30952 | 1.58 |
| TCONS_00045309 | SEQ 1771 | 0.30952 | 1.57 |
| TCONS_00062327 | SEQ 2005 | 0.30952 | 1.56 |
| TCONS_00027493 | SEQ 1467 | 0.30952 | 1.52 |
| TCONS_00059139 | SEQ 1923 | 0.30952 | 1.52 |
| TCONS_00021559 | SEQ 1333 | 0.30952 | 1.49 |
| TCONS_00027495 | SEQ 1471 | 0.30952 | 1.49 |
| TCONS_00050207 | SEQ 1846 | 0.30952 | 1.48 |
| TCONS_00012060 | SEQ 1201 | 0.30952 | 1.45 |
| TCONS_00014141 | SEQ 1224 | 0.30952 | 1.44 |
| TCONS_00033703 | SEQ 1561 | 0.30952 | 1.41 |
| TCONS_00035095 | SEQ 1574 | 0.30952 | 1.41 |
| TCONS_00021427 | SEQ 1335 | 0.30952 | 1.40 |
| TCONS_00033615 | SEQ 1542 | 0.30952 | 1.33 |
| TCONS_00045264 | SEQ 1760 | 0.30952 | 1.33 |
| TCONS_00050203 | SEQ 1842 | 0.30952 | 1.33 |
| TCONS_00055690 | SEQ 1890 | 0.30952 | 1.31 |
| TCONS_00000437 | SEQ 1097 | 0.30952 | 1.27 |
| TCONS_00005137 | SEQ 1104 | 0.30952 | 1.15 |
| TCONS_00027501 | SEQ 1478 | 0.30952 | 1.15 |
| TCONS_00021372 | SEQ 1311 | 0.30952 | 1.10 |
| TCONS_00045398 | SEQ 1789 | 0.30952 | 0.84 |
| TCONS_00066424 | SEQ 2095 | 0.30952 | 0.83 |
| TCONS_00066441 | SEQ 2102 | 0.30952 | 0.79 |
| TCONS_00027951 | SEQ 1488 | 0.30952 | 0.74 |
| TCONS_00044932 | SEQ 1735 | 0.30952 | 0.73 |
| TCONS_00019873 | SEQ 1297 | 0.30952 | 0.73 |
| TCONS_00000438 | SEQ 1098 | 0.30952 | 0.72 |
| TCONS_00000416 | SEQ 1091 | 0.30952 | 0.71 |
| TCONS_00040733 | SEQ 1712 | 0.30952 | 0.71 |
| TCONS_00008952 | SEQ 1178 | 0.30952 | 0.70 |
| TCONS_00012038 | SEQ 1198 | 0.30952 | 0.70 |
| TCONS_00059378 | SEQ 1928 | 0.30952 | 0.69 |
| TCONS_00028120 | SEQ 1518 | 0.30952 | 0.68 |
| TCONS_00059394 | SEQ 1941 | 0.30952 | 0.67 |
| TCONS_00059321 | SEQ 1959 | 0.30952 | 0.67 |
| TCONS_00019850 | SEQ 1294 | 0.30952 | 0.66 |
| TCONS_00062349 | SEQ 2024 | 0.30952 | 0.65 |
| TCONS_00017349 | SEQ 1263 | 0.30952 | 0.64 |
| TCONS_00027658 | SEQ 1511 | 0.30952 | 0.63 |
| TCONS_00027934 | SEQ 1465 | 0.30952 | 0.60 |
| TCONS_00035030 | SEQ 1580 | 0.30952 | 0.56 |
| TCONS_00027702 | SEQ 1525 | 0.30952 | 0.54 |
| TCONS_00050192 | SEQ 1837 | 0.30952 | 0.54 |
| TCONS_00062313 | SEQ 1998 | 0.30952 | 0.52 |
| TCONS_00000002 | SEQ 1009 | 0.31430 | 5.14 |
| TCONS_00055627 | SEQ 1920 | 0.32579 | 0.31 |
| TCONS_00027725 | SEQ 1536 | 0.33827 | 2.21 |
| TCONS_00055542 | SEQ 1911 | 0.34427 | 3.03 |
| TCONS_00055450 | SEQ 1888 | 0.34427 | 2.82 |
| TCONS_00017439 | SEQ 1286 | 0.34427 | 2.36 |
| TCONS_00005307 | SEQ 1138 | 0.34427 | 1.77 |
| TCONS_00023357 | SEQ 1370 | 0.34574 | 0.49 |
| TCONS_00000147 | SEQ 1036 | 0.34574 | 0.41 |
| TCONS_00023193 | SEQ 1372 | 0.34574 | 0.41 |
| TCONS_00012126 | SEQ 1220 | 0.34574 | 2.38 |
| TCONS_00028014 | SEQ 1499 | 0.34574 | 2.35 |
| TCONS_00000427 | SEQ 1095 | 0.34574 | 1.88 |
| TCONS_00008852 | SEQ 1165 | 0.34574 | 1.80 |
| TCONS_00021588 | SEQ 1339 | 0.34574 | 1.63 |
| TCONS_00050505 | SEQ 1823 | 0.34574 | 1.33 |
| TCONS_00021547 | SEQ 1324 | 0.34574 | 1.24 |
| TCONS_00066397 | SEQ 2083 | 0.34574 | 0.75 |
| TCONS_00059405 | SEQ 1944 | 0.34574 | 0.66 |
| TCONS_00005302 | SEQ 1137 | 0.34574 | 0.64 |
| TCONS_00055591 | SEQ 1918 | 0.34652 | 0.30 |
| TCONS_00014196 | SEQ 1232 | 0.36605 | 0.14 |
| TCONS_00024813 | SEQ 1398 | 0.39614 | 1.29 |
| TCONS_00026636 | SEQ 1425 | 0.39614 | 1.16 |
| TCONS_00023192 | SEQ 1371 | 0.39761 | 5.31 |
| TCONS_00037244 | SEQ 1670 | 0.39761 | 4.55 |
| TCONS_00000122 | SEQ 1031 | 0.39761 | 1.42 |

TABLE 7-continued

The 1091 novel lncRNAs identified by the invention and fold change and p-value
(differential expression in AD group versus healthy control group).

| lncRNA | SEQ | p-value | FC |
|---|---|---|---|
| TCONS_00036983 | SEQ 1663 | 0.39761 | 1.01 |
| TCONS_00027697 | SEQ 1524 | 0.39761 | 0.87 |
| TCONS_00000305 | SEQ 1062 | 0.39761 | 0.58 |
| TCONS_00011954 | SEQ 1211 | 0.39908 | 1.81 |
| TCONS_00008860 | SEQ 1167 | 0.39908 | 1.45 |
| TCONS_00017451 | SEQ 1287 | 0.40053 | 3.43 |
| TCONS_00023333 | SEQ 1364 | 0.40053 | 2.91 |
| TCONS_00014210 | SEQ 1238 | 0.40053 | 1.59 |
| TCONS_00066400 | SEQ 2085 | 0.40053 | 1.43 |
| TCONS_00023086 | SEQ 1345 | 0.40053 | 1.20 |
| TCONS_00050221 | SEQ 1853 | 0.40053 | 0.78 |
| TCONS_00036782 | SEQ 1618 | 0.40053 | 0.61 |
| TCONS_00017363 | SEQ 1269 | 0.40053 | 0.57 |
| TCONS_00066494 | SEQ 2065 | 0.40197 | 1.89 |
| TCONS_00023122 | SEQ 1354 | 0.40197 | 1.71 |
| TCONS_00008663 | SEQ 1149 | 0.40197 | 1.40 |
| TCONS_00027714 | SEQ 1534 | 0.40197 | 0.90 |
| TCONS_00037110 | SEQ 1641 | 0.40197 | 0.74 |
| TCONS_00062521 | SEQ 1975 | 0.42063 | 0.46 |
| TCONS_00014425 | SEQ 1252 | 0.42063 | 0.43 |
| TCONS_00050494 | SEQ 1818 | 0.42063 | 0.14 |
| TCONS_00055453 | SEQ 1891 | 0.42063 | 2.33 |
| TCONS_00017372 | SEQ 1273 | 0.42063 | 2.03 |
| TCONS_00066562 | SEQ 2106 | 0.42063 | 2.00 |
| TCONS_00000343 | SEQ 1076 | 0.42063 | 1.98 |
| TCONS_00027923 | SEQ 1458 | 0.42063 | 1.77 |
| TCONS_00023114 | SEQ 1351 | 0.42063 | 1.75 |
| TCONS_00055786 | SEQ 1913 | 0.42063 | 1.68 |
| TCONS_00012029 | SEQ 1195 | 0.42063 | 1.61 |
| TCONS_00050177 | SEQ 1832 | 0.42063 | 1.57 |
| TCONS_00062728 | SEQ 2049 | 0.42063 | 1.53 |
| TCONS_00062427 | SEQ 2042 | 0.42063 | 1.50 |
| TCONS_00066420 | SEQ 2092 | 0.42063 | 1.49 |
| TCONS_00059385 | SEQ 1939 | 0.42063 | 1.47 |
| TCONS_00008693 | SEQ 1160 | 0.42063 | 1.42 |
| TCONS_00027937 | SEQ 1470 | 0.42063 | 1.42 |
| TCONS_00040601 | SEQ 1679 | 0.42063 | 1.37 |
| TCONS_00050574 | SEQ 1845 | 0.42063 | 1.36 |
| TCONS_00027496 | SEQ 1472 | 0.42063 | 1.31 |
| TCONS_00055468 | SEQ 1893 | 0.42063 | 1.25 |
| TCONS_00008918 | SEQ 1176 | 0.42063 | 1.24 |
| TCONS_00027531 | SEQ 1492 | 0.42063 | 1.24 |
| TCONS_00040919 | SEQ 1693 | 0.42063 | 1.24 |
| TCONS_00000201 | SEQ 1041 | 0.42063 | 1.22 |
| TCONS_00021541 | SEQ 1319 | 0.42063 | 1.21 |
| TCONS_00012109 | SEQ 1213 | 0.42063 | 1.16 |
| TCONS_00027754 | SEQ 1432 | 0.42063 | 1.16 |
| TCONS_00027500 | SEQ 1476 | 0.42063 | 1.07 |
| TCONS_00014326 | SEQ 1225 | 0.42063 | 0.95 |
| TCONS_00045322 | SEQ 1774 | 0.42063 | 0.93 |
| TCONS_00026552 | SEQ 1411 | 0.42063 | 0.89 |
| TCONS_00062559 | SEQ 1995 | 0.42063 | 0.87 |
| TCONS_00033704 | SEQ 1562 | 0.42063 | 0.85 |
| TCONS_00037031 | SEQ 1676 | 0.42063 | 0.84 |
| TCONS_00037216 | SEQ 1662 | 0.42063 | 0.83 |
| TCONS_00019918 | SEQ 1308 | 0.42063 | 0.82 |
| TCONS_00050212 | SEQ 1847 | 0.42063 | 0.82 |
| TCONS_00062420 | SEQ 2038 | 0.42063 | 0.81 |
| TCONS_00062314 | SEQ 1999 | 0.42063 | 0.81 |
| TCONS_00019917 | SEQ 1307 | 0.42063 | 0.80 |
| TCONS_00062315 | SEQ 2000 | 0.42063 | 0.79 |
| TCONS_00062503 | SEQ 1971 | 0.42063 | 0.78 |
| TCONS_00050088 | SEQ 1812 | 0.42063 | 0.78 |
| TCONS_00045244 | SEQ 1750 | 0.42063 | 0.77 |
| TCONS_00023220 | SEQ 1379 | 0.42063 | 0.77 |
| TCONS_00059438 | SEQ 1955 | 0.42063 | 0.76 |
| TCONS_00050204 | SEQ 1843 | 0.42063 | 0.74 |
| TCONS_00041037 | SEQ 1717 | 0.42063 | 0.74 |
| TCONS_00062348 | SEQ 2023 | 0.42063 | 0.74 |
| TCONS_00044971 | SEQ 1749 | 0.42063 | 0.73 |
| TCONS_00021570 | SEQ 1336 | 0.42063 | 0.73 |
| TCONS_00027397 | SEQ 1443 | 0.42063 | 0.70 |
| TCONS_00017374 | SEQ 1275 | 0.42063 | 0.70 |
| TCONS_00024800 | SEQ 1391 | 0.42063 | 0.69 |
| TCONS_00045249 | SEQ 1751 | 0.42063 | 0.69 |

TABLE 7-continued

The 1091 novel lncRNAs identified by the invention and fold change and p-value (differential expression in AD group versus healthy control group).

| lncRNA | SEQ | p-value | FC |
| --- | --- | --- | --- |
| TCONS_00035103 | SEQ 1581 | 0.42063 | 0.68 |
| TCONS_00027339 | SEQ 1434 | 0.42063 | 0.67 |
| TCONS_00014199 | SEQ 1233 | 0.42063 | 0.67 |
| TCONS_00066535 | SEQ 2089 | 0.42063 | 0.66 |
| TCONS_00026643 | SEQ 1427 | 0.42063 | 0.65 |
| TCONS_00066423 | SEQ 2094 | 0.42063 | 0.63 |
| TCONS_00037245 | SEQ 1671 | 0.42063 | 0.63 |
| TCONS_00027389 | SEQ 1440 | 0.42063 | 0.61 |
| TCONS_00000010 | SEQ 1012 | 0.42063 | 0.58 |
| TCONS_00035977 | SEQ 1597 | 0.42063 | 0.55 |
| TCONS_00062426 | SEQ 2041 | 0.42063 | 0.51 |
| TCONS_00033768 | SEQ 1549 | 0.42371 | <0.01 |
| TCONS_00045267 | SEQ 1764 | 0.42371 | <0.01 |
| TCONS_00055749 | SEQ 1903 | 0.42371 | <0.01 |
| TCONS_00062367 | SEQ 2029 | 0.42371 | <0.01 |
| TCONS_00000657 | SEQ 1051 | 0.42371 | >100 |
| TCONS_00021545 | SEQ 1322 | 0.42371 | >100 |
| TCONS_00027410 | SEQ 1448 | 0.42371 | >100 |
| TCONS_00040694 | SEQ 1699 | 0.42371 | >100 |
| TCONS_00050293 | SEQ 1867 | 0.43385 | 0.32 |
| TCONS_00024843 | SEQ 1402 | 0.43858 | 10.00 |
| TCONS_00000344 | SEQ 1077 | 0.44069 | >100 |
| TCONS_00045261 | SEQ 1757 | 0.44069 | >100 |
| TCONS_00000836 | SEQ 1101 | 0.45781 | 1.19 |
| TCONS_00050345 | SEQ 1876 | 0.45781 | 1.17 |
| TCONS_00027963 | SEQ 1490 | 0.46060 | 1.51 |
| TCONS_00027394 | SEQ 1442 | 0.46198 | 1.94 |
| TCONS_00027745 | SEQ 1539 | 0.46198 | 1.10 |
| TCONS_00035112 | SEQ 1587 | 0.46334 | 2.00 |
| TCONS_00021382 | SEQ 1312 | 0.46334 | 1.70 |
| TCONS_00019813 | SEQ 1309 | 0.46334 | 1.62 |
| TCONS_00023106 | SEQ 1349 | 0.46334 | 1.61 |
| TCONS_00014185 | SEQ 1230 | 0.46334 | 1.53 |
| TCONS_00045175 | SEQ 1797 | 0.46334 | 0.79 |
| TCONS_00021388 | SEQ 1314 | 0.46334 | 0.65 |
| TCONS_00050126 | SEQ 1819 | 0.50233 | 0.15 |
| TCONS_00066442 | SEQ 2103 | 0.51790 | 1.19 |
| TCONS_00040618 | SEQ 1682 | 0.51925 | 1.51 |
| TCONS_00027637 | SEQ 1507 | 0.52058 | 0.45 |
| TCONS_00050646 | SEQ 1873 | 0.52322 | 0.15 |
| TCONS_00023144 | SEQ 1362 | 0.52452 | 0.52 |
| TCONS_00021528 | SEQ 1315 | 0.52709 | 0.40 |
| TCONS_00027689 | SEQ 1523 | 0.52836 | 0.50 |
| TCONS_00059396 | SEQ 1943 | 0.52836 | 0.43 |
| TCONS_00000296 | SEQ 1059 | 0.52836 | 0.40 |
| TCONS_00023262 | SEQ 1387 | 0.52836 | 2.32 |
| TCONS_00012120 | SEQ 1219 | 0.52836 | 2.13 |
| TCONS_00000773 | SEQ 1086 | 0.52836 | 1.58 |
| TCONS_00017460 | SEQ 1259 | 0.52836 | 1.11 |
| TCONS_00066515 | SEQ 2078 | 0.52836 | 1.06 |
| TCONS_00050346 | SEQ 1877 | 0.52836 | 0.55 |
| TCONS_00066404 | SEQ 2086 | 0.52962 | 1.57 |
| TCONS_00059427 | SEQ 1949 | 0.52962 | 1.39 |
| TCONS_00014431 | SEQ 1255 | 0.52962 | 1.06 |
| TCONS_00019761 | SEQ 1298 | 0.52962 | 0.98 |
| TCONS_00044946 | SEQ 1740 | 0.52962 | 0.90 |
| TCONS_00000256 | SEQ 1053 | 0.52962 | 0.75 |
| TCONS_00062576 | SEQ 2015 | 0.54762 | 3.63 |
| TCONS_00011991 | SEQ 1221 | 0.54762 | 2.36 |
| TCONS_00037101 | SEQ 1634 | 0.54762 | 2.17 |
| TCONS_00055570 | SEQ 1914 | 0.54762 | 2.00 |
| TCONS_00055541 | SEQ 1910 | 0.54762 | 1.90 |
| TCONS_00044997 | SEQ 1756 | 0.54762 | 1.58 |
| TCONS_00026700 | SEQ 1416 | 0.54762 | 1.56 |
| TCONS_00036986 | SEQ 1666 | 0.54762 | 1.55 |
| TCONS_00033771 | SEQ 1551 | 0.54762 | 1.54 |
| TCONS_00062339 | SEQ 2010 | 0.54762 | 1.54 |
| TCONS_00008820 | SEQ 1148 | 0.54762 | 1.54 |
| TCONS_00000059 | SEQ 1018 | 0.54762 | 1.46 |
| TCONS_00055612 | SEQ 1919 | 0.54762 | 1.46 |
| TCONS_00000708 | SEQ 1057 | 0.54762 | 1.45 |
| TCONS_00023281 | SEQ 1350 | 0.54762 | 1.44 |
| TCONS_00011829 | SEQ 1189 | 0.54762 | 1.43 |
| TCONS_00023217 | SEQ 1376 | 0.54762 | 1.41 |
| TCONS_00027589 | SEQ 1503 | 0.54762 | 1.39 |

TABLE 7-continued

The 1091 novel lncRNAs identified by the invention and fold change and p-value
(differential expression in AD group versus healthy control group).

| lncRNA | SEQ | p-value | FC |
| --- | --- | --- | --- |
| TCONS_00027943 | SEQ 1481 | 0.54762 | 1.36 |
| TCONS_00027704 | SEQ 1527 | 0.54762 | 1.35 |
| TCONS_00011821 | SEQ 1187 | 0.54762 | 1.34 |
| TCONS_00027587 | SEQ 1502 | 0.54762 | 1.33 |
| TCONS_00008676 | SEQ 1153 | 0.54762 | 1.33 |
| TCONS_00005287 | SEQ 1135 | 0.54762 | 1.32 |
| TCONS_00000640 | SEQ 1046 | 0.54762 | 1.31 |
| TCONS_00045213 | SEQ 1743 | 0.54762 | 1.31 |
| TCONS_00008828 | SEQ 1150 | 0.54762 | 1.30 |
| TCONS_00066367 | SEQ 2071 | 0.54762 | 1.29 |
| TCONS_00040892 | SEQ 1684 | 0.54762 | 1.26 |
| TCONS_00021484 | SEQ 1343 | 0.54762 | 1.24 |
| TCONS_00062554 | SEQ 1984 | 0.54762 | 1.23 |
| TCONS_00027499 | SEQ 1475 | 0.54762 | 1.23 |
| TCONS_00050541 | SEQ 1830 | 0.54762 | 1.23 |
| TCONS_00062304 | SEQ 1987 | 0.54762 | 1.22 |
| TCONS_00026662 | SEQ 1405 | 0.54762 | 1.21 |
| TCONS_00037058 | SEQ 1623 | 0.54762 | 1.21 |
| TCONS_00062377 | SEQ 2034 | 0.54762 | 1.19 |
| TCONS_00027949 | SEQ 1486 | 0.54762 | 1.18 |
| TCONS_00059376 | SEQ 1926 | 0.54762 | 1.15 |
| TCONS_00000033 | SEQ 1016 | 0.54762 | 1.15 |
| TCONS_00023104 | SEQ 1348 | 0.54762 | 1.13 |
| TCONS_00055452 | SEQ 1889 | 0.54762 | 1.12 |
| TCONS_00014356 | SEQ 1229 | 0.54762 | 1.12 |
| TCONS_00004942 | SEQ 1112 | 0.54762 | 1.10 |
| TCONS_00036055 | SEQ 1613 | 0.54762 | 1.08 |
| TCONS_00021531 | SEQ 1316 | 0.54762 | 1.06 |
| TCONS_00005265 | SEQ 1124 | 0.54762 | 1.05 |
| TCONS_00000557 | SEQ 1027 | 0.54762 | 1.02 |
| TCONS_00027935 | SEQ 1466 | 0.54762 | 1.00 |
| TCONS_00023190 | SEQ 1369 | 0.54762 | 0.97 |
| TCONS_00026752 | SEQ 1423 | 0.54762 | 0.95 |
| TCONS_00050086 | SEQ 1810 | 0.54762 | 0.92 |
| TCONS_00019798 | SEQ 1305 | 0.54762 | 0.92 |
| TCONS_00062550 | SEQ 1980 | 0.54762 | 0.91 |
| TCONS_00000346 | SEQ 1079 | 0.54762 | 0.91 |
| TCONS_00000742 | SEQ 1070 | 0.54762 | 0.90 |
| TCONS_00062316 | SEQ 2001 | 0.54762 | 0.89 |
| TCONS_00021546 | SEQ 1323 | 0.54762 | 0.87 |
| TCONS_00050197 | SEQ 1839 | 0.54762 | 0.83 |
| TCONS_00027601 | SEQ 1506 | 0.54762 | 0.80 |
| TCONS_00008980 | SEQ 1184 | 0.54762 | 0.78 |
| TCONS_00008697 | SEQ 1161 | 0.54762 | 0.76 |
| TCONS_00055628 | SEQ 1921 | 0.54762 | 0.76 |
| TCONS_00045230 | SEQ 1747 | 0.54762 | 0.76 |
| TCONS_00027402 | SEQ 1445 | 0.54762 | 0.75 |
| TCONS_00035975 | SEQ 1594 | 0.54762 | 0.75 |
| TCONS_00014260 | SEQ 1248 | 0.54762 | 0.74 |
| TCONS_00027932 | SEQ 1463 | 0.54762 | 0.74 |
| TCONS_00036814 | SEQ 1625 | 0.54762 | 0.73 |
| TCONS_00011832 | SEQ 1192 | 0.54762 | 0.68 |
| TCONS_00050729 | SEQ 1881 | 0.54762 | 0.68 |
| TCONS_00033750 | SEQ 1545 | 0.54762 | 0.67 |
| TCONS_00066563 | SEQ 2107 | 0.54762 | 0.65 |
| TCONS_00027585 | SEQ 1500 | 0.54762 | 0.60 |
| TCONS_00050731 | SEQ 1882 | 0.54762 | 0.60 |
| TCONS_00000120 | SEQ 1029 | 0.54762 | 0.59 |
| TCONS_00045017 | SEQ 1766 | 0.54762 | 0.57 |
| TCONS_00059243 | SEQ 1945 | 0.54762 | 0.57 |
| TCONS_00023215 | SEQ 1375 | 0.54762 | 0.53 |
| TCONS_00005363 | SEQ 1145 | 0.59703 | 0.56 |
| TCONS_00014200 | SEQ 1234 | 0.59816 | 1.89 |
| TCONS_00037098 | SEQ 1633 | 0.59816 | 0.74 |
| TCONS_00027536 | SEQ 1494 | 0.59929 | 1.58 |
| TCONS_00035088 | SEQ 1563 | 0.59929 | 1.48 |
| TCONS_00008776 | SEQ 1180 | 0.59929 | 0.71 |
| TCONS_00019694 | SEQ 1291 | 0.59929 | 0.70 |
| TCONS_00000321 | SEQ 1069 | 0.60040 | 1.81 |
| TCONS_00017396 | SEQ 1278 | 0.60040 | 1.63 |
| TCONS_00040930 | SEQ 1700 | 0.60040 | 1.50 |
| TCONS_00066384 | SEQ 2081 | 0.60040 | 1.49 |
| TCONS_00036109 | SEQ 1601 | 0.60040 | 1.47 |
| TCONS_00050306 | SEQ 1870 | 0.60040 | 1.18 |
| TCONS_00005183 | SEQ 1111 | 0.60040 | 1.16 |

TABLE 7-continued

The 1091 novel lncRNAs identified by the invention and fold change and p-value
(differential expression in AD group versus healthy control group).

| lncRNA | SEQ | p-value | FC |
| --- | --- | --- | --- |
| TCONS_00000523 | SEQ 1019 | 0.60040 | 1.01 |
| TCONS_00062549 | SEQ 1979 | 0.60040 | 0.80 |
| TCONS_00066479 | SEQ 2064 | 0.60040 | 0.77 |
| TCONS_00062496 | SEQ 1966 | 0.60724 | >100 |
| TCONS_00027590 | SEQ 1504 | 0.60724 | 10.54 |
| TCONS_00000531 | SEQ 1020 | 0.60724 | 2.40 |
| TCONS_00028006 | SEQ 1497 | 0.60724 | 1.02 |
| TCONS_00040662 | SEQ 1694 | 0.66231 | 1.25 |
| TCONS_00040905 | SEQ 1688 | 0.66843 | 1.54 |
| TCONS_00008965 | SEQ 1181 | 0.67040 | 2.00 |
| TCONS_00014150 | SEQ 1226 | 0.67040 | 1.90 |
| TCONS_00062278 | SEQ 1970 | 0.67137 | 0.36 |
| TCONS_00008851 | SEQ 1164 | 0.67137 | 0.19 |
| TCONS_00062704 | SEQ 2046 | 0.67137 | 1.16 |
| TCONS_00055724 | SEQ 1897 | 0.67137 | 0.69 |
| TCONS_00050563 | SEQ 1836 | 0.67234 | 2.39 |
| TCONS_00044945 | SEQ 1739 | 0.67234 | 1.36 |
| TCONS_00005005 | SEQ 1127 | 0.67234 | 0.71 |
| TCONS_00019799 | SEQ 1306 | 0.67424 | 1.48 |
| TCONS_00050235 | SEQ 1856 | 0.67424 | 1.06 |
| TCONS_00008677 | SEQ 1154 | 0.67424 | 0.57 |
| TCONS_00059214 | SEQ 1938 | 0.67517 | 2.88 |
| TCONS_00059212 | SEQ 1936 | 0.67517 | 2.41 |
| TCONS_00017530 | SEQ 1282 | 0.67517 | 1.93 |
| TCONS_00000551 | SEQ 1023 | 0.67517 | 1.49 |
| TCONS_00027471 | SEQ 1454 | 0.67517 | 0.86 |
| TCONS_00027750 | SEQ 1429 | 0.67517 | 0.70 |
| TCONS_00027703 | SEQ 1526 | 0.67517 | 0.54 |
| TCONS_00036836 | SEQ 1630 | 0.69048 | 0.47 |
| TCONS_00062275 | SEQ 1968 | 0.69048 | 0.34 |
| TCONS_00050089 | SEQ 1813 | 0.69048 | 0.29 |
| TCONS_00017348 | SEQ 1262 | 0.69048 | 2.42 |
| TCONS_00044919 | SEQ 1733 | 0.69048 | 2.23 |
| TCONS_00023221 | SEQ 1380 | 0.69048 | 1.93 |
| TCONS_00023323 | SEQ 1359 | 0.69048 | 1.91 |
| TCONS_00027767 | SEQ 1438 | 0.69048 | 1.88 |
| TCONS_00036034 | SEQ 1610 | 0.69048 | 1.81 |
| TCONS_00028167 | SEQ 1537 | 0.69048 | 1.76 |
| TCONS_00012068 | SEQ 1205 | 0.69048 | 1.73 |
| TCONS_00023174 | SEQ 1368 | 0.69048 | 1.72 |
| TCONS_00028054 | SEQ 1508 | 0.69048 | 1.60 |
| TCONS_00062558 | SEQ 1994 | 0.69048 | 1.55 |
| TCONS_00045182 | SEQ 1799 | 0.69048 | 1.52 |
| TCONS_00027944 | SEQ 1482 | 0.69048 | 1.44 |
| TCONS_00040703 | SEQ 1707 | 0.69048 | 1.44 |
| TCONS_00028113 | SEQ 1515 | 0.69048 | 1.43 |
| TCONS_00045346 | SEQ 1781 | 0.69048 | 1.41 |
| TCONS_00000260 | SEQ 1054 | 0.69048 | 1.39 |
| TCONS_00055508 | SEQ 1899 | 0.69048 | 1.38 |
| TCONS_00050070 | SEQ 1806 | 0.69048 | 1.33 |
| TCONS_00035093 | SEQ 1570 | 0.69048 | 1.29 |
| TCONS_00005037 | SEQ 1136 | 0.69048 | 1.29 |
| TCONS_00000650 | SEQ 1049 | 0.69048 | 1.29 |
| TCONS_00027494 | SEQ 1468 | 0.69048 | 1.28 |
| TCONS_00066504 | SEQ 2069 | 0.69048 | 1.27 |
| TCONS_00008871 | SEQ 1169 | 0.69048 | 1.26 |
| TCONS_00027416 | SEQ 1449 | 0.69048 | 1.25 |
| TCONS_00062579 | SEQ 2018 | 0.69048 | 1.24 |
| TCONS_00014136 | SEQ 1223 | 0.69048 | 1.23 |
| TCONS_00021619 | SEQ 1341 | 0.69048 | 1.23 |
| TCONS_00000009 | SEQ 1011 | 0.69048 | 1.23 |
| TCONS_00040658 | SEQ 1689 | 0.69048 | 1.22 |
| TCONS_00059271 | SEQ 1948 | 0.69048 | 1.22 |
| TCONS_00036123 | SEQ 1605 | 0.69048 | 1.20 |
| TCONS_00000751 | SEQ 1072 | 0.69048 | 1.20 |
| TCONS_00027400 | SEQ 1444 | 0.69048 | 1.17 |
| TCONS_00045438 | SEQ 1794 | 0.69048 | 1.15 |
| TCONS_00062551 | SEQ 1981 | 0.69048 | 1.14 |
| TCONS_00012059 | SEQ 1200 | 0.69048 | 1.14 |
| TCONS_00033689 | SEQ 1560 | 0.69048 | 1.13 |
| TCONS_00050017 | SEQ 1804 | 0.69048 | 1.12 |
| TCONS_00036113 | SEQ 1603 | 0.69048 | 1.11 |
| TCONS_00004983 | SEQ 1121 | 0.69048 | 1.11 |
| TCONS_00033710 | SEQ 1540 | 0.69048 | 1.10 |
| TCONS_00040895 | SEQ 1686 | 0.69048 | 1.10 |

TABLE 7-continued

The 1091 novel lncRNAs identified by the invention and fold change and p-value
(differential expression in AD group versus healthy control group).

| lncRNA | SEQ | p-value | FC |
| --- | --- | --- | --- |
| TCONS_00014428 | SEQ 1253 | 0.69048 | 1.07 |
| TCONS_00005077 | SEQ 1142 | 0.69048 | 1.06 |
| TCONS_00059297 | SEQ 1957 | 0.69048 | 1.04 |
| TCONS_00036901 | SEQ 1646 | 0.69048 | 1.03 |
| TCONS_00055681 | SEQ 1887 | 0.69048 | 1.00 |
| TCONS_00050638 | SEQ 1871 | 0.69048 | 0.99 |
| TCONS_00062730 | SEQ 2051 | 0.69048 | 0.98 |
| TCONS_00005008 | SEQ 1129 | 0.69048 | 0.97 |
| TCONS_00023131 | SEQ 1356 | 0.69048 | 0.95 |
| TCONS_00040590 | SEQ 1677 | 0.69048 | 0.94 |
| TCONS_00023085 | SEQ 1344 | 0.69048 | 0.93 |
| TCONS_00062305 | SEQ 1988 | 0.69048 | 0.92 |
| TCONS_00000127 | SEQ 1034 | 0.69048 | 0.92 |
| TCONS_00062347 | SEQ 2021 | 0.69048 | 0.89 |
| TCONS_00036813 | SEQ 1624 | 0.69048 | 0.89 |
| TCONS_00017328 | SEQ 1260 | 0.69048 | 0.89 |
| TCONS_00036984 | SEQ 1664 | 0.69048 | 0.89 |
| TCONS_00008856 | SEQ 1166 | 0.69048 | 0.87 |
| TCONS_00004943 | SEQ 1113 | 0.69048 | 0.86 |
| TCONS_00062572 | SEQ 2007 | 0.69048 | 0.86 |
| TCONS_00037090 | SEQ 1632 | 0.69048 | 0.85 |
| TCONS_00036093 | SEQ 1595 | 0.69048 | 0.83 |
| TCONS_00066409 | SEQ 2090 | 0.69048 | 0.83 |
| TCONS_00019776 | SEQ 1302 | 0.69048 | 0.82 |
| TCONS_00026614 | SEQ 1421 | 0.69048 | 0.82 |
| TCONS_00059284 | SEQ 1952 | 0.69048 | 0.82 |
| TCONS_00035978 | SEQ 1598 | 0.69048 | 0.82 |
| TCONS_00044941 | SEQ 1737 | 0.69048 | 0.81 |
| TCONS_00000345 | SEQ 1078 | 0.69048 | 0.81 |
| TCONS_00033664 | SEQ 1552 | 0.69048 | 0.80 |
| TCONS_00062302 | SEQ 1985 | 0.69048 | 0.79 |
| TCONS_00035096 | SEQ 1576 | 0.69048 | 0.79 |
| TCONS_00000006 | SEQ 1010 | 0.69048 | 0.79 |
| TCONS_00024807 | SEQ 1393 | 0.69048 | 0.77 |
| TCONS_00000735 | SEQ 1067 | 0.69048 | 0.73 |
| TCONS_00050598 | SEQ 1857 | 0.69048 | 0.71 |
| TCONS_00014211 | SEQ 1239 | 0.69048 | 0.71 |
| TCONS_00027711 | SEQ 1533 | 0.69048 | 0.69 |
| TCONS_00059424 | SEQ 1947 | 0.69048 | 0.69 |
| TCONS_00017350 | SEQ 1264 | 0.69048 | 0.65 |
| TCONS_00044948 | SEQ 1741 | 0.69048 | 0.64 |
| TCONS_00050219 | SEQ 1851 | 0.69048 | 0.64 |
| TCONS_00033649 | SEQ 1546 | 0.69048 | 0.64 |
| TCONS_00066412 | SEQ 2091 | 0.69048 | 0.63 |
| TCONS_00019765 | SEQ 1299 | 0.69048 | 0.59 |
| TCONS_00014453 | SEQ 1256 | 0.69048 | 0.59 |
| TCONS_00000723 | SEQ 1058 | 0.69048 | 0.54 |
| TCONS_00027530 | SEQ 1491 | 0.72408 | 2.29 |
| TCONS_00050316 | SEQ 1872 | 0.74568 | 0.27 |
| TCONS_00055421 | SEQ 1885 | 0.75033 | 2.82 |
| TCONS_00005243 | SEQ 1120 | 0.75033 | 1.39 |
| TCONS_00000338 | SEQ 1074 | 0.75033 | 0.78 |
| TCONS_00066451 | SEQ 2105 | 0.75257 | 0.48 |
| TCONS_00027505 | SEQ 1480 | 0.75257 | 1.29 |
| TCONS_00040947 | SEQ 1704 | 0.75257 | 1.14 |
| TCONS_00021392 | SEQ 1317 | 0.75257 | 0.69 |
| TCONS_00005182 | SEQ 1110 | 0.75257 | 0.69 |
| TCONS_00026597 | SEQ 1420 | 0.75330 | 1.73 |
| TCONS_00062376 | SEQ 2033 | 0.75330 | 1.43 |
| TCONS_00024847 | SEQ 1403 | 0.75330 | 1.25 |
| TCONS_00035994 | SEQ 1602 | 0.75330 | 1.23 |
| TCONS_00045240 | SEQ 1748 | 0.75330 | 1.15 |
| TCONS_00050459 | SEQ 1808 | 0.75330 | 1.13 |
| TCONS_00059174 | SEQ 1924 | 0.75330 | 1.09 |
| TCONS_00050703 | SEQ 1879 | 0.75330 | 1.04 |
| TCONS_00050115 | SEQ 1817 | 0.75330 | 1.00 |
| TCONS_00066517 | SEQ 2082 | 0.75330 | 0.96 |
| TCONS_00008889 | SEQ 1172 | 0.75330 | 0.95 |
| TCONS_00024818 | SEQ 1399 | 0.75330 | 0.88 |
| TCONS_00040697 | SEQ 1701 | 0.75330 | 0.85 |
| TCONS_00028140 | SEQ 1532 | 0.75330 | 0.82 |
| TCONS_00024808 | SEQ 1394 | 0.75330 | 0.78 |
| TCONS_00059185 | SEQ 1927 | 0.75330 | 0.76 |
| TCONS_00019685 | SEQ 1289 | 0.75330 | 0.70 |
| TCONS_00024812 | SEQ 1397 | 0.75330 | 0.64 |

TABLE 7-continued

The 1091 novel lncRNAs identified by the invention and fold change and p-value
(differential expression in AD group versus healthy control group).

| lncRNA | SEQ | p-value | FC |
| --- | --- | --- | --- |
| TCONS_00055414 | SEQ 1883 | 0.79625 | 0.32 |
| TCONS_00068985 | SEQ 2108 | 0.79625 | 1.50 |
| TCONS_00045134 | SEQ 1793 | 0.79717 | <0.01 |
| TCONS_00066372 | SEQ 2075 | 0.79717 | <0.01 |
| TCONS_00014398 | SEQ 1241 | 0.79717 | 0.41 |
| TCONS_00019846 | SEQ 1293 | 0.79717 | 0.28 |
| TCONS_00037193 | SEQ 1658 | 0.79717 | 0.09 |
| TCONS_00045108 | SEQ 1783 | 0.82306 | 0.56 |
| TCONS_00026535 | SEQ 1406 | 0.82366 | 0.70 |
| TCONS_00026562 | SEQ 1415 | 0.82881 | 0.67 |
| TCONS_00023171 | SEQ 1367 | 0.82936 | 3.24 |
| TCONS_00059213 | SEQ 1937 | 0.82936 | 1.57 |
| TCONS_00019869 | SEQ 1296 | 0.82936 | 1.50 |
| TCONS_00040700 | SEQ 1703 | 0.82936 | 1.29 |
| TCONS_00008901 | SEQ 1173 | 0.83148 | 0.32 |
| TCONS_00024904 | SEQ 1401 | 0.83148 | 2.25 |
| TCONS_00000121 | SEQ 1030 | 0.83148 | 1.17 |
| TCONS_00062636 | SEQ 2035 | 0.83200 | 1.11 |
| TCONS_00023219 | SEQ 1378 | 0.83252 | 0.32 |
| TCONS_00027819 | SEQ 1441 | 0.83252 | 2.35 |
| TCONS_00044998 | SEQ 1763 | 0.83252 | 1.57 |
| TCONS_00045396 | SEQ 1788 | 0.83252 | 1.32 |
| TCONS_00045394 | SEQ 1787 | 0.83252 | 1.23 |
| TCONS_00062458 | SEQ 2048 | 0.83252 | 1.18 |
| TCONS_00066383 | SEQ 2080 | 0.83252 | 0.78 |
| TCONS_00027705 | SEQ 1528 | 0.83252 | 0.71 |
| TCONS_00059433 | SEQ 1953 | 0.83303 | 0.12 |
| TCONS_00008716 | SEQ 1168 | 0.83353 | 0.49 |
| TCONS_00045024 | SEQ 1767 | 0.83353 | 2.93 |
| TCONS_00040829 | SEQ 1723 | 0.83353 | 1.89 |
| TCONS_00055425 | SEQ 1886 | 0.83353 | 1.37 |
| TCONS_00008905 | SEQ 1174 | 0.83353 | 1.35 |
| TCONS_00005111 | SEQ 1144 | 0.83353 | 1.15 |
| TCONS_00055652 | SEQ 1884 | 0.83353 | 1.13 |
| TCONS_00011967 | SEQ 1215 | 0.83353 | 1.12 |
| TCONS_00017420 | SEQ 1283 | 0.83353 | 0.91 |
| TCONS_00045003 | SEQ 1765 | 0.83353 | 0.78 |
| TCONS_00027533 | SEQ 1493 | 0.83404 | 1.18 |
| TCONS_00062369 | SEQ 2032 | 0.83404 | 1.14 |
| TCONS_00008955 | SEQ 1179 | 0.83404 | 1.06 |
| TCONS_00036780 | SEQ 1615 | 0.83404 | 1.03 |
| TCONS_00066327 | SEQ 2060 | 0.83404 | 0.92 |
| TCONS_00000826 | SEQ 1093 | 0.83404 | 0.83 |
| TCONS_00021579 | SEQ 1338 | 0.83404 | 0.80 |
| TCONS_00012010 | SEQ 1186 | 0.83404 | 0.65 |
| TCONS_00062411 | SEQ 2036 | 0.83404 | 0.64 |
| TCONS_00045214 | SEQ 1744 | 0.84127 | 0.33 |
| TCONS_00008880 | SEQ 1171 | 0.84127 | 2.77 |
| TCONS_00014402 | SEQ 1243 | 0.84127 | 1.82 |
| TCONS_00036891 | SEQ 1639 | 0.84127 | 1.66 |
| TCONS_00033686 | SEQ 1557 | 0.84127 | 1.60 |
| TCONS_00012031 | SEQ 1196 | 0.84127 | 1.54 |
| TCONS_00044995 | SEQ 1754 | 0.84127 | 1.47 |
| TCONS_00023324 | SEQ 1360 | 0.84127 | 1.40 |
| TCONS_00037122 | SEQ 1647 | 0.84127 | 1.39 |
| TCONS_00040917 | SEQ 1691 | 0.84127 | 1.35 |
| TCONS_00050198 | SEQ 1840 | 0.84127 | 1.33 |
| TCONS_00037148 | SEQ 1653 | 0.84127 | 1.32 |
| TCONS_00059205 | SEQ 1933 | 0.84127 | 1.31 |
| TCONS_00037198 | SEQ 1659 | 0.84127 | 1.31 |
| TCONS_00005001 | SEQ 1125 | 0.84127 | 1.30 |
| TCONS_00014417 | SEQ 1247 | 0.84127 | 1.29 |
| TCONS_00050274 | SEQ 1863 | 0.84127 | 1.28 |
| TCONS_00062556 | SEQ 1992 | 0.84127 | 1.27 |
| TCONS_00055750 | SEQ 1904 | 0.84127 | 1.25 |
| TCONS_00059386 | SEQ 1940 | 0.84127 | 1.22 |
| TCONS_00028112 | SEQ 1514 | 0.84127 | 1.22 |
| TCONS_00000041 | SEQ 1017 | 0.84127 | 1.21 |
| TCONS_00045078 | SEQ 1777 | 0.84127 | 1.21 |
| TCONS_00050275 | SEQ 1864 | 0.84127 | 1.18 |
| TCONS_00005140 | SEQ 1107 | 0.84127 | 1.18 |
| TCONS_00040821 | SEQ 1722 | 0.84127 | 1.17 |
| TCONS_00050193 | SEQ 1838 | 0.84127 | 1.17 |
| TCONS_00036032 | SEQ 1609 | 0.84127 | 1.17 |
| TCONS_00036900 | SEQ 1645 | 0.84127 | 1.16 |

TABLE 7-continued

The 1091 novel lncRNAs identified by the invention and fold change and p-value
(differential expression in AD group versus healthy control group).

| lncRNA | SEQ | p-value | FC |
| --- | --- | --- | --- |
| TCONS_00026539 | SEQ 1409 | 0.84127 | 1.16 |
| TCONS_00023164 | SEQ 1365 | 0.84127 | 1.16 |
| TCONS_00036886 | SEQ 1637 | 0.84127 | 1.15 |
| TCONS_00000727 | SEQ 1060 | 0.84127 | 1.15 |
| TCONS_00062577 | SEQ 2016 | 0.84127 | 1.14 |
| TCONS_00014408 | SEQ 1246 | 0.84127 | 1.14 |
| TCONS_00028114 | SEQ 1516 | 0.84127 | 1.13 |
| TCONS_00050609 | SEQ 1862 | 0.84127 | 1.13 |
| TCONS_00014465 | SEQ 1258 | 0.84127 | 1.12 |
| TCONS_00000628 | SEQ 1039 | 0.84127 | 1.12 |
| TCONS_00062574 | SEQ 2013 | 0.84127 | 1.12 |
| TCONS_00014168 | SEQ 1228 | 0.84127 | 1.12 |
| TCONS_00005006 | SEQ 1128 | 0.84127 | 1.11 |
| TCONS_00062301 | SEQ 1982 | 0.84127 | 1.11 |
| TCONS_00050673 | SEQ 1878 | 0.84127 | 1.11 |
| TCONS_00027497 | SEQ 1473 | 0.84127 | 1.11 |
| TCONS_00055751 | SEQ 1905 | 0.84127 | 1.10 |
| TCONS_00012069 | SEQ 1206 | 0.84127 | 1.10 |
| TCONS_00062345 | SEQ 2020 | 0.84127 | 1.09 |
| TCONS_00021571 | SEQ 1337 | 0.84127 | 1.09 |
| TCONS_00000439 | SEQ 1099 | 0.84127 | 1.08 |
| TCONS_00050474 | SEQ 1816 | 0.84127 | 1.06 |
| TCONS_00000180 | SEQ 1038 | 0.84127 | 1.06 |
| TCONS_00023199 | SEQ 1373 | 0.84127 | 1.05 |
| TCONS_00012021 | SEQ 1193 | 0.84127 | 1.05 |
| TCONS_00062575 | SEQ 2014 | 0.84127 | 1.04 |
| TCONS_00017371 | SEQ 1272 | 0.84127 | 1.02 |
| TCONS_00023325 | SEQ 1361 | 0.84127 | 1.01 |
| TCONS_00027938 | SEQ 1477 | 0.84127 | 1.01 |
| TCONS_00017408 | SEQ 1279 | 0.84127 | 1.00 |
| TCONS_00028093 | SEQ 1509 | 0.84127 | 1.00 |
| TCONS_00045472 | SEQ 1800 | 0.84127 | 0.99 |
| TCONS_00000032 | SEQ 1015 | 0.84127 | 0.99 |
| TCONS_00005340 | SEQ 1143 | 0.84127 | 0.98 |
| TCONS_00008833 | SEQ 1151 | 0.84127 | 0.95 |
| TCONS_00062359 | SEQ 2028 | 0.84127 | 0.95 |
| TCONS_00050129 | SEQ 1821 | 0.84127 | 0.93 |
| TCONS_00066371 | SEQ 2074 | 0.84127 | 0.92 |
| TCONS_00021405 | SEQ 1325 | 0.84127 | 0.91 |
| TCONS_00062307 | SEQ 1990 | 0.84127 | 0.90 |
| TCONS_00000733 | SEQ 1065 | 0.84127 | 0.89 |
| TCONS_00035023 | SEQ 1568 | 0.84127 | 0.89 |
| TCONS_00050262 | SEQ 1859 | 0.84127 | 0.89 |
| TCONS_00059274 | SEQ 1950 | 0.84127 | 0.88 |
| TCONS_00033688 | SEQ 1559 | 0.84127 | 0.88 |
| TCONS_00062421 | SEQ 2039 | 0.84127 | 0.86 |
| TCONS_00036132 | SEQ 1606 | 0.84127 | 0.85 |
| TCONS_00036919 | SEQ 1650 | 0.84127 | 0.84 |
| TCONS_00000347 | SEQ 1080 | 0.84127 | 0.83 |
| TCONS_00005011 | SEQ 1132 | 0.84127 | 0.81 |
| TCONS_00035105 | SEQ 1584 | 0.84127 | 0.80 |
| TCONS_00024809 | SEQ 1395 | 0.84127 | 0.80 |
| TCONS_00062350 | SEQ 2025 | 0.84127 | 0.79 |
| TCONS_00021416 | SEQ 1328 | 0.84127 | 0.78 |
| TCONS_00035973 | SEQ 1593 | 0.84127 | 0.77 |
| TCONS_00066532 | SEQ 2087 | 0.84127 | 0.77 |
| TCONS_00000537 | SEQ 1022 | 0.84127 | 0.76 |
| TCONS_00027954 | SEQ 1489 | 0.84127 | 0.72 |
| TCONS_00045402 | SEQ 1791 | 0.84127 | 0.71 |
| TCONS_00036031 | SEQ 1608 | 0.84127 | 0.69 |
| TCONS_00008840 | SEQ 1157 | 0.84127 | 0.66 |
| TCONS_00005136 | SEQ 1103 | 0.84127 | 0.65 |
| TCONS_00036816 | SEQ 1626 | 0.84127 | 0.65 |
| TCONS_00000440 | SEQ 1100 | 0.84127 | 0.60 |
| TCONS_00040802 | SEQ 1718 | 0.84127 | 0.59 |
| TCONS_00027586 | SEQ 1501 | 0.84127 | 0.53 |
| TCONS_00021419 | SEQ 1329 | 0.91098 | 1.42 |
| TCONS_00027825 | SEQ 1446 | 0.91418 | 0.96 |
| TCONS_00005121 | SEQ 1146 | 0.91553 | 0.47 |
| TCONS_00027470 | SEQ 1452 | 0.91553 | 0.45 |
| TCONS_00066456 | SEQ 2056 | 0.91553 | 2.45 |
| TCONS_00021397 | SEQ 1321 | 0.91553 | 1.52 |
| TCONS_00040996 | SEQ 1714 | 0.91605 | 1.11 |
| TCONS_00045110 | SEQ 1786 | 0.91631 | 4.00 |
| TCONS_00026688 | SEQ 1412 | 0.91631 | 2.52 |

TABLE 7-continued

The 1091 novel lncRNAs identified by the invention and fold change and p-value
(differential expression in AD group versus healthy control group).

| lncRNA | SEQ | p-value | FC |
| --- | --- | --- | --- |
| TCONS_00000553 | SEQ 1025 | 0.91631 | 1.52 |
| TCONS_00055512 | SEQ 1900 | 0.91631 | 0.96 |
| TCONS_00055543 | SEQ 1912 | 0.91631 | 0.96 |
| TCONS_00033770 | SEQ 1550 | 0.91631 | 0.94 |
| TCONS_00027706 | SEQ 1529 | 0.91631 | 0.91 |
| TCONS_00059333 | SEQ 1961 | 0.91656 | 0.41 |
| TCONS_00028099 | SEQ 1510 | 0.91656 | 0.38 |
| TCONS_00000792 | SEQ 1088 | 0.91656 | 2.28 |
| TCONS_00062664 | SEQ 2037 | 0.91656 | 1.67 |
| TCONS_00000552 | SEQ 1024 | 0.91656 | 1.34 |
| TCONS_00066463 | SEQ 2062 | 0.91656 | 1.34 |
| TCONS_00008683 | SEQ 1156 | 0.91656 | 1.32 |
| TCONS_00000315 | SEQ 1068 | 0.91656 | 1.27 |
| TCONS_00005264 | SEQ 1123 | 0.91656 | 1.20 |
| TCONS_00000420 | SEQ 1092 | 0.91656 | 1.10 |
| TCONS_00050059 | SEQ 1805 | 0.91656 | 1.10 |
| TCONS_00059183 | SEQ 1925 | 0.91656 | 1.08 |
| TCONS_00000461 | SEQ 1013 | 0.91656 | 1.01 |
| TCONS_00059435 | SEQ 1954 | 0.91656 | 0.99 |
| TCONS_00011961 | SEQ 1212 | 0.91656 | 0.95 |
| TCONS_00000559 | SEQ 1028 | 0.91656 | 0.92 |
| TCONS_00066444 | SEQ 2104 | 0.91656 | 0.87 |
| TCONS_00066318 | SEQ 2057 | 0.91656 | 0.61 |
| TCONS_00011903 | SEQ 1207 | 1.00000 | 0.50 |
| TCONS_00045299 | SEQ 1768 | 1.00000 | 0.48 |
| TCONS_00059464 | SEQ 1958 | 1.00000 | 0.32 |
| TCONS_00017426 | SEQ 1284 | 1.00000 | 0.27 |
| TCONS_00050543 | SEQ 1834 | 1.00000 | 0.24 |
| TCONS_00062333 | SEQ 2006 | 1.00000 | 0.14 |
| TCONS_00027922 | SEQ 1456 | 1.00000 | 0.07 |
| TCONS_00069000 | SEQ 2114 | 1.00000 | 56.73 |
| TCONS_00004967 | SEQ 1119 | 1.00000 | 11.00 |
| TCONS_00004966 | SEQ 1117 | 1.00000 | 5.60 |
| TCONS_00000732 | SEQ 1064 | 1.00000 | 3.88 |
| TCONS_00008879 | SEQ 1170 | 1.00000 | 2.91 |
| TCONS_00023170 | SEQ 1366 | 1.00000 | 2.68 |
| TCONS_00012016 | SEQ 1188 | 1.00000 | 2.66 |
| TCONS_00050175 | SEQ 1827 | 1.00000 | 1.90 |
| TCONS_00000793 | SEQ 1089 | 1.00000 | 1.79 |
| TCONS_00050502 | SEQ 1822 | 1.00000 | 1.73 |
| TCONS_00005241 | SEQ 1116 | 1.00000 | 1.65 |
| TCONS_00005010 | SEQ 1131 | 1.00000 | 1.59 |
| TCONS_00000203 | SEQ 1043 | 1.00000 | 1.52 |
| TCONS_00021599 | SEQ 1340 | 1.00000 | 1.48 |
| TCONS_00062343 | SEQ 2019 | 1.00000 | 1.39 |
| TCONS_00040834 | SEQ 1725 | 1.00000 | 1.39 |
| TCONS_00000837 | SEQ 1102 | 1.00000 | 1.38 |
| TCONS_00062520 | SEQ 1974 | 1.00000 | 1.38 |
| TCONS_00055634 | SEQ 1922 | 1.00000 | 1.37 |
| TCONS_00036922 | SEQ 1651 | 1.00000 | 1.36 |
| TCONS_00050295 | SEQ 1868 | 1.00000 | 1.36 |
| TCONS_00021481 | SEQ 1342 | 1.00000 | 1.36 |
| TCONS_00024798 | SEQ 1390 | 1.00000 | 1.35 |
| TCONS_00036838 | SEQ 1631 | 1.00000 | 1.33 |
| TCONS_00050214 | SEQ 1848 | 1.00000 | 1.31 |
| TCONS_00014187 | SEQ 1231 | 1.00000 | 1.28 |
| TCONS_00062454 | SEQ 2047 | 1.00000 | 1.28 |
| TCONS_00017352 | SEQ 1266 | 1.00000 | 1.27 |
| TCONS_00035075 | SEQ 1590 | 1.00000 | 1.26 |
| TCONS_00012032 | SEQ 1197 | 1.00000 | 1.24 |
| TCONS_00036985 | SEQ 1665 | 1.00000 | 1.24 |
| TCONS_00000348 | SEQ 1081 | 1.00000 | 1.24 |
| TCONS_00000300 | SEQ 1061 | 1.00000 | 1.23 |
| TCONS_00004987 | SEQ 1122 | 1.00000 | 1.22 |
| TCONS_00026734 | SEQ 1419 | 1.00000 | 1.21 |
| TCONS_00050526 | SEQ 1824 | 1.00000 | 1.20 |
| TCONS_00011994 | SEQ 1222 | 1.00000 | 1.20 |
| TCONS_00008682 | SEQ 1155 | 1.00000 | 1.20 |
| TCONS_00026557 | SEQ 1413 | 1.00000 | 1.18 |
| TCONS_00019797 | SEQ 1304 | 1.00000 | 1.18 |
| TCONS_00045042 | SEQ 1770 | 1.00000 | 1.16 |
| TCONS_00011830 | SEQ 1190 | 1.00000 | 1.16 |
| TCONS_00037176 | SEQ 1656 | 1.00000 | 1.16 |
| TCONS_00041064 | SEQ 1726 | 1.00000 | 1.15 |
| TCONS_00017376 | SEQ 1277 | 1.00000 | 1.15 |

TABLE 7-continued

The 1091 novel lncRNAs identified by the invention and fold change and p-value (differential expression in AD group versus healthy control group).

| lncRNA | SEQ | p-value | FC |
| --- | --- | --- | --- |
| TCONS_00037147 | SEQ 1652 | 1.00000 | 1.14 |
| TCONS_00033755 | SEQ 1547 | 1.00000 | 1.14 |
| TCONS_00017375 | SEQ 1276 | 1.00000 | 1.13 |
| TCONS_00005274 | SEQ 1133 | 1.00000 | 1.13 |
| TCONS_00037212 | SEQ 1661 | 1.00000 | 1.13 |
| TCONS_00036781 | SEQ 1617 | 1.00000 | 1.13 |
| TCONS_00036095 | SEQ 1599 | 1.00000 | 1.12 |
| TCONS_00037152 | SEQ 1654 | 1.00000 | 1.12 |
| TCONS_00027948 | SEQ 1485 | 1.00000 | 1.11 |
| TCONS_00066382 | SEQ 2079 | 1.00000 | 1.11 |
| TCONS_00050168 | SEQ 1825 | 1.00000 | 1.10 |
| TCONS_00008698 | SEQ 1162 | 1.00000 | 1.10 |
| TCONS_00037000 | SEQ 1669 | 1.00000 | 1.09 |
| TCONS_00062548 | SEQ 1978 | 1.00000 | 1.09 |
| TCONS_00040916 | SEQ 1690 | 1.00000 | 1.08 |
| TCONS_00062552 | SEQ 1983 | 1.00000 | 1.08 |
| TCONS_00014387 | SEQ 1235 | 1.00000 | 1.06 |
| TCONS_00059500 | SEQ 1964 | 1.00000 | 1.06 |
| TCONS_00011969 | SEQ 1216 | 1.00000 | 1.05 |
| TCONS_00023276 | SEQ 1347 | 1.00000 | 1.05 |
| TCONS_00012043 | SEQ 1199 | 1.00000 | 1.05 |
| TCONS_00014237 | SEQ 1242 | 1.00000 | 1.05 |
| TCONS_00066440 | SEQ 2101 | 1.00000 | 1.05 |
| TCONS_00066373 | SEQ 2076 | 1.00000 | 1.04 |
| TCONS_00023115 | SEQ 1352 | 1.00000 | 1.04 |
| TCONS_00000349 | SEQ 1082 | 1.00000 | 1.04 |
| TCONS_00023218 | SEQ 1377 | 1.00000 | 1.04 |
| TCONS_00055486 | SEQ 1895 | 1.00000 | 1.04 |
| TCONS_00027760 | SEQ 1433 | 1.00000 | 1.04 |
| TCONS_00066370 | SEQ 2073 | 1.00000 | 1.04 |
| TCONS_00040762 | SEQ 1716 | 1.00000 | 1.03 |
| TCONS_00040893 | SEQ 1685 | 1.00000 | 1.03 |
| TCONS_00050604 | SEQ 1858 | 1.00000 | 1.03 |
| TCONS_00014165 | SEQ 1227 | 1.00000 | 1.03 |
| TCONS_00035022 | SEQ 1567 | 1.00000 | 1.03 |
| TCONS_00008675 | SEQ 1152 | 1.00000 | 1.02 |
| TCONS_00008699 | SEQ 1163 | 1.00000 | 1.02 |
| TCONS_00040890 | SEQ 1683 | 1.00000 | 1.02 |
| TCONS_00000224 | SEQ 1048 | 1.00000 | 1.02 |
| TCONS_00055758 | SEQ 1908 | 1.00000 | 1.02 |
| TCONS_00026652 | SEQ 1428 | 1.00000 | 1.02 |
| TCONS_00026558 | SEQ 1414 | 1.00000 | 1.02 |
| TCONS_00062589 | SEQ 2027 | 1.00000 | 1.01 |
| TCONS_00045341 | SEQ 1778 | 1.00000 | 1.01 |
| TCONS_00000655 | SEQ 1050 | 1.00000 | 1.01 |
| TCONS_00027670 | SEQ 1520 | 1.00000 | 1.01 |
| TCONS_00027708 | SEQ 1530 | 1.00000 | 1.00 |
| TCONS_00062581 | SEQ 2022 | 1.00000 | 1.00 |
| TCONS_00037199 | SEQ 1660 | 1.00000 | 0.99 |
| TCONS_00014388 | SEQ 1236 | 1.00000 | 0.99 |
| TCONS_00050301 | SEQ 1869 | 1.00000 | 0.99 |
| TCONS_00026766 | SEQ 1426 | 1.00000 | 0.98 |
| TCONS_00050728 | SEQ 1880 | 1.00000 | 0.97 |
| TCONS_00040670 | SEQ 1696 | 1.00000 | 0.97 |
| TCONS_00050653 | SEQ 1874 | 1.00000 | 0.97 |
| TCONS_00050536 | SEQ 1826 | 1.00000 | 0.96 |
| TCONS_00027752 | SEQ 1430 | 1.00000 | 0.96 |
| TCONS_00040692 | SEQ 1697 | 1.00000 | 0.96 |
| TCONS_00017410 | SEQ 1281 | 1.00000 | 0.96 |
| TCONS_00023300 | SEQ 1353 | 1.00000 | 0.96 |
| TCONS_00062337 | SEQ 2008 | 1.00000 | 0.96 |
| TCONS_00040918 | SEQ 1692 | 1.00000 | 0.95 |
| TCONS_00059276 | SEQ 1951 | 1.00000 | 0.95 |
| TCONS_00066553 | SEQ 2100 | 1.00000 | 0.95 |
| TCONS_00040901 | SEQ 1687 | 1.00000 | 0.95 |
| TCONS_00062578 | SEQ 2017 | 1.00000 | 0.95 |
| TCONS_00035061 | SEQ 1589 | 1.00000 | 0.95 |
| TCONS_00000281 | SEQ 1056 | 1.00000 | 0.95 |
| TCONS_00066505 | SEQ 2070 | 1.00000 | 0.94 |
| TCONS_00014293 | SEQ 1257 | 1.00000 | 0.94 |
| TCONS_00040974 | SEQ 1710 | 1.00000 | 0.94 |
| TCONS_00040857 | SEQ 1727 | 1.00000 | 0.94 |
| TCONS_00040922 | SEQ 1695 | 1.00000 | 0.94 |
| TCONS_00027709 | SEQ 1531 | 1.00000 | 0.94 |
| TCONS_00019822 | SEQ 1288 | 1.00000 | 0.94 |

TABLE 7-continued

The 1091 novel lncRNAs identified by the invention and fold change and p-value
(differential expression in AD group versus healthy control group).

| lncRNA | SEQ | p-value | FC |
|---|---|---|---|
| TCONS_00036143 | SEQ 1611 | 1.00000 | 0.94 |
| TCONS_00055516 | SEQ 1902 | 1.00000 | 0.94 |
| TCONS_00005003 | SEQ 1126 | 1.00000 | 0.93 |
| TCONS_00035036 | SEQ 1586 | 1.00000 | 0.93 |
| TCONS_00033779 | SEQ 1556 | 1.00000 | 0.93 |
| TCONS_00027753 | SEQ 1431 | 1.00000 | 0.89 |
| TCONS_00044942 | SEQ 1738 | 1.00000 | 0.88 |
| TCONS_00037139 | SEQ 1648 | 1.00000 | 0.88 |
| TCONS_00036041 | SEQ 1612 | 1.00000 | 0.86 |
| TCONS_00036835 | SEQ 1629 | 1.00000 | 0.86 |
| TCONS_00068992 | SEQ 2109 | 1.00000 | 0.85 |
| TCONS_00028116 | SEQ 1517 | 1.00000 | 0.85 |
| TCONS_00059207 | SEQ 1934 | 1.00000 | 0.85 |
| TCONS_00062561 | SEQ 2003 | 1.00000 | 0.84 |
| TCONS_00005060 | SEQ 1140 | 1.00000 | 0.84 |
| TCONS_00066323 | SEQ 2059 | 1.00000 | 0.79 |
| TCONS_00000199 | SEQ 1040 | 1.00000 | 0.78 |
| TCONS_00014424 | SEQ 1251 | 1.00000 | 0.77 |
| TCONS_00050206 | SEQ 1844 | 1.00000 | 0.73 |
| TCONS_00050096 | SEQ 1815 | 1.00000 | 0.72 |
| TCONS_00040833 | SEQ 1724 | 1.00000 | 0.71 |
| TCONS_00059322 | SEQ 1960 | 1.00000 | 0.67 |
| TCONS_00036887 | SEQ 1638 | 1.00000 | 0.61 |
| TCONS_00027663 | SEQ 1512 | 1.00000 | 0.61 |
| TCONS_00055573 | SEQ 1916 | 1.00000 | 0.58 |
| TCONS_00027826 | SEQ 1447 | 1.00000 | 0.52 |

Out of 1091 novel brain lncRNAs (Table 7), 492 lncRNAs showed a fold change >1.1 and 431 lncRNAs showed a fold change <0.9 and represent potential novel therapeutic candidates for silencing or to enhancing such lncRNA in the brain respectively, for treatment of brain disorder, in particular a cognitive disorder such as MCI and Alzheimer.

Out of the 1091 novel brain lncRNAs, some preferred novel lncRNA candidates for use for therapeutic applications with no or limited peripheral side effects are, for example, those novel brain lncRNAs with fold change <0.5 or ≥2 and p value <0.05 in brain and with low or no expression in the peripheral tissues and peripheral body fluids, such as blood.

Out of the total number of 10122 novel and lncRNAs from LINCipedia sequenced by the invention in the AD and control brains and having an expression >5 CPM (median), 1202 lncRNAs, including 42 novel lncRNAs, which all showed a statistically significant differential expression when comparing AD brains to HC brains were identified. These 1202 lncRNAs are listed in Table 8 and represent therapeutic candidates for treatment of cognitive disorders in particular MCI and Alzheimer.

TABLE 8

The 1202 lncRNAs with known sequence identified by the present invention having
a deficient expression (FC ≤ 0.84) or over-expression (FC ≥ 1.22) in human AD brain
temporal cortex versus human healthy control brain temporal cortex.

| lncRNA | SEQ | p-value | FC | AUC | lncRNA | SEQ | p-value | FC | AUC |
|---|---|---|---|---|---|---|---|---|---|
| MIR100HG:20 | SEQ2115 | 0.00794 | 0.01 | 1.00 | NIFK-AS1:24 | SEQ3168 | 0.01587 | 2.70 | 0.96 |
| lnc-CBSL-1:6 | SEQ2117 | 0.00794 | 0.04 | 1.00 | lnc-RABEP2-7:2 | SEQ3172 | 0.01587 | 2.74 | 0.96 |
| lnc-SMIM11B-4:3 | SEQ2118 | 0.00794 | 0.04 | 1.00 | lnc-ZBED4-7:1 | SEQ3173 | 0.01587 | 2.74 | 0.96 |
| CD27-AS1:18 | SEQ2123 | 0.00794 | 0.08 | 1.00 | lnc-GSG1L-1:12 | SEQ3175 | 0.01587 | 2.77 | 0.96 |
| lnc-ZRANB2-2:1 | SEQ0654 | 0.00794 | 0.09 | 1.00 | lnc-SBDS-4:11 | SEQ3176 | 0.01587 | 2.78 | 0.96 |
| MIR4500HG:2 | SEQ2125 | 0.00794 | 0.09 | 1.00 | lnc-OR4F21-3:4 | SEQ3178 | 0.01587 | 2.80 | 0.96 |
| LINC02338:2 | SEQ2127 | 0.00794 | 0.09 | 1.00 | LINC00574:9 | SEQ3179 | 0.01587 | 2.80 | 0.96 |
| lnc-GNA13-2:1 | SEQ2128 | 0.00794 | 0.10 | 1.00 | PSG8-AS1:2 | SEQ3188 | 0.01587 | 2.97 | 0.96 |
| lnc-FOXD4L6-1:5 | SEQ2129 | 0.00794 | 0.11 | 1.00 | lnc-TMEM144-3:1 | SEQ3189 | 0.01587 | 2.97 | 0.96 |
| lnc-ZNF644-1:16 | SEQ2130 | 0.00794 | 0.11 | 1.00 | lnc-RNF24-2:5 | SEQ3190 | 0.01587 | 2.97 | 0.96 |
| lnc-SYT16-4:9 | SEQ2131 | 0.00794 | 0.11 | 1.00 | lnc-ZNF236-7:1 | SEQ3191 | 0.01587 | 2.98 | 0.96 |
| THUMPD3-AS1:27 | SEQ2132 | 0.00794 | 0.12 | 1.00 | lnc-ZNF366-1:1 | SEQ3197 | 0.01587 | 3.05 | 0.96 |
| lnc-POM121L2-2:1 | SEQ2133 | 0.00794 | 0.12 | 1.00 | lnc-ZNF366-1:2 | SEQ3198 | 0.01587 | 3.05 | 0.96 |
| LY86-AS1:12 | SEQ2134 | 0.00794 | 0.13 | 1.00 | ITPKB-AS1:3 | SEQ3199 | 0.01587 | 3.06 | 0.96 |
| lnc-ZEB1-10:2 | SEQ2135 | 0.00794 | 0.14 | 1.00 | DUBR:16 | SEQ3200 | 0.01587 | 3.06 | 0.96 |
| lnc-SLC6A12-2:31 | SEQ2137 | 0.00794 | 0.15 | 1.00 | lnc-FAM71E1-2:9 | SEQ3219 | 0.01587 | 3.34 | 0.96 |
| lnc-SETSIP-2:8 | SEQ2141 | 0.00794 | 0.17 | 1.00 | lnc-ZNF131-1:24 | SEQ3221 | 0.01587 | 3.38 | 0.96 |
| lnc-ST3GAL4-10:12 | SEQ2143 | 0.00794 | 0.17 | 1.00 | XIST:8 | SEQ3227 | 0.01587 | 3.56 | 0.96 |
| lnc-DIS3-4:1 | SEQ2144 | 0.00794 | 0.18 | 1.00 | lnc-GOLGA6L6-14:1 | SEQ3228 | 0.01587 | 3.60 | 0.96 |
| lnc-PMM2-6:2 | SEQ2146 | 0.00794 | 0.18 | 1.00 | lnc-CAPN15-4:1 | SEQ3229 | 0.01587 | 3.66 | 0.96 |
| lnc-S100P-4:9 | SEQ2152 | 0.00794 | 0.20 | 1.00 | lnc-PAICS-3:5 | SEQ3230 | 0.01587 | 3.67 | 0.96 |

TABLE 8-continued

The 1202 lncRNAs with known sequence identified by the present invention having a deficient expression (FC ≤ 0.84) or over-expression (FC ≥ 1.22) in human AD brain temporal cortex versus human healthy control brain temporal cortex.

| lncRNA | SEQ | p-value | FC | AUC | lncRNA | SEQ | p-value | FC | AUC |
|---|---|---|---|---|---|---|---|---|---|
| lnc-KAAG1-1:1 | SEQ2154 | 0.00794 | 0.20 | 1.00 | XIST:10 | SEQ3233 | 0.01587 | 3.74 | 0.96 |
| lnc-POTEI-2:8 | SEQ2155 | 0.00794 | 0.21 | 1.00 | LINC01608:15 | SEQ3240 | 0.01587 | 4.17 | 0.96 |
| lnc-BANP-1:9 | SEQ2160 | 0.00794 | 0.23 | 1.00 | lnc-EMCN-1:1 | SEQ3241 | 0.01587 | 4.17 | 0.96 |
| lnc-ACSBG1-4:1 | SEQ2161 | 0.00794 | 0.23 | 1.00 | LINC02199:5 | SEQ3244 | 0.01587 | 4.21 | 0.96 |
| TPT1-AS1:42 | SEQ2164 | 0.00794 | 0.24 | 1.00 | lnc-ST18-4:2 | SEQ3245 | 0.01587 | 4.22 | 0.96 |
| RFPL1S:26 | SEQ2166 | 0.00794 | 0.24 | 1.00 | XIST:43 | SEQ3248 | 0.01587 | 4.46 | 0.96 |
| RFPL1S:5 | SEQ2167 | 0.00794 | 0.24 | 1.00 | LINC01608:16 | SEQ3250 | 0.01587 | 4.56 | 0.96 |
| lnc-ZMAT3-3:11 | SEQ2169 | 0.00794 | 0.24 | 1.00 | lnc-ENGASE-1:1 | SEQ3252 | 0.01587 | 4.89 | 0.96 |
| SNHG16:10 | SEQ2173 | 0.00794 | 0.25 | 1.00 | WAC-AS1:21 | SEQ3255 | 0.01587 | 5.31 | 0.96 |
| SNHG16:36 | SEQ2174 | 0.00794 | 0.25 | 1.00 | lnc-SLC38A8-4:5 | SEQ3261 | 0.01587 | 5.93 | 0.96 |
| LINC01122:9 | SEQ2175 | 0.00794 | 0.25 | 1.00 | lnc-SBDS-4:6 | SEQ3263 | 0.01587 | 6.66 | 0.96 |
| lnc-SVOP-1:1 | SEQ2179 | 0.00794 | 0.26 | 1.00 | lnc-EIF2AK3-1:6 | SEQ3267 | 0.01587 | 6.96 | 0.96 |
| lnc-ZNF644-1:29 | SEQ2180 | 0.00794 | 0.26 | 1.00 | lnc-LTBP3-2:2 | SEQ3275 | 0.01587 | 24.44 | 0.96 |
| PWRN1:28 | SEQ2187 | 0.00794 | 0.28 | 1.00 | lnc-LTBP3-2:3 | SEQ3277 | 0.01587 | 25.74 | 0.96 |
| RFPL1S:1 | SEQ2191 | 0.00794 | 0.29 | 1.00 | lnc-B3GNT5-11:1 | SEQ2120 | 0.03175 | 0.06 | 0.92 |
| LINC-PINT:16 | SEQ2192 | 0.00794 | 0.29 | 1.00 | lnc-DRICH1-3:22 | SEQ2122 | 0.03175 | 0.08 | 0.92 |
| lnc-LMF1-3:4 | SEQ2202 | 0.00794 | 0.30 | 1.00 | lnc-LAMTOR5-1:1 | SEQ2124 | 0.03175 | 0.09 | 0.92 |
| PWRN1:9 | SEQ2208 | 0.00794 | 0.31 | 1.00 | SLC26A4-AS1:17 | SEQ2136 | 0.03175 | 0.14 | 0.92 |
| ILF3-AS1:6 | SEQ2209 | 0.00794 | 0.31 | 1.00 | lnc-DGCR6-7:12 | SEQ2138 | 0.03175 | 0.16 | 0.92 |
| lnc-ACO1-10:1 | SEQ2213 | 0.00794 | 0.31 | 1.00 | LINC02389:3 | SEQ2140 | 0.03175 | 0.16 | 0.92 |
| lnc-LMF1-3:19 | SEQ2218 | 0.00794 | 0.32 | 1.00 | SNHG16:1 | SEQ2142 | 0.03175 | 0.17 | 0.92 |
| lnc-ZNF518B-2:2 | SEQ2224 | 0.00794 | 0.32 | 1.00 | lnc-SOWAHB-5:10 | SEQ2145 | 0.03175 | 0.18 | 0.92 |
| lnc-NEK6-2:2 | SEQ2226 | 0.00794 | 0.32 | 1.00 | lnc-GRAP-3:3 | SEQ2147 | 0.03175 | 0.18 | 0.92 |
| lnc-SPON2-1:2 | SEQ2237 | 0.00794 | 0.35 | 1.00 | lnc-GRAP-3:1 | SEQ2148 | 0.03175 | 0.18 | 0.92 |
| lnc-DFNA5-2:9 | SEQ2239 | 0.00794 | 0.35 | 1.00 | lnc-SRRD-1:6 | SEQ2149 | 0.03175 | 0.19 | 0.92 |
| lnc-DUSP1-2:1 | SEQ2242 | 0.00794 | 0.35 | 1.00 | lnc-POTEI-2:6 | SEQ2151 | 0.03175 | 0.20 | 0.92 |
| lnc-GABRA2-1:1 | SEQ2243 | 0.00794 | 0.36 | 1.00 | lnc-SNRPN-1:5 | SEQ2153 | 0.03175 | 0.20 | 0.92 |
| lnc-FNBP1L-2:6 | SEQ2246 | 0.00794 | 0.36 | 1.00 | DANT2:6 | SEQ2157 | 0.03175 | 0.21 | 0.92 |
| LY86-AS1:11 | SEQ2252 | 0.00794 | 0.36 | 1.00 | lnc-FBRSL1-3:6 | SEQ2162 | 0.03175 | 0.23 | 0.92 |
| SNHG8:9 | SEQ2255 | 0.00794 | 0.37 | 1.00 | lnc-GLB1L2-4:1 | SEQ2163 | 0.03175 | 0.24 | 0.92 |
| TTC28-AS1:1 | SEQ2262 | 0.00794 | 0.38 | 1.00 | LINC02009:2 | SEQ2170 | 0.03175 | 0.24 | 0.92 |
| lnc-ZCCHC7-2:24 | SEQ2279 | 0.00794 | 0.40 | 1.00 | lnc-FBXO28-1:12 | SEQ2181 | 0.03175 | 0.26 | 0.92 |
| lnc-IER5-3:1 | SEQ2286 | 0.00794 | 0.40 | 1.00 | lnc-EMP1-6:1 | SEQ2182 | 0.03175 | 0.26 | 0.92 |
| lnc-GABBR1-1:2 | SEQ2290 | 0.00794 | 0.40 | 1.00 | MRPL23-AS1:9 | SEQ2183 | 0.03175 | 0.26 | 0.92 |
| lnc-COMMD1-1:1 | SEQ2294 | 0.00794 | 0.41 | 1.00 | MAGI2-AS3:83 | SEQ2184 | 0.03175 | 0.26 | 0.92 |
| lnc-ZNF45-2:5 | SEQ2301 | 0.00794 | 0.41 | 1.00 | LINC00664:11 | SEQ2185 | 0.03175 | 0.27 | 0.92 |
| lnc-ATP6V1C1-12:1 | SEQ2310 | 0.00794 | 0.42 | 1.00 | lnc-ZNF721-4:1 | SEQ2186 | 0.03175 | 0.27 | 0.92 |
| lnc-KPNA2-6:15 | SEQ2322 | 0.00794 | 0.43 | 1.00 | lnc-NPBWR1-11:6 | SEQ2188 | 0.03175 | 0.28 | 0.92 |
| lnc-C11orf94-6:1 | SEQ2324 | 0.00794 | 0.43 | 1.00 | CADM3-AS1:3 | SEQ2189 | 0.03175 | 0.28 | 0.92 |
| lnc-COL3A1-3:1 | SEQ2332 | 0.00794 | 0.43 | 1.00 | lnc-COX7B2-1:1 | SEQ2190 | 0.03175 | 0.29 | 0.92 |
| lnc-AP3S1-4:15 | SEQ2335 | 0.00794 | 0.43 | 1.00 | LINC01476:4 | SEQ2193 | 0.03175 | 0.29 | 0.92 |
| lnc-PUM3-7:1 | SEQ2337 | 0.00794 | 0.44 | 1.00 | lnc-C14orf166-2:5 | SEQ2194 | 0.03175 | 0.30 | 0.92 |
| lnc-EML 1-1:1 | SEQ2344 | 0.00794 | 0.44 | 1.00 | LINC01007:2 | SEQ2196 | 0.03175 | 0.30 | 0.92 |
| lnc-TUBB2A-1:1 | SEQ2358 | 0.00794 | 0.45 | 1.00 | LINC01007:6 | SEQ2197 | 0.03175 | 0.30 | 0.92 |
| OTUD6B-AS1:11 | SEQ2360 | 0.00794 | 0.46 | 1.00 | LINC01007:4 | SEQ2198 | 0.03175 | 0.30 | 0.92 |
| OTUD6B-AS1:9 | SEQ2361 | 0.00794 | 0.46 | 1.00 | lnc-FZD4-1:5 | SEQ2199 | 0.03175 | 0.30 | 0.92 |
| lnc-PRSS22-4:1 | SEQ2362 | 0.00794 | 0.46 | 1.00 | lnc-WNT5A-3:4 | SEQ2200 | 0.03175 | 0.30 | 0.92 |
| lnc-FNDC10-1:4 | SEQ2367 | 0.00794 | 0.46 | 1.00 | lnc-SRGAP2C-5:2 | SEQ2201 | 0.03175 | 0.30 | 0.92 |
| ATP2B1-AS1:5 | SEQ2369 | 0.00794 | 0.46 | 1.00 | MIR4500HG:1 | SEQ2203 | 0.03175 | 0.31 | 0.92 |
| lnc-C7orf77-5:1 | SEQ2370 | 0.00794 | 0.46 | 1.00 | lnc-LRCH1-1:1 | SEQ0437 | 0.03175 | 0.31 | 0.92 |
| lnc-CMTM7-2:3 | SEQ2376 | 0.00794 | 0.46 | 1.00 | lnc-LIPI-11:1 | SEQ2204 | 0.03175 | 0.31 | 0.92 |
| lnc-TEX15-4:1 | SEQ2382 | 0.00794 | 0.46 | 1.00 | LINC00507:2 | SEQ2205 | 0.03175 | 0.31 | 0.92 |
| LINC01128:37 | SEQ2391 | 0.00794 | 0.47 | 1.00 | lnc-KCNA3-4:2 | SEQ2206 | 0.03175 | 0.31 | 0.92 |
| lnc-SNAPC2-2:2 | SEQ2400 | 0.00794 | 0.48 | 1.00 | COPG2IT1:2 | SEQ2207 | 0.03175 | 0.31 | 0.92 |
| lnc-DUSP1-2:2 | SEQ2407 | 0.00794 | 0.48 | 1.00 | HTR5A-AS1:4 | SEQ2210 | 0.03175 | 0.31 | 0.92 |
| lnc-TINCR-3:1 | SEQ2415 | 0.00794 | 0.48 | 1.00 | lnc-KCNA3-4:1 | SEQ2212 | 0.03175 | 0.31 | 0.92 |
| lnc-VSTM5-1:13 | SEQ2419 | 0.00794 | 0.49 | 1.00 | lnc-APH1B-1:1 | SEQ2215 | 0.03175 | 0.31 | 0.92 |
| lnc-MACROD1-5:1 | SEQ2422 | 0.00794 | 0.49 | 1.00 | lnc-NPY5R-4:1 | SEQ0823 | 0.03175 | 0.31 | 0.92 |
| lnc-MASTL-6:1 | SEQ2430 | 0.00794 | 0.49 | 1.00 | lnc-ABCD2-4:1 | SEQ2216 | 0.03175 | 0.32 | 0.92 |
| ZNF529-AS1:14 | SEQ2434 | 0.00794 | 0.49 | 1.00 | lnc-NOL6-6:1 | SEQ2217 | 0.03175 | 0.32 | 0.92 |
| lnc-DPP7-2:2 | SEQ2436 | 0.00794 | 0.49 | 1.00 | lnc-ACOD1-5:1 | SEQ2222 | 0.03175 | 0.32 | 0.92 |
| lnc-EMC3-3:4 | SEQ2441 | 0.00794 | 0.50 | 1.00 | lnc-SIPA1L1-5:1 | SEQ2225 | 0.03175 | 0.32 | 0.92 |
| LINC00667:14 | SEQ2442 | 0.00794 | 0.50 | 1.00 | lnc-CADPS-1:1 | SEQ2227 | 0.03175 | 0.32 | 0.92 |
| lnc-SCPEP1-3:1 | SEQ2448 | 0.00794 | 0.50 | 1.00 | lnc-HDX-2:1 | SEQ2228 | 0.03175 | 0.33 | 0.92 |
| lnc-BBOX1-1:11 | SEQ2450 | 0.00794 | 0.50 | 1.00 | lnc-ZNF816-2:17 | SEQ2229 | 0.03175 | 0.33 | 0.92 |
| lnc-DFNB59-2:22 | SEQ2451 | 0.00794 | 0.50 | 1.00 | lnc-SENP6-3:11 | SEQ2230 | 0.03175 | 0.33 | 0.92 |
| lnc-MTMR2-4:1 | SEQ2456 | 0.00794 | 0.51 | 1.00 | lnc-KCNH5-3:1 | SEQ2232 | 0.03175 | 0.34 | 0.92 |
| lnc-KLHL10-2:1 | SEQ2459 | 0.00794 | 0.51 | 1.00 | lnc-TENM1-4:2 | SEQ2234 | 0.03175 | 0.34 | 0.92 |
| lnc-CCDC7-2:2 | SEQ2460 | 0.00794 | 0.51 | 1.00 | lnc-NYAP2-2:2 | SEQ2236 | 0.03175 | 0.34 | 0.92 |
| RASSF8-AS1:42 | SEQ2467 | 0.00794 | 0.51 | 1.00 | lnc-IL 12RB2-1:1 | SEQ2238 | 0.03175 | 0.35 | 0.92 |
| lnc-POTEI-2:7 | SEQ2476 | 0.00794 | 0.52 | 1.00 | lnc-FAM106A-2:10 | SEQ2240 | 0.03175 | 0.35 | 0.92 |
| lnc-SLC10A7-8:1 | SEQ2484 | 0.00794 | 0.53 | 1.00 | lnc-ENC1-5:1 | SEQ2244 | 0.03175 | 0.36 | 0.92 |
| lnc-TRIML 1-9:1 | SEQ2490 | 0.00794 | 0.53 | 1.00 | lnc-MYF5-2:3 | SEQ2245 | 0.03175 | 0.36 | 0.92 |
| VLDLR-AS1:21 | SEQ2501 | 0.00794 | 0.53 | 1.00 | lnc-TGS1-3:1 | SEQ2251 | 0.03175 | 0.36 | 0.92 |

TABLE 8-continued

The 1202 lncRNAs with known sequence identified by the present invention having a deficient expression (FC ≤ 0.84) or over-expression (FC ≥ 1.22) in human AD brain temporal cortex versus human healthy control brain temporal cortex.

| lncRNA | SEQ | p-value | FC | AUC | lncRNA | SEQ | p-value | FC | AUC |
|---|---|---|---|---|---|---|---|---|---|
| lnc-VAT1-4:1 | SEQ2511 | 0.00794 | 0.54 | 1.00 | lnc-UBE2B-2:1 | SEQ2253 | 0.03175 | 0.37 | 0.92 |
| lnc-NPIPB4-3:2 | SEQ2518 | 0.00794 | 0.54 | 1.00 | lnc-XKR4-3:1 | SEQ2254 | 0.03175 | 0.37 | 0.92 |
| CASC15:17 | SEQ2522 | 0.00794 | 0.54 | 1.00 | lnc-MPPED2-4:1 | SEQ2256 | 0.03175 | 0.37 | 0.92 |
| lnc-PCSK1N-3:3 | SEQ2523 | 0.00794 | 0.54 | 1.00 | LINC01197:31 | SEQ2258 | 0.03175 | 0.37 | 0.92 |
| lnc-MAVS-3:1 | SEQ2534 | 0.00794 | 0.55 | 1.00 | lnc-SMARCA5-4:18 | SEQ0253 | 0.03175 | 0.37 | 0.92 |
| lnc-LRRC57-1:1 | SEQ2537 | 0.00794 | 0.55 | 1.00 | MIR583HG:2 | SEQ2260 | 0.03175 | 0.38 | 0.92 |
| lnc-ESCO2-1:3 | SEQ2554 | 0.00794 | 0.56 | 1.00 | lnc-COL9A2-1:3 | SEQ2261 | 0.03175 | 0.38 | 0.92 |
| lnc-IL31RA-2:1 | SEQ2557 | 0.00794 | 0.56 | 1.00 | lnc-POM121L2-2:3 | SEQ2263 | 0.03175 | 0.38 | 0.92 |
| lnc-ATG12-3:2 | SEQ2558 | 0.00794 | 0.56 | 1.00 | lnc-SYT16-4:15 | SEQ2264 | 0.03175 | 0.38 | 0.92 |
| lnc-FGFBP3-2:3 | SEQ2559 | 0.00794 | 0.56 | 1.00 | lnc-NAA50-3:1 | SEQ2266 | 0.03175 | 0.38 | 0.92 |
| lnc-SPOPL-10:1 | SEQ2567 | 0.00794 | 0.57 | 1.00 | lnc-CTXN1-1:1 | SEQ2267 | 0.03175 | 0.38 | 0.92 |
| lnc-EIF5-2:1 | SEQ2571 | 0.00794 | 0.57 | 1.00 | lnc-DNAH9-4:1 | SEQ2270 | 0.03175 | 0.39 | 0.92 |
| lnc-RAI2-5:1 | SEQ2575 | 0.00794 | 0.57 | 1.00 | lnc-SNRPN-8:19 | SEQ2271 | 0.03175 | 0.39 | 0.92 |
| lnc-MAP1B-2:1 | SEQ2587 | 0.00794 | 0.58 | 1.00 | lnc-PKIA-3:2 | SEQ2273 | 0.03175 | 0.39 | 0.92 |
| lnc-ABTB2-4:2 | SEQ2589 | 0.00794 | 0.58 | 1.00 | lnc-CALN1-2:1 | SEQ2274 | 0.03175 | 0.39 | 0.92 |
| lnc-EIF2B1-1:1 | SEQ2595 | 0.00794 | 0.59 | 1.00 | lnc-CXorf67-1:5 | SEQ2275 | 0.03175 | 0.39 | 0.92 |
| lnc-CHD1L-5:1 | SEQ2596 | 0.00794 | 0.59 | 1.00 | lnc-CES5A-3:14 | SEQ2276 | 0.03175 | 0.39 | 0.92 |
| lnc-ERAL 1-3:2 | SEQ2598 | 0.00794 | 0.59 | 1.00 | SLC8A1-AS1:1 | SEQ2277 | 0.03175 | 0.39 | 0.92 |
| lnc-ERAL 1-3:4 | SEQ2599 | 0.00794 | 0.59 | 1.00 | lnc-STRAP-5:1 | SEQ2280 | 0.03175 | 0.40 | 0.92 |
| lnc-CCDC85C-2:1 | SEQ2601 | 0.00794 | 0.59 | 1.00 | KRTAP5-AS1:12 | SEQ2281 | 0.03175 | 0.40 | 0.92 |
| lnc-DUXA-4:1 | SEQ2603 | 0.00794 | 0.59 | 1.00 | lnc-FAM110C-1:11 | SEQ2282 | 0.03175 | 0.40 | 0.92 |
| lnc-CHMP2B-1:11 | SEQ0679 | 0.00794 | 0.60 | 1.00 | lnc-SOWAHB-5:3 | SEQ2283 | 0.03175 | 0.40 | 0.92 |
| lnc-SSTR2-1:2 | SEQ2604 | 0.00794 | 0.60 | 1.00 | lnc-NEUROD1-3:1 | SEQ2284 | 0.03175 | 0.40 | 0.92 |
| lnc-PAX1-5:1 | SEQ2611 | 0.00794 | 0.60 | 1.00 | lnc-SV2B-3:1 | SEQ2285 | 0.03175 | 0.40 | 0.92 |
| lnc-ASPHD2-2:2 | SEQ2612 | 0.00794 | 0.60 | 1.00 | lnc-METTL22-5:1 | SEQ2287 | 0.03175 | 0.40 | 0.92 |
| lnc-CDC42SE2-1:10 | SEQ2613 | 0.00794 | 0.60 | 1.00 | lnc-LINGO2-2:3 | SEQ2288 | 0.03175 | 0.40 | 0.92 |
| lnc-TMEM154-2:1 | SEQ2616 | 0.00794 | 0.60 | 1.00 | lnc-SPIDR-1:1 | SEQ2292 | 0.03175 | 0.40 | 0.92 |
| lnc-FEM1B-4:1 | SEQ2624 | 0.00794 | 0.61 | 1.00 | lnc-KNSTRN-2:1 | SEQ2293 | 0.03175 | 0.41 | 0.92 |
| lnc-PYGO1-1:1 | SEQ2626 | 0.00794 | 0.61 | 1.00 | lnc-TACR1-1:5 | SEQ2295 | 0.03175 | 0.41 | 0.92 |
| lnc-F2RL2-6:1 | SEQ2628 | 0.00794 | 0.61 | 1.00 | lnc-MYF5-2:4 | SEQ2296 | 0.03175 | 0.41 | 0.92 |
| LINC00205:7 | SEQ2630 | 0.00794 | 0.61 | 1.00 | lnc-SYT16-1:1 | SEQ2297 | 0.03175 | 0.41 | 0.92 |
| THUMPD3-AS1:78 | SEQ2636 | 0.00794 | 0.62 | 1.00 | lnc-FAAP100-2:1 | SEQ2299 | 0.03175 | 0.41 | 0.92 |
| lnc-SLC35F5-3:11 | SEQ2639 | 0.00794 | 0.62 | 1.00 | lnc-DLG5-5:1 | SEQ2302 | 0.03175 | 0.41 | 0.92 |
| lnc-SH3BGRL2-2:14 | SEQ2644 | 0.00794 | 0.62 | 1.00 | lnc-GTF2F2-14:1 | SEQ2304 | 0.03175 | 0.41 | 0.92 |
| lnc-NEMF-2:2 | SEQ2656 | 0.00794 | 0.63 | 1.00 | lnc-ITFG1-2:1 | SEQ2307 | 0.03175 | 0.41 | 0.92 |
| lnc-CCNG1-1:4 | SEQ2660 | 0.00794 | 0.63 | 1.00 | lnc-SYNE2-4:1 | SEQ2308 | 0.03175 | 0.42 | 0.92 |
| lnc-NEMF-2:1 | SEQ2662 | 0.00794 | 0.64 | 1.00 | lnc-CD59-2:5 | SEQ2309 | 0.03175 | 0.42 | 0.92 |
| lnc-NPR2-2:3 | SEQ2685 | 0.00794 | 0.65 | 1.00 | lnc-TNFRSF13B-2:1 | SEQ2311 | 0.03175 | 0.42 | 0.92 |
| lnc-HDGFL2-6:2 | SEQ2688 | 0.00794 | 0.65 | 1.00 | lnc-CHRM3-1:1 | SEQ2312 | 0.03175 | 0.42 | 0.92 |
| lnc-PLEKHA8-3:8 | SEQ2689 | 0.00794 | 0.65 | 1.00 | lnc-PPP5D1-1:1 | SEQ2313 | 0.03175 | 0.42 | 0.92 |
| lnc-TIMM21-5:8 | SEQ2693 | 0.00794 | 0.65 | 1.00 | lnc-ZNF674-1:12 | SEQ2314 | 0.03175 | 0.42 | 0.92 |
| lnc-EYA3-2:2 | SEQ2694 | 0.00794 | 0.65 | 1.00 | lnc-CBLN2-1:1 | SEQ2318 | 0.03175 | 0.43 | 0.92 |
| lnc-ATP6V1C2-2:2 | SEQ2695 | 0.00794 | 0.66 | 1.00 | lnc-SCN2A-7:1 | SEQ2321 | 0.03175 | 0.43 | 0.92 |
| lnc-RBPMS2-3:1 | SEQ2697 | 0.00794 | 0.66 | 1.00 | lnc-ZSCAN2-5:11 | SEQ2323 | 0.03175 | 0.43 | 0.92 |
| lnc-ADAM30-1:1 | SEQ2698 | 0.00794 | 0.66 | 1.00 | lnc-PPFIA4-1:1 | SEQ2325 | 0.03175 | 0.43 | 0.92 |
| lnc-GPR39-9:1 | SEQ2704 | 0.00794 | 0.67 | 1.00 | lnc-XRCC5-3:1 | SEQ2326 | 0.03175 | 0.43 | 0.92 |
| lnc-ITGB8-10:1 | SEQ2706 | 0.00794 | 0.67 | 1.00 | lnc-PLEKHB2-4:3 | SEQ2327 | 0.03175 | 0.43 | 0.92 |
| lnc-ANKRD55-6:1 | SEQ2711 | 0.00794 | 0.68 | 1.00 | LINC00665:2 | SEQ2328 | 0.03175 | 0.43 | 0.92 |
| lnc-CCDC186-1:1 | SEQ2713 | 0.00794 | 0.68 | 1.00 | lnc-CTAGE6-1:1 | SEQ2329 | 0.03175 | 0.43 | 0.92 |
| lnc-YIF1A-8:3 | SEQ2715 | 0.00794 | 0.68 | 1.00 | lnc-MEST-2:1 | SEQ2333 | 0.03175 | 0.43 | 0.92 |
| lnc-NUDT3-1:3 | SEQ2725 | 0.00794 | 0.69 | 1.00 | LINC00630:5 | SEQ2334 | 0.03175 | 0.43 | 0.92 |
| lnc-NAXD-4:1 | SEQ2736 | 0.00794 | 0.70 | 1.00 | MEF2C-AS1:49 | SEQ2336 | 0.03175 | 0.44 | 0.92 |
| lnc-AMMECR1L-1:2 | SEQ2743 | 0.00794 | 0.72 | 1.00 | THAP9-AS1:24 | SEQ2338 | 0.03175 | 0.44 | 0.92 |
| lnc-ZNF718-5:1 | SEQ2744 | 0.00794 | 0.73 | 1.00 | lnc-NHS-2:1 | SEQ2339 | 0.03175 | 0.44 | 0.92 |
| lnc-FAM72D-8:1 | SEQ2753 | 0.00794 | 0.75 | 1.00 | SNHG1:49 | SEQ2340 | 0.03175 | 0.44 | 0.92 |
| DLEU2:32 | SEQ2776 | 0.00794 | 1.32 | 1.00 | lnc-POM121L2-2:2 | SEQ2341 | 0.03175 | 0.44 | 0.92 |
| lnc-FAAH2-1:9 | SEQ2785 | 0.00794 | 1.38 | 1.00 | LIMD1-AS1:5 | SEQ2342 | 0.03175 | 0.44 | 0.92 |
| lnc-NEK6-2:4 | SEQ2786 | 0.00794 | 1.38 | 1.00 | lnc-APOL5-4:1 | SEQ2343 | 0.03175 | 0.44 | 0.92 |
| lnc-NEK6-2:1 | SEQ2787 | 0.00794 | 1.38 | 1.00 | lnc-PAM-1:10 | SEQ2345 | 0.03175 | 0.44 | 0.92 |
| lnc-PTPN14-2:6 | SEQ2790 | 0.00794 | 1.40 | 1.00 | lnc-ZFP69B-1:2 | SEQ2346 | 0.03175 | 0.44 | 0.92 |
| lnc-MAFF-6:1 | SEQ2792 | 0.00794 | 1.41 | 1.00 | lnc-ZFP69B-1:1 | SEQ2347 | 0.03175 | 0.44 | 0.92 |
| lnc-ANXA2R-6:1 | SEQ2793 | 0.00794 | 1.41 | 1.00 | lnc-PDK3-1:1 | SEQ2348 | 0.03175 | 0.44 | 0.92 |
| lnc-SPATA21-4:6 | SEQ2798 | 0.00794 | 1.42 | 1.00 | lnc-KBTBD6-2:1 | SEQ2349 | 0.03175 | 0.45 | 0.92 |
| lnc-ECHDC3-8:1 | SEQ2799 | 0.00794 | 1.44 | 1.00 | lnc-VPS33B-6:1 | SEQ2350 | 0.03175 | 0.45 | 0.92 |
| lnc-RBM19-2:1 | SEQ2800 | 0.00794 | 1.45 | 1.00 | lnc-SMURF1-2:1 | SEQ2351 | 0.03175 | 0.45 | 0.92 |
| CAHM:3 | SEQ2810 | 0.00794 | 1.49 | 1.00 | lnc-CLEC18B-7:5 | SEQ2353 | 0.03175 | 0.45 | 0.92 |
| lnc-OSBPL7-3:2 | SEQ2813 | 0.00794 | 1.49 | 1.00 | lnc-UGT3A2-3:1 | SEQ0389 | 0.03175 | 0.45 | 0.92 |
| lnc-ZNF331-1:1 | SEQ2814 | 0.00794 | 1.49 | 1.00 | lnc-PTPMT1-2:1 | SEQ2354 | 0.03175 | 0.45 | 0.92 |
| lnc-ZNF124-2:4 | SEQ2822 | 0.00794 | 1.52 | 1.00 | lnc-KIF1C-1:14 | SEQ2355 | 0.03175 | 0.45 | 0.92 |
| lnc-MID1-1:14 | SEQ2829 | 0.00794 | 1.53 | 1.00 | lnc-WBP4-2:9 | SEQ2356 | 0.03175 | 0.45 | 0.92 |
| lnc-DERL3-6:1 | SEQ2835 | 0.00794 | 1.55 | 1.00 | LINC01963:3 | SEQ2357 | 0.03175 | 0.45 | 0.92 |
| lnc-NPIPA8-3:1 | SEQ2836 | 0.00794 | 1.55 | 1.00 | LINC-PINT:59 | SEQ2363 | 0.03175 | 0.46 | 0.92 |
| lnc-PIGP-6:2 | SEQ2843 | 0.00794 | 1.56 | 1.00 | lnc-NMD3-1:1 | SEQ2364 | 0.03175 | 0.46 | 0.92 |
| lnc-LRRC56-1:4 | SEQ2844 | 0.00794 | 1.57 | 1.00 | lnc-MPPE1-8:2 | SEQ2365 | 0.03175 | 0.46 | 0.92 |

TABLE 8-continued

The 1202 lncRNAs with known sequence identified by the present invention having a deficient expression (FC ≤ 0.84) or over-expression (FC ≥ 1.22) in human AD brain temporal cortex versus human healthy control brain temporal cortex.

| lncRNA | SEQ | p-value | FC | AUC | lncRNA | SEQ | p-value | FC | AUC |
|---|---|---|---|---|---|---|---|---|---|
| lnc-C19orf47-1:1 | SEQ2848 | 0.00794 | 1.58 | 1.00 | NIPBL-AS1:8 | SEQ2366 | 0.03175 | 0.46 | 0.92 |
| lnc-OCIAD2-3:5 | SEQ2849 | 0.00794 | 1.58 | 1.00 | lnc-HIST2H3D-1:1 | SEQ2368 | 0.03175 | 0.46 | 0.92 |
| lnc-KCNRG-1:1 | SEQ2856 | 0.00794 | 1.59 | 1.00 | lnc-ERCC4-7:1 | SEQ2371 | 0.03175 | 0.46 | 0.92 |
| lnc-ZNF 169-7:4 | SEQ2857 | 0.00794 | 1.59 | 1.00 | lnc-PPP5C-1:2 | SEQ2372 | 0.03175 | 0.46 | 0.92 |
| lnc-NMS-4:1 | SEQ2859 | 0.00794 | 1.59 | 1.00 | lnc-GCGR-1:2 | SEQ2373 | 0.03175 | 0.46 | 0.92 |
| ASAP1-IT2:1 | SEQ2868 | 0.00794 | 1.61 | 1.00 | lnc-TBL1XR1-17:1 | SEQ2374 | 0.03175 | 0.46 | 0.92 |
| lnc-WDR4-2:5 | SEQ2874 | 0.00794 | 1.62 | 1.00 | lnc-AKAP12-2:1 | SEQ2375 | 0.03175 | 0.46 | 0.92 |
| lnc-MAP3K2-4:1 | SEQ2875 | 0.00794 | 1.62 | 1.00 | lnc-KHDC3L-2:3 | SEQ2377 | 0.03175 | 0.46 | 0.92 |
| LINC01000:7 | SEQ2877 | 0.00794 | 1.62 | 1.00 | lnc-RBMS2-4:1 | SEQ2378 | 0.03175 | 0.46 | 0.92 |
| lnc-C19orf47-3:1 | SEQ2881 | 0.00794 | 1.63 | 1.00 | lnc-CACNA2D1-1:1 | SEQ0897 | 0.03175 | 0.46 | 0.92 |
| lnc-ZNF778-1:10 | SEQ2882 | 0.00794 | 1.64 | 1.00 | lnc-IPO5-7:1 | SEQ0521 | 0.03175 | 0.46 | 0.92 |
| LCMT1-AS1:9 | SEQ2883 | 0.00794 | 1.64 | 1.00 | lnc-SOWAHB-5:4 | SEQ2381 | 0.03175 | 0.46 | 0.92 |
| lnc-BIN3-2:1 | SEQ2884 | 0.00794 | 1.64 | 1.00 | MIF-AS1:8 | SEQ2383 | 0.03175 | 0.46 | 0.92 |
| lnc-FABP2-1:1 | SEQ2886 | 0.00794 | 1.65 | 1.00 | lnc-NXNL 1-5:1 | SEQ2384 | 0.03175 | 0.47 | 0.92 |
| lnc-WDR70-5:4 | SEQ2893 | 0.00794 | 1.67 | 1.00 | lnc-ARHGAP6-2:1 | SEQ2385 | 0.03175 | 0.47 | 0.92 |
| lnc-ILKAP-6:1 | SEQ2895 | 0.00794 | 1.68 | 1.00 | lnc-CACNB2-1:1 | SEQ2386 | 0.03175 | 0.47 | 0.92 |
| lnc-CYP2E1-13:1 | SEQ2901 | 0.00794 | 1.69 | 1.00 | lnc-FAM120C-1:1 | SEQ2388 | 0.03175 | 0.47 | 0.92 |
| lnc-ZFP36L1-2:13 | SEQ2904 | 0.00794 | 1.70 | 1.00 | lnc-CENPVL2-3:1 | SEQ2389 | 0.03175 | 0.47 | 0.92 |
| lnc-SCAF11-4:1 | SEQ2908 | 0.00794 | 1.71 | 1.00 | LINC00884:15 | SEQ2390 | 0.03175 | 0.47 | 0.92 |
| lnc-NMRAL 1-4:1 | SEQ2910 | 0.00794 | 1.71 | 1.00 | lnc-LINC00890-7:1 | SEQ2393 | 0.03175 | 0.47 | 0.92 |
| lnc-MNX1-10:1 | SEQ0322 | 0.00794 | 1.72 | 1.00 | lnc-TMCC2-2:1 | SEQ2395 | 0.03175 | 0.47 | 0.92 |
| CACTIN-AS1:5 | SEQ2914 | 0.00794 | 1.73 | 1.00 | lnc-ZNF333-4:2 | SEQ2397 | 0.03175 | 0.48 | 0.92 |
| lnc-FAHD2B-1:2 | SEQ2915 | 0.00794 | 1.73 | 1.00 | PEG3-AS1:1 | SEQ2398 | 0.03175 | 0.48 | 0.92 |
| lnc-LHFPL 1-2:1 | SEQ2916 | 0.00794 | 1.73 | 1.00 | lnc-APTX-3:1 | SEQ2399 | 0.03175 | 0.48 | 0.92 |
| lnc-TAF9-2:3 | SEQ2917 | 0.00794 | 1.74 | 1.00 | lnc-PSEN2-4:1 | SEQ2403 | 0.03175 | 0.48 | 0.92 |
| lnc-PAG1-4:1 | SEQ2928 | 0.00794 | 1.76 | 1.00 | lnc-CMBL-8:2 | SEQ2404 | 0.03175 | 0.48 | 0.92 |
| lnc-ARMCX4-3:1 | SEQ2939 | 0.00794 | 1.79 | 1.00 | LINC00174:21 | SEQ2406 | 0.03175 | 0.48 | 0.92 |
| lnc-ZNF852-2:3 | SEQ2944 | 0.00794 | 1.79 | 1.00 | lnc-C8B-4:1 | SEQ2410 | 0.03175 | 0.48 | 0.92 |
| lnc-STARD10-1:6 | SEQ0840 | 0.00794 | 1.80 | 1.00 | lnc-EVX1-15:1 | SEQ2412 | 0.03175 | 0.48 | 0.92 |
| lnc-SERPIND1-2:1 | SEQ2948 | 0.00794 | 1.80 | 1.00 | lnc-BICD1-1:1 | SEQ2413 | 0.03175 | 0.48 | 0.92 |
| lnc-PMM2-2:4 | SEQ2955 | 0.00794 | 1.82 | 1.00 | lnc-SESN1-5:1 | SEQ2414 | 0.03175 | 0.48 | 0.92 |
| lnc-CRYM-4:1 | SEQ2958 | 0.00794 | 1.84 | 1.00 | lnc-DTNA-5:1 | SEQ2416 | 0.03175 | 0.48 | 0.92 |
| lnc-PRR26-5:1 | SEQ2961 | 0.00794 | 1.85 | 1.00 | MIR 100HG:97 | SEQ2417 | 0.03175 | 0.49 | 0.92 |
| lnc-THAP3-2:2 | SEQ2979 | 0.00794 | 1.91 | 1.00 | OIP5-AS1:4 | SEQ2423 | 0.03175 | 0.49 | 0.92 |
| lnc-NOP9-1:2 | SEQ2990 | 0.00794 | 1.94 | 1.00 | lnc-AP3S1-4:3 | SEQ2424 | 0.03175 | 0.49 | 0.92 |
| lnc-PRPF40B-1:2 | SEQ2997 | 0.00794 | 1.95 | 1.00 | lnc-SCAF4-1:2 | SEQ2425 | 0.03175 | 0.49 | 0.92 |
| lnc-SAMD11-14:1 | SEQ3001 | 0.00794 | 1.97 | 1.00 | lnc-SNRPN-8:5 | SEQ2426 | 0.03175 | 0.49 | 0.92 |
| lnc-STX8-4:1 | SEQ3002 | 0.00794 | 1.97 | 1.00 | lnc-SRPRB-1:1 | SEQ2427 | 0.03175 | 0.49 | 0.92 |
| lnc-NRDE2-3:1 | SEQ3003 | 0.00794 | 1.98 | 1.00 | lnc-SLC3A2-6:1 | SEQ2428 | 0.03175 | 0.49 | 0.92 |
| lnc-SLC29A4-5:5 | SEQ3004 | 0.00794 | 1.99 | 1.00 | lnc-TMEM185B-9:1 | SEQ2432 | 0.03175 | 0.49 | 0.92 |
| lnc-SZT2-2:3 | SEQ3006 | 0.00794 | 2.00 | 1.00 | lnc-FGF13-1:1 | SEQ2435 | 0.03175 | 0.49 | 0.92 |
| lnc-SLC39A11-1:34 | SEQ3008 | 0.00794 | 2.00 | 1.00 | lnc-CHMP2B-5:1 | SEQ2437 | 0.03175 | 0.50 | 0.92 |
| lnc-MAFF-2:1 | SEQ3013 | 0.00794 | 2.01 | 1.00 | lnc-LASP1-5:1 | SEQ2438 | 0.03175 | 0.50 | 0.92 |
| lnc-ATP6VOE2-1:1 | SEQ3014 | 0.00794 | 2.01 | 1.00 | lnc-DAPP1-8:3 | SEQ2439 | 0.03175 | 0.50 | 0.92 |
| lnc-PHB2-7:1 | SEQ3018 | 0.00794 | 2.02 | 1.00 | SOX1-OT:5 | SEQ2440 | 0.03175 | 0.50 | 0.92 |
| lnc-AGRP-1:26 | SEQ3020 | 0.00794 | 2.04 | 1.00 | lnc-AADACL2-4:1 | SEQ2443 | 0.03175 | 0.50 | 0.92 |
| lnc-PPARA-3:13 | SEQ3022 | 0.00794 | 2.04 | 1.00 | SLC8A1-AS1:32 | SEQ2444 | 0.03175 | 0.50 | 0.92 |
| lnc-USP6-2:20 | SEQ3027 | 0.00794 | 2.05 | 1.00 | SNHG6:10 | SEQ2446 | 0.03175 | 0.50 | 0.92 |
| lnc-CANX-1:10 | SEQ3029 | 0.00794 | 2.06 | 1.00 | lnc-SLC25A3-7:1 | SEQ2447 | 0.03175 | 0.50 | 0.92 |
| lnc-ZMYND19-2:1 | SEQ3032 | 0.00794 | 2.06 | 1.00 | lnc-GBP2-1:2 | SEQ2449 | 0.03175 | 0.50 | 0.92 |
| lnc-DHRS7B-1:6 | SEQ3034 | 0.00794 | 2.06 | 1.00 | lnc-MRPS14-1:6 | SEQ2452 | 0.03175 | 0.50 | 0.92 |
| lnc-LEF1-3:13 | SEQ3036 | 0.00794 | 2.07 | 1.00 | lnc-FZD4-1:6 | SEQ2454 | 0.03175 | 0.51 | 0.92 |
| SMCR5:1 | SEQ3037 | 0.00794 | 2.07 | 1.00 | lnc-ZNF275-4:1 | SEQ2455 | 0.03175 | 0.51 | 0.92 |
| SRP14-AS1:20 | SEQ3039 | 0.00794 | 2.08 | 1.00 | lnc-CIB1-1:1 | SEQ2457 | 0.03175 | 0.51 | 0.92 |
| lnc-ERMARD-2:6 | SEQ3042 | 0.00794 | 2.09 | 1.00 | lnc-TMEM57-1:2 | SEQ2461 | 0.03175 | 0.51 | 0.92 |
| lnc-C8orf48-7:1 | SEQ3046 | 0.00794 | 2.10 | 1.00 | lnc-FOXM1-1:1 | SEQ2462 | 0.03175 | 0.51 | 0.92 |
| lnc-PPARA-3:7 | SEQ3050 | 0.00794 | 2.12 | 1.00 | lnc-CKAP2L-2:1 | SEQ2463 | 0.03175 | 0.51 | 0.92 |
| lnc-MISP3-5:1 | SEQ3052 | 0.00794 | 2.13 | 1.00 | RNF219-AS1:17 | SEQ2464 | 0.03175 | 0.51 | 0.92 |
| lnc-NAV1-9:6 | SEQ3053 | 0.00794 | 2.13 | 1.00 | lnc-DEFB115-5:2 | SEQ2465 | 0.03175 | 0.51 | 0.92 |
| lnc-HEATR4-5:1 | SEQ3063 | 0.00794 | 2.16 | 1.00 | lnc-POLD3-1:2 | SEQ2469 | 0.03175 | 0.52 | 0.92 |
| lnc-TEF-1:1 | SEQ3075 | 0.00794 | 2.21 | 1.00 | lnc-ZNF587-2:1 | SEQ2470 | 0.03175 | 0.52 | 0.92 |
| lnc-ZNF541-4:1 | SEQ3078 | 0.00794 | 2.21 | 1.00 | lnc-CENPM-4:1 | SEQ2475 | 0.03175 | 0.52 | 0.92 |
| HDAC2-AS2:10 | SEQ3080 | 0.00794 | 2.22 | 1.00 | lnc-MTA3-7:2 | SEQ2477 | 0.03175 | 0.52 | 0.92 |
| lnc-CAND2-2:5 | SEQ3083 | 0.00794 | 2.23 | 1.00 | lnc-GPR180-8:1 | SEQ2478 | 0.03175 | 0.52 | 0.92 |
| lnc-CAND2-2:6 | SEQ3084 | 0.00794 | 2.23 | 1.00 | lnc-DNAL 1-1:1 | SEQ2480 | 0.03175 | 0.52 | 0.92 |
| lnc-CD40LG-2:9 | SEQ3085 | 0.00794 | 2.24 | 1.00 | lnc-SUMF1-18:1 | SEQ2482 | 0.03175 | 0.52 | 0.92 |
| lnc-PHYHD1-1:1 | SEQ3086 | 0.00794 | 2.24 | 1.00 | lnc-BAZ1A-2:1 | SEQ2485 | 0.03175 | 0.53 | 0.92 |
| lnc-PDYN-1:9 | SEQ3089 | 0.00794 | 2.26 | 1.00 | lnc-POTEI-2:11 | SEQ2488 | 0.03175 | 0.53 | 0.92 |
| lnc-MB-6:1 | SEQ3094 | 0.00794 | 2.27 | 1.00 | lnc-AACS-5:1 | SEQ2489 | 0.03175 | 0.53 | 0.92 |
| lnc-DNAL4-4:1 | SEQ3095 | 0.00794 | 2.28 | 1.00 | lnc-MOCS1-3:1 | SEQ2491 | 0.03175 | 0.53 | 0.92 |
| lnc-CTXN1-6:1 | SEQ3096 | 0.00794 | 2.28 | 1.00 | lnc-TFRC-7:2 | SEQ2492 | 0.03175 | 0.53 | 0.92 |
| lnc-TUBA1C-1:14 | SEQ3099 | 0.00794 | 2.29 | 1.00 | lnc-PSMC5-4:1 | SEQ2496 | 0.03175 | 0.53 | 0.92 |
| lnc-SHC3-5:3 | SEQ3102 | 0.00794 | 2.30 | 1.00 | lnc-CCDC125-1:6 | SEQ2497 | 0.03175 | 0.53 | 0.92 |
| lnc-SNRNP35-2:1 | SEQ3103 | 0.00794 | 2.30 | 1.00 | lnc-NDUFAB1-1:1 | SEQ2498 | 0.03175 | 0.53 | 0.92 |

TABLE 8-continued

The 1202 lncRNAs with known sequence identified by the present invention having a deficient expression (FC ≤ 0.84) or over-expression (FC ≥ 1.22) in human AD brain temporal cortex versus human healthy control brain temporal cortex.

| lncRNA | SEQ | p-value | FC | AUC | lncRNA | SEQ | p-value | FC | AUC |
|---|---|---|---|---|---|---|---|---|---|
| ATXN2-AS:5 | SEQ3104 | 0.00794 | 2.30 | 1.00 | lnc-ZNF41-2:1 | SEQ2499 | 0.03175 | 0.53 | 0.92 |
| lnc-CHRNE-4:1 | SEQ3106 | 0.00794 | 2.32 | 1.00 | lnc-C12orf40-1:1 | SEQ2500 | 0.03175 | 0.53 | 0.92 |
| lnc-MEGF6-2:1 | SEQ3107 | 0.00794 | 2.32 | 1.00 | lnc-EXTL3-2:2 | SEQ2502 | 0.03175 | 0.53 | 0.92 |
| lnc-CCDC146-4:6 | SEQ3108 | 0.00794 | 2.32 | 1.00 | lnc-ZFYVE9-2:2 | SEQ2503 | 0.03175 | 0.53 | 0.92 |
| lnc-UBE2H-2:3 | SEQ3112 | 0.00794 | 2.32 | 1.00 | lnc-PXN-1:1 | SEQ2506 | 0.03175 | 0.53 | 0.92 |
| lnc-SLC25A6-4:1 | SEQ3114 | 0.00794 | 2.32 | 1.00 | lnc-RPIA-1:4 | SEQ2507 | 0.03175 | 0.54 | 0.92 |
| lnc-POFUT2-5:1 | SEQ3120 | 0.00794 | 2.37 | 1.00 | lnc-REL-1:3 | SEQ2508 | 0.03175 | 0.54 | 0.92 |
| lnc-GNG13-5:1 | SEQ3121 | 0.00794 | 2.37 | 1.00 | lnc-SBDS-19:2 | SEQ2509 | 0.03175 | 0.54 | 0.92 |
| lnc-SEC24A-1:1 | SEQ3126 | 0.00794 | 2.41 | 1.00 | lnc-GFOD1-2:1 | SEQ2510 | 0.03175 | 0.54 | 0.92 |
| lnc-USP34-1:10 | SEQ3127 | 0.00794 | 2.42 | 1.00 | lnc-ZNF33B-6:1 | SEQ0394 | 0.03175 | 0.54 | 0.92 |
| lnc-RDH13-4:1 | SEQ3134 | 0.00794 | 2.44 | 1.00 | lnc-TACSTD2-2:4 | SEQ0020 | 0.03175 | 0.54 | 0.92 |
| lnc-PHB2-6:1 | SEQ3135 | 0.00794 | 2.45 | 1.00 | lnc-YTHDF3-6:3 | SEQ2514 | 0.03175 | 0.54 | 0.92 |
| lnc-DPH1-1:2 | SEQ3136 | 0.00794 | 2.45 | 1.00 | lnc-YTHDF3-6:1 | SEQ2515 | 0.03175 | 0.54 | 0.92 |
| lnc-BAZ1A-4:1 | SEQ3138 | 0.00794 | 2.46 | 1.00 | lnc-CENPV-2:1 | SEQ2516 | 0.03175 | 0.54 | 0.92 |
| lnc-PDE6B-1:11 | SEQ3140 | 0.00794 | 2.47 | 1.00 | lnc-DUSP1-6:1 | SEQ2517 | 0.03175 | 0.54 | 0.92 |
| lnc-SBDS-4:9 | SEQ3145 | 0.00794 | 2.50 | 1.00 | lnc-MOV10-2:1 | SEQ2519 | 0.03175 | 0.54 | 0.92 |
| lnc-PAXIP1-3:2 | SEQ3147 | 0.00794 | 2.50 | 1.00 | lnc-SHC3-1:2 | SEQ2520 | 0.03175 | 0.54 | 0.92 |
| lnc-NKX2-2-2:2 | SEQ3150 | 0.00794 | 2.52 | 1.00 | lnc-LEKR1-4:9 | SEQ2521 | 0.03175 | 0.54 | 0.92 |
| lnc-NLN-3:1 | SEQ3152 | 0.00794 | 2.53 | 1.00 | lnc-EIF2B1-6:1 | SEQ2524 | 0.03175 | 0.54 | 0.92 |
| lnc-SMG1-1:9 | SEQ3156 | 0.00794 | 2.57 | 1.00 | lnc-HSD11B2-1:1 | SEQ2525 | 0.03175 | 0.54 | 0.92 |
| lnc-RIPOR1-1:7 | SEQ3158 | 0.00794 | 2.57 | 1.00 | lnc-UGDH-3:3 | SEQ2526 | 0.03175 | 0.54 | 0.92 |
| lnc-SAMD11-10:1 | SEQ3159 | 0.00794 | 2.59 | 1.00 | lnc-CBY3-3:2 | SEQ2527 | 0.03175 | 0.54 | 0.92 |
| lnc-MOCS1-1:6 | SEQ3160 | 0.00794 | 2.59 | 1.00 | lnc-C14orf28-2:1 | SEQ2528 | 0.03175 | 0.54 | 0.92 |
| lnc-ANKRD9-1:1 | SEQ3162 | 0.00794 | 2.62 | 1.00 | lnc-FAM60A-3:1 | SEQ2531 | 0.03175 | 0.54 | 0.92 |
| MIR663AHG:66 | SEQ3165 | 0.00794 | 2.67 | 1.00 | lnc-DHX33-1:1 | SEQ2533 | 0.03175 | 0.55 | 0.92 |
| lnc-MOCS1-6:1 | SEQ3167 | 0.00794 | 2.70 | 1.00 | lnc-ARSG-2:8 | SEQ2535 | 0.03175 | 0.55 | 0.92 |
| lnc-HNRNPU-8:1 | SEQ3170 | 0.00794 | 2.72 | 1.00 | lnc-CA6-8:1 | SEQ2536 | 0.03175 | 0.55 | 0.92 |
| lnc-KIAA0141-1:2 | SEQ3171 | 0.00794 | 2.74 | 1.00 | lnc-DEFB115-5:3 | SEQ2538 | 0.03175 | 0.55 | 0.92 |
| lnc-HMOX1-2:2 | SEQ3174 | 0.00794 | 2.75 | 1.00 | lnc-PNLIPRP1-1:2 | SEQ2540 | 0.03175 | 0.55 | 0.92 |
| lnc-HDGFL2-7:1 | SEQ3180 | 0.00794 | 2.83 | 1.00 | lnc-FAM104A-2:1 | SEQ2542 | 0.03175 | 0.55 | 0.92 |
| lnc-UBASH3A-6:2 | SEQ3182 | 0.00794 | 2.91 | 1.00 | lnc-KCNA3-3:6 | SEQ2546 | 0.03175 | 0.55 | 0.92 |
| SLC2A1-AS1:15 | SEQ3183 | 0.00794 | 2.94 | 1.00 | lnc-PNLIPRP1-1:3 | SEQ2548 | 0.03175 | 0.55 | 0.92 |
| TRPM2-AS:5 | SEQ3184 | 0.00794 | 2.95 | 1.00 | lnc-KIAA1586-4:1 | SEQ2549 | 0.03175 | 0.55 | 0.92 |
| lnc-AGO2-2:3 | SEQ0668 | 0.00794 | 2.95 | 1.00 | lnc-H2AFJ-2:7 | SEQ2551 | 0.03175 | 0.56 | 0.92 |
| lnc-DENND1A-5:1 | SEQ3185 | 0.00794 | 2.96 | 1.00 | lnc-MED14-6:1 | SEQ2552 | 0.03175 | 0.56 | 0.92 |
| lnc-MOCS1-1:5 | SEQ3186 | 0.00794 | 2.96 | 1.00 | lnc-LRRC63-6:2 | SEQ2555 | 0.03175 | 0.56 | 0.92 |
| lnc-IL3RA-1:24 | SEQ3193 | 0.00794 | 3.02 | 1.00 | lnc-MAPK6-5:1 | SEQ2556 | 0.03175 | 0.56 | 0.92 |
| lnc-GRAP-1:1 | SEQ3195 | 0.00794 | 3.04 | 1.00 | lnc-CHN1-5:11 | SEQ0419 | 0.03175 | 0.56 | 0.92 |
| lnc-ANKRD13A-5:1 | SEQ3196 | 0.00794 | 3.05 | 1.00 | lnc-ARHGAP28-10:4 | SEQ2560 | 0.03175 | 0.56 | 0.92 |
| lnc-SPANXB1-5:4 | SEQ3202 | 0.00794 | 3.10 | 1.00 | lnc-AIDA-1:1 | SEQ2562 | 0.03175 | 0.56 | 0.92 |
| PACRG-AS3:6 | SEQ3204 | 0.00794 | 3.13 | 1.00 | lnc-CLDN19-3:1 | SEQ2564 | 0.03175 | 0.56 | 0.92 |
| lnc-ANKRD13A-5:3 | SEQ3206 | 0.00794 | 3.14 | 1.00 | lnc-TOR1AIP1-2:1 | SEQ2565 | 0.03175 | 0.57 | 0.92 |
| lnc-BCL2L13-4:1 | SEQ3208 | 0.00794 | 3.15 | 1.00 | lnc-DLGAP5-2:1 | SEQ2566 | 0.03175 | 0.57 | 0.92 |
| lnc-TFF3-1:1 | SEQ3209 | 0.00794 | 3.15 | 1.00 | lnc-TMEM55A-6:1 | SEQ2568 | 0.03175 | 0.57 | 0.92 |
| lnc-ZNF585B-5:7 | SEQ3212 | 0.00794 | 3.20 | 1.00 | lnc-ABTB1-1:1 | SEQ2569 | 0.03175 | 0.57 | 0.92 |
| MALAT1:25 | SEQ3213 | 0.00794 | 3.21 | 1.00 | lnc-KMT2C-1:1 | SEQ2570 | 0.03175 | 0.57 | 0.92 |
| lnc-ACSBG2-2:3 | SEQ3214 | 0.00794 | 3.23 | 1.00 | lnc-GNA14-3:1 | SEQ2572 | 0.03175 | 0.57 | 0.92 |
| lnc-HIPK2-1:1 | SEQ3215 | 0.00794 | 3.23 | 1.00 | lnc-ATG2B-9:2 | SEQ2576 | 0.03175 | 0.57 | 0.92 |
| LINC01159:14 | SEQ3216 | 0.00794 | 3.27 | 1.00 | lnc-IL 13RA2-3:1 | SEQ2577 | 0.03175 | 0.57 | 0.92 |
| lnc-TMEM53-2:1 | SEQ3218 | 0.00794 | 3.29 | 1.00 | lnc-SHB-4:1 | SEQ2579 | 0.03175 | 0.57 | 0.92 |
| MIR646HG:26 | SEQ3222 | 0.00794 | 3.38 | 1.00 | lnc-SLC25A32-9:1 | SEQ2581 | 0.03175 | 0.58 | 0.92 |
| lnc-MUSK-3:1 | SEQ3224 | 0.00794 | 3.39 | 1.00 | OIP5-AS1:10 | SEQ2582 | 0.03175 | 0.58 | 0.92 |
| lnc-TMEM53-1:1 | SEQ3226 | 0.00794 | 3.47 | 1.00 | OIP5-AS1:34 | SEQ2583 | 0.03175 | 0.58 | 0.92 |
| lnc-NAIP-5:1 | SEQ3231 | 0.00794 | 3.68 | 1.00 | lnc-SPRED2-22:1 | SEQ2584 | 0.03175 | 0.58 | 0.92 |
| lnc-ZNF236-1:7 | SEQ3232 | 0.00794 | 3.73 | 1.00 | NORAD:8 | SEQ2585 | 0.03175 | 0.58 | 0.92 |
| TSIX:1 | SEQ3234 | 0.00794 | 3.78 | 1.00 | lnc-PHIP-3:1 | SEQ2586 | 0.03175 | 0.58 | 0.92 |
| lnc-MPHOSPH10-2:1 | SEQ3236 | 0.00794 | 3.86 | 1.00 | lnc-MAN2A2-2:3 | SEQ2588 | 0.03175 | 0.58 | 0.92 |
| lnc-ENGASE-4:1 | SEQ3237 | 0.00794 | 3.97 | 1.00 | lnc-DCAF8-1:1 | SEQ2590 | 0.03175 | 0.58 | 0.92 |
| HDAC2-AS2:35 | SEQ3239 | 0.00794 | 4.10 | 1.00 | lnc-MBOAT4-2:1 | SEQ2592 | 0.03175 | 0.58 | 0.92 |
| lnc-SPANXB1-5:3 | SEQ3242 | 0.00794 | 4.19 | 1.00 | lnc-FOXD4L5-18:4 | SEQ2593 | 0.03175 | 0.58 | 0.92 |
| lnc-ZNF236-1:6 | SEQ3246 | 0.00794 | 4.26 | 1.00 | lnc-SPINK2-4:1 | SEQ2594 | 0.03175 | 0.59 | 0.92 |
| lnc-THOC1-3:1 | SEQ3247 | 0.00794 | 4.41 | 1.00 | lnc-MLH1-1:1 | SEQ2597 | 0.03175 | 0.59 | 0.92 |
| lnc-TARDBP-5:6 | SEQ3249 | 0.00794 | 4.51 | 1.00 | lnc-AHCY-4:1 | SEQ2600 | 0.03175 | 0.59 | 0.92 |
| lnc-GPR37-1:1 | SEQ0926 | 0.00794 | 4.72 | 1.00 | lnc-MCTS1-2:1 | SEQ2602 | 0.03175 | 0.59 | 0.92 |
| LINC01608:9 | SEQ3251 | 0.00794 | 4.76 | 1.00 | lnc-SCD-2:4 | SEQ2606 | 0.03175 | 0.60 | 0.92 |
| SRP14-AS1:28 | SEQ3253 | 0.00794 | 5.10 | 1.00 | lnc-FAM103A1-2:5 | SEQ2607 | 0.03175 | 0.60 | 0.92 |
| lnc-CXorf51B-1:1 | SEQ3257 | 0.00794 | 5.47 | 1.00 | lnc-SURF2-4:1 | SEQ2609 | 0.03175 | 0.60 | 0.92 |
| lnc-ZNF608-20:2 | SEQ3258 | 0.00794 | 5.65 | 1.00 | lnc-HAO2-2:26 | SEQ2610 | 0.03175 | 0.60 | 0.92 |
| lnc-LEF1-3:4 | SEQ3259 | 0.00794 | 5.77 | 1.00 | SNHG7:15 | SEQ2614 | 0.03175 | 0.60 | 0.92 |
| LINC01515:31 | SEQ3260 | 0.00794 | 5.90 | 1.00 | lnc-HMG20A-6:1 | SEQ2615 | 0.03175 | 0.60 | 0.92 |
| lnc-BCL2L13-5:2 | SEQ3262 | 0.00794 | 6.65 | 1.00 | lnc-PANK3-13:2 | SEQ2618 | 0.03175 | 0.60 | 0.92 |
| lnc-LTBP3-2:6 | SEQ3264 | 0.00794 | 6.67 | 1.00 | lnc-ATCAY-1:1 | SEQ2619 | 0.03175 | 0.60 | 0.92 |
| NR2F1-AS1:49 | SEQ3265 | 0.00794 | 6.78 | 1.00 | EIF3J-AS1:21 | SEQ0261 | 0.03175 | 0.61 | 0.92 |
| LINC01608:12 | SEQ3266 | 0.00794 | 6.91 | 1.00 | lnc-DNAH8-2:6 | SEQ2620 | 0.03175 | 0.61 | 0.92 |

TABLE 8-continued

The 1202 lncRNAs with known sequence identified by the present invention having a deficient expression (FC ≤ 0.84) or over-expression (FC ≥ 1.22) in human AD brain temporal cortex versus human healthy control brain temporal cortex.

| lncRNA | SEQ | p-value | FC | AUC | lncRNA | SEQ | p-value | FC | AUC |
|---|---|---|---|---|---|---|---|---|---|
| lnc-NMUR2-4:1 | SEQ3268 | 0.00794 | 6.99 | 1.00 | lnc-ATOX1-4:1 | SEQ2621 | 0.03175 | 0.61 | 0.92 |
| LINC-PINT:27 | SEQ3269 | 0.00794 | 8.08 | 1.00 | lnc-AGAP2-1:4 | SEQ2622 | 0.03175 | 0.61 | 0.92 |
| lnc-DRICH1-3:26 | SEQ3271 | 0.00794 | 8.28 | 1.00 | lnc-HRASLS-5:3 | SEQ2623 | 0.03175 | 0.61 | 0.92 |
| MALAT1:23 | SEQ3272 | 0.00794 | 10.88 | 1.00 | lnc-HMGCS1-3:1 | SEQ2627 | 0.03175 | 0.61 | 0.92 |
| MALAT1:48 | SEQ3273 | 0.00794 | 10.88 | 1.00 | lnc-PANK3-13:1 | SEQ2629 | 0.03175 | 0.61 | 0.92 |
| lnc-BAHCC1-2:1 | SEQ3274 | 0.00794 | 12.21 | 1.00 | lnc-FAM174A-6:2 | SEQ2631 | 0.03175 | 0.62 | 0.92 |
| lnc-NDUFB4-1:3 | SEQ2116 | 0.01116 | 0.02 | 1.00 | lnc-UCHL3-1:1 | SEQ2632 | 0.03175 | 0.62 | 0.92 |
| lnc-CTH-14:1 | SEQ2121 | 0.01193 | 0.07 | 1.00 | lnc-PALLD-8:1 | SEQ2633 | 0.03175 | 0.62 | 0.92 |
| lnc-ZNF717-4:8 | SEQ2119 | 0.01587 | 0.04 | 0.96 | lnc-ZNF596-9:2 | SEQ2634 | 0.03175 | 0.62 | 0.92 |
| lnc-PSMB9-6:1 | SEQ2126 | 0.01587 | 0.09 | 0.96 | lnc-PTAR1-4:1 | SEQ2638 | 0.03175 | 0.62 | 0.92 |
| lnc-SYT16-4:11 | SEQ2139 | 0.01587 | 0.16 | 0.96 | lnc-GLRX2-1:2 | SEQ2640 | 0.03175 | 0.62 | 0.92 |
| lnc-ZNF705B-3:1 | SEQ2150 | 0.01587 | 0.20 | 0.96 | lnc-PHOSPHO2-2:1 | SEQ2641 | 0.03175 | 0.62 | 0.92 |
| lnc-DIRC3-1:4 | SEQ2156 | 0.01587 | 0.21 | 0.96 | lnc-KLHL28-3:5 | SEQ2642 | 0.03175 | 0.62 | 0.92 |
| lnc-NID2-2:1 | SEQ2158 | 0.01587 | 0.22 | 0.96 | CASC2:1 | SEQ2645 | 0.03175 | 0.62 | 0.92 |
| lnc-SYT16-4:10 | SEQ2159 | 0.01587 | 0.23 | 0.96 | lnc-KIF1C-1:2 | SEQ2646 | 0.03175 | 0.62 | 0.92 |
| lnc-MED10-3:1 | SEQ2165 | 0.01587 | 0.24 | 0.96 | lnc-STARD8-3:1 | SEQ2647 | 0.03175 | 0.63 | 0.92 |
| lnc-PRSS27-4:24 | SEQ2168 | 0.01587 | 0.24 | 0.96 | lnc-ASXL 1-3:1 | SEQ2650 | 0.03175 | 0.63 | 0.92 |
| lnc-SCARB2-1:4 | SEQ2171 | 0.01587 | 0.25 | 0.96 | lnc-LPCAT3-1:1 | SEQ2652 | 0.03175 | 0.63 | 0.92 |
| lnc-GAPT-10:1 | SEQ2172 | 0.01587 | 0.25 | 0.96 | MCPH1-AS1:2 | SEQ0308 | 0.03175 | 0.63 | 0.92 |
| CERNA1:2 | SEQ2176 | 0.01587 | 0.25 | 0.96 | ZFAS1:23 | SEQ2657 | 0.03175 | 0.63 | 0.92 |
| lnc-HNRNPA2B1-15:16 | SEQ2177 | 0.01587 | 0.25 | 0.96 | lnc-SSB-2:1 | SEQ2661 | 0.03175 | 0.63 | 0.92 |
| THAP9-AS1:27 | SEQ2178 | 0.01587 | 0.25 | 0.96 | lnc-KANSL2-1:2 | SEQ2664 | 0.03175 | 0.64 | 0.92 |
| lnc-LIPI-7:1 | SEQ2195 | 0.01587 | 0.30 | 0.96 | lnc-BICRAL-3:1 | SEQ2666 | 0.03175 | 0.64 | 0.92 |
| lnc-PRDM4-6:5 | SEQ2211 | 0.01587 | 0.31 | 0.96 | lnc-USP53-8:5 | SEQ2668 | 0.03175 | 0.64 | 0.92 |
| lnc-SOCS6-10:1 | SEQ2214 | 0.01587 | 0.31 | 0.96 | LINC01124:11 | SEQ2670 | 0.03175 | 0.64 | 0.92 |
| lnc-UNC80-1:1 | SEQ2219 | 0.01587 | 0.32 | 0.96 | lnc-TARBP1-6:1 | SEQ2671 | 0.03175 | 0.64 | 0.92 |
| lnc-SYT16-4:3 | SEQ2220 | 0.01587 | 0.32 | 0.96 | lnc-MRPS16-2:4 | SEQ2674 | 0.03175 | 0.64 | 0.92 |
| lnc-SYT16-4:6 | SEQ2221 | 0.01587 | 0.32 | 0.96 | lnc-SIDT2-2:2 | SEQ2675 | 0.03175 | 0.64 | 0.92 |
| lnc-SMARCA5-4:7 | SEQ2223 | 0.01587 | 0.32 | 0.96 | lnc-C11orf94-1:1 | SEQ2676 | 0.03175 | 0.64 | 0.92 |
| lnc-USP17L7-1:1 | SEQ0746 | 0.01587 | 0.33 | 0.96 | lnc-GNA11-3:1 | SEQ2681 | 0.03175 | 0.65 | 0.92 |
| LINC00630:38 | SEQ2231 | 0.01587 | 0.33 | 0.96 | lnc-BTBD1-2:1 | SEQ2683 | 0.03175 | 0.65 | 0.92 |
| lnc-GUCY1A3-1:1 | SEQ0520 | 0.01587 | 0.34 | 0.96 | lnc-MZT2A-19:1 | SEQ2684 | 0.03175 | 0.65 | 0.92 |
| lnc-GLIPR1L1-2:3 | SEQ0427 | 0.01587 | 0.34 | 0.96 | lnc-SMC5-6:1 | SEQ2686 | 0.03175 | 0.65 | 0.92 |
| RFPL1S:11 | SEQ2233 | 0.01587 | 0.34 | 0.96 | lnc-NPIPB4-3:5 | SEQ2687 | 0.03175 | 0.65 | 0.92 |
| lnc-PPIE-5:1 | SEQ2235 | 0.01587 | 0.34 | 0.96 | lnc-TOX4-4:2 | SEQ2696 | 0.03175 | 0.66 | 0.92 |
| lnc-ITGBL 1-2:1 | SEQ2241 | 0.01587 | 0.35 | 0.96 | lnc-KCNT1-6:1 | SEQ2699 | 0.03175 | 0.66 | 0.92 |
| NR2F1-AS1:6 | SEQ2247 | 0.01587 | 0.36 | 0.96 | lnc-ATPIF1-2:1 | SEQ2700 | 0.03175 | 0.66 | 0.92 |
| RFPL1S:10 | SEQ2248 | 0.01587 | 0.36 | 0.96 | lnc-ITGB1BP2-2:1 | SEQ2701 | 0.03175 | 0.66 | 0.92 |
| CHMP1B-AS1:2 | SEQ2249 | 0.01587 | 0.36 | 0.96 | lnc-TMEM186-1:2 | SEQ2702 | 0.03175 | 0.66 | 0.92 |
| lnc-PPP1R3C-4:1 | SEQ2250 | 0.01587 | 0.36 | 0.96 | lnc-INAFM2-1:1 | SEQ2705 | 0.03175 | 0.67 | 0.92 |
| lnc-SUSD1-1:5 | SEQ0638 | 0.01587 | 0.37 | 0.96 | lnc-RGP D8-5:2 | SEQ2707 | 0.03175 | 0.67 | 0.92 |
| LINC01184:30 | SEQ2257 | 0.01587 | 0.37 | 0.96 | lnc-CDT1-1:1 | SEQ2708 | 0.03175 | 0.67 | 0.92 |
| lnc-TMSB15A-3:1 | SEQ2259 | 0.01587 | 0.37 | 0.96 | lnc-BTBD6-2:1 | SEQ2709 | 0.03175 | 0.67 | 0.92 |
| lnc-COPG2-3:1 | SEQ2265 | 0.01587 | 0.38 | 0.96 | lnc-CRHR2-3:1 | SEQ2710 | 0.03175 | 0.67 | 0.92 |
| lnc-SNRPN-8:36 | SEQ2268 | 0.01587 | 0.38 | 0.96 | PINK1-AS:1 | SEQ2712 | 0.03175 | 0.68 | 0.92 |
| lnc-TYRO3-3:1 | SEQ2269 | 0.01587 | 0.39 | 0.96 | lnc-GUSB-4:1 | SEQ2716 | 0.03175 | 0.68 | 0.92 |
| lnc-ZNF736-1:2 | SEQ2272 | 0.01587 | 0.39 | 0.96 | lnc-GP1BA-1:1 | SEQ2718 | 0.03175 | 0.68 | 0.92 |
| lnc-NT5E-11:3 | SEQ2278 | 0.01587 | 0.39 | 0.96 | lnc-EDEM3-7:3 | SEQ0272 | 0.03175 | 0.68 | 0.92 |
| lnc-MUC20-5:2 | SEQ2289 | 0.01587 | 0.40 | 0.96 | lnc-PRCP-1:1 | SEQ2720 | 0.03175 | 0.68 | 0.92 |
| lnc-FANCM-8:3 | SEQ2291 | 0.01587 | 0.40 | 0.96 | lnc-ALX4-17:1 | SEQ2722 | 0.03175 | 0.68 | 0.92 |
| lnc-FSHR-4:1 | SEQ2298 | 0.01587 | 0.41 | 0.96 | lnc-AP3S1-1:3 | SEQ2723 | 0.03175 | 0.68 | 0.92 |
| lnc-LIPI-4:6 | SEQ2300 | 0.01587 | 0.41 | 0.96 | lnc-FUT9-1:1 | SEQ2724 | 0.03175 | 0.69 | 0.92 |
| lnc-VPREB1-7:3 | SEQ2303 | 0.01587 | 0.41 | 0.96 | lnc-CHD2-13:2 | SEQ2726 | 0.03175 | 0.69 | 0.92 |
| lnc-KHDC3L-2:16 | SEQ2305 | 0.01587 | 0.41 | 0.96 | lnc-BAG3-1:1 | SEQ2727 | 0.03175 | 0.69 | 0.92 |
| lnc-CHST7-2:1 | SEQ2306 | 0.01587 | 0.41 | 0.96 | lnc-TMEM243-1:1 | SEQ2728 | 0.03175 | 0.69 | 0.92 |
| lnc-PARD3B-4:1 | SEQ2315 | 0.01587 | 0.42 | 0.96 | lnc-RPS6KB1-1:7 | SEQ2729 | 0.03175 | 0.69 | 0.92 |
| SNHG3:5 | SEQ2316 | 0.01587 | 0.42 | 0.96 | lnc-ZC3HC1-4:1 | SEQ2731 | 0.03175 | 0.70 | 0.92 |
| lnc-ZNF704-7:6 | SEQ2317 | 0.01587 | 0.42 | 0.96 | lnc-PINK1-2:1 | SEQ2734 | 0.03175 | 0.70 | 0.92 |
| lnc-PRMT6-9:1 | SEQ2319 | 0.01587 | 0.43 | 0.96 | lnc-RTL9-2:1 | SEQ2735 | 0.03175 | 0.70 | 0.92 |
| lnc-GNA13-2:13 | SEQ2320 | 0.01587 | 0.43 | 0.96 | lnc-MAML3-2:1 | SEQ0438 | 0.03175 | 0.71 | 0.92 |
| lnc-FGFBP3-2:2 | SEQ2330 | 0.01587 | 0.43 | 0.96 | lnc-NOB1-1:1 | SEQ2738 | 0.03175 | 0.71 | 0.92 |
| lnc-NOL4-6:1 | SEQ2331 | 0.01587 | 0.43 | 0.96 | lnc-ANAPC11-2:9 | SEQ2739 | 0.03175 | 0.71 | 0.92 |
| IDI2-AS1:5 | SEQ2352 | 0.01587 | 0.45 | 0.96 | lnc-C14orf177-5:1 | SEQ2740 | 0.03175 | 0.72 | 0.92 |
| lnc-ZNF316-3:8 | SEQ2359 | 0.01587 | 0.45 | 0.96 | lnc-ACTRT3-5:1 | SEQ2741 | 0.03175 | 0.72 | 0.92 |
| ADIRF-AS1:2 | SEQ2379 | 0.01587 | 0.46 | 0.96 | lnc-GPBP1L1-1:8 | SEQ2745 | 0.03175 | 0.73 | 0.92 |
| lnc-CA6-8:2 | SEQ2380 | 0.01587 | 0.46 | 0.96 | lnc-ZNF221-2:6 | SEQ2746 | 0.03175 | 0.73 | 0.92 |
| lnc-DCAF4L1-2:1 | SEQ2387 | 0.01587 | 0.47 | 0.96 | lnc-LEAP2-2:1 | SEQ2749 | 0.03175 | 0.74 | 0.92 |
| SNAI3-AS1:6 | SEQ2392 | 0.01587 | 0.47 | 0.96 | lnc-CIB3-1:2 | SEQ2750 | 0.03175 | 0.74 | 0.92 |
| lnc-COX7B-2:1 | SEQ2394 | 0.01587 | 0.47 | 0.96 | lnc-SLTM-1:2 | SEQ0982 | 0.03175 | 0.75 | 0.92 |
| lnc-TAOK3-9:1 | SEQ2396 | 0.01587 | 0.48 | 0.96 | lnc-NR2C2-1:1 | SEQ2751 | 0.03175 | 0.75 | 0.92 |
| LINC01006:1 | SEQ2401 | 0.01587 | 0.48 | 0.96 | lnc-DFFA-12:2 | SEQ2754 | 0.03175 | 0.75 | 0.92 |
| LINC01006:2 | SEQ2402 | 0.01587 | 0.48 | 0.96 | lnc-PLEKHA8-3:5 | SEQ0962 | 0.03175 | 0.75 | 0.92 |
| lnc-AP3S1-1:2 | SEQ2405 | 0.01587 | 0.48 | 0.96 | lnc-PGBD5-1:1 | SEQ2755 | 0.03175 | 0.75 | 0.92 |
| OIP5-AS1:2 | SEQ2408 | 0.01587 | 0.48 | 0.96 | lnc-CDH8-4:1 | SEQ2756 | 0.03175 | 0.76 | 0.92 |

TABLE 8-continued

The 1202 lncRNAs with known sequence identified by the present invention having a deficient expression (FC ≤ 0.84) or over-expression (FC ≥ 1.22) in human AD brain temporal cortex versus human healthy control brain temporal cortex.

| lncRNA | SEQ | p-value | FC | AUC | lncRNA | SEQ | p-value | FC | AUC |
|---|---|---|---|---|---|---|---|---|---|
| lnc-FAM172A-7:8 | SEQ2409 | 0.01587 | 0.48 | 0.96 | lnc-TCTA-2:1 | SEQ2757 | 0.03175 | 0.76 | 0.92 |
| lnc-PMM2-6:4 | SEQ2411 | 0.01587 | 0.48 | 0.96 | lnc-ERVV-2-9:1 | SEQ2758 | 0.03175 | 0.76 | 0.92 |
| UGDH-AS1:10 | SEQ0407 | 0.01587 | 0.49 | 0.96 | lnc-DDX49-1:1 | SEQ2759 | 0.03175 | 0.76 | 0.92 |
| lnc-S100P-4:13 | SEQ2418 | 0.01587 | 0.49 | 0.96 | lnc-HSD11B1L-1:1 | SEQ2760 | 0.03175 | 0.77 | 0.92 |
| lnc-ZNF449-3:5 | SEQ2420 | 0.01587 | 0.49 | 0.96 | lnc-MOGAT2-4:1 | SEQ2762 | 0.03175 | 0.78 | 0.92 |
| lnc-ZNF449-3:4 | SEQ2421 | 0.01587 | 0.49 | 0.96 | lnc-C20orf96-1:1 | SEQ2764 | 0.03175 | 0.79 | 0.92 |
| lnc-GRAP2-2:1 | SEQ2429 | 0.01587 | 0.49 | 0.96 | lnc-TRIM59-1:1 | SEQ2766 | 0.03175 | 0.79 | 0.92 |
| lnc-TPTE2-4:1 | SEQ2431 | 0.01587 | 0.49 | 0.96 | lnc-GSDMB-1:1 | SEQ2767 | 0.03175 | 0.84 | 0.92 |
| lnc-H2AFV-3:1 | SEQ2433 | 0.01587 | 0.49 | 0.96 | lnc-RFNG-1:7 | SEQ2768 | 0.03175 | 1.22 | 0.92 |
| lnc-XXYLT1-5:1 | SEQ0221 | 0.01587 | 0.50 | 0.96 | lnc-SCRN1-1:5 | SEQ2769 | 0.03175 | 1.25 | 0.92 |
| lnc-EPC1-5:1 | SEQ2445 | 0.01587 | 0.50 | 0.96 | lnc-RRN3-3:5 | SEQ2770 | 0.03175 | 1.26 | 0.92 |
| lnc-NUB1-4:1 | SEQ0126 | 0.01587 | 0.50 | 0.96 | lnc-ANKS3-2:1 | SEQ2771 | 0.03175 | 1.28 | 0.92 |
| lnc-GPRIN2-2:1 | SEQ2453 | 0.01587 | 0.50 | 0.96 | lnc-ADAT3-5:1 | SEQ2772 | 0.03175 | 1.28 | 0.92 |
| lnc-ACTR10-6:1 | SEQ2458 | 0.01587 | 0.51 | 0.96 | lnc-TMC8-4:1 | SEQ2775 | 0.03175 | 1.32 | 0.92 |
| lnc-KCNE4-7:1 | SEQ2466 | 0.01587 | 0.51 | 0.96 | EP300-AS1:13 | SEQ2778 | 0.03175 | 1.34 | 0.92 |
| lnc-RMDN2-3:24 | SEQ2468 | 0.01587 | 0.52 | 0.96 | lnc-SLC22A18-1:1 | SEQ2779 | 0.03175 | 1.34 | 0.92 |
| OTUD6B-AS1:5 | SEQ2471 | 0.01587 | 0.52 | 0.96 | lnc-PARVG-5:1 | SEQ2781 | 0.03175 | 1.35 | 0.92 |
| lnc-CGREF1-2:1 | SEQ2472 | 0.01587 | 0.52 | 0.96 | lnc-MRPL3-2:6 | SEQ2782 | 0.03175 | 1.36 | 0.92 |
| lnc-FGF23-5:3 | SEQ2473 | 0.01587 | 0.52 | 0.96 | DUBR:25 | SEQ2783 | 0.03175 | 1.38 | 0.92 |
| lnc-FGF23-5:1 | SEQ2474 | 0.01587 | 0.52 | 0.96 | HDHD5-AS1:6 | SEQ2784 | 0.03175 | 1.38 | 0.92 |
| lnc-DLK1-18:121 | SEQ2479 | 0.01587 | 0.52 | 0.96 | lnc-NPIPB12-1:1 | SEQ0822 | 0.03175 | 1.39 | 0.92 |
| lnc-SMARCC2-5:1 | SEQ2481 | 0.01587 | 0.52 | 0.96 | lnc-CMTM3-1:1 | SEQ2789 | 0.03175 | 1.39 | 0.92 |
| lnc-ARHGAP15-2:3 | SEQ2483 | 0.01587 | 0.52 | 0.96 | lnc-SSH3-5:1 | SEQ2791 | 0.03175 | 1.40 | 0.92 |
| EIF3J-AS1:1 | SEQ2486 | 0.01587 | 0.53 | 0.96 | WDFY3-AS2:5 | SEQ2794 | 0.03175 | 1.41 | 0.92 |
| SNHG22:7 | SEQ2487 | 0.01587 | 0.53 | 0.96 | LINC00342:1 | SEQ2795 | 0.03175 | 1.41 | 0.92 |
| lnc-ST7L-5:1 | SEQ2493 | 0.01587 | 0.53 | 0.96 | lnc-TMEM211-1:1 | SEQ2797 | 0.03175 | 1.42 | 0.92 |
| NORAD:9 | SEQ2494 | 0.01587 | 0.53 | 0.96 | lnc-USP35-11:2 | SEQ2802 | 0.03175 | 1.45 | 0.92 |
| lnc-LEKR1-4:10 | SEQ2495 | 0.01587 | 0.53 | 0.96 | lnc-DHX38-4:13 | SEQ2803 | 0.03175 | 1.45 | 0.92 |
| lnc-CT47A1-1:1 | SEQ2504 | 0.01587 | 0.53 | 0.96 | lnc-RPP25-3:1 | SEQ2804 | 0.03175 | 1.46 | 0.92 |
| lnc-SOCS2-1:2 | SEQ2505 | 0.01587 | 0.53 | 0.96 | SEMA6A-AS1:1 | SEQ2805 | 0.03175 | 1.47 | 0.92 |
| lnc-ADGRA3-7:1 | SEQ2512 | 0.01587 | 0.54 | 0.96 | TRAF3IP2-AS1:58 | SEQ2806 | 0.03175 | 1.47 | 0.92 |
| lnc-CHODL-2:2 | SEQ2513 | 0.01587 | 0.54 | 0.96 | lnc-HBEGF-2:8 | SEQ2807 | 0.03175 | 1.47 | 0.92 |
| lnc-SSR3-11:1 | SEQ2529 | 0.01587 | 0.54 | 0.96 | HYI-AS1:3 | SEQ2809 | 0.03175 | 1.48 | 0.92 |
| NORAD:3 | SEQ2530 | 0.01587 | 0.54 | 0.96 | lnc-WDFY4-2:1 | SEQ2812 | 0.03175 | 1.49 | 0.92 |
| NORAD:4 | SEQ2532 | 0.01587 | 0.55 | 0.96 | lnc-KLHDC4-2:2 | SEQ2815 | 0.03175 | 1.49 | 0.92 |
| lnc-CIB3-6:1 | SEQ2539 | 0.01587 | 0.55 | 0.96 | lnc-CTNS-1:1 | SEQ2816 | 0.03175 | 1.50 | 0.92 |
| lnc-LRRK2-1:5 | SEQ2541 | 0.01587 | 0.55 | 0.96 | lnc-TRPM1-3:1 | SEQ0388 | 0.03175 | 1.51 | 0.92 |
| LINC01537:4 | SEQ2543 | 0.01587 | 0.55 | 0.96 | lnc-AUNIP-1:12 | SEQ2821 | 0.03175 | 1.52 | 0.92 |
| lnc-ANAPC11-2:12 | SEQ2544 | 0.01587 | 0.55 | 0.96 | lnc-MYOM1-4:5 | SEQ2823 | 0.03175 | 1.52 | 0.92 |
| lnc-COL20A1-3:2 | SEQ2545 | 0.01587 | 0.55 | 0.96 | lnc-SPATA21-6:3 | SEQ2824 | 0.03175 | 1.52 | 0.92 |
| lnc-JAG1-6:1 | SEQ2547 | 0.01587 | 0.55 | 0.96 | lnc-AGBL3-2:1 | SEQ2825 | 0.03175 | 1.52 | 0.92 |
| NORAD:1 | SEQ2550 | 0.01587 | 0.55 | 0.96 | lnc-NPIPB12-2:1 | SEQ2827 | 0.03175 | 1.53 | 0.92 |
| lnc-WDR77-1:2 | SEQ2553 | 0.01587 | 0.56 | 0.96 | lnc-C11orf95-1:2 | SEQ2828 | 0.03175 | 1.53 | 0.92 |
| lnc-TBCB-1:2 | SEQ2561 | 0.01587 | 0.56 | 0.96 | lnc-TPT1-2:1 | SEQ2830 | 0.03175 | 1.54 | 0.92 |
| lnc-ARMCX1-2:1 | SEQ2563 | 0.01587 | 0.56 | 0.96 | lnc-SLC25A16-1:2 | SEQ2831 | 0.03175 | 1.54 | 0.92 |
| lnc-SRD5A1-2:1 | SEQ2573 | 0.01587 | 0.57 | 0.96 | lnc-USP6-2:22 | SEQ2832 | 0.03175 | 1.54 | 0.92 |
| lnc-ZNF613-7:1 | SEQ2574 | 0.01587 | 0.57 | 0.96 | lnc-MED9-1:2 | SEQ2833 | 0.03175 | 1.54 | 0.92 |
| lnc-MPPE1-8:3 | SEQ2578 | 0.01587 | 0.57 | 0.96 | lnc-NOP14-3:4 | SEQ2834 | 0.03175 | 1.54 | 0.92 |
| lnc-RSPH10B2-1:3 | SEQ2580 | 0.01587 | 0.57 | 0.96 | lnc-ADAP1-1:1 | SEQ2837 | 0.03175 | 1.55 | 0.92 |
| GABPB1-IT1:5 | SEQ2591 | 0.01587 | 0.58 | 0.96 | lnc-ZFP3-3:1 | SEQ2838 | 0.03175 | 1.55 | 0.92 |
| lnc-ARHGEF2-3:4 | SEQ2605 | 0.01587 | 0.60 | 0.96 | KIAA1614-AS1:1 | SEQ2839 | 0.03175 | 1.56 | 0.92 |
| lnc-WASHC4-4:1 | SEQ2608 | 0.01587 | 0.60 | 0.96 | lnc-PLD3-3:1 | SEQ2840 | 0.03175 | 1.56 | 0.92 |
| lnc-ZNF639-4:1 | SEQ2617 | 0.01587 | 0.60 | 0.96 | lnc-TARBP2-2:1 | SEQ2845 | 0.03175 | 1.57 | 0.92 |
| lnc-MFSD4A-1:1 | SEQ2625 | 0.01587 | 0.61 | 0.96 | LINC01410:8 | SEQ2846 | 0.03175 | 1.57 | 0.92 |
| OIP5-AS1:1 | SEQ2635 | 0.01587 | 0.62 | 0.96 | lnc-CYP4F22-5:1 | SEQ2850 | 0.03175 | 1.58 | 0.92 |
| lnc-ZNF613-6:1 | SEQ2637 | 0.01587 | 0.62 | 0.96 | PPP3CB-AS1:22 | SEQ2852 | 0.03175 | 1.58 | 0.92 |
| lnc-SNX20-5:3 | SEQ2643 | 0.01587 | 0.62 | 0.96 | lnc-PPARA-3:8 | SEQ2854 | 0.03175 | 1.58 | 0.92 |
| lnc-KDM3A-1:3 | SEQ2648 | 0.01587 | 0.63 | 0.96 | lnc-MTG1-2:1 | SEQ2858 | 0.03175 | 1.59 | 0.92 |
| lnc-NOL6-6:2 | SEQ2649 | 0.01587 | 0.63 | 0.96 | DLEU2:26 | SEQ0862 | 0.03175 | 1.60 | 0.92 |
| lnc-FGL2-4:1 | SEQ2651 | 0.01587 | 0.63 | 0.96 | lnc-ABCE1-5:1 | SEQ2862 | 0.03175 | 1.60 | 0.92 |
| lnc-EIF1AD-1:1 | SEQ2653 | 0.01587 | 0.63 | 0.96 | IRAIN:2 | SEQ2863 | 0.03175 | 1.60 | 0.92 |
| lnc-TEX37-1:2 | SEQ2654 | 0.01587 | 0.63 | 0.96 | IRAIN:3 | SEQ2864 | 0.03175 | 1.60 | 0.92 |
| lnc-TEX37-1:1 | SEQ2655 | 0.01587 | 0.63 | 0.96 | lnc-ZNF778-1:4 | SEQ2865 | 0.03175 | 1.60 | 0.92 |
| lnc-POM121-2:5 | SEQ2658 | 0.01587 | 0.63 | 0.96 | MAGI2-AS3:85 | SEQ2867 | 0.03175 | 1.61 | 0.92 |
| lnc-SLC16A11-7:7 | SEQ2659 | 0.01587 | 0.63 | 0.96 | TPT1-AS1:54 | SEQ2870 | 0.03175 | 1.61 | 0.92 |
| lnc-PIGU-3:1 | SEQ2663 | 0.01587 | 0.64 | 0.96 | LINC02482:2 | SEQ2871 | 0.03175 | 1.61 | 0.92 |
| lnc-AGAP4-2:1 | SEQ2665 | 0.01587 | 0.64 | 0.96 | lnc-PPP6R2-2:2 | SEQ2876 | 0.03175 | 1.62 | 0.92 |
| lnc-URGCP-MRPS24-2:1 | SEQ2667 | 0.01587 | 0.64 | 0.96 | lnc-CLEC18B-5:1 | SEQ2878 | 0.03175 | 1.63 | 0.92 |
| lnc-EFEMP1-3:12 | SEQ2669 | 0.01587 | 0.64 | 0.96 | lnc-MYOZ1-1:2 | SEQ2879 | 0.03175 | 1.63 | 0.92 |
| lnc-SHISA5-1:2 | SEQ2672 | 0.01587 | 0.64 | 0.96 | LINC00599:13 | SEQ2880 | 0.03175 | 1.63 | 0.92 |
| lnc-GLOD4-3:1 | SEQ2673 | 0.01587 | 0.64 | 0.96 | LIMD1-AS1:2 | SEQ2885 | 0.03175 | 1.64 | 0.92 |
| lnc-STX10-3:1 | SEQ2677 | 0.01587 | 0.64 | 0.96 | lnc-TELO2-3:2 | SEQ2887 | 0.03175 | 1.65 | 0.92 |
| lnc-MAOA-5:1 | SEQ2678 | 0.01587 | 0.64 | 0.96 | lnc-DLK1-18:77 | SEQ2888 | 0.03175 | 1.65 | 0.92 |

TABLE 8-continued

The 1202 lncRNAs with known sequence identified by the present invention having a deficient expression (FC ≤ 0.84) or over-expression (FC ≥ 1.22) in human AD brain temporal cortex versus human healthy control brain temporal cortex.

| lncRNA | SEQ | p-value | FC | AUC | lncRNA | SEQ | p-value | FC | AUC |
|---|---|---|---|---|---|---|---|---|---|
| lnc-MB-5:1 | SEQ2679 | 0.01587 | 0.64 | 0.96 | lnc-MACC1-3:6 | SEQ2890 | 0.03175 | 1.66 | 0.92 |
| lnc-IL31RA-1:1 | SEQ2680 | 0.01587 | 0.64 | 0.96 | SVIL-AS1:39 | SEQ2891 | 0.03175 | 1.66 | 0.92 |
| lnc-FNTB-2:1 | SEQ2682 | 0.01587 | 0.65 | 0.96 | lnc-CELF4-10:1 | SEQ2892 | 0.03175 | 1.67 | 0.92 |
| lnc-FANCL-4:1 | SEQ2690 | 0.01587 | 0.65 | 0.96 | lnc-MED15-1:2 | SEQ0620 | 0.03175 | 1.68 | 0.92 |
| lnc-CES5A-1:2 | SEQ2691 | 0.01587 | 0.65 | 0.96 | lnc-LIPG-11:1 | SEQ2894 | 0.03175 | 1.68 | 0.92 |
| lnc-NOP53-2:1 | SEQ2692 | 0.01587 | 0.65 | 0.96 | lnc-TOB2-3:1 | SEQ2902 | 0.03175 | 1.69 | 0.92 |
| lnc-CPM-3:1 | SEQ0228 | 0.01587 | 0.66 | 0.96 | lnc-PLA2G1B-2:3 | SEQ2905 | 0.03175 | 1.70 | 0.92 |
| lnc-PTBP3-7:1 | SEQ2703 | 0.01587 | 0.67 | 0.96 | lnc-SLC37A2-2:1 | SEQ2906 | 0.03175 | 1.71 | 0.92 |
| lnc-FAM228B-2:1 | SEQ2714 | 0.01587 | 0.68 | 0.96 | lnc-RNF208-3:1 | SEQ2911 | 0.03175 | 1.72 | 0.92 |
| lnc-ABCC6-11:1 | SEQ2717 | 0.01587 | 0.68 | 0.96 | lnc-ANKRD36B-3:9 | SEQ2913 | 0.03175 | 1.72 | 0.92 |
| lnc-VLDLR-4:1 | SEQ2719 | 0.01587 | 0.68 | 0.96 | lnc-CD40LG-2:12 | SEQ2919 | 0.03175 | 1.74 | 0.92 |
| lnc-CYTIP-2:1 | SEQ0200 | 0.01587 | 0.68 | 0.96 | lnc-EVI5L-3:1 | SEQ2920 | 0.03175 | 1.74 | 0.92 |
| lnc-EPM2AIP1-9:2 | SEQ2721 | 0.01587 | 0.68 | 0.96 | lnc-ZNF587-1:1 | SEQ2921 | 0.03175 | 1.74 | 0.92 |
| lnc-LYN-8:1 | SEQ0619 | 0.01587 | 0.69 | 0.96 | lnc-SERPINE3-2:1 | SEQ2922 | 0.03175 | 1.74 | 0.92 |
| lnc-PSMC3IP-5:1 | SEQ2730 | 0.01587 | 0.70 | 0.96 | lnc-SHC3-5:1 | SEQ2924 | 0.03175 | 1.75 | 0.92 |
| lnc-P4HTM-2:1 | SEQ2732 | 0.01587 | 0.70 | 0.96 | lnc-RABEP2-6:1 | SEQ2929 | 0.03175 | 1.77 | 0.92 |
| lnc-GDPD4-1:3 | SEQ2733 | 0.01587 | 0.70 | 0.96 | lnc-NUDT4P1-1:12 | SEQ2932 | 0.03175 | 1.78 | 0.92 |
| lnc-KIFC2-1:8 | SEQ2737 | 0.01587 | 0.70 | 0.96 | lnc-CRYM-3:1 | SEQ2933 | 0.03175 | 1.78 | 0.92 |
| lnc-GAMT-6:2 | SEQ2742 | 0.01587 | 0.72 | 0.96 | GEMIN7-AS1:2 | SEQ2934 | 0.03175 | 1.78 | 0.92 |
| lnc-PRPF4B-5:1 | SEQ2747 | 0.01587 | 0.73 | 0.96 | lnc-FGFR1OP-11:1 | SEQ2935 | 0.03175 | 1.78 | 0.92 |
| lnc-CXorf65-2:1 | SEQ2748 | 0.01587 | 0.74 | 0.96 | lnc-NTAN1-5:1 | SEQ2936 | 0.03175 | 1.78 | 0.92 |
| lnc-AGO1-1:1 | SEQ2752 | 0.01587 | 0.75 | 0.96 | lnc-GOLGA8F-7:1 | SEQ2938 | 0.03175 | 1.78 | 0.92 |
| lnc-PMM1-1:1 | SEQ2761 | 0.01587 | 0.77 | 0.96 | lnc-LTC4S-1:1 | SEQ2942 | 0.03175 | 1.79 | 0.92 |
| lnc-GPAT4-2:2 | SEQ2763 | 0.01587 | 0.78 | 0.96 | lnc-RIPOR1-1:6 | SEQ2943 | 0.03175 | 1.79 | 0.92 |
| BACE1-AS:5 | SEQ2765 | 0.01587 | 0.79 | 0.96 | lnc-TIGD5-1:1 | SEQ2945 | 0.03175 | 1.80 | 0.92 |
| lnc-MFSD14B-18:1 | SEQ2773 | 0.01587 | 1.30 | 0.96 | lnc-NAIP-4:1 | SEQ2946 | 0.03175 | 1.80 | 0.92 |
| lnc-RARRES2-2:2 | SEQ2774 | 0.01587 | 1.31 | 0.96 | lnc-OR4F29-8:25 | SEQ2949 | 0.03175 | 1.81 | 0.92 |
| lnc-DNAH10-2:1 | SEQ2777 | 0.01587 | 1.33 | 0.96 | lnc-BDH1-5:8 | SEQ2950 | 0.03175 | 1.81 | 0.92 |
| lnc-OR4F15-4:5 | SEQ2780 | 0.01587 | 1.35 | 0.96 | lnc-SKI-5:1 | SEQ2951 | 0.03175 | 1.81 | 0.92 |
| lnc-IL17RA-33:6 | SEQ2788 | 0.01587 | 1.39 | 0.96 | MIR9-3HG:11 | SEQ2957 | 0.03175 | 1.82 | 0.92 |
| lnc-SEPT7-4:1 | SEQ2796 | 0.01587 | 1.42 | 0.96 | lnc-C1orf198-6:3 | SEQ2959 | 0.03175 | 1.84 | 0.92 |
| lnc-CCL27-2:1 | SEQ2801 | 0.01587 | 1.45 | 0.96 | CCDC183-AS1:3 | SEQ2960 | 0.03175 | 1.85 | 0.92 |
| lnc-ZNF417-1:2 | SEQ2808 | 0.01587 | 1.48 | 0.96 | lnc-OAZ3-2:12 | SEQ2965 | 0.03175 | 1.86 | 0.92 |
| lnc-PPP6R2-5:1 | SEQ2811 | 0.01587 | 1.49 | 0.96 | LHX4-AS1:3 | SEQ2966 | 0.03175 | 1.86 | 0.92 |
| lnc-PNOC-2:1 | SEQ2817 | 0.01587 | 1.51 | 0.96 | lnc-EPHA6-1:2 | SEQ2967 | 0.03175 | 1.87 | 0.92 |
| lnc-SPATA21-4:8 | SEQ2818 | 0.01587 | 1.51 | 0.96 | UGDH-AS1:8 | SEQ2968 | 0.03175 | 1.87 | 0.92 |
| lnc-EFCAB12-2:17 | SEQ2819 | 0.01587 | 1.51 | 0.96 | lnc-GRINA-2:1 | SEQ2969 | 0.03175 | 1.87 | 0.92 |
| lnc-TCP11-2:6 | SEQ2820 | 0.01587 | 1.51 | 0.96 | lnc-SAMD11-12:3 | SEQ2970 | 0.03175 | 1.87 | 0.92 |
| lnc-PDGFB-2:1 | SEQ2826 | 0.01587 | 1.52 | 0.96 | lnc-PLA2G6-1:2 | SEQ2971 | 0.03175 | 1.88 | 0.92 |
| lnc-YRDC-3:1 | SEQ2841 | 0.01587 | 1.56 | 0.96 | SVIL-AS1:17 | SEQ2972 | 0.03175 | 1.88 | 0.92 |
| lnc-RIOX2-3:4 | SEQ2842 | 0.01587 | 1.56 | 0.96 | SVIL-AS1:35 | SEQ2973 | 0.03175 | 1.88 | 0.92 |
| lnc-KMT2C-3:1 | SEQ2847 | 0.01587 | 1.58 | 0.96 | LINC01372:8 | SEQ2975 | 0.03175 | 1.89 | 0.92 |
| lnc-SULT1A4-4:1 | SEQ2851 | 0.01587 | 1.58 | 0.96 | lnc-IGIP-5:1 | SEQ2977 | 0.03175 | 1.90 | 0.92 |
| lnc-TSPAN33-1:1 | SEQ2853 | 0.01587 | 1.58 | 0.96 | lnc-ELK4-1:4 | SEQ2978 | 0.03175 | 1.90 | 0.92 |
| lnc-HMGCS2-1:2 | SEQ2855 | 0.01587 | 1.59 | 0.96 | MAGI2-AS3:51 | SEQ2983 | 0.03175 | 1.92 | 0.92 |
| lnc-NTN3-1:2 | SEQ2860 | 0.01587 | 1.59 | 0.96 | lnc-ZNF467-4:1 | SEQ2985 | 0.03175 | 1.92 | 0.92 |
| lnc-LAT-2:1 | SEQ2861 | 0.01587 | 1.60 | 0.96 | lnc-PABPN1L-1:1 | SEQ2986 | 0.03175 | 1.93 | 0.92 |
| lnc-HIST3H2BB-1:8 | SEQ2866 | 0.01587 | 1.60 | 0.96 | lnc-IGSF9B-2:1 | SEQ2987 | 0.03175 | 1.93 | 0.92 |
| lnc-CPLX1-2:8 | SEQ2869 | 0.01587 | 1.61 | 0.96 | lnc-MC5R-11:1 | SEQ2989 | 0.03175 | 1.93 | 0.92 |
| lnc-CXorf40B-3:1 | SEQ2872 | 0.01587 | 1.62 | 0.96 | lnc-CLRN2-1:2 | SEQ2991 | 0.03175 | 1.94 | 0.92 |
| lnc-FXYD2-2:1 | SEQ2873 | 0.01587 | 1.62 | 0.96 | lnc-COPZ2-1:8 | SEQ2992 | 0.03175 | 1.94 | 0.92 |
| lnc-FAAP20-2:1 | SEQ2889 | 0.01587 | 1.66 | 0.96 | lnc-DHRS7B-1:7 | SEQ2993 | 0.03175 | 1.94 | 0.92 |
| lnc-ANKRD34B-4:1 | SEQ2896 | 0.01587 | 1.69 | 0.96 | lnc-FAM184B-4:1 | SEQ2994 | 0.03175 | 1.94 | 0.92 |
| lnc-CA7-4:3 | SEQ2897 | 0.01587 | 1.69 | 0.96 | lnc-ISOC2-3:1 | SEQ2996 | 0.03175 | 1.95 | 0.92 |
| NTM-AS1:3 | SEQ2898 | 0.01587 | 1.69 | 0.96 | lnc-CSPG4-1:12 | SEQ2998 | 0.03175 | 1.95 | 0.92 |
| NTM-AS1:4 | SEQ2899 | 0.01587 | 1.69 | 0.96 | lnc-PPM1H-6:1 | SEQ3011 | 0.03175 | 2.01 | 0.92 |
| lnc-TCP10L-2:1 | SEQ2900 | 0.01587 | 1.69 | 0.96 | lnc-TTYH3-2:1 | SEQ3012 | 0.03175 | 2.01 | 0.92 |
| lnc-NAA38-4:1 | SEQ2903 | 0.01587 | 1.70 | 0.96 | lnc-TMC5-3:1 | SEQ3015 | 0.03175 | 2.01 | 0.92 |
| lnc-FAAP20-3:1 | SEQ2907 | 0.01587 | 1.71 | 0.96 | lnc-TMEM211-7:1 | SEQ3023 | 0.03175 | 2.04 | 0.92 |
| lnc-PGAM2-1:1 | SEQ2909 | 0.01587 | 1.71 | 0.96 | lnc-NBPF1-1:6 | SEQ3026 | 0.03175 | 2.05 | 0.92 |
| lnc-FBXO11-1:10 | SEQ2912 | 0.01587 | 1.72 | 0.96 | lnc-ATG4B-2:1 | SEQ3030 | 0.03175 | 2.06 | 0.92 |
| lnc-NEUROD1-2:3 | SEQ2918 | 0.01587 | 1.74 | 0.96 | lnc-PRKN-17:1 | SEQ3031 | 0.03175 | 2.06 | 0.92 |
| lnc-KLHL18-6:1 | SEQ2923 | 0.01587 | 1.75 | 0.96 | lnc-ATAD5-2:1 | SEQ3035 | 0.03175 | 2.07 | 0.92 |
| CCDC183-AS1:5 | SEQ2925 | 0.01587 | 1.76 | 0.96 | CNTFR-AS1:14 | SEQ3038 | 0.03175 | 2.08 | 0.92 |
| lnc-CNTN2-4:1 | SEQ2926 | 0.01587 | 1.76 | 0.96 | lnc-TRUB2-8:1 | SEQ3040 | 0.03175 | 2.08 | 0.92 |
| lnc-TAX1BP3-1:2 | SEQ2927 | 0.01587 | 1.76 | 0.96 | ASB16-AS1:9 | SEQ3041 | 0.03175 | 2.08 | 0.92 |
| lnc-UNC5B-1:1 | SEQ2930 | 0.01587 | 1.77 | 0.96 | lnc-RNF24-2:8 | SEQ3043 | 0.03175 | 2.10 | 0.92 |
| LMCD1-AS1:11 | SEQ2931 | 0.01587 | 1.77 | 0.96 | lnc-DNAJB6-10:3 | SEQ3044 | 0.03175 | 2.10 | 0.92 |
| lnc-ATAD5-5:1 | SEQ2937 | 0.01587 | 1.78 | 0.96 | lnc-DNAJB6-10:2 | SEQ3045 | 0.03175 | 2.10 | 0.92 |
| lnc-CASP9-5:1 | SEQ2940 | 0.01587 | 1.79 | 0.96 | lnc-DNAAF5-1:6 | SEQ3048 | 0.03175 | 2.11 | 0.92 |
| lnc-PEX6-1:1 | SEQ2942 | 0.01587 | 1.79 | 0.96 | lnc-SCIMP-1:1 | SEQ3051 | 0.03175 | 2.13 | 0.92 |
| lnc-SMAD7-2:3 | SEQ2947 | 0.01587 | 1.80 | 0.96 | lnc-PFDN4-11:4 | SEQ3054 | 0.03175 | 2.13 | 0.92 |
| lnc-RHNO1-1:1 | SEQ0026 | 0.01587 | 1.81 | 0.96 | PPP3CB-AS1:5 | SEQ3057 | 0.03175 | 2.14 | 0.92 |
| lnc-GTF2H2C-3:1 | SEQ2952 | 0.01587 | 1.82 | 0.96 | lnc-MSLNL-3:1 | SEQ3059 | 0.03175 | 2.15 | 0.92 |

TABLE 8-continued

The 1202 lncRNAs with known sequence identified by the present invention having
a deficient expression (FC ≤ 0.84) or over-expression (FC ≥ 1.22) in human AD brain
temporal cortex versus human healthy control brain temporal cortex.

| lncRNA | SEQ | p-value | FC | AUC | lncRNA | SEQ | p-value | FC | AUC |
|---|---|---|---|---|---|---|---|---|---|
| lnc-PPEF1-7:2 | SEQ2953 | 0.01587 | 1.82 | 0.96 | lnc-HAS1-2:1 | SEQ3061 | 0.03175 | 2.15 | 0.92 |
| lnc-SDCCAG8-5:1 | SEQ2954 | 0.01587 | 1.82 | 0.96 | lnc-CPLX1-11:1 | SEQ3064 | 0.03175 | 2.16 | 0.92 |
| lnc-BDH1-5:11 | SEQ2956 | 0.01587 | 1.82 | 0.96 | lnc-PPDPF-2:1 | SEQ3067 | 0.03175 | 2.18 | 0.92 |
| lnc-CRYM-3:2 | SEQ2962 | 0.01587 | 1.85 | 0.96 | lnc-GLRX5-2:2 | SEQ3070 | 0.03175 | 2.20 | 0.92 |
| lnc-CRABP2-3:1 | SEQ2963 | 0.01587 | 1.86 | 0.96 | TNRC6C-AS1:1 | SEQ3072 | 0.03175 | 2.20 | 0.92 |
| lnc-PRKN-10:1 | SEQ2964 | 0.01587 | 1.86 | 0.96 | ITPK1-AS1:2 | SEQ3073 | 0.03175 | 2.20 | 0.92 |
| lnc-PACRG-2:1 | SEQ2974 | 0.01587 | 1.88 | 0.96 | ITPK1-AS1:1 | SEQ3074 | 0.03175 | 2.20 | 0.92 |
| PCBP1-AS1:201 | SEQ2976 | 0.01587 | 1.90 | 0.96 | lnc-SLC7A14-3:12 | SEQ3079 | 0.03175 | 2.22 | 0.92 |
| lnc-NPTX1-4:1 | SEQ2980 | 0.01587 | 1.91 | 0.96 | MALAT1:26 | SEQ3081 | 0.03175 | 2.23 | 0.92 |
| lnc-CHN2-2:4 | SEQ2981 | 0.01587 | 1.92 | 0.96 | lnc-GPC2-2:6 | SEQ3088 | 0.03175 | 2.25 | 0.92 |
| lnc-ZNF705D-6:1 | SEQ2982 | 0.01587 | 1.92 | 0.96 | lnc-GSG1L-1:9 | SEQ3090 | 0.03175 | 2.26 | 0.92 |
| lnc-PCIF1-1:1 | SEQ2984 | 0.01587 | 1.92 | 0.96 | lnc-COX19-2:1 | SEQ3091 | 0.03175 | 2.26 | 0.92 |
| lnc-OSGIN1-1:9 | SEQ2988 | 0.01587 | 1.93 | 0.96 | lnc-LGR6-8:1 | SEQ3092 | 0.03175 | 2.27 | 0.92 |
| lnc-PEX10-6:1 | SEQ2995 | 0.01587 | 1.95 | 0.96 | lnc-LRIG2-5:1 | SEQ3093 | 0.03175 | 2.27 | 0.92 |
| lnc-OTOA-3:4 | SEQ2999 | 0.01587 | 1.96 | 0.96 | lnc-IL3RA-1:22 | SEQ3101 | 0.03175 | 2.29 | 0.92 |
| ADNP-AS1:7 | SEQ3000 | 0.01587 | 1.96 | 0.96 | lnc-POM121L2-2:5 | SEQ3110 | 0.03175 | 2.32 | 0.92 |
| lnc-LRRK1-3:4 | SEQ0242 | 0.01587 | 1.97 | 0.96 | lnc-NMRK2-5:9 | SEQ3111 | 0.03175 | 2.32 | 0.92 |
| lnc-TMEM211-2:8 | SEQ0644 | 0.01587 | 1.99 | 0.96 | lnc-COA6-1:2 | SEQ3113 | 0.03175 | 2.32 | 0.92 |
| lnc-LRRC56-1:7 | SEQ3005 | 0.01587 | 2.00 | 0.96 | lnc-ATAD2B-2:1 | SEQ3116 | 0.03175 | 2.34 | 0.92 |
| lnc-OR4F29-8:23 | SEQ3007 | 0.01587 | 2.00 | 0.96 | lnc-SSH3-5:2 | SEQ3117 | 0.03175 | 2.35 | 0.92 |
| lnc-PILRB-1:5 | SEQ3009 | 0.01587 | 2.00 | 0.96 | ZMIZ1-AS1:22 | SEQ3122 | 0.03175 | 2.38 | 0.92 |
| lnc-CEP83-7:1 | SEQ3010 | 0.01587 | 2.01 | 0.96 | lnc-GLRX5-7:2 | SEQ3123 | 0.03175 | 2.38 | 0.92 |
| lnc-ALG12-5:3 | SEQ3016 | 0.01587 | 2.01 | 0.96 | lnc-FAM184B-6:1 | SEQ3128 | 0.03175 | 2.42 | 0.92 |
| lnc-GTPBP1-1:2 | SEQ3017 | 0.01587 | 2.02 | 0.96 | lnc-PRR26-2:1 | SEQ3129 | 0.03175 | 2.42 | 0.92 |
| lnc-PPIF-1:3 | SEQ3019 | 0.01587 | 2.02 | 0.96 | MALAT1:14 | SEQ3130 | 0.03175 | 2.43 | 0.92 |
| lnc-TOP1MT-5:1 | SEQ3021 | 0.01587 | 2.04 | 0.96 | lnc-SPANXB1-7:1 | SEQ3131 | 0.03175 | 2.44 | 0.92 |
| lnc-RPL12-1:3 | SEQ3024 | 0.01587 | 2.04 | 0.96 | lnc-CEL-5:2 | SEQ3132 | 0.03175 | 2.44 | 0.92 |
| lnc-NKPD1-1:1 | SEQ3025 | 0.01587 | 2.04 | 0.96 | lnc-CANT1-3:1 | SEQ3133 | 0.03175 | 2.44 | 0.92 |
| lnc-NEURL4-1:4 | SEQ3028 | 0.01587 | 2.05 | 0.96 | OLMALINC:4 | SEQ3137 | 0.03175 | 2.45 | 0.92 |
| DLG5-AS1:5 | SEQ3033 | 0.01587 | 2.06 | 0.96 | lnc-CRLF3-3:1 | SEQ3139 | 0.03175 | 2.46 | 0.92 |
| lnc-GRINA-3:1 | SEQ3047 | 0.01587 | 2.10 | 0.96 | LINC01759:10 | SEQ3141 | 0.03175 | 2.48 | 0.92 |
| lnc-PLPP2-2:1 | SEQ3049 | 0.01587 | 2.11 | 0.96 | lnc-RGS9-16:1 | SEQ3149 | 0.03175 | 2.52 | 0.92 |
| lnc-TMEM163-2:1 | SEQ3055 | 0.01587 | 2.14 | 0.96 | lnc-KCNQ2-2:2 | SEQ3151 | 0.03175 | 2.52 | 0.92 |
| lnc-LGALS7B-1:4 | SEQ3056 | 0.01587 | 2.14 | 0.96 | lnc-FAM104A-8:2 | SEQ3153 | 0.03175 | 2.56 | 0.92 |
| lnc-CNP-1:1 | SEQ3058 | 0.01587 | 2.14 | 0.96 | lnc-EMX1-1:1 | SEQ3154 | 0.03175 | 2.56 | 0.92 |
| lnc-HGH1-1:1 | SEQ3060 | 0.01587 | 2.15 | 0.96 | lnc-SPANXB1-7:5 | SEQ3157 | 0.03175 | 2.57 | 0.92 |
| lnc-ERV3-1-10:8 | SEQ3062 | 0.01587 | 2.16 | 0.96 | lnc-MINDY1-2:1 | SEQ3163 | 0.03175 | 2.66 | 0.92 |
| ZMIZ1-AS1:31 | SEQ3065 | 0.01587 | 2.17 | 0.96 | lnc-PLEKHA2-4:1 | SEQ3164 | 0.03175 | 2.67 | 0.92 |
| lnc-SPANXB1-7:7 | SEQ3066 | 0.01587 | 2.17 | 0.96 | lnc-CDCA2-4:1 | SEQ3166 | 0.03175 | 2.68 | 0.92 |
| lnc-ERLEC1-6:1 | SEQ3068 | 0.01587 | 2.18 | 0.96 | SNHG12:10 | SEQ3169 | 0.03175 | 2.71 | 0.92 |
| lnc-NAV1-8:1 | SEQ3069 | 0.01587 | 2.20 | 0.96 | lnc-TXNDC15-1:1 | SEQ3177 | 0.03175 | 2.79 | 0.92 |
| lnc-SELENON-2:2 | SEQ3071 | 0.01587 | 2.20 | 0.96 | lnc-LRRC56-1:11 | SEQ3181 | 0.03175 | 2.87 | 0.92 |
| lnc-MYO15B-3:1 | SEQ3076 | 0.01587 | 2.21 | 0.96 | lnc-DRICH1-3:35 | SEQ3187 | 0.03175 | 2.97 | 0.92 |
| lnc-ARFRP1-1:1 | SEQ3077 | 0.01587 | 2.21 | 0.96 | lnc-SNX20-8:1 | SEQ3192 | 0.03175 | 2.98 | 0.92 |
| lnc-RFPL3S-4:1 | SEQ3082 | 0.01587 | 2.23 | 0.96 | lnc-SLC7A7-1:6 | SEQ3194 | 0.03175 | 3.04 | 0.92 |
| lnc-NPC1-1:1 | SEQ3087 | 0.01587 | 2.24 | 0.96 | lnc-ST18-4:4 | SEQ3201 | 0.03175 | 3.09 | 0.92 |
| LINC01608:19 | SEQ3097 | 0.01587 | 2.29 | 0.96 | lnc-CANT1-2:5 | SEQ3203 | 0.03175 | 3.11 | 0.92 |
| lnc-DRICH1-3:51 | SEQ3098 | 0.01587 | 2.29 | 0.96 | lnc-TRUB2-8:2 | SEQ3205 | 0.03175 | 3.13 | 0.92 |
| lnc-KIF13B-2:1 | SEQ3100 | 0.01587 | 2.29 | 0.96 | lnc-SLC29A4-5:9 | SEQ3207 | 0.03175 | 3.15 | 0.92 |
| lnc-TCF19-1:54 | SEQ3105 | 0.01587 | 2.31 | 0.96 | lnc-DCP1B-6:1 | SEQ3210 | 0.03175 | 3.17 | 0.92 |
| lnc-CCL25-1:5 | SEQ3109 | 0.01587 | 2.32 | 0.96 | lnc-SFTPA2-6:1 | SEQ3211 | 0.03175 | 3.18 | 0.92 |
| lnc-GOLGA80-3:6 | SEQ3115 | 0.01587 | 2.32 | 0.96 | lnc-FAM187A-2:1 | SEQ3217 | 0.03175 | 3.28 | 0.92 |
| lnc-GRINA-1:1 | SEQ3118 | 0.01587 | 2.36 | 0.96 | DANT2:3 | SEQ3220 | 0.03175 | 3.36 | 0.92 |
| lnc-ANKRD20A3-19:1 | SEQ3119 | 0.01587 | 2.36 | 0.96 | lnc-BLM-6:5 | SEQ3223 | 0.03175 | 3.39 | 0.92 |
| lnc-CLRN2-1:1 | SEQ3124 | 0.01587 | 2.40 | 0.96 | lnc-OR4F3-5:9 | SEQ3225 | 0.03175 | 3.42 | 0.92 |
| NORAD:2 | SEQ3125 | 0.01587 | 2.41 | 0.96 | LINC00639:9 | SEQ3235 | 0.03175 | 3.85 | 0.92 |
| TNRC6C-AS1:5 | SEQ3142 | 0.01587 | 2.48 | 0.96 | lnc-SSTR2-5:1 | SEQ3238 | 0.03175 | 4.08 | 0.92 |
| TNRC6C-AS1:2 | SEQ3143 | 0.01587 | 2.48 | 0.96 | LINC01608:17 | SEQ3243 | 0.03175 | 4.20 | 0.92 |
| lnc-NBPF3-3:6 | SEQ3144 | 0.01587 | 2.49 | 0.96 | lnc-CD46-7:4 | SEQ3254 | 0.03175 | 5.19 | 0.92 |
| GSN-AS1:1 | SEQ3146 | 0.01587 | 2.50 | 0.96 | LINC01715:4 | SEQ3256 | 0.03175 | 5.35 | 0.92 |
| MIR646HG:31 | SEQ3148 | 0.01587 | 2.51 | 0.96 | TDRG1:6 | SEQ3270 | 0.03175 | 8.23 | 0.92 |
| lnc-IL3RA-1:18 | SEQ3155 | 0.01587 | 2.57 | 0.96 | MALAT1:11 | SEQ3276 | 0.03175 | 25.39 | 0.92 |
| lnc-SULT1A3-5:1 | SEQ3161 | 0.01587 | 2.59 | 0.96 | LINC00092:11 | SEQ3278 | 0.03175 | 41.83 | 0.92 |

386 lncRNAs comprising 28 novel lncRNAs showed (i) high expression in postmortem brain (CPM>25), (ii) significant differential expression in AD brain versus HC brain, and (iii) no or low expression (<5 CPM) in plasma and blood (Paxgene) of living AD patients or healthy controls. These 386 lncRNAs are listed and their profile included in Tables 7 and 8.

To identify for diagnostic and therapeutic applications, circulating lncRNAs in the peripheral body fluids, blood and plasma lncRNA signatures involved specifically in the pathogenesis of brain disorders, including but not limited to cognitive disorders such as mild cognitive impairment (MCI), Alzheimer (AD), frontotemporal (FTD) dementia and/or dementia with Lewy bodies (DLB), a total of 128,893 lncRNAs comprising the 1091 novel lncRNAs and the 127802 lncRNAs based on LNCipedia were screened and profiled in the brain from AD cases and from non-demented cases as well as in plasma and/or whole blood samples from different groups of subjects, including a group of patients with MCI, a group of patients with mild AD, a group of patients with moderate-to-severe AD, a group of patients with DLB and a group of patients with FTD as well as a control reference group of cognitively intact healthy controls having normal neurocognitive scores and with no brain imaging abnormalities, have been screened.

Subsequently, out of 128 894 lncRNAs in all samples, 53747 lncRNAs in brain samples, 35618 lncRNAs in plasma samples, 71132 lncRNAs in whole blood (Paxgene RNA tubes) samples have been detected with the level of at least one count in a sample among the samples included in the experiments. Further applying an additional threshold of expression level >5CPM in 50% of samples from at least one of the subject groups studied, the following numbers of lncRNAs were retained for Statistical analysis: 10122 brain lncRNAs, 3774 plasma lncRNAs and 9367 whole blood lncRNAs.

For each lncRNA, the differential expression level was determined by comparing the expression level between two groups (for example AD group and healthy control group), using a two-tailed Welch t test and/or Wilcoxon Mann-Whitney test. Significant differential expression was identified as $p<0.05$. 410 lncRNAs were differentially expressed in AD plasma versus HC plasma, with statistically significance ($p<0.05$, Wilcoxon test) and a fold change FC<0.80 or >1.20. Table 9 shows the 410 plasma lncRNAs.

TABLE 9

The 410 plasma lncRNAs that are differentially expressed in AD plasma versus HC plasma.

| lncRNA | SEQ | p value | FC | AUC | lncRNA | SEQ | p value | FC | AUC |
|---|---|---|---|---|---|---|---|---|---|
| lnc-KLHL36-2:2 | SEQ3279 | 0.0022 | 2.46 | 1.00 | lnc-PYDC2-5:1 | SEQ3459 | 0.0022 | 10.28 | 1.00 |
| LINC01000:5 | SEQ3280 | 0.0022 | 0.20 | 1.00 | lnc-PPIAL4D-5:7 | SEQ3460 | 0.0411 | 0.38 | 0.86 |
| lnc-ABCC5-3:1 | SEQ3281 | 0.0022 | 2.44 | 1.00 | lnc-REL-6:3 | SEQ3461 | 0.0043 | 13.49 | 0.97 |
| lnc-ABCC5-3:4 | SEQ3282 | 0.0022 | 3.49 | 1.00 | lnc-ZNF460-2:1 | SEQ0473 | 0.0450 | 6.14 | 0.86 |
| lnc-ANAPC11-2:8 | SEQ3283 | 0.0022 | 2.51 | 1.00 | lnc-TOP1-9:1 | SEQ3462 | 0.0260 | 4.56 | 0.89 |
| lnc-CLLU1-2:6 | SEQ3284 | 0.0022 | 3.65 | 1.00 | TCONS_00050494 | SEQ1818 | 0.0087 | 3.27 | 0.94 |
| lnc-CREB3L1-1:6 | SEQ3285 | 0.0022 | 0.30 | 1.00 | lnc-TAF9-10:1 | SEQ0639 | 0.0411 | 3.12 | 0.86 |
| lnc-FGL2-3:1 | SEQ3286 | 0.0022 | 3.99 | 1.00 | lnc-UROC1-1:1 | SEQ3463 | 0.0115 | 12.52 | 0.94 |
| lnc-HERC3-1:7 | SEQ3287 | 0.0022 | 2.87 | 1.00 | lnc-PMM2-6:4 | SEQ2411 | 0.0260 | 3.55 | 0.89 |
| lnc-IL9R-1:5 | SEQ3288 | 0.0022 | 0.00 | 1.00 | lnc-SPATA32-2:4 | SEQ3464 | 0.0411 | 4.81 | 0.86 |
| lnc-LCOR-4:3 | SEQ3289 | 0.0022 | 4.31 | 1.00 | lnc-ZNF843-2:4 | SEQ3465 | 0.0303 | 347 | 0.89 |
| lnc-LRRC10-1:1 | SEQ3290 | 0.0022 | 3.26 | 1.00 | lnc-RIPOR2-7:1 | SEQ3466 | 0.0411 | 3.56 | 0.86 |
| lnc-MAGEE2-2:1 | SEQ3291 | 0.0050 | 5.09 | 1.00 | lnc-NUTM1-6:4 | SEQ3467 | 0.0043 | 6.40 | 0.97 |
| lnc-NEK6-2:1 | SEQ2787 | 0.0022 | 5.82 | 1.00 | lnc-PFDN6-2:3 | SEQ3468 | 0.0411 | 3.59 | 0.86 |
| lnc-NEK6-2:4 | SEQ2786 | 0.0022 | 4.65 | 1.00 | lnc-SSH3-5:1 | SEQ2791 | 0.0152 | 2.07 | 0.92 |
| CCDC183-AS1:5 | SEQ2925 | 0.0260 | 4.07 | 0.89 | lnc-USP47-2:1 | SEQ3469 | 0.0022 | 3.87 | 1.00 |
| CRTC3-AS1:3 | SEQ3292 | 0.0022 | 3.33 | 1.00 | lnc-STX10-2:1 | SEQ3470 | 0.0022 | 6.21 | 1.00 |
| FGD5-AS1:14 | SEQ3293 | 0.0152 | 2.71 | 0.92 | lnc-SMN2-4:2 | SEQ3471 | 0.0022 | 19.3 | 1.00 |
| LINC02288:8 | SEQ3294 | 0.0087 | 5.60 | 0.94 | lnc-TCF7-1:3 | SEQ0990 | 0.0022 | 3.05 | 1.00 |
| lnc-ABTB2-3:1 | SEQ3295 | 0.0129 | 4.23 | 0.94 | lnc-SBK1-1:1 | SEQ3472 | 0.0050 | 6.05 | 1.00 |
| lnc-ARAF-4:1 | SEQ3296 | 0.0260 | 2.34 | 0.89 | lnc-RBM12B-10:1 | SEQ3473 | 0.0087 | 0.42 | 0.94 |
| lnc-ATP6V1C2-2:2 | SEQ2695 | 0.0260 | 4.33 | 0.89 | lnc-RNF39-9:1 | SEQ3474 | 0.0087 | 1.54 | 0.94 |
| lnc-ATXN2-1:1 | SEQ0099 | 0.0087 | 1.62 | 0.94 | lnc-ZC3H12B-1:5 | SEQ3475 | 0.0043 | 0.51 | 0.97 |
| lnc-BORA-25:1 | SEQ3297 | 0.0260 | 3.39 | 0.89 | lnc-RMDN2-3:24 | SEQ2468 | 0.0022 | 2.35 | 1.00 |
| lnc-DEFB115-5:1 | SEQ3298 | 0.0081 | 174.03 | 0.97 | lnc-ZNF552-3:1 | SEQ3476 | 0.0022 | 2.28 | 1.00 |
| lnc-DTX1-1:1 | SEQ3299 | 0.0450 | 3.40 | 0.86 | lnc-SPRYD3-1:17 | SEQ3477 | 0.0043 | 2.84 | 0.97 |
| lnc-EXOSC6-1:2 | SEQ3300 | 0.0411 | 3.95 | 0.86 | lnc-ROM1-7:1 | SEQ3478 | 0.0022 | 2.57 | 1.00 |
| lnc-FAM174A-6:2 | SEQ2631 | 0.0411 | 2.87 | 0.86 | lnc-OSBPL7-1:1 | SEQ3479 | 0.0050 | 4.81 | 1.00 |
| lnc-GCN1-3:1 | SEQ3301 | 0.0450 | 3.14 | 0.86 | lnc-ZNF559-ZNF177-1:1 | SEQ3480 | 0.0043 | 11.85 | 1.00 |
| lnc-GIMAP5-1:1 | SEQ3302 | 0.0152 | 6.09 | 0.92 | lnc-SLC45A3-3:1 | SEQ3481 | 0.0022 | 3.96 | 1.00 |
| lnc-IL18BP-1:1 | SEQ3303 | 0.0411 | 2.29 | 0.86 | lnc-PMM2-2:1 | SEQ3482 | 0.0028 | Inf | 1.00 |
| lnc-MIS12-3:1 | SEQ3304 | 0.0260 | 1.66 | 0.89 | SNHG12:13 | SEQ3483 | 0.0022 | 26.17 | 1.00 |
| lnc-NLRC4-3:3 | SEQ3305 | 0.0087 | 3.16 | 0.94 | TSPOAP1-AS1:39 | SEQ3484 | 0.0022 | 169 | 1.00 |
| lnc-NPIPB13-3:1 | SEQ3306 | 0.0152 | 3.15 | 0.92 | TCONS_00019798 | SEQ1305 | 0.0022 | 4.07 | 1.00 |
| CA3-AS1:13 | SEQ3307 | 0.0087 | 0.25 | 0.94 | lnc-PAPLN-1:1 | SEQ3485 | 0.0411 | 2.41 | 0.86 |
| CSTF3-AS1:10 | SEQ3308 | 0.0152 | 2.30 | 0.92 | lnc-SYCP1-7:1 | SEQ3486 | 0.0260 | 1.50 | 0.89 |
| EP300-AS1:13 | SEQ2778 | 0.0043 | 0.45 | 0.97 | lnc-RABL2B-3:1 | SEQ3487 | 0.0411 | 6.26 | 0.86 |
| FAM239A:16 | SEQ3309 | 0.0260 | 2.85 | 0.89 | lnc-SIAH1-1:1 | SEQ3488 | 0.0152 | 1.80 | 0.92 |
| FGD5-AS1:29 | SEQ3310 | 0.0260 | 3.67 | 0.89 | lnc-RAB17-2:1 | SEQ3489 | 0.0087 | 2.41 | 0.94 |
| FGD5-AS1:8 | SEQ3311 | 0.0411 | 0.10 | 0.86 | lnc-ZCCHC7-2:12 | SEQ3490 | 0.0260 | 7.75 | 0.89 |
| GAS5:31 | SEQ3312 | 0.0411 | 4.65 | 0.86 | lnc-NRGN-1:6 | SEQ3491 | 0.0411 | 0.41 | 0.86 |
| H1FX-AS1:15 | SEQ3313 | 0.0260 | 3.93 | 0.89 | lnc-TEKT1-2:1 | SEQ3492 | 0.0087 | 2.51 | 0.94 |
| HCG11:10 | SEQ3314 | 0.0043 | 30.61 | 0.97 | TCONS_00066544 | SEQ2098 | 0.0303 | 6.13 | 0.89 |
| HCG11:2 | SEQ3315 | 0.0043 | 30.61 | 0.97 | lnc-REL-1:3 | SEQ2508 | 0.0260 | 2.57 | 0.89 |
| HCG11:9 | SEQ3316 | 0.0043 | 30.61 | 0.97 | lnc-SATB1-8:1 | SEQ3493 | 0.0043 | 4.01 | 0.97 |
| IL10RB-AS1:3 | SEQ3317 | 0.0022 | 4.E+11 | 1.00 | lnc-RNMT-8:1 | SEQ3494 | 0.0284 | 0.00 | 0.83 |
| IQCH-AS1:17 | SEQ3318 | 0.0129 | 6.46 | 0.94 | lnc-YPEL5-5:1 | SEQ0750 | 0.0152 | 2.94 | 0.92 |
| JHDM1D-AS1:2 | SEQ3319 | 0.0260 | 0.07 | 0.89 | THRIL:1 | SEQ3495 | 0.0115 | 30.93 | 0.94 |
| LINC00869:69 | SEQ3320 | 0.0411 | 0.23 | 0.86 | TCONS_00050563 | SEQ1836 | 0.0411 | 2.84 | 0.86 |
| LINC00909:10 | SEQ3321 | 0.0411 | 4.91 | 0.86 | lnc-SYNJ2-1:1 | SEQ3496 | 0.0152 | 2.94 | 0.92 |
| LINC00926:6 | SEQ3322 | 0.0260 | 27.17 | 0.89 | lnc-STAT1-2:4 | SEQ3497 | 0.0087 | 2.75 | 0.94 |
| LINC01000:15 | SEQ3323 | 0.0411 | 2.95 | 0.86 | TCONS_00023171 | SEQ1367 | 0.0284 | Inf | 0.83 |
| LINC01419:1 | SEQ3324 | 0.0411 | 7.61 | 0.86 | PSMA3-AS1:27 | SEQ3498 | 0.0152 | 0.41 | 0.92 |
| LINC01473:6 | SEQ3325 | 0.0078 | 0.07 | 0.97 | TCONS_00045364 | SEQ1785 | 0.0152 | 3.23 | 0.92 |

TABLE 9-continued

The 410 plasma lncRNAs that are differentially expressed in AD plasma versus HC plasma.

| lncRNA | SEQ | p value | FC | AUC | lncRNA | SEQ | p value | FC | AUC |
|---|---|---|---|---|---|---|---|---|---|
| LINC01952:8 | SEQ3326 | 0.0411 | 1.90 | 0.86 | LRRC75A-AS1:3 | SEQ3499 | 0.0260 | 4.37 | 0.89 |
| LINC02062:2 | SEQ3327 | 0.0152 | 179.88 | 0.92 | lnc-TEAD2-2:4 | SEQ3500 | 0.0260 | 3.19 | 0.89 |
| LINC02397:10 | SEQ3328 | 0.0152 | 8.19 | 0.92 | lnc-YY1AP1-2:1 | SEQ3501 | 0.0303 | 3.93 | 0.89 |
| LIX1-AS1:2 | SEQ3329 | 0.0152 | 13.41 | 0.92 | lnc-STPG1-3:4 | SEQ3502 | 0.0087 | 4.72 | 0.94 |
| lnc-ACOT9-2:1 | SEQ3330 | 0.0087 | 2.32 | 0.94 | lnc-SH3D19-2:1 | SEQ3503 | 0.0260 | 2.86 | 0.89 |
| lnc-ADAM30-1:1 | SEQ2698 | 0.0295 | 6.92 | 0.89 | lnc-TRDMT1-5:3 | SEQ3504 | 0.0087 | 2.45 | 0.94 |
| lnc-AGO1-1:1 | SEQ2752 | 0.0129 | 5.66 | 0.94 | NNT-AS1:11 | SEQ3505 | 0.0411 | 0.18 | 0.86 |
| lnc-AGO3-3:1 | SEQ3331 | 0.0411 | 3.66 | 0.86 | lnc-OST4-6:2 | SEQ0954 | 0.0260 | 6.67 | 0.89 |
| lnc-AHSA2-5:6 | SEQ3332 | 0.0438 | 6.26 | 0.86 | lnc-SMG1-3:1 | SEQ3506 | 0.0200 | 3.60 | 0.92 |
| lnc-AIM2-3:3 | SEQ3333 | 0.0411 | 2.53 | 0.86 | lnc-ZNF613-2:1 | SEQ3507 | 0.0438 | 2.87 | 0.86 |
| lnc-AKAP12-2:1 | SEQ2375 | 0.0260 | 2.25 | 0.89 | lnc-ZNF891-1:1 | SEQ3508 | 0.0260 | 5.52 | 0.89 |
| lnc-AMPH-10:8 | SEQ3334 | 0.0115 | 7.51 | 0.94 | lnc-PTPA-3:4 | SEQ3509 | 0.0152 | 6.31 | 0.92 |
| lnc-ANAPC11-2:2 | SEQ3335 | 0.0411 | 3.91 | 0.86 | lnc-RAB37-1:6 | SEQ3510 | 0.0152 | 2.19 | 0.92 |
| lnc-ANGPTL1-2:1 | SEQ3336 | 0.0411 | 2.22 | 0.86 | lnc-TMEM212-1:4 | SEQ3511 | 0.0152 | 0.09 | 0.92 |
| lnc-ANKRD13A-4:1 | SEQ3337 | 0.0048 | 8.02 | 1.00 | lnc-RPL39L-3:1 | SEQ3512 | 0.0303 | 4.08 | 0.89 |
| lnc-ANKRD20A2-22:3 | SEQ3338 | 0.0411 | 3.36 | 0.86 | lnc-SLC25A47-5:1 | SEQ3513 | 0.0043 | 2.75 | 0.97 |
| lnc-ANO8-1:2 | SEQ3339 | 0.0250 | 22.08 | 0.89 | lnc-PLEKHA3-20:1 | SEQ3514 | 0.0260 | 2.39 | 0.89 |
| lnc-APBA2-5:4 | SEQ3340 | 0.0129 | 6.87 | 0.94 | lnc-TMEM30B-9:2 | SEQ3515 | 0.0411 | 4.59 | 0.86 |
| lnc-APTX-3:1 | SEQ2399 | 0.0411 | 1.92 | 0.86 | THAP9-AS1:28 | SEQ3516 | 0.0043 | 5.97 | 0.97 |
| lnc-ARF6-3:1 | SEQ3341 | 0.0087 | 2.93 | 0.94 | lnc-PAX8-6:1 | SEQ3517 | 0.0200 | 7.45 | 0.92 |
| lnc-ARL14EP-4:1 | SEQ3342 | 0.0043 | 10.23 | 1.00 | lnc-TAF1B-2:1 | SEQ3518 | 0.0167 | 162 | 0.90 |
| lnc-BCL2L13-3:1 | SEQ3343 | 0.0260 | 2.56 | 0.89 | lnc-ZNF121-1:1 | SEQ3519 | 0.0043 | 3.91 | 0.97 |
| lnc-BLACE-2:15 | SEQ3344 | 0.0087 | 0.27 | 0.94 | TCONS_00011972 | SEQ1217 | 0.0087 | 2.22 | 0.94 |
| lnc-BLACE-2:5 | SEQ3345 | 0.0152 | 0.03 | 0.92 | lnc-TIGD5-3:1 | SEQ3520 | 0.0087 | 2.50 | 0.94 |
| lnc-C10orf10-2:22 | SEQ3346 | 0.0260 | 1.67 | 0.89 | lnc-ROM1-7:5 | SEQ3521 | 0.0411 | 2.36 | 0.86 |
| lnc-C10orf10-2:23 | SEQ3347 | 0.0260 | 1.67 | 0.89 | lnc-RNF123-1:3 | SEQ3522 | 0.0260 | 4.31 | 0.89 |
| lnc-C11orf21-3:1 | SEQ3348 | 0.0411 | 2.71 | 0.86 | UGDH-AS1:10 | SEQ0407 | 0.0411 | 6.05 | 0.86 |
| lnc-C12orf73-1:1 | SEQ3349 | 0.0411 | 2.02 | 0.86 | lnc-RAB3C-1:1 | SEQ3523 | 0.0411 | 2.75 | 0.86 |
| lnc-C1orf112-4:2 | SEQ3350 | 0.0200 | 4.47 | 0.92 | lnc-ZNF506-2:3 | SEQ3524 | 0.0152 | 5.13 | 0.92 |
| lnc-C1QBP-1:1 | SEQ3351 | 0.0438 | 3.96 | 0.86 | WAC-AS1:12 | SEQ3525 | 0.0043 | 3.99 | 0.97 |
| lnc-C20orf96-1:1 | SEQ2764 | 0.0152 | 2.76 | 0.92 | SNHG16:2 | SEQ3526 | 0.0411 | 7.48 | 0.86 |
| lnc-C6orf106-2:2 | SEQ3352 | 0.0043 | 1.79 | 0.97 | TCONS_00037052 | SEQ1619 | 0.0438 | 6.17 | 0.86 |
| lnc-C9orf152-5:1 | SEQ3353 | 0.0303 | 4.54 | 0.89 | lnc-TMTC3-1:1 | SEQ3527 | 0.0411 | 0.44 | 0.86 |
| lnc-C9orf57-1:1 | SEQ3354 | 0.0152 | 6.22 | 0.92 | lnc-TSTD3-1:3 | SEQ3528 | 0.0043 | 2.63 | 0.97 |
| lnc-CBARP-2:1 | SEQ3355 | 0.0411 | 2.34 | 0.86 | ZMYM4-AS1:1 | SEQ3529 | 0.0087 | 2.47 | 0.94 |
| lnc-CCT4-1:8 | SEQ3356 | 0.0411 | 2.60 | 0.86 | lnc-PPP4C-2:7 | SEQ3530 | 0.0087 | 2.23 | 0.94 |
| lnc-CDC42BPB-4:1 | SEQ3357 | 0.0411 | 3.25 | 0.86 | lnc-TM2D2-1:1 | SEQ3531 | 0.0260 | 2.74 | 0.89 |
| lnc-CDH20-3:1 | SEQ3358 | 0.0087 | 3.08 | 0.94 | lnc-PCED1B-5:3 | SEQ3532 | 0.0260 | 0.11 | 0.89 |
| lnc-CDIPT-1:11 | SEQ3359 | 0.0152 | 2.30 | 0.92 | lnc-ZGRF1-8:1 | SEQ3533 | 0.0260 | 2.15 | 0.89 |
| lnc-CDK12-2:5 | SEQ3360 | 0.0411 | 19.25 | 0.86 | lnc-SAG-3:1 | SEQ3534 | 0.0260 | 6.89 | 0.89 |
| lnc-CDK2AP1-1:9 | SEQ3361 | 0.0411 | 2.20 | 0.86 | lnc-ZCCHC7-2:1 | SEQ3535 | 0.0411 | 2.28 | 0.86 |
| lnc-CEACAM21-5:6 | SEQ3362 | 0.0087 | 5.09 | 0.94 | lnc-TMX2-1:1 | SEQ3536 | 0.0078 | 9.44 | 0.97 |
| lnc-CECR2-1:4 | SEQ3363 | 0.0152 | 74.37 | 0.92 | lnc-SULT1A4-1:30 | SEQ3537 | 0.0411 | 3.45 | 0.86 |
| lnc-CELA3A-5:11 | SEQ3364 | 0.0303 | 2.E+09 | 0.89 | lnc-TET3-2:2 | SEQ3538 | 0.0124 | 5.24 | 0.94 |
| lnc-CEMP1-5:1 | SEQ3365 | 0.0200 | 4.68 | 0.92 | NDUFA6-AS1:42 | SEQ3539 | 0.0260 | 2.90 | 0.89 |
| lnc-CISD2-1:3 | SEQ3366 | 0.0152 | 2.57 | 0.92 | lnc-UBAC1-2:2 | SEQ3540 | 0.0303 | 14.74 | 0.89 |
| lnc-CKS1B-3:1 | SEQ3367 | 0.0087 | 3.27 | 0.94 | lnc-SNX14-5:1 | SEQ3541 | 0.0152 | 2.14 | 0.92 |
| lnc-CLDN11-7:1 | SEQ3368 | 0.0260 | 0.32 | 0.89 | lnc-PPA2-1:1 | SEQ3542 | 0.0087 | 3.28 | 0.94 |
| lnc-CLEC2D-8:7 | SEQ3369 | 0.0152 | 4.52 | 0.92 | lnc-S1PR1-6:1 | SEQ3543 | 0.0260 | 2.34 | 0.89 |
| lnc-CNTRL-6:8 | SEQ3370 | 0.0250 | 5.E+05 | 0.89 | lnc-TARS-6:1 | SEQ3544 | 0.0260 | 2.32 | 0.89 |
| lnc-CPM-1:1 | SEQ3371 | 0.0048 | 21.75 | 1.00 | lnc-USP35-11:2 | SEQ2802 | 0.0411 | 1.87 | 0.86 |
| lnc-CTSV-3:1 | SEQ3372 | 0.0411 | 2.91 | 0.86 | PSMA3-AS1:8 | SEQ3545 | 0.0260 | 0.20 | 0.89 |
| lnc-CXCL2-3:1 | SEQ3373 | 0.0411 | 0.53 | 0.86 | TCONS_00027402 | SEQ1445 | 0.0295 | 0.07 | 0.89 |
| lnc-DALRD3-1:4 | SEQ3374 | 0.0260 | 3.91 | 0.89 | OR2A1-AS1:19 | SEQ3546 | 0.0129 | 24.12 | 0.94 |
| lnc-DAO-3:1 | SEQ0685 | 0.0043 | 1.70 | 0.97 | lnc-POLR3E-3:4 | SEQ3547 | 0.0152 | 1.71 | 0.92 |
| lnc-DCAF1-1:1 | SEQ3375 | 0.0087 | 2.54 | 0.94 | lnc-RMDN2-3:2 | SEQ3548 | 0.0411 | 3.24 | 0.86 |
| lnc-DEF8-1:1 | SEQ3376 | 0.0303 | 5.60 | 0.89 | lnc-SLC25A29-1:2 | SEQ3549 | 0.0081 | 8.76 | 0.97 |
| lnc-DNAL4-4:1 | SEQ3095 | 0.0411 | 4.63 | 0.86 | ZBTB11-AS1:9 | SEQ3550 | 0.0411 | 54.24 | 0.86 |
| lnc-DPH5-5:1 | SEQ3377 | 0.0048 | 17.28 | 1.00 | PEG13:2 | SEQ3551 | 0.0411 | 3.20 | 0.86 |
| lnc-DUSP26-14:1 | SEQ3378 | 0.0043 | 1.99 | 0.97 | lnc-PHF3-12:1 | SEQ3552 | 0.0152 | 2.20 | 0.92 |
| lnc-EBF3-6:2 | SEQ3379 | 0.0152 | 0.33 | 0.92 | lnc-ZNF16-2:11 | SEQ3553 | 0.0152 | 3.42 | 0.92 |
| lnc-EFCAB8-1:3 | SEQ3380 | 0.0411 | 2.73 | 0.86 | RAD51-AS1:7 | SEQ3554 | 0.0341 | 264.44 | 0.88 |
| lnc-EIF1AD-1:1 | SEQ2653 | 0.0152 | 2.12 | 0.92 | lnc-SLC17A5-1:7 | SEQ3555 | 0.0260 | 0.18 | 0.89 |
| lnc-ENOPH1-3:3 | SEQ3381 | 0.0087 | 2.42 | 0.94 | lnc-TMEM155-3:1 | SEQ3556 | 0.0043 | 3.02 | 0.97 |
| lnc-EPGN-4:1 | SEQ3382 | 0.0411 | 0.05 | 0.86 | SH3BP5-AS1:2 | SEQ3557 | 0.0260 | 2.54 | 0.89 |
| lnc-ERCC6L2-14:1 | SEQ3383 | 0.0152 | 2.20 | 0.92 | lnc-SPRED2-22:1 | SEQ2584 | 0.0260 | 2.44 | 0.89 |
| lnc-ESRP2-2:9 | SEQ3384 | 0.0260 | 2.54 | 0.89 | lnc-NSUN5-2:1 | SEQ3558 | 0.0411 | 2.72 | 0.86 |
| lnc-EXOC3L4-3:1 | SEQ3385 | 0.0043 | 13.96 | 0.97 | lnc-TAGLN-2:1 | SEQ3559 | 0.0043 | 2.88 | 0.97 |
| lnc-EYS-1:1 | SEQ3386 | 0.0411 | 3.12 | 0.86 | lnc-OR1A2-1:1 | SEQ3560 | 0.0411 | 2.72 | 0.86 |
| lnc-FAAP100-2:1 | SEQ2299 | 0.0260 | 1.40 | 0.89 | lnc-SYNGR1-5:1 | SEQ3561 | 0.0260 | 0.52 | 0.89 |
| lnc-FAM103A1-2:5 | SEQ2607 | 0.0087 | 2.37 | 0.94 | POT1-AS1:2 | SEQ3562 | 0.0260 | 5.77 | 0.89 |
| lnc-FAM156A-2:1 | SEQ3387 | 0.0129 | 3.46 | 0.94 | TCONS_00011974 | SEQ1218 | 0.0411 | 2.10 | 0.86 |
| lnc-FAM177B-1:1 | SEQ3388 | 0.0411 | 1.86 | 0.86 | lnc-TMEM234-1:4 | SEQ3563 | 0.0260 | 3.40 | 0.89 |
| lnc-FAM231C-7:6 | SEQ3389 | 0.0260 | 2.23 | 0.89 | lnc-RRN3-3:5 | SEQ2770 | 0.0043 | 3.61 | 0.97 |
| lnc-FAM72B-7:2 | SEQ3390 | 0.0152 | 4.07 | 0.92 | lnc-STAU2-3:4 | SEQ3564 | 0.0072 | 33.24 | 0.97 |
| lnc-FAM72D-4:1 | SEQ3391 | 0.0260 | 2.98 | 0.89 | lnc-PLA2G15-2:2 | SEQ3565 | 0.0411 | 2.29 | 0.86 |

TABLE 9-continued

The 410 plasma lncRNAs that are differentially expressed in AD plasma versus HC plasma.

| lncRNA | SEQ | p value | FC | AUC | lncRNA | SEQ | p value | FC | AUC |
|---|---|---|---|---|---|---|---|---|---|
| lnc-FANCL-4:1 | SEQ2690 | 0.0152 | 2.43 | 0.92 | lnc-PXN-1:1 | SEQ2506 | 0.0411 | 3.05 | 0.86 |
| lnc-FBN1-3:2 | SEQ3392 | 0.0043 | 7.16 | 0.97 | lnc-UBAC1-2:1 | SEQ3566 | 0.0411 | 4.42 | 0.86 |
| lnc-FER-6:1 | SEQ3393 | 0.0260 | 3.17 | 0.89 | TUG1:21 | SEQ3567 | 0.0411 | 0.36 | 0.86 |
| lnc-FKBP6-4:1 | SEQ3394 | 0.0152 | 2.65 | 0.92 | MIR4453HG:2 | SEQ3568 | 0.0411 | 2.78 | 0.86 |
| lnc-FNDC1-9:9 | SEQ3395 | 0.0411 | 2.55 | 0.86 | lnc-SUGT1-3:1 | SEQ0131 | 0.0341 | 56.87 | 0.88 |
| lnc-GAPT-6:2 | SEQ3396 | 0.0152 | 5.48 | 0.92 | lnc-OSBPL7-3:1 | SEQ3569 | 0.0260 | 0.44 | 0.89 |
| lnc-GAS2-1:15 | SEQ3397 | 0.0411 | 2.21 | 0.86 | lnc-SLA2-1:1 | SEQ3570 | 0.0411 | 2.70 | 0.86 |
| lnc-GDAP2-3:2 | SEQ3398 | 0.0411 | 1.82 | 0.86 | lnc-TRIM28-13:1 | SEQ3571 | 0.0152 | 3.75 | 0.92 |
| lnc-GNA11-3:1 | SEQ2681 | 0.0411 | 2.23 | 0.86 | lnc-ZBTB20-1:4 | SEQ3572 | 0.0411 | 3.11 | 0.86 |
| lnc-GNA11-3:2 | SEQ3399 | 0.0438 | 5.64 | 0.86 | PXN-AS1:15 | SEQ3573 | 0.0411 | 4.12 | 0.86 |
| lnc-GOLGA8F-8:1 | SEQ3400 | 0.0295 | 3.85 | 0.89 | PSMA3-AS1:6 | SEQ3574 | 0.0087 | 14.53 | 0.94 |
| lnc-GPR160-2:1 | SEQ3401 | 0.0411 | 1.49 | 0.86 | lnc-SP140-3:4 | SEQ3575 | 0.0124 | 11.42 | 0.94 |
| lnc-GPR37L1-7:4 | SEQ3402 | 0.0260 | 3.80 | 0.89 | VIM-AS1:7 | SEQ3576 | 0.0411 | 5.99 | 0.86 |
| lnc-GPR83-5:1 | SEQ3403 | 0.0043 | 1.86 | 0.97 | lnc-TUFM-3:3 | SEQ3577 | 0.0260 | 2.21 | 0.89 |
| lnc-GRB7-1:1 | SEQ3404 | 0.0043 | 48.62 | 0.97 | lnc-SLC45A4-8:1 | SEQ3578 | 0.0152 | 3.34 | 0.92 |
| lnc-GRINA-2:1 | SEQ2969 | 0.0411 | 2.10 | 0.86 | lnc-RLIM-4:1 | SEQ3579 | 0.0260 | 2.41 | 0.89 |
| lnc-GRK4-2:7 | SEQ3405 | 0.0411 | 1.97 | 0.86 | lnc-RACK1-1:2 | SEQ3580 | 0.0260 | 4.55 | 0.89 |
| lnc-HAAO-7:6 | SEQ3406 | 0.0411 | 0.25 | 0.86 | lnc-TRIM28-13:2 | SEQ3581 | 0.0260 | 10.16 | 0.89 |
| lnc-HAO2-2:1 | SEQ3407 | 0.0078 | 27.85 | 0.97 | lnc-SPOCK2-1:2 | SEQ3582 | 0.0416 | 2.43 | 0.86 |
| lnc-HARS-1:1 | SEQ3408 | 0.0411 | 0.50 | 0.86 | lnc-USP44-3:1 | SEQ3583 | 0.0411 | 3.20 | 0.86 |
| lnc-HBG2-1:1 | SEQ3409 | 0.0043 | 3.45 | 0.97 | ZNF341-AS1:10 | SEQ3584 | 0.0087 | 1.96 | 0.94 |
| lnc-HEATR4-6:1 | SEQ3410 | 0.0341 | 12.48 | 0.88 | lnc-RBM11-5:4 | SEQ3585 | 0.0278 | 6.38 | 0.89 |
| lnc-HELB-2:1 | SEQ3411 | 0.0260 | 3.55 | 0.89 | TCONS 00066563 | SEQ2107 | 0.0260 | 0.19 | 0.89 |
| lnc-HLA-DOB-1:1 | SEQ3412 | 0.0450 | 4.00 | 0.86 | lnc-ROM1-7:3 | SEQ3586 | 0.0152 | 2.37 | 0.92 |
| lnc-HMBOX1-1:1 | SEQ3413 | 0.0087 | 33.72 | 0.94 | lnc-WNT1-5:1 | SEQ3587 | 0.0411 | 2.54 | 0.86 |
| lnc-HMGA1-2:11 | SEQ3414 | 0.0411 | 5.75 | 0.86 | lnc-WDR45B-1:2 | SEQ3588 | 0.0194 | 9.06 | 0.92 |
| lnc-HMGA1-2:4 | SEQ3415 | 0.0260 | 2.70 | 0.89 | lnc-ROM1-7:6 | SEQ3589 | 0.0411 | 2.31 | 0.86 |
| lnc-HMGN5-3:1 | SEQ3416 | 0.0260 | 2.42 | 0.89 | ST7-AS1:1 | SEQ3590 | 0.0411 | 1.76 | 0.86 |
| lnc-HMHB1-6:2 | SEQ3417 | 0.0087 | 4.03 | 0.94 | lnc-TBP-3:1 | SEQ3591 | 0.0411 | 2.93 | 0.86 |
| lnc-HTR1B-1:4 | SEQ3418 | 0.0411 | 3.85 | 0.86 | lnc-RASGRP1-6:1 | SEQ3592 | 0.0200 | 6.95 | 0.92 |
| lnc-IER5-3:1 | SEQ2286 | 0.0284 | Inf | 0.83 | lnc-ZNF726-5:2 | SEQ3593 | 0.0260 | 2.69 | 0.89 |
| lnc-IFFO1-3:1 | SEQ3419 | 0.0152 | 1.35 | 0.92 | TUG1:9 | SEQ3594 | 0.0411 | 2.02 | 0.86 |
| lnc-IFNG-3:1 | SEQ3420 | 0.0450 | 5.01 | 0.86 | lnc-SLC9A3-1:2 | SEQ3595 | 0.0200 | 9.54 | 0.92 |
| lnc-IGIP-2:3 | SEQ3421 | 0.0087 | 3.95 | 0.94 | lnc-RBL2-4:3 | SEQ3596 | 0.0081 | 9.83 | 0.97 |
| lnc-IGSF9B-2:1 | SEQ2987 | 0.0152 | 3.85 | 0.92 | lnc-VSNL1-5:1 | SEQ3597 | 0.0260 | 2.45 | 0.89 |
| lnc-IL18BP-1:2 | SEQ3422 | 0.0411 | 2.29 | 0.86 | TCONS 00059492 | SEQ1962 | 0.0438 | 3.97 | 0.86 |
| lnc-IL18BP-1:3 | SEQ3423 | 0.0411 | 2.29 | 0.86 | lnc-RIPOR2-3:1 | SEQ3598 | 0.0411 | 2.37 | 0.86 |
| lnc-IL20RA-3:1 | SEQ3424 | 0.0260 | 0.27 | 0.89 | lnc-TCTA-2:1 | SEQ2757 | 0.0260 | 1.35 | 0.89 |
| lnc-ITGB4-2:3 | SEQ3425 | 0.0260 | 2.59 | 0.89 | lnc-PSMC3IP-1:1 | SEQ3599 | 0.0260 | 3.02 | 0.89 |
| lnc-JAM2-11:1 | SEQ3426 | 0.0152 | 1.77 | 0.92 | lnc-PROC-1:11 | SEQ3600 | 0.0152 | 4.36 | 0.92 |
| lnc-JMJD6-1:5 | SEQ3427 | 0.0411 | 4.30 | 0.86 | TP53TG1:3 | SEQ3601 | 0.0043 | 21.53 | 0.97 |
| lnc-JMJD7-PLA2G4B-2:8 | SEQ3428 | 0.0411 | 3.59 | 0.86 | MALAT1:11 | SEQ3276 | 0.0260 | 2.03 | 0.89 |
| lnc-KALRN-5:10 | SEQ3429 | 0.0260 | 3.54 | 0.89 | lnc-PCGF2-4:1 | SEQ3602 | 0.0260 | 6.82 | 0.89 |
| lnc-KIAA1644-1:1 | SEQ3430 | 0.0411 | 3.72 | 0.86 | lnc-SQSTM1-2:2 | SEQ3603 | 0.0411 | 1.77 | 0.86 |
| lnc-KLHDC9-5:4 | SEQ3431 | 0.0260 | 3.67 | 0.89 | TUG1:44 | SEQ3604 | 0.0411 | 6.33 | 0.86 |
| lnc-KLHL25-6:1 | SEQ3432 | 0.0152 | 2.93 | 0.92 | SH3BP5-AS1:6 | SEQ3605 | 0.0260 | 2.54 | 0.89 |
| lnc-KRT80-3:1 | SEQ3433 | 0.0438 | 3.65 | 0.86 | TRG-AS1:14 | SEQ3606 | 0.0152 | 20.18 | 0.92 |
| lnc-LAMA5-1:4 | SEQ3434 | 0.0022 | 10.44 | 1.00 | lnc-RSC1A1-1:1 | SEQ3607 | 0.0411 | 2.65 | 0.86 |
| lnc-LAMA5-4:1 | SEQ3435 | 0.0260 | 2.18 | 0.89 | lnc-NUP153-3:5 | SEQ3608 | 0.0450 | 3.13 | 0.86 |
| lnc-LHPP-6:6 | SEQ3436 | 0.0411 | 3.85 | 0.86 | lnc-TAOK1-4:1 | SEQ3609 | 0.0043 | 3.26 | 0.97 |
| lnc-LIN7A-3:1 | SEQ3437 | 0.0167 | 12.31 | 0.90 | lnc-ZBTB2-6:1 | SEQ3610 | 0.0411 | 3.43 | 0.86 |
| lnc-LPIN3-1:1 | SEQ3438 | 0.0124 | 5.66 | 0.94 | lnc-PILRB-1:3 | SEQ3611 | 0.0411 | 39.86 | 0.86 |
| lnc-LRCH1-6:1 | SEQ3439 | 0.0152 | 1.86 | 0.92 | lnc-RBMS2-4:1 | SEQ2378 | 0.0087 | 4.62 | 0.94 |
| lnc-LRIG2-10:1 | SEQ3440 | 0.0411 | 1.81 | 0.86 | lnc-SUGCT-4:1 | SEQ3612 | 0.0152 | 2.79 | 0.92 |
| lnc-LRR1-1:2 | SEQ0813 | 0.0411 | 0.29 | 0.86 | lnc-RNF24-3:1 | SEQ3613 | 0.0411 | 1.57 | 0.86 |
| lnc-LRR1-1:3 | SEQ0814 | 0.0411 | 0.81 | 0.86 | lnc-NUS1-5:1 | SEQ3614 | 0.0411 | 2.03 | 0.86 |
| lnc-LRRC10-1:2 | SEQ3441 | 0.0087 | 3.06 | 0.94 | ZNF341-AS1:9 | SEQ3615 | 0.0152 | 1.81 | 0.92 |
| lnc-LRRC37A3-5:8 | SEQ3442 | 0.0050 | 1.E+21 | 1.00 | lnc-STAR-1:2 | SEQ3616 | 0.0043 | 2.51 | 0.97 |
| lnc-MANBA-2:9 | SEQ3443 | 0.0260 | 2.39 | 0.89 | TRHDE-AS1:14 | SEQ3617 | 0.0087 | 0.23 | 0.94 |
| lnc-MARCH7-3:1 | SEQ3444 | 0.0260 | 3.61 | 0.89 | lnc-SLC3A2-6:1 | SEQ2428 | 0.0411 | 1.89 | 0.86 |
| lnc-MASTL-6:1 | SEQ2430 | 0.0278 | 5.38 | 0.89 | lnc-WRB-7:2 | SEQ3618 | 0.0411 | 2.32 | 0.86 |
| lnc-MAX-16:1 | SEQ3445 | 0.0260 | 1.68 | 0.89 | lnc-PSMB9-6:5 | SEQ3619 | 0.0260 | 3.91 | 0.89 |
| lnc-MCTP2-7:4 | SEQ3446 | 0.0411 | 3.33 | 0.86 | lnc-TIPIN-1:1 | SEQ3620 | 0.0303 | 5.03 | 0.89 |
| lnc-MEP1B-2:1 | SEQ3447 | 0.0260 | 2.36 | 0.89 | lnc-SPATA32-4:1 | SEQ3621 | 0.0087 | 3.81 | 0.94 |
| lnc-MFSD13A-2:1 | SEQ3448 | 0.0152 | 2.34 | 0.92 | lnc-VSIG4-2:1 | SEQ3622 | 0.0087 | 3.33 | 0.94 |
| lnc-MIEN1-1:1 | SEQ3449 | 0.0411 | 2.60 | 0.86 | lnc-TRAK1-1:1 | SEQ3623 | 0.0379 | 41.45 | 0.86 |
| lnc-MLLT1-2:1 | SEQ3450 | 0.0152 | 2.16 | 0.92 | lnc-TMEM178A-1:7 | SEQ3624 | 0.0295 | 21.47 | 0.89 |
| lnc-MLX-3:1 | SEQ3451 | 0.0087 | 3.16 | 0.94 | PITPNA-AS1:3 | SEQ3625 | 0.0260 | 3.07 | 0.89 |
| lnc-MNX1-11:1 | SEQ3452 | 0.0124 | 5.74 | 0.94 | lnc-RNF135-1:27 | SEQ3626 | 0.0129 | 117.53 | 0.94 |
| lnc-MROH6-1:1 | SEQ3453 | 0.0129 | 17.08 | 0.94 | lnc-OTULIN-1:1 | SEQ3627 | 0.0260 | 3.04 | 0.89 |
| lnc-MYOM1-6:3 | SEQ3454 | 0.0022 | 5.94 | 1.00 | PSMA3-AS1:40 | SEQ3628 | 0.0152 | 7.16 | 0.92 |
| lnc-NAMPT-1:2 | SEQ3455 | 0.0260 | 2.03 | 0.89 | lnc-TSSK6-1:1 | SEQ3629 | 0.0152 | 4.37 | 0.92 |
| lnc-NINJ1-2:1 | SEQ3456 | 0.0043 | 2.75 | 0.97 | lnc-PLPP2-5:3 | SEQ3630 | 0.0411 | 1.71 | 0.86 |

TABLE 9-continued

The 410 plasma lncRNAs that are differentially expressed in AD plasma versus HC plasma.

| lncRNA | SEQ | p value | FC | AUC | lncRNA | SEQ | p value | FC | AUC |
|---|---|---|---|---|---|---|---|---|---|
| lnc-NR2F6-5:1 | SEQ3457 | 0.0043 | 2.51 | 0.97 | lnc-STON2-5:1 | SEQ3631 | 0.0087 | 1.92 | 0.94 |
| PCBP1-AS1:217 | SEQ3458 | 0.0087 | 1.54 | 0.94 | ZNF528-AS1:16 | SEQ3632 | 0.0194 | 4.E+08 | 0.92 |

2847 lncRNAs were differentially expressed in whole blood (Paxgene RNA tube) of MCI group or mild AD group or moderate-to-severe AD group or both of these AD groups or FTD group or DLB group as compared to healthy control group, and having statistical significance (p value <0.05, Wilcoxon test) and a fold change FC≤0.80 or ≥1.20. These lncRNAs showed a differential expression with a statistical significance for at least one disease group when compared to healthy control group (p value<0.05, Wilcoxon). The 2847 lncRNAs are shown in Table 10.

TABLE 10

2847 whole blood (Paxgene RNA tube) lncRNAs differentially expressed in MCI group or mild AD group or moderate-to-severe AD group or both of these AD groups or FTD group or DLB group as compared to healthy control group.

| Group | lncRNA | SEQ | p-value | FC | Group | lncRNA | SEQ | p-value | FC |
|---|---|---|---|---|---|---|---|---|---|
| DLB | A1BG-AS1:13 | SEQ5267 | 1.E-04 | 1.8 | DLB | lnc-MRPS5-2:2 | SEQ4304 | 1.E-03 | 1.8 |
| MCI | A1BG-AS1:13 | SEQ5267 | 5.E-04 | 1.6 | miAD | lnc-MRPS5-2:2 | SEQ4304 | 7.E-03 | 1.4 |
| DLB | A2M-AS1:3 | SEQ5584 | 2.E-04 | 2.5 | All AD | lnc-MRPS5-2:2 | SEQ4304 | 1.E-02 | 1.4 |
| DLB | AATBC:4 | SEQ4566 | 2.E-03 | 1.4 | MCI | lnc-MRPS5-2:3 | SEQ4165 | 1.E-04 | 2.1 |
| DLB | AATBC:5 | SEQ4567 | 2.E-03 | 1.4 | miAD | lnc-MRPS5-2:3 | SEQ4165 | 1.E-02 | 1.4 |
| DLB | ACBD3-AS1:14 | SEQ5759 | 8.E-05 | 2.2 | All AD | lnc-MRPS5-2:3 | SEQ4165 | 2.E-02 | 1.3 |
| msAD | ACTN1-AS1:6 | SEQ3638 | 3.E-02 | 1.2 | MCI | lnc-MRPS5-4:3 | SEQ5499 | 2.E-04 | 2.2 |
| All AD | ACTN1-AS1:6 | SEQ3638 | 4.E-02 | 1.2 | DLB | lnc-MTERF1-5:1 | SEQ4758 | 1.E-03 | 1.5 |
| All AD | ADAMTSL4-AS1:1 | SEQ3640 | 2.E-02 | 0.8 | All AD | lnc-MTFR1L-1:4 | SEQ5202 | 3.E-02 | 1.3 |
| msAD | ADAMTSL4-AS1:1 | SEQ3640 | 2.E-02 | 0.8 | FTD | lnc-MTHFD1-3:1 | SEQ4184 | 8.E-07 | 0.5 |
| FTD | ADNP-AS1:12 | SEQ0340 | 3.E-04 | 0.6 | All AD | lnc-MTHFD1-3:1 | SEQ4184 | 8.E-03 | 0.7 |
| MCI | AGAP2-AS1:1 | SEQ3643 | 4.E-05 | 2.0 | miAD | lnc-MTHFD1-3:1 | SEQ4184 | 1.E-02 | 0.6 |
| All AD | AGAP2-AS1:1 | SEQ3643 | 3.E-02 | 1.3 | FTD | lnc-MTPN-1:1 | SEQ4462 | 2.E-05 | 0.3 |
| All AD | AIRN:2 | SEQ3645 | 2.E-02 | 0.8 | miAD | lnc-MTPN-1:1 | SEQ4462 | 2.E-04 | 0.4 |
| FTD | ANKRD10-IT1:2 | SEQ5990 | 1.E-06 | 0.4 | All AD | lnc-MTPN-1:1 | SEQ4462 | 3.E-04 | 0.5 |
| FTD | ANKRD44-IT1:1 | SEQ4807 | 1.E-03 | 0.7 | msAD | lnc-MTPN-1:1 | SEQ4462 | 2.E-03 | 0.5 |
| DLB | APOBEC3B-AS1:2 | SEQ5079 | 2.E-05 | 0.4 | miAD | lnc-MTRNR2L3-1:2 | SEQ4241 | 1.E-02 | 1.3 |
| MCI | APOBEC3B-AS1:2 | SEQ5079 | 1.E-04 | 0.5 | All AD | lnc-MTRNR2L3-1:2 | SEQ4241 | 1.E-02 | 1.2 |
| FTD | APOBEC3B-AS1:2 | SEQ5079 | 6.E-04 | 0.5 | DLB | lnc-MTUS2-9:1 | SEQ4829 | 9.E-04 | 1.3 |
| miAD | APTR:15 | SEQ3651 | 4.E-03 | 0.7 | DLB | lnc-MUC17-4:1 | SEQ5244 | 5.E-04 | 1.4 |
| All AD | APTR:15 | SEQ3651 | 5.E-03 | 0.7 | DLB | lnc-MUC20-16:1 | SEQ4224 | 6.E-05 | 1.5 |
| msAD | APTR:15 | SEQ3651 | 3.E-02 | 0.8 | MCI | lnc-MUC20-16:1 | SEQ4224 | 6.E-05 | 1.5 |
| All AD | APTR:16 | SEQ3636 | 2.E-02 | 0.8 | miAD | lnc-MUC20-16:1 | SEQ4224 | 7.E-04 | 1.3 |
| msAD | APTR:16 | SEQ3636 | 5.E-02 | 0.8 | All AD | lnc-MUC20-16:1 | SEQ4224 | 1.E-03 | 1.3 |
| miAD | APTR:17 | SEQ0260 | 5.E-03 | 0.7 | msAD | lnc-MUC20-16:1 | SEQ4224 | 1.E-02 | 1.3 |
| All AD | APTR:17 | SEQ0260 | 9.E-03 | 0.7 | MCI | lnc-MUC20-16:2 | SEQ4127 | 4.E-07 | 2.1 |
| DLB | ARAP1-AS1:1 | SEQ4621 | 1.E-03 | 1.4 | DLB | lnc-MUC20-16:2 | SEQ4127 | 6.E-06 | 2.0 |
| MCI | ASH1L-AS1:1 | SEQ4883 | 9.E-04 | 2.3 | FTD | lnc-MUC20-16:2 | SEQ4127 | 1.E-05 | 1.9 |
| DLB | ATP1A1-AS1:5 | SEQ5498 | 2.E-04 | 2.0 | miAD | lnc-MUC20-16:2 | SEQ4127 | 2.E-03 | 1.4 |
| DLB | ATP2A1-AS1:12 | SEQ5180 | 5.E-04 | 1.4 | All AD | lnc-MUC20-16:2 | SEQ4127 | 2.E-03 | 1.3 |
| DLB | ATP6VOE2-AS1:1 | SEQ4643 | 1.E-03 | 1.6 | msAD | lnc-MUC20-16:2 | SEQ4127 | 1.E-02 | 1.3 |
| MCI | ATP6VOE2-AS1:14 | SEQ3659 | 3.E-06 | 2.3 | DLB | lnc-MUC5B-1:1 | SEQ5724 | 9.E-05 | 1.4 |
| FTD | ATP6VOE2-AS1:14 | SEQ3659 | 6.E-04 | 1.6 | DLB | lnc-MUSTN1-1:1 | SEQ5656 | 1.E-04 | 1.4 |
| miAD | ATP6VOE2-AS1:14 | SEQ3659 | 7.E-04 | 1.6 | FTD | lnc-MVB12B-7:1 | SEQ5716 | 1.E-04 | 0.5 |
| All AD | ATP6VOE2-AS1:14 | SEQ3659 | 2.E-02 | 1.3 | DLB | lnc-MVP-3:6 | SEQ5362 | 7.E-06 | 2.1 |
| DLB | ATP6VOE2-AS1:18 | SEQ3663 | 4.E-04 | 1.9 | MCI | lnc-MVP-3:6 | SEQ5362 | 1.E-05 | 2.3 |
| MCI | ATP6VOE2-AS1:18 | SEQ3663 | 2.E-03 | 1.6 | FTD | lnc-MVP-3:6 | SEQ5362 | 4.E-04 | 1.8 |
| msAD | ATP6VOE2-AS1:18 | SEQ3663 | 2.E-02 | 1.2 | msAD | lnc-MYBBP1A-2:1 | SEQ4100 | 1.E-02 | 1.4 |
| All AD | ATP6VOE2-AS1:18 | SEQ3663 | 2.E-02 | 1.2 | All AD | lnc-MYBBP1A-2:1 | SEQ4100 | 2.E-02 | 1.4 |
| MCI | ATP6VOE2-AS1:19 | SEQ4794 | 1.E-03 | 2.4 | FTD | lnc-MYF5-2:3 | SEQ2245 | 4.E-08 | 0.4 |
| DLB | ATP6VOE2-AS1:22 | SEQ5142 | 6.E-04 | 1.8 | DLB | lnc-MYF5-2:3 | SEQ2245 | 9.E-05 | 0.5 |
| MCI | ATP6VOE2-AS1:27 | SEQ5188 | 3.E-04 | 1.5 | MCI | lnc-MYF5-2:3 | SEQ2245 | 1.E-04 | 0.5 |
| DLB | ATP6VOE2-AS1:27 | SEQ5188 | 5.E-04 | 1.5 | miAD | lnc-MYF5-2:3 | SEQ2245 | 1.E-03 | 0.6 |
| FTD | BACH1-IT1:1 | SEQ5153 | 5.E-04 | 0.6 | All AD | lnc-MYF5-2:3 | SEQ2245 | 6.E-03 | 0.6 |
| DLB | BISPR:20 | SEQ5519 | 2.E-04 | 1.4 | FTD | lnc-MYF5-2:4 | SEQ2296 | 4.E-09 | 0.4 |
| miAD | BOLA3-AS1:14 | SEQ3673 | 9.E-05 | 2.3 | MCI | lnc-MYF5-2:4 | SEQ2296 | 3.E-05 | 0.4 |
| All AD | BOLA3-AS1:14 | SEQ3673 | 2.E-04 | 2.0 | DLB | lnc-MYF5-2:4 | SEQ2296 | 4.E-05 | 0.5 |
| FTD | BOLA3-AS1:14 | SEQ3673 | 3.E-04 | 2.8 | miAD | lnc-MYF5-2:4 | SEQ2296 | 2.E-04 | 0.5 |
| msAD | BOLA3-AS1:14 | SEQ3673 | 4.E-03 | 1.7 | All AD | lnc-MYF5-2:4 | SEQ2296 | 2.E-03 | 0.6 |
| FTD | BOLA3-AS1:25 | SEQ3677 | 1.E-05 | 0.6 | msAD | lnc-MYF5-2:4 | SEQ2296 | 4.E-02 | 0.6 |
| All AD | BOLA3-AS1:25 | SEQ3677 | 3.E-02 | 0.8 | FTD | lnc-MYF5-2:5 | SEQ4262 | 4.E-05 | 0.5 |
| DLB | C6orf47-AS1:1 | SEQ4838 | 9.E-04 | 1.4 | miAD | lnc-MYF5-2:5 | SEQ4262 | 9.E-03 | 0.7 |
| DLB | CACTIN-AS1:2 | SEQ3680 | 4.E-05 | 1.7 | All AD | lnc-MYF5-2:5 | SEQ4262 | 2.E-02 | 0.7 |
| msAD | CACTIN-AS1:2 | SEQ3680 | 1.E-03 | 1.3 | All AD | lnc-MYH9-1:1 | SEQ4021 | 1.E-02 | 0.7 |
| All AD | CACTIN-AS1:2 | SEQ3680 | 1.E-03 | 1.3 | msAD | lnc-MYH9-1:1 | SEQ4021 | 2.E-02 | 0.7 |
| MCI | CACTIN-AS1:2 | SEQ3680 | 1.E-03 | 1.3 | DLB | lnc-MYLPF-3:2 | SEQ5847 | 4.E-05 | 1.5 |

TABLE 10-continued 2847 whole blood (Paxgene RNA tube) lncRNAs differentially expressed in
MCI group or mild AD group or moderate-to-severe AD group or both of these
AD groups or FTD group or DLB group as compared to healthy control group.

| Group | lncRNA | SEQ | p-value | FC | Group | lncRNA | SEQ | p-value | FC |
|---|---|---|---|---|---|---|---|---|---|
| miAD | CACTIN-AS1:2 | SEQ3680 | 6.E-03 | 1.3 | MCI | lnc-MYO16-7:1 | SEQ4673 | 1.E-03 | 0.8 |
| DLB | CACTIN-AS1:5 | SEQ2914 | 3.E-04 | 1.7 | DLB | lnc-MYO1D-1:2 | SEQ5020 | 7.E-04 | 1.4 |
| MCI | CACTIN-AS1:5 | SEQ2914 | 7.E-03 | 1.7 | FTD | lnc-MYO6-1:1 | SEQ4205 | 8.E-06 | 0.5 |
| All AD | CACTIN-AS1:6 | SEQ3686 | 5.E-02 | 1.2 | miAD | lnc-MY06-1:1 | SEQ4205 | 1.E-02 | 0.7 |
| DLB | CAPN10-AS1:2 | SEQ5209 | 5.E-04 | 1.8 | All AD | lnc-MYO6-1:1 | SEQ4205 | 1.E-02 | 0.7 |
| DLB | CARD8-AS1:5 | SEQ4426 | 2.E-03 | 1.5 | FTD | lnc-MYOM1-6:2 | SEQ5872 | 3.E-05 | 0.6 |
| DLB | CASC2:1 | SEQ2645 | 5.E-05 | 1.5 | DLB | lnc-N4BP2-3:1 | SEQ3688 | 5.E-05 | 2.4 |
| All AD | CATIP-AS1:6 | SEQ3690 | 5.E-02 | 0.8 | All AD | lnc-N4BP2-3:1 | SEQ3688 | 3.E-02 | 1.3 |
| DLB | CCDC144NL-AS1:22 | SEQ4979 | 5.E-05 | 1.9 | msAD | lnc-N4BP2-3:1 | SEQ3688 | 5.E-02 | 1.3 |
| MCI | CCDC144NL-AS1:22 | SEQ4979 | 8.E-04 | 1.8 | DLB | lnc-N4BP2L1-4:1 | SEQ5458 | 3.E-04 | 2.0 |
| DLB | CCDC144NL-AS1:50 | SEQ3693 | 2.E-05 | 1.9 | All AD | lnc-NAA35-13:2 | SEQ5233 | 4.E-02 | 0.8 |
| MCI | CCDC144NL-AS1:50 | SEQ3693 | 2.E-05 | 2.1 | FTD | lnc-NAA38-5:1 | SEQ4193 | 5.E-04 | 0.7 |
| msAD | CCDC144NL-AS1:50 | SEQ3693 | 2.E-02 | 1.2 | miAD | lnc-NAA38-5:1 | SEQ4193 | 1.E-02 | 0.8 |
| All AD | CCDC144NL-AS1:50 | SEQ3693 | 4.E-02 | 1.2 | All AD | lnc-NAA38-5:1 | SEQ4193 | 4.E-02 | 0.8 |
| DLB | CCDC144NL-AS1:51 | SEQ3697 | 2.E-05 | 1.9 | FTD | lnc-NABP1-1:1 | SEQ5416 | 3.E-04 | 0.7 |
| MCI | CCDC144NL-AS1:51 | SEQ3697 | 4.E-05 | 2.0 | FTD | lnc-NABP1-1:2 | SEQ4356 | 1.E-05 | 0.6 |
| FTD | CCDC144NL-AS1:51 | SEQ3697 | 6.E-04 | 1.4 | miAD | lnc-NABP1-1:2 | SEQ4356 | 4.E-03 | 0.7 |
| All AD | CCDC144NL-AS1:51 | SEQ3697 | 1.E-02 | 1.2 | All AD | lnc-NABP1-1:2 | SEQ4356 | 1.E-02 | 0.7 |
| msAD | CCDC144NL-AS1:51 | SEQ3697 | 3.E-02 | 1.2 | MCI | lnc-NABP1-5:1 | SEQ4160 | 1.E-03 | 1.6 |
| DLB | CCDC183-AS1:4 | SEQ3701 | 2.E-05 | 1.5 | All AD | lnc-NABP1-5:1 | SEQ4160 | 7.E-03 | 1.3 |
| MCI | CCDC183-AS1:4 | SEQ3701 | 6.E-04 | 1.3 | msAD | lnc-NABP1-5:1 | SEQ4160 | 1.E-02 | 1.3 |
| All AD | CCDC183-AS1:4 | SEQ3701 | 2.E-02 | 1.1 | FTD | lnc-NAMPT-1:2 | SEQ3455 | 8.E-05 | 0.6 |
| msAD | CCDC183-AS1:4 | SEQ3701 | 2.E-02 | 1.1 | DLB | lnc-NAT1-7:2 | SEQ4687 | 1.E-03 | 1.4 |
| MCI | CCDC183-AS1:5 | SEQ2925 | 7.E-04 | 1.6 | FTD | lnc-NAT9-1:1 | SEQ4159 | 3.E-07 | 1.7 |
| All AD | CCDC18-AS1:45 | SEQ3706 | 5.E-02 | 1.3 | MCI | lnc-NAT9-1:1 | SEQ4159 | 1.E-06 | 2.1 |
| miAD | CD27-AS1:1 | SEQ3707 | 1.E-02 | 1.4 | DLB | lnc-NAT9-1:1 | SEQ4159 | 3.E-06 | 2.0 |
| All AD | CD27-AS1:1 | SEQ3707 | 2.E-02 | 1.3 | miAD | lnc-NAT9-1:1 | SEQ4159 | 1.E-02 | 1.2 |
| FTD | CEBPB-AS1:2 | SEQ4719 | 2.E-04 | 1.8 | All AD | lnc-NAT9-1:1 | SEQ4159 | 2.E-02 | 1.2 |
| MCI | CEBPB-AS1:2 | SEQ4719 | 5.E-04 | 1.9 | DLB | lnc-NAT9-1:4 | SEQ5013 | 7.E-04 | 1.4 |
| DLB | CEBPB-AS1:2 | SEQ4719 | 1.E-03 | 1.7 | MCI | lnc-NAV1-9:1 | SEQ5343 | 5.E-05 | 2.1 |
| miAD | CFAP58-AS1:4 | SEQ0109 | 1.E-02 | 0.7 | DLB | lnc-NAV1-9:1 | SEQ5343 | 4.E-04 | 2.2 |
| All AD | CFAP58-AS1:4 | SEQ0109 | 3.E-02 | 0.7 | DLB | lnc-NAXD-4:1 | SEQ2736 | 2.E-03 | 1.3 |
| FTD | CFLAR-AS1:22 | SEQ3712 | 2.E-05 | 0.6 | FTD | lnc-NBN-2:1 | SEQ3838 | 1.E-05 | 0.6 |
| All AD | CFLAR-AS1:22 | SEQ3712 | 2.E-02 | 0.7 | All AD | lnc-NBN-2:1 | SEQ3838 | 1.E-02 | 0.7 |
| FTD | CHMP1B-AS1:2 | SEQ2249 | 1.E-07 | 0.4 | miAD | lnc-NBN-2:1 | SEQ3838 | 1.E-02 | 0.7 |
| MCI | CHMP1B-AS1:2 | SEQ2249 | 4.E-04 | 0.4 | msAD | lnc-NBN-2:1 | SEQ3838 | 3.E-02 | 0.8 |
| DLB | CHMP1B-AS1:2 | SEQ2249 | 2.E-03 | 0.5 | DLB | lnc-NBPF1-1:12 | SEQ4728 | 2.E-04 | 3.1 |
| All AD | CHMP1B-AS1:2 | SEQ2249 | 2.E-02 | 0.6 | MCI | lnc-NBPF1-1:12 | SEQ4728 | 1.E-03 | 2.5 |
| miAD | CKMT2-AS1:32 | SEQ3713 | 3.E-03 | 1.7 | DLB | lnc-NBPF1-1:6 | SEQ3026 | 8.E-05 | 2.4 |
| All AD | CKMT2-AS1:32 | SEQ3713 | 9.E-03 | 1.5 | FTD | lnc-NBPF1-1:6 | SEQ3026 | 5.E-04 | 2.0 |
| MCI | CPEB2-AS1:4 | SEQ4788 | 1.E-03 | 1.8 | MCI | lnc-NBPF1-1:6 | SEQ3026 | 1.E-03 | 2.0 |
| DLB | CTBP1-AS:2 | SEQ4927 | 8.E-04 | 1.4 | FTD | lnc-NBPF15-1:2 | SEQ4591 | 1.E-03 | 1.6 |
| DLB | CTBP1-AS:3 | SEQ5245 | 2.E-05 | 1.6 | MCI | lnc-NBPF15-1:2 | SEQ4591 | 2.E-03 | 1.6 |
| MCI | CTBP1-AS:3 | SEQ5245 | 5.E-02 | 1.4 | DLB | lnc-NBPF15-1:2 | SEQ4591 | 2.E-02 | 1.8 |
| FTD | CYTOR:49 | SEQ3721 | 4.E-04 | 0.5 | MCI | lnc-NBPF3-3:6 | SEQ3144 | 1.E-03 | 1.7 |
| miAD | CYTOR:49 | SEQ3721 | 7.E-03 | 0.6 | MCI | lnc-NBPF3-3:7 | SEQ4651 | 2.E-04 | 1.8 |
| All AD | CYTOR:49 | SEQ3721 | 7.E-03 | 0.7 | DLB | lnc-NBPF3-3:7 | SEQ4651 | 1.E-03 | 1.8 |
| msAD | CYTOR:49 | SEQ3721 | 2.E-02 | 0.7 | miAD | lnc-NBPF3-8:1 | SEQ3929 | 4.E-03 | 0.6 |
| DLB | CYTOR:50 | SEQ5178 | 5.E-04 | 1.4 | All AD | lnc-NBPF3-8:1 | SEQ3929 | 5.E-03 | 0.7 |
| FTD | DARS-AS1:43 | SEQ3725 | 7.E-04 | 0.7 | msAD | lnc-NBPF3-8:1 | SEQ3929 | 3.E-02 | 0.7 |
| All AD | DARS-AS1:43 | SEQ3725 | 1.E-02 | 0.7 | FTD | lnc-NCKAP1-5:2 | SEQ4381 | 4.E-04 | 0.6 |
| msAD | DARS-AS1:43 | SEQ3725 | 3.E-02 | 0.7 | miAD | lnc-NCKAP1-5:2 | SEQ4381 | 4.E-03 | 0.7 |
| MCI | DDIT4-AS1:2 | SEQ5738 | 9.E-05 | 1.7 | All AD | lnc-NCKAP1-5:2 | SEQ4381 | 9.E-03 | 0.7 |
| DLB | DGUOK-AS1:7 | SEQ5186 | 5.E-04 | 1.5 | FTD | lnc-NCOA4-6:1 | SEQ5061 | 7.E-04 | 0.6 |
| FTD | DIAPH2-AS1:8 | SEQ4994 | 8.E-04 | 0.6 | FTD | lnc-NDFIP2-13:1 | SEQ4472 | 1.E-04 | 0.5 |
| FTD | DLEU1:2 | SEQ3732 | 3.E-07 | 0.5 | MCI | lnc-NDFIP2-13:1 | SEQ4472 | 2.E-03 | 0.6 |
| miAD | DLEU1:2 | SEQ3732 | 3.E-04 | 0.6 | All AD | lnc-NDFIP2-13:1 | SEQ4472 | 3.E-02 | 0.7 |
| MCI | DLEU1:2 | SEQ3732 | 2.E-03 | 0.6 | DLB | lnc-NDFIP2-26:2 | SEQ3696 | 4.E-04 | 1.4 |
| All AD | DLEU1:2 | SEQ3732 | 2.E-03 | 0.6 | All AD | lnc-NDFIP2-26:2 | SEQ3696 | 4.E-02 | 1.1 |
| msAD | DLEU1:2 | SEQ3732 | 3.E-02 | 0.7 | msAD | lnc-NDFIP2-26:2 | SEQ3696 | 5.E-02 | 1.1 |
| FTD | DLEU1:3 | SEQ3735 | 8.E-05 | 0.6 | DLB | lnc-NDRG1-2:1 | SEQ4828 | 2.E-04 | 1.4 |
| All AD | DLEU1:3 | SEQ3735 | 4.E-02 | 0.7 | MCI | lnc-NDRG1-2:1 | SEQ4828 | 9.E-04 | 1.3 |
| FTD | DLEU1:54 | SEQ3736 | 2.E-05 | 0.6 | DLB | lnc-NDRG1-5:1 | SEQ4864 | 2.E-05 | 1.8 |
| All AD | DLEU1:54 | SEQ3736 | 5.E-02 | 0.7 | MCI | lnc-NDRG1-5:1 | SEQ4864 | 9.E-04 | 1.6 |
| All AD | DLEU2:26 | SEQ0862 | 2.E-02 | 0.7 | DLB | lnc-NDRG1-7:2 | SEQ5432 | 3.E-04 | 1.4 |
| All AD | DLEU2:32 | SEQ2776 | 7.E-03 | 0.7 | MCI | lnc-NDRG1-7:2 | SEQ5432 | 3.E-04 | 1.4 |
| miAD | DLEU2:32 | SEQ2776 | 1.E-02 | 0.7 | DLB | lnc-NDRG1-7:4 | SEQ4677 | 2.E-04 | 1.3 |
| msAD | DLEU2:32 | SEQ2776 | 2.E-02 | 0.8 | MCI | lnc-NDRG1-7:4 | SEQ4677 | 1.E-03 | 1.3 |
| FTD | DLEU2:45 | SEQ0863 | 9.E-05 | 0.7 | All AD | lnc-NDUFA4-2:1 | SEQ5260 | 5.E-03 | 1.2 |
| All AD | DLEU2:45 | SEQ0863 | 2.E-03 | 0.7 | msAD | lnc-NDUFA6-2:2 | SEQ3899 | 3.E-02 | 1.2 |
| miAD | DLEU2:45 | SEQ0863 | 2.E-03 | 0.7 | DLB | lnc-NDUFAF8-1:3 | SEQ5031 | 7.E-04 | 1.5 |
| msAD | DLEU2:45 | SEQ0863 | 1.E-02 | 0.8 | DLB | lnc-NDUFAF8-1:4 | SEQ4629 | 1.E-03 | 1.4 |
| MCI | DLEU2:5 | SEQ5943 | 9.E-06 | 0.1 | FTD | lnc-NDUFB3-3:3 | SEQ3750 | 2.E-04 | 0.5 |
| FTD | DLG5-AS1:10 | SEQ5411 | 3.E-04 | 0.6 | miAD | lnc-NDUFB3-3:3 | SEQ3750 | 6.E-04 | 0.6 |

TABLE 10-continued 2847 whole blood (Paxgene RNA tube) lncRNAs differentially expressed in
MCI group or mild AD group or moderate-to-severe AD group or both of these
AD groups or FTD group or DLB group as compared to healthy control group.

| Group | lncRNA | SEQ | p-value | FC | Group | lncRNA | SEQ | p-value | FC |
| --- | --- | --- | --- | --- | --- | --- | --- | --- | --- |
| DLB | DLGAP4-AS1:11 | SEQ4702 | 1.E-03 | 1.5 | All AD | lnc-NDUFB3-3:3 | SEQ3750 | 3.E-03 | 0.6 |
| MCI | DNAJC9-AS1:9 | SEQ4869 | 9.E-04 | 1.6 | msAD | lnc-NDUFB3-3:3 | SEQ3750 | 4.E-02 | 0.7 |
| DLB | DPP9-AS1:1 | SEQ4563 | 2.E-03 | 1.4 | DLB | lnc-NECAB3-1:1 | SEQ5198 | 3.E-04 | 1.8 |
| FTD | DPYD-AS1:3 | SEQ3747 | 5.E-05 | 0.7 | MCI | lnc-NECAB3-1:1 | SEQ5198 | 5.E-04 | 1.7 |
| All AD | DPYD-AS1:3 | SEQ3747 | 3.E-02 | 0.7 | DLB | lnc-NEIL1-1:2 | SEQ5266 | 7.E-06 | 1.7 |
| msAD | DPYD-AS1:3 | SEQ3747 | 4.E-02 | 0.8 | FTD | lnc-NEIL1-1:2 | SEQ5266 | 1.E-04 | 1.4 |
| FTD | DPYD-AS2:1 | SEQ4360 | 8.E-05 | 0.6 | All AD | lnc-NEIL1-1:2 | SEQ5266 | 4.E-02 | 1.2 |
| miAD | DPYD-AS2:1 | SEQ4360 | 4.E-03 | 0.7 | DLB | lnc-NEK5-1:3 | SEQ5482 | 2.E-04 | 1.5 |
| FTD | EAF1-AS1:15 | SEQ5886 | 3.E-05 | 0.7 | FTD | lnc-NEK7-4:1 | SEQ4217 | 4.E-06 | 0.5 |
| FTD | EIF1B-AS1:18 | SEQ5465 | 3.E-04 | 0.6 | miAD | lnc-NEK7-4:1 | SEQ4217 | 1.E-02 | 0.7 |
| FTD | EIF3J-AS1:21 | SEQ0261 | 9.E-04 | 0.6 | All AD | lnc-NEK7-4:1 | SEQ4217 | 2.E-02 | 0.7 |
| DLB | ELOA-AS1:4 | SEQ5251 | 5.E-04 | 1.5 | FTD | lnc-NEMF-1:4 | SEQ3674 | 3.E-11 | 4.2 |
| FTD | ENTPD1-AS1:12 | SEQ3757 | 9.E-04 | 0.6 | MCI | lnc-NEMF-1:4 | SEQ3674 | 3.E-05 | 3.0 |
| miAD | ENTPD1-AS1:12 | SEQ3757 | 3.E-03 | 0.6 | msAD | lnc-NEMF-1:4 | SEQ3674 | 5.E-02 | 1.3 |
| All AD | ENTPD1-AS1:12 | SEQ3757 | 8.E-03 | 0.7 | FTD | lnc-NEMF-2:2 | SEQ2656 | 6.E-08 | 5.6 |
| All AD | ENTPD1-AS1:23 | SEQ3758 | 3.E-02 | 0.8 | MCI | lnc-NEMF-2:2 | SEQ2656 | 6.E-05 | 4.1 |
| FTD | ENTPD1-AS1:34 | SEQ5552 | 2.E-04 | 0.7 | DLB | lnc-NEMF-2:2 | SEQ2656 | 2.E-03 | 3.0 |
| All AD | ENTPD1-AS1:5 | SEQ3760 | 5.E-02 | 0.8 | All AD | lnc-NEMF-2:2 | SEQ2656 | 2.E-02 | 2.3 |
| FTD | FAM13A-AS1:1 | SEQ3762 | 1.E-04 | 0.6 | DLB | lnc-NEMF-4:1 | SEQ4738 | 8.E-05 | 1.4 |
| All AD | FAM13A-AS1:1 | SEQ3762 | 8.E-03 | 0.7 | MCI | lnc-NEMF-4:1 | SEQ4738 | 1.E-03 | 1.3 |
| miAD | FAM13A-AS1:1 | SEQ3762 | 1.E-02 | 0.7 | DLB | lnc-NEMP2-4:1 | SEQ5668 | 1.E-04 | 1.7 |
| msAD | FAM13A-AS1:1 | SEQ3762 | 2.E-02 | 0.8 | FTD | lnc-NETO2-3:1 | SEQ5273 | 8.E-05 | 0.6 |
| DLB | FAM13A-AS1:5 | SEQ5865 | 4.E-05 | 3.2 | All AD | lnc-NETO2-3:1 | SEQ5273 | 4.E-02 | 0.8 |
| MCI | FAM157C:3 | SEQ5767 | 4.E-07 | 0.1 | DLB | lnc-NEURL4-1:3 | SEQ4617 | 1.E-03 | 1.4 |
| FTD | FAM157C:3 | SEQ5767 | 7.E-05 | 0.1 | DLB | lnc-NEURL4-1:4 | SEQ3028 | 1.E-04 | 1.6 |
| DLB | FAM182A:4 | SEQ4636 | 1.E-03 | 1.5 | MCI | lnc-NEURL4-1:4 | SEQ3028 | 2.E-04 | 1.6 |
| miAD | FAM198B-AS1:7 | SEQ3768 | 1.E-02 | 0.7 | MCI | lnc-NFAM1-4:1 | SEQ5147 | 1.E-04 | 2.0 |
| All AD | FAM198B-AS1:7 | SEQ3768 | 2.E-02 | 0.8 | DLB | lnc-NFAM1-4:1 | SEQ5147 | 6.E-04 | 2.0 |
| DLB | FAM215B:1 | SEQ4971 | 8.E-04 | 1.6 | All AD | lnc-NFAM1-4:1 | SEQ5147 | 3.E-02 | 1.2 |
| MCI | FAM239A:9 | SEQ3770 | 2.E-04 | 2.1 | DLB | lnc-NGFR-1:1 | SEQ3671 | 1.E-03 | 1.3 |
| DLB | FAM239A:9 | SEQ3770 | 2.E-03 | 1.8 | All AD | lnc-NGFR-1:1 | SEQ3671 | 1.E-02 | 1.2 |
| All AD | FAM239A:9 | SEQ3770 | 3.E-02 | 1.3 | msAD | lnc-NGFR-1:1 | SEQ3671 | 5.E-02 | 1.1 |
| msAD | FAM30A:2 | SEQ3772 | 1.E-02 | 1.6 | All AD | lnc-NHS-2:1 | SEQ2339 | 2.E-02 | 0.8 |
| All AD | FAM30A:2 | SEQ3772 | 2.E-02 | 1.5 | FTD | lnc-NID1-4:4 | SEQ4463 | 3.E-10 | 0.3 |
| DLB | FAM53B-AS1:1 | SEQ5494 | 2.E-04 | 1.8 | MCI | lnc-NID1-4:4 | SEQ4463 | 4.E-07 | 0.4 |
| miAD | FAM99A:4 | SEQ3775 | 7.E-03 | 0.6 | miAD | lnc-NID1-4:4 | SEQ4463 | 4.E-05 | 0.5 |
| All AD | FAM99A:4 | SEQ3775 | 2.E-02 | 0.7 | All AD | lnc-NID1-4:4 | SEQ4463 | 1.E-05 | 0.5 |
| miAD | FAM99B:7 | SEQ3777 | 1.E-02 | 0.7 | DLB | lnc-NID1-4:4 | SEQ4463 | 2.E-03 | 0.4 |
| All AD | FAM99B:7 | SEQ3777 | 3.E-02 | 0.7 | msAD | lnc-NID1-4:4 | SEQ4463 | 2.E-03 | 0.6 |
| FTD | FGD5-AS1:11 | SEQ3778 | 3.E-07 | 3.1 | FTD | lnc-NIF3L1-3:1 | SEQ5283 | 4.E-04 | 0.6 |
| MCI | FGD5-AS1:11 | SEQ3778 | 9.E-06 | 3.3 | All AD | lnc-NIF3L1-3:1 | SEQ5283 | 3.E-02 | 0.8 |
| DLB | FGD5-AS1:11 | SEQ3778 | 1.E-04 | 2.5 | miAD | lnc-NIN-1:1 | SEQ4149 | 1.E-02 | 0.6 |
| msAD | FGD5-AS1:11 | SEQ3778 | 1.E-02 | 1.4 | All AD | lnc-NIN-1:1 | SEQ4149 | 1.E-02 | 0.7 |
| All AD | FGD5-AS1:11 | SEQ3778 | 2.E-02 | 1.4 | FTD | lnc-NINJ2-3:1 | SEQ6000 | 3.E-07 | 0.4 |
| DLB | FGD5-AS1:28 | SEQ3782 | 5.E-04 | 2.4 | FTD | lnc-NIPBL-3:1 | SEQ5604 | 2.E-04 | 0.6 |
| All AD | FGD5-AS1:28 | SEQ3782 | 8.E-03 | 1.6 | msAD | lnc-NKAP-4:2 | SEQ4178 | 1.E-02 | 2.0 |
| msAD | FGD5-AS1:28 | SEQ3782 | 2.E-02 | 1.7 | All AD | lnc-NKX2-4-6:3 | SEQ4164 | 3.E-03 | 1.3 |
| FTD | FGD5-AS1:30 | SEQ3785 | 1.E-07 | 3.1 | msAD | lnc-NKX2-4-6:3 | SEQ4164 | 4.E-03 | 1.3 |
| MCI | FGD5-AS1:30 | SEQ3785 | 2.E-05 | 2.9 | miAD | lnc-NKX2-4-6:3 | SEQ4164 | 1.E-02 | 1.3 |
| DLB | FGD5-AS1:30 | SEQ3785 | 3.E-04 | 2.3 | DLB | lnc-NKX6-3-1:1 | SEQ5030 | 9.E-05 | 1.7 |
| All AD | FGD5-AS1:30 | SEQ3785 | 8.E-03 | 1.4 | MCI | lnc-NKX6-3-1:1 | SEQ5030 | 7.E-04 | 1.5 |
| msAD | FGD5-AS1:30 | SEQ3785 | 8.E-03 | 1.4 | All AD | lnc-NKX6-3-1:1 | SEQ5030 | 3.E-02 | 1.1 |
| MCI | FGD5-AS1:6 | SEQ4466 | 3.E-06 | 0.2 | FTD | lnc-NLN-2:1 | SEQ5286 | 4.E-06 | 0.5 |
| FTD | FGD5-AS1:6 | SEQ4466 | 9.E-04 | 0.2 | All AD | lnc-NLN-2:1 | SEQ5286 | 2.E-02 | 0.7 |
| DLB | FGD5-AS1:6 | SEQ4466 | 2.E-03 | 0.3 | FTD | lnc-NLRC4-3:3 | SEQ3305 | 3.E-04 | 0.7 |
| miAD | FGD5-AS1:7 | SEQ3784 | 2.E-03 | 0.4 | All AD | lnc-NLRC4-3:3 | SEQ3305 | 9.E-03 | 0.8 |
| All AD | FGD5-AS1:7 | SEQ3784 | 4.E-03 | 0.4 | miAD | lnc-NLRC4-3:3 | SEQ3305 | 1.E-02 | 0.7 |
| msAD | FGD5-AS1:7 | SEQ3784 | 4.E-02 | 0.5 | msAD | lnc-NLRC4-3:3 | SEQ3305 | 3.E-02 | 0.8 |
| DLB | FGD5-AS1:9 | SEQ4423 | 2.E-03 | 1.5 | MCI | lnc-NLRC4-4:1 | SEQ5821 | 2.E-05 | 1.9 |
| DLB | FLNB-AS1:1 | SEQ3796 | 2.E-04 | 1.9 | DLB | lnc-NLRC4-4:1 | SEQ5821 | 5.E-05 | 1.9 |
| MCI | FLNB-AS1:1 | SEQ3796 | 1.E-03 | 1.7 | DLB | lnc-NLRP12-1:12 | SEQ5265 | 5.E-04 | 1.6 |
| All AD | FLNB-AS1:1 | SEQ3796 | 3.E-03 | 1.5 | FTD | lnc-NMD3-1:1 | SEQ2364 | 4.E-04 | 0.6 |
| msAD | FLNB-AS1:1 | SEQ3796 | 6.E-03 | 1.5 | DLB | lnc-NME3-1:2 | SEQ5256 | 5.E-04 | 1.5 |
| miAD | FLNB-AS1:1 | SEQ3796 | 8.E-03 | 1.5 | DLB | lnc-NMT1-1:2 | SEQ3980 | 2.E-04 | 1.6 |
| DLB | FLNB-AS1:3 | SEQ3800 | 2.E-03 | 2.4 | MCI | lnc-NMT1-1:2 | SEQ3980 | 1.E-03 | 1.4 |
| MCI | FLNB-AS1:3 | SEQ3800 | 1.E-04 | 2.0 | All AD | lnc-NMT1-1:2 | SEQ3980 | 2.E-02 | 1.2 |
| All AD | FLNB-AS1:3 | SEQ3800 | 4.E-04 | 1.5 | msAD | lnc-NMT1-1:2 | SEQ3980 | 2.E-02 | 1.2 |
| msAD | FLNB-AS1:3 | SEQ3800 | 1.E-03 | 1.5 | FTD | lnc-NNT-3:5 | SEQ4905 | 9.E-04 | 0.7 |
| miAD | FLNB-AS1:3 | SEQ3800 | 1.E-03 | 1.6 | DLB | lnc-NOB1-1:1 | SEQ2738 | 1.E-03 | 1.5 |
| FTD | FOXP1-IT1:1 | SEQ3805 | 1.E-05 | 0.6 | All AD | lnc-NOB1-1:1 | SEQ2738 | 3.E-02 | 1.1 |
| miAD | FOXP1-IT1:1 | SEQ3805 | 1.E-02 | 0.7 | FTD | lnc-NOD1-1:1 | SEQ5295 | 2.E-05 | 0.6 |
| All AD | FOXP1-IT1:1 | SEQ3805 | 3.E-02 | 0.7 | All AD | lnc-NOD1-1:1 | SEQ5295 | 4.E-02 | 0.7 |
| FTD | FRY-AS1:6 | SEQ5829 | 5.E-05 | 0.6 | DLB | lnc-NOL6-7:1 | SEQ5516 | 2.E-04 | 1.4 |
| FTD | FTX:19 | SEQ3811 | 3.E-09 | 0.1 | DLB | lnc-NOP14-3:4 | SEQ2834 | 4.E-04 | 1.6 |

TABLE 10-continued 2847 whole blood (Paxgene RNA tube) lncRNAs differentially expressed in MCI group or mild AD group or moderate-to-severe AD group or both of these AD groups or FTD group or DLB group as compared to healthy control group.

| Group | lncRNA | SEQ | p-value | FC | Group | lncRNA | SEQ | p-value | FC |
|---|---|---|---|---|---|---|---|---|---|
| MCI | FTX:19 | SEQ3811 | 2.E-07 | 0.1 | MCI | lnc-NOP16-2:6 | SEQ4973 | 5.E-04 | 1.7 |
| DLB | FTX:19 | SEQ3811 | 7.E-06 | 0.1 | DLB | lnc-NOP16-2:6 | SEQ4973 | 8.E-04 | 1.7 |
| All AD | FTX:19 | SEQ3811 | 4.E-03 | 0.1 | DLB | lnc-NOP9-1:2 | SEQ2990 | 3.E-04 | 1.4 |
| miAD | FTX:19 | SEQ3811 | 5.E-03 | 0.1 | DLB | lnc-NOS2-2:1 | SEQ4307 | 1.E-03 | 1.7 |
| msAD | FTX:19 | SEQ3811 | 1.E-02 | 0.2 | msAD | lnc-NOS2-2:1 | SEQ4307 | 7.E-03 | 1.4 |
| FTD | FTX:24 | SEQ5089 | 6.E-04 | 0.7 | All AD | lnc-NOS2-2:1 | SEQ4307 | 3.E-02 | 1.3 |
| FTD | FTX:28 | SEQ4395 | 1.E-04 | 0.5 | DLB | lnc-NPB-1:5 | SEQ4837 | 8.E-04 | 1.4 |
| MCI | FTX:28 | SEQ4395 | 2.E-03 | 0.5 | MCI | lnc-NPB-1:5 | SEQ4837 | 9.E-04 | 1.4 |
| All AD | FTX:37 | SEQ3814 | 3.E-02 | 0.7 | FTD | lnc-NPEPL1-3:1 | SEQ5470 | 3.E-04 | 0.7 |
| DLB | FTX:4 | SEQ4793 | 1.E-03 | 2.1 | MCI | lnc-NPIPA7-4:1 | SEQ4441 | 2.E-03 | 1.6 |
| DLB | FTX:44 | SEQ4642 | 1.E-03 | 1.6 | FTD | lnc-NPIPB12-2:2 | SEQ5357 | 4.E-04 | 0.6 |
| FTD | FTX:50 | SEQ3819 | 3.E-08 | 0.3 | FTD | lnc-NPIPB12-4:1 | SEQ5858 | 4.E-05 | 0.7 |
| MCI | FTX:50 | SEQ3819 | 8.E-05 | 0.4 | DLB | lnc-NPIPB3-1:1 | SEQ4519 | 6.E-05 | 1.7 |
| All AD | FTX:50 | SEQ3819 | 3.E-02 | 0.6 | MCI | lnc-NPIPB3-1:1 | SEQ4519 | 2.E-03 | 1.5 |
| DLB | FTX:52 | SEQ5282 | 3.E-05 | 2.2 | DLB | lnc-NPIPB3-2:1 | SEQ4765 | 1.E-03 | 1.5 |
| MCI | FTX:52 | SEQ5282 | 5.E-04 | 1.9 | All AD | lnc-NPL-2:1 | SEQ5306 | 2.E-02 | 0.7 |
| FTD | FTX:54 | SEQ4798 | 1.E-03 | 0.4 | FTD | lnc-NPL-2:2 | SEQ3740 | 3.E-04 | 0.6 |
| DLB | GABPB1-AS1:24 | SEQ3823 | 7.E-06 | 3.8 | All AD | lnc-NPL-2:2 | SEQ3740 | 1.E-02 | 0.7 |
| FTD | GABPB1-AS1:24 | SEQ3823 | 1.E-03 | 1.9 | msAD | lnc-NPL-2:2 | SEQ3740 | 4.E-02 | 0.8 |
| MCI | GABPB1-AS1:24 | SEQ3823 | 1.E-03 | 2.4 | FTD | lnc-NPM2-3:1 | SEQ5780 | 7.E-05 | 0.6 |
| miAD | GABPB1-AS1:24 | SEQ3823 | 3.E-03 | 1.6 | DLB | lnc-NPTX1-2:12 | SEQ4521 | 2.E-03 | 1.6 |
| All AD | GABPB1-AS1:24 | SEQ3823 | 8.E-03 | 1.4 | DLB | lnc-NPTX1-2:2 | SEQ5131 | 6.E-04 | 1.6 |
| FTD | GABPB1-IT1:2 | SEQ3828 | 2.E-04 | 2.4 | msAD | lnc-NPTX1-2:5 | SEQ4251 | 9.E-03 | 0.6 |
| All AD | GABPB1-IT1:2 | SEQ3828 | 4.E-02 | 1.3 | All AD | lnc-NPTX1-2:5 | SEQ4251 | 4.E-02 | 0.6 |
| miAD | GABPB1-IT1:5 | SEQ2591 | 7.E-03 | 1.6 | msAD | lnc-NPTX1-2:6 | SEQ3742 | 4.E-02 | 0.8 |
| All AD | GABPB1-IT1:5 | SEQ2591 | 1.E-02 | 1.4 | DLB | lnc-NPTX1-2:9 | SEQ5130 | 6.E-04 | 1.6 |
| msAD | GABPB1-IT1:5 | SEQ2591 | 5.E-02 | 1.3 | miAD | lnc-NR1D1-1:6 | SEQ4228 | 1.E-02 | 0.7 |
| DLB | GAS6-AS1:3 | SEQ5908 | 2.E-05 | 2.3 | All AD | lnc-NR1D1-1:6 | SEQ4228 | 4.E-02 | 0.8 |
| msAD | GFOD1-AS1:3 | SEQ3957 | 3.E-02 | 1.5 | FTD | lnc-NR1I2-3:1 | SEQ5229 | 5.E-04 | 0.6 |
| DLB | GHRLOS:9 | SEQ5051 | 7.E-04 | 2.0 | DLB | lnc-NR2C2-1:1 | SEQ2751 | 8.E-04 | 1.3 |
| miAD | GK-AS1:1 | SEQ3749 | 7.E-03 | 0.6 | DLB | lnc-NR2F6-5:1 | SEQ3457 | 6.E-04 | 1.4 |
| All AD | GK-AS1:1 | SEQ3749 | 9.E-03 | 0.7 | MCI | lnc-NR2F6-5:1 | SEQ3457 | 2.E-03 | 1.4 |
| msAD | GK-AS1:1 | SEQ3749 | 4.E-02 | 0.7 | FTD | lnc-NRBF2-2:1 | SEQ4087 | 1.E-08 | 0.4 |
| DLB | GLYCTK-AS1:7 | SEQ5124 | 6.E-04 | 1.6 | MCI | lnc-NRBF2-2:1 | SEQ4087 | 5.E-04 | 0.6 |
| DLB | GLYCTK-AS1:8 | SEQ5015 | 7.E-04 | 1.4 | miAD | lnc-NRBF2-2:1 | SEQ4087 | 2.E-03 | 0.5 |
| miAD | GSEC:2 | SEQ3835 | 4.E-03 | 0.6 | All AD | lnc-NRBF2-2:1 | SEQ4087 | 2.E-03 | 0.6 |
| All AD | GSEC:2 | SEQ3835 | 3.E-02 | 0.7 | msAD | lnc-NRBF2-2:1 | SEQ4087 | 1.E-02 | 0.6 |
| MCI | H1FX-AS1:15 | SEQ3313 | 2.E-05 | 1.6 | FTD | lnc-NRF1-2:1 | SEQ5313 | 4.E-05 | 0.5 |
| DLB | H1FX-AS1:15 | SEQ3313 | 5.E-05 | 1.6 | All AD | lnc-NRF1-2:1 | SEQ5313 | 4.E-02 | 0.7 |
| FTD | H1FX-AS1:15 | SEQ3313 | 2.E-04 | 1.5 | FTD | lnc-NT5C2-2:1 | SEQ3787 | 1.E-04 | 0.6 |
| All AD | H1FX-AS1:15 | SEQ3313 | 3.E-03 | 1.3 | miAD | lnc-NT5C2-2:1 | SEQ3787 | 6.E-03 | 0.7 |
| msAD | H1FX-AS1:15 | SEQ3313 | 5.E-03 | 1.3 | All AD | lnc-NT5C2-2:1 | SEQ3787 | 8.E-03 | 0.7 |
| miAD | H1FX-AS1:15 | SEQ3313 | 8.E-03 | 1.3 | msAD | lnc-NT5C2-2:1 | SEQ3787 | 4.E-02 | 0.8 |
| DLB | H1FX-AS1:16 | SEQ3841 | 2.E-04 | 1.8 | DLB | lnc-NT5M-1:3 | SEQ5274 | 5.E-04 | 1.7 |
| miAD | H1FX-AS1:16 | SEQ3841 | 1.E-03 | 1.5 | FTD | lnc-NTNG1-4:1 | SEQ4301 | 1.E-05 | 0.6 |
| All AD | H1FX-AS1:16 | SEQ3841 | 1.E-03 | 1.4 | miAD | lnc-NTNG1-4:1 | SEQ4301 | 7.E-03 | 0.7 |
| msAD | H1FX-AS1:16 | SEQ3841 | 8.E-03 | 1.4 | All AD | lnc-NTNG1-4:1 | SEQ4301 | 1.E-02 | 0.8 |
| DLB | HCG26:5 | SEQ5696 | 1.E-04 | 1.6 | DLB | lnc-NTNG2-2:1 | SEQ5661 | 1.E-04 | 1.5 |
| DLB | HCP5:1 | SEQ5322 | 4.E-04 | 1.5 | All AD | lnc-NUAK1-5:1 | SEQ5317 | 4.E-02 | 0.9 |
| DLB | HCP5:3 | SEQ5476 | 2.E-04 | 1.3 | FTD | lnc-NUCB2-1:1 | SEQ4907 | 9.E-04 | 0.7 |
| FTD | HCP5:4 | SEQ5344 | 3.E-04 | 2.4 | All AD | lnc-NUDT3-1:3 | SEQ2725 | 3.E-02 | 1.2 |
| MCI | HCP5:4 | SEQ5344 | 4.E-04 | 2.2 | FTD | lnc-NUDT4P1-1:11 | SEQ5954 | 7.E-06 | 0.5 |
| DLB | HCP5:7 | SEQ5321 | 4.E-04 | 1.5 | DLB | lnc-NUDT4P1-1:13 | SEQ4757 | 1.E-03 | 1.5 |
| FTD | HCP5:9 | SEQ5345 | 3.E-04 | 2.4 | DLB | lnc-NUDT4P1-1:2 | SEQ4564 | 2.E-03 | 1.4 |
| MCI | HCP5:9 | SEQ5345 | 4.E-04 | 2.2 | FTD | lnc-NUDT4P1-1:5 | SEQ5899 | 2.E-05 | 0.6 |
| FTD | HOTAIRM1:14 | SEQ3852 | 2.E-04 | 0.7 | FTD | lnc-NUDT4P1-9:1 | SEQ4171 | 1.E-07 | 0.5 |
| msAD | HOTAIRM1:14 | SEQ3852 | 9.E-03 | 0.7 | MCI | lnc-NUDT4P1-9:1 | SEQ4171 | 4.E-05 | 0.6 |
| All AD | HOTAIRM1:14 | SEQ3852 | 1.E-02 | 0.6 | All AD | lnc-NUDT4P1-9:1 | SEQ4171 | 3.E-03 | 0.7 |
| DLB | IL21R-AS1:1 | SEQ4596 | 2.E-03 | 1.7 | miAD | lnc-NUDT4P1-9:1 | SEQ4171 | 4.E-03 | 0.6 |
| DLB | IL21R-AS1:2 | SEQ5206 | 5.E-04 | 1.7 | msAD | lnc-NUDT4P1-9:1 | SEQ4171 | 1.E-02 | 0.7 |
| DLB | IL21R-AS1:3 | SEQ4595 | 2.E-03 | 1.7 | All AD | lnc-NUMB-1:11 | SEQ5325 | 2.E-02 | 0.8 |
| MCI | IRAIN:2 | SEQ2863 | 1.E-03 | 1.6 | All AD | lnc-NUMB-1:6 | SEQ5326 | 4.E-02 | 0.8 |
| MCI | IRAIN:3 | SEQ2864 | 1.E-03 | 1.6 | All AD | lnc-NUMB-2:1 | SEQ5327 | 2.E-02 | 0.8 |
| DLB | ITFG2-AS1:3 | SEQ5620 | 2.E-04 | 1.6 | DLB | lnc-NUP188-1:1 | SEQ4556 | 2.E-03 | 1.3 |
| DLB | ITPKB-IT1:1 | SEQ4587 | 2.E-03 | 1.6 | All AD | lnc-NUS1-5:1 | SEQ3614 | 2.E-02 | 1.2 |
| FTD | JMJD1C-AS1:6 | SEQ5643 | 1.E-04 | 0.6 | DLB | lnc-NXNL1-7:2 | SEQ4402 | 2.E-03 | 1.3 |
| FTD | JPX:13 | SEQ4473 | 3.E-07 | 0.5 | FTD | lnc-NXPH2-1:1 | SEQ4903 | 9.E-04 | 0.6 |
| MCI | JPX:13 | SEQ4473 | 2.E-03 | 0.7 | All AD | lnc-NXPH2-1:1 | SEQ4903 | 2.E-02 | 0.8 |
| FTD | JPX:20 | SEQ5292 | 4.E-04 | 0.6 | FTD | lnc-NXPH2-3:10 | SEQ4666 | 7.E-05 | 0.3 |
| FTD | JPX:22 | SEQ5885 | 3.E-05 | 0.5 | MCI | lnc-NXPH2-3:10 | SEQ4666 | 9.E-05 | 0.3 |
| FTD | KCNJ2-AS1:3 | SEQ3865 | 5.E-04 | 0.6 | DLB | lnc-NXPH2-3:10 | SEQ4666 | 1.E-03 | 0.3 |
| miAD | KCNJ2-AS1:3 | SEQ3865 | 2.E-03 | 0.6 | miAD | lnc-NXPH2-3:5 | SEQ3634 | 1.E-02 | 0.6 |
| All AD | KCNJ2-AS1:3 | SEQ3865 | 7.E-03 | 0.6 | All AD | lnc-NXPH2-3:5 | SEQ3634 | 1.E-02 | 0.7 |
| DLB | KCNQ10T1:1 | SEQ4434 | 2.E-03 | 1.5 | msAD | lnc-NXPH2-3:5 | SEQ3634 | 5.E-02 | 0.8 |

TABLE 10-continued 2847 whole blood (Paxgene RNA tube) lncRNAs differentially expressed in
MCI group or mild AD group or moderate-to-severe AD group or both of these
AD groups or FTD group or DLB group as compared to healthy control group.

| Group | lncRNA | SEQ | p-value | FC | Group | lncRNA | SEQ | p-value | FC |
|---|---|---|---|---|---|---|---|---|---|
| FTD | KCNQ1OT1:2 | SEQ5774 | 7.E-05 | 0.5 | MCI | lnc-OBSCN-AS1-2:1 | SEQ5039 | 7.E-04 | 1.6 |
| DLB | KCNQ1OT1:3 | SEQ4433 | 2.E-03 | 1.5 | DLB | lnc-OCM-3:4 | SEQ5076 | 2.E-08 | 3.3 |
| FTD | KCNQ1OT1:5 | SEQ5762 | 8.E-05 | 0.5 | MCI | lnc-OCM-3:4 | SEQ5076 | 4.E-08 | 3.1 |
| FTD | KCNQ1OT1:8 | SEQ0139 | 2.E-04 | 0.6 | msAD | lnc-OCM-3:4 | SEQ5076 | 6.E-05 | 1.7 |
| DLB | KDM4A-AS1:5 | SEQ4616 | 1.E-03 | 1.4 | All AD | lnc-OCM-3:4 | SEQ5076 | 7.E-05 | 1.7 |
| DLB | KIF9-AS1:9 | SEQ4492 | 2.E-03 | 1.4 | miAD | lnc-OCM-3:4 | SEQ5076 | 7.E-04 | 1.7 |
| DLB | LAMTOR5-AS1:1 | SEQ5672 | 1.E-04 | 1.7 | FTD | lnc-ODF1-9:1 | SEQ0824 | 2.E-06 | 0.6 |
| DLB | LCMT1-AS2:4 | SEQ4657 | 1.E-03 | 1.9 | DLB | lnc-OGDH-2:3 | SEQ4682 | 1.E-03 | 1.4 |
| MCI | LEF1-AS1:1 | SEQ3877 | 1.E-03 | 1.9 | DLB | lnc-OIP5-1:1 | SEQ5863 | 4.E-05 | 1.9 |
| DLB | LEF1-AS1:1 | SEQ3877 | 2.E-03 | 1.9 | FTD | lnc-OIT3-1:1 | SEQ5230 | 5.E-04 | 0.6 |
| miAD | LEF1-AS1:1 | SEQ3877 | 3.E-03 | 1.6 | msAD | lnc-OLIG1-3:2 | SEQ4101 | 1.E-02 | 1.6 |
| All AD | LEF1-AS1:1 | SEQ3877 | 4.E-03 | 1.5 | DLB | lnc-OPLAH-1:1 | SEQ5811 | 5.E-05 | 1.4 |
| msAD | LEF1-AS1:1 | SEQ3877 | 2.E-02 | 1.4 | miAD | lnc-OR10V1-1:1 | SEQ4329 | 6.E-03 | 0.8 |
| MCI | LEF1-AS1:2 | SEQ3882 | 3.E-04 | 2.3 | All AD | lnc-OR10V1-1:1 | SEQ4329 | 3.E-02 | 0.8 |
| DLB | LEF1-AS1:2 | SEQ3882 | 4.E-04 | 2.3 | DLB | lnc-OR1A2-1:1 | SEQ3560 | 1.E-03 | 1.4 |
| miAD | LEF1-AS1:2 | SEQ3882 | 2.E-03 | 1.7 | msAD | lnc-OR1J1-2:1 | SEQ3840 | 3.E-02 | 1.3 |
| All AD | LEF1-AS1:2 | SEQ3882 | 3.E-03 | 1.6 | DLB | lnc-OR4F15-4:5 | SEQ2780 | 4.E-07 | 1.7 |
| msAD | LEF1-AS1:2 | SEQ3882 | 2.E-02 | 1.5 | MCI | lnc-OR4F15-4:5 | SEQ2780 | 3.E-05 | 1.3 |
| All AD | LEF1-AS1:24 | SEQ3886 | 4.E-02 | 1.3 | FTD | lnc-OR4F15-4:5 | SEQ2780 | 8.E-04 | 1.3 |
| DLB | LIMD1-AS1:2 | SEQ2885 | 2.E-03 | 1.5 | msAD | lnc-OR4F15-4:5 | SEQ2780 | 1.E-02 | 1.2 |
| msAD | LINC00205:10 | SEQ3689 | 5.E-02 | 1.3 | All AD | lnc-OR4F15-4:5 | SEQ2780 | 4.E-02 | 1.1 |
| MCI | LINC00205:26 | SEQ4533 | 6.E-04 | 1.9 | All AD | lnc-OR4F16-15:5 | SEQ5342 | 5.E-02 | 0.7 |
| DLB | LINC00205:26 | SEQ4533 | 2.E-03 | 1.9 | FTD | lnc-OR4F17-5:1 | SEQ5002 | 8.E-04 | 0.7 |
| MCI | LINC00211:13 | SEQ4965 | 8.E-04 | 1.6 | miAD | lnc-OR4F17-8:1 | SEQ4085 | 3.E-03 | 0.6 |
| FTD | LINC00211:15 | SEQ3890 | 3.E-04 | 0.4 | All AD | lnc-OR4F17-8:1 | SEQ4085 | 3.E-03 | 0.6 |
| All AD | LINC00211:15 | SEQ3890 | 6.E-03 | 0.5 | msAD | lnc-OR4F17-8:1 | SEQ4085 | 1.E-02 | 0.6 |
| msAD | LINC00211:15 | SEQ3890 | 7.E-03 | 0.4 | All AD | lnc-OR4F29-1:10 | SEQ5346 | 4.E-02 | 0.6 |
| MCI | LINC00235:1 | SEQ3731 | 5.E-04 | 2.1 | DLB | lnc-OR4F29-11:1 | SEQ4438 | 2.E-03 | 1.5 |
| DLB | LINC00235:1 | SEQ3731 | 9.E-04 | 2.3 | DLB | lnc-OR4F29-11:5 | SEQ5967 | 4.E-06 | 1.9 |
| All AD | LINC00235:1 | SEQ3731 | 2.E-02 | 1.4 | DLB | lnc-OR4F29-11:6 | SEQ5611 | 2.E-04 | 1.4 |
| msAD | LINC00235:1 | SEQ3731 | 4.E-02 | 1.4 | miAD | lnc-OR4F29-3:11 | SEQ0044 | 2.E-03 | 0.5 |
| All AD | LINC00402:4 | SEQ3893 | 2.E-02 | 1.3 | All AD | lnc-OR4F29-3:11 | SEQ0044 | 4.E-03 | 0.6 |
| FTD | LINC00472:23 | SEQ4670 | 5.E-04 | 0.7 | msAD | lnc-OR4F29-3:11 | SEQ0044 | 4.E-02 | 0.7 |
| MCI | LINC00472:23 | SEQ4670 | 1.E-03 | 0.8 | miAD | lnc-OR4F29-3:7 | SEQ4602 | 1.E-03 | 0.6 |
| FTD | LINC00472:38 | SEQ5930 | 1.E-05 | 0.6 | All AD | lnc-OR4F29-3:7 | SEQ4602 | 7.E-03 | 0.7 |
| FTD | LINC00472:41 | SEQ3848 | 3.E-11 | 0.1 | All AD | lnc-OR4F29-8:3 | SEQ3836 | 2.E-02 | 0.7 |
| MCI | LINC00472:41 | SEQ3848 | 2.E-08 | 0.2 | msAD | lnc-OR4F29-8:3 | SEQ3836 | 3.E-02 | 0.7 |
| miAD | LINC00472:41 | SEQ3848 | 3.E-05 | 0.3 | DLB | lnc-OR4F29-8:30 | SEQ5241 | 5.E-04 | 1.4 |
| DLB | LINC00472:41 | SEQ3848 | 9.E-05 | 0.2 | FTD | lnc-OR4F29-8:48 | SEQ5882 | 3.E-05 | 0.4 |
| All AD | LINC00472:41 | SEQ3848 | 7.E-03 | 0.3 | All AD | lnc-OR4F3-5:4 | SEQ5350 | 3.E-02 | 0.6 |
| msAD | LINC00472:41 | SEQ3848 | 3.E-02 | 0.3 | msAD | lnc-OR4F4-4:3 | SEQ3996 | 2.E-02 | 1.7 |
| All AD | LINC00476:1 | SEQ3719 | 2.E-02 | 1.3 | miAD | lnc-OR4F5-2:1 | SEQ4371 | 4.E-03 | 0.6 |
| msAD | LINC00476:1 | SEQ3719 | 4.E-02 | 1.3 | All AD | lnc-OR4F5-2:1 | SEQ4371 | 8.E-03 | 0.6 |
| FTD | LINC00533:8 | SEQ3864 | 5.E-04 | 0.5 | DLB | lnc-OR4F6-1:1 | SEQ4266 | 6.E-05 | 2.0 |
| miAD | LINC00533:8 | SEQ3864 | 6.E-03 | 0.5 | msAD | lnc-OR4F6-1:1 | SEQ4266 | 9.E-03 | 1.4 |
| All AD | LINC00533:8 | SEQ3864 | 7.E-03 | 0.6 | All AD | lnc-OR4F6-1:1 | SEQ4266 | 2.E-02 | 1.3 |
| msAD | LINC00533:8 | SEQ3864 | 3.E-02 | 0.6 | msAD | lnc-OR52K2-1:1 | SEQ4300 | 7.E-03 | 0.7 |
| DLB | LINC00649:37 | SEQ5639 | 2.E-04 | 2.1 | All AD | lnc-OR52K2-1:1 | SEQ4300 | 1.E-02 | 0.8 |
| MCI | LINC00659:10 | SEQ4726 | 1.E-03 | 2.2 | DLB | lnc-OR6C65-3:1 | SEQ5441 | 3.E-04 | 1.5 |
| FTD | LINC00667:21 | SEQ5085 | 6.E-04 | 0.6 | DLB | lnc-OR7C2-1:2 | SEQ5740 | 9.E-05 | 1.9 |
| FTD | LINC00667:3 | SEQ5304 | 4.E-04 | 1.9 | MCI | lnc-OSBPL7-3:1 | SEQ3569 | 5.E-05 | 1.6 |
| DLB | LINC00677:6 | SEQ4555 | 2.E-03 | 1.3 | FTD | lnc-OSBPL7-3:1 | SEQ3569 | 1.E-04 | 1.6 |
| DLB | LINC00685:6 | SEQ4963 | 3.E-04 | 1.8 | DLB | lnc-OSBPL7-3:1 | SEQ3569 | 2.E-03 | 1.5 |
| MCI | LINC00685:6 | SEQ4963 | 8.E-04 | 1.6 | All AD | lnc-OSBPL7-3:2 | SEQ2813 | 4.E-02 | 0.8 |
| DLB | LINC00847:2 | SEQ4857 | 9.E-04 | 1.5 | FTD | lnc-OSBPL7-3:3 | SEQ0534 | 2.E-05 | 0.7 |
| miAD | LINC00847:3 | SEQ3912 | 5.E-03 | 1.7 | miAD | lnc-OSBPL7-3:3 | SEQ0534 | 1.E-02 | 0.8 |
| All AD | LINC00847:3 | SEQ3912 | 3.E-02 | 1.4 | All AD | lnc-OSBPL7-3:3 | SEQ0534 | 2.E-02 | 0.8 |
| FTD | LINC00861:6 | SEQ3915 | 3.E-08 | 5.9 | FTD | lnc-OSBPL7-3:4 | SEQ0535 | 4.E-05 | 0.7 |
| DLB | LINC00861:6 | SEQ3915 | 6.E-08 | 6.6 | FTD | lnc-OSBPL7-3:6 | SEQ0536 | 4.E-05 | 0.7 |
| MCI | LINC00861:6 | SEQ3915 | 3.E-06 | 5.1 | All AD | lnc-OSBPL7-3:6 | SEQ0536 | 3.E-02 | 0.8 |
| All AD | LINC00861:6 | SEQ3915 | 1.E-03 | 1.8 | msAD | lnc-OSMR-2:2 | SEQ4340 | 5.E-03 | 0.6 |
| miAD | LINC00861:6 | SEQ3915 | 3.E-04 | 1.8 | FTD | lnc-OTOA-1:2 | SEQ3943 | 1.E-04 | 0.5 |
| msAD | LINC00861:6 | SEQ3915 | 1.E-03 | 1.8 | All AD | lnc-OTOA-1:2 | SEQ3943 | 6.E-03 | 0.6 |
| MCI | LINC00869:68 | SEQ3730 | 3.E-04 | 2.1 | miAD | lnc-OTOA-1:2 | SEQ3943 | 7.E-03 | 0.6 |
| DLB | LINC00869:68 | SEQ3730 | 8.E-04 | 1.9 | msAD | lnc-OTOA-1:2 | SEQ3943 | 3.E-02 | 0.7 |
| miAD | LINC00869:68 | SEQ3730 | 1.E-03 | 1.7 | DLB | lnc-OTULIN-4:1 | SEQ5694 | 1.E-04 | 1.5 |
| All AD | LINC00869:68 | SEQ3730 | 4.E-03 | 1.5 | DLB | lnc-P4HTM-4:1 | SEQ5334 | 4.E-04 | 1.7 |
| msAD | LINC00869:68 | SEQ3730 | 4.E-02 | 1.4 | MCI | lnc-PABPC1L2B-3:1 | SEQ4448 | 3.E-04 | 1.7 |
| miAD | LINC00869:73 | SEQ3922 | 3.E-03 | 0.5 | DLB | lnc-PABPC1L2B-3:1 | SEQ4448 | 2.E-03 | 1.6 |
| All AD | LINC00869:73 | SEQ3922 | 3.E-03 | 0.6 | DLB | lnc-PABPN1L-1:1 | SEQ2986 | 2.E-03 | 1.6 |
| msAD | LINC00869:73 | SEQ3922 | 2.E-02 | 0.6 | MCI | lnc-PACSIN1-1:1 | SEQ5452 | 1.E-04 | 1.6 |
| All AD | LINC00877:15 | SEQ3743 | 3.E-02 | 0.8 | DLB | lnc-PACSIN1-1:1 | SEQ5452 | 3.E-04 | 1.8 |
| msAD | LINC00877:15 | SEQ3743 | 4.E-02 | 0.8 | DLB | lnc-PADI2-1:1 | SEQ5936 | 1.E-05 | 1.8 |
| FTD | LINC00894:50 | SEQ3925 | 6.E-05 | 0.6 | DLB | lnc-PAF1-3:1 | SEQ5113 | 6.E-04 | 1.4 |

TABLE 10-continued 2847 whole blood (Paxgene RNA tube) lncRNAs differentially expressed in
MCI group or mild AD group or moderate-to-severe AD group or both of these
AD groups or FTD group or DLB group as compared to healthy control group.

| Group | lncRNA | SEQ | p-value | FC | Group | lncRNA | SEQ | p-value | FC |
|---|---|---|---|---|---|---|---|---|---|
| All AD | LINC00894:50 | SEQ3925 | 4.E-02 | 0.7 | MCI | lnc-PAGR1-2:8 | SEQ5430 | 1.E-04 | 1.4 |
| msAD | LINC00910:32 | SEQ3926 | 2.E-02 | 1.3 | DLB | lnc-PAGR1-2:8 | SEQ5430 | 3.E-04 | 1.4 |
| All AD | LINC00910:32 | SEQ3926 | 4.E-02 | 1.2 | FTD | lnc-PAIP2B-2:1 | SEQ5874 | 3.E-05 | 0.6 |
| msAD | LINC00926:2 | SEQ3927 | 2.E-02 | 1.6 | FTD | lnc-PALLD-8:1 | SEQ2633 | 2.E-05 | 0.6 |
| All AD | LINC00926:2 | SEQ3927 | 4.E-02 | 1.5 | DLB | lnc-PANK3-13:1 | SEQ2629 | 5.E-04 | 1.5 |
| miAD | LINC00937:21 | SEQ3930 | 1.E-02 | 0.6 | FTD | lnc-PANK3-13:2 | SEQ2618 | 7.E-05 | 0.6 |
| All AD | LINC00937:21 | SEQ3930 | 2.E-02 | 0.7 | DLB | lnc-PANO1-1:1 | SEQ5485 | 2.E-04 | 1.5 |
| msAD | LINC00938:7 | SEQ3931 | 2.E-02 | 1.4 | MCI | lnc-PAPD5-2:1 | SEQ5851 | 4.E-05 | 1.8 |
| All AD | LINC00938:7 | SEQ3931 | 3.E-02 | 1.2 | DLB | lnc-PAPD5-2:1 | SEQ5851 | 4.E-05 | 1.9 |
| DLB | LINC00957:7 | SEQ5252 | 4.E-05 | 1.7 | FTD | lnc-PAPLN-2:1 | SEQ5163 | 5.E-04 | 0.8 |
| MCI | LINC00957:7 | SEQ5252 | 5.E-04 | 1.5 | FTD | lnc-PAPPA2-2:1 | SEQ4328 | 2.E-05 | 0.6 |
| MCI | LINC00963:12 | SEQ5349 | 2.E-04 | 0.5 | miAD | lnc-PAPPA2-2:1 | SEQ4328 | 6.E-03 | 0.7 |
| FTD | LINC00963:12 | SEQ5349 | 4.E-04 | 0.5 | All AD | lnc-PAPPA2-2:1 | SEQ4328 | 1.E-02 | 0.8 |
| DLB | LINC00963:7 | SEQ4528 | 2.E-03 | 1.7 | FTD | lnc-PAPPA2-6:1 | SEQ4247 | 5.E-04 | 0.7 |
| MCI | LINC00989:1 | SEQ3938 | 6.E-04 | 1.6 | miAD | lnc-PAPPA2-6:1 | SEQ4247 | 9.E-03 | 0.7 |
| msAD | LINC00989:1 | SEQ3938 | 4.E-03 | 1.4 | All AD | lnc-PAPPA2-6:1 | SEQ4247 | 1.E-02 | 0.8 |
| All AD | LINC00989:1 | SEQ3938 | 5.E-03 | 1.3 | FTD | lnc-PAPPA2-7:1 | SEQ0165 | 2.E-04 | 0.6 |
| DLB | LINCO1000:7 | SEQ2877 | 2.E-04 | 1.5 | All AD | lnc-PAPPA2-7:1 | SEQ0165 | 2.E-03 | 0.7 |
| MCI | LINC01002:1 | SEQ5287 | 3.E-02 | 0.6 | miAD | lnc-PAPPA2-7:1 | SEQ0165 | 2.E-03 | 0.7 |
| FTD | LINC01002:1 | SEQ5287 | 4.E-04 | 0.5 | msAD | lnc-PAPPA2-7:1 | SEQ0165 | 8.E-03 | 0.7 |
| miAD | LINC01002:27 | SEQ3945 | 2.E-03 | 0.5 | miAD | lnc-PAPSS2-10:1 | SEQ4072 | 1.E-02 | 0.7 |
| All AD | LINC01002:27 | SEQ3945 | 1.E-02 | 0.6 | All AD | lnc-PAPSS2-10:1 | SEQ4072 | 3.E-02 | 0.8 |
| miAD | LINC01002:9 | SEQ3759 | 5.E-03 | 0.5 | All AD | lnc-PATL2-9:1 | SEQ3944 | 1.E-02 | 0.7 |
| All AD | LINC01002:9 | SEQ3759 | 7.E-03 | 0.6 | msAD | lnc-PATL2-9:1 | SEQ3944 | 3.E-02 | 0.7 |
| msAD | LINC01002:9 | SEQ3759 | 4.E-02 | 0.7 | FTD | lnc-PAWR-14:1 | SEQ4343 | 3.E-05 | 0.5 |
| DLB | LINC01089:27 | SEQ5862 | 2.E-05 | 1.9 | miAD | lnc-PAWR-14:1 | SEQ4343 | 5.E-03 | 0.6 |
| MCI | LINC01089:27 | SEQ5862 | 4.E-05 | 1.9 | All AD | lnc-PAWR-14:1 | SEQ4343 | 7.E-03 | 0.6 |
| DLB | LINC01089:3 | SEQ5705 | 5.E-05 | 1.9 | All AD | lnc-PAXX-2:1 | SEQ3639 | 4.E-02 | 0.8 |
| MCI | LINC01089:3 | SEQ5705 | 1.E-04 | 1.8 | msAD | lnc-PAXX-2:1 | SEQ3639 | 5.E-02 | 0.9 |
| DLB | LINC01128:4 | SEQ3953 | 1.E-04 | 1.9 | miAD | lnc-PCBP1-2:1 | SEQ3999 | 2.E-03 | 0.6 |
| MCI | LINC01128:4 | SEQ3953 | 3.E-04 | 1.7 | All AD | lnc-PCBP1-2:1 | SEQ3999 | 3.E-03 | 0.6 |
| All AD | LINC01128:4 | SEQ3953 | 6.E-03 | 1.3 | msAD | lnc-PCBP1-2:1 | SEQ3999 | 2.E-02 | 0.6 |
| miAD | LINC01128:4 | SEQ3953 | 6.E-03 | 1.3 | FTD | lnc-PCDHGA1-1:3 | SEQ5923 | 1.E-05 | 0.6 |
| msAD | LINC01128:4 | SEQ3953 | 2.E-02 | 1.3 | FTD | lnc-PCDHGA1-1:4 | SEQ5922 | 1.E-05 | 0.6 |
| All AD | LINC01136:8 | SEQ3958 | 2.E-03 | 0.5 | FTD | lnc-PCDHGA1-3:2 | SEQ4819 | 4.E-07 | 0.4 |
| miAD | LINC01136:8 | SEQ3958 | 2.E-03 | 0.5 | MCI | lnc-PCDHGA1-3:2 | SEQ4819 | 4.E-04 | 0.5 |
| msAD | LINC01136:8 | SEQ3958 | 8.E-03 | 0.5 | miAD | lnc-PCDHGA1-3:2 | SEQ4819 | 1.E-03 | 0.5 |
| DLB | LINC01138:20 | SEQ3672 | 6.E-04 | 1.7 | DLB | lnc-PCGF2-3:1 | SEQ5700 | 1.E-04 | 1.6 |
| msAD | LINC01138:20 | SEQ3672 | 5.E-02 | 1.2 | DLB | lnc-PCGF2-4:1 | SEQ3602 | 4.E-05 | 1.5 |
| msAD | LINC01138:23 | SEQ3889 | 3.E-02 | 0.8 | FTD | lnc-PCNX4-3:1 | SEQ4285 | 1.E-08 | 0.5 |
| All AD | LINC01138:23 | SEQ3889 | 3.E-02 | 0.8 | MCI | lnc-PCNX4-3:1 | SEQ4285 | 8.E-05 | 0.5 |
| FTD | LINCO1154:11 | SEQ5747 | 9.E-05 | 0.7 | miAD | lnc-PCNX4-3:1 | SEQ4285 | 7.E-03 | 0.7 |
| MCI | LINC01215:3 | SEQ3963 | 2.E-04 | 2.5 | All AD | lnc-PCNX4-3:1 | SEQ4285 | 1.E-02 | 0.7 |
| msAD | LINC01215:3 | SEQ3963 | 1.E-02 | 1.5 | FTD | lnc-PCP4L1-3:2 | SEQ4902 | 9.E-04 | 0.6 |
| All AD | LINCO1215:3 | SEQ3963 | 4.E-02 | 1.3 | DLB | lnc-PCSK7-1:4 | SEQ5619 | 2.E-04 | 1.6 |
| DLB | LINCO1224:32 | SEQ5454 | 3.E-04 | 1.8 | FTD | lnc-PCYOX1-4:1 | SEQ5998 | 2.E-07 | 0.3 |
| DLB | LINC01224:33 | SEQ4653 | 2.E-04 | 2.1 | MCI | lnc-PCYOX1-4:1 | SEQ5998 | 4.E-07 | 0.4 |
| MCI | LINC01224:33 | SEQ4653 | 1.E-03 | 1.8 | FTD | lnc-PDCD4-6:1 | SEQ5384 | 2.E-05 | 0.6 |
| DLB | LINC01224:56 | SEQ5278 | 5.E-04 | 1.8 | All AD | lnc-PDCD4-6:1 | SEQ5384 | 5.E-02 | 0.8 |
| DLB | LINC01311:5 | SEQ3967 | 6.E-04 | 1.5 | FTD | lnc-PDCL2-4:1 | SEQ5475 | 2.E-07 | 0.6 |
| MCI | LINC01311:5 | SEQ3967 | 1.E-03 | 1.5 | MCI | lnc-PDCL2-4:1 | SEQ5475 | 2.E-04 | 0.7 |
| All AD | LINC01311:5 | SEQ3967 | 4.E-02 | 1.2 | msAD | lnc-PDE6D-3:1 | SEQ3793 | 4.E-02 | 1.3 |
| FTD | LINC01355:1 | SEQ5509 | 2.E-04 | 0.6 | MCI | lnc-PDGFA-6:2 | SEQ5057 | 4.E-08 | 6.3 |
| miAD | LINC01359:11 | SEQ3826 | 1.E-03 | 0.6 | FTD | lnc-PDGFA-6:2 | SEQ5057 | 7.E-06 | 3.3 |
| All AD | LINC01359:11 | SEQ3826 | 4.E-03 | 0.6 | DLB | lnc-PDGFA-6:2 | SEQ5057 | 7.E-04 | 3.1 |
| msAD | LINC01359:11 | SEQ3826 | 4.E-02 | 0.7 | All AD | lnc-PDGFA-6:5 | SEQ5389 | 4.E-02 | 0.6 |
| FTD | LINC01410:15 | SEQ5978 | 5.E-07 | 0.2 | miAD | lnc-PDGFA-6:6 | SEQ4378 | 3.E-03 | 0.7 |
| MCI | LINC01410:15 | SEQ5978 | 3.E-06 | 0.2 | All AD | lnc-PDGFA-6:6 | SEQ4378 | 1.E-02 | 0.7 |
| FTD | LINC01410:17 | SEQ3799 | 9.E-05 | 0.5 | DLB | lnc-PDGFB-2:1 | SEQ2826 | 5.E-04 | 1.6 |
| All AD | LINCO1410:17 | SEQ3799 | 1.E-02 | 0.6 | FTD | lnc-PDK3-1:1 | SEQ2348 | 7.E-04 | 0.7 |
| msAD | LINCO1410:17 | SEQ3799 | 4.E-02 | 0.7 | All AD | lnc-PDK3-1:1 | SEQ2348 | 3.E-02 | 0.8 |
| DLB | LINC01465:1 | SEQ4432 | 1.E-04 | 1.8 | FTD | lnc-PDS5B-2:1 | SEQ5392 | 5.E-06 | 0.6 |
| FTD | LINC01465:1 | SEQ4432 | 6.E-04 | 1.6 | All AD | lnc-PDS5B-2:1 | SEQ5392 | 3.E-02 | 0.8 |
| MCI | LINC01465:1 | SEQ4432 | 2.E-03 | 1.5 | FTD | lnc-PDSS1-4:1 | SEQ5363 | 1.E-08 | 0.5 |
| FTD | LINC01481:13 | SEQ5902 | 1.E-08 | 0.1 | MCI | lnc-PDSS1-4:1 | SEQ5363 | 2.E-06 | 0.5 |
| MCI | LINC01481:13 | SEQ5902 | 2.E-05 | 0.1 | miAD | lnc-PDSS1-4:1 | SEQ5363 | 4.E-04 | 0.7 |
| FTD | LINC01481:8 | SEQ0478 | 4.E-06 | 0.5 | All AD | lnc-PDSS1-4:1 | SEQ5363 | 4.E-03 | 0.7 |
| All AD | LINC01550:1 | SEQ3981 | 4.E-02 | 1.3 | FTD | lnc-PDSS1-6:1 | SEQ4152 | 2.E-07 | 0.5 |
| MCI | LINC01550:11 | SEQ5742 | 9.E-05 | 3.5 | miAD | lnc-PDSS1-6:1 | SEQ4152 | 1.E-02 | 0.6 |
| FTD | LINC01578:13 | SEQ3985 | 6.E-09 | 0.4 | FTD | lnc-PDSS1-7:1 | SEQ3851 | 2.E-04 | 0.6 |
| MCI | LINC01578:13 | SEQ3985 | 4.E-05 | 0.4 | miAD | lnc-PDSS1-7:1 | SEQ3851 | 7.E-03 | 0.7 |
| miAD | LINC01578:13 | SEQ3985 | 8.E-04 | 0.6 | All AD | lnc-PDSS1-7:1 | SEQ3851 | 8.E-03 | 0.7 |
| DLB | LINC01578:13 | SEQ3985 | 1.E-03 | 0.6 | msAD | lnc-PDSS1-7:1 | SEQ3851 | 3.E-02 | 0.7 |
| All AD | LINC01578:13 | SEQ3985 | 8.E-03 | 0.6 | FTD | lnc-PDSS1-9:1 | SEQ3667 | 4.E-05 | 0.7 |

TABLE 10-continued 2847 whole blood (Paxgene RNA tube) lncRNAs differentially expressed in
MCI group or mild AD group or moderate-to-severe AD group or both of these
AD groups or FTD group or DLB group as compared to healthy control group.

| Group | lncRNA | SEQ | p-value | FC | Group | lncRNA | SEQ | p-value | FC |
|---|---|---|---|---|---|---|---|---|---|
| FTD | LINC01578:2 | SEQ3987 | 2.E-04 | 0.6 | All AD | lnc-PDSS1-9:1 | SEQ3667 | 2.E-02 | 0.8 |
| All AD | LINC01578:2 | SEQ3987 | 3.E-02 | 0.7 | msAD | lnc-PDSS1-9:1 | SEQ3667 | 5.E-02 | 0.8 |
| DLB | LINC01623:9 | SEQ5725 | 9.E-05 | 1.4 | FTD | lnc-PDYN-1:13 | SEQ4327 | 6.E-04 | 0.6 |
| DLB | LINC01678:2 | SEQ5580 | 2.E-04 | 1.9 | miAD | lnc-PDYN-1:13 | SEQ4327 | 6.E-03 | 0.6 |
| DLB | LINC01715:4 | SEQ3256 | 1.E-05 | 0.4 | All AD | lnc-PDYN-1:13 | SEQ4327 | 2.E-02 | 0.7 |
| MCI | LINC01715:4 | SEQ3256 | 5.E-04 | 0.3 | miAD | lnc-PDYN-1:16 | SEQ4111 | 1.E-02 | 0.7 |
| DLB | LINC01762:6 | SEQ5671 | 1.E-04 | 1.7 | All AD | lnc-PDYN-1:16 | SEQ4111 | 3.E-02 | 0.7 |
| DLB | LINC01762:7 | SEQ5670 | 1.E-04 | 1.7 | All AD | lnc-PDYN-1:9 | SEQ3089 | 5.E-02 | 0.7 |
| FTD | LINC01814:4 | SEQ3869 | 9.E-04 | 0.7 | DLB | lnc-PDZD2-1:1 | SEQ3861 | 8.E-05 | 1.5 |
| miAD | LINC01814:4 | SEQ3869 | 2.E-03 | 0.6 | All AD | lnc-PDZD2-1:1 | SEQ3861 | 2.E-02 | 1.2 |
| All AD | LINC01814:4 | SEQ3869 | 4.E-03 | 0.7 | msAD | lnc-PDZD2-1:1 | SEQ3861 | 3.E-02 | 1.2 |
| msAD | LINC01814:4 | SEQ3869 | 3.E-02 | 0.8 | DLB | lnc-PEA15-1:2 | SEQ4931 | 8.E-04 | 1.4 |
| MCI | LINC01891:2 | SEQ4455 | 2.E-03 | 1.8 | DLB | lnc-PEBP4-1:3 | SEQ4055 | 2.E-04 | 1.4 |
| All AD | LINC02035:2 | SEQ3993 | 6.E-03 | 0.8 | msAD | lnc-PEBP4-1:3 | SEQ4055 | 2.E-02 | 1.2 |
| miAD | LINC02035:2 | SEQ3993 | 1.E-02 | 0.8 | MCI | lnc-PELP1-2:1 | SEQ5134 | 6.E-04 | 1.7 |
| msAD | LINC02035:2 | SEQ3993 | 2.E-02 | 0.8 | DLB | lnc-PER2-5:1 | SEQ5695 | 1.E-04 | 1.6 |
| msAD | LINC02035:4 | SEQ3780 | 4.E-02 | 1.3 | DLB | lnc-PEX11G-3:1 | SEQ5315 | 9.E-06 | 1.6 |
| FTD | LINC02062:11 | SEQ5912 | 2.E-05 | 0.5 | FTD | lnc-PEX11G-3:1 | SEQ5315 | 3.E-04 | 1.4 |
| FTD | LINC02062:12 | SEQ3998 | 8.E-05 | 0.6 | MCI | lnc-PEX11G-3:1 | SEQ5315 | 4.E-04 | 1.5 |
| miAD | LINC02062:12 | SEQ3998 | 9.E-03 | 0.7 | DLB | lnc-PEX11G-4:3 | SEQ5281 | 2.E-05 | 2.0 |
| All AD | LINC02062:12 | SEQ3998 | 2.E-02 | 0.7 | MCI | lnc-PEX11G-4:3 | SEQ5281 | 5.E-04 | 1.9 |
| miAD | LINC02068:5 | SEQ4145 | 1.E-02 | 0.6 | DLB | lnc-PEX6-1:1 | SEQ2942 | 6.E-05 | 1.6 |
| All AD | LINC02100:2 | SEQ4000 | 3.E-02 | 0.7 | FTD | lnc-PEX6-3:1 | SEQ5896 | 2.E-06 | 1.7 |
| FTD | LINC02100:8 | SEQ5150 | 5.E-04 | 0.6 | DLB | lnc-PEX6-3:1 | SEQ5896 | 4.E-06 | 1.8 |
| MCI | LINC02288:2 | SEQ5435 | 3.E-04 | 1.5 | MCI | lnc-PEX6-3:1 | SEQ5896 | 2.E-05 | 1.8 |
| MCI | LINC02288:4 | SEQ4002 | 2.E-05 | 2.1 | All AD | lnc-PEX7-1:4 | SEQ5402 | 3.E-02 | 0.8 |
| FTD | LINC02288:4 | SEQ4002 | 2.E-04 | 1.7 | FTD | lnc-PEX7-1:7 | SEQ5606 | 2.E-04 | 0.7 |
| DLB | LINC02288:4 | SEQ4002 | 5.E-04 | 1.8 | All AD | lnc-PEX7-4:1 | SEQ3855 | 1.E-02 | 0.8 |
| All AD | LINC02288:4 | SEQ4002 | 2.E-02 | 1.2 | msAD | lnc-PEX7-4:1 | SEQ3855 | 3.E-02 | 0.8 |
| FTD | LINC02328:9 | SEQ4007 | 3.E-05 | 0.5 | FTD | lnc-PFDN4-11:2 | SEQ5086 | 6.E-04 | 0.6 |
| All AD | LINC02328:9 | SEQ4007 | 1.E-02 | 0.7 | All AD | lnc-PFDN4-11:2 | SEQ5086 | 2.E-02 | 0.7 |
| msAD | LINC02328:9 | SEQ4007 | 1.E-02 | 0.7 | MCI | lnc-PFDN6-2:3 | SEQ3468 | 1.E-07 | 2.5 |
| MCI | LINC02361:3 | SEQ4009 | 2.E-04 | 1.7 | FTD | lnc-PFDN6-2:3 | SEQ3468 | 2.E-07 | 2.0 |
| All AD | LINC02361:3 | SEQ4009 | 3.E-02 | 1.2 | DLB | lnc-PFDN6-2:3 | SEQ3468 | 4.E-06 | 2.4 |
| miAD | LINC02362:13 | SEQ4012 | 1.E-02 | 0.6 | miAD | lnc-PFDN6-2:3 | SEQ3468 | 1.E-03 | 1.3 |
| All AD | LINC02362:13 | SEQ4012 | 2.E-02 | 0.7 | All AD | lnc-PFDN6-2:3 | SEQ3468 | 5.E-03 | 1.2 |
| miAD | LINC02362:14 | SEQ4014 | 1.E-02 | 0.6 | All AD | lnc-PFKFB3-3:5 | SEQ5408 | 5.E-02 | 0.7 |
| All AD | LINC02362:14 | SEQ4014 | 2.E-02 | 0.7 | DLB | lnc-PGAM2-1:1 | SEQ2909 | 6.E-04 | 1.5 |
| FTD | LINC02362:17 | SEQ4825 | 6.E-06 | 0.4 | FTD | lnc-PGAP1-2:1 | SEQ4147 | 1.E-09 | 0.4 |
| MCI | LINC02362:17 | SEQ4825 | 3.E-04 | 0.5 | MCI | lnc-PGAP1-2:1 | SEQ4147 | 4.E-05 | 0.5 |
| DLB | LINC02362:17 | SEQ4825 | 9.E-04 | 0.5 | miAD | lnc-PGAP1-2:1 | SEQ4147 | 1.E-02 | 0.6 |
| miAD | LINC02363:2 | SEQ4017 | 1.E-02 | 0.7 | All AD | lnc-PGAP1-2:1 | SEQ4147 | 2.E-02 | 0.7 |
| All AD | LINC02363:2 | SEQ4017 | 3.E-02 | 0.8 | DLB | lnc-PGBD5-1:1 | SEQ2755 | 4.E-04 | 1.5 |
| miAD | LINC02363:6 | SEQ4019 | 7.E-03 | 0.6 | FTD | lnc-PGGT1B-1:1 | SEQ5999 | 3.E-07 | 0.2 |
| All AD | LINC02363:6 | SEQ4019 | 3.E-02 | 0.7 | FTD | lnc-PGM1-1:1 | SEQ5646 | 1.E-04 | 0.6 |
| All AD | LINC02384:5 | SEQ4020 | 3.E-02 | 0.6 | DLB | lnc-PHB2-2:1 | SEQ4561 | 2.E-03 | 1.4 |
| All AD | LINC02397:10 | SEQ3328 | 3.E-02 | 1.5 | All AD | lnc-PHB2-4:3 | SEQ5414 | 3.E-02 | 1.3 |
| msAD | LINC02397:10 | SEQ3328 | 4.E-02 | 1.5 | FTD | lnc-PHF20L1-6:1 | SEQ4316 | 1.E-08 | 0.4 |
| msAD | LINC02397:15 | SEQ3901 | 3.E-02 | 1.5 | MCI | lnc-PHF20L1-6:1 | SEQ4316 | 6.E-05 | 0.5 |
| All AD | LINC02397:15 | SEQ3901 | 4.E-02 | 1.4 | miAD | lnc-PHF20L1-6:1 | SEQ4316 | 6.E-03 | 0.6 |
| FTD | LINC02422:5 | SEQ4022 | 6.E-05 | 0.7 | All AD | lnc-PHF20L1-6:1 | SEQ4316 | 1.E-02 | 0.6 |
| All AD | LINC02422:5 | SEQ4022 | 5.E-02 | 0.8 | FTD | lnc-PHLDA1-1:2 | SEQ5221 | 5.E-04 | 0.4 |
| miAD | LINC02471:3 | SEQ3866 | 2.E-03 | 0.6 | DLB | lnc-PHYHD1-1:1 | SEQ3086 | 8.E-05 | 1.7 |
| All AD | LINC02471:3 | SEQ3866 | 4.E-03 | 0.6 | All AD | lnc-PIGBOS1-2:1 | SEQ5417 | 3.E-02 | 0.8 |
| msAD | LINC02471:3 | SEQ3866 | 3.E-02 | 0.7 | All AD | lnc-PIGBOS1-3:1 | SEQ5418 | 4.E-02 | 0.8 |
| MCI | LINC02482:12 | SEQ3880 | 6.E-05 | 2.0 | FTD | lnc-PIGBOS1-4:1 | SEQ5062 | 7.E-04 | 0.6 |
| All AD | LINC02482:12 | SEQ3880 | 1.E-02 | 1.3 | FTD | lnc-PIGBOS1-5:1 | SEQ5546 | 2.E-04 | 0.6 |
| msAD | LINC02482:12 | SEQ3880 | 3.E-02 | 1.4 | msAD | lnc-PIGN-7:3 | SEQ4342 | 5.E-03 | 0.6 |
| FTD | LINC-PINT:10 | SEQ4029 | 4.E-04 | 0.7 | All AD | lnc-PIGN-7:3 | SEQ4342 | 8.E-03 | 0.6 |
| miAD | LINC-PINT:10 | SEQ4029 | 1.E-02 | 0.8 | FTD | lnc-PIK3AP1-2:1 | SEQ5136 | 5.E-04 | 1.6 |
| All AD | LINC-PINT:10 | SEQ4029 | 2.E-02 | 0.8 | MCI | lnc-PIK3AP1-2:1 | SEQ5136 | 6.E-04 | 1.7 |
| DLB | LINC-PINT:11 | SEQ5167 | 3.E-06 | 5.E-02 | All AD | lnc-PIK3AP1-2:1 | SEQ5136 | 4.E-02 | 1.2 |
| FTD | LINC-PINT:11 | SEQ5167 | 2.E-04 | 0.1 | miAD | lnc-PIK3IP1-2:1 | SEQ4299 | 7.E-03 | 0.7 |
| MCI | LINC-PINT:11 | SEQ5167 | 5.E-04 | 4.E-02 | All AD | lnc-PIK3IP1-2:1 | SEQ4299 | 1.E-02 | 0.7 |
| FTD | LINC-PINT:16 | SEQ2192 | 7.E-02 | 0.6 | MCI | lnc-PILRB-1:5 | SEQ3009 | 2.E-03 | 1.8 |
| FTD | LINC-PINT:25 | SEQ5971 | 4.E-08 | 0.2 | DLB | lnc-PILRB-1:5 | SEQ3009 | 3.E-04 | 1.7 |
| MCI | LINC-PINT:25 | SEQ5971 | 3.E-06 | 0.3 | FTD | lnc-PINK1-2:1 | SEQ2734 | 1.E-10 | 0.3 |
| All AD | LINC-PINT:33 | SEQ4036 | 1.E-02 | 0.7 | MCI | lnc-PINK1-2:1 | SEQ2734 | 3.E-05 | 0.3 |
| msAD | LINC-PINT:33 | SEQ4036 | 1.E-02 | 0.7 | DLB | lnc-PINK1-2:1 | SEQ2734 | 1.E-03 | 0.4 |
| MCI | LINC-PINT:36 | SEQ5836 | 4.E-05 | 0.1 | DLB | lnc-PKHD1-2:3 | SEQ4646 | 1.E-03 | 1.6 |
| FTD | LINC-PINT:39 | SEQ4999 | 8.E-04 | 0.7 | DLB | lnc-PKHD1-6:1 | SEQ4967 | 8.E-04 | 1.6 |
| DLB | LINC-PINT:4 | SEQ5555 | 2.E-04 | 0.2 | msAD | lnc-PKN2-5:1 | SEQ4089 | 1.E-02 | 0.7 |
| miAD | LINC-PINT:46 | SEQ4040 | 2.E-03 | 1.4 | FTD | lnc-PLA2G15-1:2 | SEQ3907 | 1.E-04 | 2.4 |
| All AD | LINC-PINT:46 | SEQ4040 | 7.E-03 | 1.3 | MCI | lnc-PLA2G15-1:2 | SEQ3907 | 2.E-04 | 2.3 |

TABLE 10-continued 2847 whole blood (Paxgene RNA tube) lncRNAs differentially expressed in
MCI group or mild AD group or moderate-to-severe AD group or both of these
AD groups or FTD group or DLB group as compared to healthy control group.

| Group | lncRNA | SEQ | p-value | FC | Group | lncRNA | SEQ | p-value | FC |
|---|---|---|---|---|---|---|---|---|---|
| FTD | LINC-PINT:70 | SEQ4033 | 3.E-07 | 0.2 | DLB | lnc-PLA2G15-1:2 | SEQ3907 | 2.E-03 | 2.1 |
| MCI | LINC-PINT:70 | SEQ4033 | 4.E-06 | 0.1 | msAD | lnc-PLA2G15-1:2 | SEQ3907 | 3.E-02 | 1.4 |
| msAD | LINC-PINT:70 | SEQ4033 | 2.E-02 | 0.3 | All AD | lnc-PLA2G15-1:2 | SEQ3907 | 5.E-02 | 1.3 |
| All AD | LINC-PINT:70 | SEQ4033 | 2.E-02 | 0.3 | DLB | lnc-PLA2G15-2:2 | SEQ3565 | 2.E-03 | 1.5 |
| FTD | LINC-PINT:71 | SEQ3665 | 7.E-06 | 0.6 | DLB | lnc-PLA2G6-1:2 | SEQ2971 | 2.E-04 | 1.6 |
| All AD | LINC-PINT:71 | SEQ3665 | 3.E-02 | 0.7 | MCI | lnc-PLA2G6-1:2 | SEQ2971 | 2.E-03 | 1.5 |
| msAD | LINC-PINT:71 | SEQ3665 | 5.E-02 | 0.8 | All AD | lnc-PLAGL2-6:1 | SEQ5429 | 5.E-02 | 0.8 |
| FTD | LINC-PINT:77 | SEQ4909 | 9.E-04 | 0.7 | DLB | lnc-PLCB1-1:7 | SEQ5490 | 7.E-07 | 1.8 |
| DLB | LIPE-AS1:16 | SEQ3727 | 6.E-05 | 2.0 | MCI | lnc-PLCB1-1:7 | SEQ5490 | 2.E-04 | 1.6 |
| MCI | LIPE-AS1:16 | SEQ3727 | 9.E-04 | 1.7 | DLB | lnc-PLCD3-4:4 | SEQ4841 | 9.E-04 | 1.4 |
| All AD | LIPE-AS1:16 | SEQ3727 | 3.E-02 | 1.2 | FTD | lnc-PLCD3-4:7 | SEQ5433 | 6.E-05 | 0.5 |
| msAD | LIPE-AS1:16 | SEQ3727 | 4.E-02 | 1.2 | All AD | lnc-PLCD3-4:7 | SEQ5433 | 4.E-02 | 0.6 |
| All AD | LMNB1-DT:3 | SEQ4051 | 5.E-03 | 1.3 | FTD | lnc-PLCG1-2:1 | SEQ5645 | 1.E-04 | 0.6 |
| miAD | LMNB1-DT:3 | SEQ4051 | 1.E-02 | 1.3 | FTD | lnc-PLEKHB2-4:3 | SEQ2327 | 1.E-05 | 0.6 |
| msAD | LMNB1-DT:3 | SEQ4051 | 1.E-02 | 1.3 | MCI | lnc-PLEKHB2-4:3 | SEQ2327 | 4.E-05 | 0.6 |
| DLB | lnc-A1BG-1:8 | SEQ4706 | 1.E-03 | 1.5 | FTD | lnc-PLEKHD1-4:1 | SEQ5353 | 4.E-04 | 0.6 |
| FTD | lnc-ABCA5-7:1 | SEQ0014 | 1.E-05 | 0.6 | All AD | lnc-PLEKHD1-4:1 | SEQ5353 | 4.E-02 | 0.7 |
| All AD | lnc-ABCA5-7:1 | SEQ0014 | 5.E-02 | 0.8 | DLB | lnc-PLEKHH2-4:1 | SEQ4483 | 2.E-03 | 1.3 |
| DLB | lnc-ABCC5-3:1 | SEQ3281 | 3.E-04 | 1.5 | DLB | lnc-PLEKHH2-4:2 | SEQ4482 | 2.E-03 | 1.3 |
| FTD | lnc-ABCC5-3:4 | SEQ3282 | 5.E-05 | 1.8 | DLB | lnc-PLPP2-5:5 | SEQ5632 | 2.E-04 | 1.8 |
| MCI | lnc-ABCC5-3:4 | SEQ3282 | 5.E-05 | 1.9 | FTD | lnc-PLPPR5-4:1 | SEQ5684 | 1.E-04 | 0.5 |
| DLB | lnc-ABCC5-3:4 | SEQ3282 | 2.E-03 | 1.7 | FTD | lnc-PLSCR2-2:1 | SEQ0964 | 2.E-05 | 0.5 |
| All AD | lnc-ABCC5-3:4 | SEQ3282 | 2.E-02 | 1.3 | All AD | lnc-PLSCR2-2:1 | SEQ0964 | 7.E-03 | 0.6 |
| DLB | lnc-ABCC6-11:1 | SEQ2717 | 2.E-03 | 1.4 | miAD | lnc-PLSCR2-2:1 | SEQ0964 | 8.E-03 | 0.6 |
| MCI | lnc-ABCF2-2:1 | SEQ5473 | 3.E-06 | 1.6 | msAD | lnc-PLSCR2-2:1 | SEQ0964 | 2.E-02 | 0.6 |
| DLB | lnc-ABCF2-2:1 | SEQ5473 | 2.E-05 | 1.6 | FTD | lnc-PLXND1-1:1 | SEQ5223 | 5.E-04 | 0.5 |
| FTD | lnc-ABCF2-2:1 | SEQ5473 | 3.E-04 | 1.4 | FTD | lnc-PLXND1-3:1 | SEQ5715 | 1.E-04 | 0.5 |
| miAD | lnc-ABHD12B-2:1 | SEQ4060 | 4.E-03 | 0.7 | FTD | lnc-PLXND1-3:2 | SEQ3703 | 3.E-10 | 0.3 |
| All AD | lnc-ABHD12B-2:1 | SEQ4060 | 8.E-03 | 0.7 | MCI | lnc-PLXND1-3:2 | SEQ3703 | 4.E-05 | 0.5 |
| msAD | lnc-ABTB1-2:1 | SEQ3881 | 3.E-02 | 1.4 | All AD | lnc-PLXND1-3:2 | SEQ3703 | 2.E-02 | 0.5 |
| All AD | lnc-ABTB1-2:1 | SEQ3881 | 5.E-02 | 1.3 | msAD | lnc-PLXND1-3:2 | SEQ3703 | 5.E-02 | 0.6 |
| MCI | lnc-ABTB2-4:1 | SEQ4062 | 6.E-06 | 1.6 | DLB | lnc-PMM2-2:1 | SEQ3482 | 6.E-04 | 1.5 |
| DLB | lnc-ABTB2-4:1 | SEQ4062 | 2.E-05 | 1.6 | DLB | lnc-PMM2-6:1 | SEQ4792 | 1.E-03 | 2.0 |
| FTD | lnc-ABTB2-4:1 | SEQ4062 | 1.E-04 | 1.4 | FTD | lnc-PMM2-6:3 | SEQ5443 | 2.E-09 | 0.2 |
| All AD | lnc-ABTB2-4:1 | SEQ4062 | 8.E-03 | 1.2 | DLB | lnc-PMM2-6:3 | SEQ5443 | 1.E-06 | 0.2 |
| msAD | lnc-ABTB2-4:1 | SEQ4062 | 1.E-02 | 1.2 | MCI | lnc-PMM2-6:3 | SEQ5443 | 3.E-06 | 0.2 |
| DLB | lnc-ACBD6-2:1 | SEQ5444 | 3.E-04 | 1.6 | All AD | lnc-PMM2-6:3 | SEQ5443 | 4.E-02 | 0.4 |
| msAD | lnc-ACO1-1:1 | SEQ0590 | 9.E-03 | 0.7 | FTD | lnc-PNMA2-1:1 | SEQ5162 | 5.E-04 | 0.7 |
| All AD | lnc-ACO1-1:1 | SEQ0590 | 1.E-02 | 0.7 | FTD | lnc-PNO1-1:1 | SEQ4348 | 9.E-10 | 0.4 |
| FTD | lnc-ACTA2-1:1 | SEQ5550 | 2.E-04 | 0.6 | MCI | lnc-PNO1-1:1 | SEQ4348 | 5.E-05 | 0.5 |
| DLB | lnc-ACTR2-11:1 | SEQ3921 | 6.E-06 | 1.6 | All AD | lnc-PNO1-1:1 | SEQ4348 | 1.E-03 | 0.6 |
| msAD | lnc-ACTR2-11:1 | SEQ3921 | 3.E-02 | 1.1 | miAD | lnc-PNO1-1:1 | SEQ4348 | 3.E-03 | 0.6 |
| All AD | lnc-ACTR2-11:1 | SEQ3921 | 3.E-02 | 1.1 | msAD | lnc-PNO1-1:1 | SEQ4348 | 5.E-03 | 0.7 |
| All AD | lnc-ACTR3-2:1 | SEQ4067 | 5.E-02 | 0.8 | miAD | lnc-PNOC-2:1 | SEQ2817 | 9.E-03 | 1.3 |
| miAD | lnc-ACTR6-4:1 | SEQ4069 | 8.E-03 | 0.7 | All AD | lnc-PNOC-2:1 | SEQ2817 | 1.E-02 | 1.2 |
| All AD | lnc-ACTR6-4:1 | SEQ4069 | 1.E-02 | 0.7 | FTD | lnc-POC5-4:2 | SEQ5161 | 5.E-04 | 0.7 |
| FTD | lnc-ACTRT3-2:5 | SEQ3699 | 6.E-04 | 1.7 | All AD | lnc-POLD3-2:1 | SEQ5447 | 5.E-02 | 0.9 |
| All AD | lnc-ACTRT3-2:5 | SEQ3699 | 2.E-02 | 1.3 | DLB | lnc-POLR2J2-2:1 | SEQ5533 | 2.E-04 | 1.8 |
| msAD | lnc-ACTRT3-2:5 | SEQ3699 | 5.E-02 | 1.2 | MCI | lnc-POLR2J2-2:1 | SEQ5533 | 2.E-04 | 1.7 |
| All AD | lnc-ACTRT3-5:1 | SEQ2741 | 5.E-02 | 1.2 | DLB | lnc-POLR3E-3:4 | SEQ3547 | 1.E-03 | 1.5 |
| All AD | lnc-ACY1-2:1 | SEQ4071 | 2.E-02 | 1.2 | DLB | lnc-POLR3GL-10:1 | SEQ4515 | 2.E-03 | 1.5 |
| FTD | lnc-ADAD1-3:1 | SEQ0774 | 9.E-10 | 0.4 | msAD | lnc-POLR3GL-6:4 | SEQ3974 | 2.E-02 | 1.5 |
| MCI | lnc-ADAD1-3:1 | SEQ0774 | 3.E-06 | 0.4 | DLB | lnc-POLR3K-1:7 | SEQ4703 | 1.E-03 | 1.5 |
| miAD | lnc-ADAD1-3:1 | SEQ0774 | 2.E-04 | 0.5 | DLB | lnc-POLR3K-1:9 | SEQ4481 | 2.E-03 | 1.3 |
| All AD | lnc-ADAD1-3:1 | SEQ0774 | 3.E-04 | 0.6 | All AD | lnc-POTEH-1:1 | SEQ4048 | 1.E-02 | 1.2 |
| msAD | lnc-ADAD1-3:1 | SEQ0774 | 3.E-03 | 0.6 | msAD | lnc-POTEH-1:1 | SEQ4048 | 2.E-02 | 1.2 |
| FTD | lnc-ADAM22-2:10 | SEQ4076 | 6.E-05 | 0.5 | FTD | lnc-POU5F2-5:1 | SEQ5608 | 2.E-04 | 0.7 |
| miAD | lnc-ADAM22-2:10 | SEQ4076 | 1.E-02 | 0.6 | DLB | lnc-PPARA-3:11 | SEQ5621 | 2.E-04 | 1.6 |
| All AD | lnc-ADAM22-2:10 | SEQ4076 | 2.E-03 | 0.6 | MCI | lnc-PPARA-3:8 | SEQ2854 | 2.E-03 | 1.5 |
| msAD | lnc-ADAM22-2:10 | SEQ4076 | 1.E-02 | 0.6 | DLB | lnc-PPARA-4:1 | SEQ4739 | 1.E-03 | 1.4 |
| FTD | lnc-ADAM22-2:13 | SEQ4079 | 3.E-04 | 0.6 | miAD | lnc-PPEF1-7:4 | SEQ4078 | 1.E-02 | 0.8 |
| miAD | lnc-ADAM22-2:13 | SEQ4079 | 2.E-03 | 0.5 | All AD | lnc-PPEF1-7:4 | SEQ4078 | 3.E-02 | 0.8 |
| All AD | lnc-ADAM22-2:13 | SEQ4079 | 2.E-03 | 0.6 | DLB | lnc-PPIAL4D-5:15 | SEQ5493 | 2.E-04 | 1.6 |
| msAD | lnc-ADAM22-2:13 | SEQ4079 | 1.E-02 | 0.6 | MCI | lnc-PPIAL4D-5:4 | SEQ3660 | 7.E-04 | 2.6 |
| miAD | lnc-ADAM30-1:1 | SEQ2698 | 1.E-02 | 0.7 | DLB | lnc-PPIAL4D-5:4 | SEQ3660 | 1.E-03 | 2.1 |
| All AD | lnc-ADAM30-1:1 | SEQ2698 | 2.E-02 | 0.7 | All AD | lnc-PPIAL4D-5:4 | SEQ3660 | 4.E-02 | 1.5 |
| DLB | lnc-ADAMTS12-2:6 | SEQ4081 | 1.E-03 | 1.8 | msAD | lnc-PPIAL4D-5:4 | SEQ3660 | 5.E-02 | 1.5 |
| MCI | lnc-ADAMTS12-2:6 | SEQ4081 | 1.E-03 | 1.7 | miAD | lnc-PPIAL4F-3:2 | SEQ0828 | 5.E-03 | 0.6 |
| All AD | lnc-ADAMTS12-2:6 | SEQ4081 | 3.E-02 | 1.2 | All AD | lnc-PPIAL4F-3:2 | SEQ0828 | 8.E-03 | 0.5 |
| miAD | lnc-ADAMTSL4-4:1 | SEQ3903 | 6.E-03 | 0.6 | msAD | lnc-PPIAL4F-3:2 | SEQ0828 | 2.E-02 | 0.5 |
| All AD | lnc-ADAMTSL4-4:1 | SEQ3903 | 6.E-03 | 0.7 | miAD | lnc-PPIAL4F-3:3 | SEQ3932 | 5.E-03 | 0.6 |
| msAD | lnc-ADAMTSL4-4:1 | SEQ3903 | 3.E-02 | 0.7 | All AD | lnc-PPIAL4F-3:3 | SEQ3932 | 6.E-03 | 0.5 |
| DLB | lnc-ADAMTSL4-7:2 | SEQ4676 | 1.E-03 | 1.3 | msAD | lnc-PPIAL4F-3:3 | SEQ3932 | 3.E-02 | 0.5 |
| miAD | lnc-ADAP2-1:1 | SEQ4086 | 1.E-02 | 0.7 | miAD | lnc-PPIAL4F-6:13 | SEQ4192 | 1.E-02 | 0.8 |

TABLE 10-continued 2847 whole blood (Paxgene RNA tube) lncRNAs differentially expressed in
MCI group or mild AD group or moderate-to-severe AD group or both of these
AD groups or FTD group or DLB group as compared to healthy control group.

| Group | lncRNA | SEQ | p-value | FC | Group | lncRNA | SEQ | p-value | FC |
|---|---|---|---|---|---|---|---|---|---|
| All AD | lnc-ADAP2-1:1 | SEQ4086 | 3.E−02 | 0.8 | All AD | lnc-PPIAL4F-6:13 | SEQ4192 | 3.E−02 | 0.8 |
| msAD | lnc-ADGRL4-6:1 | SEQ3810 | 4.E−02 | 0.6 | msAD | lnc-PPIAL4G-11:1 | SEQ3641 | 3.E−02 | 0.9 |
| FTD | lnc-ADGRV1-6:1 | SEQ4088 | 1.E−04 | 0.6 | FTD | lnc-PPIAL4G-3:5 | SEQ3650 | 3.E−04 | 0.6 |
| All AD | lnc-ADGRV1-6:1 | SEQ4088 | 4.E−02 | 0.7 | All AD | lnc-PPIAL4G-3:5 | SEQ3650 | 2.E−02 | 0.7 |
| FTD | lnc-ADGRV1-8:1 | SEQ4091 | 2.E−05 | 0.5 | msAD | lnc-PPIAL4G-3:5 | SEQ3650 | 5.E−02 | 0.8 |
| MCI | lnc-ADGRV1-8:1 | SEQ4091 | 1.E−03 | 0.6 | DLB | lnc-PPIL2-1:4 | SEQ4551 | 2.E−03 | 1.3 |
| All AD | lnc-ADGRV1-8:1 | SEQ4091 | 2.E−02 | 0.7 | DLB | lnc-PPIL4-9:1 | SEQ4781 | 1.E−03 | 1.7 |
| FTD | lnc-ADH5-6:1 | SEQ5409 | 3.E−04 | 0.6 | MCI | lnc-PPP1R10-1:3 | SEQ4826 | 2.E−06 | 0.6 |
| DLB | lnc-ADIPOQ-3:2 | SEQ4093 | 1.E−03 | 1.8 | FTD | lnc-PPP1R10-1:3 | SEQ4826 | 2.E−06 | 0.6 |
| All AD | lnc-ADIPOQ-3:2 | SEQ4093 | 5.E−02 | 1.2 | DLB | lnc-PPP1R10-1:3 | SEQ4826 | 9.E−04 | 0.6 |
| DLB | lnc-ADIPOQ-3:3 | SEQ5336 | 4.E−04 | 1.7 | All AD | lnc-PPP1R10-1:3 | SEQ4826 | 2.E−02 | 0.8 |
| miAD | lnc-ADO-2:1 | SEQ4096 | 1.E−03 | 0.7 | DLB | lnc-PPP1R1A-2:1 | SEQ5879 | 3.E−05 | 1.6 |
| All AD | lnc-ADO-2:1 | SEQ4096 | 3.E−02 | 0.8 | DLB | lnc-PPP1R27-2:1 | SEQ4761 | 4.E−05 | 1.6 |
| FTD | lnc-ADRB1-4:1 | SEQ0118 | 1.E−03 | 0.7 | FTD | lnc-PPP1R27-2:1 | SEQ4761 | 3.E−04 | 1.4 |
| miAD | lnc-ADRB2-1:1 | SEQ4099 | 9.E−03 | 0.7 | MCI | lnc-PPP1R27-2:1 | SEQ4761 | 1.E−03 | 1.5 |
| All AD | lnc-ADRB2-1:1 | SEQ4099 | 2.E−02 | 0.8 | All AD | lnc-PPP1R27-2:1 | SEQ4761 | 5.E−02 | 1.1 |
| All AD | lnc-ADSS-4:1 | SEQ3813 | 3.E−02 | 0.8 | DLB | lnc-PPP1R3B-11:4 | SEQ5277 | 5.E−04 | 1.8 |
| msAD | lnc-ADSS-4:1 | SEQ3813 | 4.E−02 | 0.8 | DLB | lnc-PPP4C-2:7 | SEQ3530 | 2.E−04 | 1.4 |
| DLB | lnc-AEBP1-1:1 | SEQ4975 | 2.E−04 | 1.6 | MCI | lnc-PPP4C-2:7 | SEQ3530 | 3.E−04 | 1.5 |
| MCI | lnc-AEBP1-1:1 | SEQ4975 | 8.E−04 | 1.7 | DLB | lnc-PPP4R1-18:3 | SEQ5377 | 3.E−04 | 1.5 |
| DLB | lnc-AES-6:3 | SEQ4772 | 9.E−06 | 1.7 | MCI | lnc-PPP4R1-18:3 | SEQ5377 | 3.E−04 | 1.5 |
| MCI | lnc-AES-6:3 | SEQ4772 | 1.E−03 | 1.5 | DLB | lnc-PPP5D1-1:1 | SEQ2313 | 1.E−03 | 1.3 |
| DLB | lnc-AES-8:1 | SEQ4930 | 8.E−04 | 1.4 | DLB | lnc-PPP6R2-5:1 | SEQ2811 | 1.E−05 | 1.7 |
| FTD | lnc-AFG1L-5:1 | SEQ0263 | 1.E−05 | 0.5 | FTD | lnc-PPP6R2-5:1 | SEQ2811 | 1.E−03 | 1.4 |
| FTD | lnc-AFG1L-7:1 | SEQ6011 | 3.E−10 | 0.1 | MCI | lnc-PPP6R2-5:1 | SEQ2811 | 2.E−03 | 1.4 |
| miAD | lnc-AFG1L-8:1 | SEQ4107 | 9.E−03 | 0.8 | All AD | lnc-PQLC1-9:1 | SEQ5467 | 3.E−02 | 1.2 |
| All AD | lnc-AFG1L-8:1 | SEQ4107 | 2.E−02 | 0.8 | DLB | lnc-PQLC2-1:1 | SEQ5794 | 6.E−05 | 1.7 |
| DLB | lnc-AGAP2-2:1 | SEQ4693 | 5.E−04 | 1.4 | DLB | lnc-PRAME-7:1 | SEQ4053 | 5.E−05 | 2.4 |
| MCI | lnc-AGAP2-2:1 | SEQ4693 | 1.E−03 | 1.4 | All AD | lnc-PRAME-7:1 | SEQ4053 | 2.E−02 | 1.3 |
| DLB | lnc-AGAP5-6:1 | SEQ5626 | 2.E−04 | 1.7 | msAD | lnc-PRAME-7:1 | SEQ4053 | 2.E−02 | 1.4 |
| FTD | lnc-AGAP5-6:4 | SEQ4803 | 1.E−03 | 0.5 | miAD | lnc-PRCD-2:2 | SEQ4106 | 1.E−02 | 0.6 |
| FTD | lnc-AGBL1-7:1 | SEQ5809 | 6.E−05 | 0.7 | All AD | lnc-PRCD-2:2 | SEQ4106 | 3.E−02 | 0.7 |
| DLB | lnc-AGBL2-1:1 | SEQ5126 | 6.E−04 | 1.6 | FTD | lnc-PRDM14-4:1 | SEQ6009 | 2.E−09 | 0.3 |
| FTD | lnc-AGBL3-1:1 | SEQ4046 | 1.E−06 | 0.5 | All AD | lnc-PRDM7-1:2 | SEQ5472 | 5.E−02 | 0.8 |
| MCI | lnc-AGBL3-1:1 | SEQ4046 | 2.E−03 | 0.7 | FTD | lnc-PRDX6-3:1 | SEQ4997 | 8.E−04 | 0.6 |
| All AD | lnc-AGBL3-1:1 | SEQ4046 | 4.E−03 | 0.7 | All AD | lnc-PRDX6-3:1 | SEQ4997 | 4.E−02 | 0.8 |
| miAD | lnc-AGBL3-1:1 | SEQ4046 | 4.E−03 | 0.7 | DLB | lnc-PRELID1-1:1 | SEQ5613 | 2.E−04 | 1.4 |
| msAD | lnc-AGBL3-1:1 | SEQ4046 | 2.E−02 | 0.7 | DLB | lnc-PRICKLE4-1:1 | SEQ5195 | 5.E−04 | 1.6 |
| All AD | lnc-AGO1-1:1 | SEQ2752 | 5.E−02 | 0.8 | MCI | lnc-PRKCQ-3:1 | SEQ4886 | 3.E−04 | 6.5 |
| DLB | lnc-AGO2-2:2 | SEQ0119 | 2.E−04 | 1.6 | DLB | lnc-PRKCQ-3:1 | SEQ4886 | 9.E−04 | 5.0 |
| DLB | lnc-AGRP-1:13 | SEQ4599 | 2.E−03 | 1.8 | FTD | lnc-PRKD3-2:1 | SEQ5911 | 2.E−05 | 0.5 |
| MCI | lnc-AGRP-1:8 | SEQ5330 | 9.E−05 | 1.6 | FTD | lnc-PRKN-4:1 | SEQ3854 | 4.E−05 | 0.6 |
| DLB | lnc-AGRP-1:8 | SEQ5330 | 4.E−04 | 1.6 | All AD | lnc-PRKN-4:1 | SEQ3854 | 1.E−02 | 0.8 |
| DLB | lnc-AHNAK2-1:1 | SEQ5698 | 1.E−04 | 1.6 | msAD | lnc-PRKN-4:1 | SEQ3854 | 3.E−02 | 0.8 |
| FTD | lnc-AHSA2-2:1 | SEQ5800 | 6.E−05 | 0.6 | FTD | lnc-PRLHR-2:1 | SEQ3635 | 3.E−07 | 0.6 |
| FTD | lnc-AHSA2-5:6 | SEQ3332 | 2.E−09 | 3.E−02 | miAD | lnc-PRLHR-2:1 | SEQ3635 | 1.E−02 | 0.7 |
| MCI | lnc-AHSA2-5:6 | SEQ3332 | 9.E−06 | 2.E−02 | All AD | lnc-PRLHR-2:1 | SEQ3635 | 1.E−02 | 0.7 |
| DLB | lnc-AHSA2-5:6 | SEQ3332 | 2.E−04 | 3.E−02 | msAD | lnc-PRLHR-2:1 | SEQ3635 | 5.E−02 | 0.8 |
| FTD | lnc-AIDA-2:1 | SEQ4124 | 3.E−04 | 0.7 | FTD | lnc-PRPF4B-1:1 | SEQ5654 | 5.E−07 | 0.5 |
| miAD | lnc-AIDA-2:1 | SEQ4124 | 8.E−03 | 0.8 | MCI | lnc-PRPF4B-1:1 | SEQ5654 | 1.E−04 | 0.6 |
| All AD | lnc-AIDA-2:1 | SEQ4124 | 2.E−02 | 0.8 | DLB | lnc-PRR14-1:7 | SEQ5531 | 2.E−04 | 1.6 |
| All AD | lnc-AIM2-3:2 | SEQ4125 | 5.E−02 | 0.8 | DLB | lnc-PRRG2-1:1 | SEQ4499 | 8.E−04 | 1.5 |
| FTD | lnc-AIM2-3:3 | SEQ3333 | 7.E−05 | 0.6 | MCI | lnc-PRRG2-1:1 | SEQ4499 | 2.E−03 | 1.4 |
| All AD | lnc-AIM2-3:3 | SEQ3333 | 4.E−03 | 0.7 | DLB | lnc-PRSS2-5:1 | SEQ5208 | 3.E−04 | 1.9 |
| miAD | lnc-AIM2-3:3 | SEQ3333 | 5.E−03 | 0.7 | MCI | lnc-PRSS2-5:1 | SEQ5208 | 5.E−04 | 1.8 |
| msAD | lnc-AIM2-3:3 | SEQ3333 | 2.E−02 | 0.7 | All AD | lnc-PRSS2-5:1 | SEQ5208 | 3.E−02 | 1.2 |
| All AD | lnc-AIM2-3:4 | SEQ4128 | 4.E−02 | 0.7 | DLB | lnc-PRSS27-2:20 | SEQ5557 | 1.E−03 | 1.3 |
| FTD | lnc-AIM2-3:5 | SEQ4130 | 5.E−05 | 0.6 | DLB | lnc-PRSS27-4:12 | SEQ5703 | 1.E−04 | 1.7 |
| All AD | lnc-AIM2-3:5 | SEQ4130 | 2.E−03 | 0.7 | DLB | lnc-PRSS27-4:14 | SEQ5216 | 5.E−04 | 2.0 |
| miAD | lnc-AIM2-3:5 | SEQ4130 | 2.E−03 | 0.7 | FTD | lnc-PRSS27-4:24 | SEQ2168 | 8.E−09 | 0.1 |
| msAD | lnc-AIM2-3:5 | SEQ4130 | 9.E−03 | 0.7 | MCI | lnc-PRSS27-4:24 | SEQ2168 | 3.E−08 | 0.1 |
| All AD | lnc-AK4-2:1 | SEQ3741 | 2.E−02 | 0.7 | All AD | lnc-PRSS27-4:24 | SEQ2168 | 4.E−04 | 0.1 |
| msAD | lnc-AK4-2:1 | SEQ3741 | 4.E−02 | 0.8 | DLB | lnc-PRSS27-4:6 | SEQ4532 | 2.E−03 | 1.9 |
| FTD | lnc-AK7-6:1 | SEQ4134 | 2.E−06 | 0.5 | DLB | lnc-PSMA7-1:1 | SEQ5951 | 7.E−06 | 1.9 |
| MCI | lnc-AK7-6:1 | SEQ4134 | 9.E−04 | 0.6 | DLB | lnc-PSMB1-1:1 | SEQ4416 | 2.E−03 | 1.4 |
| miAD | lnc-AK7-6:1 | SEQ4134 | 4.E−03 | 0.7 | DLB | lnc-PSMB7-2:1 | SEQ5622 | 2.E−04 | 1.6 |
| All AD | lnc-AK7-6:1 | SEQ4134 | 2.E−02 | 0.7 | DLB | lnc-PSMB9-6:3 | SEQ5503 | 2.E−04 | 2.9 |
| FTD | lnc-AKAP11-1:1 | SEQ5677 | 1.E−04 | 0.4 | DLB | lnc-PSMC3-1:1 | SEQ4929 | 2.E−04 | 1.5 |
| All AD | lnc-AKIRIN1-1:10 | SEQ4135 | 3.E−02 | 0.8 | MCI | lnc-PSMC3-1:1 | SEQ4929 | 5.E−04 | 1.4 |
| All AD | lnc-AKNAD1-3:1 | SEQ4136 | 2.E−02 | 0.8 | DLB | lnc-PSMC3IP-1:1 | SEQ3599 | 3.E−04 | 1.3 |
| FTD | lnc-AKR1D1-5:2 | SEQ0098 | 3.E−04 | 0.6 | MCI | lnc-PSMC3IP-3:1 | SEQ3754 | 8.E−05 | 1.7 |
| DLB | lnc-AKR7A2-2:1 | SEQ0145 | 1.E−03 | 1.4 | FTD | lnc-PSMC3IP-3:1 | SEQ3754 | 9.E−04 | 1.5 |
| FTD | lnc-AKTIP-3:1 | SEQ4139 | 1.E−05 | 0.6 | DLB | lnc-PSMC3IP-3:1 | SEQ3754 | 1.E−03 | 1.6 |
| All AD | lnc-AKTIP-3:1 | SEQ4139 | 3.E−02 | 0.8 | All AD | lnc-PSMC3IP-3:1 | SEQ3754 | 2.E−02 | 1.2 |

TABLE 10-continued 2847 whole blood (Paxgene RNA tube) lncRNAs differentially expressed in MCI group or mild AD group or moderate-to-severe AD group or both of these AD groups or FTD group or DLB group as compared to healthy control group.

| Group | lncRNA | SEQ | p-value | FC | Group | lncRNA | SEQ | p-value | FC |
|---|---|---|---|---|---|---|---|---|---|
| FTD | lnc-ALB-7:2 | SEQ4141 | 1.E-07 | 0.4 | msAD | lnc-PSMC3IP-3:1 | SEQ3754 | 4.E-02 | 1.2 |
| MCI | lnc-ALB-7:2 | SEQ4141 | 2.E-04 | 0.5 | DLB | lnc-PSMC3IP-3:11 | SEQ4960 | 2.E-04 | 1.6 |
| miAD | lnc-ALB-7:2 | SEQ4141 | 7.E-03 | 0.6 | MCI | lnc-PSMC3IP-3:11 | SEQ4960 | 8.E-03 | 1.6 |
| All AD | lnc-ALB-7:2 | SEQ4141 | 2.E-02 | 0.7 | DLB | lnc-PSMC3IP-3:13 | SEQ3726 | 5.E-04 | 1.7 |
| MCI | lnc-ALDH3B2-1:1 | SEQ5648 | 1.E-04 | 2.4 | MCI | lnc-PSMC3IP-3:13 | SEQ3726 | 1.E-03 | 1.5 |
| FTD | lnc-ALDH3B2-1:1 | SEQ5648 | 1.E-04 | 1.8 | msAD | lnc-PSMC3IP-3:13 | SEQ3726 | 4.E-02 | 1.2 |
| DLB | lnc-ALG12-5:3 | SEQ3016 | 2.E-03 | 1.4 | All AD | lnc-PSMC3IP-3:13 | SEQ3726 | 5.E-02 | 1.2 |
| All AD | lnc-ALPK1-2:3 | SEQ4144 | 4.E-02 | 0.7 | FTD | lnc-PSMC3IP-3:6 | SEQ3982 | 2.E-04 | 1.6 |
| FTD | lnc-ALPK1-2:4 | SEQ4148 | 1.E-08 | 0.4 | MCI | lnc-PSMC3IP-3:6 | SEQ3982 | 2.E-04 | 1.6 |
| MCI | lnc-ALPK1-2:4 | SEQ4148 | 3.E-05 | 0.4 | DLB | lnc-PSMC3IP-3:6 | SEQ3982 | 1.E-03 | 1.6 |
| miAD | lnc-ALPK1-2:4 | SEQ4148 | 3.E-04 | 0.5 | All AD | lnc-PSMC3IP-3:6 | SEQ3982 | 6.E-03 | 1.3 |
| DLB | lnc-ALPK1-2:4 | SEQ4148 | 4.E-04 | 0.5 | miAD | lnc-PSMC3IP-3:6 | SEQ3982 | 8.E-03 | 1.3 |
| All AD | lnc-ALPK1-2:4 | SEQ4148 | 5.E-04 | 0.5 | msAD | lnc-PSMC3IP-3:6 | SEQ3982 | 2.E-02 | 1.2 |
| msAD | lnc-ALPK1-2:4 | SEQ4148 | 5.E-03 | 0.6 | FTD | lnc-PSMC6-1:1 | SEQ5982 | 2.E-06 | 0.4 |
| FTD | lnc-AMDHD1-1:2 | SEQ4073 | 3.E-05 | 0.6 | FTD | lnc-PSMD6-1:1 | SEQ5926 | 1.E-05 | 0.6 |
| MCI | lnc-AMDHD1-1:2 | SEQ4073 | 2.E-04 | 0.6 | DLB | lnc-PSMD7-2:1 | SEQ4720 | 1.E-03 | 1.8 |
| miAD | lnc-AMDHD1-1:2 | SEQ4073 | 1.E-02 | 0.7 | DLB | lnc-PSMG4-1:1 | SEQ3724 | 7.E-04 | 1.5 |
| All AD | lnc-AMDHD1-1:2 | SEQ4073 | 3.E-02 | 0.8 | All AD | lnc-PSMG4-1:1 | SEQ3724 | 2.E-02 | 1.2 |
| FTD | lnc-AMY1B-1:10 | SEQ5686 | 1.E-04 | 0.6 | msAD | lnc-PSMG4-1:1 | SEQ3724 | 4.E-02 | 1.2 |
| FTD | lnc-AMZ2-5:5 | SEQ4154 | 1.E-05 | 0.4 | FTD | lnc-PTBP2-11:1 | SEQ3669 | 7.E-06 | 0.6 |
| MCI | lnc-AMZ2-5:5 | SEQ4154 | 2.E-04 | 0.5 | All AD | lnc-PTBP2-11:1 | SEQ3669 | 3.E-02 | 0.8 |
| miAD | lnc-AMZ2-5:5 | SEQ4154 | 7.E-03 | 0.6 | msAD | lnc-PTBP2-11:1 | SEQ3669 | 5.E-02 | 0.8 |
| All AD | lnc-AMZ2-5:5 | SEQ4154 | 2.E-02 | 0.7 | DLB | lnc-PTBP3-7:1 | SEQ2703 | 5.E-04 | 1.3 |
| MCI | lnc-AMZ2-8:1 | SEQ4396 | 2.E-03 | 0.5 | FTD | lnc-PTP4A2-3:4 | SEQ5007 | 8.E-04 | 2.9 |
| All AD | lnc-ANAPC11-2:11 | SEQ3746 | 2.E-02 | 1.2 | FTD | lnc-PTP4A2-3:6 | SEQ5107 | 8.E-05 | 0.6 |
| msAD | lnc-ANAPC11-2:11 | SEQ3746 | 4.E-02 | 1.2 | MCI | lnc-PTP4A2-3:6 | SEQ5107 | 6.E-04 | 0.7 |
| MCI | lnc-ANAPC11-2:2 | SEQ3335 | 1.E-05 | 2.0 | DLB | lnc-PTPMT1-2:1 | SEQ2354 | 5.E-05 | 1.5 |
| FTD | lnc-ANAPC11-2:2 | SEQ3335 | 1.E-05 | 1.8 | DLB | lnc-PTPN23-1:2 | SEQ4934 | 8.E-04 | 1.4 |
| DLB | lnc-ANAPC11-2:2 | SEQ3335 | 3.E-05 | 2.1 | FTD | lnc-PUM3-2:1 | SEQ5291 | 4.E-04 | 0.6 |
| All AD | lnc-ANAPC11-2:2 | SEQ3335 | 2.E-03 | 1.3 | FTD | lnc-PUM3-7:1 | SEQ2337 | 8.E-04 | 0.6 |
| miAD | lnc-ANAPC11-2:2 | SEQ3335 | 3.E-03 | 1.3 | FTD | lnc-PUS7-2:1 | SEQ3909 | 4.E-08 | 0.5 |
| msAD | lnc-ANAPC11-2:2 | SEQ3335 | 9.E-03 | 1.2 | miAD | lnc-PUS7-2:1 | SEQ3909 | 1.E-03 | 0.6 |
| DLB | lnc-ANAPC11-2:8 | SEQ3283 | 1.E-05 | 1.5 | All AD | lnc-PUS7-2:1 | SEQ3909 | 3.E-03 | 0.7 |
| MCI | lnc-ANAPC11-2:8 | SEQ3283 | 4.E-05 | 1.4 | msAD | lnc-PUS7-2:1 | SEQ3909 | 3.E-02 | 0.7 |
| DLB | lnc-ANGPTL1-2:1 | SEQ3336 | 5.E-05 | 1.8 | FTD | lnc-PUS7-3:1 | SEQ6014 | 3.E-11 | 0.2 |
| FTD | lnc-ANKFY1-5:1 | SEQ5997 | 4.E-07 | 0.6 | DLB | lnc-PXDC1-12:3 | SEQ4641 | 1.E-03 | 1.5 |
| MCI | lnc-ANKH-1:8 | SEQ5053 | 3.E-04 | 2.3 | All AD | lnc-PXDC1-12:3 | SEQ4641 | 5.E-02 | 1.2 |
| FTD | lnc-ANKH-1:8 | SEQ5053 | 6.E-04 | 1.9 | DLB | lnc-PYCARD-1:2 | SEQ4964 | 8.E-04 | 1.6 |
| DLB | lnc-ANKH-1:8 | SEQ5053 | 7.E-04 | 2.6 | DLB | lnc-QPRT-3:1 | SEQ5329 | 4.E-04 | 1.6 |
| DLB | lnc-ANKRD20A2-22:3 | SEQ3338 | 1.E-05 | 1.7 | MCI | lnc-RAB1A-6:1 | SEQ5185 | 2.E-04 | 1.5 |
| FTD | lnc-ANKRD20A2-22:3 | SEQ3338 | 6.E-04 | 1.4 | DLB | lnc-RAB1A-6:1 | SEQ5185 | 5.E-04 | 1.5 |
| All AD | lnc-ANKRD20A2-22:3 | SEQ3338 | 5.E-02 | 1.1 | DLB | lnc-RAB23-20:13 | SEQ4851 | 9.E-04 | 1.5 |
| miAD | lnc-ANKRD20A4-5:4 | SEQ4167 | 7.E-03 | 0.7 | FTD | lnc-RAB2B-2:2 | SEQ5644 | 1.E-04 | 0.6 |
| All AD | lnc-ANKRD20A4-5:4 | SEQ4167 | 1.E-02 | 0.7 | DLB | lnc-RAB37-1:5 | SEQ5380 | 3.E-04 | 1.6 |
| miAD | lnc-ANKRD27-9:1 | SEQ4169 | 6.E-03 | 0.7 | DLB | lnc-RAB3A-5:1 | SEQ5567 | 2.E-04 | 1.6 |
| All AD | lnc-ANKRD27-9:1 | SEQ4169 | 4.E-02 | 0.8 | MCI | lnc-RABEP2-4:1 | SEQ5391 | 3.E-04 | 1.8 |
| msAD | lnc-ANKRD33B-2:1 | SEQ3825 | 4.E-02 | 1.4 | DLB | lnc-RABEP2-7:1 | SEQ5341 | 2.E-05 | 2.1 |
| FTD | lnc-ANKRD34B-2:12 | SEQ4174 | 8.E-05 | 0.6 | MCI | lnc-RABEP2-7:1 | SEQ5341 | 4.E-04 | 2.0 |
| MCI | lnc-ANKRD34B-2:12 | SEQ4174 | 9.E-04 | 0.6 | DLB | lnc-RABEP2-7:2 | SEQ3172 | 7.E-04 | 1.7 |
| miAD | lnc-ANKRD34B-2:12 | SEQ4174 | 5.E-03 | 0.7 | MCI | lnc-RACK1-1:2 | SEQ3580 | 9.E-06 | 1.6 |
| All AD | lnc-ANKRD34B-2:12 | SEQ4174 | 2.E-02 | 0.7 | DLB | lnc-RACK1-1:2 | SEQ3580 | 2.E-05 | 1.6 |
| FTD | lnc-ANKRD34B-2:13 | SEQ4176 | 8.E-05 | 0.6 | DLB | lnc-RADIL-1:1 | SEQ5262 | 9.E-05 | 1.6 |
| MCI | lnc-ANKRD34B-2:13 | SEQ4176 | 1.E-03 | 0.6 | MCI | lnc-RADIL-1:1 | SEQ5262 | 5.E-04 | 1.5 |
| miAD | lnc-ANKRD34B-2:13 | SEQ4176 | 5.E-03 | 0.7 | All AD | lnc-RAG1-4:1 | SEQ5504 | 4.E-02 | 0.8 |
| All AD | lnc-ANKRD34B-2:13 | SEQ4176 | 2.E-02 | 0.7 | DLB | lnc-RAI1-2:2 | SEQ5573 | 2.E-04 | 1.6 |
| FTD | lnc-ANKRD34B-2:7 | SEQ4179 | 1.E-04 | 0.5 | All AD | lnc-RAMP3-1:1 | SEQ5506 | 2.E-02 | 0.7 |
| miAD | lnc-ANKRD34B-2:7 | SEQ4179 | 7.E-04 | 0.6 | DLB | lnc-RANBP9-1:3 | SEQ4092 | 2.E-04 | 1.4 |
| All AD | lnc-ANKRD34B-2:7 | SEQ4179 | 1.E-02 | 0.7 | All AD | lnc-RANBP9-1:3 | SEQ4092 | 6.E-03 | 1.2 |
| FTD | lnc-ANKRD34B-2:8 | SEQ4181 | 3.E-04 | 0.4 | miAD | lnc-RANBP9-1:3 | SEQ4092 | 1.E-02 | 1.2 |
| MCI | lnc-ANKRD34B-2:8 | SEQ4181 | 1.E-03 | 0.5 | msAD | lnc-RANBP9-1:3 | SEQ4092 | 1.E-02 | 1.2 |
| All AD | lnc-ANKRD34B-2:8 | SEQ4181 | 4.E-02 | 0.6 | FTD | lnc-RAP2C-4:1 | SEQ4377 | 1.E-06 | 0.5 |
| miAD | lnc-ANKRD34B-4:1 | SEQ2896 | 4.E-03 | 1.2 | MCI | lnc-RAP2C-4:1 | SEQ4377 | 2.E-04 | 0.5 |
| All AD | lnc-ANKRD34B-4:1 | SEQ2896 | 5.E-03 | 1.2 | miAD | lnc-RAP2C-4:1 | SEQ4377 | 3.E-03 | 0.6 |
| msAD | lnc-ANKRD34B-4:1 | SEQ2896 | 2.E-02 | 1.2 | All AD | lnc-RAP2C-4:1 | SEQ4377 | 8.E-03 | 0.7 |
| All AD | lnc-ANKRD36-1:4 | SEQ4183 | 4.E-03 | 1.5 | DLB | lnc-RAPSN-1:1 | SEQ4610 | 1.E-03 | 1.3 |
| msAD | lnc-ANKRD36-1:4 | SEQ4183 | 8.E-03 | 1.5 | FTD | lnc-RARB-4:1 | SEQ5210 | 2.E-04 | 1.6 |
| miAD | lnc-ANKRD36-1:4 | SEQ4183 | 1.E-02 | 1.5 | MCI | lnc-RARB-4:1 | SEQ5210 | 3.E-04 | 2.0 |
| DLB | lnc-ANKRD39-1:1 | SEQ4491 | 2.E-03 | 1.4 | DLB | lnc-RARB-4:1 | SEQ5210 | 5.E-04 | 1.8 |
| FTD | lnc-ANKS1B-1:1 | SEQ3860 | 1.E-07 | 0.5 | MCI | lnc-RARRES2-2:2 | SEQ2774 | 4.E-06 | 1.6 |
| MCI | lnc-ANKS1B-1:1 | SEQ3860 | 6.E-05 | 0.6 | DLB | lnc-RARRES2-2:2 | SEQ2774 | 9.E-06 | 1.6 |
| All AD | lnc-ANKS1B-1:1 | SEQ3860 | 1.E-03 | 0.7 | FTD | lnc-RARRES2-2:2 | SEQ2774 | 6.E-05 | 1.4 |
| msAD | lnc-ANKS1B-1:1 | SEQ3860 | 3.E-02 | 0.8 | All AD | lnc-RARRES2-2:2 | SEQ2774 | 3.E-03 | 1.2 |
| DLB | lnc-ANKS3-2:1 | SEQ2771 | 2.E-03 | 1.5 | miAD | lnc-RARRES2-2:2 | SEQ2774 | 5.E-03 | 1.2 |
| All AD | lnc-ANLN-6:1 | SEQ4186 | 4.E-02 | 0.8 | msAD | lnc-RARRES2-2:2 | SEQ2774 | 8.E-03 | 1.2 |

TABLE 10-continued 2847 whole blood (Paxgene RNA tube) lncRNAs differentially expressed in MCI group or mild AD group or moderate-to-severe AD group or both of these AD groups or FTD group or DLB group as compared to healthy control group.

| Group | lncRNA | SEQ | p-value | FC | Group | lncRNA | SEQ | p-value | FC |
|---|---|---|---|---|---|---|---|---|---|
| DLB | lnc-ANP32E-1:1 | SEQ4400 | 2.E-03 | 1.2 | DLB | lnc-RARRES2-5:1 | SEQ5383 | 2.E-04 | 1.7 |
| FTD | lnc-ANTXR2-1:8 | SEQ5547 | 2.E-04 | 0.6 | MCI | lnc-RARRES2-5:1 | SEQ5383 | 3.E-04 | 1.6 |
| FTD | lnc-ANXA3-7:1 | SEQ5781 | 7.E-05 | 0.6 | All AD | lnc-RARS2-4:1 | SEQ3642 | 3.E-02 | 0.8 |
| FTD | lnc-ANXA3-8:1 | SEQ0670 | 1.E-06 | 0.6 | msAD | lnc-RARS2-4:1 | SEQ3642 | 5.E-02 | 0.9 |
| MCI | lnc-ANXA3-8:1 | SEQ0670 | 1.E-04 | 0.6 | FTD | lnc-RASA2-1:1 | SEQ5294 | 4.E-04 | 0.7 |
| All AD | lnc-ANXA3-8:1 | SEQ0670 | 4.E-02 | 0.8 | miAD | lnc-RASSF3-1:1 | SEQ4155 | 1.E-02 | 0.7 |
| FTD | lnc-AP1AR-1:1 | SEQ4189 | 4.E-08 | 0.5 | All AD | lnc-RASSF3-1:1 | SEQ4155 | 2.E-02 | 0.8 |
| miAD | lnc-AP1AR-1:1 | SEQ4189 | 4.E-02 | 0.5 | DLB | lnc-RBAK-RBAKDN-2:13 | SEQ5129 | 6.E-04 | 1.6 |
| All AD | lnc-AP1AR-1:1 | SEQ4189 | 8.E-04 | 0.6 | MCI | lnc-RBBP8NL-2:1 | SEQ5128 | 6.E-04 | 1.6 |
| MCI | lnc-AP1AR-1:1 | SEQ4189 | 2.E-03 | 0.6 | FTD | lnc-RBL2-1:10 | SEQ4900 | 9.E-04 | 0.6 |
| msAD | lnc-AP1AR-1:1 | SEQ4189 | 9.E-03 | 0.6 | FTD | lnc-RBL2-1:11 | SEQ5587 | 2.E-02 | 0.5 |
| FTD | lnc-AP3S1-4:3 | SEQ2424 | 1.E-08 | 0.3 | MCI | lnc-RBL2-1:3 | SEQ4730 | 4.E-04 | 3.5 |
| MCI | lnc-AP3S1-4:3 | SEQ2424 | 1.E-04 | 0.4 | DLB | lnc-RBL2-1:3 | SEQ4730 | 1.E-03 | 2.7 |
| MCI | lnc-APAF1-3:1 | SEQ5059 | 2.E-05 | 0.4 | FTD | lnc-RBM12B-4:2 | SEQ5071 | 7.E-04 | 0.7 |
| FTD | lnc-APAF1-3:1 | SEQ5059 | 7.E-04 | 0.6 | MCI | lnc-RBM23-3:1 | SEQ4562 | 3.E-05 | 1.6 |
| miAD | lnc-APBB2-3:1 | SEQ4195 | 8.E-03 | 0.6 | DLB | lnc-RBM23-3:1 | SEQ4562 | 2.E-03 | 1.4 |
| All AD | lnc-APBB2-3:1 | SEQ4195 | 1.E-02 | 0.7 | DLB | lnc-RBM28-3:2 | SEQ5532 | 2.E-04 | 1.7 |
| DLB | lnc-APCDD1L-3:2 | SEQ5727 | 9.E-05 | 1.4 | FTD | lnc-RC3H1-2:1 | SEQ4355 | 6.E-08 | 0.5 |
| FTD | lnc-APLNR-3:1 | SEQ5227 | 5.E-04 | 0.6 | miAD | lnc-RC3H1-2:1 | SEQ4355 | 4.E-03 | 0.7 |
| All AD | lnc-APOBEC3A-2:1 | SEQ3666 | 2.E-02 | 0.8 | All AD | lnc-RC3H1-2:1 | SEQ4355 | 1.E-02 | 0.7 |
| msAD | lnc-APOBEC3A-2:1 | SEQ3666 | 5.E-02 | 0.8 | All AD | lnc-RC3H2-1:1 | SEQ5518 | 4.E-02 | 0.8 |
| DLB | lnc-APOBEC3H-3:1 | SEQ5259 | 4.E-04 | 1.5 | FTD | lnc-RCC1L-3:1 | SEQ3975 | 7.E-07 | 0.5 |
| DLB | lnc-APOC3-2:7 | SEQ4685 | 1.E-03 | 1.4 | MCI | lnc-RCC1L-3:1 | SEQ3975 | 2.E-05 | 0.6 |
| DLB | lnc-APOL2-5:1 | SEQ5264 | 5.E-04 | 1.6 | All AD | lnc-RCC1L-3:1 | SEQ3975 | 2.E-02 | 0.7 |
| msAD | lnc-APOL4-1:5 | SEQ4202 | 8.E-03 | 0.8 | msAD | lnc-RCC1L-3:1 | SEQ3975 | 2.E-02 | 0.7 |
| All AD | lnc-APOL4-1:5 | SEQ4202 | 1.E-02 | 0.8 | All AD | lnc-RCSD1-4:1 | SEQ0831 | 5.E-02 | 0.8 |
| MCI | lnc-APOL5-4:1 | SEQ2343 | 2.E-05 | 0.6 | FTD | lnc-RDH10-3:1 | SEQ5869 | 4.E-05 | 0.6 |
| FTD | lnc-APOL5-4:1 | SEQ2343 | 4.E-05 | 0.6 | DLB | lnc-RDH13-1:2 | SEQ0250 | 1.E-03 | 1.5 |
| All AD | lnc-APOL5-4:1 | SEQ2343 | 2.E-03 | 0.7 | DLB | lnc-REC8-2:1 | SEQ4479 | 9.E-06 | 1.5 |
| msAD | lnc-APOL5-4:1 | SEQ2343 | 3.E-03 | 0.6 | MCI | lnc-REC8-2:1 | SEQ4479 | 2.E-03 | 1.3 |
| miAD | lnc-APOL5-4:1 | SEQ2343 | 6.E-03 | 0.7 | FTD | lnc-REL-1:3 | SEQ2508 | 2.E-05 | 0.6 |
| All AD | lnc-AQP8-2:1 | SEQ3756 | 3.E-02 | 1.4 | FTD | lnc-REL-6:3 | SEQ3461 | 1.E-04 | 0.7 |
| msAD | lnc-AQP8-2:1 | SEQ3756 | 4.E-02 | 1.5 | All AD | lnc-REL-6:3 | SEQ3461 | 5.E-02 | 0.8 |
| DLB | lnc-AQP8-2:5 | SEQ4835 | 9.E-04 | 1.4 | msAD | lnc-REXO5-1:2 | SEQ4665 | 1.E-03 | 2.0 |
| DLB | lnc-ARAF-1:1 | SEQ5459 | 2.E-04 | 1.9 | All AD | lnc-REX05-1:2 | SEQ4665 | 5.E-03 | 1.7 |
| MCI | lnc-ARAF-1:1 | SEQ5459 | 3.E-04 | 2.0 | MCI | lnc-RFNG-1:7 | SEQ2768 | 3.E-05 | 1.5 |
| DLB | lnc-ARF5-7:1 | SEQ4756 | 1.E-05 | 1.6 | DLB | lnc-RFNG-1:7 | SEQ2768 | 4.E-05 | 1.4 |
| MCI | lnc-ARF5-7:1 | SEQ4756 | 1.E-03 | 1.4 | miAD | lnc-RFNG-1:7 | SEQ2768 | 6.E-03 | 1.2 |
| MCI | lnc-ARF6-1:1 | SEQ4542 | 3.E-05 | 2.E-04 | All AD | lnc-RFNG-1:7 | SEQ2768 | 2.E-02 | 1.1 |
| DLB | lnc-ARF6-1:1 | SEQ4542 | 2.E-03 | 2.E-04 | msAD | lnc-RFT1-3:1 | SEQ4061 | 2.E-02 | 1.5 |
| All AD | lnc-ARHGAP10-5:2 | SEQ3781 | 2.E-02 | 1.3 | All AD | lnc-RFT1-3:1 | SEQ4061 | 3.E-02 | 1.3 |
| msAD | lnc-ARHGAP10-5:2 | SEQ3781 | 4.E-02 | 1.3 | FTD | lnc-RGPD2-2:1 | SEQ5354 | 4.E-04 | 0.6 |
| MCI | lnc-ARHGEF1-5:1 | SEQ4210 | 1.E-05 | 1.6 | FTD | lnc-RGS6-3:1 | SEQ5974 | 3.E-02 | 0.6 |
| FTD | lnc-ARHGEF1-5:1 | SEQ4210 | 4.E-05 | 1.5 | FTD | lnc-RGS9-15:4 | SEQ4117 | 1.E-03 | 0.7 |
| DLB | lnc-ARHGEF1-5:1 | SEQ4210 | 2.E-04 | 1.5 | All AD | lnc-RGS9-15:4 | SEQ4117 | 1.E-02 | 0.8 |
| All AD | lnc-ARHGEF1-5:1 | SEQ4210 | 4.E-02 | 1.1 | miAD | lnc-RGS9-15:4 | SEQ4117 | 1.E-02 | 0.8 |
| FTD | lnc-ARHGEF39-1:1 | SEQ3834 | 6.E-05 | 1.5 | FTD | lnc-RICTOR-2:1 | SEQ5065 | 7.E-04 | 0.7 |
| All AD | lnc-ARHGEF39-1:1 | SEQ3834 | 3.E-02 | 1.2 | MCI | lnc-RIMBP3C-3:1 | SEQ5754 | 8.E-05 | 1.7 |
| msAD | lnc-ARHGEF39-1:1 | SEQ3834 | 3.E-02 | 1.2 | DLB | lnc-RIMBP3C-5:1 | SEQ4637 | 3.E-04 | 1.7 |
| FTD | lnc-ARHGEF39-1:3 | SEQ3718 | 2.E-04 | 1.5 | MCI | lnc-RIMBP3C-5:1 | SEQ4637 | 1.E-03 | 1.5 |
| All AD | lnc-ARHGEF39-1:3 | SEQ3718 | 4.E-02 | 1.2 | MCI | lnc-RIMKLB-6:5 | SEQ4663 | 1.E-03 | 3.4 |
| msAD | lnc-ARHGEF39-1:3 | SEQ3718 | 4.E-02 | 1.2 | msAD | lnc-RIPOR1-1:5 | SEQ3647 | 5.E-02 | 1.2 |
| MCI | lnc-ARID2-8:1 | SEQ3792 | 1.E-03 | 1.7 | DLB | lnc-RIPOR1-1:6 | SEQ2943 | 2.E-03 | 1.4 |
| DLB | lnc-ARID2-8:1 | SEQ3792 | 2.E-03 | 1.7 | DLB | lnc-RIPOR1-1:7 | SEQ3158 | 5.E-04 | 1.5 |
| All AD | lnc-ARID2-8:1 | SEQ3792 | 1.E-02 | 1.3 | DLB | lnc-RIPOR1-1:8 | SEQ4771 | 1.E-03 | 1.5 |
| miAD | lnc-ARID2-8:1 | SEQ3792 | 1.E-02 | 1.3 | DLB | lnc-RIPOR2-7:1 | SEQ3466 | 2.E-03 | 1.5 |
| msAD | lnc-ARID2-8:1 | SEQ3792 | 4.E-02 | 1.3 | DLB | lnc-RIPOR2-7:2 | SEQ4506 | 2.E-03 | 1.5 |
| MCI | lnc-ARID3B-4:1 | SEQ4216 | 3.E-04 | 1.6 | DLB | lnc-RIPOR3-1:1 | SEQ4925 | 8.E-04 | 1.4 |
| All AD | lnc-ARID3B-4:1 | SEQ4216 | 4.E-02 | 1.1 | DLB | lnc-RLBP1-3:1 | SEQ4750 | 1.E-03 | 1.4 |
| DLB | lnc-ARID5A-2:1 | SEQ4523 | 2.E-04 | 1.7 | DLB | lnc-RLIM-4:1 | SEQ3579 | 1.E-03 | 1.5 |
| MCI | lnc-ARID5A-2:1 | SEQ4523 | 2.E-03 | 1.6 | All AD | lnc-RMDN2-3:24 | SEQ2468 | 3.E-02 | 0.8 |
| MCI | lnc-ARL14-2:3 | SEQ4782 | 1.E-03 | 1.7 | All AD | lnc-RMI2-3:1 | SEQ5534 | 4.E-02 | 0.7 |
| DLB | lnc-ARL16-1:1 | SEQ5616 | 2.E-04 | 1.4 | MCI | lnc-RNASET2-1:4 | SEQ4516 | 2.E-04 | 1.5 |
| DLB | lnc-ARL16-1:2 | SEQ4559 | 1.E-04 | 1.5 | DLB | lnc-RNASET2-1:4 | SEQ4516 | 2.E-03 | 1.5 |
| MCI | lnc-ARL16-1:2 | SEQ4559 | 2.E-03 | 1.4 | FTD | lnc-RNASET2-1:5 | SEQ5545 | 2.E-04 | 0.6 |
| FTD | lnc-ARL5A-1:1 | SEQ5745 | 9.E-05 | 0.6 | FTD | lnc-RNASET2-1:9 | SEQ4282 | 4.E-08 | 0.3 |
| DLB | lnc-ARMC6-1:1 | SEQ4624 | 1.E-03 | 1.4 | MCI | lnc-RNASET2-1:9 | SEQ4282 | 1.E-03 | 0.5 |
| DLB | lnc-ARMC6-1:2 | SEQ4854 | 9.E-04 | 1.5 | miAD | lnc-RNASET2-1:9 | SEQ4282 | 3.E-03 | 0.5 |
| DLB | lnc-ARMC7-1:1 | SEQ5527 | 2.E-04 | 1.5 | All AD | lnc-RNASET2-1:9 | SEQ4282 | 1.E-02 | 0.6 |
| DLB | lnc-ARRDC2-3:1 | SEQ5618 | 2.E-04 | 1.6 | FTD | lnc-RNF111-3:1 | SEQ5468 | 3.E-04 | 0.6 |
| All AD | lnc-ARSG-2:8 | SEQ2535 | 3.E-02 | 0.6 | DLB | lnc-RNF123-1:1 | SEQ4013 | 2.E-04 | 1.6 |
| MCI | lnc-ARVCF-4:11 | SEQ5818 | 3.E-05 | 1.6 | MCI | lnc-RNF123-1:1 | SEQ4013 | 8.E-04 | 1.5 |
| DLB | lnc-ARVCF-4:11 | SEQ5818 | 5.E-05 | 1.6 | msAD | lnc-RNF123-1:1 | SEQ4013 | 2.E-02 | 1.2 |

TABLE 10-continued 2847 whole blood (Paxgene RNA tube) lncRNAs differentially expressed in
MCI group or mild AD group or moderate-to-severe AD group or both of these
AD groups or FTD group or DLB group as compared to healthy control group.

| Group | lncRNA | SEQ | p-value | FC | Group | lncRNA | SEQ | p-value | FC |
|---|---|---|---|---|---|---|---|---|---|
| MCI | lnc-ARVCF-4:13 | SEQ4194 | 1.E-05 | 2.0 | All AD | lnc-RNF123-1:1 | SEQ4013 | 3.E-02 | 1.2 |
| FTD | lnc-ARVCF-4:13 | SEQ4194 | 2.E-04 | 1.6 | miAD | lnc-RNF125-2:1 | SEQ4605 | 1.E-03 | 1.6 |
| All AD | lnc-ARVCF-4:13 | SEQ4194 | 4.E-03 | 1.2 | DLB | lnc-RNF125-2:2 | SEQ5760 | 8.E-05 | 2.3 |
| miAD | lnc-ARVCF-4:13 | SEQ4194 | 8.E-03 | 1.2 | FTD | lnc-RNF13-4:1 | SEQ5837 | 4.E-09 | 0.2 |
| msAD | lnc-ARVCF-4:13 | SEQ4194 | 1.E-02 | 1.2 | MCI | lnc-RNF13-4:1 | SEQ5837 | 6.E-08 | 0.3 |
| FTD | lnc-ASCC2-1:1 | SEQ3888 | 1.E-04 | 0.6 | DLB | lnc-RNF13-4:1 | SEQ5837 | 4.E-05 | 0.3 |
| All AD | lnc-ASCC2-1:1 | SEQ3888 | 8.E-03 | 0.7 | miAD | lnc-RNF149-3:1 | SEQ3914 | 1.E-03 | 0.7 |
| miAD | lnc-ASCC2-1:1 | SEQ3888 | 8.E-03 | 0.6 | All AD | lnc-RNF149-3:1 | SEQ3914 | 3.E-03 | 0.7 |
| msAD | lnc-ASCC2-1:1 | SEQ3888 | 3.E-02 | 0.8 | msAD | lnc-RNF149-3:1 | SEQ3914 | 3.E-02 | 0.8 |
| FTD | lnc-ASF1A-6:1 | SEQ4225 | 4.E-04 | 0.7 | FTD | lnc-RNF219-3:1 | SEQ5989 | 2.E-06 | 0.5 |
| MCI | lnc-ASF1A-6:1 | SEQ4225 | 5.E-04 | 0.7 | FTD | lnc-RNF219-6:1 | SEQ5653 | 4.E-07 | 0.5 |
| All AD | lnc-ASF1A-6:1 | SEQ4225 | 7.E-03 | 0.7 | MCI | lnc-RNF219-6:1 | SEQ5653 | 1.E-04 | 0.5 |
| msAD | lnc-ASF1A-6:1 | SEQ4225 | 8.E-03 | 0.7 | DLB | lnc-RNF24-2:5 | SEQ3190 | 5.E-04 | 1.7 |
| All AD | lnc-ASPHD2-2:2 | SEQ2612 | 4.E-03 | 1.1 | DLB | lnc-RNF24-2:9 | SEQ5790 | 6.E-05 | 1.5 |
| msAD | lnc-ASPHD2-2:2 | SEQ2612 | 5.E-03 | 1.2 | DLB | lnc-RNF40-1:1 | SEQ3839 | 8.E-05 | 1.6 |
| miAD | lnc-ASPHD2-2:2 | SEQ2612 | 1.E-02 | 1.1 | MCI | lnc-RNF40-1:1 | SEQ3839 | 6.E-04 | 1.5 |
| FTD | lnc-ASPRV1-2:1 | SEQ4229 | 4.E-05 | 0.6 | msAD | lnc-RNF40-1:1 | SEQ3839 | 3.E-02 | 1.2 |
| All AD | lnc-ASPRV1-2:1 | SEQ4229 | 3.E-02 | 0.8 | DLB | lnc-RNFT2-1:7 | SEQ4939 | 8.E-04 | 1.5 |
| DLB | lnc-ASXL1-3:1 | SEQ2650 | 3.E-04 | 1.5 | MCI | lnc-RNMT-7:1 | SEQ4875 | 8.E-04 | 1.8 |
| MCI | lnc-ASXL1-4:3 | SEQ4231 | 2.E-04 | 1.8 | DLB | lnc-RNMT-7:1 | SEQ4875 | 9.E-04 | 1.9 |
| DLB | lnc-ASXL1-4:3 | SEQ4231 | 7.E-04 | 1.8 | FTD | lnc-ROCK1-1:1 | SEQ5980 | 3.E-06 | 0.6 |
| All AD | lnc-ASXL1-4:3 | SEQ4231 | 4.E-02 | 1.2 | DLB | lnc-ROGDI-1:1 | SEQ5950 | 7.E-06 | 1.4 |
| DLB | lnc-ATAD2-1:1 | SEQ4447 | 2.E-03 | 1.6 | DLB | lnc-ROM1-4:1 | SEQ5258 | 5.E-04 | 1.5 |
| FTD | lnc-ATAD5-9:9 | SEQ3904 | 1.E-06 | 0.5 | DLB | lnc-ROM1-7:1 | SEQ3478 | 3.E-04 | 1.5 |
| miAD | lnc-ATAD5-9:9 | SEQ3904 | 4.E-03 | 0.7 | DLB | lnc-ROM1-7:3 | SEQ3586 | 2.E-04 | 1.6 |
| All AD | lnc-ATAD5-9:9 | SEQ3904 | 6.E-03 | 0.7 | DLB | lnc-ROM1-7:6 | SEQ3589 | 2.E-03 | 1.5 |
| msAD | lnc-ATAD5-9:9 | SEQ3904 | 3.E-02 | 0.7 | FTD | lnc-ROPN1L-2:2 | SEQ5554 | 3.E-08 | 0.5 |
| MCI | lnc-ATG12-3:2 | SEQ2558 | 2.E-03 | 1.8 | MCI | lnc-ROPN1L-2:2 | SEQ5554 | 2.E-05 | 0.6 |
| All AD | lnc-ATG3-1:1 | SEQ4191 | 5.E-03 | 0.7 | All AD | lnc-ROPN1L-2:2 | SEQ5554 | 4.E-02 | 0.7 |
| miAD | lnc-ATG3-1:1 | SEQ4191 | 1.E-02 | 0.7 | FTD | lnc-RORA-2:1 | SEQ3798 | 8.E-06 | 0.4 |
| msAD | lnc-ATG3-1:1 | SEQ4191 | 1.E-02 | 0.7 | All AD | lnc-RORA-2:1 | SEQ3798 | 2.E-02 | 0.7 |
| FTD | lnc-ATL1-4:1 | SEQ5001 | 8.E-04 | 0.7 | msAD | lnc-RORA-2:1 | SEQ3798 | 4.E-02 | 0.7 |
| FTD | lnc-ATOH7-3:3 | SEQ3867 | 3.E-07 | 0.5 | FTD | lnc-RPE-4:2 | SEQ5964 | 5.E-06 | 0.6 |
| MCI | lnc-ATOH7-3:3 | SEQ3867 | 6.E-04 | 0.6 | DLB | lnc-RPIA-4:2 | SEQ4656 | 1.E-03 | 1.9 |
| miAD | lnc-ATOH7-3:3 | SEQ3867 | 3.E-03 | 0.7 | DLB | lnc-RPIA-5:1 | SEQ4982 | 8.E-04 | 2.1 |
| All AD | lnc-ATOH7-3:3 | SEQ3867 | 5.E-03 | 0.7 | All AD | lnc-RPIA-5:1 | SEQ4982 | 3.E-02 | 1.3 |
| msAD | lnc-ATOH7-3:3 | SEQ3867 | 3.E-02 | 0.7 | DLB | lnc-RPL12-1:3 | SEQ3024 | 1.E-03 | 1.5 |
| DLB | lnc-ATOX1-4:1 | SEQ2621 | 1.E-03 | 1.4 | DLB | lnc-RPL13-5:1 | SEQ5446 | 3.E-04 | 1.6 |
| FTD | lnc-ATP11B-6:1 | SEQ4668 | 7.E-07 | 0.5 | DLB | lnc-RPL36AL-1:1 | SEQ4550 | 2.E-03 | 1.3 |
| MCI | lnc-ATP11B-6:1 | SEQ4668 | 1.E-03 | 0.6 | DLB | lnc-RPP38-5:1 | SEQ5046 | 7.E-04 | 1.8 |
| miAD | lnc-ATP1A1-1:2 | SEQ4077 | 1.E-02 | 0.8 | FTD | lnc-RPP38-6:2 | SEQ5782 | 7.E-05 | 0.6 |
| All AD | lnc-ATP1A1-1:2 | SEQ4077 | 2.E-02 | 0.8 | miAD | lnc-RPS12-1:1 | SEQ4218 | 1.E-02 | 0.7 |
| DLB | lnc-ATP6AP2-3:1 | SEQ5197 | 5.E-04 | 1.6 | All AD | lnc-RPS12-1:1 | SEQ4218 | 2.E-02 | 0.7 |
| FTD | lnc-ATP6V1C1-9:4 | SEQ3802 | 7.E-07 | 0.6 | MCI | lnc-RPS25-5:1 | SEQ4968 | 8.E-04 | 1.6 |
| All AD | lnc-ATP6V1C1-9:4 | SEQ3802 | 2.E-02 | 0.7 | MCI | lnc-RRN3-4:1 | SEQ4461 | 1.E-06 | 2.1 |
| msAD | lnc-ATP6V1C1-9:4 | SEQ3802 | 4.E-02 | 0.8 | DLB | lnc-RRN3-4:1 | SEQ4461 | 3.E-06 | 2.1 |
| MCI | lnc-ATP6V1E2-5:2 | SEQ4243 | 8.E-05 | 1.7 | FTD | lnc-RRN3-4:1 | SEQ4461 | 3.E-05 | 1.8 |
| DLB | lnc-ATP6V1E2-5:2 | SEQ4243 | 3.E-04 | 1.5 | miAD | lnc-RRN3-4:1 | SEQ4461 | 2.E-03 | 1.3 |
| All AD | lnc-ATP6V1E2-5:2 | SEQ4243 | 3.E-02 | 1.2 | All AD | lnc-RRN3-4:1 | SEQ4461 | 7.E-03 | 1.3 |
| DLB | lnc-ATP6V1G1-2:1 | SEQ5199 | 5.E-04 | 1.7 | FTD | lnc-RSBN1-1:1 | SEQ5104 | 1.E-05 | 0.5 |
| FTD | lnc-ATP6V1G3-2:1 | SEQ4045 | 3.E-07 | 0.5 | MCI | lnc-RSBN1-1:1 | SEQ5104 | 6.E-04 | 0.6 |
| MCI | lnc-ATP6V1G3-2:1 | SEQ4045 | 4.E-05 | 0.6 | DLB | lnc-RSPH10B2-1:3 | SEQ2580 | 1.E-03 | 1.5 |
| All AD | lnc-ATP6V1G3-2:1 | SEQ4045 | 5.E-03 | 0.7 | DLB | lnc-RSPH1-7:2 | SEQ4513 | 2.E-03 | 1.5 |
| miAD | lnc-ATP6V1G3-2:1 | SEQ4045 | 6.E-03 | 0.6 | DLB | lnc-RTL8B-1:2 | SEQ5693 | 1.E-04 | 1.5 |
| msAD | lnc-ATP6V1G3-2:1 | SEQ4045 | 2.E-02 | 0.7 | FTD | lnc-RTN4-1:1 | SEQ5361 | 4.E-04 | 0.7 |
| MCI | lnc-ATPAF2-2:1 | SEQ4451 | 2.E-03 | 1.6 | All AD | lnc-RTP2-1:1 | SEQ3786 | 1.E-02 | 0.7 |
| DLB | lnc-ATPAF2-2:1 | SEQ4451 | 2.E-03 | 1.7 | msAD | lnc-RTP2-1:1 | SEQ3786 | 3.E-02 | 0.7 |
| DLB | lnc-ATXN7L3-1:3 | SEQ4480 | 2.E-03 | 1.3 | miAD | lnc-RTP2-1:2 | SEQ3661 | 1.E-02 | 0.7 |
| DLB | lnc-AUNIP-1:1 | SEQ5492 | 2.E-04 | 1.6 | All AD | lnc-RTP2-1:2 | SEQ3661 | 1.E-02 | 0.7 |
| DLB | lnc-AUNIP-1:12 | SEQ2821 | 2.E-05 | 1.6 | msAD | lnc-RTP2-1:2 | SEQ3661 | 5.E-02 | 0.7 |
| msAD | lnc-AUNIP-1:12 | SEQ2821 | 7.E-03 | 1.2 | All AD | lnc-RTP4-5:2 | SEQ5563 | 4.E-02 | 0.8 |
| All AD | lnc-AUNIP-1:12 | SEQ2821 | 1.E-02 | 1.2 | FTD | lnc-RXFP2-2:2 | SEQ5941 | 1.E-05 | 0.6 |
| MCI | lnc-AUNIP-2:1 | SEQ4658 | 1.E-03 | 2.0 | FTD | lnc-RXFP2-3:1 | SEQ5289 | 4.E-04 | 0.6 |
| msAD | lnc-B2M-1:1 | SEQ3816 | 4.E-02 | 0.8 | MCI | lnc-SAG-3:1 | SEQ3534 | 2.E-03 | 1.8 |
| msAD | lnc-B2M-1:2 | SEQ3986 | 2.E-02 | 0.7 | FTD | lnc-SAMD11-12:4 | SEQ4200 | 8.E-07 | 0.2 |
| All AD | lnc-B2M-1:2 | SEQ3986 | 3.E-02 | 0.8 | MCI | lnc-SAMD11-12:4 | SEQ4200 | 1.E-06 | 0.2 |
| All AD | lnc-B4GALNT3-2:11 | SEQ4249 | 5.E-02 | 0.8 | DLB | lnc-SAMD11-12:4 | SEQ4200 | 4.E-05 | 0.3 |
| MCI | lnc-B4GALNT3-4:2 | SEQ4583 | 2.E-03 | 1.5 | All AD | lnc-SAMD11-12:4 | SEQ4200 | 4.E-03 | 0.5 |
| MCI | lnc-BANP-10:1 | SEQ4430 | 2.E-03 | 1.6 | msAD | lnc-SAMD11-12:4 | SEQ4200 | 9.E-03 | 0.6 |
| MCI | lnc-BANP-10:1 | SEQ4430 | 2.E-03 | 1.5 | miAD | lnc-SAMD11-12:4 | SEQ4200 | 1.E-02 | 0.5 |
| DLB | lnc-BASP1-1:1 | SEQ5255 | 5.E-04 | 1.5 | All AD | lnc-SAMD11-13:2 | SEQ3700 | 4.E-02 | 1.2 |
| MCI | lnc-BAZ1A-2:1 | SEQ2485 | 5.E-05 | 1.7 | msAD | lnc-SAMD11-13:2 | SEQ3700 | 5.E-02 | 1.3 |
| FTD | lnc-BAZ1A-2:1 | SEQ2485 | 1.E-04 | 1.7 | FTD | lnc-SAMD11-14:1 | SEQ3001 | 1.E-04 | 0.7 |
| miAD | lnc-BAZ1A-2:1 | SEQ2485 | 7.E-03 | 1.3 | MCI | lnc-SAMD11-14:1 | SEQ3001 | 1.E-03 | 0.7 |

TABLE 10-continued 2847 whole blood (Paxgene RNA tube) lncRNAs differentially expressed in
MCI group or mild AD group or moderate-to-severe AD group or both of these
AD groups or FTD group or DLB group as compared to healthy control group.

| Group | lncRNA | SEQ | p-value | FC | Group | lncRNA | SEQ | p-value | FC |
|---|---|---|---|---|---|---|---|---|---|
| All AD | lnc-BAZ1A-2:1 | SEQ2485 | 1.E-02 | 1.2 | FTD | lnc-SAMD12-4:1 | SEQ5404 | 3.E-04 | 0.6 |
| FTD | lnc-BAZ2B-1:7 | SEQ3737 | 7.E-05 | 0.6 | All AD | lnc-SAMD12-4:1 | SEQ5404 | 5.E-02 | 0.7 |
| miAD | lnc-BAZ2B-1:7 | SEQ3737 | 4.E-03 | 0.6 | DLB | lnc-SAMD4A-3:1 | SEQ4442 | 7.E-04 | 1.8 |
| All AD | lnc-BAZ2B-1:7 | SEQ3737 | 7.E-03 | 0.7 | MCI | lnc-SAMD4A-3:1 | SEQ4442 | 2.E-03 | 1.6 |
| msAD | lnc-BAZ2B-1:7 | SEQ3737 | 4.E-02 | 0.7 | FTD | lnc-SAMD5-1:10 | SEQ0090 | 3.E-06 | 0.5 |
| FTD | lnc-BAZ2B-2:1 | SEQ3649 | 3.E-05 | 0.6 | miAD | lnc-SAMD5-1:10 | SEQ0090 | 4.E-03 | 0.6 |
| miAD | lnc-BAZ2B-2:1 | SEQ3649 | 1.E-02 | 0.7 | msAD | lnc-SAMD9L-1:1 | SEQ4296 | 7.E-03 | 0.6 |
| All AD | lnc-BAZ2B-2:1 | SEQ3649 | 1.E-02 | 0.7 | All AD | lnc-SAMD9L-1:1 | SEQ4296 | 1.E-02 | 0.7 |
| msAD | lnc-BAZ2B-2:1 | SEQ3649 | 5.E-02 | 0.8 | FTD | lnc-SAR1B-1:1 | SEQ5839 | 1.E-05 | 0.5 |
| FTD | lnc-BCL2L11-3:1 | SEQ5605 | 2.E-04 | 0.7 | MCI | lnc-SAR1B-1:1 | SEQ5839 | 4.E-05 | 0.5 |
| FTD | lnc-BCL2L11-3:3 | SEQ5234 | 5.E-04 | 0.7 | FTD | lnc-SBDS-3:1 | SEQ5159 | 5.E-04 | 0.7 |
| All AD | lnc-BCL2L11-6:1 | SEQ4257 | 4.E-02 | 0.8 | DLB | lnc-SBDS-4:3 | SEQ5480 | 2.E-04 | 1.4 |
| All AD | lnc-BDH1-5:10 | SEQ4258 | 5.E-03 | 1.8 | DLB | lnc-SBDS-4:9 | SEQ3145 | 6.E-05 | 1.7 |
| msAD | lnc-BDH1-5:10 | SEQ4258 | 6.E-03 | 1.9 | FTD | lnc-SBF2-1:5 | SEQ4028 | 4.E-05 | 0.6 |
| FTD | lnc-BDH1-5:12 | SEQ4105 | 8.E-08 | 0.4 | All AD | lnc-SBF2-1:5 | SEQ4028 | 5.E-03 | 0.6 |
| miAD | lnc-BDH1-5:12 | SEQ4105 | 1.E-02 | 0.6 | miAD | lnc-SBF2-1:5 | SEQ4028 | 6.E-03 | 0.6 |
| All AD | lnc-BDH1-5:12 | SEQ4105 | 2.E-02 | 0.6 | msAD | lnc-SBF2-1:5 | SEQ4028 | 2.E-02 | 0.7 |
| MCI | lnc-BICD1-5:1 | SEQ4439 | 5.E-04 | 1.8 | DLB | lnc-SBK1-1:1 | SEQ3472 | 2.E-03 | 1.8 |
| DLB | lnc-BICD1-5:1 | SEQ4439 | 2.E-03 | 1.5 | DLB | lnc-SBNO1-1:1 | SEQ4866 | 9.E-04 | 1.6 |
| DLB | lnc-BICRAL-3:1 | SEQ2666 | 4.E-04 | 1.5 | DLB | lnc-SBNO2-1:3 | SEQ5440 | 3.E-04 | 1.5 |
| DLB | lnc-BIN3-1:1 | SEQ5614 | 2.E-04 | 1.4 | FTD | lnc-SCAF8-5:3 | SEQ5959 | 7.E-06 | 0.6 |
| DLB | lnc-BIN3-2:1 | SEQ2884 | 9.E-04 | 1.4 | DLB | lnc-SCARB1-4:1 | SEQ5040 | 7.E-04 | 1.6 |
| FTD | lnc-BIRC6-1:4 | SEQ0892 | 5.E-04 | 0.7 | MCI | lnc-SCEL-6:1 | SEQ3655 | 6.E-06 | 2.0 |
| FTD | lnc-BOLA2B-1:5 | SEQ5096 | 6.E-04 | 1.6 | DLB | lnc-SCEL-6:1 | SEQ3655 | 6.E-06 | 2.1 |
| DLB | lnc-BOLA2B-1:7 | SEQ4698 | 7.E-04 | 1.4 | FTD | lnc-SCEL-6:1 | SEQ3655 | 2.E-05 | 1.8 |
| MCI | lnc-BOLA2B-1:7 | SEQ4698 | 1.E-03 | 1.5 | All AD | lnc-SCEL-6:1 | SEQ3655 | 3.E-02 | 1.2 |
| DLB | lnc-BOLL-1:1 | SEQ3744 | 3.E-05 | 1.9 | msAD | lnc-SCEL-6:1 | SEQ3655 | 5.E-02 | 1.2 |
| MCI | lnc-BOLL-1:1 | SEQ3744 | 4.E-04 | 1.6 | DLB | lnc-SCG3-5:1 | SEQ4780 | 1.E-03 | 1.6 |
| All AD | lnc-BOLL-1:1 | SEQ3744 | 3.E-02 | 1.2 | DLB | lnc-SCGB2B2-11:1 | SEQ5561 | 5.E-05 | 1.6 |
| msAD | lnc-BOLL-1:1 | SEQ3744 | 4.E-02 | 1.2 | MCI | lnc-SCGB2B2-11:1 | SEQ5561 | 2.E-04 | 1.5 |
| FTD | lnc-BOLL-6:1 | SEQ5586 | 2.E-04 | 0.4 | msAD | lnc-SCGB3A1-3:5 | SEQ3842 | 3.E-02 | 1.3 |
| MCI | lnc-BORCS5-1:2 | SEQ3820 | 1.E-03 | 1.5 | All AD | lnc-SCGB3A1-3:5 | SEQ3842 | 4.E-02 | 1.3 |
| DLB | lnc-BORCS5-1:2 | SEQ3820 | 1.E-03 | 1.5 | All AD | lnc-SCO1-1:1 | SEQ5582 | 5.E-02 | 1.2 |
| msAD | lnc-BORCS5-1:2 | SEQ3820 | 4.E-02 | 1.2 | FTD | lnc-SCRN3-5:1 | SEQ3830 | 2.E-04 | 0.7 |
| DLB | lnc-BPNT1-2:5 | SEQ4510 | 2.E-03 | 1.5 | msAD | lnc-SCRN3-5:1 | SEQ3830 | 3.E-02 | 0.8 |
| MCI | lnc-BRAT1-2:1 | SEQ3709 | 1.E-04 | 2.0 | All AD | lnc-SCRN3-5:1 | SEQ3830 | 4.E-02 | 0.8 |
| DLB | lnc-BRAT1-2:1 | SEQ3709 | 1.E-03 | 1.6 | FTD | lnc-SCRN3-7:1 | SEQ5236 | 5.E-04 | 0.7 |
| All AD | lnc-BRAT1-2:1 | SEQ3709 | 3.E-02 | 1.3 | MCI | lnc-SCTR-2:1 | SEQ5676 | 3.E-05 | 2.4 |
| msAD | lnc-BRAT1-2:1 | SEQ3709 | 5.E-02 | 1.3 | FTD | lnc-SCTR-2:1 | SEQ5676 | 9.E-05 | 1.8 |
| msAD | lnc-BRD1-7:1 | SEQ3908 | 3.E-02 | 1.6 | DLB | lnc-SCTR-2:1 | SEQ5676 | 1.E-02 | 2.0 |
| DLB | lnc-BRF1-12:1 | SEQ4271 | 2.E-04 | 2.6 | All AD | lnc-SDCBP-2:8 | SEQ3720 | 4.E-02 | 0.8 |
| msAD | lnc-BRF1-12:1 | SEQ4271 | 8.E-04 | 1.9 | msAD | lnc-SDCBP-2:8 | SEQ3720 | 4.E-02 | 0.8 |
| All AD | lnc-BRF1-12:1 | SEQ4271 | 1.E-03 | 1.8 | FTD | lnc-SDE2-1:15 | SEQ5367 | 5.E-05 | 0.4 |
| miAD | lnc-BRF1-12:1 | SEQ4271 | 7.E-03 | 1.7 | MCI | lnc-SDE2-1:15 | SEQ5367 | 5.E-04 | 0.5 |
| DLB | lnc-BRF2-2:1 | SEQ5012 | 7.E-04 | 1.3 | MCI | lnc-SDE2-1:5 | SEQ5211 | 5.E-04 | 1.8 |
| DLB | lnc-BRI3-2:1 | SEQ4573 | 1.E-04 | 1.6 | FTD | lnc-SEC22C-2:12 | SEQ5469 | 3.E-04 | 0.6 |
| MCI | lnc-BRI3-2:1 | SEQ4573 | 2.E-03 | 1.5 | All AD | lnc-SEC22C-2:12 | SEQ5469 | 5.E-02 | 0.8 |
| FTD | lnc-BST1-2:1 | SEQ4736 | 7.E-04 | 0.7 | DLB | lnc-SEC24A-2:2 | SEQ4707 | 1.E-03 | 1.5 |
| MCI | lnc-BST1-2:1 | SEQ4736 | 1.E-03 | 0.6 | miAD | lnc-SELENOP-5:1 | SEQ5077 | 6.E-04 | 1.3 |
| FTD | lnc-BTBD1-2:1 | SEQ2683 | 4.E-04 | 0.7 | All AD | lnc-SELENOP-5:1 | SEQ5077 | 5.E-03 | 1.2 |
| DLB | lnc-BTBD6-2:1 | SEQ2709 | 2.E-05 | 1.7 | FTD | lnc-SEMA4B-6:2 | SEQ5588 | 2.E-04 | 0.5 |
| FTD | lnc-BTD-2:1 | SEQ5307 | 8.E-05 | 1.5 | All AD | lnc-SEMA4D-5:3 | SEQ5589 | 4.E-02 | 0.8 |
| MCI | lnc-BTD-2:1 | SEQ5307 | 4.E-04 | 1.3 | FTD | lnc-SENP6-12:1 | SEQ4188 | 5.E-06 | 0.5 |
| All AD | lnc-BTN2A2-1:1 | SEQ4230 | 9.E-03 | 0.7 | miAD | lnc-SENP6-12:1 | SEQ4188 | 1.E-02 | 0.7 |
| msAD | lnc-BTN2A2-1:1 | SEQ4230 | 1.E-02 | 0.7 | All AD | lnc-SENP6-12:1 | SEQ4188 | 2.E-02 | 0.7 |
| FTD | lnc-BTNL8-7:1 | SEQ4119 | 1.E-06 | 1.7 | DLB | lnc-SENP8-2:1 | SEQ3941 | 3.E-05 | 1.5 |
| MCI | lnc-BTNL8-7:1 | SEQ4119 | 1.E-05 | 2.0 | MCI | lnc-SENP8-2:1 | SEQ3941 | 1.E-03 | 1.4 |
| DLB | lnc-BTNL8-7:1 | SEQ4119 | 1.E-03 | 1.8 | All AD | lnc-SENP8-2:1 | SEQ3941 | 8.E-03 | 1.2 |
| miAD | lnc-BTNL8-7:1 | SEQ4119 | 1.E-02 | 1.2 | miAD | lnc-SENP8-2:1 | SEQ3941 | 1.E-02 | 1.2 |
| All AD | lnc-BTNL8-7:1 | SEQ4119 | 2.E-02 | 1.2 | msAD | lnc-SENP8-2:1 | SEQ3941 | 3.E-02 | 1.2 |
| DLB | lnc-BYSL-2:1 | SEQ3918 | 6.E-05 | 1.7 | DLB | lnc-SEPT14-4:1 | SEQ5254 | 5.E-04 | 1.5 |
| MCI | lnc-BYSL-2:1 | SEQ3918 | 4.E-04 | 1.6 | DLB | lnc-SEPT3-4:1 | SEQ4635 | 1.E-03 | 1.5 |
| FTD | lnc-BYSL-2:1 | SEQ3918 | 6.E-04 | 1.3 | MCI | lnc-SERF1B-1:4 | SEQ5583 | 9.E-05 | 2.4 |
| All AD | lnc-BYSL-2:1 | SEQ3918 | 2.E-02 | 1.2 | DLB | lnc-SERF1B-1:4 | SEQ5583 | 2.E-04 | 2.2 |
| msAD | lnc-BYSL-2:1 | SEQ3918 | 3.E-02 | 1.2 | All AD | lnc-SERF1B-1:4 | SEQ5583 | 5.E-02 | 1.2 |
| DLB | lnc-BYSL-3:2 | SEQ4613 | 1.E-03 | 1.3 | MCI | lnc-SERHL2-1:11 | SEQ3755 | 7.E-04 | 1.7 |
| miAD | lnc-BZW1-1:1 | SEQ4153 | 1.E-02 | 0.7 | DLB | lnc-SERHL2-1:11 | SEQ3755 | 2.E-03 | 1.7 |
| All AD | lnc-BZW1-1:1 | SEQ4153 | 4.E-02 | 0.8 | All AD | lnc-SERHL2-1:11 | SEQ3755 | 3.E-02 | 1.2 |
| DLB | lnc-C11orf54-1:1 | SEQ5712 | 1.E-03 | 2.1 | msAD | lnc-SERHL2-1:11 | SEQ3755 | 4.E-02 | 1.3 |
| FTD | lnc-C11orf63-5:4 | SEQ4816 | 1.E-03 | 1.4 | MCI | lnc-SERHL2-1:6 | SEQ4318 | 2.E-05 | 1.8 |
| FTD | lnc-C12orf40-7:1 | SEQ4278 | 3.E-06 | 0.5 | DLB | lnc-SERHL2-1:6 | SEQ4318 | 9.E-04 | 1.6 |
| All AD | lnc-C12orf40-7:1 | SEQ4278 | 2.E-04 | 0.6 | FTD | lnc-SERHL2-1:6 | SEQ4318 | 1.E-03 | 1.5 |
| miAD | lnc-C12orf40-7:1 | SEQ4278 | 3.E-04 | 0.5 | All AD | lnc-SERHL2-1:6 | SEQ4318 | 3.E-03 | 1.3 |
| msAD | lnc-C12orf40-7:1 | SEQ4278 | 2.E-03 | 0.6 | msAD | lnc-SERHL2-1:6 | SEQ4318 | 6.E-03 | 1.3 |

TABLE 10-continued 2847 whole blood (Paxgene RNA tube) lncRNAs differentially expressed in MCI group or mild AD group or moderate-to-severe AD group or both of these AD groups or FTD group or DLB group as compared to healthy control group.

| Group | lncRNA | SEQ | p-value | FC | Group | lncRNA | SEQ | p-value | FC |
|---|---|---|---|---|---|---|---|---|---|
| DLB | lnc-C12orf73-1:1 | SEQ3349 | 2.E-05 | 1.5 | miAD | lnc-SERHL2-1:6 | SEQ4318 | 6.E-03 | 1.3 |
| miAD | lnc-C13orf42-1:1 | SEQ4110 | 1.E-02 | 0.7 | FTD | lnc-SERHL2-1:7 | SEQ4881 | 4.E-04 | 2.4 |
| All AD | lnc-C13orf42-1:1 | SEQ4110 | 3.E-02 | 0.7 | MCI | lnc-SERHL2-1:7 | SEQ4881 | 8.E-04 | 2.5 |
| FTD | lnc-C14orf28-2:1 | SEQ2528 | 6.E-05 | 0.5 | DLB | lnc-SERHL2-1:7 | SEQ4881 | 9.E-04 | 2.2 |
| All AD | lnc-C14orf28-2:1 | SEQ2528 | 2.E-02 | 0.7 | MCI | lnc-SERHL2-1:8 | SEQ0546 | 7.E-04 | 1.6 |
| msAD | lnc-C14orf28-2:1 | SEQ2528 | 5.E-02 | 0.7 | All AD | lnc-SERHL2-1:8 | SEQ0546 | 6.E-03 | 1.3 |
| msAD | lnc-C14orf79-5:1 | SEQ3897 | 3.E-02 | 1.2 | msAD | lnc-SERHL2-1:8 | SEQ0546 | 9.E-03 | 1.3 |
| All AD | lnc-C14orf79-5:1 | SEQ3897 | 4.E-02 | 1.2 | MCI | lnc-SERHL2-4:2 | SEQ4393 | 2.E-03 | 0.5 |
| All AD | lnc-C15orf39-1:1 | SEQ4281 | 2.E-02 | 0.8 | MCI | lnc-SERHL2-4:4 | SEQ4394 | 2.E-03 | 0.5 |
| DLB | lnc-C16orf45-4:1 | SEQ5312 | 4.E-04 | 1.4 | miAD | lnc-SERHL2-8:1 | SEQ4540 | 2.E-03 | 1.3 |
| DLB | lnc-C17orf97-5:2 | SEQ5523 | 2.E-04 | 1.4 | All AD | lnc-SERHL2-8:1 | SEQ4540 | 9.E-03 | 1.2 |
| DLB | lnc-C19orf44-5:1 | SEQ5788 | 6.E-05 | 1.5 | FTD | lnc-SERINC1-3:1 | SEQ5720 | 1.E-04 | 0.6 |
| DLB | lnc-C19orf44-8:3 | SEQ4697 | 1.E-03 | 1.5 | MCI | lnc-SERP1-4:1 | SEQ5692 | 2.E-05 | 1.4 |
| All AD | lnc-C19orf57-6:6 | SEQ4283 | 4.E-02 | 0.8 | DLB | lnc-SERP1-4:1 | SEQ5692 | 1.E-04 | 1.4 |
| All AD | lnc-C19orf57-6:7 | SEQ4284 | 3.E-02 | 0.8 | All AD | lnc-SERPINA1-1:1 | SEQ3844 | 2.E-02 | 0.7 |
| FTD | lnc-C1orf186-6:1 | SEQ6003 | 6.E-08 | 0.5 | msAD | lnc-SERPINA1-1:1 | SEQ3844 | 3.E-02 | 0.8 |
| MCI | lnc-C1orf35-3:1 | SEQ4052 | 8.E-05 | 1.7 | FTD | lnc-SERPINA11-1:1 | SEQ3698 | 1.E-04 | 2.0 |
| DLB | lnc-C1orf35-3:1 | SEQ4052 | 7.E-04 | 1.6 | MCI | lnc-SERPINA11-1:1 | SEQ3698 | 3.E-04 | 2.3 |
| msAD | lnc-C1orf35-3:1 | SEQ4052 | 2.E-02 | 1.2 | msAD | lnc-SERPINA11-1:1 | SEQ3698 | 5.E-02 | 1.2 |
| All AD | lnc-C1orf35-3:1 | SEQ4052 | 3.E-02 | 1.2 | DLB | lnc-SERPINB1-1:10 | SEQ5697 | 1.E-04 | 1.6 |
| MCI | lnc-C1orf35-3:2 | SEQ4274 | 4.E-05 | 1.7 | DLB | lnc-SERPINF1-1:1 | SEQ4683 | 1.E-03 | 1.4 |
| DLB | lnc-C1orf35-3:2 | SEQ4274 | 5.E-04 | 1.6 | DLB | lnc-SERTAD2-1:3 | SEQ5660 | 1.E-04 | 1.5 |
| msAD | lnc-C1orf35-3:2 | SEQ4274 | 8.E-03 | 1.3 | msAD | lnc-SERTAD2-3:4 | SEQ3883 | 3.E-02 | 1.5 |
| All AD | lnc-C1orf35-3:2 | SEQ4274 | 2.E-02 | 1.2 | FTD | lnc-SETD7-3:3 | SEQ5235 | 5.E-04 | 0.7 |
| DLB | lnc-C1QBP-1:1 | SEQ3351 | 8.E-04 | 1.5 | DLB | lnc-SFMBT2-3:1 | SEQ5024 | 7.E-04 | 1.5 |
| FTD | lnc-C1QTNF1-9:1 | SEQ3652 | 3.E-04 | 0.6 | DLB | lnc-SFPQ-2:1 | SEQ0169 | 1.E-03 | 1.5 |
| All AD | lnc-C1QTNF1-9:1 | SEQ3652 | 2.E-02 | 0.7 | FTD | lnc-SFPQ-2:2 | SEQ5549 | 2.E-04 | 0.6 |
| msAD | lnc-C1QTNF1-9:1 | SEQ3652 | 5.E-02 | 0.8 | DLB | lnc-SFPQ-2:4 | SEQ4721 | 1.E-03 | 1.8 |
| DLB | lnc-C1QTNF8-4:1 | SEQ5257 | 5.E-04 | 1.5 | miAD | lnc-SFRP4-3:1 | SEQ4187 | 1.E-02 | 0.7 |
| FTD | lnc-C1R-1:1 | SEQ4288 | 2.E-06 | 0.5 | All AD | lnc-SFRP4-3:1 | SEQ4187 | 1.E-02 | 0.7 |
| All AD | lnc-C1R-1:1 | SEQ4288 | 2.E-02 | 0.7 | FTD | lnc-SFRP4-3:3 | SEQ4215 | 4.E-04 | 0.6 |
| FTD | lnc-C20orf196-4:1 | SEQ4290 | 4.E-04 | 0.6 | All AD | lnc-SFRP4-3:3 | SEQ4215 | 4.E-03 | 0.7 |
| All AD | lnc-C20orf196-4:1 | SEQ4290 | 5.E-02 | 0.7 | msAD | lnc-SFRP4-3:3 | SEQ4215 | 9.E-03 | 0.7 |
| msAD | lnc-C20orf85-3:1 | SEQ3946 | 3.E-02 | 0.8 | miAD | lnc-SFRP4-3:3 | SEQ4215 | 1.E-02 | 0.6 |
| All AD | lnc-C20orf85-3:1 | SEQ3946 | 3.E-02 | 0.8 | DLB | lnc-SGCA-4:2 | SEQ5566 | 2.E-04 | 1.6 |
| DLB | lnc-C20orf96-1:1 | SEQ2764 | 3.E-05 | 1.5 | DLB | lnc-SGSM3-6:1 | SEQ4748 | 1.E-03 | 1.4 |
| DLB | lnc-C21orf58-1:2 | SEQ0033 | 2.E-04 | 1.7 | FTD | lnc-SGTB-5:1 | SEQ4353 | 1.E-04 | 0.6 |
| DLB | lnc-C21orf58-1:5 | SEQ5207 | 5.E-04 | 1.7 | miAD | lnc-SGTB-5:1 | SEQ4353 | 4.E-03 | 0.6 |
| All AD | lnc-C21orf58-1:8 | SEQ4293 | 4.E-02 | 1.4 | All AD | lnc-SGTB-5:1 | SEQ4353 | 2.E-02 | 0.7 |
| All AD | lnc-C5orf56-3:1 | SEQ4294 | 3.E-02 | 0.8 | MCI | lnc-SH2D7-3:1 | SEQ5864 | 7.E-06 | 2.1 |
| miAD | lnc-C6orf132-5:1 | SEQ4197 | 7.E-04 | 1.4 | DLB | lnc-SH2D7-3:1 | SEQ5864 | 4.E-05 | 2.1 |
| All AD | lnc-C6orf132-5:1 | SEQ4197 | 1.E-03 | 1.4 | FTD | lnc-SH3BGRL-1:1 | SEQ5743 | 9.E-05 | 0.6 |
| msAD | lnc-C6orf132-5:1 | SEQ4197 | 1.E-02 | 1.3 | DLB | lnc-SH3GL1-1:1 | SEQ5375 | 3.E-04 | 1.5 |
| FTD | lnc-C6orf201-6:2 | SEQ5871 | 3.E-05 | 0.5 | FTD | lnc-SH3KBP1-1:1 | SEQ5090 | 6.E-04 | 0.7 |
| FTD | lnc-C6orf222-4:2 | SEQ4297 | 4.E-04 | 0.7 | miAD | lnc-SHANK2-1:7 | SEQ4349 | 5.E-03 | 0.7 |
| miAD | lnc-C6orf222-4:2 | SEQ4297 | 4.E-03 | 0.6 | All AD | lnc-SHANK2-1:7 | SEQ4349 | 9.E-03 | 0.8 |
| All AD | lnc-C6orf222-4:2 | SEQ4297 | 1.E-02 | 0.7 | FTD | lnc-SHANK2-5:1 | SEQ4366 | 8.E-07 | 0.5 |
| FTD | lnc-C6orf62-1:1 | SEQ3990 | 4.E-07 | 0.5 | All AD | lnc-SHANK2-5:1 | SEQ4366 | 9.E-04 | 0.7 |
| MCI | lnc-C6orf62-1:1 | SEQ3990 | 8.E-04 | 0.6 | miAD | lnc-SHANK2-5:1 | SEQ4366 | 1.E-03 | 0.7 |
| All AD | lnc-C6orf62-1:1 | SEQ3990 | 8.E-03 | 0.7 | msAD | lnc-SHANK2-5:1 | SEQ4366 | 4.E-03 | 0.7 |
| miAD | lnc-C6orf62-1:1 | SEQ3990 | 1.E-02 | 0.6 | DLB | lnc-SHISA5-2:1 | SEQ4926 | 8.E-04 | 1.4 |
| msAD | lnc-C6orf62-1:1 | SEQ3990 | 2.E-02 | 0.7 | FTD | lnc-SHOC2-1:2 | SEQ4604 | 1.E-05 | 0.6 |
| All AD | lnc-C9orf3-6:1 | SEQ4302 | 3.E-02 | 0.8 | MCI | lnc-SHOC2-1:2 | SEQ4604 | 1.E-03 | 0.7 |
| All AD | lnc-CA4-2:1 | SEQ4303 | 2.E-02 | 0.8 | miAD | lnc-SHOC2-1:2 | SEQ4604 | 1.E-03 | 0.7 |
| DLB | lnc-CA6-8:1 | SEQ2536 | 2.E-04 | 1.4 | All AD | lnc-SHOC2-1:2 | SEQ4604 | 9.E-03 | 0.7 |
| miAD | lnc-CA6-8:1 | SEQ2536 | 2.E-04 | 1.3 | FTD | lnc-SHOC2-3:1 | SEQ5833 | 5.E-05 | 0.6 |
| All AD | lnc-CA6-8:1 | SEQ2536 | 2.E-03 | 1.2 | FTD | lnc-SHOC2-3:2 | SEQ5985 | 2.E-06 | 0.6 |
| msAD | lnc-CA6-8:1 | SEQ2536 | 2.E-03 | 1.2 | FTD | lnc-SHOX2-8:1 | SEQ5290 | 4.E-04 | 0.6 |
| DLB | lnc-CA6-8:2 | SEQ2380 | 4.E-06 | 1.6 | DLB | lnc-SIKE1-2:2 | SEQ5110 | 6.E-04 | 1.4 |
| FTD | lnc-CA6-8:2 | SEQ2380 | 4.E-05 | 1.3 | DLB | lnc-SIPA1-2:1 | SEQ5438 | 3.E-04 | 1.5 |
| MCI | lnc-CA6-8:2 | SEQ2380 | 4.E-05 | 1.5 | FTD | lnc-SIPA1L1-2:8 | SEQ5681 | 1.E-04 | 0.5 |
| msAD | lnc-CA6-8:2 | SEQ2380 | 2.E-04 | 1.2 | FTD | lnc-SIPA1L1-2:8 | SEQ5856 | 4.E-05 | 0.5 |
| All AD | lnc-CA6-8:2 | SEQ2380 | 5.E-04 | 1.2 | DLB | lnc-SIPA1L3-4:2 | SEQ4764 | 2.E-04 | 1.5 |
| miAD | lnc-CA6-8:2 | SEQ2380 | 6.E-03 | 1.2 | MCI | lnc-SIPA1L3-4:2 | SEQ4764 | 1.E-03 | 1.5 |
| FTD | lnc-CACNB2-1:1 | SEQ2386 | 5.E-04 | 0.6 | miAD | lnc-SIRPG-5:3 | SEQ4357 | 2.E-03 | 0.7 |
| FTD | lnc-CACNG1-1:2 | SEQ5592 | 2.E-04 | 0.6 | All AD | lnc-SIRPG-5:3 | SEQ4357 | 3.E-02 | 0.8 |
| FTD | lnc-CALCB-4:1 | SEQ5939 | 1.E-05 | 0.6 | DLB | lnc-SIVA1-1:1 | SEQ5249 | 5.E-04 | 1.5 |
| DLB | lnc-CALHM1-1:3 | SEQ3992 | 1.E-03 | 1.5 | FTD | lnc-SKIL-4:1 | SEQ3966 | 8.E-06 | 0.4 |
| All AD | lnc-CALHM1-1:3 | SEQ3992 | 2.E-02 | 1.2 | MCI | lnc-SKIL-4:1 | SEQ3966 | 6.E-04 | 0.4 |
| msAD | lnc-CALHM1-1:3 | SEQ3992 | 2.E-02 | 1.2 | All AD | lnc-SKIL-4:1 | SEQ3966 | 7.E-03 | 0.6 |
| DLB | lnc-CAMK2D-1:1 | SEQ4309 | 2.E-03 | 2.0 | miAD | lnc-SKIL-4:1 | SEQ3966 | 9.E-03 | 0.6 |
| All AD | lnc-CAMK2D-1:1 | SEQ4309 | 4.E-02 | 1.3 | msAD | lnc-SKIL-4:1 | SEQ3966 | 2.E-02 | 0.6 |
| FTD | lnc-CAND2-2:2 | SEQ5507 | 2.E-04 | 0.3 | DLB | lnc-SKIV2L2-1:2 | SEQ4745 | 1.E-03 | 1.4 |
| FTD | lnc-CAND2-2:4 | SEQ5098 | 2.E-04 | 0.2 | DLB | lnc-SLA2-1:1 | SEQ3570 | 2.E-03 | 1.4 |

TABLE 10-continued 2847 whole blood (Paxgene RNA tube) lncRNAs differentially expressed in
MCI group or mild AD group or moderate-to-severe AD group or both of these
AD groups or FTD group or DLB group as compared to healthy control group.

| Group | lncRNA | SEQ | p-value | FC | Group | lncRNA | SEQ | p-value | FC |
|---|---|---|---|---|---|---|---|---|---|
| MCI | lnc-CAND2-2:4 | SEQ5098 | 6.E-04 | 0.2 | FTD | lnc-SLAMF7-2:13 | SEQ5719 | 1.E-04 | 0.6 |
| MCI | lnc-CARD14-1:1 | SEQ4701 | 1.E-03 | 1.5 | DLB | lnc-SLC10A1-1:1 | SEQ5022 | 7.E-04 | 1.4 |
| MCI | lnc-CASC1-1:1 | SEQ4548 | 2.E-03 | 0.6 | DLB | lnc-SLC11A2-8:1 | SEQ4443 | 1.E-04 | 1.7 |
| FTD | lnc-CASC1-2:1 | SEQ4146 | 3.E-03 | 0.5 | MCI | lnc-SLC11A2-8:1 | SEQ4443 | 2.E-03 | 1.6 |
| miAD | lnc-CASC1-2:1 | SEQ4146 | 1.E-02 | 0.6 | FTD | lnc-SLC12A6-1:1 | SEQ4113 | 1.E-06 | 0.6 |
| All AD | lnc-CASC1-2:1 | SEQ4146 | 2.E-02 | 0.7 | miAD | lnc-SLC12A6-1:1 | SEQ4113 | 1.E-02 | 0.7 |
| FTD | lnc-CASC1-3:1 | SEQ4315 | 1.E-05 | 0.6 | All AD | lnc-SLC12A6-1:1 | SEQ4113 | 4.E-02 | 0.7 |
| miAD | lnc-CASC1-3:1 | SEQ4315 | 4.E-03 | 0.7 | FTD | lnc-SLC12A8-3:1 | SEQ5629 | 6.E-06 | 0.5 |
| All AD | lnc-CASC1-3:1 | SEQ4315 | 1.E-02 | 0.8 | All AD | lnc-SLC12A8-3:1 | SEQ5629 | 3.E-02 | 0.7 |
| FTD | lnc-CASP10-1:3 | SEQ4317 | 3.E-05 | 0.6 | DLB | lnc-SLC15A3-2:1 | SEQ5708 | 9.E-05 | 1.9 |
| All AD | lnc-CASP10-1:3 | SEQ4317 | 3.E-02 | 0.8 | MCI | lnc-SLC15A3-2:1 | SEQ5708 | 1.E-04 | 1.8 |
| DLB | lnc-CASTOR2-1:1 | SEQ4415 | 2.E-03 | 1.4 | DLB | lnc-SLC16A11-7:11 | SEQ4711 | 1.E-03 | 1.5 |
| DLB | lnc-CATSPERB-1:1 | SEQ4695 | 1.E-03 | 1.4 | FTD | lnc-SLC16A3-7:1 | SEQ5963 | 5.E-06 | 0.5 |
| FTD | lnc-CAV2-2:1 | SEQ5984 | 2.E-06 | 0.5 | All AD | lnc-SLC16A3-8:1 | SEQ3859 | 8.E-03 | 0.7 |
| FTD | lnc-CAVIN2-1:1 | SEQ4219 | 1.E-07 | 0.5 | miAD | lnc-SLC16A3-8:1 | SEQ3859 | 9.E-03 | 0.7 |
| miAD | lnc-CAVIN2-1:1 | SEQ4219 | 2.E-03 | 0.6 | msAD | lnc-SLC16A3-8:1 | SEQ3859 | 3.E-02 | 0.7 |
| All AD | lnc-CAVIN2-1:1 | SEQ4219 | 2.E-03 | 0.7 | FTD | lnc-SLC1A3-1:1 | SEQ0547 | 2.E-07 | 0.5 |
| msAD | lnc-CAVIN2-1:1 | SEQ4219 | 1.E-02 | 0.7 | MCI | lnc-SLC1A3-1:1 | SEQ0547 | 5.E-04 | 0.6 |
| DLB | lnc-CBARP-6:1 | SEQ5560 | 2.E-04 | 1.5 | All AD | lnc-SLC1A3-1:1 | SEQ0547 | 2.E-02 | 0.7 |
| FTD | lnc-CBR3-2:2 | SEQ5972 | 2.E-06 | 0.5 | miAD | lnc-SLC22A1-2:1 | SEQ4277 | 8.E-03 | 0.7 |
| MCI | lnc-CBR3-2:2 | SEQ5972 | 3.E-06 | 0.5 | All AD | lnc-SLC22A1-2:1 | SEQ4277 | 1.E-02 | 0.8 |
| DLB | lnc-CBS-2:1 | SEQ5386 | 3.E-04 | 1.7 | miAD | lnc-SLC22A1-3:2 | SEQ4114 | 1.E-02 | 0.7 |
| miAD | lnc-CBWD5-1:1 | SEQ3662 | 5.E-03 | 0.6 | All AD | lnc-SLC22A1-3:2 | SEQ4114 | 1.E-02 | 0.8 |
| All AD | lnc-CBWD5-1:1 | SEQ3662 | 8.E-03 | 0.7 | All AD | lnc-SLC22A2-1:1 | SEQ5638 | 5.E-02 | 0.8 |
| msAD | lnc-CBWD5-1:1 | SEQ3662 | 5.E-02 | 0.7 | miAD | lnc-SLC22A2-3:1 | SEQ4286 | 7.E-03 | 0.7 |
| All AD | lnc-CBX6-2:1 | SEQ3911 | 8.E-03 | 0.7 | All AD | lnc-SLC22A2-3:1 | SEQ4286 | 1.E-02 | 0.7 |
| miAD | lnc-CBX6-2:1 | SEQ3911 | 9.E-03 | 0.7 | DLB | lnc-SLC22A31-2:1 | SEQ4490 | 1.E-03 | 1.4 |
| msAD | lnc-CBX6-2:1 | SEQ3911 | 3.E-02 | 0.7 | MCI | lnc-SLC22A31-2:1 | SEQ4490 | 2.E-03 | 1.4 |
| DLB | lnc-CCDC146-1:12 | SEQ4553 | 2.E-03 | 1.3 | DLB | lnc-SLC22A31-4:1 | SEQ5559 | 2.E-04 | 1.4 |
| FTD | lnc-CCDC146-2:1 | SEQ5407 | 3.E-04 | 0.6 | FTD | lnc-SLC25A3-7:1 | SEQ2447 | 2.E-07 | 0.5 |
| FTD | lnc-CCDC150-3:1 | SEQ4325 | 1.E-06 | 0.6 | MCI | lnc-SLC25A3-7:1 | SEQ2447 | 2.E-05 | 0.6 |
| All AD | lnc-CCDC150-3:1 | SEQ4325 | 4.E-02 | 0.8 | All AD | lnc-SLC25A3-7:1 | SEQ2447 | 4.E-03 | 0.7 |
| FTD | lnc-CCDC150-4:1 | SEQ5948 | 8.E-06 | 0.6 | miAD | lnc-SLC25A3-7:1 | SEQ2447 | 5.E-03 | 0.7 |
| DLB | lnc-CCDC150-7:1 | SEQ5217 | 3.E-04 | 2.2 | msAD | lnc-SLC25A3-7:1 | SEQ2447 | 1.E-02 | 0.7 |
| MCI | lnc-CCDC150-7:1 | SEQ5217 | 5.E-04 | 2.0 | DLB | lnc-SLC25A39-2:1 | SEQ5393 | 4.E-05 | 0.2 |
| FTD | lnc-CCDC17-1:1 | SEQ5415 | 3.E-04 | 0.7 | MCI | lnc-SLC25A39-2:1 | SEQ5393 | 3.E-04 | 0.2 |
| DLB | lnc-CCDC173-6:1 | SEQ4524 | 2.E-03 | 1.6 | FTD | lnc-SLC25A39-2:1 | SEQ5393 | 3.E-04 | 0.2 |
| FTD | lnc-CCDC175-2:1 | SEQ4894 | 9.E-04 | 0.6 | DLB | lnc-SLC25A51-1:2 | SEQ4740 | 1.E-03 | 1.4 |
| DLB | lnc-CCDC22-1:1 | SEQ4414 | 2.E-03 | 1.4 | DLB | lnc-SLC25A6-4:1 | SEQ3114 | 2.E-04 | 1.6 |
| DLB | lnc-CCDC54-6:4 | SEQ5385 | 3.E-04 | 1.7 | MCI | lnc-SLC25A6-4:1 | SEQ3114 | 1.E-04 | 1.5 |
| FTD | lnc-CCDC68-1:1 | SEQ5424 | 7.E-07 | 0.4 | msAD | lnc-SLC25A6-4:1 | SEQ3114 | 3.E-02 | 1.2 |
| MCI | lnc-CCDC68-1:1 | SEQ5424 | 3.E-04 | 0.5 | MCI | lnc-SLC27A5-2:1 | SEQ4504 | 6.E-04 | 1.5 |
| DLB | lnc-CCDC69-1:1 | SEQ5374 | 3.E-04 | 1.5 | DLB | lnc-SLC27A5-2:1 | SEQ4504 | 2.E-03 | 1.4 |
| FTD | lnc-CCDC7-1:6 | SEQ3656 | 1.E-05 | 2.1 | DLB | lnc-SLC27A5-3:2 | SEQ4552 | 4.E-05 | 1.4 |
| MCI | lnc-CCDC7-1:6 | SEQ3656 | 8.E-05 | 2.1 | MCI | lnc-SLC27A5-3:2 | SEQ4552 | 2.E-03 | 1.3 |
| DLB | lnc-CCDC7-1:6 | SEQ3656 | 2.E-04 | 1.8 | FTD | lnc-SLC2A13-2:3 | SEQ4541 | 6.E-08 | 0.4 |
| All AD | lnc-CCDC7-1:6 | SEQ3656 | 2.E-02 | 1.3 | MCI | lnc-SLC2A13-2:3 | SEQ4541 | 6.E-05 | 0.4 |
| msAD | lnc-CCDC7-1:6 | SEQ3656 | 5.E-02 | 1.3 | All AD | lnc-SLC2A13-2:3 | SEQ4541 | 4.E-04 | 0.5 |
| FTD | lnc-CCDC71L-1:13 | SEQ4331 | 8.E-05 | 0.5 | msAD | lnc-SLC2A13-2:3 | SEQ4541 | 9.E-04 | 0.5 |
| All AD | lnc-CCDC71L-1:13 | SEQ4331 | 3.E-02 | 0.7 | miAD | lnc-SLC2A13-2:3 | SEQ4541 | 2.E-03 | 0.5 |
| FTD | lnc-CCDC71L-1:14 | SEQ4332 | 8.E-05 | 0.5 | DLB | lnc-SLC2A9-3:1 | SEQ5173 | 5.E-04 | 1.3 |
| All AD | lnc-CCDC71L-1:14 | SEQ4332 | 2.E-02 | 0.7 | DLB | lnc-SLC30A5-6:1 | SEQ4050 | 4.E-04 | 1.5 |
| DLB | lnc-CCDC74A-1:3 | SEQ3824 | 2.E-05 | 1.9 | MCI | lnc-SLC30A5-6:1 | SEQ4050 | 4.E-04 | 1.4 |
| MCI | lnc-CCDC74A-1:3 | SEQ3824 | 5.E-04 | 1.6 | miAD | lnc-SLC30A5-6:1 | SEQ4050 | 2.E-03 | 1.2 |
| msAD | lnc-CCDC74A-1:3 | SEQ3824 | 4.E-02 | 1.2 | All AD | lnc-SLC30A5-6:1 | SEQ4050 | 2.E-03 | 1.2 |
| MCI | lnc-CCDC78-4:1 | SEQ5880 | 3.E-05 | 1.7 | msAD | lnc-SLC30A5-6:1 | SEQ4050 | 2.E-02 | 1.2 |
| FTD | lnc-CCDC83-1:1 | SEQ4001 | 8.E-07 | 0.5 | FTD | lnc-SLC35E3-7:1 | SEQ5993 | 1.E-06 | 0.6 |
| miAD | lnc-CCDC83-1:1 | SEQ4001 | 2.E-03 | 0.6 | DLB | lnc-SLC35E3-8:1 | SEQ5769 | 2.E-07 | 0.3 |
| All AD | lnc-CCDC83-1:1 | SEQ4001 | 3.E-03 | 0.6 | MCI | lnc-SLC35E3-8:1 | SEQ5769 | 2.E-06 | 0.2 |
| msAD | lnc-CCDC83-1:1 | SEQ4001 | 2.E-02 | 0.7 | FTD | lnc-SLC35E3-8:1 | SEQ5769 | 7.E-05 | 0.2 |
| FTD | lnc-CCDC85C-2:1 | SEQ2601 | 3.E-04 | 0.7 | FTD | lnc-SLC35E3-8:2 | SEQ4267 | 8.E-07 | 0.4 |
| FTD | lnc-CCNB1IP1-1:2 | SEQ0903 | 1.E-07 | 1.8 | All AD | lnc-SLC35E3-8:2 | SEQ4267 | 3.E-03 | 0.5 |
| MCI | lnc-CCNB1IP1-1:2 | SEQ0903 | 4.E-05 | 1.7 | msAD | lnc-SLC35E3-8:2 | SEQ4267 | 7.E-03 | 0.6 |
| DLB | lnc-CCNB1IP1-1:2 | SEQ0903 | 2.E-04 | 1.5 | miAD | lnc-SLC35E3-8:2 | SEQ4267 | 8.E-03 | 0.5 |
| FTD | lnc-CCNB1IP1-1:3 | SEQ4026 | 4.E-08 | 0.5 | DLB | lnc-SLC35F5-3:11 | SEQ2639 | 1.E-04 | 1.3 |
| DLB | lnc-CCNB1IP1-1:3 | SEQ4026 | 4.E-05 | 0.6 | MCI | lnc-SLC35F5-3:11 | SEQ2639 | 5.E-04 | 1.2 |
| MCI | lnc-CCNB1IP1-1:3 | SEQ4026 | 2.E-04 | 0.6 | MCI | lnc-SLC35G3-1:3 | SEQ3900 | 1.E-04 | 2.9 |
| All AD | lnc-CCNB1IP1-1:3 | SEQ4026 | 6.E-03 | 0.7 | DLB | lnc-SLC35G3-1:3 | SEQ3900 | 6.E-04 | 2.5 |
| miAD | lnc-CCNB1IP1-1:3 | SEQ4026 | 1.E-02 | 0.7 | All AD | lnc-SLC35G3-1:3 | SEQ3900 | 1.E-02 | 1.5 |
| msAD | lnc-CCNB1IP1-1:3 | SEQ4026 | 2.E-02 | 0.7 | msAD | lnc-SLC35G3-1:3 | SEQ3900 | 3.E-02 | 1.5 |
| FTD | lnc-CCNB1IP1-1:4 | SEQ5261 | 1.E-07 | 1.9 | DLB | lnc-SLC37A2-2:1 | SEQ2906 | 2.E-04 | 1.5 |
| MCI | lnc-CCNB1IP1-1:4 | SEQ5261 | 3.E-05 | 1.7 | DLB | lnc-SLC38A3-1:1 | SEQ4724 | 6.E-05 | 2.3 |
| DLB | lnc-CCNB1IP1-1:4 | SEQ5261 | 5.E-04 | 1.5 | MCI | lnc-SLC38A3-1:1 | SEQ4724 | 1.E-03 | 1.9 |
| FTD | lnc-CCNB1IP1-1:5 | SEQ4027 | 2.E-08 | 0.5 | FTD | lnc-SLC39A10-10:1 | SEQ3806 | 6.E-08 | 1.7 |

TABLE 10-continued 2847 whole blood (Paxgene RNA tube) lncRNAs differentially expressed in
MCI group or mild AD group or moderate-to-severe AD group or both of these
AD groups or FTD group or DLB group as compared to healthy control group.

| Group | lncRNA | SEQ | p-value | FC | Group | lncRNA | SEQ | p-value | FC |
|---|---|---|---|---|---|---|---|---|---|
| DLB | lnc-CCNB1IP1-1:5 | SEQ4027 | 4.E-05 | 0.6 | MCI | lnc-SLC39A10-10:1 | SEQ3806 | 4.E-06 | 1.8 |
| MCI | lnc-CCNB1IP1-1:5 | SEQ4027 | 2.E-04 | 0.6 | DLB | lnc-SLC39A10-10:1 | SEQ3806 | 5.E-05 | 1.6 |
| All AD | lnc-CCNB1IP1-1:5 | SEQ4027 | 7.E-03 | 0.7 | miAD | lnc-SLC39A10-10:1 | SEQ3806 | 2.E-03 | 1.3 |
| miAD | lnc-CCNB1IP1-1:5 | SEQ4027 | 1.E-02 | 0.7 | All AD | lnc-SLC39A10-10:1 | SEQ3806 | 4.E-03 | 1.2 |
| msAD | lnc-CCNB1IP1-1:5 | SEQ4027 | 2.E-02 | 0.7 | msAD | lnc-SLC39A10-10:1 | SEQ3806 | 4.E-02 | 1.2 |
| FTD | lnc-CCNYL1-2:1 | SEQ5810 | 1.E-06 | 0.3 | FTD | lnc-SLC39A10-3:1 | SEQ3934 | 1.E-08 | 0.5 |
| MCI | lnc-CCNYL1-2:1 | SEQ5810 | 5.E-05 | 0.3 | MCI | lnc-SLC39A10-3:1 | SEQ3934 | 4.E-04 | 0.7 |
| FTD | lnc-CCNYL1-2:2 | SEQ4344 | 2.E-05 | 0.6 | All AD | lnc-SLC39A10-3:1 | SEQ3934 | 1.E-02 | 0.7 |
| All AD | lnc-CCNYL1-2:2 | SEQ4344 | 3.E-02 | 0.7 | msAD | lnc-SLC39A10-3:1 | SEQ3934 | 3.E-02 | 0.7 |
| DLB | lnc-CCT4-1:8 | SEQ3356 | 2.E-03 | 1.9 | miAD | lnc-SLC45A1-1:7 | SEQ4103 | 1.E-02 | 0.6 |
| miAD | lnc-CCT8-6:4 | SEQ4292 | 7.E-03 | 0.6 | All AD | lnc-SLC45A1-1:7 | SEQ4103 | 2.E-02 | 0.7 |
| All AD | lnc-CCT8-6:4 | SEQ4292 | 2.E-02 | 0.6 | All AD | lnc-SLC48A1-1:8 | SEQ3648 | 2.E-02 | 0.7 |
| miAD | lnc-CD300C-2:1 | SEQ4256 | 9.E-03 | 0.5 | msAD | lnc-SLC48A1-1:8 | SEQ3648 | 5.E-02 | 0.7 |
| All AD | lnc-CD300C-2:1 | SEQ4256 | 2.E-02 | 0.5 | DLB | lnc-SLC4A11-1:1 | SEQ5515 | 2.E-04 | 1.4 |
| DLB | lnc-CD3D-3:1 | SEQ4140 | 6.E-04 | 1.8 | DLB | lnc-SLC6A18-2:1 | SEQ4175 | 8.E-05 | 2.5 |
| MCI | lnc-CD3D-3:1 | SEQ4140 | 7.E-04 | 1.6 | All AD | lnc-SLC6A18-2:1 | SEQ4175 | 8.E-03 | 1.4 |
| miAD | lnc-CD3D-3:1 | SEQ4140 | 1.E-02 | 1.2 | msAD | lnc-SLC6A18-2:1 | SEQ4175 | 1.E-02 | 1.5 |
| FTD | lnc-CD47-8:1 | SEQ5884 | 3.E-05 | 0.5 | DLB | lnc-SLC6A9-6:1 | SEQ5663 | 1.E-04 | 1.7 |
| FTD | lnc-CD53-1:1 | SEQ5092 | 6.E-04 | 0.7 | All AD | lnc-SLC6A9-6:1 | SEQ5663 | 4.E-02 | 1.2 |
| DLB | lnc-CDC42-2:1 | SEQ4880 | 9.E-04 | 2.2 | DLB | lnc-SLC9A3-1:3 | SEQ5148 | 6.E-04 | 2.1 |
| DLB | lnc-CDC42BPB-4:3 | SEQ4486 | 2.E-03 | 1.4 | All AD | lnc-SLC9A3-1:3 | SEQ5148 | 4.E-02 | 1.3 |
| DLB | lnc-CDC42SE2-1:10 | SEQ2613 | 1.E-04 | 1.6 | DLB | lnc-SLC9A6-1:2 | SEQ4755 | 2.E-04 | 1.5 |
| MCI | lnc-CDC42SE2-1:10 | SEQ2613 | 7.E-04 | 1.5 | MCI | lnc-SLC9A6-1:2 | SEQ4755 | 1.E-03 | 1.4 |
| DLB | lnc-CDC42SE2-1:3 | SEQ4652 | 1.E-04 | 2.1 | All AD | lnc-SLC9A8-3:4 | SEQ5665 | 2.E-02 | 0.6 |
| MCI | lnc-CDC42SE2-1:3 | SEQ4652 | 1.E-03 | 1.8 | miAD | lnc-SLC9A8-3:5 | SEQ4190 | 1.E-02 | 0.7 |
| FTD | lnc-CDC73-5:1 | SEQ5969 | 4.E-06 | 0.6 | FTD | lnc-SLCO4C1-5:1 | SEQ3971 | 8.E-08 | 0.4 |
| DLB | lnc-CDC73-6:2 | SEQ4609 | 1.E-03 | 1.3 | miAD | lnc-SLCO4C1-5:1 | SEQ3971 | 5.E-04 | 0.5 |
| miAD | lnc-CDCA2-4:1 | SEQ3166 | 7.E-03 | 0.7 | MCI | lnc-SLCO4C1-5:1 | SEQ3971 | 9.E-04 | 0.5 |
| All AD | lnc-CDCA2-4:1 | SEQ3166 | 2.E-02 | 0.7 | All AD | lnc-SLCO4C1-5:1 | SEQ3971 | 2.E-03 | 0.6 |
| FTD | lnc-CDH26-9:1 | SEQ5746 | 9.E-05 | 0.7 | msAD | lnc-SLCO4C1-5:1 | SEQ3971 | 2.E-02 | 0.6 |
| All AD | lnc-CDHR3-7:1 | SEQ4352 | 5.E-02 | 0.7 | FTD | lnc-SLCO6A1-3:1 | SEQ5678 | 1.E-04 | 0.4 |
| DLB | lnc-CDIPT-1:11 | SEQ3359 | 2.E-03 | 1.4 | FTD | lnc-SLF1-4:2 | SEQ4985 | 8.E-06 | 0.5 |
| msAD | lnc-CDIPT-1:9 | SEQ3716 | 4.E-02 | 1.2 | miAD | lnc-SLF1-4:2 | SEQ4985 | 8.E-05 | 0.5 |
| FTD | lnc-CDIPT-2:1 | SEQ4354 | 8.E-08 | 1.5 | All AD | lnc-SLF1-4:2 | SEQ4985 | 5.E-03 | 0.6 |
| DLB | lnc-CDIPT-2:1 | SEQ4354 | 2.E-07 | 1.9 | FTD | lnc-SLF1-7:1 | SEQ3722 | 1.E-03 | 0.6 |
| MCI | lnc-CDIPT-2:1 | SEQ4354 | 6.E-07 | 1.7 | All AD | lnc-SLF1-7:1 | SEQ3722 | 1.E-02 | 0.8 |
| All AD | lnc-CDIPT-2:1 | SEQ4354 | 1.E-04 | 1.3 | miAD | lnc-SLF1-7:1 | SEQ3722 | 1.E-02 | 0.7 |
| msAD | lnc-CDIPT-2:1 | SEQ4354 | 2.E-04 | 1.3 | msAD | lnc-SLF1-7:1 | SEQ3722 | 4.E-02 | 0.8 |
| miAD | lnc-CDIPT-2:1 | SEQ4354 | 8.E-04 | 1.3 | DLB | lnc-SLFN12-1:1 | SEQ5272 | 5.E-04 | 1.7 |
| DLB | lnc-CDIPT-3:1 | SEQ3833 | 3.E-05 | 1.6 | DLB | lnc-SLFN14-2:1 | SEQ4717 | 2.E-04 | 1.9 |
| MCI | lnc-CDIPT-3:1 | SEQ3833 | 8.E-05 | 1.5 | MCI | lnc-SLFN14-2:1 | SEQ4717 | 1.E-03 | 1.7 |
| All AD | lnc-CDIPT-3:1 | SEQ3833 | 1.E-02 | 1.2 | FTD | lnc-SLTM-1:2 | SEQ0982 | 2.E-05 | 0.5 |
| msAD | lnc-CDIPT-3:1 | SEQ3833 | 3.E-02 | 1.2 | MCI | lnc-SLTM-1:2 | SEQ0982 | 3.E-04 | 0.6 |
| FTD | lnc-CDK19-4:1 | SEQ4090 | 7.E-05 | 0.6 | All AD | lnc-SLTM-1:2 | SEQ0982 | 5.E-02 | 0.8 |
| miAD | lnc-CDK19-4:1 | SEQ4090 | 2.E-03 | 0.6 | MCI | lnc-SMARCC2-3:2 | SEQ4314 | 6.E-06 | 1.7 |
| All AD | lnc-CDK19-4:1 | SEQ4090 | 3.E-03 | 0.7 | DLB | lnc-SMARCC2-3:2 | SEQ4314 | 3.E-05 | 1.6 |
| msAD | lnc-CDK19-4:1 | SEQ4090 | 1.E-02 | 0.8 | FTD | lnc-SMARCC2-3:2 | SEQ4314 | 1.E-04 | 1.5 |
| FTD | lnc-CDK2AP1-1:10 | SEQ4667 | 1.E-05 | 0.4 | All AD | lnc-SMARCC2-3:2 | SEQ4314 | 3.E-03 | 1.2 |
| MCI | lnc-CDK2AP1-1:10 | SEQ4667 | 1.E-03 | 0.5 | msAD | lnc-SMARCC2-3:2 | SEQ4314 | 6.E-03 | 1.3 |
| DLB | lnc-CDK2AP1-1:9 | SEQ3361 | 1.E-03 | 1.4 | miAD | lnc-SMARCC2-3:2 | SEQ4314 | 7.E-03 | 1.2 |
| FTD | lnc-CDNF-2:3 | SEQ4361 | 2.E-06 | 0.4 | DLB | lnc-SMARCC2-9:1 | SEQ4833 | 9.E-04 | 1.4 |
| MCI | lnc-CDNF-2:3 | SEQ4361 | 5.E-04 | 0.6 | MCI | lnc-SMC5-6:1 | SEQ2686 | 4.E-04 | 2.0 |
| All AD | lnc-CDNF-2:3 | SEQ4361 | 4.E-02 | 0.7 | FTD | lnc-SMCO1-2:2 | SEQ5398 | 3.E-04 | 0.6 |
| DLB | lnc-CDPF1-2:1 | SEQ4059 | 5.E-04 | 1.5 | All AD | lnc-SMCO1-2:2 | SEQ5398 | 2.E-02 | 0.7 |
| msAD | lnc-CDPF1-2:1 | SEQ4059 | 2.E-02 | 1.3 | MCI | lnc-SMCO4-3:1 | SEQ4543 | 2.E-03 | 0.6 |
| All AD | lnc-CDPF1-2:1 | SEQ4059 | 4.E-02 | 1.2 | DLB | lnc-SMCR8-1:1 | SEQ4498 | 8.E-05 | 1.5 |
| msAD | lnc-CDR2-1:4 | SEQ3808 | 4.E-02 | 1.3 | MCI | lnc-SMCR8-1:1 | SEQ4498 | 2.E-03 | 1.4 |
| DLB | lnc-CDR2-4:2 | SEQ5484 | 2.E-04 | 1.5 | FTD | lnc-SMG1-3:1 | SEQ3506 | 3.E-04 | 0.7 |
| DLB | lnc-CDS2-2:1 | SEQ4741 | 1.E-04 | 1.5 | MCI | lnc-SMIM11B-11:1 | SEQ3891 | 6.E-07 | 2.8 |
| MCI | lnc-CDS2-2:1 | SEQ4741 | 1.E-03 | 1.4 | DLB | lnc-SMIM11B-11:1 | SEQ3891 | 1.E-06 | 2.5 |
| FTD | lnc-CEACAM20-2:5 | SEQ5360 | 4.E-04 | 0.7 | FTD | lnc-SMIM11B-11:1 | SEQ3891 | 2.E-05 | 2.2 |
| MCI | lnc-CEBPB-13:10 | SEQ4547 | 2.E-03 | 0.6 | All AD | lnc-SMIM11B-11:1 | SEQ3891 | 9.E-03 | 1.4 |
| DLB | lnc-CEL-5:2 | SEQ3132 | 1.E-03 | 1.7 | miAD | lnc-SMIM11B-11:1 | SEQ3891 | 1.E-02 | 1.4 |
| MCI | lnc-CEMP1-1:1 | SEQ5146 | 3.E-04 | 2.1 | msAD | lnc-SMIM11B-11:1 | SEQ3891 | 3.E-02 | 1.3 |
| DLB | lnc-CEMP1-1:1 | SEQ5146 | 6.E-04 | 1.9 | miAD | lnc-SMIM13-5:1 | SEQ4279 | 8.E-03 | 0.8 |
| MCI | lnc-CEMP1-1:2 | SEQ5799 | 6.E-05 | 2.0 | All AD | lnc-SMIM13-5:1 | SEQ4279 | 2.E-02 | 0.8 |
| DLB | lnc-CEMP1-1:6 | SEQ4620 | 1.E-03 | 1.4 | msAD | lnc-SMTNL2-4:1 | SEQ3997 | 2.E-02 | 2.6 |
| DLB | lnc-CEMP1-1:7 | SEQ4876 | 9.E-04 | 2.0 | All AD | lnc-SMTNL2-4:1 | SEQ3997 | 3.E-02 | 2.2 |
| DLB | lnc-CEMP1-10:1 | SEQ4839 | 9.E-04 | 1.4 | DLB | lnc-SNAP47-2:1 | SEQ5143 | 2.E-04 | 2.1 |
| DLB | lnc-CEMP1-5:1 | SEQ3365 | 4.E-05 | 1.6 | MCI | lnc-SNAP47-2:1 | SEQ5143 | 6.E-04 | 1.8 |
| MCI | lnc-CEMP1-5:1 | SEQ3365 | 6.E-04 | 1.6 | FTD | lnc-SNAPC1-4:1 | SEQ5682 | 3.E-07 | 0.5 |
| All AD | lnc-CENPB-3:1 | SEQ4367 | 3.E-02 | 0.7 | All AD | lnc-SNAPC1-4:1 | SEQ5682 | 5.E-02 | 0.7 |
| All AD | lnc-CENPB-3:2 | SEQ4368 | 3.E-02 | 0.7 | DLB | lnc-SNAPC2-2:3 | SEQ4933 | 5.E-04 | 1.5 |
| DLB | lnc-CENPBD1-2:8 | SEQ4696 | 3.E-04 | 1.5 | MCI | lnc-SNAPC2-2:3 | SEQ4933 | 8.E-04 | 1.4 |

TABLE 10-continued 2847 whole blood (Paxgene RNA tube) lncRNAs differentially expressed in
MCI group or mild AD group or moderate-to-severe AD group or both of these
AD groups or FTD group or DLB group as compared to healthy control group.

| Group | lncRNA | SEQ | p-value | FC | Group | lncRNA | SEQ | p-value | FC |
|---|---|---|---|---|---|---|---|---|---|
| MCI | lnc-CENPBD1-2:8 | SEQ4696 | 1.E-03 | 1.4 | DLB | lnc-SNAPC5-1:2 | SEQ3920 | 5.E-04 | 1.6 |
| FTD | lnc-CENPT-1:5 | SEQ4369 | 3.E-07 | 2.3 | msAD | lnc-SNAPC5-1:2 | SEQ3920 | 3.E-02 | 1.3 |
| MCI | lnc-CENPT-1:5 | SEQ4369 | 4.E-06 | 2.5 | All AD | lnc-SNAPC5-1:2 | SEQ3920 | 4.E-02 | 1.2 |
| DLB | lnc-CENPT-1:5 | SEQ4369 | 1.E-05 | 2.0 | MCI | lnc-SNF8-1:3 | SEQ5169 | 5.E-04 | 0.8 |
| All AD | lnc-CENPT-1:5 | SEQ4369 | 9.E-04 | 1.3 | msAD | lnc-SNPH-5:1 | SEQ4233 | 1.E-02 | 2.4 |
| msAD | lnc-CENPT-1:5 | SEQ4369 | 2.E-03 | 1.3 | All AD | lnc-SNPH-5:1 | SEQ4233 | 3.E-02 | 1.7 |
| miAD | lnc-CENPT-1:5 | SEQ4369 | 2.E-03 | 1.3 | FTD | lnc-SNPH-6:5 | SEQ4544 | 3.E-06 | 0.6 |
| MCI | lnc-CENPT-1:6 | SEQ5048 | 2.E-04 | 1.8 | MCI | lnc-SNPH-6:5 | SEQ4544 | 2.E-03 | 0.6 |
| DLB | lnc-CENPT-1:6 | SEQ5048 | 7.E-04 | 1.8 | DLB | lnc-SNRPC-2:6 | SEQ3685 | 7.E-06 | 2.0 |
| All AD | lnc-CENPU-1:1 | SEQ4373 | 3.E-02 | 0.7 | MCI | lnc-SNRPC-2:6 | SEQ3685 | 2.E-05 | 1.8 |
| DLB | lnc-CENPVL2-3:1 | SEQ2389 | 2.E-03 | 1.6 | FTD | lnc-SNRPC-2:6 | SEQ3685 | 2.E-04 | 1.6 |
| DLB | lnc-CEP19-1:2 | SEQ5673 | 1.E-04 | 1.7 | All AD | lnc-SNRPC-2:6 | SEQ3685 | 1.E-02 | 1.2 |
| All AD | lnc-CEP350-3:4 | SEQ4375 | 4.E-02 | 0.8 | msAD | lnc-SNRPC-2:6 | SEQ3685 | 5.E-02 | 1.2 |
| FTD | lnc-CEP83-7:1 | SEQ3010 | 5.E-04 | 0.6 | FTD | lnc-SNRPN-8:18 | SEQ5060 | 7.E-04 | 0.6 |
| FTD | lnc-CERKL-7:1 | SEQ5970 | 4.E-06 | 0.6 | MCI | lnc-SNRPN-8:44 | SEQ4445 | 2.E-03 | 1.6 |
| DLB | lnc-CETP-2:2 | SEQ5324 | 4.E-04 | 1.6 | DLB | lnc-SNRPN-8:44 | SEQ4445 | 2.E-03 | 1.8 |
| FTD | lnc-CFAP36-3:10 | SEQ5826 | 5.E-05 | 0.4 | MCI | lnc-SNRPN-8:7 | SEQ5640 | 2.E-04 | 2.8 |
| FTD | lnc-CFAP36-3:2 | SEQ0786 | 7.E-04 | 0.6 | FTD | lnc-SNRPN-8:85 | SEQ5091 | 6.E-04 | 0.7 |
| DLB | lnc-CFAP36-3:3 | SEQ4977 | 8.E-04 | 1.8 | MCI | lnc-SNRPN-8:92 | SEQ5103 | 6.E-04 | 0.6 |
| DLB | lnc-CFAP36-3:4 | SEQ5451 | 3.E-04 | 1.7 | DLB | lnc-SNTG2-4:3 | SEQ4961 | 8.E-04 | 1.6 |
| miAD | lnc-CFLAR-1:4 | SEQ4116 | 1.E-02 | 0.7 | FTD | lnc-SNX11-2:1 | SEQ5679 | 1.E-04 | 0.5 |
| All AD | lnc-CFLAR-1:4 | SEQ4116 | 2.E-02 | 0.8 | FTD | lnc-SNX11-2:2 | SEQ5403 | 3.E-04 | 0.5 |
| DLB | lnc-CGA-2:2 | SEQ4437 | 2.E-03 | 1.5 | DLB | lnc-SNX2-1:2 | SEQ4824 | 3.E-06 | 0.4 |
| FTD | lnc-CGREF1-2:1 | SEQ2472 | 4.E-08 | 0.6 | MCI | lnc-SNX2-1:2 | SEQ4824 | 9.E-04 | 0.5 |
| MCI | lnc-CGREF1-2:1 | SEQ2472 | 5.E-05 | 0.7 | All AD | lnc-SNX33-6:1 | SEQ5691 | 3.E-02 | 1.2 |
| DLB | lnc-CGREF1-2:1 | SEQ2472 | 4.E-04 | 0.8 | FTD | lnc-SNX7-11:1 | SEQ4115 | 1.E-05 | 0.5 |
| DLB | lnc-CHADL-1:7 | SEQ5196 | 5.E-04 | 1.6 | All AD | lnc-SNX7-11:1 | SEQ4115 | 3.E-03 | 0.7 |
| FTD | lnc-CHIC2-2:1 | SEQ5765 | 8.E-05 | 0.7 | miAD | lnc-SNX7-11:1 | SEQ4115 | 3.E-03 | 0.6 |
| FTD | lnc-CHN2-5:1 | SEQ3761 | 6.E-06 | 0.6 | msAD | lnc-SNX7-11:1 | SEQ4115 | 1.E-02 | 0.7 |
| miAD | lnc-CHN2-5:1 | SEQ3761 | 1.E-03 | 0.6 | DLB | lnc-SNX8-1:1 | SEQ4465 | 7.E-06 | 2.1 |
| All AD | lnc-CHN2-5:1 | SEQ3761 | 3.E-03 | 0.7 | MCI | lnc-SNX8-1:1 | SEQ4465 | 7.E-04 | 1.6 |
| msAD | lnc-CHN2-5:1 | SEQ3761 | 4.E-02 | 0.7 | msAD | lnc-SNX8-1:1 | SEQ4465 | 2.E-03 | 1.3 |
| DLB | lnc-CHRAC1-6:1 | SEQ0420 | 4.E-04 | 1.7 | All AD | lnc-SNX8-1:1 | SEQ4465 | 1.E-02 | 1.2 |
| MCI | lnc-CHRAC1-6:1 | SEQ0420 | 1.E-03 | 1.6 | MCI | lnc-SOCS3-3:1 | SEQ5667 | 1.E-04 | 1.7 |
| MCI | lnc-CHRDL2-3:1 | SEQ4264 | 1.E-05 | 3.0 | FTD | lnc-SOCS6-10:1 | SEQ2214 | 2.E-04 | 0.5 |
| FTD | lnc-CHRDL2-3:1 | SEQ4264 | 2.E-03 | 2.4 | All AD | lnc-SOCS6-10:1 | SEQ2214 | 2.E-03 | 0.7 |
| miAD | lnc-CHRDL2-3:1 | SEQ4264 | 9.E-03 | 1.4 | msAD | lnc-SOCS6-10:1 | SEQ2214 | 2.E-03 | 0.7 |
| All AD | lnc-CHRDL2-3:1 | SEQ4264 | 2.E-02 | 1.3 | miAD | lnc-SOCS6-10:1 | SEQ2214 | 1.E-02 | 0.7 |
| miAD | lnc-CHRNA9-2:1 | SEQ4275 | 8.E-03 | 0.6 | FTD | lnc-SOWAHB-6:1 | SEQ5688 | 1.E-04 | 0.6 |
| All AD | lnc-CHRNA9-2:1 | SEQ4275 | 2.E-02 | 0.7 | DLB | lnc-SOX15-1:6 | SEQ5525 | 2.E-04 | 1.5 |
| msAD | lnc-CHRNE-3:3 | SEQ4054 | 2.E-02 | 1.5 | DLB | lnc-SP110-8:1 | SEQ5578 | 2.E-04 | 1.7 |
| All AD | lnc-CHRNE-3:3 | SEQ4054 | 2.E-02 | 1.4 | FTD | lnc-SP110-8:4 | SEQ3913 | 8.E-08 | 0.5 |
| All AD | lnc-CHST3-1:1 | SEQ3822 | 1.E-02 | 1.3 | MCI | lnc-SP110-8:4 | SEQ3913 | 5.E-05 | 0.6 |
| miAD | lnc-CHST3-1:1 | SEQ3822 | 1.E-02 | 1.3 | All AD | lnc-SP110-8:4 | SEQ3913 | 2.E-02 | 0.7 |
| msAD | lnc-CHST3-1:1 | SEQ3822 | 4.E-02 | 1.2 | msAD | lnc-SP110-8:4 | SEQ3913 | 3.E-02 | 0.7 |
| DLB | lnc-CIB3-1:1 | SEQ5176 | 5.E-04 | 1.4 | All AD | lnc-SP110-8:5 | SEQ3738 | 2.E-02 | 0.7 |
| DLB | lnc-CIB3-1:2 | SEQ2750 | 5.E-04 | 1.3 | msAD | lnc-SP110-8:5 | SEQ3738 | 4.E-02 | 0.7 |
| DLB | lnc-CIB3-1:3 | SEQ5179 | 5.E-04 | 1.4 | FTD | lnc-SP110-9:1 | SEQ5228 | 5.E-04 | 0.6 |
| FTD | lnc-CISD2-1:2 | SEQ4031 | 1.E-04 | 0.6 | All AD | lnc-SP140-3:4 | SEQ3575 | 4.E-02 | 0.8 |
| All AD | lnc-CISD2-1:2 | SEQ4031 | 7.E-03 | 0.7 | DLB | lnc-SP140-3:7 | SEQ5250 | 5.E-04 | 1.5 |
| miAD | lnc-CISD2-1:2 | SEQ4031 | 1.E-02 | 0.7 | miAD | lnc-SP9-13:4 | SEQ4245 | 9.E-03 | 0.6 |
| msAD | lnc-CISD2-1:2 | SEQ4031 | 2.E-02 | 0.7 | miAD | lnc-SP9-8:1 | SEQ4209 | 1.E-02 | 0.7 |
| FTD | lnc-CISD2-1:3 | SEQ3366 | 4.E-04 | 1.4 | FTD | lnc-SPACA5-1:1 | SEQ5830 | 5.E-05 | 0.6 |
| MCI | lnc-CISD2-1:3 | SEQ3366 | 5.E-04 | 1.3 | miAD | lnc-SPAG1-7:1 | SEQ4333 | 1.E-04 | 1.3 |
| DLB | lnc-CISD2-11:1 | SEQ3654 | 5.E-05 | 1.6 | All AD | lnc-SPAG1-7:1 | SEQ4333 | 4.E-04 | 1.3 |
| MCI | lnc-CISD2-11:1 | SEQ3654 | 2.E-03 | 1.5 | msAD | lnc-SPAG1-7:1 | SEQ4333 | 6.E-03 | 1.2 |
| msAD | lnc-CISD2-11:1 | SEQ3654 | 5.E-02 | 1.2 | DLB | lnc-SPATA21-3:1 | SEQ3769 | 6.E-05 | 1.5 |
| DLB | lnc-CKB-1:1 | SEQ4952 | 8.E-04 | 1.5 | msAD | lnc-SPATA21-3:1 | SEQ3769 | 4.E-02 | 1.1 |
| DLB | lnc-CKS1B-2:2 | SEQ5479 | 2.E-04 | 1.4 | DLB | lnc-SPATA21-4:9 | SEQ5177 | 5.E-04 | 1.4 |
| MCI | lnc-CKS1B-3:1 | SEQ3367 | 3.E-06 | 1.7 | DLB | lnc-SPATA21-6:3 | SEQ2824 | 2.E-04 | 1.6 |
| DLB | lnc-CKS1B-3:1 | SEQ3367 | 1.E-03 | 1.6 | All AD | lnc-SPATA31A1-3:1 | SEQ5702 | 4.E-02 | 0.7 |
| All AD | lnc-CKS1B-3:1 | SEQ3367 | 4.E-02 | 1.1 | MCI | lnc-SPATA32-1:1 | SEQ4779 | 1.E-03 | 1.6 |
| MCI | lnc-CKS1B-3:3 | SEQ5798 | 6.E-05 | 1.9 | All AD | lnc-SPATA32-2:16 | SEQ4238 | 7.E-03 | 0.8 |
| FTD | lnc-CLASP2-1:2 | SEQ4047 | 7.E-07 | 1.5 | msAD | lnc-SPATA32-2:16 | SEQ4238 | 1.E-02 | 0.8 |
| DLB | lnc-CLASP2-1:2 | SEQ4047 | 1.E-06 | 1.7 | DLB | lnc-SPATA32-2:4 | SEQ3464 | 2.E-03 | 1.8 |
| MCI | lnc-CLASP2-1:2 | SEQ4047 | 5.E-05 | 1.6 | All AD | lnc-SPATA32-2:7 | SEQ5704 | 4.E-02 | 0.8 |
| All AD | lnc-CLASP2-1:2 | SEQ4047 | 1.E-02 | 1.2 | FTD | lnc-SPERT-4:1 | SEQ5777 | 7.E-05 | 0.6 |
| msAD | lnc-CLASP2-1:2 | SEQ4047 | 2.E-02 | 1.2 | miAD | lnc-SPOCK2-1:2 | SEQ3582 | 1.E-03 | 1.4 |
| FTD | lnc-CLDN10-7:1 | SEQ5913 | 2.E-06 | 0.5 | All AD | lnc-SPOCK2-1:2 | SEQ3582 | 2.E-03 | 1.3 |
| DLB | lnc-CLDN4-2:1 | SEQ5371 | 3.E-04 | 1.4 | msAD | lnc-SPOCK2-1:2 | SEQ3582 | 1.E-02 | 1.3 |
| DLB | lnc-CLEC16A-1:1 | SEQ4387 | 5.E-05 | 1.8 | miAD | lnc-SPON2-1:2 | SEQ2237 | 1.E-02 | 0.7 |
| MCI | lnc-CLEC16A-1:1 | SEQ4387 | 2.E-03 | 1.5 | All AD | lnc-SPON2-1:2 | SEQ2237 | 2.E-02 | 0.7 |
| All AD | lnc-CLEC16A-1:1 | SEQ4387 | 2.E-02 | 1.3 | MCI | lnc-SPOPL-10:1 | SEQ2567 | 8.E-05 | 0.4 |
| DLB | lnc-CLEC18B-5:1 | SEQ2878 | 2.E-03 | 1.5 | DLB | lnc-SPOPL-10:1 | SEQ2567 | 8.E-04 | 0.4 |

TABLE 10-continued 2847 whole blood (Paxgene RNA tube) lncRNAs differentially expressed in
MCI group or mild AD group or moderate-to-severe AD group or both of these
AD groups or FTD group or DLB group as compared to healthy control group.

| Group | lncRNA | SEQ | p-value | FC | Group | lncRNA | SEQ | p-value | FC |
|---|---|---|---|---|---|---|---|---|---|
| miAD | lnc-CLEC2D-8:4 | SEQ4386 | 2.E-03 | 0.3 | FTD | lnc-SPOPL-2:3 | SEQ4138 | 8.E-04 | 0.6 |
| DLB | lnc-CLEC2D-8:7 | SEQ3369 | 3.E-04 | 1.6 | miAD | lnc-SPOPL-2:3 | SEQ4138 | 1.E-02 | 0.8 |
| MCI | lnc-CLEC2D-8:7 | SEQ3369 | 1.E-03 | 1.5 | All AD | lnc-SPOPL-2:3 | SEQ4138 | 2.E-02 | 0.8 |
| All AD | lnc-CLEC2D-8:7 | SEQ3369 | 4.E-03 | 1.3 | FTD | lnc-SPOPL-2:4 | SEQ5101 | 4.E-08 | 0.3 |
| msAD | lnc-CLEC2D-8:7 | SEQ3369 | 5.E-03 | 1.3 | miAD | lnc-SPOPL-2:4 | SEQ5101 | 3.E-04 | 0.4 |
| FTD | lnc-CLEC3A-2:2 | SEQ4802 | 1.E-03 | 0.5 | MCI | lnc-SPOPL-2:4 | SEQ5101 | 6.E-04 | 0.5 |
| FTD | lnc-CLIC6-5:1 | SEQ5544 | 2.E-04 | 0.6 | All AD | lnc-SPOPL-2:4 | SEQ5101 | 9.E-04 | 0.5 |
| All AD | lnc-CLK3-1:1 | SEQ4389 | 4.E-02 | 1.1 | FTD | lnc-SPPL2A-2:1 | SEQ4363 | 2.E-09 | 0.5 |
| DLB | lnc-CLLU1-2:1 | SEQ4390 | 2.E-03 | 1.2 | MCI | lnc-SPPL2A-2:1 | SEQ4363 | 3.E-06 | 0.5 |
| All AD | lnc-CLLU1-2:1 | SEQ4390 | 4.E-02 | 1.1 | All AD | lnc-SPPL2A-2:1 | SEQ4363 | 1.E-03 | 0.7 |
| msAD | lnc-CLLU1-2:2 | SEQ4016 | 2.E-02 | 1.4 | miAD | lnc-SPPL2A-2:1 | SEQ4363 | 2.E-03 | 0.7 |
| All AD | lnc-CLLU1-2:2 | SEQ4016 | 5.E-02 | 1.2 | msAD | lnc-SPPL2A-2:1 | SEQ4363 | 4.E-03 | 0.7 |
| All AD | lnc-CLSPN-2:1 | SEQ4392 | 4.E-02 | 0.8 | DLB | lnc-SPPL3-2:1 | SEQ5246 | 5.E-04 | 1.4 |
| DLB | lnc-CLUAP1-1:2 | SEQ4705 | 1.E-03 | 1.5 | DLB | lnc-SPPL3-3:1 | SEQ5726 | 9.E-05 | 1.4 |
| DLB | lnc-CLUAP1-8:2 | SEQ5247 | 6.E-05 | 1.5 | DLB | lnc-SPPL3-4:1 | SEQ4776 | 3.E-04 | 1.7 |
| MCI | lnc-CLUAP1-8:2 | SEQ5247 | 5.E-04 | 1.4 | MCI | lnc-SPPL3-4:1 | SEQ4776 | 1.E-03 | 1.6 |
| DLB | lnc-CLUAP1-9:1 | SEQ5428 | 3.E-04 | 1.4 | FTD | lnc-SPRTN-2:1 | SEQ4204 | 6.E-08 | 0.5 |
| FTD | lnc-CLUH-2:1 | SEQ4815 | 1.E-03 | 0.8 | miAD | lnc-SPRTN-2:1 | SEQ4204 | 1.E-03 | 0.6 |
| DLB | lnc-CMTM3-1:1 | SEQ2789 | 4.E-04 | 1.3 | MCI | lnc-SPRTN-2:1 | SEQ4204 | 1.E-03 | 0.6 |
| DLB | lnc-CMTM4-5:1 | SEQ5706 | 1.E-04 | 1.8 | All AD | lnc-SPRTN-2:1 | SEQ4204 | 2.E-03 | 0.6 |
| DLB | lnc-CMTM7-2:1 | SEQ3789 | 9.E-04 | 1.3 | msAD | lnc-SPRTN-2:1 | SEQ4204 | 1.E-02 | 0.6 |
| msAD | lnc-CMTM7-2:1 | SEQ3789 | 4.E-02 | 1.2 | DLB | lnc-SPRYD3-1:12 | SEQ3876 | 2.E-05 | 2.2 |
| FTD | lnc-CMTR1-10:1 | SEQ0788 | 4.E-09 | 0.4 | MCI | lnc-SPRYD3-1:12 | SEQ3876 | 3.E-05 | 2.0 |
| MCI | lnc-CMTR1-10:1 | SEQ0788 | 7.E-04 | 0.6 | FTD | lnc-SPRYD3-1:12 | SEQ3876 | 2.E-04 | 1.6 |
| miAD | lnc-CMTR1-10:1 | SEQ0788 | 1.E-02 | 0.5 | All AD | lnc-SPRYD3-1:12 | SEQ3876 | 9.E-03 | 1.3 |
| All AD | lnc-CMTR1-10:1 | SEQ0788 | 2.E-02 | 0.6 | miAD | lnc-SPRYD3-1:12 | SEQ3876 | 1.E-02 | 1.3 |
| DLB | lnc-CNN1-6:1 | SEQ5036 | 9.E-05 | 1.7 | msAD | lnc-SPRYD3-1:12 | SEQ3876 | 3.E-02 | 1.3 |
| MCI | lnc-CNN1-6:1 | SEQ5036 | 7.E-04 | 1.5 | DLB | lnc-SPRYD3-1:8 | SEQ4196 | 7.E-04 | 1.5 |
| DLB | lnc-CNP-1:1 | SEQ3058 | 6.E-04 | 1.5 | miAD | lnc-SPRYD3-1:8 | SEQ4196 | 1.E-02 | 1.3 |
| FTD | lnc-CNTNAP3B-10:1 | SEQ4987 | 8.E-04 | 0.4 | All AD | lnc-SPRYD3-1:8 | SEQ4196 | 3.E-02 | 1.2 |
| msAD | lnc-CNTRL-6:6 | SEQ3795 | 4.E-02 | 1.6 | DLB | lnc-SPTBN4-1:5 | SEQ3774 | 3.E-04 | 1.6 |
| DLB | lnc-COA6-4:1 | SEQ4752 | 3.E-05 | 1.5 | All AD | lnc-SPTBN4-1:5 | SEQ3774 | 3.E-02 | 1.2 |
| MCI | lnc-COA6-4:1 | SEQ4752 | 1.E-03 | 1.4 | msAD | lnc-SPTBN4-1:5 | SEQ3774 | 4.E-02 | 1.2 |
| DLB | lnc-COG7-1:1 | SEQ4630 | 1.E-03 | 1.5 | MCI | lnc-SQSTM1-2:3 | SEQ4572 | 4.E-04 | 1.7 |
| DLB | lnc-COG7-3:3 | SEQ5741 | 9.E-05 | 2.1 | DLB | lnc-SQSTM1-2:3 | SEQ4572 | 2.E-03 | 1.5 |
| DLB | lnc-COG8-2:1 | SEQ4580 | 8.E-05 | 1.7 | DLB | lnc-SQSTM1-4:1 | SEQ5526 | 2.E-04 | 1.5 |
| MCI | lnc-COG8-2:1 | SEQ4580 | 2.E-03 | 1.5 | FTD | lnc-SRD5A3-4:1 | SEQ5600 | 2.E-04 | 0.6 |
| All AD | lnc-COIL-7:1 | SEQ4411 | 4.E-02 | 0.8 | miAD | lnc-SRGN-4:1 | SEQ4157 | 1.E-02 | 0.8 |
| All AD | lnc-COPG1-2:3 | SEQ4412 | 3.E-02 | 0.7 | All AD | lnc-SRGN-4:1 | SEQ4157 | 3.E-02 | 0.8 |
| DLB | lnc-COPG1-1:3 | SEQ5135 | 6.E-04 | 1.7 | MCI | lnc-SRP54-1:2 | SEQ4762 | 1.E-03 | 1.5 |
| FTD | lnc-COPS5-2:1 | SEQ5834 | 5.E-05 | 0.7 | FTD | lnc-SRPK2-1:16 | SEQ5859 | 3.E-08 | 0.1 |
| DLB | lnc-COPS7A-4:3 | SEQ5655 | 1.E-04 | 1.4 | MCI | lnc-SRPK2-1:16 | SEQ5859 | 3.E-06 | 0.1 |
| msAD | lnc-COQ4-1:3 | SEQ3653 | 5.E-02 | 0.9 | DLB | lnc-SRPK2-1:16 | SEQ5859 | 4.E-05 | 0.1 |
| DLB | lnc-COQ9-1:1 | SEQ4440 | 2.E-03 | 1.6 | FTD | lnc-SRPK2-1:17 | SEQ4662 | 2.E-07 | 7.3 |
| MCI | lnc-COX19-2:1 | SEQ3091 | 8.E-05 | 2.1 | MCI | lnc-SRPK2-1:17 | SEQ4662 | 7.E-06 | 4.6 |
| DLB | lnc-COX19-2:1 | SEQ3091 | 5.E-04 | 1.8 | DLB | lnc-SRPK2-1:17 | SEQ4662 | 1.E-03 | 2.7 |
| DLB | lnc-COX4I1-6:1 | SEQ4446 | 2.E-03 | 1.6 | FTD | lnc-SRPK2-1:18 | SEQ5722 | 1.E-05 | 0.6 |
| miAD | lnc-COX6A2-5:1 | SEQ4280 | 8.E-05 | 0.8 | All AD | lnc-SRPK2-1:18 | SEQ5722 | 3.E-02 | 0.8 |
| All AD | lnc-COX6A2-5:1 | SEQ4280 | 2.E-02 | 0.8 | DLB | lnc-SRPK2-1:5 | SEQ4647 | 1.E-03 | 1.7 |
| MCI | lnc-COX7A2L-4:9 | SEQ4095 | 3.E-04 | 1.4 | FTD | lnc-SRPK2-1:7 | SEQ6004 | 5.E-08 | 0.2 |
| DLB | lnc-COX7A2L-4:9 | SEQ4095 | 8.E-04 | 1.5 | FTD | lnc-SRPK2-5:4 | SEQ5352 | 4.E-04 | 0.6 |
| All AD | lnc-COX7A2L-4:9 | SEQ4095 | 3.E-03 | 1.3 | FTD | lnc-SRPK2-6:1 | SEQ6012 | 2.E-10 | 0.3 |
| miAD | lnc-COX7A2L-4:9 | SEQ4095 | 3.E-03 | 1.3 | FTD | lnc-SRPK2-7:1 | SEQ5931 | 1.E-05 | 0.7 |
| msAD | lnc-COX7A2L-4:9 | SEQ4095 | 1.E-02 | 1.3 | FTD | lnc-SRPK2-8:1 | SEQ4380 | 7.E-06 | 0.4 |
| FTD | lnc-COX7B-4:2 | SEQ4421 | 1.E-04 | 0.6 | miAD | lnc-SRPK2-8:1 | SEQ4380 | 3.E-03 | 0.5 |
| All AD | lnc-COX7B-4:2 | SEQ4421 | 3.E-02 | 0.8 | DLB | lnc-SRRM2-1:2 | SEQ4244 | 5.E-04 | 2.1 |
| MCI | lnc-CPLX1-2:15 | SEQ5214 | 5.E-04 | 2.0 | FTD | lnc-SRRM2-1:2 | SEQ4244 | 7.E-04 | 2.1 |
| DLB | lnc-CPLX1-2:17 | SEQ5918 | 2.E-05 | 1.9 | All AD | lnc-SRRM2-1:2 | SEQ4244 | 9.E-03 | 1.5 |
| MCI | lnc-CPLX1-2:6 | SEQ5464 | 8.E-05 | 4.5 | msAD | lnc-SRRM2-1:2 | SEQ4244 | 1.E-02 | 1.5 |
| FTD | lnc-CPLX1-2:6 | SEQ5464 | 1.E-04 | 3.2 | MCI | lnc-SRSF12-2:1 | SEQ3670 | 1.E-06 | 1.8 |
| DLB | lnc-CPLX1-2:6 | SEQ5464 | 3.E-04 | 3.5 | DLB | lnc-SRSF12-2:1 | SEQ3670 | 3.E-04 | 1.8 |
| DLB | lnc-CPLX1-2:8 | SEQ2869 | 4.E-04 | 1.6 | FTD | lnc-SRSF12-2:1 | SEQ3670 | 6.E-04 | 1.4 |
| FTD | lnc-CPM-1:1 | SEQ3371 | 4.E-05 | 0.6 | miAD | lnc-SRSF12-2:1 | SEQ3670 | 4.E-03 | 1.1 |
| FTD | lnc-CPM-3:1 | SEQ0228 | 1.E-07 | 0.5 | All AD | lnc-SRSF12-2:1 | SEQ3670 | 8.E-03 | 1.1 |
| MCI | lnc-CPM-3:1 | SEQ0228 | 3.E-04 | 0.5 | msAD | lnc-SRSF12-2:1 | SEQ3670 | 5.E-02 | 1.1 |
| All AD | lnc-CPM-3:1 | SEQ0228 | 3.E-02 | 0.8 | DLB | lnc-SRSF2-1:1 | SEQ4861 | 9.E-04 | 1.5 |
| DLB | lnc-CPM-6:1 | SEQ5338 | 4.E-04 | 1.8 | MCI | lnc-SRSF2-10:1 | SEQ4626 | 2.E-04 | 1.5 |
| DLB | lnc-CPPED1-1:1 | SEQ3862 | 2.E-04 | 1.7 | DLB | lnc-SRSF2-10:1 | SEQ4626 | 1.E-03 | 1.4 |
| All AD | lnc-CPPED1-1:1 | SEQ3862 | 1.E-02 | 1.2 | DLB | lnc-SRSF2-9:1 | SEQ5120 | 6.E-04 | 1.5 |
| msAD | lnc-CPPED1-1:1 | SEQ3862 | 3.E-02 | 1.3 | MCI | lnc-SRSF2-9:2 | SEQ4935 | 2.E-04 | 1.6 |
| miAD | lnc-CPSF2-5:1 | SEQ4384 | 3.E-05 | 1.7 | DLB | lnc-SRSF2-9:2 | SEQ4935 | 8.E-04 | 1.4 |
| FTD | lnc-CPSF2-5:1 | SEQ4384 | 8.E-05 | 1.8 | DLB | lnc-SRY-11:1 | SEQ4418 | 2.E-03 | 1.4 |
| All AD | lnc-CPSF2-5:1 | SEQ4384 | 1.E-04 | 1.6 | DLB | lnc-SSBP4-2:1 | SEQ4638 | 1.E-03 | 1.5 |
| MCI | lnc-CPSF2-5:1 | SEQ4384 | 2.E-04 | 1.8 | All AD | lnc-SSH3-4:1 | SEQ5734 | 3.E-02 | 0.8 |

TABLE 10-continued 2847 whole blood (Paxgene RNA tube) lncRNAs differentially expressed in
MCI group or mild AD group or moderate-to-severe AD group or both of these
AD groups or FTD group or DLB group as compared to healthy control group.

| Group | lncRNA | SEQ | p-value | FC | Group | lncRNA | SEQ | p-value | FC |
|---|---|---|---|---|---|---|---|---|---|
| DLB | lnc-CPSF2-5:1 | SEQ4384 | 2.E-04 | 1.7 | DLB | lnc-SSH3-5:1 | SEQ2791 | 3.E-04 | 1.4 |
| msAD | lnc-CPSF2-5:1 | SEQ4384 | 3.E-03 | 1.4 | MCI | lnc-SSH3-5:1 | SEQ2791 | 7.E-04 | 1.3 |
| MCI | lnc-CRACR2A-5:2 | SEQ5302 | 2.E-04 | 1.6 | MCI | lnc-SSR2-1:4 | SEQ4922 | 8.E-03 | 0.7 |
| DLB | lnc-CRACR2A-5:2 | SEQ5302 | 3.E-04 | 1.6 | FTD | lnc-SSTR4-9:1 | SEQ4890 | 9.E-04 | 0.5 |
| FTD | lnc-CRACR2A-5:2 | SEQ5302 | 4.E-04 | 1.4 | DLB | lnc-ST3GAL2-1:1 | SEQ5310 | 4.E-04 | 1.4 |
| FTD | lnc-CRCP-1:1 | SEQ4805 | 1.E-03 | 0.6 | FTD | lnc-STARD8-3:1 | SEQ2647 | 2.E-04 | 0.7 |
| msAD | lnc-CREG1-3:1 | SEQ3949 | 3.E-02 | 1.2 | All AD | lnc-STARD8-3:1 | SEQ2647 | 1.E-02 | 0.8 |
| All AD | lnc-CREG1-3:1 | SEQ3949 | 3.E-02 | 1.2 | msAD | lnc-STARD8-3:1 | SEQ2647 | 3.E-02 | 0.8 |
| FTD | lnc-CRIPT-5:1 | SEQ5900 | 2.E-05 | 0.6 | FTD | lnc-STARD9-1:6 | SEQ5009 | 5.E-04 | 0.4 |
| DLB | lnc-CRLF1-1:2 | SEQ4674 | 1.E-03 | 1.3 | MCI | lnc-STARD9-1:6 | SEQ5009 | 7.E-04 | 0.4 |
| DLB | lnc-CRLF1-1:4 | SEQ4435 | 2.E-03 | 1.5 | FTD | lnc-STAT1-1:1 | SEQ5513 | 8.E-05 | 0.5 |
| FTD | lnc-CRYBA4-23:40 | SEQ4888 | 9.E-04 | 0.5 | MCI | lnc-STAT1-1:1 | SEQ5513 | 2.E-04 | 0.5 |
| FTD | lnc-CRYBB1-1:3 | SEQ4444 | 1.E-03 | 1.5 | All AD | lnc-STAT1-1:1 | SEQ5513 | 3.E-02 | 0.7 |
| All AD | lnc-CRYBB1-1:3 | SEQ4444 | 3.E-02 | 1.2 | DLB | lnc-STAT3-1:2 | SEQ4918 | 2.E-04 | 3.9 |
| DLB | lnc-CRYM-4:1 | SEQ2958 | 3.E-04 | 1.6 | FTD | lnc-STAT3-1:2 | SEQ4918 | 9.E-04 | 2.6 |
| FTD | lnc-CSNK1A1L-1:1 | SEQ3695 | 5.E-04 | 0.5 | FTD | lnc-STAT3-1:3 | SEQ3739 | 2.E-08 | 0.6 |
| miAD | lnc-CSNK1A1L-1:1 | SEQ3695 | 1.E-03 | 0.6 | All AD | lnc-STAT3-1:3 | SEQ3739 | 2.E-02 | 0.7 |
| All AD | lnc-CSNK1A1L-1:1 | SEQ3695 | 4.E-03 | 0.6 | msAD | lnc-STAT3-1:3 | SEQ3739 | 4.E-02 | 0.8 |
| msAD | lnc-CSNK1A1L-1:1 | SEQ3695 | 5.E-02 | 0.7 | FTD | lnc-STAU2-3:4 | SEQ3564 | 2.E-04 | 0.6 |
| FTD | lnc-CSNK1E-1:4 | SEQ4474 | 5.E-04 | 0.7 | miAD | lnc-STAU2-3:4 | SEQ3564 | 1.E-02 | 0.7 |
| MCI | lnc-CSNK1E-1:4 | SEQ4474 | 2.E-03 | 0.7 | All AD | lnc-STAU2-3:4 | SEQ3564 | 2.E-02 | 0.8 |
| DLB | lnc-CSNK1G2-4:2 | SEQ5529 | 5.E-05 | 1.7 | FTD | lnc-STEAP4-1:1 | SEQ3694 | 7.E-04 | 0.5 |
| MCI | lnc-CSNK1G2-4:2 | SEQ5529 | 2.E-04 | 1.6 | miAD | lnc-STEAP4-1:1 | SEQ3694 | 7.E-03 | 0.6 |
| FTD | lnc-CSPP1-1:5 | SEQ4452 | 4.E-05 | 1.8 | All AD | lnc-STEAP4-1:1 | SEQ3694 | 9.E-03 | 0.7 |
| MCI | lnc-CSPP1-1:5 | SEQ4452 | 4.E-05 | 1.8 | msAD | lnc-STEAP4-1:1 | SEQ3694 | 5.E-02 | 0.7 |
| DLB | lnc-CSPP1-1:5 | SEQ4452 | 1.E-04 | 1.8 | DLB | lnc-STK38-1:1 | SEQ5520 | 2.E-04 | 1.4 |
| All AD | lnc-CSPP1-1:5 | SEQ4452 | 4.E-02 | 1.2 | miAD | lnc-STK39-3:9 | SEQ3878 | 6.E-03 | 1.4 |
| FTD | lnc-CSRP2-1:1 | SEQ3936 | 5.E-04 | 0.7 | All AD | lnc-STK39-3:9 | SEQ3878 | 7.E-03 | 1.3 |
| miAD | lnc-CSRP2-1:1 | SEQ3936 | 2.E-03 | 0.7 | msAD | lnc-STK39-3:9 | SEQ3878 | 3.E-02 | 1.3 |
| All AD | lnc-CSRP2-1:1 | SEQ3936 | 3.E-03 | 0.7 | FTD | lnc-STK4-1:1 | SEQ5420 | 3.E-04 | 0.7 |
| msAD | lnc-CSRP2-1:1 | SEQ3936 | 3.E-02 | 0.8 | DLB | lnc-STOM-1:1 | SEQ4855 | 9.E-04 | 1.5 |
| DLB | lnc-CT47A1-1:1 | SEQ2504 | 4.E-06 | 1.6 | FTD | lnc-STON2-5:1 | SEQ3631 | 4.E-05 | 0.6 |
| FTD | lnc-CTAGE5-8:4 | SEQ4898 | 9.E-04 | 0.6 | MCI | lnc-STON2-5:1 | SEQ3631 | 3.E-04 | 0.6 |
| DLB | lnc-CTC1-2:8 | SEQ4631 | 7.E-04 | 1.5 | All AD | lnc-STON2-5:1 | SEQ3631 | 4.E-02 | 0.8 |
| MCI | lnc-CTC1-2:8 | SEQ4631 | 1.E-03 | 1.5 | FTD | lnc-STRN-1:1 | SEQ4399 | 1.E-06 | 0.6 |
| FTD | lnc-CTNNBIP1-1:1 | SEQ5155 | 5.E-04 | 0.6 | MCI | lnc-STRN-1:1 | SEQ4399 | 2.E-03 | 0.7 |
| DLB | lnc-CTNS-1:1 | SEQ2816 | 4.E-05 | 1.6 | DLB | lnc-STUB1-2:1 | SEQ5253 | 5.E-04 | 1.5 |
| msAD | lnc-CTNS-1:1 | SEQ2816 | 4.E-03 | 1.2 | DLB | lnc-STX10-2:1 | SEQ3470 | 9.E-06 | 1.6 |
| All AD | lnc-CTNS-1:1 | SEQ2816 | 9.E-03 | 1.1 | MCI | lnc-STX10-2:1 | SEQ3470 | 9.E-06 | 1.7 |
| All AD | lnc-CTSZ-2:11 | SEQ4037 | 1.E-02 | 1.4 | FTD | lnc-STX10-2:1 | SEQ3470 | 2.E-05 | 1.5 |
| msAD | lnc-CTSZ-2:11 | SEQ4037 | 2.E-02 | 1.4 | DLB | lnc-STX10-2:2 | SEQ4686 | 6.E-04 | 1.5 |
| FTD | lnc-CTSZ-7:1 | SEQ5690 | 3.E-07 | 0.5 | MCI | lnc-STX10-2:2 | SEQ4686 | 1.E-03 | 1.4 |
| MCI | lnc-CTSZ-7:1 | SEQ5690 | 1.E-04 | 0.6 | FTD | lnc-STX3-4:2 | SEQ4242 | 2.E-05 | 2.0 |
| DLB | lnc-CTU2-1:1 | SEQ5116 | 6.E-04 | 1.4 | DLB | lnc-STX3-4:2 | SEQ4242 | 4.E-05 | 2.2 |
| DLB | lnc-CTU2-3:2 | SEQ5540 | 2.E-04 | 2.0 | MCI | lnc-STX3-4:2 | SEQ4242 | 6.E-05 | 2.4 |
| MCI | lnc-CTU2-3:4 | SEQ5448 | 3.E-04 | 1.7 | All AD | lnc-STX3-4:2 | SEQ4242 | 2.E-03 | 1.5 |
| DLB | lnc-CTXN1-2:1 | SEQ5946 | 9.E-06 | 1.7 | msAD | lnc-STX3-4:2 | SEQ4242 | 3.E-03 | 1.6 |
| DLB | lnc-CUL2-3:5 | SEQ4848 | 9.E-04 | 1.5 | miAD | lnc-STX3-4:2 | SEQ4242 | 1.E-02 | 1.4 |
| FTD | lnc-CWC15-1:1 | SEQ4464 | 2.E-07 | 0.5 | All AD | lnc-STX3-4:7 | SEQ4065 | 8.E-03 | 0.7 |
| MCI | lnc-CWC15-1:1 | SEQ4464 | 4.E-05 | 0.5 | msAD | lnc-STX3-4:7 | SEQ4065 | 2.E-02 | 0.7 |
| All AD | lnc-CWC15-1:1 | SEQ4464 | 4.E-02 | 0.8 | FTD | lnc-STX3-4:8 | SEQ4268 | 8.E-04 | 0.6 |
| FTD | lnc-CWC15-1:2 | SEQ4374 | 2.E-06 | 3.4 | All AD | lnc-STX3-4:8 | SEQ4268 | 3.E-03 | 0.6 |
| DLB | lnc-CWC15-1:2 | SEQ4374 | 2.E-04 | 2.4 | msAD | lnc-STX3-4:8 | SEQ4268 | 7.E-03 | 0.6 |
| All AD | lnc-CWC15-1:2 | SEQ4374 | 7.E-04 | 1.6 | miAD | lnc-STX3-4:8 | SEQ4268 | 8.E-03 | 0.7 |
| miAD | lnc-CWC15-1:2 | SEQ4374 | 1.E-03 | 1.7 | FTD | lnc-STXBP4-1:2 | SEQ5962 | 6.E-06 | 0.4 |
| msAD | lnc-CWC15-1:2 | SEQ4374 | 3.E-03 | 1.6 | DLB | lnc-SUGCT-4:1 | SEQ3612 | 2.E-03 | 1.4 |
| DLB | lnc-CWC15-5:1 | SEQ4118 | 4.E-05 | 1.5 | FTD | lnc-SUGCT-5:1 | SEQ4035 | 6.E-06 | 0.5 |
| MCI | lnc-CWC15-5:1 | SEQ4118 | 2.E-03 | 1.3 | MCI | lnc-SUGCT-5:1 | SEQ4035 | 3.E-04 | 0.7 |
| miAD | lnc-CWC15-5:1 | SEQ4118 | 1.E-02 | 1.2 | All AD | lnc-SUGCT-5:1 | SEQ4035 | 9.E-03 | 0.7 |
| All AD | lnc-CWC15-5:1 | SEQ4118 | 2.E-02 | 1.2 | msAD | lnc-SUGCT-5:1 | SEQ4035 | 2.E-02 | 0.7 |
| FTD | lnc-CWF19L2-1:2 | SEQ5599 | 2.E-04 | 0.6 | DLB | lnc-SULT1A4-1:9 | SEQ4582 | 2.E-03 | 1.5 |
| miAD | lnc-CXorf21-2:1 | SEQ4180 | 1.E-02 | 0.6 | MCI | lnc-SUMF1-5:1 | SEQ5751 | 1.E-06 | 2.2 |
| All AD | lnc-CXorf21-2:1 | SEQ4180 | 2.E-02 | 0.7 | FTD | lnc-SUMF1-5:1 | SEQ5751 | 2.E-06 | 1.8 |
| DLB | lnc-CXorf65-2:1 | SEQ2748 | 3.E-05 | 1.5 | DLB | lnc-SUMF1-5:1 | SEQ5751 | 6.E-06 | 2.4 |
| FTD | lnc-CYB5D2-2:2 | SEQ5297 | 4.E-04 | 0.7 | All AD | lnc-SUMF1-5:1 | SEQ5751 | 4.E-02 | 1.2 |
| msAD | lnc-CYB5R2-3:10 | SEQ4322 | 6.E-03 | 1.4 | FTD | lnc-SUMO4-2:1 | SEQ5857 | 4.E-05 | 0.6 |
| All AD | lnc-CYB5R2-3:10 | SEQ4322 | 4.E-02 | 1.2 | FTD | lnc-SUPT16H-3:1 | SEQ4923 | 5.E-04 | 0.8 |
| DLB | lnc-CYGB-1:1 | SEQ5753 | 8.E-05 | 1.6 | MCI | lnc-SUPT16H-3:1 | SEQ4923 | 8.E-04 | 0.8 |
| msAD | lnc-CYGB-2:2 | SEQ3872 | 3.E-02 | 0.9 | FTD | lnc-SUPT16H-3:2 | SEQ4030 | 3.E-09 | 0.4 |
| DLB | lnc-CYGB-4:1 | SEQ5318 | 4.E-04 | 1.5 | MCI | lnc-SUPT16H-3:2 | SEQ4030 | 8.E-05 | 0.5 |
| miAD | lnc-CYP1B1-1:3 | SEQ4468 | 2.E-03 | 0.7 | All AD | lnc-SUPT16H-3:2 | SEQ4030 | 6.E-03 | 0.7 |
| All AD | lnc-CYP1B1-1:3 | SEQ4468 | 5.E-03 | 0.7 | miAD | lnc-SUPT16H-3:2 | SEQ4030 | 1.E-02 | 0.7 |
| DLB | lnc-CYP4F22-2:2 | SEQ5815 | 5.E-05 | 1.6 | msAD | lnc-SUPT16H-3:2 | SEQ4030 | 2.E-02 | 0.7 |
| DLB | lnc-CYP4F22-6:1 | SEQ5038 | 7.E-04 | 1.6 | DLB | lnc-SUPT6H-1:2 | SEQ5860 | 4.E-05 | 1.5 |

TABLE 10-continued 2847 whole blood (Paxgene RNA tube) lncRNAs differentially expressed in
MCI group or mild AD group or moderate-to-severe AD group or both of these
AD groups or FTD group or DLB group as compared to healthy control group.

| Group | lncRNA | SEQ | p-value | FC | Group | lncRNA | SEQ | p-value | FC |
|---|---|---|---|---|---|---|---|---|---|
| All AD | lnc-CYP4F8-1:1 | SEQ4470 | 4.E−02 | 1.2 | DLB | lnc-SUSD1-1:4 | SEQ5144 | 6.E−04 | 1.9 |
| All AD | lnc-CYP4F8-1:2 | SEQ4471 | 4.E−02 | 1.2 | FTD | lnc-SUSD1-1:5 | SEQ0638 | 6.E−04 | 0.6 |
| msAD | lnc-CYR61-3:5 | SEQ3687 | 5.E−02 | 1.2 | miAD | lnc-SUSD1-1:5 | SEQ0638 | 1.E−02 | 0.7 |
| FTD | lnc-CYTIP-2:1 | SEQ0200 | 9.E−04 | 0.7 | All AD | lnc-SUSD1-1:5 | SEQ0638 | 4.E−02 | 0.8 |
| DLB | lnc-DALRD3-1:11 | SEQ4791 | 1.E−03 | 1.9 | DLB | lnc-SWSAP1-4:1 | SEQ4126 | 4.E−05 | 1.5 |
| DLB | lnc-DALRD3-1:4 | SEQ3374 | 2.E−04 | 1.5 | All AD | lnc-SWSAP1-4:1 | SEQ4126 | 3.E−03 | 1.2 |
| DLB | lnc-DALRD3-6:1 | SEQ4475 | 1.E−04 | 1.5 | miAD | lnc-SWSAP1-4:1 | SEQ4126 | 4.E−03 | 1.2 |
| All AD | lnc-DALRD3-6:1 | SEQ4475 | 2.E−02 | 1.2 | msAD | lnc-SWSAP1-4:1 | SEQ4126 | 1.E−02 | 1.2 |
| FTD | lnc-DAPP1-8:3 | SEQ2439 | 5.E−04 | 0.6 | FTD | lnc-SYCE3-1:2 | SEQ3976 | 4.E−04 | 0.7 |
| FTD | lnc-DARS2-3:2 | SEQ4913 | 9.E−04 | 0.8 | msAD | lnc-SYCE3-1:2 | SEQ3976 | 2.E−02 | 0.7 |
| MCI | lnc-DAZAP2-3:1 | SEQ0056 | 2.E−03 | 1.6 | All AD | lnc-SYCE3-1:2 | SEQ3976 | 2.E−02 | 0.7 |
| DLB | lnc-DBT-3:1 | SEQ5340 | 4.E−05 | 1.9 | DLB | lnc-SYNE3-1:1 | SEQ5369 | 3.E−04 | 1.4 |
| MCI | lnc-DBT-3:1 | SEQ5340 | 4.E−04 | 1.8 | DLB | lnc-SYNE3-1:2 | SEQ5368 | 3.E−04 | 1.4 |
| All AD | lnc-DBX2-4:3 | SEQ4477 | 5.E−02 | 1.1 | DLB | lnc-SYNE3-1:3 | SEQ5309 | 4.E−04 | 1.4 |
| DLB | lnc-DCAF1-1:1 | SEQ3375 | 1.E−04 | 1.3 | All AD | lnc-SYNE3-5:1 | SEQ5757 | 3.E−02 | 1.4 |
| FTD | lnc-DCAF4L1-2:1 | SEQ2387 | 1.E−04 | 0.6 | MCI | lnc-SYT13-8:1 | SEQ3708 | 2.E−06 | 1.7 |
| All AD | lnc-DCAF4L1-2:1 | SEQ2387 | 1.E−02 | 0.7 | DLB | lnc-SYT13-8:1 | SEQ3708 | 1.E−05 | 1.6 |
| msAD | lnc-DCAF4L1-2:1 | SEQ2387 | 3.E−02 | 0.7 | All AD | lnc-SYT13-8:1 | SEQ3708 | 4.E−02 | 1.2 |
| MCI | lnc-DCLRE1B-3:1 | SEQ5928 | 2.E−06 | 0.4 | msAD | lnc-SYT13-8:1 | SEQ3708 | 5.E−02 | 1.2 |
| FTD | lnc-DCLRE1B-3:1 | SEQ5928 | 1.E−05 | 0.4 | DLB | lnc-SYT2-4:2 | SEQ5097 | 6.E−04 | 2.E−03 |
| FTD | lnc-DCUN1D1-10:1 | SEQ4291 | 1.E−09 | 0.3 | FTD | lnc-TAAR9-3:4 | SEQ5364 | 3.E−05 | 0.3 |
| MCI | lnc-DCUN1D1-10:1 | SEQ4291 | 2.E−05 | 0.4 | MCI | lnc-TAAR9-3:4 | SEQ5364 | 3.E−04 | 0.3 |
| DLB | lnc-DCUN1D1-10:1 | SEQ4291 | 9.E−05 | 0.4 | FTD | lnc-TAAR9-3:5 | SEQ4732 | 2.E−10 | 0.4 |
| miAD | lnc-DCUN1D1-10:1 | SEQ4291 | 7.E−03 | 0.4 | MCI | lnc-TAAR9-3:5 | SEQ4732 | 6.E−06 | 0.4 |
| All AD | lnc-DCUN1D1-10:1 | SEQ4291 | 1.E−02 | 0.5 | miAD | lnc-TAAR9-3:5 | SEQ4732 | 1.E−03 | 0.6 |
| DLB | lnc-DDB1-1:2 | SEQ5421 | 8.E−05 | 1.7 | All AD | lnc-TAAR9-3:5 | SEQ4732 | 6.E−03 | 0.6 |
| MCI | lnc-DDB1-1:2 | SEQ5421 | 2.E−04 | 1.6 | DLB | lnc-TAF12-5:1 | SEQ3964 | 2.E−04 | 1.4 |
| FTD | lnc-DDB1-1:2 | SEQ5421 | 3.E−02 | 1.5 | msAD | lnc-TAF12-5:1 | SEQ3964 | 2.E−02 | 1.2 |
| MCI | lnc-DDIAS-6:1 | SEQ3745 | 5.E−04 | 1.4 | DLB | lnc-TAF6-1:2 | SEQ5219 | 5.E−04 | 2.7 |
| DLB | lnc-DDIAS-6:1 | SEQ3745 | 7.E−04 | 1.6 | DLB | lnc-TAF9-1:8 | SEQ4558 | 2.E−03 | 1.3 |
| miAD | lnc-DDIAS-6:1 | SEQ3745 | 8.E−03 | 1.3 | miAD | lnc-TAF9-2:2 | SEQ4102 | 1.E−02 | 0.5 |
| All AD | lnc-DDIAS-6:1 | SEQ3745 | 1.E−02 | 1.2 | DLB | lnc-TAF9-6:6 | SEQ4969 | 8.E−04 | 1.6 |
| msAD | lnc-DDIAS-6:1 | SEQ3745 | 4.E−02 | 1.2 | DLB | lnc-TAGLN-2:1 | SEQ3559 | 4.E−04 | 1.4 |
| MCI | lnc-DDX39A-3:1 | SEQ4785 | 1.E−03 | 1.7 | FTD | lnc-TANC1-1:3 | SEQ5238 | 1.E−08 | 0.3 |
| FTD | lnc-DDX58-3:1 | SEQ4044 | 1.E−03 | 0.7 | miAD | lnc-TANC1-1:3 | SEQ5238 | 5.E−04 | 0.5 |
| All AD | lnc-DDX58-3:1 | SEQ4044 | 1.E−02 | 0.7 | FTD | lnc-TAOK1-4:1 | SEQ3609 | 7.E−04 | 0.7 |
| msAD | lnc-DDX58-3:1 | SEQ4044 | 2.E−02 | 0.7 | MCI | lnc-TAOK1-4:2 | SEQ5761 | 1.E−05 | 0.2 |
| DLB | lnc-DDX6-1:1 | SEQ5115 | 6.E−04 | 1.4 | FTD | lnc-TAOK1-4:2 | SEQ5761 | 8.E−05 | 0.2 |
| DLB | lnc-DEC1-7:1 | SEQ3804 | 2.E−04 | 1.6 | DLB | lnc-TAOK3-9:1 | SEQ2396 | 6.E−04 | 1.5 |
| MCI | lnc-DEC1-7:1 | SEQ3804 | 9.E−04 | 1.6 | miAD | lnc-TAOK3-9:1 | SEQ2396 | 2.E−03 | 1.3 |
| msAD | lnc-DEC1-7:1 | SEQ3804 | 4.E−02 | 1.2 | All AD | lnc-TAOK3-9:1 | SEQ2396 | 3.E−03 | 1.2 |
| DLB | lnc-DEFB115-3:1 | SEQ5595 | 9.E−06 | 2.4 | msAD | lnc-TAOK3-9:1 | SEQ2396 | 2.E−02 | 1.2 |
| FTD | lnc-DEFB115-3:1 | SEQ5595 | 2.E−04 | 1.8 | MCI | lnc-TARBP1-6:1 | SEQ2671 | 5.E−05 | 1.7 |
| DLB | lnc-DEFB115-5:2 | SEQ2465 | 8.E−05 | 2.0 | DLB | lnc-TARBP1-6:1 | SEQ2671 | 1.E−04 | 1.7 |
| FTD | lnc-DEFB115-5:2 | SEQ2465 | 6.E−04 | 1.7 | FTD | lnc-TARBP1-6:1 | SEQ2671 | 2.E−04 | 1.6 |
| All AD | lnc-DEFB115-5:2 | SEQ2465 | 4.E−02 | 1.3 | All AD | lnc-TARBP1-6:1 | SEQ2671 | 4.E−04 | 1.5 |
| All AD | lnc-DEFB131B-5:1 | SEQ3683 | 4.E−02 | 1.2 | msAD | lnc-TARBP1-6:1 | SEQ2671 | 1.E−03 | 1.4 |
| msAD | lnc-DEFB131B-5:1 | SEQ3683 | 5.E−02 | 1.2 | miAD | lnc-TARBP1-6:1 | SEQ2671 | 1.E−03 | 1.5 |
| DLB | lnc-DEGS2-2:2 | SEQ4003 | 9.E−06 | 1.6 | MCI | lnc-TARS-6:1 | SEQ3544 | 1.E−03 | 1.7 |
| FTD | lnc-DEGS2-2:2 | SEQ4003 | 9.E−04 | 1.4 | FTD | lnc-TAS2R30-1:2 | SEQ5288 | 4.E−04 | 0.6 |
| MCI | lnc-DEGS2-2:2 | SEQ4003 | 9.E−04 | 1.4 | FTD | lnc-TBC1D19-8:1 | SEQ5084 | 6.E−04 | 0.6 |
| All AD | lnc-DEGS2-2:2 | SEQ4003 | 8.E−03 | 1.2 | FTD | lnc-TBC1D19-8:2 | SEQ5960 | 6.E−06 | 4.E−02 |
| miAD | lnc-DEGS2-2:2 | SEQ4003 | 1.E−02 | 1.3 | FTD | lnc-TBC1D31-3:1 | SEQ5594 | 2.E−04 | 0.6 |
| msAD | lnc-DEGS2-2:2 | SEQ4003 | 2.E−02 | 1.2 | DLB | lnc-TBX19-2:1 | SEQ5795 | 6.E−05 | 1.7 |
| DLB | lnc-DENND1A-5:1 | SEQ3185 | 8.E−05 | 1.6 | DLB | lnc-TBX2-7:1 | SEQ5201 | 5.E−04 | 1.8 |
| MCI | lnc-DENND3-7:1 | SEQ4306 | 2.E−04 | 1.7 | MCI | lnc-TBX2-7:1 | SEQ5201 | 5.E−04 | 1.7 |
| DLB | lnc-DENND3-7:1 | SEQ4306 | 3.E−04 | 1.6 | DLB | lnc-TBXA2R-2:1 | SEQ4459 | 2.E−03 | 2.5 |
| msAD | lnc-DENND3-7:1 | SEQ4306 | 7.E−03 | 1.3 | FTD | lnc-TC2N-1:1 | SEQ4893 | 9.E−04 | 0.6 |
| All AD | lnc-DENND3-7:1 | SEQ4306 | 2.E−02 | 1.2 | FTD | lnc-TCEANC2-1:1 | SEQ5000 | 8.E−04 | 0.7 |
| DLB | lnc-DENND3-9:1 | SEQ4263 | 3.E−04 | 1.7 | All AD | lnc-TCF19-1:104 | SEQ5768 | 4.E−02 | 0.7 |
| MCI | lnc-DENND3-9:1 | SEQ4263 | 8.E−04 | 1.8 | FTD | lnc-TCF19-1:107 | SEQ5466 | 3.E−04 | 0.6 |
| msAD | lnc-DENND3-9:1 | SEQ4263 | 9.E−03 | 1.3 | All AD | lnc-TCF19-1:107 | SEQ5466 | 3.E−02 | 0.7 |
| All AD | lnc-DENND3-9:1 | SEQ4263 | 2.E−02 | 1.2 | DLB | lnc-TCF7-1:3 | SEQ0990 | 2.E−04 | 1.4 |
| DLB | lnc-DFNB59-2:28 | SEQ5937 | 1.E−05 | 2.4 | MCI | lnc-TCFL5-6:1 | SEQ5564 | 1.E−04 | 1.5 |
| DLB | lnc-DHRS7B-7:2 | SEQ5187 | 5.E−04 | 1.5 | FTD | lnc-TCFL5-6:1 | SEQ5564 | 2.E−04 | 1.3 |
| DLB | lnc-DHRSX-1:6 | SEQ5311 | 4.E−04 | 1.4 | DLB | lnc-TCFL5-6:1 | SEQ5564 | 2.E−04 | 1.5 |
| FTD | lnc-DHX33-1:1 | SEQ2533 | 6.E−04 | 0.7 | All AD | lnc-TCP1-4:1 | SEQ5772 | 1.E−02 | 0.8 |
| msAD | lnc-DHX38-4:13 | SEQ2803 | 5.E−02 | 1.2 | DLB | lnc-TCTA-1:1 | SEQ4966 | 8.E−04 | 1.6 |
| DLB | lnc-DLGAP5-2:1 | SEQ2566 | 9.E−04 | 1.3 | FTD | lnc-TCTA-2:1 | SEQ2757 | 1.E−05 | 0.7 |
| DLB | lnc-DMTN-5:1 | SEQ5269 | 2.E−05 | 1.8 | MCI | lnc-TCTA-2:1 | SEQ2757 | 7.E−04 | 0.8 |
| MCI | lnc-DMTN-5:1 | SEQ5269 | 5.E−04 | 1.6 | All AD | lnc-TCTN3-2:1 | SEQ5775 | 3.E−02 | 0.8 |
| All AD | lnc-DMXL1-7:1 | SEQ4018 | 1.E−02 | 1.2 | FTD | lnc-TDP1-6:2 | SEQ5680 | 1.E−04 | 0.5 |
| msAD | lnc-DMXL1-7:1 | SEQ4018 | 2.E−02 | 1.2 | miAD | lnc-TEAD2-2:4 | SEQ3500 | 8.E−03 | 1.3 |
| MCI | lnc-DNAH10OS-6:1 | SEQ5010 | 7.E−04 | 0.5 | All AD | lnc-TEAD2-2:4 | SEQ3500 | 9.E−03 | 1.3 |

TABLE 10-continued 2847 whole blood (Paxgene RNA tube) lncRNAs differentially expressed in
MCI group or mild AD group or moderate-to-severe AD group or both of these
AD groups or FTD group or DLB group as compared to healthy control group.

| Group | lncRNA | SEQ | p-value | FC | Group | lncRNA | SEQ | p-value | FC |
|---|---|---|---|---|---|---|---|---|---|
| DLB | lnc-DNAH10OS-8:2 | SEQ5044 | 7.E-04 | 1.7 | msAD | lnc-TEAD2-2:4 | SEQ3500 | 4.E-02 | 1.2 |
| DLB | lnc-DNAJA1-1:1 | SEQ5797 | 6.E-05 | 1.9 | MCI | lnc-TEC-2:1 | SEQ5141 | 5.E-05 | 1.8 |
| msAD | lnc-DNAJC15-5:1 | SEQ3843 | 3.E-02 | 0.6 | FTD | lnc-TEC-2:1 | SEQ5141 | 2.E-04 | 1.6 |
| msAD | lnc-DNAJC15-6:1 | SEQ3924 | 3.E-02 | 0.6 | DLB | lnc-TEC-2:1 | SEQ5141 | 6.E-04 | 1.8 |
| All AD | lnc-DNAJC15-6:1 | SEQ3924 | 3.E-02 | 0.6 | DLB | lnc-TEF-1:1 | SEQ3075 | 5.E-05 | 1.6 |
| DLB | lnc-DNAJC16-1:2 | SEQ4625 | 1.E-03 | 1.4 | MCI | lnc-TEF-1:1 | SEQ3075 | 7.E-04 | 1.5 |
| FTD | lnc-DNAJC19-8:1 | SEQ5867 | 4.E-05 | 0.6 | DLB | lnc-TEKT2-1:2 | SEQ4568 | 2.E-03 | 1.4 |
| DLB | lnc-DNAJC5-1:3 | SEQ5372 | 3.E-04 | 1.4 | DLB | lnc-TELO2-3:2 | SEQ2887 | 4.E-07 | 2.1 |
| FTD | lnc-DNAJC5B-1:3 | SEQ5405 | 3.E-04 | 0.6 | MCI | lnc-TELO2-3:2 | SEQ2887 | 1.E-05 | 2.0 |
| DLB | lnc-DNAJC7-1:1 | SEQ4518 | 9.E-06 | 1.6 | DLB | lnc-TELO2-3:3 | SEQ5003 | 4.E-06 | 1.7 |
| All AD | lnc-DNAJC7-1:1 | SEQ4518 | 5.E-02 | 1.1 | MCI | lnc-TELO2-3:3 | SEQ5003 | 2.E-05 | 1.6 |
| DLB | lnc-DNAL1-2:1 | SEQ4509 | 2.E-03 | 1.5 | FTD | lnc-TELO2-3:3 | SEQ5003 | 8.E-04 | 1.3 |
| MCI | lnc-DNAL4-4:1 | SEQ3095 | 4.E-05 | 1.7 | FTD | lnc-TENM1-6:1 | SEQ3849 | 1.E-05 | 0.5 |
| DLB | lnc-DNAL4-4:1 | SEQ3095 | 1.E-04 | 1.8 | miAD | lnc-TENM1-6:1 | SEQ3849 | 1.E-03 | 0.6 |
| DLB | lnc-DNASE1L2-2:11 | SEQ5947 | 9.E-06 | 1.7 | All AD | lnc-TENM1-6:1 | SEQ3849 | 3.E-03 | 0.6 |
| DLB | lnc-DNASE1L2-2:12 | SEQ4422 | 2.E-06 | 1.7 | msAD | lnc-TENM1-6:1 | SEQ3849 | 3.E-02 | 0.6 |
| MCI | lnc-DNASE1L2-2:12 | SEQ4422 | 2.E-03 | 1.4 | All AD | lnc-TEX37-1:1 | SEQ2655 | 4.E-02 | 1.2 |
| FTD | lnc-DOCK11-1:1 | SEQ5358 | 4.E-04 | 0.7 | All AD | lnc-TEX37-1:2 | SEQ2654 | 4.E-02 | 1.2 |
| FTD | lnc-DOCK7-7:1 | SEQ0015 | 3.E-05 | 0.6 | DLB | lnc-TFDP2-5:1 | SEQ4709 | 1.E-03 | 1.5 |
| DLB | lnc-DOLPP1-3:1 | SEQ4598 | 1.E-04 | 1.6 | DLB | lnc-TFEC-7:1 | SEQ4248 | 8.E-05 | 1.4 |
| MCI | lnc-DOLPP1-3:1 | SEQ4598 | 2.E-03 | 1.8 | MCI | lnc-TFEC-7:1 | SEQ4248 | 1.E-03 | 1.3 |
| FTD | lnc-DPP4-10:1 | SEQ5512 | 2.E-04 | 0.6 | All AD | lnc-TFEC-7:1 | SEQ4248 | 4.E-03 | 1.2 |
| DLB | lnc-DPP7-1:1 | SEQ4708 | 1.E-03 | 1.5 | msAD | lnc-TFEC-7:1 | SEQ4248 | 8.E-03 | 1.2 |
| DLB | lnc-DR1-2:1 | SEQ4684 | 1.E-03 | 1.4 | miAD | lnc-TFEC-7:1 | SEQ4248 | 9.E-03 | 1.2 |
| FTD | lnc-DR1-2:2 | SEQ5300 | 4.E-04 | 0.8 | DLB | lnc-TFPT-1:1 | SEQ4694 | 1.E-03 | 1.4 |
| miAD | lnc-DRD2-1:7 | SEQ3704 | 1.E-02 | 0.6 | FTD | lnc-TGFBR2-1:1 | SEQ5419 | 3.E-04 | 0.7 |
| All AD | lnc-DRD2-1:7 | SEQ3704 | 1.E-02 | 0.6 | FTD | lnc-TGM5-1:3 | SEQ5787 | 8.E-08 | 0.5 |
| msAD | lnc-DRD2-1:7 | SEQ3704 | 5.E-02 | 0.7 | MCI | lnc-TGM5-1:3 | SEQ5787 | 6.E-05 | 0.6 |
| DLB | lnc-DRD5-23:2 | SEQ5314 | 4.E-04 | 1.4 | All AD | lnc-TGM5-1:3 | SEQ5787 | 5.E-02 | 0.7 |
| msAD | lnc-DRD5-29:1 | SEQ3847 | 3.E-02 | 1.6 | FTD | lnc-TGM5-1:5 | SEQ6001 | 3.E-07 | 4.1 |
| DLB | lnc-DRICH1-3:10 | SEQ4972 | 1.E-04 | 1.7 | DLB | lnc-TGM6-4:1 | SEQ3919 | 1.E-03 | 1.5 |
| MCI | lnc-DRICH1-3:10 | SEQ4972 | 8.E-04 | 1.7 | All AD | lnc-TGM6-4:1 | SEQ3919 | 2.E-02 | 1.2 |
| FTD | lnc-DRICH1-3:9 | SEQ4454 | 6.E-04 | 1.6 | msAD | lnc-TGM6-4:1 | SEQ3919 | 3.E-02 | 1.2 |
| DLB | lnc-DRICH1-3:9 | SEQ4454 | 7.E-04 | 1.8 | All AD | lnc-TGS1-1:2 | SEQ5789 | 4.E-02 | 0.6 |
| MCI | lnc-DRICH1-3:9 | SEQ4454 | 2.E-03 | 1.7 | msAD | lnc-THBS1-7:1 | SEQ3779 | 4.E-02 | 1.3 |
| DLB | lnc-DSCR3-2:2 | SEQ4408 | 1.E-04 | 1.5 | DLB | lnc-THTPA-2:27 | SEQ5732 | 9.E-05 | 1.5 |
| MCI | lnc-DSCR3-2:2 | SEQ4408 | 2.E-03 | 1.4 | DLB | lnc-THTPA-2:28 | SEQ5733 | 9.E-05 | 1.5 |
| FTD | lnc-DSCR8-4:1 | SEQ4538 | 2.E-04 | 0.5 | DLB | lnc-THTPA-2:33 | SEQ5731 | 9.E-05 | 1.5 |
| All AD | lnc-DSCR8-4:1 | SEQ4538 | 3.E-02 | 0.6 | FTD | lnc-THUMPD2-2:1 | SEQ3837 | 3.E-04 | 0.5 |
| FTD | lnc-DTNBP1-14:1 | SEQ4539 | 2.E-05 | 0.6 | miAD | lnc-THUMPD2-2:1 | SEQ3837 | 9.E-03 | 0.6 |
| All AD | lnc-DTNBP1-14:1 | SEQ4539 | 3.E-02 | 0.7 | All AD | lnc-THUMPD2-2:1 | SEQ3837 | 9.E-03 | 0.6 |
| msAD | lnc-DTNBP1-5:22 | SEQ3658 | 5.E-02 | 1.5 | msAD | lnc-THUMPD2-2:1 | SEQ3837 | 3.E-02 | 0.8 |
| DLB | lnc-DTYMK-1:2 | SEQ5043 | 4.E-05 | 1.7 | FTD | lnc-THUMPD3-6:1 | SEQ4222 | 1.E-06 | 0.6 |
| MCI | lnc-DTYMK-1:2 | SEQ5043 | 7.E-04 | 1.7 | miAD | lnc-THUMPD3-6:1 | SEQ4222 | 1.E-02 | 0.7 |
| DLB | lnc-DUSP28-1:1 | SEQ4846 | 9.E-04 | 1.5 | DLB | lnc-TICAM1-1:2 | SEQ5514 | 4.E-06 | 1.4 |
| FTD | lnc-DUXA-4:1 | SEQ2603 | 5.E-07 | 0.5 | MCI | lnc-TICAM1-1:2 | SEQ5514 | 2.E-04 | 1.3 |
| All AD | lnc-DUXA-4:1 | SEQ2603 | 4.E-02 | 0.7 | All AD | lnc-TICAM1-1:2 | SEQ5514 | 3.E-02 | 1.1 |
| DLB | lnc-DYNLL2-3:1 | SEQ3803 | 2.E-05 | 1.4 | DLB | lnc-TIGD1-1:16 | SEQ5522 | 2.E-04 | 1.4 |
| All AD | lnc-DYNLL2-3:1 | SEQ3803 | 4.E-02 | 1.1 | FTD | lnc-TIGD4-3:1 | SEQ5397 | 3.E-04 | 0.6 |
| msAD | lnc-DYNLL2-3:1 | SEQ3803 | 4.E-02 | 1.1 | DLB | lnc-TIGD5-1:1 | SEQ2945 | 6.E-05 | 1.7 |
| MCI | lnc-DYNLL2-4:1 | SEQ4868 | 9.E-04 | 1.6 | All AD | lnc-TIGD5-1:1 | SEQ2945 | 3.E-02 | 1.2 |
| DLB | lnc-DYNLT1-1:1 | SEQ4431 | 2.E-03 | 1.5 | msAD | lnc-TIGD5-1:1 | SEQ2945 | 4.E-02 | 1.2 |
| FTD | lnc-DYSF-2:2 | SEQ5779 | 7.E-05 | 0.6 | All AD | lnc-TIMM9-4:1 | SEQ4177 | 3.E-03 | 1.8 |
| FTD | lnc-DYSF-4:1 | SEQ3751 | 7.E-05 | 0.6 | miAD | lnc-TIMM9-4:1 | SEQ4177 | 4.E-03 | 2.0 |
| miAD | lnc-DYSF-4:1 | SEQ3751 | 2.E-03 | 0.7 | msAD | lnc-TIMM9-4:1 | SEQ4177 | 1.E-02 | 1.6 |
| All AD | lnc-DYSF-4:1 | SEQ3751 | 5.E-03 | 0.7 | All AD | lnc-TLCD1-1:2 | SEQ5796 | 4.E-02 | 1.1 |
| msAD | lnc-DYSF-4:1 | SEQ3751 | 4.E-02 | 0.7 | DLB | lnc-TLDC2-4:1 | SEQ0555 | 5.E-05 | 1.7 |
| MCI | lnc-EBLN1-1:1 | SEQ3983 | 1.E-04 | 1.7 | MCI | lnc-TLR10-2:1 | SEQ4427 | 2.E-03 | 1.5 |
| FTD | lnc-EBLN1-1:1 | SEQ3983 | 7.E-04 | 1.7 | FTD | lnc-TLR1-1:1 | SEQ5944 | 3.E-08 | 0.4 |
| DLB | lnc-EBLN1-1:1 | SEQ3983 | 9.E-04 | 1.8 | MCI | lnc-TLR1-1:1 | SEQ5944 | 4.E-07 | 0.4 |
| msAD | lnc-EBLN1-1:1 | SEQ3983 | 2.E-03 | 1.3 | DLB | lnc-TLR1-1:1 | SEQ5944 | 9.E-06 | 0.4 |
| All AD | lnc-EBLN1-1:2 | SEQ4545 | 4.E-02 | 1.3 | FTD | lnc-TLR1-1:4 | SEQ3887 | 7.E-07 | 0.5 |
| All AD | lnc-EBPL-1:1 | SEQ4546 | 3.E-02 | 0.8 | All AD | lnc-TLR1-1:4 | SEQ3887 | 2.E-02 | 0.7 |
| miAD | lnc-ECE1-1:1 | SEQ4182 | 1.E-02 | 0.6 | msAD | lnc-TLR1-1:4 | SEQ3887 | 3.E-02 | 0.7 |
| All AD | lnc-ECE1-1:1 | SEQ4182 | 1.E-02 | 0.7 | MCI | lnc-TMA16-1:1 | SEQ4896 | 8.E-04 | 0.6 |
| DLB | lnc-ECSCR-2:5 | SEQ5431 | 8.E-05 | 1.6 | FTD | lnc-TMA16-1:1 | SEQ4896 | 9.E-04 | 0.6 |
| MCI | lnc-ECSCR-2:5 | SEQ5431 | 3.E-04 | 1.4 | FTD | lnc-TMC5-1:1 | SEQ4737 | 8.E-06 | 0.7 |
| MCI | lnc-EDC3-2:10 | SEQ5714 | 1.E-04 | 3.1 | MCI | lnc-TMC5-1:1 | SEQ4737 | 1.E-04 | 0.7 |
| MCI | lnc-EDC3-2:16 | SEQ4760 | 1.E-03 | 1.5 | DLB | lnc-TMC5-1:1 | SEQ4737 | 1.E-03 | 0.8 |
| All AD | lnc-EDEM3-7:3 | SEQ0272 | 3.E-02 | 0.7 | All AD | lnc-TMC5-1:1 | SEQ4737 | 3.E-02 | 0.9 |
| msAD | lnc-EDEM3-7:3 | SEQ0272 | 5.E-02 | 0.7 | DLB | lnc-TMEM105-1:1 | SEQ4951 | 8.E-04 | 1.5 |
| DLB | lnc-EFCAB12-2:16 | SEQ5894 | 2.E-05 | 1.7 | DLB | lnc-TMEM109-2:1 | SEQ5133 | 2.E-04 | 1.9 |
| DLB | lnc-EFCAB12-2:4 | SEQ4612 | 1.E-03 | 1.3 | MCI | lnc-TMEM109-2:1 | SEQ5133 | 6.E-04 | 1.6 |
| DLB | lnc-EFCAB12-2:8 | SEQ4436 | 2.E-03 | 1.5 | DLB | lnc-TMEM120B-4:2 | SEQ4586 | 2.E-03 | 1.6 |

TABLE 10-continued 2847 whole blood (Paxgene RNA tube) lncRNAs differentially expressed in MCI group or mild AD group or moderate-to-severe AD group or both of these AD groups or FTD group or DLB group as compared to healthy control group.

| Group | lncRNA | SEQ | p-value | FC | Group | lncRNA | SEQ | p-value | FC |
|---|---|---|---|---|---|---|---|---|---|
| DLB | lnc-EFCAB8-1:3 | SEQ3380 | 5.E-04 | 1.4 | DLB | lnc-TMEM120B-4:4 | SEQ4853 | 9.E-04 | 1.5 |
| DLB | lnc-EFCAB9-5:2 | SEQ4496 | 2.E-03 | 1.4 | DLB | lnc-TMEM121-2:15 | SEQ4057 | 2.E-03 | 2.3 |
| FTD | lnc-EFHB-6:1 | SEQ4989 | 8.E-04 | 0.5 | All AD | lnc-TMEM121-2:15 | SEQ4057 | 1.E-02 | 1.6 |
| FTD | lnc-EFR3A-6:1 | SEQ5956 | 7.E-06 | 0.6 | msAD | lnc-TMEM121-2:15 | SEQ4057 | 2.E-02 | 1.6 |
| MCI | lnc-EGFL7-3:1 | SEQ4645 | 1.E-03 | 1.6 | DLB | lnc-TMEM121-2:16 | SEQ4214 | 8.E-04 | 1.8 |
| miAD | lnc-EGR2-5:1 | SEQ4460 | 2.E-03 | 0.6 | All AD | lnc-TMEM121-2:16 | SEQ4214 | 3.E-03 | 1.4 |
| All AD | lnc-EGR2-5:1 | SEQ4460 | 6.E-03 | 0.6 | miAD | lnc-TMEM121-2:16 | SEQ4214 | 3.E-03 | 1.5 |
| DLB | lnc-EIF1AD-1:1 | SEQ2653 | 5.E-04 | 1.4 | msAD | lnc-TMEM121-2:16 | SEQ4214 | 1.E-02 | 1.3 |
| All AD | lnc-EIF2AK3-26:2 | SEQ4334 | 2.E-03 | 1.3 | DLB | lnc-TMEM121-2:17 | SEQ4379 | 5.E-04 | 3.6 |
| msAD | lnc-EIF2AK3-26:2 | SEQ4334 | 4.E-03 | 1.1 | All AD | lnc-TMEM121-2:17 | SEQ4379 | 6.E-04 | 2.3 |
| miAD | lnc-EIF2AK3-26:2 | SEQ4334 | 6.E-03 | 1.5 | msAD | lnc-TMEM121-2:17 | SEQ4379 | 1.E-03 | 2.5 |
| DLB | lnc-EIF2AK3-4:58 | SEQ4358 | 1.E-03 | 3.1 | miAD | lnc-TMEM121-2:17 | SEQ4379 | 3.E-03 | 2.1 |
| miAD | lnc-EIF2AK3-4:58 | SEQ4358 | 4.E-03 | 1.9 | msAD | lnc-TMEM121-2:19 | SEQ3733 | 4.E-02 | 1.5 |
| All AD | lnc-EIF2AK3-4:58 | SEQ4358 | 2.E-02 | 1.7 | miAD | lnc-TMEM121-2:20 | SEQ4041 | 3.E-03 | 1.7 |
| DLB | lnc-EIF2AK3-4:59 | SEQ4232 | 2.E-04 | 2.8 | All AD | lnc-TMEM121-2:20 | SEQ4041 | 4.E-03 | 1.7 |
| FTD | lnc-EIF2AK3-4:59 | SEQ4232 | 6.E-04 | 2.8 | msAD | lnc-TMEM121-2:20 | SEQ4041 | 2.E-02 | 1.6 |
| msAD | lnc-EIF2AK3-4:59 | SEQ4232 | 1.E-02 | 1.7 | All AD | lnc-TMEM121-2:21 | SEQ5806 | 4.E-02 | 1.4 |
| All AD | lnc-EIF2AK3-4:59 | SEQ4232 | 1.E-02 | 1.6 | miAD | lnc-TMEM132D-5:1 | SEQ4212 | 1.E-02 | 0.7 |
| DLB | lnc-EIF2AK3-4:65 | SEQ3873 | 4.E-05 | 2.4 | All AD | lnc-TMEM132D-5:1 | SEQ4212 | 2.E-02 | 0.8 |
| MCI | lnc-EIF2AK3-4:65 | SEQ3873 | 1.E-03 | 1.8 | All AD | lnc-TMEM140-1:2 | SEQ5808 | 3.E-02 | 0.7 |
| All AD | lnc-EIF2AK3-4:65 | SEQ3873 | 1.E-02 | 1.1 | FTD | lnc-TMEM155-3:1 | SEQ3556 | 7.E-06 | 0.5 |
| msAD | lnc-EIF2AK3-4:65 | SEQ3873 | 3.E-02 | 1.1 | MCI | lnc-TMEM155-3:1 | SEQ3556 | 2.E-05 | 0.5 |
| miAD | lnc-EIF2AK3-4:75 | SEQ4250 | 9.E-03 | 1.4 | DLB | lnc-TMEM160-1:1 | SEQ5181 | 5.E-04 | 1.4 |
| All AD | lnc-EIF2AK3-4:75 | SEQ4250 | 1.E-02 | 1.3 | MCI | lnc-TMEM167B-1:2 | SEQ4004 | 7.E-07 | 2.4 |
| All AD | lnc-EIF2AK3-4:77 | SEQ4571 | 4.E-02 | 1.2 | FTD | lnc-TMEM167B-1:2 | SEQ4004 | 2.E-06 | 2.0 |
| MCI | lnc-EIF2B1-1:1 | SEQ2595 | 2.E-05 | 1.5 | DLB | lnc-TMEM167B-1:2 | SEQ4004 | 1.E-04 | 2.1 |
| FTD | lnc-EIF2B1-1:1 | SEQ2595 | 3.E-04 | 1.3 | miAD | lnc-TMEM167B-1:2 | SEQ4004 | 4.E-03 | 1.3 |
| All AD | lnc-EIF2B1-1:1 | SEQ2595 | 3.E-02 | 1.2 | All AD | lnc-TMEM167B-1:2 | SEQ4004 | 4.E-03 | 1.3 |
| DLB | lnc-EIF2D-3:1 | SEQ4850 | 9.E-04 | 1.5 | msAD | lnc-TMEM167B-1:2 | SEQ4004 | 2.E-02 | 1.2 |
| FTD | lnc-EIF2S3-1:1 | SEQ5351 | 4.E-04 | 0.6 | MCI | lnc-TMEM167B-1:3 | SEQ5635 | 1.E-06 | 2.2 |
| DLB | lnc-EIF3B-2:3 | SEQ3940 | 1.E-05 | 1.8 | FTD | lnc-TMEM167B-1:3 | SEQ5635 | 2.E-05 | 1.7 |
| MCI | lnc-EIF3B-2:3 | SEQ3940 | 2.E-05 | 1.5 | DLB | lnc-TMEM167B-1:3 | SEQ5635 | 2.E-04 | 1.9 |
| miAD | lnc-EIF3B-2:3 | SEQ3940 | 4.E-04 | 1.3 | All AD | lnc-TMEM167B-1:3 | SEQ5635 | 2.E-02 | 1.2 |
| FTD | lnc-EIF3B-2:3 | SEQ3940 | 8.E-04 | 1.3 | MCI | lnc-TMEM167B-1:4 | SEQ5541 | 3.E-06 | 2.1 |
| All AD | lnc-EIF3B-2:3 | SEQ3940 | 2.E-03 | 1.2 | FTD | lnc-TMEM167B-1:4 | SEQ5541 | 2.E-04 | 1.7 |
| msAD | lnc-EIF3B-2:3 | SEQ3940 | 3.E-03 | 1.2 | DLB | lnc-TMEM167B-1:4 | SEQ5541 | 2.E-04 | 2.0 |
| miAD | lnc-EIF4E3-2:1 | SEQ4132 | 1.E-02 | 0.6 | All AD | lnc-TMEM167B-1:4 | SEQ5541 | 4.E-02 | 1.2 |
| All AD | lnc-EIF4E3-2:1 | SEQ4132 | 1.E-02 | 0.7 | FTD | lnc-TMEM167B-1:5 | SEQ3821 | 2.E-06 | 1.9 |
| All AD | lnc-EIF4E3-2:2 | SEQ4579 | 3.E-02 | 0.7 | MCI | lnc-TMEM167B-1:5 | SEQ3821 | 6.E-06 | 2.4 |
| DLB | lnc-EIF4ENIF1-3:1 | SEQ3788 | 3.E-04 | 1.6 | DLB | lnc-TMEM167B-1:5 | SEQ3821 | 2.E-04 | 2.2 |
| MCI | lnc-EIF4ENIF1-3:1 | SEQ3788 | 2.E-03 | 1.4 | All AD | lnc-TMEM167B-1:5 | SEQ3821 | 1.E-02 | 1.2 |
| msAD | lnc-EIF4ENIF1-3:1 | SEQ3788 | 4.E-02 | 1.2 | miAD | lnc-TMEM167B-1:5 | SEQ3821 | 1.E-02 | 1.3 |
| All AD | lnc-EIF4G3-4:1 | SEQ4581 | 3.E-02 | 0.8 | msAD | lnc-TMEM167B-1:5 | SEQ3821 | 4.E-02 | 1.2 |
| MCI | lnc-EIF5-2:1 | SEQ2571 | 1.E-05 | 1.7 | DLB | lnc-TMEM173-3:3 | SEQ5194 | 5.E-04 | 1.6 |
| DLB | lnc-EIF5-2:1 | SEQ2571 | 5.E-05 | 1.9 | FTD | lnc-TMEM178A-5:1 | SEQ4104 | 1.E-04 | 0.5 |
| FTD | lnc-EIF5-2:1 | SEQ2571 | 1.E-04 | 1.4 | miAD | lnc-TMEM178A-5:1 | SEQ4104 | 1.E-02 | 0.6 |
| All AD | lnc-EIF5-2:1 | SEQ2571 | 2.E-02 | 1.1 | All AD | lnc-TMEM178A-5:1 | SEQ4104 | 3.E-02 | 0.7 |
| msAD | lnc-EIF5-2:1 | SEQ2571 | 3.E-02 | 1.1 | FTD | lnc-TMEM178A-6:5 | SEQ3797 | 3.E-05 | 0.5 |
| FTD | lnc-ELF2-5:2 | SEQ4109 | 1.E-04 | 0.6 | miAD | lnc-TMEM178A-6:5 | SEQ3797 | 5.E-03 | 0.5 |
| miAD | lnc-ELF2-5:2 | SEQ4109 | 1.E-02 | 0.7 | All AD | lnc-TMEM178A-6:5 | SEQ3797 | 7.E-03 | 0.6 |
| All AD | lnc-ELF2-5:2 | SEQ4109 | 3.E-02 | 0.7 | msAD | lnc-TMEM178A-6:5 | SEQ3797 | 4.E-02 | 0.6 |
| DLB | lnc-ELFN1-3:2 | SEQ4585 | 3.E-05 | 1.7 | msAD | lnc-TMEM183A-1:1 | SEQ3991 | 2.E-02 | 1.2 |
| All AD | lnc-ELFN1-3:2 | SEQ4585 | 4.E-02 | 1.2 | All AD | lnc-TMEM185B-1:6 | SEQ5817 | 5.E-02 | 0.8 |
| DLB | lnc-ELFN1-6:2 | SEQ4594 | 2.E-04 | 1.9 | msAD | lnc-TMEM185B-12:2 | SEQ4025 | 2.E-02 | 0.5 |
| MCI | lnc-ELFN1-6:2 | SEQ4594 | 2.E-03 | 1.7 | All AD | lnc-TMEM185B-12:2 | SEQ4025 | 2.E-02 | 0.6 |
| MCI | lnc-ELL3-1:2 | SEQ4383 | 2.E-06 | 1.7 | All AD | lnc-TMEM185B-12:3 | SEQ4226 | 8.E-03 | 0.6 |
| FTD | lnc-ELL3-1:2 | SEQ4383 | 8.E-06 | 1.6 | msAD | lnc-TMEM185B-12:3 | SEQ4226 | 1.E-02 | 0.5 |
| DLB | lnc-ELL3-1:2 | SEQ4383 | 9.E-05 | 1.7 | msAD | lnc-TMEM186-1:2 | SEQ2702 | 2.E-02 | 1.3 |
| miAD | lnc-ELL3-1:2 | SEQ4383 | 4.E-04 | 1.3 | DLB | lnc-TMEM202-2:2 | SEQ5373 | 3.E-04 | 1.5 |
| All AD | lnc-ELL3-1:2 | SEQ4383 | 4.E-04 | 1.3 | FTD | lnc-TMEM206-3:2 | SEQ3714 | 4.E-05 | 0.6 |
| msAD | lnc-ELL3-1:2 | SEQ4383 | 3.E-03 | 1.3 | miAD | lnc-TMEM206-3:2 | SEQ3714 | 1.E-02 | 0.7 |
| FTD | lnc-EMC3-2:1 | SEQ4593 | 2.E-04 | 0.7 | All AD | lnc-TMEM206-3:2 | SEQ3714 | 1.E-02 | 0.7 |
| All AD | lnc-EMC3-2:1 | SEQ4593 | 3.E-02 | 0.8 | msAD | lnc-TMEM206-3:2 | SEQ3714 | 4.E-02 | 0.8 |
| FTD | lnc-EMCN-4:1 | SEQ4137 | 1.E-04 | 0.6 | All AD | lnc-TMEM212-5:1 | SEQ5819 | 4.E-02 | 0.8 |
| miAD | lnc-EMCN-4:1 | SEQ4137 | 1.E-02 | 0.7 | DLB | lnc-TMEM231-2:1 | SEQ5792 | 6.E-05 | 1.6 |
| All AD | lnc-EMCN-4:1 | SEQ4137 | 3.E-02 | 0.8 | DLB | lnc-TMEM234-4:1 | SEQ5877 | 3.E-05 | 1.6 |
| All AD | lnc-EME2-1:1 | SEQ3682 | 2.E-02 | 1.2 | DLB | lnc-TMEM240-1:1 | SEQ4946 | 8.E-04 | 1.5 |
| msAD | lnc-EME2-1:1 | SEQ3682 | 5.E-02 | 1.2 | All AD | lnc-TMEM255B-5:13 | SEQ5820 | 3.E-02 | 1.5 |
| MCI | lnc-EMG1-1:1 | SEQ4928 | 8.E-04 | 1.4 | FTD | lnc-TMEM30B-9:1 | SEQ4108 | 6.E-11 | 0.3 |
| DLB | lnc-EMG1-1:2 | SEQ5636 | 2.E-04 | 1.9 | MCI | lnc-TMEM30B-9:1 | SEQ4108 | 7.E-06 | 0.4 |
| All AD | lnc-EML6-6:1 | SEQ3684 | 3.E-02 | 1.2 | DLB | lnc-TMEM30B-9:1 | SEQ4108 | 2.E-03 | 0.4 |
| msAD | lnc-EML6-6:1 | SEQ3684 | 5.E-02 | 1.2 | miAD | lnc-TMEM30B-9:1 | SEQ4108 | 1.E-02 | 0.6 |
| FTD | lnc-EMX2-3:4 | SEQ5359 | 4.E-04 | 0.7 | FTD | lnc-TMEM43-1:4 | SEQ5285 | 4.E-04 | 0.5 |
| DLB | lnc-ENC1-5:1 | SEQ2244 | 2.E-03 | 1.7 | DLB | lnc-TMEM50B-4:2 | SEQ4870 | 9.E-04 | 1.7 |

TABLE 10-continued 2847 whole blood (Paxgene RNA tube) lncRNAs differentially expressed in
MCI group or mild AD group or moderate-to-severe AD group or both of these
AD groups or FTD group or DLB group as compared to healthy control group.

| Group | lncRNA | SEQ | p-value | FC | Group | lncRNA | SEQ | p-value | FC |
|---|---|---|---|---|---|---|---|---|---|
| All AD | lnc-ENOPH1-3:3 | SEQ3381 | 3.E−03 | 1.2 | All AD | lnc-TMEM63A-2:1 | SEQ5822 | 3.E−02 | 1.2 |
| miAD | lnc-ENOPH1-3:3 | SEQ3381 | 3.E−03 | 1.3 | DLB | lnc-TMEM88B-6:1 | SEQ5055 | 2.E−05 | 3.8 |
| msAD | lnc-ENOPH1-3:3 | SEQ3381 | 1.E−02 | 1.2 | MCI | lnc-TMEM88B-6:1 | SEQ5055 | 7.E−04 | 2.7 |
| DLB | lnc-EPHA1-1:4 | SEQ5276 | 5.E−04 | 1.7 | FTD | lnc-TMTC3-13:11 | SEQ3765 | 2.E−05 | 0.6 |
| DLB | lnc-EPHA6-7:1 | SEQ4574 | 1.E−05 | 1.7 | miAD | lnc-TMTC3-13:11 | SEQ3765 | 9.E−03 | 0.7 |
| MCI | lnc-EPHA6-7:1 | SEQ4574 | 2.E−03 | 1.5 | All AD | lnc-TMTC3-13:11 | SEQ3765 | 1.E−02 | 0.7 |
| FTD | lnc-EPHB3-5:1 | SEQ4809 | 1.E−03 | 0.7 | msAD | lnc-TMTC3-13:11 | SEQ3765 | 4.E−02 | 0.7 |
| DLB | lnc-EPM2AIP1-5:2 | SEQ4648 | 1.E−03 | 1.7 | DLB | lnc-TMUB2-1:11 | SEQ5664 | 1.E−04 | 1.5 |
| FTD | lnc-EPN2-3:2 | SEQ4005 | 2.E−06 | 2.9 | DLB | lnc-TMUB2-2:1 | SEQ5814 | 5.E−05 | 1.5 |
| DLB | lnc-EPN2-3:2 | SEQ4005 | 2.E−04 | 2.5 | All AD | lnc-TNFAIP6-5:1 | SEQ5824 | 5.E−02 | 0.7 |
| MCI | lnc-EPN2-3:2 | SEQ4005 | 5.E−02 | 2.2 | DLB | lnc-TNFAIP8L1-2:1 | SEQ4950 | 8.E−04 | 1.5 |
| msAD | lnc-EPN2-3:2 | SEQ4005 | 2.E−02 | 1.2 | All AD | lnc-TNFAIP8L1-2:1 | SEQ4950 | 4.E−02 | 1.2 |
| All AD | lnc-EPN2-3:2 | SEQ4005 | 2.E−02 | 1.2 | FTD | lnc-TNFRSF11A-5:1 | SEQ5825 | 8.E−08 | 0.5 |
| FTD | lnc-EPN2-3:3 | SEQ5074 | 7.E−04 | 1.8 | All AD | lnc-TNFRSF11A-5:1 | SEQ5825 | 2.E−02 | 0.7 |
| FTD | lnc-ERAP2-4:3 | SEQ5601 | 2.E−04 | 0.6 | DLB | lnc-TNFRSF13C-1:1 | SEQ4142 | 3.E−04 | 2.2 |
| DLB | lnc-ERCC6L2-14:1 | SEQ3383 | 2.E−04 | 1.5 | All AD | lnc-TNFRSF13C-1:1 | SEQ4142 | 3.E−03 | 1.5 |
| MCI | lnc-ERCC6L2-14:1 | SEQ3383 | 8.E−04 | 1.4 | msAD | lnc-TNFRSF13C-1:1 | SEQ4142 | 4.E−03 | 1.6 |
| miAD | lnc-ERCC6L2-14:1 | SEQ3383 | 8.E−03 | 1.2 | miAD | lnc-TNFRSF13C-1:1 | SEQ4142 | 1.E−02 | 1.4 |
| All AD | lnc-ERCC6L2-14:1 | SEQ3383 | 9.E−03 | 1.2 | miAD | lnc-TNFRSF14-2:7 | SEQ4234 | 1.E−02 | 0.5 |
| msAD | lnc-ERCC6L2-14:1 | SEQ3383 | 4.E−02 | 1.2 | All AD | lnc-TNFRSF14-2:7 | SEQ4234 | 1.E−02 | 0.6 |
| FTD | lnc-ERRFI1-3:1 | SEQ5607 | 2.E−04 | 0.7 | MCI | lnc-TNFRSF14-4:2 | SEQ5213 | 4.E−07 | 1.9 |
| DLB | lnc-ERV3-1-1:4 | SEQ4405 | 2.E−03 | 1.3 | FTD | lnc-TNFRSF14-4:2 | SEQ5213 | 5.E−06 | 1.7 |
| FTD | lnc-ERV3-1-2:1 | SEQ3853 | 1.E−04 | 0.6 | miAD | lnc-TNFRSF14-4:2 | SEQ5213 | 8.E−04 | 1.5 |
| miAD | lnc-ERV3-1-2:1 | SEQ3853 | 4.E−03 | 0.7 | DLB | lnc-TNFRSF14-4:2 | SEQ5213 | 5.E−04 | 1.9 |
| All AD | lnc-ERV3-1-2:1 | SEQ3853 | 6.E−03 | 0.7 | All AD | lnc-TNFRSF14-4:2 | SEQ5213 | 3.E−03 | 1.4 |
| msAD | lnc-ERV3-1-2:1 | SEQ3853 | 3.E−02 | 0.8 | msAD | lnc-TNFRSF1A-3:1 | SEQ3977 | 2.E−02 | 0.7 |
| miAD | lnc-ESM1-3:3 | SEQ4203 | 1.E−02 | 0.6 | All AD | lnc-TNFRSF1A-3:1 | SEQ3977 | 3.E−02 | 0.7 |
| DLB | lnc-ESRP2-4:1 | SEQ4417 | 2.E−03 | 1.4 | DLB | lnc-TNFRSF8-2:1 | SEQ4710 | 1.E−03 | 1.5 |
| DLB | lnc-ESRRB-1:1 | SEQ4575 | 9.E−04 | 1.4 | FTD | lnc-TNFSF4-3:2 | SEQ5063 | 7.E−04 | 0.6 |
| MCI | lnc-ESRRB-1:1 | SEQ4575 | 2.E−03 | 1.5 | All AD | lnc-TNFSF4-3:2 | SEQ5063 | 4.E−02 | 0.7 |
| FTD | lnc-ESRRB-3:1 | SEQ4912 | 9.E−04 | 0.7 | DLB | lnc-TNIP2-1:1 | SEQ4845 | 9.E−04 | 1.4 |
| MCI | lnc-EVL-6:10 | SEQ4872 | 1.E−04 | 1.7 | All AD | lnc-TNRC6A-3:2 | SEQ5831 | 3.E−02 | 1.2 |
| DLB | lnc-EVL-6:10 | SEQ4872 | 9.E−04 | 1.7 | MCI | lnc-TNRC6C-3:1 | SEQ5627 | 2.E−05 | 1.9 |
| FTD | lnc-EVPL-1:1 | SEQ4064 | 1.E−04 | 0.5 | DLB | lnc-TNRC6C-3:1 | SEQ5627 | 2.E−04 | 1.7 |
| All AD | lnc-EVPL-1:1 | SEQ4064 | 5.E−03 | 0.6 | FTD | lnc-TOB1-4:1 | SEQ5647 | 1.E−04 | 0.7 |
| miAD | lnc-EVPL-1:1 | SEQ4064 | 7.E−03 | 0.6 | MCI | lnc-TOB2-2:1 | SEQ3968 | 2.E−04 | 1.4 |
| msAD | lnc-EVPL-1:1 | SEQ4064 | 2.E−02 | 0.7 | DLB | lnc-TOB2-2:1 | SEQ3968 | 2.E−03 | 1.4 |
| DLB | lnc-EVX1-15:1 | SEQ2412 | 4.E−05 | 1.3 | msAD | lnc-TOB2-2:1 | SEQ3968 | 2.E−02 | 1.2 |
| DLB | lnc-EVX2-8:1 | SEQ4082 | 2.E−04 | 1.7 | All AD | lnc-TOMM20-2:22 | SEQ5835 | 4.E−02 | 0.7 |
| miAD | lnc-EVX2-8:1 | SEQ4082 | 1.E−02 | 1.3 | DLB | lnc-TOMM22-2:2 | SEQ4766 | 9.E−04 | 1.4 |
| All AD | lnc-EVX2-8:1 | SEQ4082 | 3.E−02 | 1.2 | MCI | lnc-TOMM22-2:2 | SEQ4766 | 1.E−03 | 1.5 |
| All AD | lnc-EXOSC1-1:2 | SEQ4611 | 5.E−02 | 0.8 | DLB | lnc-TOR1AIP1-2:1 | SEQ2565 | 1.E−03 | 1.7 |
| FTD | lnc-EXOSC6-1:2 | SEQ3300 | 5.E−05 | 0.6 | FTD | lnc-TOX4-4:2 | SEQ2696 | 4.E−05 | 0.6 |
| DLB | lnc-EXOSC6-1:6 | SEQ5218 | 4.E−04 | 2.4 | DLB | lnc-TOX4-4:2 | SEQ2696 | 6.E−04 | 0.7 |
| MCI | lnc-EXOSC6-1:6 | SEQ5218 | 5.E−04 | 2.4 | miAD | lnc-TOX4-4:2 | SEQ2696 | 5.E−03 | 0.7 |
| All AD | lnc-EXOSC8-4:1 | SEQ4615 | 5.E−02 | 0.7 | All AD | lnc-TOX4-4:2 | SEQ2696 | 3.E−02 | 0.8 |
| FTD | lnc-EXTL2-2:1 | SEQ5225 | 5.E−04 | 0.6 | All AD | lnc-TP53BP2-8:2 | SEQ5838 | 3.E−02 | 0.7 |
| FTD | lnc-F2RL2-1:2 | SEQ3827 | 3.E−06 | 0.5 | MCI | lnc-TP53TG5-3:1 | SEQ4914 | 6.E−06 | 1.9 |
| miAD | lnc-F2RL2-1:2 | SEQ3827 | 9.E−03 | 0.7 | DLB | lnc-TP53TG5-3:1 | SEQ4914 | 4.E−05 | 1.8 |
| All AD | lnc-F2RL2-1:2 | SEQ3827 | 9.E−03 | 0.7 | FTD | lnc-TP53TG5-3:1 | SEQ4914 | 9.E−04 | 1.4 |
| msAD | lnc-F2RL2-1:2 | SEQ3827 | 4.E−02 | 0.8 | DLB | lnc-TPBGL-2:1 | SEQ4424 | 2.E−03 | 1.5 |
| DLB | lnc-FAAP100-2:1 | SEQ2299 | 5.E−04 | 1.3 | MCI | lnc-TPBGL-2:1 | SEQ4424 | 2.E−03 | 1.5 |
| MCI | lnc-FAAP20-2:1 | SEQ2889 | 4.E−04 | 1.7 | DLB | lnc-TPCN1-1:1 | SEQ4584 | 4.E−04 | 1.6 |
| DLB | lnc-FAAP20-2:1 | SEQ2889 | 5.E−04 | 1.7 | MCI | lnc-TPCN1-1:1 | SEQ4584 | 2.E−03 | 1.5 |
| DLB | lnc-FAHD2B-1:1 | SEQ5339 | 4.E−04 | 1.8 | FTD | lnc-TRAF5-8:1 | SEQ5763 | 8.E−05 | 0.6 |
| DLB | lnc-FAHD2B-1:2 | SEQ2915 | 2.E−04 | 1.9 | All AD | lnc-TRAF6-3:1 | SEQ5842 | 4.E−02 | 0.8 |
| All AD | lnc-FAM106A-2:10 | SEQ2240 | 7.E−03 | 0.5 | DLB | lnc-TRAPPC2L-2:4 | SEQ4777 | 1.E−03 | 1.6 |
| miAD | lnc-FAM106A-2:10 | SEQ2240 | 8.E−03 | 0.5 | MCI | lnc-TRDMT1-5:1 | SEQ4984 | 9.E−05 | 3.6 |
| msAD | lnc-FAM106A-2:10 | SEQ2240 | 3.E−02 | 0.6 | FTD | lnc-TRDMT1-5:1 | SEQ4984 | 2.E−04 | 2.5 |
| All AD | lnc-FAM106A-2:7 | SEQ4623 | 3.E−02 | 0.6 | DLB | lnc-TRDMT1-5:1 | SEQ4984 | 8.E−04 | 3.1 |
| DLB | lnc-FAM111B-1:3 | SEQ4406 | 2.E−03 | 1.3 | All AD | lnc-TRDMT1-5:1 | SEQ4984 | 4.E−02 | 1.4 |
| FTD | lnc-FAM114A1-1:1 | SEQ4326 | 6.E−08 | 0.5 | FTD | lnc-TREML2-4:1 | SEQ4995 | 8.E−04 | 0.6 |
| MCI | lnc-FAM114A1-1:1 | SEQ4326 | 7.E−04 | 0.6 | DLB | lnc-TREX1-10:5 | SEQ5200 | 5.E−04 | 1.7 |
| miAD | lnc-FAM114A1-1:1 | SEQ4326 | 6.E−03 | 0.6 | miAD | lnc-TREX1-5:1 | SEQ3723 | 1.E−02 | 0.8 |
| All AD | lnc-FAM114A1-1:1 | SEQ4326 | 1.E−02 | 0.7 | All AD | lnc-TREX1-5:1 | SEQ3723 | 3.E−02 | 0.8 |
| All AD | lnc-FAM126B-1:2 | SEQ3668 | 2.E−02 | 0.8 | msAD | lnc-TREX1-5:1 | SEQ3723 | 4.E−02 | 0.8 |
| msAD | lnc-FAM126B-1:2 | SEQ3668 | 5.E−02 | 0.8 | FTD | lnc-TRIL-3:1 | SEQ4347 | 2.E−04 | 0.5 |
| FTD | lnc-FAM131B-2:1 | SEQ3679 | 8.E−05 | 0.5 | miAD | lnc-TRIL-3:1 | SEQ4347 | 5.E−03 | 0.6 |
| miAD | lnc-FAM131B-2:1 | SEQ3679 | 1.E−02 | 0.6 | All AD | lnc-TRIL-3:1 | SEQ4347 | 3.E−02 | 0.7 |
| All AD | lnc-FAM131B-2:1 | SEQ3679 | 1.E−02 | 0.6 | miAD | lnc-TRIL-3:2 | SEQ4206 | 1.E−02 | 0.7 |
| msAD | lnc-FAM131B-2:1 | SEQ3679 | 5.E−02 | 0.6 | All AD | lnc-TRIL-3:2 | SEQ4206 | 2.E−02 | 0.7 |
| FTD | lnc-FAM133B-1:1 | SEQ5226 | 5.E−04 | 0.6 | FTD | lnc-TRIM23-1:1 | SEQ5102 | 1.E−08 | 0.5 |
| FTD | lnc-FAM13C-5:1 | SEQ4372 | 7.E−05 | 0.6 | MCI | lnc-TRIM23-1:1 | SEQ5102 | 6.E−04 | 0.5 |
| miAD | lnc-FAM13C-5:1 | SEQ4372 | 4.E−03 | 0.7 | All AD | lnc-TRIM25-1:1 | SEQ5849 | 1.E−02 | 0.7 |

TABLE 10-continued 2847 whole blood (Paxgene RNA tube) lncRNAs differentially expressed in
MCI group or mild AD group or moderate-to-severe AD group or both of these
AD groups or FTD group or DLB group as compared to healthy control group.

| Group | lncRNA | SEQ | p-value | FC | Group | lncRNA | SEQ | p-value | FC |
|---|---|---|---|---|---|---|---|---|---|
| All AD | lnc-FAM13C-5:1 | SEQ4372 | 9.E-03 | 0.7 | DLB | lnc-TRIM26-2:27 | SEQ4644 | 1.E-03 | 1.6 |
| DLB | lnc-FAM156A-1:2 | SEQ5434 | 3.E-04 | 1.4 | MCI | lnc-TRIM26-2:53 | SEQ5649 | 1.E-04 | 0.1 |
| DLB | lnc-FAM156A-3:5 | SEQ5881 | 3.E-03 | 1.7 | DLB | lnc-TRIM28-13:2 | SEQ3581 | 2.E-03 | 1.4 |
| FTD | lnc-FAM162A-2:12 | SEQ4634 | 7.E-05 | 0.7 | DLB | lnc-TRIM39-2:1 | SEQ5205 | 5.E-04 | 1.7 |
| All AD | lnc-FAM162A-2:12 | SEQ4634 | 4.E-02 | 0.8 | FTD | lnc-TRIM55-1:14 | SEQ4916 | 9.E-04 | 1.8 |
| FTD | lnc-FAM162A-2:6 | SEQ6002 | 8.E-08 | 0.3 | FTD | lnc-TRIM59-1:1 | SEQ2766 | 8.E-07 | 0.6 |
| FTD | lnc-FAM167A-5:2 | SEQ5898 | 2.E-05 | 0.5 | miAD | lnc-TRIM59-1:1 | SEQ2766 | 1.E-02 | 0.7 |
| DLB | lnc-FAM167B-2:1 | SEQ4453 | 2.E-03 | 1.7 | All AD | lnc-TRIM59-1:1 | SEQ2766 | 2.E-02 | 0.8 |
| DLB | lnc-FAM168A-1:1 | SEQ4858 | 9.E-04 | 1.5 | FTD | lnc-TRIM61-6:1 | SEQ5220 | 2.E-04 | 2.3 |
| FTD | lnc-FAM174A-6:1 | SEQ4639 | 5.E-05 | 0.5 | MCI | lnc-TRIM61-6:1 | SEQ5220 | 5.E-04 | 2.9 |
| All AD | lnc-FAM174A-6:1 | SEQ4639 | 3.E-02 | 0.7 | DLB | lnc-TRIM62-2:1 | SEQ5263 | 5.E-04 | 1.6 |
| All AD | lnc-FAM174A-6:6 | SEQ4640 | 5.E-02 | 0.6 | FTD | lnc-TRIM69-2:8 | SEQ4814 | 1.E-03 | 0.7 |
| FTD | lnc-FAM177B-1:1 | SEQ3388 | 1.E-04 | 0.6 | MCI | lnc-TRIM74-1:6 | SEQ4254 | 7.E-06 | 3.3 |
| miAD | lnc-FAM177B-1:1 | SEQ3388 | 8.E-03 | 0.7 | DLB | lnc-TRIM74-1:6 | SEQ4254 | 2.E-03 | 2.0 |
| All AD | lnc-FAM177B-1:1 | SEQ3388 | 1.E-02 | 0.8 | All AD | lnc-TRIM74-1:6 | SEQ4254 | 6.E-03 | 1.6 |
| DLB | lnc-FAM184B-1:2 | SEQ5791 | 6.E-05 | 1.5 | msAD | lnc-TRIM74-1:6 | SEQ4254 | 9.E-03 | 1.6 |
| DLB | lnc-FAM187B-3:1 | SEQ5109 | 6.E-04 | 1.2 | FTD | lnc-TRMT10B-4:1 | SEQ5609 | 3.E-07 | 0.5 |
| FTD | lnc-FAM192A-3:1 | SEQ4170 | 4.E-05 | 0.6 | MCI | lnc-TRMT10B-4:1 | SEQ5609 | 2.E-04 | 0.6 |
| All AD | lnc-FAM192A-3:1 | SEQ4170 | 3.E-03 | 0.6 | All AD | lnc-TRMT10B-4:1 | SEQ5609 | 2.E-02 | 0.8 |
| miAD | lnc-FAM192A-3:1 | SEQ4170 | 4.E-03 | 0.6 | FTD | lnc-TRMT10C-3:1 | SEQ4398 | 1.E-07 | 0.5 |
| msAD | lnc-FAM192A-3:1 | SEQ4170 | 1.E-02 | 0.6 | MCI | lnc-TRMT10C-3:1 | SEQ4398 | 2.E-03 | 0.7 |
| msAD | lnc-FAM192A-4:1 | SEQ4298 | 7.E-03 | 0.7 | All AD | lnc-TRMT10C-3:1 | SEQ4398 | 2.E-02 | 0.7 |
| All AD | lnc-FAM192A-4:1 | SEQ4298 | 2.E-02 | 0.7 | FTD | lnc-TRMT10C-4:1 | SEQ4992 | 8.E-04 | 0.6 |
| msAD | lnc-FAM192A-4:3 | SEQ4603 | 1.E-03 | 0.7 | MCI | lnc-TRMT1-1:1 | SEQ4158 | 7.E-04 | 1.3 |
| All AD | lnc-FAM192A-4:3 | SEQ4603 | 5.E-03 | 0.7 | miAD | lnc-TRMT1-1:1 | SEQ4158 | 1.E-02 | 1.1 |
| msAD | lnc-FAM192A-4:5 | SEQ4150 | 1.E-02 | 0.7 | All AD | lnc-TRMT1-1:1 | SEQ4158 | 2.E-02 | 1.1 |
| All AD | lnc-FAM192A-4:5 | SEQ4150 | 2.E-02 | 0.7 | All AD | lnc-TRMT61B-5:3 | SEQ5853 | 3.E-02 | 0.8 |
| DLB | lnc-FAM193B-2:1 | SEQ5387 | 3.E-04 | 1.7 | All AD | lnc-TRPC5-3:1 | SEQ5854 | 3.E-02 | 1.2 |
| FTD | lnc-FAM200A-1:1 | SEQ5687 | 1.E-04 | 0.6 | FTD | lnc-TRPC5OS-5:1 | SEQ5597 | 2.E-04 | 0.4 |
| FTD | lnc-FAM200B-3:1 | SEQ3664 | 2.E-04 | 0.7 | DLB | lnc-TRPM5-1:1 | SEQ4867 | 9.E-04 | 1.6 |
| miAD | lnc-FAM200B-3:1 | SEQ3664 | 8.E-03 | 0.7 | DLB | lnc-TRPT1-1:2 | SEQ5701 | 1.E-04 | 1.7 |
| All AD | lnc-FAM200B-3:1 | SEQ3664 | 1.E-02 | 0.7 | DLB | lnc-TRRAP-1:1 | SEQ5570 | 2.E-04 | 1.6 |
| msAD | lnc-FAM200B-3:1 | SEQ3664 | 5.E-02 | 0.7 | DLB | lnc-TRRAP-1:4 | SEQ5571 | 2.E-04 | 1.6 |
| DLB | lnc-FAM207A-7:1 | SEQ5711 | 1.E-04 | 1.9 | MCI | lnc-TRRAP-1:5 | SEQ4747 | 1.E-03 | 1.4 |
| MCI | lnc-FAM208B-5:3 | SEQ3973 | 2.E-05 | 1.6 | DLB | lnc-TRRAP-1:6 | SEQ5628 | 2.E-04 | 1.7 |
| FTD | lnc-FAM208B-5:3 | SEQ3973 | 2.E-05 | 1.5 | FTD | lnc-TSPOAP1-1:1 | SEQ5299 | 4.E-04 | 0.7 |
| DLB | lnc-FAM208B-5:3 | SEQ3973 | 8.E-05 | 1.7 | DLB | lnc-TSPOAP1-1:2 | SEQ5674 | 2.E-05 | 1.8 |
| All AD | lnc-FAM208B-5:3 | SEQ3973 | 2.E-02 | 1.2 | MCI | lnc-TSPOAP1-1:2 | SEQ5674 | 1.E-04 | 1.7 |
| msAD | lnc-FAM208B-5:3 | SEQ3973 | 2.E-02 | 1.2 | DLB | lnc-TSPOAP1-1:4 | SEQ4597 | 2.E-03 | 1.7 |
| FTD | lnc-FAM217A-1:7 | SEQ4988 | 4.E-04 | 0.5 | FTD | lnc-TSPYL5-4:1 | SEQ4804 | 1.E-03 | 0.6 |
| DLB | lnc-FAM231C-7:7 | SEQ5203 | 3.E-04 | 1.7 | All AD | lnc-TSPYL5-4:1 | SEQ4804 | 3.E-02 | 0.7 |
| MCI | lnc-FAM231C-7:7 | SEQ5203 | 5.E-04 | 1.7 | DLB | lnc-TSR3-1:2 | SEQ0339 | 1.E-04 | 1.6 |
| All AD | lnc-FAM3B-3:2 | SEQ4659 | 4.E-02 | 0.8 | MCI | lnc-TSR3-1:2 | SEQ0339 | 3.E-04 | 1.5 |
| All AD | lnc-FAM49B-1:1 | SEQ4660 | 4.E-02 | 0.7 | MCI | lnc-TSSK2-1:1 | SEQ5709 | 4.E-05 | 2.0 |
| FTD | lnc-FAM71D-1:2 | SEQ4895 | 9.E-04 | 0.6 | DLB | lnc-TSSK2-1:1 | SEQ5709 | 1.E-04 | 1.8 |
| DLB | lnc-FAM71E1-2:10 | SEQ5752 | 8.E-05 | 1.5 | DLB | lnc-TSSK3-2:2 | SEQ4428 | 2.E-03 | 1.5 |
| All AD | lnc-FAM71E1-2:9 | SEQ3219 | 1.E-02 | 1.3 | DLB | lnc-TSSK4-3:2 | SEQ5308 | 4.E-04 | 1.4 |
| msAD | lnc-FAM71E1-2:9 | SEQ3219 | 2.E-02 | 1.3 | DLB | lnc-TSSK6-1:2 | SEQ5823 | 2.E-05 | 1.6 |
| miAD | lnc-FAM72B-17:1 | SEQ3884 | 4.E-03 | 0.6 | MCI | lnc-TSSK6-1:2 | SEQ5823 | 5.E-05 | 1.9 |
| All AD | lnc-FAM72B-17:1 | SEQ3884 | 5.E-03 | 0.5 | DLB | lnc-TSTA3-2:1 | SEQ4409 | 2.E-03 | 1.4 |
| msAD | lnc-FAM72B-17:1 | SEQ3884 | 3.E-02 | 0.5 | FTD | lnc-TTC27-10:1 | SEQ5976 | 3.E-06 | 0.6 |
| DLB | lnc-FAM72D-8:1 | SEQ2753 | 3.E-04 | 1.4 | DLB | lnc-TTC4-1:1 | SEQ3776 | 4.E-05 | 1.7 |
| miAD | lnc-FAM84B-20:1 | SEQ3995 | 3.E-03 | 1.4 | msAD | lnc-TTC4-1:1 | SEQ3776 | 4.E-02 | 1.2 |
| All AD | lnc-FAM84B-20:1 | SEQ3995 | 4.E-03 | 1.4 | DLB | lnc-TTC9-3:1 | SEQ5917 | 2.E-05 | 1.7 |
| msAD | lnc-FAM84B-20:1 | SEQ3995 | 2.E-02 | 1.4 | FTD | lnc-TTC9-4:1 | SEQ5224 | 5.E-04 | 0.5 |
| MCI | lnc-FAM84B-21:1 | SEQ4956 | 3.E-04 | 1.5 | DLB | lnc-TUBA1C-1:15 | SEQ4456 | 2.E-03 | 1.8 |
| DLB | lnc-FAM84B-21:1 | SEQ4956 | 8.E-04 | 1.5 | DLB | lnc-TUBA1C-1:8 | SEQ5558 | 2.E-04 | 1.4 |
| DLB | lnc-FAM84B-4:3 | SEQ0083 | 9.E-04 | 1.8 | FTD | lnc-TUBA1C-3:2 | SEQ3773 | 9.E-05 | 0.6 |
| DLB | lnc-FAM84B-6:5 | SEQ4529 | 2.E-03 | 1.7 | miAD | lnc-TUBA1C-3:2 | SEQ3773 | 2.E-03 | 0.6 |
| DLB | lnc-FAM8A1-2:5 | SEQ4622 | 2.E-04 | 1.5 | All AD | lnc-TUBA1C-3:2 | SEQ3773 | 5.E-03 | 0.7 |
| MCI | lnc-FAM8A1-2:5 | SEQ4622 | 1.E-03 | 1.4 | msAD | lnc-TUBA1C-3:2 | SEQ3773 | 4.E-02 | 0.7 |
| DLB | lnc-FAM92A-2:1 | SEQ4503 | 2.E-03 | 1.4 | FTD | lnc-TUBA3C-16:1 | SEQ4801 | 1.E-03 | 0.5 |
| DLB | lnc-FAM92B-4:1 | SEQ5535 | 2.E-04 | 1.7 | DLB | lnc-TUBA3D-1:3 | SEQ4712 | 1.E-03 | 1.5 |
| MCI | lnc-FANCA-3:1 | SEQ4011 | 4.E-05 | 1.5 | All AD | lnc-TUBB2A-7:2 | SEQ3767 | 2.E-02 | 0.8 |
| DLB | lnc-FANCA-3:1 | SEQ4011 | 9.E-04 | 1.6 | msAD | lnc-TUBB2A-7:2 | SEQ3767 | 4.E-02 | 0.8 |
| All AD | lnc-FANCA-3:1 | SEQ4011 | 2.E-02 | 1.2 | All AD | lnc-TUBD1-1:1 | SEQ3961 | 7.E-03 | 0.7 |
| msAD | lnc-FANCA-3:1 | SEQ4011 | 2.E-02 | 1.2 | miAD | lnc-TUBD1-1:1 | SEQ3961 | 8.E-03 | 0.7 |
| DLB | lnc-FANCL-4:1 | SEQ2690 | 7.E-04 | 1.5 | msAD | lnc-TUBD1-1:1 | SEQ3961 | 2.E-02 | 0.8 |
| All AD | lnc-FANCL-4:1 | SEQ2690 | 2.E-02 | 1.2 | MCI | lnc-TUBGCP6-5:4 | SEQ5689 | 9.E-06 | 1.7 |
| msAD | lnc-FANCL-4:1 | SEQ2690 | 3.E-02 | 1.2 | DLB | lnc-TUBGCP6-5:4 | SEQ5689 | 9.E-05 | 1.7 |
| All AD | lnc-FAP-3:1 | SEQ0206 | 2.E-02 | 0.7 | FTD | lnc-TUBGCP6-5:4 | SEQ5689 | 1.E-04 | 1.5 |
| msAD | lnc-FAP-3:1 | SEQ0206 | 4.E-02 | 0.7 | MCI | lnc-TUBGCP6-5:6 | SEQ4865 | 7.E-04 | 1.7 |
| All AD | lnc-FAS-1:1 | SEQ4671 | 3.E-02 | 0.8 | DLB | lnc-TUBGCP6-5:6 | SEQ4865 | 9.E-04 | 1.6 |
| FTD | lnc-FAS-2:2 | SEQ5399 | 3.E-04 | 0.7 | MCI | lnc-TULP2-4:1 | SEQ5890 | 1.E-05 | 1.6 |

TABLE 10-continued 2847 whole blood (Paxgene RNA tube) lncRNAs differentially expressed in
MCI group or mild AD group or moderate-to-severe AD group or both of these
AD groups or FTD group or DLB group as compared to healthy control group.

| Group | lncRNA | SEQ | p-value | FC | Group | lncRNA | SEQ | p-value | FC |
| --- | --- | --- | --- | --- | --- | --- | --- | --- | --- |
| DLB | lnc-FBXL22-1:1 | SEQ3898 | 9.E−04 | 1.4 | DLB | lnc-TULP2-4:1 | SEQ5890 | 2.E−05 | 1.6 |
| MCI | lnc-FBXL22-1:1 | SEQ3898 | 2.E−03 | 1.4 | DLB | lnc-TUSC5-5:2 | SEQ3875 | 1.E−05 | 1.7 |
| All AD | lnc-FBXL22-1:1 | SEQ3898 | 2.E−02 | 1.2 | MCI | lnc-TUSC5-5:2 | SEQ3875 | 1.E−03 | 1.4 |
| msAD | lnc-FBXL22-1:1 | SEQ3898 | 3.E−02 | 1.2 | msAD | lnc-TUSC5-5:2 | SEQ3875 | 3.E−02 | 1.2 |
| DLB | lnc-FBXO11-1:8 | SEQ5237 | 9.E−06 | 1.9 | All AD | lnc-TUSC5-5:2 | SEQ3875 | 4.E−02 | 1.2 |
| MCI | lnc-FBXO11-1:8 | SEQ5237 | 9.E−05 | 1.6 | DLB | lnc-TVP23A-6:1 | SEQ5530 | 2.E−04 | 1.6 |
| FTD | lnc-FBXO11-1:8 | SEQ5237 | 5.E−04 | 1.6 | FTD | lnc-TWSG1-1:1 | SEQ5776 | 7.E−05 | 0.5 |
| miAD | lnc-FBXO11-4:1 | SEQ3717 | 7.E−03 | 1.4 | All AD | lnc-TWSG1-1:1 | SEQ5776 | 3.E−02 | 0.7 |
| All AD | lnc-FBXO11-4:1 | SEQ3717 | 9.E−03 | 1.3 | FTD | lnc-TWSG1-2:1 | SEQ0047 | 6.E−10 | 0.4 |
| msAD | lnc-FBXO11-4:1 | SEQ3717 | 4.E−02 | 1.2 | MCI | lnc-TWSG1-2:1 | SEQ0047 | 1.E−05 | 0.4 |
| All AD | lnc-FBXO28-1:10 | SEQ4679 | 5.E−02 | 0.8 | miAD | lnc-TWSG1-2:1 | SEQ0047 | 2.E−03 | 0.6 |
| FTD | lnc-FBXO28-1:13 | SEQ5785 | 4.E−06 | 0.3 | All AD | lnc-TWSG1-2:1 | SEQ0047 | 3.E−02 | 0.6 |
| MCI | lnc-FBXO28-1:13 | SEQ5785 | 6.E−05 | 0.4 | FTD | lnc-TXLNB-3:4 | SEQ5914 | 2.E−05 | 0.5 |
| FTD | lnc-FBXO30-2:1 | SEQ5683 | 1.E−04 | 0.5 | FTD | lnc-TXLNB-3:6 | SEQ5988 | 2.E−06 | 0.4 |
| FTD | lnc-FBXO45-4:1 | SEQ4199 | 3.E−07 | 2.1 | DLB | lnc-TXNRD2-2:1 | SEQ5328 | 1.E−04 | 1.7 |
| MCI | lnc-FBXO45-4:1 | SEQ4199 | 1.E−05 | 2.6 | MCI | lnc-TXNRD2-2:1 | SEQ5328 | 4.E−04 | 1.6 |
| DLB | lnc-FBXO45-4:1 | SEQ4199 | 1.E−04 | 2.1 | DLB | lnc-TYW1-7:8 | SEQ5952 | 7.E−06 | 2.0 |
| miAD | lnc-FBXO45-4:1 | SEQ4199 | 2.E−03 | 1.3 | MCI | lnc-U2AF2-1:4 | SEQ5174 | 3.E−04 | 1.3 |
| All AD | lnc-FBXO45-4:1 | SEQ4199 | 2.E−03 | 1.3 | DLB | lnc-U2AF2-1:4 | SEQ5174 | 1.E−04 | 1.4 |
| msAD | lnc-FBXO45-4:1 | SEQ4199 | 1.E−02 | 1.3 | MCI | lnc-UACA-5:1 | SEQ4784 | 2.E−04 | 1.9 |
| DLB | lnc-FBXO47-1:1 | SEQ4419 | 2.E−03 | 1.4 | DLB | lnc-UACA-5:1 | SEQ4784 | 1.E−03 | 1.7 |
| FTD | lnc-FCAR-1:1 | SEQ3850 | 9.E−05 | 0.6 | FTD | lnc-UAP1-4:1 | SEQ4669 | 5.E−06 | 0.6 |
| All AD | lnc-FCAR-1:1 | SEQ3850 | 1.E−02 | 0.7 | MCI | lnc-UAP1-4:1 | SEQ4669 | 1.E−03 | 0.6 |
| miAD | lnc-FCAR-1:1 | SEQ3850 | 1.E−02 | 0.7 | All AD | lnc-UAP1-4:1 | SEQ4669 | 2.E−02 | 0.8 |
| msAD | lnc-FCAR-1:1 | SEQ3850 | 3.E−02 | 0.7 | DLB | lnc-UBAC1-2:2 | SEQ3540 | 1.E−03 | 2.3 |
| All AD | lnc-FCGR2B-5:1 | SEQ4688 | 3.E−02 | 0.7 | DLB | lnc-UBALD1-1:1 | SEQ5739 | 9.E−05 | 1.9 |
| All AD | lnc-FCGR3A-4:1 | SEQ4689 | 3.E−02 | 0.8 | DLB | lnc-UBAP2L-1:1 | SEQ4401 | 2.E−03 | 1.3 |
| FTD | lnc-FEM1B-4:1 | SEQ2624 | 6.E−10 | 0.3 | DLB | lnc-UBE2D2-2:1 | SEQ4832 | 5.E−05 | 1.6 |
| MCI | lnc-FEM1B-4:1 | SEQ2624 | 9.E−06 | 0.4 | MCI | lnc-UBE2D2-2:1 | SEQ4832 | 9.E−04 | 1.4 |
| All AD | lnc-FEM1B-4:1 | SEQ2624 | 1.E−02 | 0.6 | msAD | lnc-UBL5-1:4 | SEQ3948 | 3.E−02 | 1.2 |
| msAD | lnc-FEM1B-4:1 | SEQ2624 | 2.E−02 | 0.6 | All AD | lnc-UBR2-4:2 | SEQ5873 | 4.E−02 | 0.8 |
| FTD | lnc-FFAR2-1:1 | SEQ4692 | 3.E−05 | 0.6 | DLB | lnc-UCK1-3:2 | SEQ5850 | 4.E−05 | 1.6 |
| All AD | lnc-FFAR2-1:1 | SEQ4692 | 3.E−02 | 0.8 | DLB | lnc-UCP3-2:3 | SEQ3728 | 4.E−05 | 2.2 |
| DLB | lnc-FGF23-5:1 | SEQ2474 | 2.E−04 | 1.5 | MCI | lnc-UCP3-2:3 | SEQ3728 | 9.E−05 | 2.4 |
| DLB | lnc-FGF23-5:3 | SEQ2473 | 2.E−04 | 1.6 | FTD | lnc-UCP3-2:3 | SEQ3728 | 1.E−04 | 1.9 |
| DLB | lnc-FGF9-11:1 | SEQ4915 | 5.E−05 | 1.8 | All AD | lnc-UCP3-2:3 | SEQ3728 | 1.E−02 | 1.3 |
| MCI | lnc-FGF9-11:1 | SEQ4915 | 2.E−04 | 1.7 | msAD | lnc-UCP3-2:3 | SEQ3728 | 4.E−02 | 1.2 |
| FTD | lnc-FGF9-11:1 | SEQ4915 | 9.E−04 | 1.5 | All AD | lnc-UGDH-3:3 | SEQ2526 | 2.E−02 | 0.8 |
| All AD | lnc-FGFBP2-1:2 | SEQ3763 | 2.E−02 | 0.7 | FTD | lnc-UGP2-3:2 | SEQ5158 | 5.E−04 | 0.7 |
| msAD | lnc-FGFBP2-1:2 | SEQ3763 | 4.E−02 | 0.7 | All AD | lnc-UGT3A2-3:1 | SEQ0389 | 1.E−02 | 0.8 |
| MCI | lnc-FGL2-3:1 | SEQ3286 | 5.E−05 | 0.4 | DLB | lnc-ULK4-1:2 | SEQ5565 | 2.E−04 | 1.5 |
| FTD | lnc-FGL2-3:1 | SEQ3286 | 2.E−04 | 0.5 | All AD | lnc-UPK3B-5:5 | SEQ5875 | 4.E−02 | 1.3 |
| DLB | lnc-FGL2-3:1 | SEQ3286 | 9.E−04 | 0.6 | All AD | lnc-UQCC3-1:1 | SEQ3979 | 1.E−02 | 1.2 |
| miAD | lnc-FGL2-3:1 | SEQ3286 | 1.E−02 | 0.7 | msAD | lnc-UQCC3-1:1 | SEQ3979 | 2.E−02 | 1.2 |
| All AD | lnc-FGL2-3:1 | SEQ3286 | 1.E−02 | 0.6 | FTD | lnc-UQCC3-2:1 | SEQ4084 | 2.E−09 | 3.3 |
| msAD | lnc-FGL2-3:1 | SEQ3286 | 4.E−02 | 0.6 | MCI | lnc-UQCC3-2:1 | SEQ4084 | 4.E−05 | 2.3 |
| FTD | lnc-FIGNL1-4:1 | SEQ5548 | 2.E−04 | 0.6 | DLB | lnc-UQCC3-2:1 | SEQ4084 | 2.E−04 | 2.0 |
| FTD | lnc-FILIP1-2:2 | SEQ6005 | 4.E−08 | 0.4 | All AD | lnc-UQCC3-2:1 | SEQ4084 | 6.E−03 | 1.5 |
| DLB | lnc-FKBP6-3:1 | SEQ4501 | 2.E−03 | 1.4 | msAD | lnc-UQCC3-2:1 | SEQ4084 | 1.E−02 | 1.5 |
| DLB | lnc-FLII-1:4 | SEQ4273 | 2.E−07 | 1.8 | miAD | lnc-UQCC3-2:1 | SEQ4084 | 1.E−02 | 1.4 |
| FTD | lnc-FLII-1:4 | SEQ4273 | 3.E−07 | 1.5 | FTD | lnc-UQCRHL-1:4 | SEQ4295 | 1.E−04 | 0.5 |
| MCI | lnc-FLII-1:4 | SEQ4273 | 1.E−06 | 1.7 | miAD | lnc-UQCRHL-1:4 | SEQ4295 | 7.E−03 | 0.6 |
| miAD | lnc-FLII-1:4 | SEQ4273 | 2.E−04 | 1.3 | All AD | lnc-UQCRHL-1:4 | SEQ4295 | 9.E−03 | 0.7 |
| All AD | lnc-FLII-1:4 | SEQ4273 | 6.E−04 | 1.2 | DLB | lnc-URGCP-2:11 | SEQ5906 | 2.E−05 | 1.8 |
| msAD | lnc-FLII-1:4 | SEQ4273 | 8.E−03 | 1.2 | MCI | lnc-URGCP-2:8 | SEQ5108 | 6.E−04 | 0.8 |
| FTD | lnc-FLNB-3:1 | SEQ4220 | 3.E−05 | 0.6 | FTD | lnc-URGCP-MRPS24-2:1 | SEQ2667 | 1.E−04 | 0.7 |
| miAD | lnc-FLNB-3:1 | SEQ4220 | 1.E−02 | 0.7 | DLB | lnc-USE1-4:1 | SEQ5041 | 7.E−04 | 1.6 |
| All AD | lnc-FLNB-3:1 | SEQ4220 | 1.E−02 | 0.8 | DLB | lnc-USP10-3:1 | SEQ5320 | 4.E−04 | 1.5 |
| DLB | lnc-FLOT1-1:1 | SEQ4403 | 2.E−05 | 1.5 | msAD | lnc-USP12-9:4 | SEQ4097 | 1.E−02 | 1.3 |
| MCI | lnc-FLOT1-1:1 | SEQ4403 | 1.E−03 | 1.3 | FTD | lnc-USP14-2:3 | SEQ4269 | 6.E−05 | 0.5 |
| DLB | lnc-FLOT1-1:2 | SEQ5889 | 2.E−05 | 1.5 | MCI | lnc-USP14-2:3 | SEQ4269 | 1.E−05 | 0.5 |
| DLB | lnc-FMR1NB-3:1 | SEQ4949 | 8.E−04 | 1.5 | miAD | lnc-USP14-2:3 | SEQ4269 | 8.E−03 | 0.7 |
| DLB | lnc-FNBP1-4:1 | SEQ5121 | 6.E−04 | 1.5 | All AD | lnc-USP14-2:3 | SEQ4269 | 2.E−02 | 0.7 |
| msAD | lnc-FNBP1L-1:12 | SEQ4163 | 2.E−03 | 1.4 | DLB | lnc-USP20-1:1 | SEQ5319 | 4.E−04 | 1.5 |
| All AD | lnc-FNBP1L-1:12 | SEQ4163 | 2.E−03 | 1.4 | FTD | lnc-USP25-1:1 | SEQ4207 | 6.E−05 | 0.6 |
| miAD | lnc-FNBP1L-1:12 | SEQ4163 | 1.E−02 | 1.3 | All AD | lnc-USP25-1:1 | SEQ4207 | 4.E−03 | 0.7 |
| miAD | lnc-FNDC1-9:10 | SEQ3845 | 5.E−03 | 1.4 | msAD | lnc-USP25-1:1 | SEQ4207 | 6.E−03 | 0.7 |
| All AD | lnc-FNDC1-9:10 | SEQ3845 | 6.E−03 | 1.4 | miAD | lnc-USP25-1:1 | SEQ4207 | 1.E−02 | 0.7 |
| msAD | lnc-FNDC1-9:10 | SEQ3845 | 3.E−02 | 1.4 | msAD | lnc-USP3-2:1 | SEQ4010 | 2.E−02 | 0.8 |
| All AD | lnc-FNDC1-9:15 | SEQ4713 | 4.E−02 | 0.8 | All AD | lnc-USP3-2:1 | SEQ4010 | 4.E−02 | 0.8 |
| MCI | lnc-FNDC1-9:22 | SEQ5027 | 2.E−04 | 1.5 | MCI | lnc-USP40-2:1 | SEQ5449 | 4.E−05 | 1.9 |
| DLB | lnc-FNDC1-9:22 | SEQ5027 | 7.E−04 | 1.5 | DLB | lnc-USP40-2:1 | SEQ5449 | 3.E−04 | 1.7 |
| miAD | lnc-FNDC1-9:3 | SEQ3846 | 5.E−03 | 1.4 | DLB | lnc-USP47-2:1 | SEQ3469 | 1.E−05 | 1.6 |

TABLE 10-continued 2847 whole blood (Paxgene RNA tube) lncRNAs differentially expressed in
MCI group or mild AD group or moderate-to-severe AD group or both of these
AD groups or FTD group or DLB group as compared to healthy control group.

| Group | lncRNA | SEQ | p-value | FC | Group | lncRNA | SEQ | p-value | FC |
|---|---|---|---|---|---|---|---|---|---|
| All AD | lnc-FNDC1-9:3 | SEQ3846 | 6.E-03 | 1.4 | msAD | lnc-USP47-2:1 | SEQ3469 | 1.E-02 | 1.2 |
| msAD | lnc-FNDC1-9:3 | SEQ3846 | 3.E-02 | 1.4 | All AD | lnc-USP47-2:1 | SEQ3469 | 3.E-02 | 1.2 |
| FTD | lnc-FNTA-1:4 | SEQ4476 | 8.E-05 | 0.6 | MCI | lnc-USP53-8:1 | SEQ5737 | 9.E-05 | 1.7 |
| MCI | lnc-FNTA-1:4 | SEQ4476 | 2.E-03 | 0.7 | FTD | lnc-USP53-8:20 | SEQ5805 | 6.E-05 | 0.6 |
| All AD | lnc-FNTA-1:4 | SEQ4476 | 5.E-02 | 0.8 | FTD | lnc-USP53-8:32 | SEQ5801 | 6.E-05 | 0.6 |
| MCI | lnc-FOXD4L5-16:1 | SEQ5462 | 1.E-05 | 2.9 | FTD | lnc-USP53-8:5 | SEQ2668 | 4.E-04 | 0.7 |
| FTD | lnc-FOXD4L5-16:1 | SEQ5462 | 2.E-04 | 2.2 | DLB | lnc-USP6-2:20 | SEQ3027 | 2.E-03 | 1.5 |
| DLB | lnc-FOXD4L5-16:1 | SEQ5462 | 3.E-04 | 2.1 | DLB | lnc-USP6-2:22 | SEQ2832 | 2.E-04 | 1.6 |
| All AD | lnc-FOXD4L5-2:2 | SEQ4718 | 3.E-02 | 0.7 | msAD | lnc-USP9Y-17:1 | SEQ3994 | 2.E-02 | 1.3 |
| All AD | lnc-FOXD4L5-26:1 | SEQ4305 | 1.E-03 | 0.5 | FTD | lnc-UTP23-10:3 | SEQ5718 | 1.E-04 | 0.6 |
| miAD | lnc-FOXD4L5-26:1 | SEQ4305 | 1.E-03 | 0.5 | FTD | lnc-UTP23-11:1 | SEQ4260 | 2.E-04 | 0.6 |
| msAD | lnc-FOXD4L5-26:1 | SEQ4305 | 7.E-03 | 0.5 | miAD | lnc-UTP23-11:1 | SEQ4260 | 9.E-03 | 0.7 |
| miAD | lnc-FOXD4L5-28:1 | SEQ4208 | 1.E-02 | 0.7 | All AD | lnc-UTP23-11:1 | SEQ4260 | 1.E-02 | 0.7 |
| All AD | lnc-FOXD4L5-28:1 | SEQ4208 | 3.E-02 | 0.8 | FTD | lnc-UTP23-11:2 | SEQ3766 | 5.E-05 | 0.6 |
| DLB | lnc-FOXL2NB-4:1 | SEQ4512 | 2.E-03 | 1.5 | All AD | lnc-UTP23-11:2 | SEQ3766 | 2.E-02 | 0.7 |
| MCI | lnc-FPGS-1:3 | SEQ5049 | 6.E-04 | 1.8 | msAD | lnc-UTP23-11:2 | SEQ3766 | 4.E-02 | 0.8 |
| DLB | lnc-FPGS-1:3 | SEQ5049 | 7.E-04 | 1.9 | All AD | lnc-UXS1-3:1 | SEQ4239 | 3.E-03 | 1.2 |
| MCI | lnc-FPGS-2:10 | SEQ4725 | 1.E-03 | 1.9 | msAD | lnc-UXS1-3:1 | SEQ4239 | 6.E-03 | 1.2 |
| All AD | lnc-FRAT1-2:1 | SEQ4723 | 2.E-02 | 0.8 | miAD | lnc-UXS1-3:1 | SEQ4239 | 1.E-02 | 1.2 |
| MCI | lnc-FRMD5-1:1 | SEQ5916 | 6.E-07 | 1.6 | FTD | lnc-UXS1-4:9 | SEQ4323 | 4.E-07 | 2.4 |
| DLB | lnc-FRMD5-1:1 | SEQ5916 | 2.E-05 | 1.5 | MCI | lnc-UXS1-4:9 | SEQ4323 | 7.E-06 | 2.3 |
| DLB | lnc-FSCN1-2:1 | SEQ4958 | 5.E-04 | 1.6 | DLB | lnc-UXS1-4:9 | SEQ4323 | 1.E-04 | 2.1 |
| MCI | lnc-FSCN1-2:1 | SEQ4958 | 8.E-04 | 1.6 | All AD | lnc-UXS1-4:9 | SEQ4323 | 2.E-03 | 1.4 |
| DLB | lnc-FSCN2-1:6 | SEQ5192 | 3.E-06 | 1.9 | miAD | lnc-UXS1-4:9 | SEQ4323 | 3.E-03 | 1.4 |
| FTD | lnc-FSCN2-1:6 | SEQ5192 | 3.E-04 | 1.4 | msAD | lnc-UXS1-4:9 | SEQ4323 | 6.E-03 | 1.4 |
| MCI | lnc-FSCN2-1:6 | SEQ5192 | 5.E-04 | 1.5 | DLB | lnc-VAV2-1:1 | SEQ5517 | 2.E-04 | 1.4 |
| DLB | lnc-FSCN2-3:1 | SEQ4608 | 1.E-03 | 1.3 | All AD | lnc-VGLL4-8:1 | SEQ3978 | 1.E-02 | 0.8 |
| FTD | lnc-FUBP1-2:5 | SEQ4729 | 4.E-05 | 0.5 | msAD | lnc-VGLL4-8:1 | SEQ3978 | 2.E-02 | 0.8 |
| All AD | lnc-FUBP1-2:5 | SEQ4729 | 4.E-02 | 0.7 | DLB | lnc-VHLL-1:1 | SEQ4962 | 8.E-04 | 1.6 |
| All AD | lnc-FZD4-1:6 | SEQ2454 | 3.E-02 | 0.7 | DLB | lnc-VIPR1-1:1 | SEQ4485 | 2.E-03 | 1.4 |
| FTD | lnc-FZD5-1:4 | SEQ5296 | 4.E-04 | 0.7 | miAD | lnc-VMP1-8:1 | SEQ3916 | 6.E-03 | 0.7 |
| DLB | lnc-GADD45B-1:2 | SEQ5496 | 2.E-04 | 1.8 | All AD | lnc-VMP1-8:1 | SEQ3916 | 6.E-03 | 0.7 |
| DLB | lnc-GADD45GIP1-1:1 | SEQ4094 | 5.E-05 | 2.0 | msAD | lnc-VMP1-8:1 | SEQ3916 | 3.E-02 | 0.8 |
| MCI | lnc-GADD45GIP1-1:1 | SEQ4094 | 6.E-05 | 2.0 | DLB | lnc-VN1R2-1:1 | SEQ5042 | 7.E-04 | 1.7 |
| FTD | lnc-GADD45GIP1-1:1 | SEQ4094 | 1.E-04 | 1.6 | All AD | lnc-VPREB1-7:15 | SEQ4198 | 3.E-03 | 1.4 |
| msAD | lnc-GADD45GIP1-1:1 | SEQ4094 | 1.E-02 | 1.2 | msAD | lnc-VPREB1-7:15 | SEQ4198 | 4.E-02 | 1.5 |
| All AD | lnc-GADD45GIP1-1:1 | SEQ4094 | 2.E-02 | 1.2 | miAD | lnc-VPREB1-7:15 | SEQ4198 | 1.E-02 | 1.4 |
| All AD | lnc-GALNT15-6:1 | SEQ3879 | 3.E-02 | 1.3 | FTD | lnc-VPS13B-1:2 | SEQ5887 | 1.E-05 | 0.6 |
| msAD | lnc-GALNT15-6:1 | SEQ3879 | 3.E-02 | 1.3 | All AD | lnc-VPS13B-1:2 | SEQ5887 | 3.E-02 | 0.8 |
| DLB | lnc-GALNTL5-2:10 | SEQ4980 | 8.E-04 | 1.9 | All AD | lnc-VRK1-10:3 | SEQ4112 | 9.E-03 | 0.6 |
| DLB | lnc-GAMT-1:2 | SEQ5378 | 3.E-04 | 1.6 | msAD | lnc-VRK1-10:3 | SEQ4112 | 1.E-02 | 0.7 |
| DLB | lnc-GAMT-4:1 | SEQ4704 | 1.E-03 | 1.5 | DLB | lnc-VRK3-2:4 | SEQ4847 | 9.E-04 | 1.5 |
| DLB | lnc-GAN-1:1 | SEQ4410 | 2.E-03 | 1.4 | FTD | lnc-VSIG10-1:1 | SEQ3871 | 2.E-05 | 0.7 |
| FTD | lnc-GAPDH-2:1 | SEQ5305 | 5.E-07 | 9.E-09 | All AD | lnc-VSIG10-1:1 | SEQ3871 | 3.E-02 | 0.8 |
| MCI | lnc-GAPDH-2:1 | SEQ5305 | 2.E-05 | 5.E-09 | msAD | lnc-VSIG10-1:1 | SEQ3871 | 3.E-02 | 0.8 |
| DLB | lnc-GAPDH-2:1 | SEQ5305 | 4.E-04 | 6.E-09 | miAD | lnc-VSNL1-5:1 | SEQ3597 | 2.E-03 | 1.4 |
| DLB | lnc-GAPDH-3:1 | SEQ5118 | 6.E-05 | 1.6 | All AD | lnc-VSNL1-5:1 | SEQ3597 | 5.E-03 | 1.3 |
| MCI | lnc-GAPDH-3:1 | SEQ5118 | 6.E-05 | 1.5 | msAD | lnc-VSNL1-5:1 | SEQ3597 | 4.E-02 | 1.2 |
| DLB | lnc-GAPDH-3:2 | SEQ4569 | 2.E-03 | 1.4 | DLB | lnc-VSTM2B-9:15 | SEQ5569 | 2.E-04 | 1.6 |
| DLB | lnc-GAPDH-6:1 | SEQ4487 | 2.E-03 | 1.4 | FTD | lnc-VSTM5-1:10 | SEQ4904 | 9.E-04 | 0.7 |
| FTD | lnc-GAPVD1-3:2 | SEQ5786 | 3.E-06 | 0.4 | FTD | lnc-VSTM5-1:13 | SEQ2419 | 8.E-04 | 2.2 |
| MCI | lnc-GAPVD1-3:2 | SEQ5786 | 6.E-04 | 0.5 | DLB | lnc-VSX1-4:1 | SEQ5675 | 1.E-04 | 1.9 |
| DLB | lnc-GAST-2:1 | SEQ4494 | 2.E-03 | 1.4 | FTD | lnc-VTI1B-1:1 | SEQ5590 | 2.E-04 | 0.6 |
| MCI | lnc-GATA5-9:1 | SEQ4488 | 9.E-04 | 1.5 | FTD | lnc-WBP4-2:9 | SEQ2356 | 4.E-04 | 0.7 |
| DLB | lnc-GATA5-9:1 | SEQ4488 | 2.E-03 | 1.4 | All AD | lnc-WBP4-2:9 | SEQ2356 | 3.E-02 | 0.8 |
| DLB | lnc-GATS-3:2 | SEQ5487 | 2.E-04 | 1.6 | FTD | lnc-WDR3-1:1 | SEQ5068 | 7.E-04 | 0.7 |
| FTD | lnc-GBP2-1:2 | SEQ2449 | 3.E-06 | 0.6 | DLB | lnc-WDR4-2:5 | SEQ2874 | 2.E-04 | 1.5 |
| MCI | lnc-GBP2-1:2 | SEQ2449 | 2.E-05 | 0.6 | DLB | lnc-WDR45B-1:2 | SEQ3588 | 3.E-05 | 1.8 |
| All AD | lnc-GBP2-1:2 | SEQ2449 | 3.E-02 | 0.8 | DLB | lnc-WDR77-1:2 | SEQ2553 | 5.E-04 | 1.6 |
| msAD | lnc-GBP2-1:2 | SEQ2449 | 3.E-02 | 0.8 | All AD | lnc-WIPF1-1:1 | SEQ5892 | 4.E-02 | 0.8 |
| FTD | lnc-GBP6-1:1 | SEQ5365 | 3.E-06 | 0.4 | All AD | lnc-WNT2-4:1 | SEQ5893 | 5.E-02 | 0.8 |
| MCI | lnc-GBP6-1:1 | SEQ5365 | 3.E-04 | 0.4 | DLB | lnc-WNT4-2:1 | SEQ4565 | 2.E-03 | 1.4 |
| MCI | lnc-GCDH-3:4 | SEQ5537 | 2.E-04 | 1.8 | FTD | lnc-WRNIP1-13:1 | SEQ5955 | 7.E-06 | 0.5 |
| FTD | lnc-GCGR-1:2 | SEQ2373 | 4.E-05 | 1.5 | FTD | lnc-WWP2-2:1 | SEQ4237 | 1.E-08 | 0.5 |
| DLB | lnc-GCGR-1:2 | SEQ2373 | 9.E-05 | 1.7 | MCI | lnc-WWP2-2:1 | SEQ4237 | 8.E-05 | 0.6 |
| miAD | lnc-GCGR-1:2 | SEQ2373 | 5.E-04 | 1.4 | All AD | lnc-WWP2-2:1 | SEQ4237 | 3.E-03 | 0.7 |
| All AD | lnc-GCGR-1:2 | SEQ2373 | 9.E-04 | 1.3 | miAD | lnc-WWP2-2:1 | SEQ4237 | 4.E-03 | 0.6 |
| MCI | lnc-GCGR-1:2 | SEQ2373 | 9.E-04 | 1.4 | msAD | lnc-WWP2-2:1 | SEQ4237 | 1.E-02 | 0.7 |
| msAD | lnc-GCGR-1:2 | SEQ2373 | 3.E-03 | 1.3 | DLB | lnc-XRCC1-2:1 | SEQ5478 | 2.E-04 | 1.4 |
| All AD | lnc-GCH1-2:4 | SEQ4749 | 4.E-02 | 1.2 | FTD | lnc-XRCC2-13:2 | SEQ5151 | 5.E-04 | 0.6 |
| DLB | lnc-GCN1-3:1 | SEQ3301 | 3.E-04 | 1.5 | DLB | lnc-XRCC3-1:1 | SEQ4763 | 1.E-03 | 1.5 |
| MCI | lnc-GCNT1-7:1 | SEQ4751 | 7.E-06 | 3.0 | DLB | lnc-XRCC3-1:2 | SEQ5437 | 3.E-04 | 1.5 |
| DLB | lnc-GCNT1-7:1 | SEQ4751 | 3.E-04 | 2.5 | FTD | lnc-XXYLT1-5:1 | SEQ0221 | 1.E-06 | 0.5 |
| FTD | lnc-GCNT1-7:1 | SEQ4751 | 6.E-04 | 2.1 | miAD | lnc-XXYLT1-5:1 | SEQ0221 | 5.E-04 | 0.6 |

TABLE 10-continued 2847 whole blood (Paxgene RNA tube) lncRNAs differentially expressed in
MCI group or mild AD group or moderate-to-severe AD group or both of these
AD groups or FTD group or DLB group as compared to healthy control group.

| Group | lncRNA | SEQ | p-value | FC | Group | lncRNA | SEQ | p-value | FC |
|---|---|---|---|---|---|---|---|---|---|
| All AD | lnc-GCNT1-7:1 | SEQ4751 | 3.E-02 | 1.4 | All AD | lnc-XXYLT1-5:1 | SEQ0221 | 2.E-03 | 0.7 |
| MCI | lnc-GDE1-1:5 | SEQ4590 | 2.E-03 | 1.6 | msAD | lnc-XXYLT1-5:1 | SEQ0221 | 4.E-02 | 0.7 |
| DLB | lnc-GDI1-1:1 | SEQ4743 | 1.E-03 | 1.4 | DLB | lnc-YIF1A-1:1 | SEQ5935 | 1.E-05 | 1.7 |
| MCI | lnc-GEMIN4-6:1 | SEQ4080 | 6.E-04 | 1.4 | DLB | lnc-YIF1B-1:1 | SEQ5461 | 3.E-04 | 2.1 |
| miAD | lnc-GEMIN4-6:1 | SEQ4080 | 1.E-02 | 1.2 | DLB | lnc-YPEL5-5:1 | SEQ0750 | 1.E-04 | 1.7 |
| All AD | lnc-GEMIN4-6:1 | SEQ4080 | 1.E-02 | 1.2 | MCI | lnc-YPEL5-5:1 | SEQ0750 | 6.E-04 | 1.5 |
| DLB | lnc-GGCT-1:31 | SEQ5630 | 2.E-04 | 1.7 | All AD | lnc-YPEL5-5:1 | SEQ0750 | 4.E-02 | 1.2 |
| DLB | lnc-GGCT-1:4 | SEQ5331 | 4.E-04 | 1.7 | FTD | lnc-YTHDF3-4:1 | SEQ6008 | 8.E-09 | 0.4 |
| FTD | lnc-GGCT-1:64 | SEQ4991 | 8.E-04 | 0.6 | FTD | lnc-YWHAZ-2:1 | SEQ5410 | 3.E-04 | 0.6 |
| FTD | lnc-GGCT-1:81 | SEQ5804 | 6.E-05 | 0.6 | All AD | lnc-YWHAZ-2:1 | SEQ5410 | 4.E-02 | 0.8 |
| FTD | lnc-GGCT-1:82 | SEQ5803 | 6.E-05 | 0.6 | DLB | lnc-YY1-1:2 | SEQ4981 | 8.E-04 | 2.0 |
| DLB | lnc-GHRL-4:2 | SEQ4753 | 2.E-04 | 1.6 | msAD | lnc-YY1AP1-2:1 | SEQ3501 | 8.E-03 | 0.7 |
| MCI | lnc-GHRL-4:2 | SEQ4753 | 1.E-03 | 1.4 | All AD | lnc-YY1AP1-2:1 | SEQ3501 | 2.E-02 | 0.8 |
| miAD | lnc-GHSR-1:1 | SEQ4221 | 1.E-02 | 0.7 | DLB | lnc-YY1AP1-3:1 | SEQ5617 | 2.E-04 | 1.5 |
| All AD | lnc-GHSR-1:1 | SEQ4221 | 2.E-02 | 0.8 | FTD | lnc-ZADH2-3:1 | SEQ5232 | 5.E-04 | 0.7 |
| MCI | lnc-GIMAP5-1:1 | SEQ3302 | 1.E-04 | 1.5 | msAD | lnc-ZBED4-2:1 | SEQ3863 | 3.E-02 | 1.4 |
| DLB | lnc-GIMAP5-1:1 | SEQ3302 | 6.E-04 | 1.4 | msAD | lnc-ZBTB2-7:1 | SEQ3675 | 5.E-02 | 1.4 |
| FTD | lnc-GIMAP7-1:1 | SEQ3984 | 2.E-10 | 0.3 | DLB | lnc-ZBTB46-2:2 | SEQ5242 | 5.E-04 | 1.4 |
| MCI | lnc-GIMAP7-1:1 | SEQ3984 | 6.E-05 | 0.3 | DLB | lnc-ZBTB46-2:3 | SEQ5111 | 6.E-04 | 1.4 |
| All AD | lnc-GIMAP7-1:1 | SEQ3984 | 9.E-03 | 0.6 | FTD | lnc-ZBTB7C-10:1 | SEQ5298 | 4.E-04 | 0.7 |
| miAD | lnc-GIMAP7-1:1 | SEQ3984 | 1.E-02 | 0.6 | MCI | lnc-ZC2HC1C-3:1 | SEQ3856 | 5.E-04 | 1.3 |
| msAD | lnc-GIMAP7-1:1 | SEQ3984 | 2.E-02 | 0.6 | DLB | lnc-ZC2HC1C-3:1 | SEQ3856 | 8.E-04 | 1.3 |
| All AD | lnc-GK5-7:1 | SEQ4767 | 4.E-02 | 0.8 | All AD | lnc-ZC2HC1C-3:1 | SEQ3856 | 2.E-02 | 1.1 |
| DLB | lnc-GLB1-2:1 | SEQ4570 | 1.E-03 | 1.6 | msAD | lnc-ZC2HC1C-3:1 | SEQ3856 | 3.E-02 | 1.1 |
| MCI | lnc-GLB1-2:1 | SEQ4570 | 2.E-03 | 1.5 | DLB | lnc-ZC3H11A-1:3 | SEQ5140 | 6.E-04 | 1.8 |
| DLB | lnc-GLDC-6:1 | SEQ3965 | 2.E-03 | 1.5 | MCI | lnc-ZC3H8-7:2 | SEQ3951 | 4.E-05 | 1.7 |
| msAD | lnc-GLDC-6:1 | SEQ3965 | 2.E-02 | 1.2 | DLB | lnc-ZC3H8-7:2 | SEQ3951 | 8.E-05 | 1.8 |
| All AD | lnc-GLDC-6:1 | SEQ3965 | 3.E-02 | 1.2 | FTD | lnc-ZC3H8-7:2 | SEQ3951 | 2.E-04 | 1.6 |
| DLB | lnc-GLG1-1:1 | SEQ5442 | 3.E-04 | 1.6 | All AD | lnc-ZC3H8-7:2 | SEQ3951 | 8.E-03 | 1.3 |
| DLB | lnc-GLOD4-2:2 | SEQ4773 | 5.E-04 | 1.7 | miAD | lnc-ZC3H8-7:2 | SEQ3951 | 1.E-02 | 1.3 |
| All AD | lnc-GLOD4-2:2 | SEQ4773 | 4.E-02 | 1.2 | msAD | lnc-ZC3H8-7:2 | SEQ3951 | 3.E-02 | 1.3 |
| DLB | lnc-GLOD4-3:1 | SEQ2673 | 8.E-05 | 1.6 | DLB | lnc-ZC3HC1-4:1 | SEQ2731 | 1.E-03 | 1.4 |
| FTD | lnc-GLRX5-7:1 | SEQ5602 | 2.E-04 | 0.6 | FTD | lnc-ZCCHC13-4:1 | SEQ4168 | 3.E-11 | 5.E-03 |
| FTD | lnc-GMNN-5:1 | SEQ5598 | 2.E-04 | 0.6 | MCI | lnc-ZCCHC13-4:1 | SEQ4168 | 9.E-06 | 6.E-03 |
| FTD | lnc-GMNN-5:2 | SEQ5087 | 6.E-04 | 0.6 | DLB | lnc-ZCCHC13-4:1 | SEQ4168 | 7.E-04 | 9.E-03 |
| FTD | lnc-GMPR2-1:1 | SEQ5666 | 3.E-07 | 1.7 | All AD | lnc-ZCCHC13-4:1 | SEQ4168 | 3.E-03 | 1.E-02 |
| MCI | lnc-GMPR2-1:1 | SEQ5666 | 2.E-06 | 1.8 | miAD | lnc-ZCCHC13-4:1 | SEQ4168 | 4.E-03 | 1.E-02 |
| DLB | lnc-GMPR2-1:1 | SEQ5666 | 1.E-04 | 1.6 | msAD | lnc-ZCCHC13-4:1 | SEQ4168 | 1.E-02 | 1.E-02 |
| DLB | lnc-GNA11-3:1 | SEQ2681 | 2.E-04 | 1.6 | DLB | lnc-ZCCHC24-8:1 | SEQ5905 | 2.E-05 | 1.7 |
| miAD | lnc-GNA11-3:1 | SEQ2681 | 3.E-03 | 1.3 | DLB | lnc-ZCCHC7-2:12 | SEQ3490 | 1.E-03 | 2.0 |
| All AD | lnc-GNA11-3:1 | SEQ2681 | 5.E-03 | 1.2 | DLB | lnc-ZCCHC7-2:22 | SEQ3657 | 4.E-05 | 4.6 |
| msAD | lnc-GNA11-3:1 | SEQ2681 | 3.E-02 | 1.2 | MCI | lnc-ZCCHC7-2:22 | SEQ3657 | 1.E-04 | 4.0 |
| DLB | lnc-GNA11-3:2 | SEQ3399 | 2.E-03 | 1.4 | FTD | lnc-ZCCHC7-2:22 | SEQ3657 | 7.E-04 | 2.8 |
| FTD | lnc-GNA14-3:1 | SEQ2572 | 1.E-06 | 0.6 | All AD | lnc-ZCCHC7-2:22 | SEQ3657 | 2.E-02 | 1.5 |
| All AD | lnc-GNA14-3:1 | SEQ2572 | 5.E-02 | 0.7 | msAD | lnc-ZCCHC7-2:22 | SEQ3657 | 5.E-02 | 1.4 |
| DLB | lnc-GNAT2-1:1 | SEQ4948 | 8.E-04 | 1.5 | MCI | lnc-ZCCHC7-2:24 | SEQ2279 | 3.E-04 | 0.5 |
| FTD | lnc-GNB4-1:1 | SEQ4783 | 3.E-05 | 0.5 | FTD | lnc-ZCCHC7-2:24 | SEQ2279 | 4.E-04 | 0.5 |
| MCI | lnc-GNB4-1:1 | SEQ4783 | 3.E-04 | 0.5 | DLB | lnc-ZFP57-11:1 | SEQ4678 | 8.E-04 | 1.4 |
| All AD | lnc-GNB4-1:1 | SEQ4783 | 2.E-02 | 0.7 | MCI | lnc-ZFP57-11:1 | SEQ4678 | 1.E-03 | 1.3 |
| DLB | lnc-GOLGA8J-4:1 | SEQ3857 | 3.E-05 | 1.4 | DLB | lnc-ZFYVE21-2:1 | SEQ5215 | 3.E-04 | 1.9 |
| All AD | lnc-GOLGA8J-4:1 | SEQ3857 | 2.E-02 | 1.1 | MCI | lnc-ZFYVE21-2:1 | SEQ5215 | 5.E-04 | 2.0 |
| msAD | lnc-GOLGA8J-4:1 | SEQ3857 | 3.E-02 | 1.1 | All AD | lnc-ZGLP1-4:1 | SEQ3935 | 9.E-03 | 0.7 |
| FTD | lnc-GOLGA80-1:1 | SEQ4908 | 9.E-04 | 0.7 | miAD | lnc-ZGLP1-4:1 | SEQ3935 | 1.E-02 | 0.7 |
| DLB | lnc-GPAT4-2:2 | SEQ2763 | 1.E-04 | 1.5 | msAD | lnc-ZGLP1-4:1 | SEQ3935 | 3.E-02 | 0.8 |
| FTD | lnc-GPBP1L1-1:8 | SEQ2745 | 1.E-08 | 0.4 | FTD | lnc-ZMAT3-4:1 | SEQ5154 | 5.E-04 | 0.6 |
| MCI | lnc-GPBP1L1-1:8 | SEQ2745 | 2.E-05 | 0.5 | DLB | lnc-ZMYM4-3:2 | SEQ4023 | 2.E-04 | 1.8 |
| All AD | lnc-GPBP1L1-1:8 | SEQ2745 | 3.E-02 | 0.7 | MCI | lnc-ZMYM4-3:2 | SEQ4023 | 1.E-03 | 1.5 |
| All AD | lnc-GPD2-1:3 | SEQ4038 | 1.E-02 | 1.4 | All AD | lnc-ZMYM4-3:2 | SEQ4023 | 1.E-02 | 1.3 |
| msAD | lnc-GPD2-1:3 | SEQ4038 | 2.E-02 | 1.5 | msAD | lnc-ZMYM4-3:2 | SEQ4023 | 2.E-02 | 1.3 |
| MCI | lnc-GPR137C-1:1 | SEQ4790 | 3.E-06 | 0.5 | DLB | lnc-ZMYND19-1:6 | SEQ4936 | 8.E-04 | 1.4 |
| FTD | lnc-GPR137C-1:1 | SEQ4790 | 1.E-05 | 0.5 | DLB | lnc-ZNF100-7:1 | SEQ5333 | 4.E-04 | 1.7 |
| All AD | lnc-GPR137C-1:1 | SEQ4790 | 4.E-02 | 0.8 | MCI | lnc-ZNF131-1:16 | SEQ4589 | 2.E-03 | 1.6 |
| miAD | lnc-GPR141-2:1 | SEQ4049 | 2.E-03 | 0.6 | DLB | lnc-ZNF131-1:24 | SEQ3221 | 4.E-04 | 1.7 |
| All AD | lnc-GPR141-2:1 | SEQ4049 | 3.E-03 | 0.7 | DLB | lnc-ZNF131-2:5 | SEQ5730 | 9.E-05 | 1.5 |
| msAD | lnc-GPR141-2:1 | SEQ4049 | 2.E-02 | 0.7 | DLB | lnc-ZNF132-1:2 | SEQ4976 | 8.E-04 | 1.7 |
| FTD | lnc-GPR141-3:1 | SEQ4382 | 8.E-08 | 0.4 | DLB | lnc-ZNF174-1:13 | SEQ5117 | 6.E-04 | 1.4 |
| MCI | lnc-GPR141-3:1 | SEQ4382 | 4.E-04 | 0.5 | DLB | lnc-ZNF212-2:2 | SEQ5271 | 5.E-04 | 1.7 |
| All AD | lnc-GPR141-3:1 | SEQ4382 | 1.E-03 | 0.5 | DLB | lnc-ZNF217-5:1 | SEQ5907 | 2.E-05 | 1.8 |
| miAD | lnc-GPR141-3:1 | SEQ4382 | 3.E-03 | 0.5 | MCI | lnc-ZNF2-2:1 | SEQ5052 | 7.E-04 | 2.2 |
| msAD | lnc-GPR141-3:1 | SEQ4382 | 3.E-03 | 0.6 | MCI | lnc-ZNF236-6:3 | SEQ5045 | 7.E-04 | 1.8 |
| FTD | lnc-GPR160-1:1 | SEQ5901 | 2.E-05 | 0.6 | DLB | lnc-ZNF236-9:4 | SEQ5268 | 5.E-04 | 1.6 |
| FTD | lnc-GPR161-4:1 | SEQ0070 | 7.E-05 | 0.5 | DLB | lnc-ZNF266-2:1 | SEQ4502 | 3.E-04 | 1.6 |
| All AD | lnc-GPR161-4:1 | SEQ0070 | 5.E-02 | 0.7 | MCI | lnc-ZNF266-2:1 | SEQ4502 | 2.E-03 | 1.4 |
| All AD | lnc-GPR183-5:6 | SEQ4068 | 1.E-02 | 0.6 | All AD | lnc-ZNF273-4:3 | SEQ5909 | 4.E-02 | 0.8 |

TABLE 10-continued 2847 whole blood (Paxgene RNA tube) lncRNAs differentially expressed in
MCI group or mild AD group or moderate-to-severe AD group or both of these
AD groups or FTD group or DLB group as compared to healthy control group.

| Group | lncRNA | SEQ | p-value | FC | Group | lncRNA | SEQ | p-value | FC |
|---|---|---|---|---|---|---|---|---|---|
| msAD | lnc-GPR183-5:6 | SEQ4068 | 1.E-02 | 0.6 | FTD | lnc-ZNF284-1:1 | SEQ4778 | 9.E-04 | 1.6 |
| All AD | lnc-GPR183-5:8 | SEQ4796 | 5.E-02 | 0.7 | DLB | lnc-ZNF284-1:1 | SEQ4778 | 1.E-03 | 1.6 |
| FTD | lnc-GPR27-5:1 | SEQ3959 | 2.E-04 | 0.6 | DLB | lnc-ZNF316-2:1 | SEQ4627 | 1.E-03 | 1.4 |
| miAD | lnc-GPR27-5:1 | SEQ3959 | 2.E-03 | 0.5 | FTD | lnc-ZNF330-4:1 | SEQ5770 | 7.E-05 | 0.4 |
| All AD | lnc-GPR27-5:1 | SEQ3959 | 4.E-03 | 0.6 | DLB | lnc-ZNF335-1:1 | SEQ4628 | 3.E-04 | 1.5 |
| msAD | lnc-GPR27-5:1 | SEQ3959 | 2.E-02 | 0.7 | MCI | lnc-ZNF335-1:1 | SEQ4628 | 1.E-03 | 1.4 |
| FTD | lnc-GPR33-14:1 | SEQ0236 | 8.E-07 | 0.5 | DLB | lnc-ZNF33B-4:4 | SEQ4578 | 2.E-03 | 1.5 |
| MCI | lnc-GPR33-14:1 | SEQ0236 | 2.E-05 | 0.5 | FTD | lnc-ZNF362-1:11 | SEQ4346 | 3.E-06 | 0.5 |
| DLB | lnc-GPR37L1-7:4 | SEQ3402 | 2.E-04 | 1.5 | DLB | lnc-ZNF362-1:11 | SEQ4346 | 3.E-04 | 0.7 |
| FTD | lnc-GPR39-9:1 | SEQ2704 | 5.E-06 | 0.5 | miAD | lnc-ZNF362-1:11 | SEQ4346 | 5.E-03 | 0.6 |
| FTD | lnc-GPR83-1:1 | SEQ5543 | 2.E-04 | 0.6 | All AD | lnc-ZNF362-1:11 | SEQ4346 | 1.E-02 | 0.6 |
| DLB | lnc-GPRC5D-3:1 | SEQ4527 | 5.E-04 | 1.9 | FTD | lnc-ZNF362-1:6 | SEQ3910 | 2.E-05 | 0.6 |
| MCI | lnc-GPRC5D-3:1 | SEQ4527 | 2.E-03 | 1.6 | DLB | lnc-ZNF362-1:6 | SEQ3910 | 8.E-04 | 0.8 |
| MCI | lnc-GPRIN2-2:1 | SEQ2453 | 2.E-03 | 0.7 | All AD | lnc-ZNF362-1:6 | SEQ3910 | 8.E-03 | 0.7 |
| DLB | lnc-GPSM1-2:1 | SEQ4554 | 2.E-05 | 1.5 | miAD | lnc-ZNF362-1:6 | SEQ3910 | 8.E-03 | 0.7 |
| MCI | lnc-GPSM1-2:1 | SEQ4554 | 2.E-04 | 1.3 | msAD | lnc-ZNF362-1:6 | SEQ3910 | 3.E-02 | 0.7 |
| DLB | lnc-GPT2-1:5 | SEQ3923 | 2.E-04 | 1.5 | FTD | lnc-ZNF362-1:7 | SEQ4917 | 9.E-04 | 2.5 |
| MCI | lnc-GPT2-1:5 | SEQ3923 | 2.E-04 | 1.5 | DLB | lnc-ZNF362-3:1 | SEQ5119 | 6.E-04 | 1.5 |
| msAD | lnc-GPT2-1:5 | SEQ3923 | 3.E-02 | 1.2 | DLB | lnc-ZNF385C-4:1 | SEQ5816 | 5.E-05 | 1.6 |
| All AD | lnc-GPT2-1:5 | SEQ3923 | 3.E-02 | 1.2 | DLB | lnc-ZNF397-4:1 | SEQ4775 | 1.E-03 | 1.6 |
| DLB | lnc-GPX3-1:1 | SEQ5729 | 9.E-05 | 1.5 | DLB | lnc-ZNF408-5:2 | SEQ5846 | 4.E-05 | 1.5 |
| MCI | lnc-GPX3-1:2 | SEQ5729 | 9.E-05 | 1.6 | All AD | lnc-ZNF408-5:2 | SEQ5846 | 4.E-02 | 1.2 |
| FTD | lnc-GRAP-1:2 | SEQ5870 | 4.E-05 | 2.8 | DLB | lnc-ZNF420-1:1 | SEQ5699 | 1.E-04 | 1.6 |
| DLB | lnc-GRAP2-2:1 | SEQ2429 | 5.E-04 | 1.6 | DLB | lnc-ZNF438-4:2 | SEQ5275 | 2.E-04 | 1.7 |
| DLB | lnc-GRAP-4:1 | SEQ4649 | 1.E-03 | 1.8 | MCI | lnc-ZNF438-4:2 | SEQ5275 | 5.E-04 | 1.7 |
| FTD | lnc-GRAP-7:2 | SEQ3752 | 2.E-06 | 2.1 | DLB | lnc-ZNF439-1:1 | SEQ4525 | 2.E-03 | 1.6 |
| DLB | lnc-GRAP-7:2 | SEQ3752 | 1.E-03 | 1.7 | DLB | lnc-ZNF460-1:1 | SEQ5610 | 2.E-03 | 1.3 |
| All AD | lnc-GRAP-7:2 | SEQ3752 | 4.E-02 | 1.2 | FTD | lnc-ZNF484-1:1 | SEQ5355 | 4.E-04 | 0.6 |
| msAD | lnc-GRAP-7:2 | SEQ3752 | 4.E-02 | 1.2 | FTD | lnc-ZNF516-14:1 | SEQ4259 | 9.E-10 | 0.3 |
| DLB | lnc-GRAPL-1:1 | SEQ3729 | 2.E-03 | 1.8 | MCI | lnc-ZNF516-14:1 | SEQ4259 | 9.E-06 | 0.4 |
| msAD | lnc-GRAPL-1:1 | SEQ3729 | 4.E-02 | 1.3 | miAD | lnc-ZNF516-14:1 | SEQ4259 | 1.E-04 | 0.5 |
| miAD | lnc-GREM1-2:3 | SEQ4143 | 1.E-02 | 0.4 | DLB | lnc-ZNF516-14:1 | SEQ4259 | 5.E-04 | 0.5 |
| DLB | lnc-GRHPR-1:1 | SEQ4500 | 2.E-03 | 1.4 | All AD | lnc-ZNF516-14:1 | SEQ4259 | 5.E-04 | 0.6 |
| MCI | lnc-GRIK2-7:1 | SEQ5652 | 1.E-04 | 0.5 | msAD | lnc-ZNF516-14:1 | SEQ4259 | 9.E-03 | 0.6 |
| DLB | lnc-GRIN3B-3:1 | SEQ5784 | 3.E-06 | 2.0 | FTD | lnc-ZNF518A-1:14 | SEQ5919 | 1.E-05 | 0.6 |
| MCI | lnc-GRIN3B-3:1 | SEQ5784 | 7.E-06 | 1.8 | All AD | lnc-ZNF518A-1:14 | SEQ5919 | 5.E-02 | 0.8 |
| FTD | lnc-GRIN3B-3:1 | SEQ5784 | 7.E-05 | 1.5 | All AD | lnc-ZNF518A-1:5 | SEQ5920 | 4.E-02 | 0.8 |
| DLB | lnc-GRINA-1:1 | SEQ3118 | 2.E-04 | 1.6 | MCI | lnc-ZNF518B-2:4 | SEQ5239 | 5.E-04 | 0.5 |
| MCI | lnc-GRINA-1:1 | SEQ3118 | 5.E-04 | 1.7 | All AD | lnc-ZNF518B-2:4 | SEQ5239 | 4.E-02 | 0.7 |
| MCI | lnc-GRINA-2:1 | SEQ2969 | 4.E-06 | 1.7 | DLB | lnc-ZNF627-3:6 | SEQ5025 | 7.E-04 | 1.5 |
| DLB | lnc-GRINA-2:1 | SEQ2969 | 1.E-04 | 1.6 | DLB | lnc-ZNF629-1:1 | SEQ4680 | 3.E-05 | 1.4 |
| FTD | lnc-GRINA-2:1 | SEQ2969 | 9.E-04 | 1.4 | MCI | lnc-ZNF629-1:1 | SEQ4680 | 1.E-03 | 1.3 |
| All AD | lnc-GRINA-2:1 | SEQ2969 | 4.E-02 | 1.2 | FTD | lnc-ZNF639-4:1 | SEQ2617 | 8.E-06 | 0.5 |
| DLB | lnc-GRINA-3:1 | SEQ3047 | 6.E-05 | 1.5 | All AD | lnc-ZNF639-4:1 | SEQ2617 | 2.E-02 | 0.7 |
| MCI | lnc-GRINA-3:1 | SEQ3047 | 5.E-04 | 1.4 | DLB | lnc-ZNF646-5:2 | SEQ4789 | 1.E-03 | 1.9 |
| DLB | lnc-GRK3-7:4 | SEQ5037 | 7.E-04 | 1.6 | miAD | lnc-ZNF654-3:1 | SEQ0857 | 6.E-03 | 0.7 |
| DLB | lnc-GRK4-2:7 | SEQ3405 | 9.E-05 | 1.4 | All AD | lnc-ZNF654-3:1 | SEQ0857 | 3.E-02 | 0.8 |
| MCI | lnc-GRK4-2:7 | SEQ3405 | 2.E-03 | 1.3 | msAD | lnc-ZNF683-3:1 | SEQ4253 | 9.E-03 | 1.2 |
| FTD | lnc-GRM1-1:2 | SEQ4887 | 9.E-04 | 0.4 | FTD | lnc-ZNF697-2:1 | SEQ5593 | 2.E-04 | 0.6 |
| DLB | lnc-GRM1-2:1 | SEQ4716 | 1.E-03 | 1.6 | All AD | lnc-ZNF697-2:1 | SEQ5593 | 4.E-02 | 0.8 |
| FTD | lnc-GRM8-2:1 | SEQ4812 | 1.E-03 | 0.7 | FTD | lnc-ZNF704-8:1 | SEQ5717 | 1.E-04 | 0.6 |
| FTD | lnc-GRM8-2:2 | SEQ0430 | 1.E-04 | 0.6 | DLB | lnc-ZNF706-1:1 | SEQ4714 | 1.E-03 | 1.6 |
| FTD | lnc-GRSF1-1:1 | SEQ4817 | 4.E-04 | 0.6 | MCI | lnc-ZNF708-13:1 | SEQ5080 | 2.E-04 | 0.4 |
| All AD | lnc-GRSF1-1:1 | SEQ4817 | 4.E-02 | 0.8 | FTD | lnc-ZNF708-13:1 | SEQ5080 | 6.E-04 | 0.5 |
| MCI | lnc-GSDMD-2:1 | SEQ4522 | 9.E-04 | 1.7 | MCI | lnc-ZNF708-3:1 | SEQ5082 | 2.E-04 | 0.6 |
| DLB | lnc-GSDMD-2:1 | SEQ4522 | 2.E-03 | 1.6 | FTD | lnc-ZNF708-3:1 | SEQ5082 | 6.E-04 | 0.5 |
| All AD | lnc-GSTO2-3:1 | SEQ4818 | 4.E-02 | 0.8 | MCI | lnc-ZNF726-1:3 | SEQ0259 | 9.E-04 | 1.6 |
| FTD | lnc-GSX2-7:1 | SEQ4820 | 1.E-08 | 0.4 | FTD | lnc-ZNF730-11:1 | SEQ4899 | 9.E-04 | 0.6 |
| MCI | lnc-GSX2-7:1 | SEQ4820 | 9.E-05 | 0.6 | All AD | lnc-ZNF740-2:1 | SEQ5924 | 3.E-02 | 0.8 |
| miAD | lnc-GSX2-7:1 | SEQ4820 | 1.E-03 | 0.6 | DLB | lnc-ZNF75D-2:2 | SEQ5659 | 1.E-04 | 1.5 |
| All AD | lnc-GSX2-7:1 | SEQ4820 | 6.E-03 | 0.6 | DLB | lnc-ZNF778-1:4 | SEQ2865 | 8.E-04 | 1.5 |
| All AD | lnc-GTDC1-1:2 | SEQ4821 | 4.E-02 | 0.7 | MCI | lnc-ZNF778-5:1 | SEQ5125 | 6.E-04 | 1.6 |
| FTD | lnc-GTDC1-12:1 | SEQ4822 | 1.E-04 | 0.6 | DLB | lnc-ZNF778-5:1 | SEQ5125 | 6.E-04 | 1.6 |
| All AD | lnc-GTDC1-12:1 | SEQ4822 | 3.E-02 | 0.7 | DLB | lnc-ZNF780B-1:1 | SEQ4526 | 2.E-03 | 1.6 |
| FTD | lnc-GTDC1-17:1 | SEQ5961 | 6.E-06 | 0.3 | FTD | lnc-ZNF792-4:1 | SEQ5866 | 4.E-05 | 0.5 |
| FTD | lnc-GTDC1-21:1 | SEQ5081 | 6.E-04 | 0.5 | DLB | lnc-ZNF8-2:1 | SEQ5379 | 3.E-04 | 1.6 |
| FTD | lnc-GTDC1-22:1 | SEQ5394 | 3.E-04 | 0.5 | DLB | lnc-ZNF835-2:1 | SEQ3790 | 4.E-04 | 1.5 |
| FTD | lnc-GTDC1-28:1 | SEQ5925 | 1.E-05 | 0.6 | msAD | lnc-ZNF835-2:1 | SEQ3790 | 4.E-02 | 1.2 |
| MCI | lnc-GTDC1-3:1 | SEQ3956 | 3.E-06 | 3.2 | All AD | lnc-ZNF835-2:1 | SEQ3790 | 4.E-02 | 1.2 |
| DLB | lnc-GTDC1-3:1 | SEQ3956 | 9.E-06 | 3.1 | DLB | lnc-ZNF836-2:4 | SEQ4699 | 3.E-05 | 1.7 |
| FTD | lnc-GTDC1-3:1 | SEQ3956 | 3.E-05 | 2.5 | MCI | lnc-ZNF836-2:4 | SEQ4699 | 1.E-03 | 1.5 |
| All AD | lnc-GTDC1-3:1 | SEQ3956 | 2.E-02 | 1.3 | DLB | lnc-ZNF837-1:2 | SEQ3783 | 2.E-05 | 2.6 |
| msAD | lnc-GTDC1-3:1 | SEQ3956 | 3.E-02 | 1.3 | MCI | lnc-ZNF837-1:2 | SEQ3783 | 3.E-05 | 2.6 |
| FTD | lnc-GTDC1-3:2 | SEQ5968 | 4.E-06 | 0.5 | FTD | lnc-ZNF837-1:2 | SEQ3783 | 8.E-05 | 2.1 |

TABLE 10-continued 2847 whole blood (Paxgene RNA tube) lncRNAs differentially expressed in
MCI group or mild AD group or moderate-to-severe AD group or both of these
AD groups or FTD group or DLB group as compared to healthy control group.

| Group | lncRNA | SEQ | p-value | FC | Group | lncRNA | SEQ | p-value | FC |
| --- | --- | --- | --- | --- | --- | --- | --- | --- | --- |
| FTD | lnc-GTDC1-5:1 | SEQ5395 | 3.E−04 | 0.5 | miAD | lnc-ZNF837-1:2 | SEQ3783 | 3.E−04 | 1.7 |
| DLB | lnc-GTF2IRD2B-3:1 | SEQ5755 | 8.E−05 | 1.7 | All AD | lnc-ZNF837-1:2 | SEQ3783 | 2.E−03 | 1.6 |
| miAD | lnc-GTPBP1-1:1 | SEQ4120 | 1.E−02 | 1.2 | msAD | lnc-ZNF837-1:2 | SEQ3783 | 4.E−02 | 1.4 |
| All AD | lnc-GTPBP1-1:1 | SEQ4120 | 2.E−02 | 1.2 | MCI | lnc-ZNF843-2:1 | SEQ5495 | 3.E−06 | 1.9 |
| DLB | lnc-GTPBP1-1:2 | SEQ3017 | 2.E−04 | 1.4 | DLB | lnc-ZNF843-2:1 | SEQ5495 | 2.E−04 | 1.8 |
| MCI | lnc-GTPBP1-1:2 | SEQ3017 | 2.E−04 | 1.4 | All AD | lnc-ZNF843-2:1 | SEQ5495 | 3.E−02 | 1.2 |
| FTD | lnc-H2AFJ-4:2 | SEQ5975 | 3.E−06 | 0.6 | MCI | lnc-ZNF843-2:4 | SEQ3465 | 2.E−05 | 2.0 |
| FTD | lnc-H2AFV-3:1 | SEQ2433 | 2.E−04 | 0.7 | DLB | lnc-ZNF843-2:4 | SEQ3465 | 1.E−04 | 1.6 |
| All AD | lnc-H3F3A-7:1 | SEQ4831 | 4.E−02 | 0.8 | FTD | lnc-ZNF843-2:4 | SEQ3465 | 5.E−04 | 1.4 |
| DLB | lnc-H6PD-2:1 | SEQ5426 | 3.E−04 | 1.4 | msAD | lnc-ZNF843-2:4 | SEQ3465 | 1.E−02 | 1.2 |
| DLB | lnc-HAGHL-1:1 | SEQ4505 | 2.E−05 | 1.8 | All AD | lnc-ZNF843-2:4 | SEQ3465 | 1.E−02 | 1.2 |
| MCI | lnc-HAGHL-1:1 | SEQ4505 | 2.E−03 | 1.5 | DLB | lnc-ZNF843-2:6 | SEQ4879 | 9.E−04 | 2.1 |
| DLB | lnc-HAND1-3:1 | SEQ5575 | 2.E−04 | 1.7 | MCI | lnc-ZNF843-2:7 | SEQ5631 | 7.E−07 | 2.1 |
| DLB | lnc-HAUS1-1:1 | SEQ4863 | 9.E−04 | 1.6 | DLB | lnc-ZNF843-2:7 | SEQ5631 | 2.E−04 | 1.8 |
| DLB | lnc-HBG2-1:1 | SEQ3409 | 1.E−03 | 1.4 | msAD | lnc-ZNF852-2:3 | SEQ2944 | 2.E−02 | 1.3 |
| DLB | lnc-HCN3-1:1 | SEQ5316 | 4.E−04 | 1.5 | MCI | lnc-ZNHIT2-1:1 | SEQ3818 | 2.E−06 | 1.9 |
| MCI | lnc-HDDC3-3:2 | SEQ4690 | 1.E−03 | 1.4 | DLB | lnc-ZNHIT2-1:1 | SEQ3818 | 3.E−05 | 1.8 |
| DLB | lnc-HDDC3-3:2 | SEQ4690 | 1.E−03 | 1.4 | FTD | lnc-ZNHIT2-1:1 | SEQ3818 | 5.E−04 | 1.4 |
| DLB | lnc-HDGFL2-7:1 | SEQ3180 | 2.E−04 | 1.8 | miAD | lnc-ZNHIT2-1:1 | SEQ3818 | 8.E−03 | 1.2 |
| MCI | lnc-HDGFL2-7:1 | SEQ3180 | 5.E−04 | 1.7 | All AD | lnc-ZNHIT2-1:1 | SEQ3818 | 9.E−03 | 1.2 |
| FTD | lnc-HELZ-4:1 | SEQ5783 | 7.E−05 | 0.7 | msAD | lnc-ZNHIT2-1:1 | SEQ3818 | 4.E−02 | 1.2 |
| FTD | lnc-HEPH-1:1 | SEQ4549 | 2.E−05 | 0.6 | msAD | lnc-ZNRD1-4:2 | SEQ4122 | 1.E−02 | 0.5 |
| MCI | lnc-HEPH-1:1 | SEQ4549 | 2.E−03 | 0.6 | DLB | lnc-ZNRF2-1:1 | SEQ4700 | 5.E−03 | 1.5 |
| DLB | lnc-HIBADH-5:1 | SEQ3962 | 3.E−05 | 1.4 | FTD | lnc-ZNRF2-4:1 | SEQ5551 | 2.E−04 | 0.7 |
| msAD | lnc-HIBADH-5:1 | SEQ3962 | 2.E−02 | 1.1 | FTD | lnc-ZRANB1-4:1 | SEQ5067 | 7.E−04 | 0.7 |
| All AD | lnc-HIBADH-5:1 | SEQ3962 | 4.E−02 | 1.1 | All AD | lnc-ZRANB1-4:1 | SEQ5067 | 4.E−02 | 0.8 |
| DLB | lnc-HIP1-1:2 | SEQ4849 | 9.E−04 | 1.5 | MCI | lnc-ZSCAN10-1:3 | SEQ5651 | 1.E−04 | 0.5 |
| DLB | lnc-HIST1H2BJ-10:5 | SEQ5707 | 1.E−04 | 1.8 | FTD | lnc-ZSCAN10-1:5 | SEQ5093 | 6.E−04 | 0.7 |
| All AD | lnc-HIST1H3A-4:1 | SEQ4172 | 1.E−02 | 0.8 | DLB | lnc-ZSCAN10-1:7 | SEQ5323 | 4.E−04 | 1.5 |
| msAD | lnc-HIST1H3A-4:1 | SEQ4172 | 1.E−02 | 0.8 | DLB | lnc-ZSCAN10-3:32 | SEQ5713 | 1.E−04 | 2.4 |
| All AD | lnc-HIST1H3D-1:1 | SEQ4844 | 3.E−02 | 0.7 | DLB | lnc-ZSCAN10-7:1 | SEQ5370 | 2.E−04 | 1.4 |
| DLB | lnc-HIST1H3F-1:1 | SEQ5878 | 3.E−05 | 1.6 | MCI | lnc-ZSCAN10-7:1 | SEQ5370 | 3.E−04 | 1.4 |
| FTD | lnc-HIST1H4D-3:1 | SEQ4032 | 2.E−05 | 1.5 | DLB | lnc-ZSCAN1-3:3 | SEQ5445 | 3.E−04 | 1.6 |
| DLB | lnc-HIST1H4D-3:1 | SEQ4032 | 2.E−05 | 1.6 | DLB | lnc-ZSCAN21-1:1 | SEQ5240 | 5.E−04 | 1.3 |
| MCI | lnc-HIST1H4D-3:1 | SEQ4032 | 3.E−05 | 1.5 | DLB | lnc-ZSCAN21-2:1 | SEQ5477 | 2.E−04 | 1.4 |
| miAD | lnc-HIST1H4D-3:1 | SEQ4032 | 2.E−03 | 1.2 | DLB | lnc-ZSCAN2-5:1 | SEQ5486 | 2.E−04 | 1.5 |
| All AD | lnc-HIST1H4D-3:1 | SEQ4032 | 3.E−03 | 1.2 | DLB | lnc-ZSCAN2-5:10 | SEQ4859 | 9.E−04 | 1.5 |
| msAD | lnc-HIST1H4D-3:1 | SEQ4032 | 2.E−02 | 1.2 | DLB | lnc-ZSWIM8-2:3 | SEQ4715 | 1.E−03 | 1.6 |
| FTD | lnc-HIST2H2AA3-1:1 | SEQ5069 | 7.E−04 | 0.7 | MCI | LRRC75A-AS1:63 | SEQ5137 | 6.E−04 | 1.8 |
| FTD | lnc-HIST2H2BF-5:1 | SEQ5366 | 3.E−06 | 0.4 | FTD | LUCAT1:1 | SEQ4330 | 3.E−05 | 0.6 |
| MCI | lnc-HIST2H2BF-5:1 | SEQ5366 | 3.E−04 | 0.5 | miAD | LUCAT1:1 | SEQ4330 | 6.E−03 | 0.6 |
| FTD | lnc-HIST2H3A-1:2 | SEQ4852 | 8.E−04 | 0.6 | All AD | LUCAT1:1 | SEQ4330 | 3.E−02 | 0.7 |
| All AD | lnc-HIST2H3A-1:2 | SEQ4852 | 2.E−02 | 0.7 | FTD | LUCAT1:14 | SEQ4151 | 3.E−04 | 0.6 |
| All AD | lnc-HIST2H3D-1:1 | SEQ2368 | 1.E−03 | 0.5 | miAD | LUCAT1:14 | SEQ4151 | 1.E−02 | 0.7 |
| msAD | lnc-HIST2H3D-1:1 | SEQ2368 | 3.E−03 | 0.5 | All AD | LUCAT1:14 | SEQ4151 | 2.E−02 | 0.7 |
| miAD | lnc-HIST2H3D-1:1 | SEQ2368 | 3.E−03 | 0.6 | miAD | LUCAT1:18 | SEQ4351 | 4.E−03 | 0.4 |
| miAD | lnc-HIST2H3PS2-10:1 | SEQ4664 | 1.E−03 | 0.4 | All AD | LUCAT1:18 | SEQ4351 | 1.E−02 | 0.5 |
| All AD | lnc-HIST2H3PS2-10:1 | SEQ4664 | 8.E−03 | 0.4 | All AD | LUCAT1:2 | SEQ5932 | 4.E−02 | 0.8 |
| DLB | lnc-HIST3H2BB-1:4 | SEQ5845 | 4.E−05 | 1.5 | All AD | LUCAT1:20 | SEQ5933 | 3.E−02 | 0.7 |
| FTD | lnc-HIST4H4-1:1 | SEQ5921 | 1.E−05 | 0.2 | All AD | LUCAT1:21 | SEQ5934 | 2.E−02 | 0.7 |
| FTD | lnc-HIST4H4-1:2 | SEQ5750 | 2.E−05 | 0.2 | FTD | LUCAT1:24 | SEQ5510 | 2.E−04 | 0.6 |
| MCI | lnc-HIST4H4-1:2 | SEQ5750 | 8.E−05 | 0.3 | All AD | LUCAT1:24 | SEQ5510 | 2.E−02 | 0.7 |
| All AD | lnc-HIST4H4-4:1 | SEQ4860 | 5.E−02 | 0.8 | FTD | LUCAT1:3 | SEQ5511 | 2.E−04 | 0.6 |
| DLB | lnc-HIST4H4-5:3 | SEQ5897 | 2.E−05 | 2.0 | All AD | LUCAT1:3 | SEQ5511 | 2.E−02 | 0.7 |
| DLB | lnc-HLA-B-2:13 | SEQ4606 | 2.E−04 | 0.2 | FTD | MALAT1:16 | SEQ4201 | 5.E−04 | 0.4 |
| MCI | lnc-HLA-B-2:13 | SEQ4606 | 1.E−03 | 0.2 | msAD | MALAT1:16 | SEQ4201 | 1.E−02 | 0.5 |
| MCI | lnc-HLA-DMA-1:1 | SEQ5942 | 2.E−07 | 1.7 | All AD | MALAT1:16 | SEQ4201 | 2.E−02 | 0.5 |
| DLB | lnc-HLA-DMA-1:1 | SEQ5942 | 4.E−06 | 1.7 | MCI | MALAT1:24 | SEQ4397 | 2.E−04 | 0.5 |
| FTD | lnc-HLA-DMA-1:1 | SEQ5942 | 1.E−05 | 1.4 | DLB | MALAT1:24 | SEQ4397 | 2.E−03 | 0.6 |
| FTD | lnc-HLA-DQA1-7:1 | SEQ5335 | 6.E−05 | 1.7 | miAD | MALAT1:32 | SEQ3633 | 7.E−03 | 0.6 |
| DLB | lnc-HLA-DQA1-7:1 | SEQ5335 | 4.E−05 | 1.7 | All AD | MALAT1:32 | SEQ3633 | 1.E−02 | 0.6 |
| DLB | lnc-HLA-DRB1-5:1 | SEQ4166 | 8.E−04 | 2.7 | msAD | MALAT1:32 | SEQ3633 | 5.E−02 | 0.7 |
| All AD | lnc-HLA-DRB1-5:1 | SEQ4166 | 4.E−03 | 1.6 | FTD | MALAT1:33 | SEQ5927 | 3.E−11 | 4.E−15 |
| msAD | lnc-HLA-DRB1-5:1 | SEQ4166 | 7.E−03 | 1.6 | DLB | MALAT1:33 | SEQ5927 | 1.E−05 | 3.E−15 |
| miAD | lnc-HLA-DRB1-5:1 | SEQ4166 | 1.E−02 | 1.5 | MCI | MALAT1:33 | SEQ5927 | 1.E−05 | 3.E−15 |
| DLB | lnc-HLA-DRB1-5:2 | SEQ5347 | 4.E−04 | 2.4 | MCI | MALAT1:38 | SEQ5650 | 1.E−06 | 0.3 |
| DLB | lnc-HMGA1-2:4 | SEQ3415 | 5.E−04 | 1.3 | FTD | MALAT1:38 | SEQ5650 | 2.E−06 | 0.3 |
| FTD | lnc-HMGB1-4:1 | SEQ5160 | 5.E−04 | 0.7 | DLB | MALAT1:38 | SEQ5650 | 1.E−04 | 0.4 |
| FTD | lnc-HMGB2-5:1 | SEQ3870 | 3.E−05 | 0.6 | DLB | MALAT1:4 | SEQ4834 | 9.E−04 | 1.4 |
| miAD | lnc-HMGB2-5:1 | SEQ3870 | 6.E−03 | 0.8 | MCI | MALAT1:40 | SEQ5556 | 2.E−04 | 0.4 |
| All AD | lnc-HMGB2-5:1 | SEQ3870 | 7.E−03 | 0.8 | DLB | MALAT1:43 | SEQ5018 | 7.E−04 | 1.4 |
| msAD | lnc-HMGB2-5:1 | SEQ3870 | 3.E−02 | 0.8 | DLB | MALAT1:5 | SEQ5019 | 7.E−04 | 1.4 |
| FTD | lnc-HMGB2-8:1 | SEQ5802 | 6.E−05 | 0.6 | DLB | MALAT1:6 | SEQ5016 | 7.E−04 | 1.4 |
| FTD | lnc-HMGN5-3:1 | SEQ3416 | 1.E−09 | 0.4 | DLB | MAP3K14-AS1:27 | SEQ5184 | 5.E−04 | 1.5 |

TABLE 10-continued 2847 whole blood (Paxgene RNA tube) lncRNAs differentially expressed in
MCI group or mild AD group or moderate-to-severe AD group or both of these
AD groups or FTD group or DLB group as compared to healthy control group.

| Group | lncRNA | SEQ | p-value | FC | Group | lncRNA | SEQ | p-value | FC |
|---|---|---|---|---|---|---|---|---|---|
| MCI | lnc-HMGN5-3:1 | SEQ3416 | 2.E-05 | 0.5 | MCI | MAP3K14-AS1:28 | SEQ4862 | 9.E-04 | 1.5 |
| All AD | lnc-HMGN5-3:1 | SEQ3416 | 1.E-03 | 0.6 | DLB | MAP3K14-AS1:28 | SEQ4862 | 9.E-04 | 1.6 |
| miAD | lnc-HMGN5-3:1 | SEQ3416 | 3.E-03 | 0.6 | FTD | MAP3K20-AS1:6 | SEQ5508 | 2.E-04 | 0.5 |
| msAD | lnc-HMGN5-3:1 | SEQ3416 | 4.E-03 | 0.6 | All AD | MATN1-AS1:2 | SEQ5940 | 3.E-02 | 1.2 |
| FTD | lnc-HNRNPA2B1-14:2 | SEQ5828 | 5.E-05 | 0.5 | DLB | MBNL1-AS1:10 | SEQ5456 | 3.E-04 | 1.9 |
| FTD | lnc-HNRNPA2B1-15:1 | SEQ4878 | 6.E-10 | 0.3 | DLB | MBNL1-AS1:5 | SEQ4754 | 1.E-03 | 1.4 |
| MCI | lnc-HNRNPA2B1-15:1 | SEQ4878 | 3.E-06 | 0.3 | miAD | MBNL1-AS1:8 | SEQ4335 | 6.E-04 | 1.5 |
| DLB | lnc-HNRNPA2B1-15:1 | SEQ4878 | 5.E-04 | 0.4 | All AD | MBNL1-AS1:8 | SEQ4335 | 1.E-02 | 1.3 |
| miAD | lnc-HNRNPA2B1-15:1 | SEQ4878 | 6.E-04 | 0.4 | DLB | MCM3AP-AS1:8 | SEQ4507 | 2.E-03 | 1.5 |
| All AD | lnc-HNRNPA2B1-15:1 | SEQ4878 | 3.E-03 | 0.5 | FTD | MIF-AS1:7 | SEQ3858 | 8.E-06 | 1.7 |
| MCI | lnc-HNRNPA2B1-15:3 | SEQ4795 | 1.E-03 | 2.8 | MCI | MIF-AS1:7 | SEQ3858 | 9.E-06 | 1.8 |
| FTD | lnc-HNRNPA2B1-15:4 | SEQ4601 | 1.E-06 | 0.5 | DLB | MIF-AS1:7 | SEQ3858 | 1.E-05 | 1.9 |
| MCI | lnc-HNRNPA2B1-15:4 | SEQ4601 | 2.E-05 | 0.5 | miAD | MIF-AS1:7 | SEQ3858 | 7.E-03 | 1.3 |
| miAD | lnc-HNRNPA2B1-15:4 | SEQ4601 | 1.E-03 | 0.6 | All AD | MIF-AS1:7 | SEQ3858 | 8.E-03 | 1.3 |
| All AD | lnc-HNRNPA2B1-15:4 | SEQ4601 | 6.E-03 | 0.6 | msAD | MIF-AS1:7 | SEQ3858 | 3.E-02 | 1.3 |
| All AD | lnc-HNRNPA2B1-15:5 | SEQ4882 | 4.E-02 | 0.7 | FTD | MIR133A1HG:2 | SEQ5642 | 1.E-04 | 0.6 |
| MCI | lnc-HNRNPA3-2:2 | SEQ5073 | 2.E-04 | 1.8 | FTD | MIR133A1HG:3 | SEQ5855 | 4.E-05 | 0.5 |
| DLB | lnc-HNRNPA3-2:2 | SEQ5073 | 5.E-04 | 1.7 | MCI | MIR17HG:13 | SEQ5996 | 7.E-07 | 3.1 |
| FTD | lnc-HNRNPA3-2:2 | SEQ5073 | 7.E-04 | 1.5 | FTD | MIR17HG:21 | SEQ4799 | 1.E-03 | 0.4 |
| FTD | lnc-HNRNPLL-4:1 | SEQ4287 | 2.E-06 | 0.5 | FTD | MIR181A2HG:1 | SEQ3905 | 9.E-04 | 0.6 |
| msAD | lnc-HNRNPLL-4:1 | SEQ4287 | 7.E-03 | 0.7 | miAD | MIR181A2HG:1 | SEQ3905 | 5.E-03 | 0.6 |
| All AD | lnc-HNRNPLL-4:1 | SEQ4287 | 8.E-03 | 0.7 | All AD | MIR181A2HG:1 | SEQ3905 | 6.E-03 | 0.7 |
| FTD | lnc-HNRNPU-1:3 | SEQ4467 | 4.E-04 | 0.4 | msAD | MIR181A2HG:1 | SEQ3905 | 3.E-02 | 0.8 |
| MCI | lnc-HNRNPU-1:3 | SEQ4467 | 2.E-03 | 0.4 | FTD | MIR222HG:26 | SEQ5396 | 3.E-04 | 0.5 |
| FTD | lnc-HNRNPU-1:6 | SEQ4889 | 7.E-05 | 0.4 | DLB | MIR29B2CHG:14 | SEQ5637 | 2.E-04 | 1.9 |
| All AD | lnc-HNRNPU-1:6 | SEQ4889 | 5.E-02 | 0.6 | DLB | MIR29B2CHG:21 | SEQ4530 | 2.E-03 | 1.8 |
| DLB | lnc-HOMEZ-1:6 | SEQ5032 | 7.E-04 | 1.5 | DLB | MIR29B2CHG:22 | SEQ4655 | 1.E-03 | 1.9 |
| All AD | lnc-HPCA-1:1 | SEQ4891 | 4.E-02 | 0.8 | MCI | MIR29B2CHG:28 | SEQ5457 | 3.E-02 | 1.9 |
| FTD | lnc-HPGD-5:1 | SEQ5827 | 5.E-05 | 0.5 | FTD | MIR29B2CHG:33 | SEQ0583 | 2.E-05 | 0.4 |
| DLB | lnc-HSD11B2-1:1 | SEQ2525 | 1.E-03 | 1.3 | All AD | MIR29B2CHG:33 | SEQ0583 | 2.E-02 | 0.7 |
| DLB | lnc-HSD17B6-3:1 | SEQ3950 | 7.E-07 | 2.0 | All AD | MIR29B2CHG:34 | SEQ5945 | 2.E-02 | 0.7 |
| MCI | lnc-HSD17B6-3:1 | SEQ3950 | 3.E-06 | 1.8 | MCI | MIR29B2CHG:48 | SEQ5099 | 7.E-06 | 0.3 |
| FTD | lnc-HSD17B6-3:1 | SEQ3950 | 6.E-06 | 1.7 | FTD | MIR29B2CHG:48 | SEQ5099 | 1.E-05 | 0.3 |
| All AD | lnc-HSD17B6-3:1 | SEQ3950 | 2.E-02 | 1.2 | DLB | MIR29B2CHG:48 | SEQ5099 | 6.E-04 | 0.3 |
| msAD | lnc-HSD17B6-3:1 | SEQ3950 | 3.E-02 | 1.2 | DLB | MIR29B2CHG:8 | SEQ4457 | 5.E-05 | 2.0 |
| All AD | lnc-HSDL1-2:1 | SEQ3753 | 2.E-02 | 1.1 | MCI | MIR29B2CHG:8 | SEQ4457 | 2.E-03 | 1.9 |
| msAD | lnc-HSDL1-2:1 | SEQ3753 | 4.E-02 | 1.2 | All AD | MIR3936HG:4 | SEQ3771 | 2.E-02 | 0.7 |
| FTD | lnc-HSP90AA1-13:1 | SEQ5591 | 2.E-04 | 0.6 | msAD | MIR3936HG:4 | SEQ3771 | 4.E-02 | 0.7 |
| All AD | lnc-HSP90AA1-15:2 | SEQ4897 | 4.E-02 | 0.8 | DLB | MIR4435-2HG:43 | SEQ4650 | 1.E-03 | 1.8 |
| DLB | lnc-HSP90AA1-2:1 | SEQ5612 | 2.E-04 | 1.4 | FTD | MIR4435-2HG:6 | SEQ5005 | 8.E-04 | 1.7 |
| DLB | lnc-HSPB1-4:4 | SEQ5813 | 5.E-05 | 1.4 | DLB | MIR4453HG:2 | SEQ3568 | 1.E-03 | 1.4 |
| DLB | lnc-HUS1B-2:1 | SEQ4588 | 2.E-03 | 1.6 | DLB | MIR600HG:4 | SEQ3892 | 6.E-04 | 1.9 |
| DLB | lnc-HYAL4-4:6 | SEQ4618 | 2.E-04 | 1.5 | msAD | MIR600HG:4 | SEQ3892 | 3.E-02 | 1.4 |
| MCI | lnc-HYAL4-4:6 | SEQ4618 | 1.E-03 | 1.4 | All AD | MIR600HG:4 | SEQ3892 | 4.E-02 | 1.3 |
| DLB | lnc-ICA1L-7:1 | SEQ4901 | 5.E-04 | 2.1 | DLB | MIR600HG:5 | SEQ3676 | 1.E-03 | 2.0 |
| MCI | lnc-ICA1L-7:1 | SEQ4901 | 5.E-04 | 2.1 | msAD | MIR600HG:5 | SEQ3676 | 5.E-02 | 1.4 |
| All AD | lnc-ICA1L-7:1 | SEQ4901 | 5.E-02 | 1.3 | FTD | MIR646HG:26 | SEQ3222 | 9.E-04 | 0.6 |
| MCI | lnc-ICAM5-1:1 | SEQ4240 | 1.E-05 | 1.7 | FTD | MIR646HG:29 | SEQ3928 | 1.E-05 | 0.5 |
| DLB | lnc-ICAM5-1:1 | SEQ4240 | 1.E-05 | 1.9 | miAD | MIR646HG:29 | SEQ3928 | 1.E-03 | 0.6 |
| FTD | lnc-ICAM5-1:1 | SEQ4240 | 2.E-04 | 1.4 | All AD | MIR646HG:29 | SEQ3928 | 3.E-03 | 0.6 |
| All AD | lnc-ICAM5-1:1 | SEQ4240 | 4.E-03 | 1.3 | msAD | MIR646HG:29 | SEQ3928 | 3.E-02 | 0.7 |
| miAD | lnc-ICAM5-1:1 | SEQ4240 | 8.E-03 | 1.3 | miAD | MIR646HG:35 | SEQ4313 | 7.E-03 | 0.7 |
| msAD | lnc-ICAM5-1:1 | SEQ4240 | 1.E-02 | 1.3 | All AD | MIR646HG:35 | SEQ4313 | 2.E-02 | 0.8 |
| DLB | lnc-ICOSLG-6:12 | SEQ4450 | 8.E-04 | 1.6 | FTD | MME-AS1:2 | SEQ4056 | 2.E-06 | 0.4 |
| MCI | lnc-ICOSLG-6:12 | SEQ4450 | 2.E-03 | 1.6 | miAD | MME-AS1:2 | SEQ4056 | 3.E-03 | 0.6 |
| miAD | lnc-IDE-3:1 | SEQ4211 | 1.E-02 | 0.7 | All AD | MME-AS1:2 | SEQ4056 | 3.E-03 | 0.6 |
| MCI | lnc-IER3-7:16 | SEQ5183 | 5.E-04 | 1.5 | msAD | MME-AS1:2 | SEQ4056 | 2.E-02 | 0.6 |
| MCI | lnc-IER3-7:17 | SEQ4560 | 1.E-04 | 1.6 | MCI | MMP25-AS1:17 | SEQ4787 | 1.E-03 | 1.8 |
| DLB | lnc-IER3-7:17 | SEQ4560 | 2.E-03 | 1.4 | All AD | MMP25-AS1:24 | SEQ5949 | 3.E-02 | 0.8 |
| DLB | lnc-IER5-4:1 | SEQ5876 | 3.E-05 | 1.5 | MCI | MRPL23-AS1:10 | SEQ3942 | 9.E-05 | 1.7 |
| DLB | lnc-IFT140-2:1 | SEQ5623 | 2.E-04 | 1.6 | DLB | MRPL23-AS1:10 | SEQ3942 | 1.E-04 | 1.7 |
| FTD | lnc-IGIP-2:3 | SEQ3421 | 8.E-06 | 0.3 | FTD | MRPL23-AS1:10 | SEQ3942 | 7.E-04 | 1.5 |
| MCI | lnc-IGIP-2:3 | SEQ3421 | 2.E-04 | 0.3 | msAD | MRPL23-AS1:10 | SEQ3942 | 3.E-02 | 1.2 |
| DLB | lnc-IGIP-2:3 | SEQ3421 | 2.E-03 | 0.4 | All AD | MRPL23-AS1:10 | SEQ3942 | 3.E-02 | 1.2 |
| miAD | lnc-IGIP-5:1 | SEQ2977 | 1.E-02 | 0.7 | MCI | MRPS30-DT:11 | SEQ4024 | 2.E-04 | 1.7 |
| All AD | lnc-IGIP-5:1 | SEQ2977 | 2.E-02 | 0.7 | DLB | MRPS30-DT:11 | SEQ4024 | 9.E-04 | 1.6 |
| MCI | lnc-IGLON5-6:10 | SEQ4600 | 8.E-05 | 2.1 | All AD | MRPS30-DT:11 | SEQ4024 | 1.E-02 | 1.3 |
| msAD | lnc-IGLON5-6:10 | SEQ4600 | 1.E-03 | 1.7 | msAD | MRPS30-DT:11 | SEQ4024 | 2.E-02 | 1.3 |
| DLB | lnc-IGLON5-6:10 | SEQ4600 | 2.E-03 | 1.9 | FTD | MRVI1-AS1:16 | SEQ5778 | 7.E-05 | 0.6 |
| All AD | lnc-IGLON5-6:10 | SEQ4600 | 4.E-03 | 1.5 | FTD | MYLK-AS1:13 | SEQ5471 | 3.E-02 | 0.7 |
| FTD | lnc-IGLON5-6:3 | SEQ4129 | 1.E-08 | 4.7 | DLB | MYLK-AS1:16 | SEQ3954 | 1.E-03 | 1.5 |
| MCI | lnc-IGLON5-6:3 | SEQ4129 | 3.E-08 | 7.5 | MCI | MYLK-AS1:16 | SEQ3954 | 2.E-03 | 1.5 |
| DLB | lnc-IGLON5-6:3 | SEQ4129 | 3.E-05 | 3.7 | msAD | MYLK-AS1:16 | SEQ3954 | 3.E-02 | 1.3 |
| All AD | lnc-IGLON5-6:3 | SEQ4129 | 1.E-02 | 1.6 | miAD | MZF1-AS1:11 | SEQ4877 | 6.E-04 | 1.9 |

TABLE 10-continued 2847 whole blood (Paxgene RNA tube) lncRNAs differentially expressed in
MCI group or mild AD group or moderate-to-severe AD group or both of these
AD groups or FTD group or DLB group as compared to healthy control group.

| Group | lncRNA | SEQ | p-value | FC | Group | lncRNA | SEQ | p-value | FC |
|---|---|---|---|---|---|---|---|---|---|
| msAD | lnc-IGLON5-6:3 | SEQ4129 | 1.E-02 | 1.7 | DLB | MZF1-AS1:11 | SEQ4877 | 9.E-04 | 2.1 |
| DLB | lnc-IGLON5-6:5 | SEQ4265 | 2.E-03 | 1.7 | All AD | MZF1-AS1:11 | SEQ4877 | 3.E-03 | 1.6 |
| msAD | lnc-IGLON5-6:5 | SEQ4265 | 9.E-03 | 1.4 | FTD | N4BP2L2-IT2:1 | SEQ5958 | 7.E-06 | 0.6 |
| FTD | lnc-IGSF10-8:1 | SEQ5929 | 1.E-05 | 0.5 | DLB | NAPA-AS1:10 | SEQ5425 | 3.E-04 | 1.4 |
| DLB | lnc-IKBIP-1:1 | SEQ4407 | 2.E-03 | 1.4 | All AD | NCAM1-AS1:1 | SEQ5953 | 4.E-02 | 0.7 |
| DLB | lnc-IL18BP-1:1 | SEQ3303 | 1.E-03 | 1.5 | miAD | NCF4-AS1:4 | SEQ4261 | 9.E-03 | 0.7 |
| DLB | lnc-IL18BP-1:2 | SEQ3422 | 8.E-04 | 1.5 | All AD | NCF4-AS1:4 | SEQ4261 | 3.E-02 | 0.8 |
| MCI | lnc-IL18BP-1:2 | SEQ3422 | 1.E-03 | 1.4 | MCI | NEAT1:11 | SEQ4370 | 1.E-08 | 6.E+04 |
| DLB | lnc-IL18BP-1:3 | SEQ3423 | 2.E-03 | 1.5 | FTD | NEAT1:11 | SEQ4370 | 8.E-07 | 16.4 |
| FTD | lnc-IL18R1-1:1 | SEQ4043 | 5.E-04 | 0.6 | DLB | NEAT1:11 | SEQ4370 | 2.E-04 | 5.6 |
| All AD | lnc-IL18R1-1:1 | SEQ4043 | 1.E-02 | 0.7 | miAD | NEAT1:11 | SEQ4370 | 4.E-03 | 2.4 |
| msAD | lnc-IL18R1-1:1 | SEQ4043 | 2.E-02 | 0.7 | All AD | NEAT1:11 | SEQ4370 | 2.E-02 | 1.9 |
| DLB | lnc-IL1RN-5:1 | SEQ4497 | 2.E-03 | 1.4 | MCI | NEAT1:12 | SEQ4350 | 2.E-06 | 3.E+02 |
| DLB | lnc-IL23A-2:5 | SEQ4425 | 2.E-03 | 1.5 | FTD | NEAT1:12 | SEQ4350 | 1.E-05 | 8.4 |
| msAD | lnc-IL23A-2:6 | SEQ4341 | 5.E-03 | 1.2 | miAD | NEAT1:12 | SEQ4350 | 5.E-03 | 2.4 |
| All AD | lnc-IL23A-2:6 | SEQ4341 | 1.E-02 | 1.2 | All AD | NEAT1:12 | SEQ4350 | 1.E-02 | 2.2 |
| DLB | lnc-IL2RA-5:1 | SEQ4484 | 2.E-03 | 1.4 | FTD | NEAT1:18 | SEQ3809 | 5.E-05 | 0.2 |
| DLB | lnc-IL31RA-1:1 | SEQ2680 | 3.E-04 | 1.6 | miAD | NEAT1:18 | SEQ3809 | 1.E-03 | 0.1 |
| MCI | lnc-IL31RA-1:1 | SEQ2680 | 2.E-03 | 1.5 | DLB | NEAT1:18 | SEQ3809 | 1.E-03 | 0.3 |
| miAD | lnc-IL31RA-1:1 | SEQ2680 | 3.E-03 | 1.4 | All AD | NEAT1:18 | SEQ3809 | 3.E-03 | 0.2 |
| All AD | lnc-IL31RA-1:1 | SEQ2680 | 4.E-03 | 1.3 | msAD | NEAT1:18 | SEQ3809 | 4.E-02 | 0.3 |
| msAD | lnc-IL31RA-1:1 | SEQ2680 | 3.E-02 | 1.3 | FTD | NEAT1:20 | SEQ4469 | 2.E-06 | 0.5 |
| MCI | lnc-IL31RA-6:2 | SEQ4535 | 2.E-03 | 2.2 | DLB | NEAT1:20 | SEQ4469 | 5.E-04 | 0.6 |
| All AD | lnc-IL31RA-6:2 | SEQ4535 | 4.E-02 | 1.4 | MCI | NEAT1:20 | SEQ4469 | 2.E-03 | 0.5 |
| DLB | lnc-IL9R-1:3 | SEQ5657 | 1.E-04 | 1.5 | All AD | NEAT1:20 | SEQ4469 | 3.E-02 | 0.7 |
| DLB | lnc-INO80E-2:2 | SEQ5191 | 5.E-04 | 1.5 | All AD | NEAT1:21 | SEQ5957 | 3.E-02 | 0.8 |
| FTD | lnc-INSL4-4:1 | SEQ5105 | 2.E-05 | 0.6 | miAD | NEAT1:22 | SEQ4986 | 2.E-06 | 0.5 |
| MCI | lnc-INSL4-4:1 | SEQ5105 | 6.E-02 | 0.6 | All AD | NEAT1:22 | SEQ4986 | 2.E-05 | 0.6 |
| FTD | lnc-INSL4-5:1 | SEQ4133 | 4.E-07 | 0.5 | msAD | NEAT1:22 | SEQ4986 | 8.E-04 | 0.6 |
| miAD | lnc-INSL4-5:1 | SEQ4133 | 1.E-02 | 0.7 | MCI | NEAT1:7 | SEQ4362 | 4.E-08 | 8.E+03 |
| All AD | lnc-INSL4-5:1 | SEQ4133 | 3.E-02 | 0.7 | FTD | NEAT1:7 | SEQ4362 | 8.E-06 | 4.8 |
| FTD | lnc-INSL4-6:1 | SEQ5423 | 1.E-07 | 0.4 | miAD | NEAT1:7 | SEQ4362 | 4.E-03 | 2.1 |
| MCI | lnc-INSL4-6:1 | SEQ5423 | 3.E-04 | 0.5 | All AD | NEAT1:7 | SEQ4362 | 1.E-02 | 2.2 |
| FTD | lnc-INSL4-8:1 | SEQ5406 | 3.E-04 | 0.6 | FTD | NEAT1:8 | SEQ4734 | 4.E-07 | 0.4 |
| FTD | lnc-INSL4-9:1 | SEQ4937 | 8.E-07 | 0.5 | MCI | NEAT1:8 | SEQ4734 | 1.E-03 | 0.5 |
| MCI | lnc-INSL4-9:1 | SEQ4937 | 1.E-04 | 0.5 | All AD | NEAT1:8 | SEQ4734 | 2.E-02 | 0.5 |
| All AD | lnc-INSL4-9:1 | SEQ4937 | 3.E-02 | 0.7 | MCI | NIPBL-AS1:1 | SEQ5100 | 6.E-04 | 0.4 |
| FTD | lnc-INSL6-3:1 | SEQ4906 | 9.E-04 | 0.7 | DLB | NIPBL-AS1:2 | SEQ4983 | 8.E-04 | 2.2 |
| FTD | lnc-INTS14-1:2 | SEQ5083 | 6.E-04 | 0.6 | FTD | NIPBL-AS1:6 | SEQ5744 | 9.E-05 | 0.6 |
| FTD | lnc-INTS9-2:1 | SEQ4940 | 8.E-05 | 0.6 | FTD | NORAD:10 | SEQ4733 | 7.E-07 | 2.1 |
| All AD | lnc-INTS9-2:1 | SEQ4940 | 3.E-02 | 0.8 | DLB | NORAD:10 | SEQ4733 | 1.E-05 | 2.0 |
| All AD | lnc-IPCEF1-2:1 | SEQ4941 | 3.E-02 | 1.2 | MCI | NORAD:10 | SEQ4733 | 9.E-05 | 2.1 |
| DLB | lnc-IQCF6-2:2 | SEQ4856 | 9.E-04 | 1.5 | All AD | NORAD:10 | SEQ4733 | 4.E-04 | 1.4 |
| All AD | lnc-IQCG-16:1 | SEQ4943 | 3.E-02 | 0.7 | miAD | NORAD:10 | SEQ4733 | 1.E-03 | 1.4 |
| All AD | lnc-IRF1-2:1 | SEQ4944 | 3.E-02 | 0.8 | msAD | NORAD:10 | SEQ4733 | 1.E-03 | 1.4 |
| All AD | lnc-IRF1-2:6 | SEQ4945 | 3.E-02 | 0.8 | FTD | NORAD:2 | SEQ3125 | 1.E-08 | 4.2 |
| DLB | lnc-IRF1-6:1 | SEQ5756 | 8.E-05 | 1.8 | MCI | NORAD:2 | SEQ3125 | 4.E-06 | 3.6 |
| DLB | lnc-IRF7-1:1 | SEQ5624 | 1.E-05 | 1.8 | DLB | NORAD:2 | SEQ3125 | 2.E-05 | 2.8 |
| MCI | lnc-IRF7-1:1 | SEQ5624 | 2.E-04 | 1.6 | All AD | NORAD:2 | SEQ3125 | 2.E-03 | 1.5 |
| All AD | lnc-IRS2-1:6 | SEQ3812 | 1.E-02 | 0.6 | miAD | NORAD:2 | SEQ3125 | 3.E-03 | 1.5 |
| miAD | lnc-IRS2-1:6 | SEQ3812 | 2.E-02 | 0.5 | msAD | NORAD:2 | SEQ3125 | 1.E-02 | 1.5 |
| msAD | lnc-IRS2-1:6 | SEQ3812 | 4.E-02 | 0.6 | All AD | NORAD:5 | SEQ3646 | 3.E-02 | 1.2 |
| msAD | lnc-IRS2-9:1 | SEQ3896 | 3.E-02 | 0.8 | msAD | NORAD:5 | SEQ3646 | 5.E-02 | 1.2 |
| All AD | lnc-IRS2-9:1 | SEQ3896 | 4.E-02 | 0.8 | FTD | NORAD:8 | SEQ2585 | 8.E-07 | 0.3 |
| MCI | lnc-ITGB1BP2-2:1 | SEQ2701 | 1.E-03 | 0.7 | MCI | NORAD:8 | SEQ2585 | 3.E-06 | 0.3 |
| DLB | lnc-ITGB1BP2-2:3 | SEQ5562 | 2.E-04 | 1.5 | All AD | NORAD:8 | SEQ2585 | 3.E-02 | 0.5 |
| DLB | lnc-ITPA-1:1 | SEQ5904 | 2.E-05 | 1.4 | FTD | NORAD:9 | SEQ2494 | 4.E-04 | 0.4 |
| MCI | lnc-ITPA-2:3 | SEQ4577 | 2.E-03 | 1.5 | MCI | NORAD:9 | SEQ2494 | 6.E-04 | 0.5 |
| DLB | lnc-ITPA-2:3 | SEQ4577 | 2.E-03 | 1.5 | All AD | NORAD:9 | SEQ2494 | 5.E-02 | 0.6 |
| FTD | lnc-JAK1-2:2 | SEQ4953 | 4.E-04 | 0.7 | DLB | NRSN2-AS1:11 | SEQ5450 | 3.E-04 | 1.7 |
| All AD | lnc-JAK1-2:2 | SEQ4953 | 2.E-02 | 0.8 | FTD | NUP50-AS1:22 | SEQ5088 | 6.E-04 | 0.6 |
| FTD | lnc-JCAD-10:1 | SEQ4954 | 1.E-05 | 0.6 | FTD | NUP50-AS1:22 | SEQ4654 | 4.E-04 | 1.7 |
| All AD | lnc-JCAD-10:1 | SEQ4954 | 3.E-02 | 0.8 | DLB | NUP50-AS1:22 | SEQ4654 | 7.E-04 | 1.9 |
| DLB | lnc-JMJD7-PLA2G4B-2:8 | SEQ3428 | 8.E-04 | 1.6 | MCI | NUP50-AS1:22 | SEQ4654 | 1.E-03 | 1.9 |
| DLB | lnc-JSRP1-1:2 | SEQ5710 | 5.E-05 | 1.8 | FTD | NUP50-AS1:27 | SEQ5356 | 4.E-04 | 0.6 |
| MCI | lnc-JSRP1-1:2 | SEQ5710 | 1.E-04 | 1.8 | MCI | NUTM2A-AS1:2 | SEQ5749 | 8.E-05 | 0.3 |
| DLB | lnc-JSRP1-2:1 | SEQ4495 | 2.E-03 | 1.4 | FTD | NUTM2A-AS1:28 | SEQ5222 | 5.E-04 | 0.5 |
| MCI | lnc-JUNB-1:1 | SEQ5422 | 1.E-05 | 1.8 | MCI | NUTM2A-AS1:30 | SEQ5903 | 2.E-05 | 0.3 |
| DLB | lnc-JUNB-1:1 | SEQ5422 | 1.E-05 | 1.6 | FTD | NUTM2A-AS1:34 | SEQ4337 | 3.E-07 | 0.5 |
| FTD | lnc-JUNB-1:1 | SEQ5422 | 3.E-04 | 1.5 | MCI | NUTM2A-AS1:34 | SEQ4337 | 2.E-04 | 0.6 |
| MCI | lnc-KANTR-2:1 | SEQ4836 | 9.E-04 | 1.4 | miAD | NUTM2A-AS1:34 | SEQ4337 | 5.E-03 | 0.7 |
| DLB | lnc-KBTBD4-4:1 | SEQ4614 | 1.E-03 | 1.3 | All AD | NUTM2A-AS1:34 | SEQ4337 | 2.E-02 | 0.7 |
| MCI | lnc-KCNC2-1:1 | SEQ4321 | 9.E-05 | 1.7 | FTD | NUTM2B-AS1:20 | SEQ5596 | 2.E-04 | 0.4 |

TABLE 10-continued 2847 whole blood (Paxgene RNA tube) lncRNAs differentially expressed in MCI group or mild AD group or moderate-to-severe AD group or both of these AD groups or FTD group or DLB group as compared to healthy control group.

| Group | lncRNA | SEQ | p-value | FC | Group | lncRNA | SEQ | p-value | FC |
|---|---|---|---|---|---|---|---|---|---|
| DLB | lnc-KCNC2-1:1 | SEQ4321 | 2.E−04 | 1.7 | FTD | NUTM2B-AS1:42 | SEQ4813 | 1.E−03 | 0.7 |
| All AD | lnc-KCNC2-1:1 | SEQ4321 | 1.E−03 | 1.3 | FTD | NUTM2B-AS1:53 | SEQ0004 | 8.E−04 | 0.5 |
| miAD | lnc-KCNC2-1:1 | SEQ4321 | 1.E−03 | 1.3 | FTD | OIP5-AS1:15 | SEQ4823 | 3.E−06 | 0.2 |
| msAD | lnc-KCNC2-1:1 | SEQ4321 | 6.E−03 | 1.3 | MCI | OIP5-AS1:15 | SEQ4823 | 6.E−06 | 0.2 |
| DLB | lnc-KCNC3-1:4 | SEQ4083 | 2.E−05 | 2.0 | DLB | OIP5-AS1:15 | SEQ4823 | 9.E−04 | 0.2 |
| msAD | lnc-KCNC3-1:4 | SEQ4083 | 1.E−02 | 1.3 | DLB | OIP5-AS1:18 | SEQ5034 | 7.E−04 | 1.5 |
| All AD | lnc-KCNC3-1:4 | SEQ4083 | 5.E−02 | 1.2 | FTD | OIP5-AS1:25 | SEQ5168 | 4.E−07 | 0.4 |
| FTD | lnc-KCNE1B-10:2 | SEQ5585 | 2.E−04 | 0.2 | MCI | OIP5-AS1:25 | SEQ5168 | 5.E−04 | 0.5 |
| msAD | lnc-KCNE1B-10:3 | SEQ4324 | 6.E−03 | 1.6 | MCI | OIP5-AS1:3 | SEQ4919 | 8.E−04 | 0.5 |
| All AD | lnc-KCNE1B-10:3 | SEQ4324 | 4.E−02 | 1.4 | FTD | OIP5-AS1:36 | SEQ5807 | 6.E−05 | 0.7 |
| miAD | lnc-KCNE1B-2:1 | SEQ4161 | 1.E−02 | 1.3 | miAD | OR2A1-AS1:20 | SEQ4272 | 8.E−03 | 1.5 |
| miAD | lnc-KCNE1B-5:1 | SEQ4162 | 1.E−02 | 1.3 | All AD | OR2A1-AS1:20 | SEQ4272 | 1.E−02 | 1.4 |
| FTD | lnc-KCNE1B-7:1 | SEQ4885 | 2.E−04 | 2.6 | DLB | PAN3-AS1:1 | SEQ4842 | 6.E−04 | 1.5 |
| MCI | lnc-KCNE1B-7:1 | SEQ4885 | 6.E−04 | 2.9 | MCI | PAN3-AS1:1 | SEQ4842 | 9.E−04 | 1.4 |
| DLB | lnc-KCNE1B-7:1 | SEQ4885 | 9.E−04 | 2.9 | DLB | PAN3-AS1:2 | SEQ4843 | 6.E−04 | 1.5 |
| DLB | lnc-KCNE1B-7:2 | SEQ5056 | 7.E−04 | 2.8 | MCI | PAN3-AS1:2 | SEQ4843 | 9.E−04 | 1.4 |
| MCI | lnc-KCNE1B-7:2 | SEQ5056 | 7.E−04 | 2.9 | All AD | PCBP1-AS1:205 | SEQ3681 | 2.E−02 | 0.7 |
| MCI | lnc-KCNE1B-7:5 | SEQ3702 | 3.E−05 | 3.2 | msAD | PCBP1-AS1:205 | SEQ3681 | 5.E−02 | 0.8 |
| miAD | lnc-KCNE1B-7:5 | SEQ3702 | 7.E−05 | 1.7 | All AD | PCBP1-AS1:213 | SEQ5966 | 3.E−02 | 0.7 |
| DLB | lnc-KCNE1B-7:5 | SEQ3702 | 1.E−03 | 2.5 | DLB | PCBP1-AS1:217 | SEQ3458 | 5.E−04 | 1.2 |
| All AD | lnc-KCNE1B-7:5 | SEQ3702 | 1.E−03 | 1.5 | FTD | PCBP1-AS1:302 | SEQ4731 | 3.E−11 | 0.2 |
| msAD | lnc-KCNE1B-7:5 | SEQ3702 | 5.E−02 | 1.3 | MCI | PCBP1-AS1:302 | SEQ4731 | 3.E−08 | 0.3 |
| FTD | lnc-KCNE1B-7:9 | SEQ4884 | 3.E−07 | 11.9 | miAD | PCBP1-AS1:302 | SEQ4731 | 2.E−06 | 0.2 |
| MCI | lnc-KCNE1B-7:9 | SEQ4884 | 9.E−04 | 2.7 | DLB | PCBP1-AS1:302 | SEQ4731 | 1.E−05 | 0.3 |
| MCI | lnc-KCNE4-7:1 | SEQ2466 | 1.E−03 | 0.6 | All AD | PCBP1-AS1:302 | SEQ4731 | 2.E−05 | 0.3 |
| FTD | lnc-KCNE5-3:1 | SEQ5723 | 3.E−06 | 0.5 | msAD | PCBP1-AS1:302 | SEQ4731 | 1.E−03 | 0.3 |
| MCI | lnc-KCNE5-3:1 | SEQ5723 | 9.E−05 | 0.6 | All AD | PCBP1-AS1:304 | SEQ3972 | 2.E−02 | 0.7 |
| FTD | lnc-KCNRG-1:1 | SEQ2856 | 6.E−08 | 0.5 | msAD | PCBP1-AS1:304 | SEQ3972 | 2.E−02 | 0.7 |
| MCI | lnc-KCNRG-1:1 | SEQ2856 | 8.E−04 | 0.6 | DLB | PCED1B-AS1:21 | SEQ5279 | 5.E−04 | 1.8 |
| miAD | lnc-KCNRG-1:1 | SEQ2856 | 6.E−03 | 0.7 | MCI | PCED1B-AS1:21 | SEQ5279 | 5.E−04 | 1.9 |
| All AD | lnc-KCNRG-1:1 | SEQ2856 | 7.E−03 | 0.7 | MCI | PCED1B-AS1:24 | SEQ4320 | 4.E−05 | 3.5 |
| msAD | lnc-KCNRG-1:1 | SEQ2856 | 3.E−02 | 0.7 | DLB | PCED1B-AS1:24 | SEQ4320 | 6.E−05 | 3.0 |
| FTD | lnc-KCNRG-2:2 | SEQ4270 | 1.E−08 | 0.5 | miAD | PCED1B-AS1:24 | SEQ4320 | 6.E−03 | 1.6 |
| MCI | lnc-KCNRG-2:2 | SEQ4270 | 1.E−05 | 0.5 | All AD | PCED1B-AS1:24 | SEQ4320 | 2.E−02 | 1.4 |
| miAD | lnc-KCNRG-2:2 | SEQ4270 | 2.E−04 | 0.6 | MCI | PCED1B-AS1:4 | SEQ5455 | 2.E−04 | 1.9 |
| All AD | lnc-KCNRG-2:2 | SEQ4270 | 5.E−04 | 0.7 | DLB | PCED1B-AS1:4 | SEQ5455 | 5.E−04 | 1.9 |
| msAD | lnc-KCNRG-2:2 | SEQ4270 | 8.E−03 | 0.7 | MCI | PCED1B-AS1:7 | SEQ5348 | 4.E−04 | 3.1 |
| FTD | lnc-KCNRG-5:2 | SEQ4075 | 1.E−08 | 0.5 | All AD | PCED1B-AS1:7 | SEQ5348 | 3.E−02 | 1.4 |
| MCI | lnc-KCNRG-5:2 | SEQ4075 | 9.E−05 | 0.6 | MCI | PCF11-AS1:12 | SEQ5841 | 4.E−05 | 0.5 |
| miAD | lnc-KCNRG-5:2 | SEQ4075 | 1.E−03 | 0.6 | FTD | PDCD4-AS1:5 | SEQ5721 | 1.E−04 | 0.6 |
| All AD | lnc-KCNRG-5:2 | SEQ4075 | 2.E−03 | 0.7 | DLB | PDCD4-AS1:6 | SEQ5401 | 1.E−05 | 1.9 |
| msAD | lnc-KCNRG-5:2 | SEQ4075 | 1.E−02 | 0.7 | MCI | PDCD4-AS1:6 | SEQ5401 | 6.E−05 | 1.7 |
| DLB | lnc-KCNT1-1:7 | SEQ5577 | 2.E−04 | 1.7 | FTD | PDCD4-AS1:6 | SEQ5401 | 3.E−04 | 1.5 |
| DLB | lnc-KCNT1-6:1 | SEQ2699 | 1.E−03 | 1.4 | DLB | PIK3CD-AS1:1 | SEQ5793 | 6.E−05 | 1.6 |
| DLB | lnc-KDM3A-1:4 | SEQ0104 | 2.E−03 | 1.4 | DLB | PIK3CD-AS2:10 | SEQ5127 | 6.E−04 | 1.6 |
| DLB | lnc-KDM4C-18:1 | SEQ5474 | 2.E−04 | 0.5 | MCI | PIK3CD-AS2:8 | SEQ5460 | 2.E−04 | 2.0 |
| MCI | lnc-KIAA0319L-1:4 | SEQ4874 | 9.E−04 | 1.8 | DLB | PIK3CD-AS2:8 | SEQ5460 | 3.E−04 | 2.0 |
| All AD | lnc-KIAA0355-1:1 | SEQ4993 | 3.E−02 | 0.8 | DLB | PIK3IP1-AS1:12 | SEQ5029 | 7.E−04 | 1.5 |
| FTD | lnc-KIAA0391-1:1 | SEQ3817 | 3.E−04 | 0.7 | All AD | PIK3IP1-AS1:12 | SEQ5029 | 4.E−02 | 1.2 |
| All AD | lnc-KIAA0391-1:1 | SEQ3817 | 3.E−02 | 0.8 | All AD | PIK3IP1-AS1:3 | SEQ5973 | 2.E−02 | 1.3 |
| msAD | lnc-KIAA0391-1:1 | SEQ3817 | 4.E−02 | 0.8 | MCI | PINK1-AS:2 | SEQ5500 | 2.E−04 | 2.3 |
| FTD | lnc-KIAA0825-1:2 | SEQ4996 | 5.E−08 | 0.5 | All AD | PLBD1-AS1:6 | SEQ3960 | 8.E−03 | 0.7 |
| MCI | lnc-KIAA0825-1:2 | SEQ4996 | 5.E−04 | 0.7 | miAD | PLBD1-AS1:6 | SEQ3960 | 1.E−02 | 0.8 |
| All AD | lnc-KIAA0825-1:2 | SEQ4996 | 2.E−02 | 0.7 | msAD | PLBD1-AS1:6 | SEQ3960 | 2.E−02 | 0.7 |
| MCI | lnc-KIAA1109-1:1 | SEQ5381 | 2.E−04 | 1.6 | miAD | PLBD1-AS1:7 | SEQ4173 | 2.E−04 | 0.8 |
| DLB | lnc-KIAA1109-1:1 | SEQ5381 | 3.E−04 | 1.6 | All AD | PLBD1-AS1:7 | SEQ4173 | 7.E−04 | 0.8 |
| DLB | lnc-KIAA1549L-1:1 | SEQ5427 | 2.E−04 | 1.3 | msAD | PLBD1-AS1:7 | SEQ4173 | 1.E−02 | 0.8 |
| MCI | lnc-KIAA1549L-1:1 | SEQ5427 | 3.E−04 | 1.4 | FTD | POC1B-AS1:8 | SEQ5156 | 5.E−04 | 0.6 |
| All AD | lnc-KIAA1551-13:1 | SEQ3715 | 3.E−02 | 0.8 | FTD | PPP3CB-AS1:4 | SEQ5981 | 2.E−06 | 0.4 |
| msAD | lnc-KIAA1551-13:1 | SEQ3715 | 4.E−02 | 0.8 | DLB | PRKAG2-AS1:1 | SEQ5488 | 1.E−04 | 1.7 |
| All AD | lnc-KIAA1551-2:1 | SEQ4066 | 9.E−03 | 0.7 | MCI | PRKAG2-AS1:1 | SEQ5488 | 2.E−04 | 1.6 |
| msAD | lnc-KIAA1551-2:1 | SEQ4066 | 2.E−02 | 0.7 | FTD | PRKCQ-AS1:11 | SEQ4800 | 1.E−03 | 0.5 |
| FTD | lnc-KIAA1551-4:1 | SEQ4359 | 3.E−06 | 0.5 | MCI | PRKCQ-AS1:3 | SEQ4536 | 3.E−06 | 4.4 |
| All AD | lnc-KIAA1551-4:1 | SEQ4359 | 9.E−04 | 0.6 | FTD | PRKCQ-AS1:3 | SEQ4536 | 1.E−03 | 2.1 |
| msAD | lnc-KIAA1551-4:1 | SEQ4359 | 1.E−03 | 0.7 | DLB | PRKCQ-AS1:3 | SEQ4536 | 2.E−03 | 2.2 |
| miAD | lnc-KIAA1551-4:1 | SEQ4359 | 4.E−03 | 0.6 | MCI | PRKCQ-AS1:36 | SEQ4537 | 3.E−06 | 4.4 |
| msAD | lnc-KIAA1551-6:1 | SEQ3988 | 2.E−02 | 0.8 | FTD | PRKCQ-AS1:36 | SEQ4537 | 1.E−03 | 2.1 |
| All AD | lnc-KIAA1551-6:1 | SEQ3988 | 3.E−02 | 0.8 | DLB | PRKCQ-AS1:36 | SEQ4537 | 2.E−03 | 2.2 |
| FTD | lnc-KIF14-1:2 | SEQ3885 | 1.E−06 | 0.5 | MCI | PRKCQ-AS1:38 | SEQ4661 | 1.E−03 | 2.1 |
| miAD | lnc-KIF14-1:2 | SEQ3885 | 4.E−04 | 0.6 | All AD | PRKCQ-AS1:45 | SEQ5977 | 3.E−02 | 1.4 |
| All AD | lnc-KIF14-1:2 | SEQ3885 | 2.E−03 | 0.6 | MCI | PRKCQ-AS1:53 | SEQ5501 | 2.E−04 | 2.3 |
| msAD | lnc-KIF14-1:2 | SEQ3885 | 3.E−02 | 0.6 | MCI | PRR7-AS1:7 | SEQ5332 | 2.E−04 | 1.7 |
| DLB | lnc-KIRREL1-1:3 | SEQ4531 | 2.E−03 | 1.8 | DLB | PRR7-AS1:7 | SEQ5332 | 4.E−04 | 1.7 |
| msAD | lnc-KLF11-1:4 | SEQ4039 | 2.E−02 | 1.5 | DLB | PRR7-AS1:8 | SEQ4420 | 1.E−03 | 1.4 |

TABLE 10-continued 2847 whole blood (Paxgene RNA tube) lncRNAs differentially expressed in
MCI group or mild AD group or moderate-to-severe AD group or both of these
AD groups or FTD group or DLB group as compared to healthy control group.

| Group | lncRNA | SEQ | p-value | FC | Group | lncRNA | SEQ | p-value | FC |
|---|---|---|---|---|---|---|---|---|---|
| FTD | lnc-KLF12-4:1 | SEQ0938 | 2.E−05 | 0.5 | MCI | PRR7-AS1:8 | SEQ4420 | 2.E−03 | 1.4 |
| FTD | lnc-KLF12-5:1 | SEQ5149 | 5.E−04 | 0.6 | All AD | PSMA3-AS1:12 | SEQ5979 | 4.E−02 | 0.8 |
| FTD | lnc-KLF5-12:1 | SEQ5008 | 5.E−07 | 0.4 | DLB | PSMA3-AS1:16 | SEQ4675 | 1.E−03 | 1.3 |
| All AD | lnc-KLF5-12:1 | SEQ5008 | 4.E−02 | 0.7 | DLB | PSMA3-AS1:27 | SEQ3498 | 1.E−03 | 1.6 |
| DLB | lnc-KLHDC9-5:1 | SEQ4478 | 2.E−03 | 1.3 | DLB | PSMA3-AS1:28 | SEQ5075 | 2.E−04 | 2.5 |
| DLB | lnc-KLHDC9-5:3 | SEQ4458 | 2.E−03 | 2.2 | FTD | PSMA3-AS1:28 | SEQ5075 | 7.E−04 | 2.2 |
| DLB | lnc-KLHDC9-5:4 | SEQ3431 | 5.E−05 | 1.5 | DLB | PSMA3-AS1:36 | SEQ5190 | 5.E−04 | 1.5 |
| MCI | lnc-KLHDC9-5:4 | SEQ3431 | 2.E−03 | 1.3 | FTD | PSMA3-AS1:40 | SEQ3628 | 6.E−06 | 0.5 |
| DLB | lnc-KLHL10-2:1 | SEQ2459 | 2.E−04 | 1.4 | FTD | PSMA3-AS1:41 | SEQ5915 | 2.E−05 | 0.6 |
| DLB | lnc-KLHL25-1:4 | SEQ4938 | 7.E−04 | 1.4 | msAD | PSMB8-AS1:11 | SEQ3937 | 3.E−02 | 0.8 |
| MCI | lnc-KLHL25-1:4 | SEQ4938 | 8.E−04 | 1.4 | MCI | PSMB8-AS1:14 | SEQ5844 | 1.E−05 | 1.6 |
| DLB | lnc-KLHL28-3:5 | SEQ2642 | 5.E−04 | 1.5 | FTD | PSMB8-AS1:14 | SEQ5844 | 1.E−05 | 1.5 |
| DLB | lnc-KLHL36-4:1 | SEQ5382 | 3.E−06 | 1.8 | DLB | PSMB8-AS1:14 | SEQ5844 | 4.E−05 | 1.5 |
| FTD | lnc-KLHL36-4:1 | SEQ5382 | 2.E−04 | 1.5 | MCI | PSMB8-AS1:15 | SEQ5888 | 2.E−05 | 0.2 |
| MCI | lnc-KLHL36-4:1 | SEQ5382 | 3.E−04 | 1.6 | MCI | PSMB8-AS1:16 | SEQ5453 | 3.E−04 | 1.8 |
| FTD | lnc-KLHL8-2:1 | SEQ4998 | 8.E−04 | 0.7 | DLB | PTOV1-AS1:8 | SEQ5212 | 5.E−04 | 1.9 |
| All AD | lnc-KLHL8-2:1 | SEQ4998 | 2.E−02 | 0.8 | DLB | PTOV1-AS2:1 | SEQ4744 | 1.E−03 | 1.4 |
| DLB | lnc-KLHL9-1:1 | SEQ5014 | 4.E−06 | 1.9 | MCI | PVT1:31 | SEQ4534 | 2.E−03 | 2.0 |
| MCI | lnc-KLHL9-1:1 | SEQ5014 | 2.E−04 | 1.6 | DLB | PXN-AS1:15 | SEQ3573 | 9.E−04 | 1.5 |
| miAD | lnc-KLHL9-1:1 | SEQ5014 | 7.E−04 | 1.4 | MCI | PXN-AS1:22 | SEQ4576 | 1.E−03 | 1.7 |
| All AD | lnc-KLHL9-1:1 | SEQ5014 | 4.E−03 | 1.3 | DLB | PXN-AS1:22 | SEQ4576 | 2.E−03 | 1.5 |
| All AD | lnc-KLLN-1:1 | SEQ5017 | 5.E−02 | 0.8 | MCI | PYCARD-AS1:1 | SEQ5028 | 1.E−04 | 1.6 |
| msAD | lnc-KLRD1-1:1 | SEQ3801 | 4.E−02 | 0.7 | FTD | PYCARD-AS1:1 | SEQ5028 | 1.E−04 | 1.5 |
| All AD | lnc-KLRD1-1:1 | SEQ3801 | 4.E−02 | 0.7 | DLB | PYCARD-AS1:1 | SEQ5028 | 7.E−04 | 1.5 |
| FTD | lnc-KMT2E-6:1 | SEQ3952 | 3.E−06 | 0.5 | DLB | RAB11B-AS1:7 | SEQ5538 | 2.E−04 | 1.8 |
| All AD | lnc-KMT2E-6:1 | SEQ3952 | 1.E−02 | 0.6 | DLB | RAD51-AS1:1 | SEQ5132 | 6.E−04 | 1.6 |
| msAD | lnc-KMT2E-6:1 | SEQ3952 | 2.E−02 | 0.7 | DLB | RALY-AS1:13 | SEQ5553 | 2.E−05 | 1.7 |
| All AD | lnc-KPNA2-6:1 | SEQ5021 | 4.E−02 | 1.2 | MCI | RALY-AS1:13 | SEQ5553 | 6.E−05 | 1.6 |
| DLB | lnc-KPNA2-6:13 | SEQ4978 | 9.E−05 | 2.2 | FTD | RALY-AS1:13 | SEQ5553 | 2.E−04 | 1.4 |
| MCI | lnc-KPNA2-6:13 | SEQ4978 | 8.E−04 | 1.8 | All AD | RALY-AS1:13 | SEQ5553 | 4.E−02 | 1.2 |
| FTD | lnc-KPNA2-6:16 | SEQ5883 | 3.E−05 | 0.5 | miAD | RARA-AS1:3 | SEQ4223 | 1.E−02 | 0.8 |
| DLB | lnc-KPNA2-6:25 | SEQ5284 | 5.E−04 | 2.4 | All AD | RARA-AS1:3 | SEQ4223 | 3.E−02 | 0.8 |
| DLB | lnc-KRT80-3:1 | SEQ3433 | 3.E−04 | 1.5 | DLB | RASSF1-AS1:2 | SEQ4746 | 6.E−04 | 1.6 |
| DLB | lnc-KRTAP5-6-3:1 | SEQ4942 | 8.E−04 | 1.5 | FTD | RASSF1-AS1:2 | SEQ4746 | 1.E−03 | 1.3 |
| miAD | lnc-KRTDAP-1:2 | SEQ4276 | 8.E−03 | 0.7 | MCI | RASSF1-AS1:2 | SEQ4746 | 1.E−03 | 1.4 |
| All AD | lnc-KRTDAP-1:2 | SEQ4276 | 1.E−02 | 0.7 | MCI | RBM26-AS1:1 | SEQ4319 | 4.E−06 | 2.0 |
| All AD | lnc-KRTDAP-1:6 | SEQ3868 | 1.E−02 | 0.7 | DLB | RBM26-AS1:1 | SEQ4319 | 1.E−05 | 2.1 |
| msAD | lnc-KRTDAP-1:6 | SEQ3868 | 3.E−02 | 0.7 | FTD | RBM26-AS1:1 | SEQ4319 | 4.E−05 | 1.7 |
| miAD | lnc-KY-4:1 | SEQ0123 | 1.E−02 | 0.6 | All AD | RBM26-AS1:1 | SEQ4319 | 2.E−03 | 1.3 |
| All AD | lnc-KY-4:1 | SEQ0123 | 2.E−02 | 0.7 | msAD | RBM26-AS1:1 | SEQ4319 | 5.E−03 | 1.3 |
| DLB | lnc-LAMA5-1:4 | SEQ3434 | 1.E−04 | 1.5 | miAD | RBM26-AS1:1 | SEQ4319 | 6.E−03 | 1.3 |
| MCI | lnc-LAMA5-1:4 | SEQ3434 | 2.E−03 | 1.3 | DLB | RBM5-AS1:1 | SEQ4691 | 1.E−03 | 1.4 |
| DLB | lnc-LAMA5-4:1 | SEQ3435 | 1.E−03 | 1.4 | DLB | RBM5-AS1:2 | SEQ4489 | 2.E−03 | 1.4 |
| All AD | lnc-LASP1-5:1 | SEQ2438 | 2.E−03 | 0.7 | All AD | RC3H1-IT1:1 | SEQ5983 | 2.E−02 | 0.7 |
| msAD | lnc-LASP1-5:1 | SEQ2438 | 3.E−03 | 0.7 | MCI | RNF219-AS1:16 | SEQ4990 | 3.E−04 | 0.6 |
| miAD | lnc-LASP1-5:1 | SEQ2438 | 8.E−03 | 0.7 | FTD | RNF219-AS1:16 | SEQ4990 | 8.E−04 | 0.6 |
| DLB | lnc-LCMT2-1:1 | SEQ4769 | 1.E−03 | 1.5 | MCI | RPARP-AS1:29 | SEQ4873 | 4.E−05 | 1.8 |
| miAD | lnc-LCOR-4:3 | SEQ3289 | 1.E−02 | 0.8 | DLB | RPARP-AS1:29 | SEQ4873 | 9.E−04 | 1.8 |
| All AD | lnc-LCOR-4:3 | SEQ3289 | 1.E−02 | 0.8 | DLB | RPARP-AS1:31 | SEQ5023 | 7.E−04 | 1.5 |
| All AD | lnc-LCOR-4:4 | SEQ5033 | 4.E−02 | 0.8 | All AD | RPS6KB2-AS1:2 | SEQ5986 | 4.E−02 | 1.2 |
| FTD | lnc-LCP2-3:1 | SEQ5766 | 8.E−05 | 0.7 | DLB | RUSC1-AS1:8 | SEQ5658 | 1.E−04 | 1.5 |
| DLB | lnc-LDAH-4:1 | SEQ4557 | 2.E−03 | 1.3 | DLB | SATB1-AS1:2 | SEQ3794 | 2.E−03 | 1.9 |
| MCI | lnc-LDHAL6A-1:2 | SEQ4830 | 9.E−04 | 1.3 | miAD | SATB1-AS1:2 | SEQ3794 | 7.E−03 | 1.5 |
| DLB | lnc-LEAP2-2:1 | SEQ2749 | 2.E−03 | 1.3 | All AD | SATB1-AS1:2 | SEQ3794 | 8.E−03 | 1.4 |
| FTD | lnc-LEKR1-7:1 | SEQ3831 | 3.E−04 | 0.6 | msAD | SATB1-AS1:2 | SEQ3794 | 4.E−02 | 1.4 |
| msAD | lnc-LEKR1-7:1 | SEQ3831 | 3.E−02 | 0.8 | All AD | SATB1-AS1:90 | SEQ5987 | 4.E−02 | 1.5 |
| All AD | lnc-LEKR1-7:1 | SEQ3831 | 4.E−02 | 0.8 | miAD | SBF2-AS1:7 | SEQ4385 | 3.E−03 | 0.7 |
| FTD | lnc-LEO1-2:1 | SEQ6013 | 1.E−10 | 0.3 | FTD | SDCBP2-AS1:4 | SEQ3711 | 3.E−04 | 2.2 |
| All AD | lnc-LEPROTL1-5:1 | SEQ4388 | 5.E−04 | 1.8 | MCI | SDCBP2-AS1:4 | SEQ3711 | 3.E−04 | 2.4 |
| msAD | lnc-LEPROTL1-5:1 | SEQ4388 | 1.E−03 | 1.8 | DLB | SDCBP2-AS1:4 | SEQ3711 | 5.E−04 | 2.3 |
| miAD | lnc-LEPROTL1-5:1 | SEQ4388 | 2.E−03 | 1.7 | msAD | SDCBP2-AS1:4 | SEQ3711 | 1.E−02 | 1.3 |
| DLB | lnc-LEPROTL1-5:2 | SEQ4449 | 2.E−03 | 1.6 | MCI | SGMS1-AS1:10 | SEQ5536 | 2.E−04 | 1.8 |
| DLB | lnc-LGALS2-1:3 | SEQ5164 | 5.E−05 | 1.6 | All AD | SGMS1-AS1:10 | SEQ5536 | 2.E−02 | 1.3 |
| FTD | lnc-LGALS2-1:3 | SEQ5164 | 5.E−04 | 1.4 | MCI | SLC25A25-AS1:1 | SEQ5910 | 2.E−05 | 2.8 |
| DLB | lnc-LGALS2-5:1 | SEQ4413 | 1.E−03 | 1.4 | DLB | SLC25A25-AS1:14 | SEQ4871 | 6.E−04 | 1.6 |
| MCI | lnc-LGALS2-5:1 | SEQ4413 | 2.E−03 | 1.4 | MCI | SLC25A25-AS1:14 | SEQ4871 | 9.E−04 | 1.7 |
| DLB | lnc-LGALS7B-1:5 | SEQ5114 | 6.E−04 | 1.4 | DLB | SLC25A25-AS1:8 | SEQ5861 | 4.E−05 | 1.8 |
| DLB | lnc-LGALSL-2:9 | SEQ4391 | 2.E−03 | 2.E−02 | DLB | SLC2A1-AS1:4 | SEQ3874 | 1.E−03 | 1.3 |
| MCI | lnc-LHFPL3-4:1 | SEQ5301 | 5.E−05 | 1.7 | miAD | SLC2A1-AS1:4 | SEQ3874 | 5.E−03 | 1.2 |
| DLB | lnc-LHFPL3-4:1 | SEQ5301 | 5.E−05 | 1.6 | All AD | SLC2A1-AS1:4 | SEQ3874 | 6.E−03 | 1.2 |
| FTD | lnc-LHFPL3-4:1 | SEQ5301 | 4.E−04 | 1.3 | msAD | SLC2A1-AS1:4 | SEQ3874 | 3.E−02 | 1.1 |
| DLB | lnc-LHPP-6:5 | SEQ5439 | 3.E−04 | 1.5 | msAD | SLC2A1-AS1:5 | SEQ3691 | 5.E−02 | 1.4 |
| DLB | lnc-LHPP-6:6 | SEQ3436 | 2.E−04 | 1.6 | FTD | SLC8A1-AS1:30 | SEQ4131 | 6.E−05 | 0.5 |
| All AD | lnc-LHPP-8:1 | SEQ3637 | 3.E−02 | 0.8 | miAD | SLC8A1-AS1:30 | SEQ4131 | 1.E−02 | 0.6 |

TABLE 10-continued 2847 whole blood (Paxgene RNA tube) lncRNAs differentially expressed in
MCI group or mild AD group or moderate-to-severe AD group or both of these
AD groups or FTD group or DLB group as compared to healthy control group.

| Group | lncRNA | SEQ | p-value | FC | Group | lncRNA | SEQ | p-value | FC |
|---|---|---|---|---|---|---|---|---|---|
| msAD | lnc-LHPP-8:1 | SEQ3637 | 5.E-02 | 0.8 | All AD | SLC8A1-AS1:30 | SEQ4131 | 3.E-02 | 0.6 |
| All AD | lnc-LIN7A-3:1 | SEQ3437 | 4.E-02 | 0.7 | FTD | SMARCA5-AS1:2 | SEQ5505 | 7.E-06 | 2.6 |
| DLB | lnc-LINC00094-2:1 | SEQ5204 | 8.E-05 | 1.9 | MCI | SMARCA5-AS1:2 | SEQ5505 | 2.E-05 | 2.6 |
| MCI | lnc-LINC00094-2:1 | SEQ5204 | 5.E-04 | 1.7 | DLB | SMARCA5-AS1:2 | SEQ5505 | 9.E-05 | 2.2 |
| DLB | lnc-LINC00672-1:1 | SEQ5376 | 3.E-04 | 1.5 | msAD | SMARCA5-AS1:2 | SEQ5505 | 2.E-04 | 1.7 |
| DLB | lnc-LINC00694-4:1 | SEQ5521 | 2.E-04 | 1.4 | All AD | SMARCA5-AS1:2 | SEQ5505 | 9.E-04 | 1.5 |
| FTD | lnc-LINC02210-CRHR1-2:4 | SEQ5641 | 1.E-04 | 0.5 | DLB | SMCR5:1 | SEQ3037 | 2.E-04 | 2.0 |
| FTD | lnc-LINC02210-CRHR1-3:1 | SEQ5938 | 1.E-05 | 0.4 | DLB | SNAI3-AS1:12 | SEQ5634 | 9.E-05 | 1.9 |
| All AD | lnc-LINS1-3:1 | SEQ5047 | 2.E-02 | 1.2 | MCI | SNAI3-AS1:12 | SEQ5634 | 2.E-04 | 1.9 |
| FTD | lnc-LIPC-2:1 | SEQ4921 | 5.E-05 | 0.4 | FTD | SND1-IT1:4 | SEQ3933 | 1.E-04 | 0.5 |
| MCI | lnc-LIPC-2:1 | SEQ4921 | 8.E-04 | 0.7 | miAD | SND1-IT1:4 | SEQ3933 | 3.E-03 | 0.6 |
| All AD | lnc-LIPC-2:1 | SEQ4921 | 2.E-02 | 0.7 | All AD | SND1-IT1:4 | SEQ3933 | 4.E-03 | 0.6 |
| FTD | lnc-LIPC-3:1 | SEQ4070 | 3.E-05 | 0.4 | msAD | SND1-IT1:4 | SEQ3933 | 2.E-02 | 0.7 |
| MCI | lnc-LIPC-3:1 | SEQ4070 | 6.E-04 | 0.6 | DLB | SND1-IT1:5 | SEQ5050 | 7.E-04 | 1.9 |
| miAD | lnc-LIPC-3:1 | SEQ4070 | 1.E-02 | 0.6 | MCI | SNHG1:1 | SEQ5463 | 3.E-04 | 2.7 |
| All AD | lnc-LIPC-3:1 | SEQ4070 | 3.E-02 | 0.7 | FTD | SNHG1:54 | SEQ5502 | 6.E-10 | 9.7 |
| FTD | lnc-LIPC-4:1 | SEQ5054 | 3.E-06 | 0.4 | MCI | SNHG1:54 | SEQ5502 | 2.E-04 | 2.6 |
| MCI | lnc-LIPC-4:1 | SEQ5054 | 9.E-05 | 0.5 | DLB | SNHG12:16 | SEQ4759 | 1.E-03 | 1.5 |
| All AD | lnc-LIPC-4:1 | SEQ5054 | 2.E-02 | 0.6 | MCI | SNHG12:17 | SEQ5303 | 4.E-05 | 1.8 |
| FTD | lnc-LIPC-5:1 | SEQ4920 | 3.E-05 | 0.4 | DLB | SNHG12:17 | SEQ5303 | 4.E-04 | 1.8 |
| MCI | lnc-LIPC-5:1 | SEQ4920 | 8.E-04 | 0.5 | FTD | SNHG12:17 | SEQ5303 | 4.E-04 | 1.7 |
| All AD | lnc-LIPC-5:1 | SEQ4920 | 4.E-02 | 0.8 | All AD | SNHG12:17 | SEQ5303 | 4.E-02 | 1.2 |
| FTD | lnc-LIPC-6:1 | SEQ3678 | 1.E-07 | 0.3 | All AD | SNHG16:31 | SEQ5992 | 4.E-02 | 0.8 |
| MCI | lnc-LIPC-6:1 | SEQ3678 | 1.E-05 | 0.3 | DLB | SNHG16:4 | SEQ4727 | 1.E-03 | 2.3 |
| DLB | lnc-LIPC-6:1 | SEQ3678 | 6.E-04 | 0.3 | All AD | SNHG16:42 | SEQ5994 | 4.E-02 | 0.8 |
| miAD | lnc-LIPC-6:1 | SEQ3678 | 1.E-02 | 0.6 | DLB | SNHG17:23 | SEQ5489 | 2.E-04 | 1.6 |
| All AD | lnc-LIPC-6:1 | SEQ3678 | 1.E-02 | 0.6 | DLB | SNHG21:11 | SEQ4768 | 1.E-03 | 1.5 |
| msAD | lnc-LIPC-6:1 | SEQ3678 | 5.E-02 | 0.6 | MCI | SNHG22:3 | SEQ5497 | 1.E-04 | 1.8 |
| FTD | lnc-LIX1-1:1 | SEQ5413 | 3.E-04 | 0.6 | DLB | SNHG22:3 | SEQ5497 | 2.E-04 | 1.9 |
| MCI | lnc-LKAAEAR1-2:1 | SEQ5026 | 5.E-04 | 1.5 | DLB | SNHG25:1 | SEQ4827 | 9.E-04 | 1.2 |
| DLB | lnc-LKAAEAR1-2:1 | SEQ5026 | 7.E-04 | 1.5 | MCI | SNHG5:12 | SEQ5542 | 1.E-04 | 0.3 |
| miAD | lnc-LMLN-4:1 | SEQ3734 | 7.E-03 | 0.5 | FTD | SNHG5:12 | SEQ5542 | 2.E-04 | 0.3 |
| All AD | lnc-LMLN-4:1 | SEQ3734 | 9.E-03 | 0.6 | All AD | SNHG6:12 | SEQ5995 | 5.E-02 | 0.8 |
| msAD | lnc-LMLN-4:1 | SEQ3734 | 4.E-02 | 0.7 | DLB | SNHG7:12 | SEQ4121 | 1.E-05 | 1.8 |
| FTD | lnc-LONP2-8:1 | SEQ4310 | 8.E-06 | 0.5 | MCI | SNHG7:12 | SEQ4121 | 2.E-04 | 1.6 |
| miAD | lnc-LONP2-8:1 | SEQ4310 | 7.E-03 | 0.6 | FTD | SNHG7:12 | SEQ4121 | 7.E-04 | 1.4 |
| All AD | lnc-LONP2-8:1 | SEQ4310 | 1.E-02 | 0.7 | All AD | SNHG7:12 | SEQ4121 | 8.E-03 | 1.2 |
| DLB | lnc-LPAR6-4:1 | SEQ5491 | 4.E-04 | 1.6 | msAD | SNHG7:12 | SEQ4121 | 1.E-02 | 1.3 |
| FTD | lnc-LPCAT3-1:1 | SEQ2652 | 5.E-06 | 1.8 | FTD | SNRK-AS1:1 | SEQ5965 | 1.E-08 | 0.5 |
| MCI | lnc-LPCAT3-1:1 | SEQ2652 | 5.E-04 | 1.9 | MCI | SNRK-AS1:1 | SEQ5965 | 4.E-06 | 0.5 |
| DLB | lnc-LPCAT3-1:1 | SEQ2652 | 2.E-03 | 1.8 | FTD | SNRK-AS1:4 | SEQ4006 | 4.E-07 | 2.3 |
| All AD | lnc-LPCAT3-1:1 | SEQ2652 | 2.E-02 | 1.2 | MCI | SNRK-AS1:4 | SEQ4006 | 1.E-06 | 2.7 |
| FTD | lnc-LPIN1-5:1 | SEQ5066 | 1.E-05 | 1.6 | DLB | SNRK-AS1:4 | SEQ4006 | 2.E-05 | 2.3 |
| MCI | lnc-LPIN1-5:1 | SEQ5066 | 2.E-04 | 1.5 | All AD | SNRK-AS1:4 | SEQ4006 | 7.E-03 | 1.3 |
| All AD | lnc-LPIN1-5:1 | SEQ5066 | 4.E-02 | 1.2 | miAD | SNRK-AS1:4 | SEQ4006 | 9.E-03 | 1.3 |
| MCI | lnc-LPIN1-7:2 | SEQ5581 | 4.E-05 | 2.2 | msAD | SNRK-AS1:4 | SEQ4006 | 2.E-02 | 1.3 |
| DLB | lnc-LPIN1-7:2 | SEQ5581 | 2.E-04 | 2.0 | FTD | SOS1-IT1:2 | SEQ4034 | 2.E-07 | 0.4 |
| DLB | lnc-LPIN3-1:1 | SEQ3438 | 3.E-04 | 1.5 | MCI | SOS1-IT1:2 | SEQ4034 | 8.E-05 | 0.5 |
| FTD | lnc-LPP-2:1 | SEQ5070 | 7.E-06 | 0.7 | All AD | SOS1-IT1:2 | SEQ4034 | 1.E-02 | 0.7 |
| All AD | lnc-LPP-2:1 | SEQ5070 | 4.E-02 | 0.8 | msAD | SOS1-IT1:2 | SEQ4034 | 2.E-02 | 0.7 |
| FTD | lnc-LPP-2:2 | SEQ5072 | 3.E-05 | 0.7 | DLB | SPAG5-AS1:8 | SEQ5843 | 4.E-05 | 1.4 |
| All AD | lnc-LPP-2:2 | SEQ5072 | 5.E-02 | 0.8 | DLB | SPAG5-AS1:9 | SEQ4632 | 1.E-03 | 1.5 |
| miAD | lnc-LRFN5-10:1 | SEQ4213 | 1.E-02 | 1.2 | DLB | SSBP3-AS1:2 | SEQ5270 | 5.E-04 | 1.6 |
| All AD | lnc-LRFN5-10:1 | SEQ4213 | 1.E-02 | 1.2 | MCI | STARD7-AS1:5 | SEQ4797 | 1.E-06 | 2.2 |
| DLB | lnc-LRP1-1:1 | SEQ4508 | 2.E-03 | 1.5 | DLB | STARD7-AS1:5 | SEQ4797 | 6.E-06 | 2.2 |
| DLB | lnc-LRP5L-14:1 | SEQ5248 | 5.E-04 | 1.5 | FTD | STARD7-AS1:5 | SEQ4797 | 3.E-05 | 2.0 |
| miAD | lnc-LRRC10-1:1 | SEQ3290 | 2.E-03 | 0.7 | All AD | STARD7-AS1:5 | SEQ4797 | 1.E-04 | 1.5 |
| All AD | lnc-LRRC10-1:1 | SEQ3290 | 5.E-03 | 0.7 | miAD | STARD7-AS1:5 | SEQ4797 | 1.E-04 | 1.5 |
| msAD | lnc-LRRC10-1:1 | SEQ3290 | 4.E-02 | 0.7 | msAD | STARD7-AS1:5 | SEQ4797 | 1.E-03 | 1.4 |
| FTD | lnc-LRRC10-1:2 | SEQ3441 | 3.E-04 | 0.5 | MCI | STXBP5-AS1:16 | SEQ5579 | 2.E-04 | 1.9 |
| miAD | lnc-LRRC10-1:2 | SEQ3441 | 1.E-02 | 0.7 | FTD | SVIL-AS1:37 | SEQ5868 | 4.E-05 | 0.6 |
| All AD | lnc-LRRC10-1:2 | SEQ3441 | 1.E-02 | 0.7 | DLB | TBC1D22A-AS1:1 | SEQ4592 | 2.E-03 | 1.7 |
| msAD | lnc-LRRC10-1:2 | SEQ3441 | 4.E-02 | 0.7 | DLB | TBX2-AS1:17 | SEQ4493 | 2.E-03 | 1.4 |
| FTD | lnc-LRRC31-2:1 | SEQ5058 | 7.E-04 | 0.5 | MCI | TCONS_00000224 | SEQ1048 | 2.E-05 | 0.5 |
| FTD | lnc-LRRC37A3-5:15 | SEQ5603 | 2.E-04 | 0.6 | DLB | TCONS_00000224 | SEQ1048 | 9.E-04 | 0.6 |
| DLB | lnc-LRRC3C-2:1 | SEQ5388 | 1.E-04 | 1.8 | FTD | TCONS_00000416 | SEQ1091 | 6.E-04 | 0.6 |
| MCI | lnc-LRRC3C-2:1 | SEQ5388 | 3.E-04 | 1.7 | FTD | TCONS_00000556 | SEQ1026 | 1.E-04 | 0.6 |
| FTD | lnc-LRRC57-1:1 | SEQ2537 | 5.E-07 | 0.5 | All AD | TCONS_00000556 | SEQ1026 | 3.E-02 | 0.8 |
| MCI | lnc-LRRC57-1:1 | SEQ2537 | 2.E-04 | 0.6 | All AD | TCONS_00000655 | SEQ1050 | 4.E-02 | 0.7 |
| All AD | lnc-LRRC57-1:1 | SEQ2537 | 5.E-02 | 0.7 | miAD | TCONS_00000773 | SEQ1086 | 1.E-02 | 0.6 |
| FTD | lnc-LRRC72-10:2 | SEQ4806 | 1.E-03 | 0.6 | All AD | TCONS_00000773 | SEQ1086 | 3.E-02 | 0.7 |
| All AD | lnc-LRRC72-10:2 | SEQ4806 | 4.E-02 | 0.7 | FTD | TCONS_00005037 | SEQ1136 | 1.E-04 | 0.6 |

TABLE 10-continued 2847 whole blood (Paxgene RNA tube) lncRNAs differentially expressed in MCI group or mild AD group or moderate-to-severe AD group or both of these AD groups or FTD group or DLB group as compared to healthy control group.

| Group | lncRNA | SEQ | p-value | FC | Group | lncRNA | SEQ | p-value | FC |
|---|---|---|---|---|---|---|---|---|---|
| miAD | lnc-LRRC72-10:4 | SEQ4336 | 5.E-03 | 0.5 | msAD | TCONS_00005060 | SEQ1140 | 5.E-02 | 1.2 |
| FTD | lnc-LRRC7-5:3 | SEQ4376 | 4.E-07 | 0.4 | FTD | TCONS_00005264 | SEQ1123 | 3.E-08 | 0.5 |
| MCI | lnc-LRRC7-5:3 | SEQ4376 | 1.E-03 | 0.6 | FTD | TCONS_00008856 | SEQ1166 | 3.E-04 | 0.5 |
| miAD | lnc-LRRC7-5:3 | SEQ4376 | 3.E-03 | 0.6 | miAD | TCONS_00008879 | SEQ1170 | 1.E-02 | 0.5 |
| All AD | lnc-LRRC7-5:3 | SEQ4376 | 8.E-03 | 0.6 | All AD | TCONS_00008879 | SEQ1170 | 2.E-02 | 0.5 |
| DLB | lnc-LRRC75A-2:1 | SEQ5568 | 2.E-04 | 1.6 | All AD | TCONS_00008889 | SEQ1172 | 2.E-02 | 0.6 |
| MCI | lnc-LRRK1-3:4 | SEQ0242 | 9.E-05 | 2.0 | msAD | TCONS_00008889 | SEQ1172 | 3.E-02 | 0.7 |
| DLB | lnc-LRRK1-3:4 | SEQ0242 | 8.E-04 | 1.7 | DLB | TCONS_00011972 | SEQ1217 | 5.E-04 | 1.3 |
| msAD | lnc-LRRK1-3:4 | SEQ0242 | 2.E-02 | 1.3 | DLB | TCONS_00011994 | SEQ1222 | 6.E-06 | 1.7 |
| All AD | lnc-LRRK1-3:4 | SEQ0242 | 4.E-02 | 1.2 | FTD | TCONS_00012062 | SEQ1202 | 4.E-05 | 0.6 |
| DLB | lnc-LSM11-1:1 | SEQ5011 | 7.E-04 | 1.3 | MCI | TCONS_00012062 | SEQ1202 | 2.E-03 | 0.6 |
| FTD | lnc-LSM14A-2:5 | SEQ5293 | 4.E-04 | 0.6 | FTD | TCONS_00012063 | SEQ1203 | 2.E-07 | 0.3 |
| DLB | lnc-LTBP2-2:1 | SEQ5625 | 2.E-04 | 1.7 | MCI | TCONS_00012063 | SEQ1203 | 2.E-04 | 0.4 |
| DLB | lnc-LTBP3-2:14 | SEQ4404 | 2.E-03 | 1.3 | All AD | TCONS_00012063 | SEQ1203 | 5.E-02 | 0.6 |
| MCI | lnc-LTBP3-2:5 | SEQ4364 | 6.E-06 | 0.2 | FTD | TCONS_00014141 | SEQ1224 | 5.E-08 | 0.4 |
| FTD | lnc-LTBP3-2:5 | SEQ4364 | 6.E-06 | 0.2 | MCI | TCONS_00014141 | SEQ1224 | 2.E-04 | 0.5 |
| miAD | lnc-LTBP3-2:5 | SEQ4364 | 4.E-03 | 0.3 | miAD | TCONS_00014141 | SEQ1224 | 3.E-03 | 0.5 |
| All AD | lnc-LTBP3-2:5 | SEQ4364 | 2.E-02 | 0.4 | FTD | TCONS_00014165 | SEQ1227 | 3.E-04 | 0.7 |
| MCI | lnc-LTC4S-1:1 | SEQ2941 | 2.E-04 | 1.6 | MCI | TCONS_00014211 | SEQ1239 | 1.E-03 | 1.8 |
| FTD | lnc-LUC7L3-6:1 | SEQ4810 | 1.E-03 | 0.7 | DLB | TCONS_00014211 | SEQ1239 | 2.E-03 | 1.8 |
| FTD | lnc-LXN-1:6 | SEQ5400 | 3.E-04 | 0.7 | All AD | TCONS_00014453 | SEQ1256 | 4.E-02 | 0.7 |
| All AD | lnc-LY86-4:8 | SEQ5094 | 4.E-02 | 0.7 | FTD | TCONS_00017372 | SEQ1273 | 6.E-09 | 4.4 |
| All AD | lnc-LYN-2:1 | SEQ5095 | 4.E-02 | 0.8 | MCI | TCONS_00017372 | SEQ1273 | 4.E-05 | 4.2 |
| DLB | lnc-LYPD6-2:1 | SEQ4429 | 8.E-05 | 1.8 | FTD | TCONS_00017375 | SEQ1276 | 2.E-04 | 3.E-08 |
| MCI | lnc-LYPD6-2:1 | SEQ4429 | 2.E-03 | 1.5 | DLB | TCONS_00017375 | SEQ1276 | 2.E-04 | 2.E-08 |
| FTD | lnc-LYPD8-4:1 | SEQ4365 | 1.E-05 | 0.4 | MCI | TCONS_00017375 | SEQ1276 | 7.E-04 | 2.E-08 |
| miAD | lnc-LYPD8-4:1 | SEQ4365 | 4.E-03 | 0.6 | DLB | TCONS_00017376 | SEQ1277 | 2.E-04 | 0.9 |
| All AD | lnc-LYPD8-4:1 | SEQ4365 | 9.E-03 | 0.6 | MCI | TCONS_00017376 | SEQ1277 | 5.E-02 | 0.9 |
| MCI | lnc-LYZL2-5:1 | SEQ4185 | 2.E-03 | 0.7 | msAD | TCONS_00017376 | SEQ1277 | 4.E-02 | 0.9 |
| miAD | lnc-LYZL2-5:1 | SEQ4185 | 1.E-02 | 0.7 | All AD | TCONS_00017376 | SEQ1277 | 5.E-02 | 0.9 |
| All AD | lnc-LYZL2-5:1 | SEQ4185 | 2.E-02 | 0.6 | FTD | TCONS_00019772 | SEQ1301 | 4.E-04 | 0.6 |
| DLB | lnc-M1AP-1:1 | SEQ4974 | 8.E-04 | 1.7 | DLB | TCONS_00019840 | SEQ1292 | 2.E-03 | 1.3 |
| DLB | lnc-M1AP-6:2 | SEQ5390 | 8.E-05 | 1.8 | FTD | TCONS_00019918 | SEQ1308 | 3.E-05 | 0.6 |
| MCI | lnc-M1AP-6:2 | SEQ5390 | 3.E-04 | 1.8 | DLB | TCONS_00021481 | SEQ1342 | 4.E-04 | 1.7 |
| DLB | lnc-M6PR-4:1 | SEQ3969 | 2.E-04 | 1.6 | MCI | TCONS_00021481 | SEQ1342 | 5.E-04 | 1.6 |
| MCI | lnc-M6PR-4:1 | SEQ3969 | 2.E-04 | 1.4 | MCI | TCONS_00023115 | SEQ1352 | 2.E-03 | 0.4 |
| All AD | lnc-M6PR-4:1 | SEQ3969 | 1.E-02 | 1.2 | FTD | TCONS_00023190 | SEQ1369 | 5.E-04 | 0.6 |
| msAD | lnc-M6PR-4:1 | SEQ3969 | 2.E-02 | 1.2 | miAD | TCONS_00023190 | SEQ1369 | 3.E-03 | 0.6 |
| MCI | lnc-MAD2L2-4:1 | SEQ5633 | 2.E-04 | 1.9 | All AD | TCONS_00023190 | SEQ1369 | 9.E-03 | 0.7 |
| MCI | lnc-MAFF-10:1 | SEQ4924 | 8.E-04 | 1.3 | FTD | TCONS_00023372 | SEQ1374 | 9.E-04 | 0.6 |
| DLB | lnc-MAFF-2:1 | SEQ3013 | 9.E-04 | 1.6 | DLB | TCONS_00026558 | SEQ1414 | 9.E-04 | 1.4 |
| MCI | lnc-MAFF-2:1 | SEQ3013 | 2.E-03 | 1.7 | DLB | TCONS_00033649 | SEQ1546 | 1.E-05 | 2.3 |
| MCI | lnc-MAFK-4:3 | SEQ3644 | 2.E-06 | 1.7 | FTD | TCONS_00033649 | SEQ1546 | 4.E-04 | 1.6 |
| DLB | lnc-MAFK-4:3 | SEQ3644 | 6.E-06 | 1.7 | DLB | TCONS_00035022 | SEQ1567 | 2.E-03 | 16.3 |
| FTD | lnc-MAFK-4:3 | SEQ3644 | 3.E-04 | 1.3 | DLB | TCONS_00035023 | SEQ1568 | 2.E-03 | 16.3 |
| msAD | lnc-MAFK-4:3 | SEQ3644 | 5.E-02 | 1.1 | MCI | TCONS_00035024 | SEQ1571 | 4.E-07 | 2.5 |
| All AD | lnc-MAGEB1-2:1 | SEQ3902 | 1.E-02 | 0.7 | DLB | TCONS_00035024 | SEQ1571 | 3.E-06 | 2.4 |
| msAD | lnc-MAGEB1-2:1 | SEQ3902 | 3.E-02 | 0.7 | FTD | TCONS_00035024 | SEQ1571 | 5.E-05 | 1.9 |
| FTD | lnc-MAGEE2-2:1 | SEQ3291 | 4.E-07 | 0.4 | All AD | TCONS_00035024 | SEQ1571 | 4.E-02 | 1.2 |
| MCI | lnc-MAGEE2-2:1 | SEQ3291 | 2.E-03 | 0.5 | All AD | TCONS_00035025 | SEQ1572 | 3.E-02 | 1.2 |
| FTD | lnc-MALRD1-11:1 | SEQ3815 | 4.E-06 | 0.6 | msAD | TCONS_00035027 | SEQ1575 | 2.E-02 | 1.4 |
| All AD | lnc-MALRD1-11:1 | SEQ3815 | 1.E-02 | 0.7 | FTD | TCONS_00035036 | SEQ1586 | 7.E-04 | 0.6 |
| miAD | lnc-MALRD1-11:1 | SEQ3815 | 1.E-02 | 0.7 | MCI | TCONS_00035091 | SEQ1565 | 2.E-02 | 1.8 |
| msAD | lnc-MALRD1-11:1 | SEQ3815 | 4.E-02 | 0.8 | DLB | TCONS_00035091 | SEQ1565 | 6.E-05 | 1.7 |
| msAD | lnc-MAN2B1-1:1 | SEQ3906 | 3.E-02 | 1.3 | FTD | TCONS_00035091 | SEQ1565 | 2.E-04 | 1.5 |
| All AD | lnc-MAN2B1-1:1 | SEQ3906 | 4.E-02 | 1.3 | DLB | TCONS_00035092 | SEQ1569 | 7.E-06 | 2.6 |
| All AD | lnc-MAN2C1-2:3 | SEQ5106 | 3.E-02 | 0.8 | MCI | TCONS_00035092 | SEQ1569 | 9.E-06 | 2.6 |
| FTD | lnc-MANBA-2:9 | SEQ3443 | 3.E-10 | 0.4 | FTD | TCONS_00035092 | SEQ1569 | 1.E-05 | 2.3 |
| MCI | lnc-MANBA-2:9 | SEQ3443 | 8.E-05 | 0.6 | All AD | TCONS_00035092 | SEQ1569 | 1.E-02 | 1.4 |
| miAD | lnc-MANBA-2:9 | SEQ3443 | 6.E-03 | 0.6 | miAD | TCONS_00035092 | SEQ1569 | 1.E-02 | 1.5 |
| All AD | lnc-MANBA-2:9 | SEQ3443 | 7.E-03 | 0.6 | msAD | TCONS_00035092 | SEQ1569 | 3.E-02 | 1.4 |
| msAD | lnc-MANBA-2:9 | SEQ3443 | 4.E-02 | 0.7 | MCI | TCONS_00035093 | SEQ1570 | 6.E-10 | 1.7 |
| FTD | lnc-MANSC4-2:2 | SEQ5685 | 1.E-04 | 0.6 | FTD | TCONS_00035093 | SEQ1570 | 6.E-06 | 1.4 |
| MCI | lnc-MAP1LC3B-1:10 | SEQ5574 | 2.E-04 | 1.6 | DLB | TCONS_00035093 | SEQ1570 | 3.E-05 | 1.5 |
| DLB | lnc-MAP1LC3B-1:9 | SEQ4514 | 2.E-03 | 1.5 | miAD | TCONS_00035093 | SEQ1570 | 1.E-02 | 1.1 |
| All AD | lnc-MAP1LC3B2-14:13 | SEQ5112 | 4.E-02 | 0.7 | All AD | TCONS_00035093 | SEQ1570 | 4.E-02 | 1.1 |
| All AD | lnc-MAP1LC3B2-14:16 | SEQ4227 | 3.E-03 | 0.6 | MCI | TCONS_00035094 | SEQ1573 | 2.E-07 | 2.6 |
| miAD | lnc-MAP1LC3B2-14:16 | SEQ4227 | 6.E-03 | 0.5 | FTD | TCONS_00035094 | SEQ1573 | 5.E-07 | 2.4 |
| msAD | lnc-MAP1LC3B2-14:16 | SEQ4227 | 1.E-02 | 0.6 | DLB | TCONS_00035094 | SEQ1573 | 9.E-06 | 2.3 |
| DLB | lnc-MAP1LC3B2-15:1 | SEQ5337 | 4.E-04 | 1.8 | All AD | TCONS_00035094 | SEQ1573 | 1.E-02 | 1.3 |
| DLB | lnc-MAP2K2-2:3 | SEQ5736 | 9.E-05 | 1.7 | msAD | TCONS_00035094 | SEQ1573 | 4.E-02 | 1.3 |
| MCI | lnc-MAP3K3-2:1 | SEQ3807 | 6.E-07 | 2.5 | FTD | TCONS_00037031 | SEQ1676 | 3.E-04 | 0.5 |
| DLB | lnc-MAP3K3-2:1 | SEQ3807 | 7.E-07 | 2.4 | DLB | TCONS_00037110 | SEQ1641 | 7.E-06 | 1.6 |
| FTD | lnc-MAP3K3-2:1 | SEQ3807 | 2.E-06 | 2.3 | DLB | TCONS_00037198 | SEQ1659 | 6.E-05 | 2.6 |

TABLE 10-continued 2847 whole blood (Paxgene RNA tube) lncRNAs differentially expressed in
MCI group or mild AD group or moderate-to-severe AD group or both of these
AD groups or FTD group or DLB group as compared to healthy control group.

| Group | lncRNA | SEQ | p-value | FC | Group | lncRNA | SEQ | p-value | FC |
|---|---|---|---|---|---|---|---|---|---|
| All AD | lnc-MAP3K3-2:1 | SEQ3807 | 1.E-02 | 1.3 | msAD | TCONS_00037198 | SEQ1659 | 4.E-02 | 1.4 |
| msAD | lnc-MAP3K3-2:1 | SEQ3807 | 4.E-02 | 1.3 | MCI | TCONS_00037216 | SEQ1662 | 6.E-05 | 0.4 |
| DLB | lnc-MAP3K3-2:5 | SEQ5175 | 5.E-04 | 1.4 | All AD | TCONS_00040803 | SEQ1719 | 4.E-02 | 0.7 |
| DLB | lnc-MAP3K6-1:1 | SEQ4742 | 3.E-04 | 1.5 | DLB | TCONS_00040994 | SEQ1713 | 2.E-05 | 1.8 |
| MCI | lnc-MAP3K6-1:1 | SEQ4742 | 1.E-03 | 1.4 | All AD | TCONS_00040994 | SEQ1713 | 4.E-02 | 1.1 |
| All AD | lnc-MAP3K7-3:3 | SEQ4255 | 8.E-03 | 1.6 | msAD | TCONS_00040994 | SEQ1713 | 5.E-02 | 1.1 |
| msAD | lnc-MAP3K7-3:3 | SEQ4255 | 9.E-03 | 1.7 | DLB | TCONS_00044932 | SEQ1735 | 1.E-06 | 2.0 |
| FTD | lnc-MAP3K8-20:1 | SEQ5064 | 7.E-04 | 0.7 | FTD | TCONS_00045041 | SEQ1769 | 5.E-05 | 0.5 |
| FTD | lnc-MAP3K9-10:2 | SEQ5122 | 7.E-06 | 0.6 | MCI | TCONS_00045041 | SEQ1769 | 9.E-04 | 0.6 |
| All AD | lnc-MAP3K9-10:2 | SEQ5122 | 5.E-02 | 0.8 | FTD | TCONS_00045125 | SEQ1790 | 2.E-07 | 0.6 |
| FTD | lnc-MAP3K9-13:1 | SEQ4811 | 1.E-04 | 0.7 | MCI | TCONS_00045125 | SEQ1790 | 1.E-04 | 0.6 |
| All AD | lnc-MAP3K9-13:1 | SEQ4811 | 3.E-02 | 0.8 | All AD | TCONS_00045125 | SEQ1790 | 3.E-02 | 0.7 |
| All AD | lnc-MAP6-4:10 | SEQ4008 | 8.E-03 | 0.7 | msAD | TCONS_00045125 | SEQ1790 | 4.E-02 | 0.7 |
| miAD | lnc-MAP6-4:10 | SEQ4008 | 1.E-02 | 0.7 | All AD | TCONS_00050017 | SEQ1804 | 3.E-02 | 1.2 |
| msAD | lnc-MAP6-4:10 | SEQ4008 | 2.E-02 | 0.7 | FTD | TCONS_00050224 | SEQ1854 | 8.E-05 | 0.6 |
| miAD | lnc-MAPK13-1:1 | SEQ4156 | 1.E-02 | 0.7 | miAD | TCONS_00050224 | SEQ1854 | 9.E-03 | 0.7 |
| All AD | lnc-MAPK13-1:1 | SEQ4156 | 2.E-02 | 0.8 | All AD | TCONS_00050224 | SEQ1854 | 1.E-02 | 0.7 |
| DLB | lnc-MAPK6-8:3 | SEQ4947 | 8.E-04 | 1.5 | MCI | TCONS_00055681 | SEQ1887 | 3.E-06 | 0.5 |
| All AD | lnc-MARC2-2:1 | SEQ3917 | 8.E-03 | 0.9 | FTD | TCONS_00059297 | SEQ1957 | 1.E-03 | 0.6 |
| miAD | lnc-MARC2-2:1 | SEQ3917 | 9.E-03 | 0.9 | MCI | TCONS_00059378 | SEQ1928 | 4.E-05 | 1.5 |
| msAD | lnc-MARC2-2:1 | SEQ3917 | 3.E-02 | 0.9 | DLB | TCONS_00059378 | SEQ1928 | 2.E-03 | 1.5 |
| DLB | lnc-MARCH10-8:2 | SEQ5669 | 1.E-04 | 1.7 | FTD | TCONS_00059405 | SEQ1944 | 2.E-06 | 0.5 |
| FTD | lnc-MARCH7-1:6 | SEQ4074 | 5.E-05 | 0.7 | FTD | TCONS_00059425 | SEQ1949 | 5.E-05 | 0.5 |
| miAD | lnc-MARCH7-1:6 | SEQ4074 | 1.E-02 | 0.7 | DLB | TCONS_00059492 | SEQ1962 | 3.E-04 | 1.6 |
| All AD | lnc-MARCH7-1:6 | SEQ4074 | 2.E-02 | 0.8 | MCI | TCONS_00059492 | SEQ1962 | 2.E-03 | 1.5 |
| FTD | lnc-MARCH7-3:1 | SEQ3444 | 2.E-07 | 0.5 | MCI | TCONS_00062313 | SEQ1998 | 2.E-04 | 0.5 |
| MCI | lnc-MARCH7-3:1 | SEQ3444 | 2.E-04 | 0.6 | miAD | TCONS_00062327 | SEQ2005 | 7.E-03 | 0.6 |
| All AD | lnc-MARCH7-3:1 | SEQ3444 | 3.E-02 | 0.7 | All AD | TCONS_00062327 | SEQ2005 | 2.E-02 | 0.7 |
| FTD | lnc-MARCH7-4:1 | SEQ3895 | 6.E-05 | 0.6 | All AD | TCONS_00062345 | SEQ2020 | 2.E-02 | 0.7 |
| miAD | lnc-MARCH7-4:1 | SEQ3895 | 7.E-03 | 0.7 | MCI | TCONS_00062359 | SEQ2028 | 3.E-05 | 1.9 |
| All AD | lnc-MARCH7-4:1 | SEQ3895 | 7.E-03 | 0.7 | miAD | TCONS_00062359 | SEQ2028 | 8.E-03 | 1.4 |
| msAD | lnc-MARCH7-4:1 | SEQ3895 | 3.E-02 | 0.7 | All AD | TCONS_00062359 | SEQ2028 | 8.E-03 | 1.3 |
| MCI | lnc-MASTL-6:1 | SEQ2430 | 2.E-04 | 0.6 | msAD | TCONS_00062359 | SEQ2028 | 3.E-02 | 1.3 |
| FTD | lnc-MASTL-7:1 | SEQ4246 | 4.E-06 | 0.6 | msAD | TCONS_00062426 | SEQ2041 | 2.E-03 | 0.5 |
| miAD | lnc-MASTL-7:1 | SEQ4246 | 9.E-03 | 0.7 | All AD | TCONS_00062426 | SEQ2041 | 4.E-03 | 0.6 |
| All AD | lnc-MASTL-7:1 | SEQ4246 | 2.E-02 | 0.7 | FTD | TCONS_00062427 | SEQ2042 | 3.E-07 | 0.2 |
| FTD | lnc-MAVS-3:1 | SEQ2534 | 3.E-08 | 0.5 | DLB | TCONS_00062427 | SEQ2042 | 1.E-05 | 0.2 |
| MCI | lnc-MAVS-3:1 | SEQ2534 | 7.E-06 | 0.5 | FTD | TCONS_00062454 | SEQ2047 | 1.E-04 | 0.6 |
| All AD | lnc-MAVS-3:1 | SEQ2534 | 4.E-03 | 0.7 | All AD | TCONS_00062454 | SEQ2047 | 5.E-02 | 0.7 |
| msAD | lnc-MAVS-3:1 | SEQ2534 | 9.E-03 | 0.7 | DLB | TCONS_00062559 | SEQ1995 | 1.E-03 | 1.4 |
| miAD | lnc-MAVS-3:1 | SEQ2534 | 1.E-02 | 0.7 | DLB | TCONS_00062700 | SEQ2045 | 4.E-04 | 1.3 |
| DLB | lnc-MB-9:1 | SEQ5524 | 2.E-04 | 1.5 | MCI | TCONS_00066312 | SEQ2053 | 2.E-03 | 0.8 |
| msAD | lnc-MBD3L2B-3:1 | SEQ4042 | 2.E-02 | 2.1 | DLB | TCONS_00066327 | SEQ2060 | 1.E-03 | 1.4 |
| All AD | lnc-MBD3L2B-3:1 | SEQ4042 | 4.E-02 | 1.8 | FTD | TCONS_00066357 | SEQ2067 | 1.E-05 | 0.5 |
| FTD | lnc-MBNL1-3:1 | SEQ5764 | 8.E-05 | 0.6 | FTD | TCONS_00066544 | SEQ2098 | 1.E-03 | 0.7 |
| FTD | lnc-MBOAT1-11:1 | SEQ5280 | 7.E-05 | 1.8 | All AD | TCONS_00066544 | SEQ2098 | 3.E-02 | 0.8 |
| MCI | lnc-MBOAT1-11:1 | SEQ5280 | 5.E-04 | 1.8 | FTD | TET2-AS1:5 | SEQ4311 | 2.E-04 | 0.6 |
| All AD | lnc-MBOAT2-2:1 | SEQ4338 | 2.E-03 | 0.7 | miAD | TET2-AS1:5 | SEQ4311 | 1.E-02 | 0.7 |
| miAD | lnc-MBOAT2-2:1 | SEQ4338 | 3.E-03 | 0.6 | All AD | TET2-AS1:5 | SEQ4311 | 2.E-02 | 0.7 |
| msAD | lnc-MBOAT2-2:1 | SEQ4338 | 5.E-03 | 0.7 | miAD | THAP9-AS1:27 | SEQ2178 | 1.E-02 | 0.6 |
| FTD | lnc-MCF2L-2:1 | SEQ5231 | 5.E-04 | 0.7 | All AD | THAP9-AS1:27 | SEQ2178 | 2.E-02 | 0.6 |
| DLB | lnc-MCHR1-1:1 | SEQ5182 | 9.E-05 | 1.5 | msAD | THRIL:2 | SEQ3970 | 2.E-02 | 1.4 |
| MCI | lnc-MCHR1-1:1 | SEQ5182 | 5.E-04 | 1.5 | All AD | THRIL:2 | SEQ3970 | 3.E-02 | 1.3 |
| All AD | lnc-MCL1-1:1 | SEQ3947 | 1.E-02 | 0.8 | FTD | THUMPD3-AS1:16 | SEQ5771 | 7.E-05 | 0.4 |
| msAD | lnc-MCL1-1:1 | SEQ3947 | 3.E-02 | 0.8 | DLB | THUMPD3-AS1:51 | SEQ5758 | 8.E-05 | 2.2 |
| All AD | lnc-MCL1-2:1 | SEQ5138 | 3.E-02 | 0.8 | MCI | TMEM161B-AS1:51 | SEQ4098 | 6.E-06 | 2.5 |
| All AD | lnc-MCL1-3:1 | SEQ5139 | 4.E-02 | 0.7 | FTD | TMEM161B-AS1:51 | SEQ4098 | 6.E-06 | 2.6 |
| FTD | lnc-MCTP2-1:1 | SEQ5748 | 9.E-05 | 0.7 | DLB | TMEM161B-AS1:51 | SEQ4098 | 2.E-05 | 2.5 |
| MCI | lnc-MCTP2-7:4 | SEQ3446 | 3.E-04 | 1.7 | miAD | TMEM161B-AS1:51 | SEQ4098 | 2.E-03 | 1.6 |
| DLB | lnc-MCTP2-7:4 | SEQ3446 | 5.E-04 | 1.8 | All AD | TMEM161B-AS1:51 | SEQ4098 | 2.E-03 | 1.5 |
| msAD | lnc-MCTP2-7:4 | SEQ3446 | 2.E-02 | 1.3 | msAD | TMEM161B-AS1:51 | SEQ4098 | 2.E-02 | 1.4 |
| All AD | lnc-MCTP2-7:4 | SEQ3446 | 2.E-02 | 1.3 | FTD | TMEM161B-AS1:52 | SEQ4308 | 1.E-09 | 0.3 |
| DLB | lnc-MCTS1-2:1 | SEQ2602 | 9.E-04 | 1.3 | MCI | TMEM161B-AS1:52 | SEQ4308 | 4.E-04 | 0.5 |
| All AD | lnc-MDM1-5:1 | SEQ3748 | 1.E-02 | 0.6 | DLB | TMEM161B-AS1:52 | SEQ4308 | 2.E-03 | 0.5 |
| msAD | lnc-MDM1-5:1 | SEQ3748 | 4.E-02 | 0.6 | miAD | TMEM161B-AS1:52 | SEQ4308 | 7.E-03 | 0.5 |
| FTD | lnc-MDM4-8:1 | SEQ0816 | 2.E-04 | 0.7 | All AD | TMEM161B-AS1:52 | SEQ4308 | 2.E-02 | 0.6 |
| All AD | lnc-MED1-4:1 | SEQ5145 | 5.E-02 | 1.1 | MCI | TMEM202-AS1:3 | SEQ4015 | 1.E-05 | 1.7 |
| DLB | lnc-MED26-1:2 | SEQ4633 | 5.E-05 | 1.8 | DLB | TMEM202-AS1:3 | SEQ4015 | 2.E-05 | 1.7 |
| MCI | lnc-MED26-1:2 | SEQ4633 | 1.E-03 | 1.5 | FTD | TMEM202-AS1:3 | SEQ4015 | 9.E-05 | 1.5 |
| DLB | lnc-MED26-1:3 | SEQ4970 | 8.E-04 | 1.6 | All AD | TMEM202-AS1:3 | SEQ4015 | 7.E-03 | 1.3 |
| DLB | lnc-MED9-1:2 | SEQ2833 | 2.E-04 | 1.9 | miAD | TMEM202-AS1:3 | SEQ4015 | 1.E-02 | 1.3 |
| FTD | lnc-MEMO1-4:1 | SEQ4312 | 3.E-08 | 0.5 | msAD | TMEM202-AS1:3 | SEQ4015 | 2.E-02 | 1.3 |
| MCI | lnc-MEMO1-4:1 | SEQ4312 | 2.E-04 | 0.6 | DLB | TMEM9B-AS1:10 | SEQ4722 | 4.E-05 | 2.2 |
| miAD | lnc-MEMO1-4:1 | SEQ4312 | 7.E-03 | 0.7 | MCI | TMEM9B-AS1:10 | SEQ4722 | 1.E-03 | 1.9 |

TABLE 10-continued 2847 whole blood (Paxgene RNA tube) lncRNAs differentially expressed in MCI group or mild AD group or moderate-to-severe AD group or both of these AD groups or FTD group or DLB group as compared to healthy control group.

| Group | lncRNA | SEQ | p-value | FC | Group | lncRNA | SEQ | p-value | FC |
|---|---|---|---|---|---|---|---|---|---|
| All AD | lnc-MEMO1-4:1 | SEQ4312 | 1.E-02 | 0.7 | DLB | TMEM9B-AS1:7 | SEQ5539 | 2.E-04 | 2.0 |
| DLB | lnc-MEP1B-2:1 | SEQ3447 | 1.E-04 | 2.1 | All AD | TMLHE-AS1:2 | SEQ6006 | 3.E-02 | 0.8 |
| MCI | lnc-MEP1B-2:1 | SEQ3447 | 5.E-04 | 1.8 | DLB | TMPO-AS1:5 | SEQ4339 | 3.E-06 | 1.8 |
| DLB | lnc-MEPCE-1:2 | SEQ5812 | 5.E-05 | 1.4 | MCI | TMPO-AS1:5 | SEQ4339 | 6.E-06 | 1.6 |
| DLB | lnc-MEPE-1:1 | SEQ4345 | 9.E-05 | 1.5 | FTD | TMPO-AS1:5 | SEQ4339 | 7.E-06 | 1.6 |
| All AD | lnc-MEPE-1:1 | SEQ4345 | 2.E-03 | 1.3 | All AD | TMPO-AS1:5 | SEQ4339 | 1.E-03 | 1.3 |
| MCI | lnc-MEPE-1:1 | SEQ4345 | 2.E-03 | 1.3 | miAD | TMPO-AS1:5 | SEQ4339 | 2.E-03 | 1.3 |
| msAD | lnc-MEPE-1:1 | SEQ4345 | 3.E-03 | 1.3 | msAD | TMPO-AS1:5 | SEQ4339 | 5.E-03 | 1.3 |
| miAD | lnc-MEPE-1:1 | SEQ4345 | 5.E-03 | 1.3 | DLB | TNK2-AS1:1 | SEQ5728 | 9.E-05 | 1.5 |
| FTD | lnc-MEST-6:1 | SEQ0124 | 1.E-07 | 0.5 | MCI | TNRC6C-AS1:1 | SEQ3072 | 6.E-06 | 1.8 |
| MCI | lnc-MEST-6:1 | SEQ0124 | 2.E-04 | 0.6 | DLB | TNRC6C-AS1:1 | SEQ3072 | 8.E-05 | 1.8 |
| miAD | lnc-MEST-6:1 | SEQ0124 | 2.E-03 | 0.6 | MCI | TNRC6C-AS1:2 | SEQ3143 | 2.E-05 | 1.6 |
| All AD | lnc-MEST-6:1 | SEQ0124 | 3.E-03 | 0.7 | DLB | TNRC6C-AS1:2 | SEQ3143 | 5.E-04 | 1.6 |
| msAD | lnc-MEST-6:1 | SEQ0124 | 2.E-02 | 0.7 | MCI | TNRC6C-AS1:5 | SEQ3142 | 2.E-05 | 1.7 |
| All AD | lnc-METTL14-3:13 | SEQ5152 | 3.E-02 | 0.8 | DLB | TNRC6C-AS1:5 | SEQ3142 | 2.E-04 | 1.6 |
| DLB | lnc-METTL26-1:2 | SEQ5891 | 2.E-05 | 1.6 | DLB | TPT1-AS1:54 | SEQ2870 | 3.E-05 | 1.8 |
| FTD | lnc-METTL2B-3:1 | SEQ3710 | 9.E-04 | 1.7 | All AD | TRAF3IP2-AS1:35 | SEQ3829 | 4.E-02 | 1.3 |
| MCI | lnc-METTL2B-3:1 | SEQ3710 | 9.E-04 | 1.7 | msAD | TRAF3IP2-AS1:35 | SEQ3829 | 4.E-02 | 1.3 |
| All AD | lnc-METTL2B-3:1 | SEQ3710 | 4.E-02 | 1.3 | FTD | TRG-AS1:1 | SEQ3894 | 7.E-04 | 0.6 |
| msAD | lnc-METTL2B-3:1 | SEQ3710 | 5.E-02 | 1.3 | All AD | TRG-AS1:1 | SEQ3894 | 8.E-03 | 0.6 |
| DLB | lnc-METTL6-5:1 | SEQ5436 | 3.E-04 | 1.5 | miAD | TRG-AS1:1 | SEQ3894 | 9.E-03 | 0.6 |
| All AD | lnc-METTL8-3:1 | SEQ5157 | 3.E-02 | 1.2 | msAD | TRG-AS1:1 | SEQ3894 | 3.E-02 | 0.7 |
| FTD | lnc-MFN1-1:2 | SEQ4058 | 3.E-07 | 0.5 | All AD | TRPM2-AS:7 | SEQ6007 | 3.E-02 | 0.7 |
| MCI | lnc-MFN1-1:2 | SEQ4058 | 2.E-05 | 0.6 | DLB | TSPOAP1-AS1:2 | SEQ5852 | 3.E-05 | 23.4 |
| miAD | lnc-MFN1-1:2 | SEQ4058 | 2.E-04 | 0.6 | MCI | TSPOAP1-AS1:2 | SEQ5852 | 4.E-05 | 13.9 |
| All AD | lnc-MFN1-1:2 | SEQ4058 | 8.E-04 | 0.7 | msAD | TSPOAP1-AS1:9 | SEQ3939 | 3.E-02 | 1.1 |
| msAD | lnc-MFN1-1:2 | SEQ4058 | 2.E-02 | 0.7 | All AD | TSPOAP1-AS1:9 | SEQ3939 | 3.E-02 | 1.1 |
| DLB | lnc-MFNG-1:2 | SEQ5035 | 7.E-04 | 1.5 | FTD | TTC21B-AS1:1 | SEQ4910 | 9.E-04 | 0.7 |
| DLB | lnc-MFSD11-1:2 | SEQ5483 | 2.E-04 | 1.5 | FTD | TTC21B-AS1:2 | SEQ4735 | 8.E-05 | 0.6 |
| DLB | lnc-MFSD13A-2:1 | SEQ3448 | 2.E-04 | 1.3 | All AD | TTC21B-AS1:2 | SEQ4735 | 1.E-04 | 0.6 |
| DLB | lnc-MFSD3-2:1 | SEQ5576 | 2.E-04 | 1.7 | miAD | TTC21B-AS1:2 | SEQ4735 | 3.E-04 | 0.6 |
| FTD | lnc-MFSD4A-1:1 | SEQ2625 | 3.E-04 | 0.6 | msAD | TTC21B-AS1:2 | SEQ4735 | 6.E-04 | 0.6 |
| FTD | lnc-MGARP-3:1 | SEQ5165 | 2.E-04 | 0.7 | MCI | TTC21B-AS1:2 | SEQ4735 | 1.E-03 | 0.6 |
| All AD | lnc-MGARP-3:1 | SEQ5165 | 3.E-02 | 0.8 | All AD | TTC21B-AS1:33 | SEQ4252 | 3.E-03 | 0.7 |
| msAD | lnc-MGAT1-4:4 | SEQ3705 | 5.E-02 | 1.2 | miAD | TTC21B-AS1:33 | SEQ4252 | 6.E-03 | 0.6 |
| DLB | lnc-MGAT5-3:1 | SEQ5166 | 5.E-04 | 1.5 | msAD | TTC21B-AS1:33 | SEQ4252 | 9.E-03 | 0.7 |
| All AD | lnc-MGAT5-3:1 | SEQ5166 | 4.E-02 | 1.2 | All AD | TTN-AS1:4 | SEQ3692 | 4.E-02 | 1.4 |
| DLB | lnc-MGLL-5:1 | SEQ4517 | 2.E-05 | 1.6 | msAD | TTN-AS1:4 | SEQ3692 | 5.E-02 | 1.4 |
| MCI | lnc-MGLL-5:1 | SEQ4517 | 2.E-03 | 1.5 | FTD | TTN-AS1:58 | SEQ5991 | 1.E-06 | 0.5 |
| MCI | lnc-MICA-9:2 | SEQ4955 | 6.E-04 | 1.5 | All AD | TTN-AS1:6 | SEQ4123 | 1.E-02 | 0.6 |
| DLB | lnc-MICA-9:2 | SEQ4955 | 8.E-04 | 1.5 | msAD | TTN-AS1:6 | SEQ4123 | 1.E-02 | 0.6 |
| DLB | lnc-MIEF2-2:1 | SEQ5243 | 5.E-04 | 1.4 | MCI | TUG1:33 | SEQ4063 | 6.E-04 | 1.5 |
| DLB | lnc-MIER3-2:1 | SEQ4681 | 1.E-03 | 1.4 | All AD | TUG1:33 | SEQ4063 | 6.E-03 | 1.3 |
| All AD | lnc-MIER3-2:1 | SEQ4681 | 5.E-02 | 1.1 | miAD | TUG1:33 | SEQ4063 | 1.E-02 | 1.3 |
| FTD | lnc-MIOS-5:2 | SEQ3764 | 8.E-06 | 0.6 | msAD | TUG1:33 | SEQ4063 | 2.E-02 | 1.3 |
| All AD | lnc-MIOS-5:2 | SEQ3764 | 1.E-02 | 0.7 | DLB | TUG1:39 | SEQ5735 | 9.E-05 | 1.6 |
| msAD | lnc-MIOS-5:2 | SEQ3764 | 4.E-02 | 0.7 | DLB | TUG1:40 | SEQ5895 | 2.E-05 | 1.8 |
| DLB | lnc-MIS12-4:1 | SEQ4840 | 9.E-04 | 1.4 | FTD | TUG1:45 | SEQ5840 | 2.E-06 | 0.5 |
| DLB | lnc-MISP3-1:7 | SEQ4619 | 1.E-03 | 1.4 | MCI | TUG1:45 | SEQ5840 | 4.E-05 | 0.5 |
| All AD | lnc-MIXL1-7:1 | SEQ5170 | 5.E-02 | 0.8 | FTD | TUG1:7 | SEQ4607 | 1.E-06 | 0.3 |
| All AD | lnc-MKI67-4:1 | SEQ5171 | 5.E-02 | 0.8 | MCI | TUG1:7 | SEQ4607 | 1.E-06 | 0.3 |
| All AD | lnc-MKI67-8:2 | SEQ5172 | 4.E-02 | 0.7 | DLB | TUG1:7 | SEQ4607 | 1.E-03 | 0.4 |
| MCI | lnc-MKLN1-1:12 | SEQ5004 | 9.E-06 | 2.0 | FTD | UBR5-AS1:10 | SEQ5412 | 3.E-04 | 0.6 |
| DLB | lnc-MKLN1-1:12 | SEQ5004 | 2.E-05 | 1.9 | MCI | UBR5-AS1:4 | SEQ5078 | 9.E-05 | 0.3 |
| FTD | lnc-MKLN1-1:12 | SEQ5004 | 8.E-04 | 1.5 | DLB | UBR5-AS1:4 | SEQ5078 | 1.E-04 | 0.3 |
| FTD | lnc-MLH1-1:1 | SEQ2597 | 8.E-06 | 0.7 | FTD | UBR5-AS1:4 | SEQ5078 | 6.E-04 | 0.3 |
| MCI | lnc-MLH1-1:1 | SEQ2597 | 2.E-04 | 0.8 | All AD | USP3-AS1:11 | SEQ6010 | 3.E-02 | 0.8 |
| All AD | lnc-MLH1-1:1 | SEQ2597 | 7.E-03 | 0.8 | FTD | USP3-AS1:9 | SEQ4289 | 9.E-10 | 0.1 |
| msAD | lnc-MLH1-1:1 | SEQ2597 | 9.E-03 | 0.8 | MCI | USP3-AS1:9 | SEQ4289 | 4.E-04 | 0.2 |
| MCI | lnc-MLLT1-2:1 | SEQ3450 | 5.E-04 | 1.4 | miAD | USP3-AS1:9 | SEQ4289 | 7.E-03 | 0.2 |
| DLB | lnc-MLLT1-2:1 | SEQ3450 | 8.E-04 | 1.4 | DLB | VAC14-AS1:3 | SEQ5572 | 2.E-04 | 1.6 |
| DLB | lnc-MLX-3:1 | SEQ3451 | 4.E-05 | 1.6 | DLB | VASH1-AS1:7 | SEQ4786 | 1.E-03 | 1.7 |
| MCI | lnc-MLX-3:1 | SEQ3451 | 2.E-03 | 1.5 | DLB | VIM-AS1:1 | SEQ3832 | 5.E-05 | 1.5 |
| All AD | lnc-MLX-3:1 | SEQ3451 | 4.E-02 | 1.1 | MCI | VIM-AS1:1 | SEQ3832 | 8.E-05 | 1.5 |
| MCI | lnc-MMP23B-1:1 | SEQ4520 | 2.E-03 | 1.5 | FTD | VIM-AS1:1 | SEQ3832 | 2.E-04 | 1.3 |
| DLB | lnc-MMP23B-4:1 | SEQ4774 | 1.E-03 | 1.5 | All AD | VIM-AS1:1 | SEQ3832 | 2.E-02 | 1.2 |
| FTD | lnc-MOCS2-9:1 | SEQ5832 | 5.E-05 | 0.6 | msAD | VIM-AS1:1 | SEQ3832 | 3.E-02 | 1.2 |
| FTD | lnc-MOV10-2:1 | SEQ2519 | 4.E-04 | 0.5 | FTD | VIM-AS1:11 | SEQ3989 | 1.E-03 | 0.7 |
| All AD | lnc-MOV10-2:1 | SEQ2519 | 3.E-02 | 0.6 | All AD | VIM-AS1:11 | SEQ3989 | 1.E-02 | 0.8 |
| MCI | lnc-MPC1-3:1 | SEQ4672 | 1.E-03 | 0.8 | msAD | VIM-AS1:11 | SEQ3989 | 2.E-02 | 0.9 |
| MCI | lnc-MPLKIP-1:1 | SEQ5848 | 1.E-05 | 1.5 | All AD | VIM-AS1:7 | SEQ3576 | 7.E-03 | 1.2 |
| DLB | lnc-MPLKIP-1:1 | SEQ5848 | 4.E-05 | 1.5 | miAD | VIM-AS1:7 | SEQ3576 | 1.E-02 | 1.2 |
| DLB | lnc-MRNIP-4:1 | SEQ4511 | 2.E-05 | 1.8 | msAD | VIM-AS1:7 | SEQ3576 | 2.E-02 | 1.2 |
| MCI | lnc-MRNIP-4:1 | SEQ4511 | 2.E-03 | 1.5 | DLB | WAC-AS1:1 | SEQ5662 | 1.E-04 | 1.5 |

TABLE 10-continued 2847 whole blood (Paxgene RNA tube) lncRNAs differentially expressed in MCI group or mild AD group or moderate-to-severe AD group or both of these AD groups or FTD group or DLB group as compared to healthy control group.

| Group | lncRNA | SEQ | p-value | FC | Group | lncRNA | SEQ | p-value | FC |
|---|---|---|---|---|---|---|---|---|---|
| DLB | lnc-MRPL11-1:11 | SEQ5481 | 2.E-04 | 1.4 | DLB | WAC-AS1:11 | SEQ4770 | 1.E-03 | 1.5 |
| FTD | lnc-MRPL16-1:1 | SEQ5189 | 4.E-04 | 0.7 | FTD | WAC-AS1:14 | SEQ4892 | 9.E-04 | 0.5 |
| All AD | lnc-MRPL16-1:1 | SEQ5189 | 5.E-02 | 0.8 | DLB | ZBED5-AS1:1 | SEQ4959 | 8.E-04 | 1.6 |
| DLB | lnc-MRPL41-1:1 | SEQ5528 | 2.E-04 | 1.6 | MCI | ZBTB11-AS1:2 | SEQ5006 | 1.E-04 | 2.4 |
| MCI | lnc-MRPL43-2:3 | SEQ3791 | 9.E-06 | 1.6 | DLB | ZBTB11-AS1:2 | SEQ5006 | 1.E-04 | 2.2 |
| DLB | lnc-MRPL43-2:3 | SEQ3791 | 2.E-05 | 1.7 | FTD | ZBTB11-AS1:2 | SEQ5006 | 8.E-04 | 2.1 |
| FTD | lnc-MRPL43-2:3 | SEQ3791 | 4.E-04 | 1.4 | All AD | ZBTB11-AS1:2 | SEQ5006 | 2.E-02 | 1.4 |
| msAD | lnc-MRPL43-2:3 | SEQ3791 | 4.E-02 | 1.2 | FTD | ZFAS1:30 | SEQ4911 | 9.E-04 | 0.7 |
| FTD | lnc-MRPL44-6:2 | SEQ5773 | 7.E-05 | 0.4 | DLB | ZFHX2-AS1:10 | SEQ4957 | 8.E-04 | 1.6 |
| MCI | lnc-MRPL48-1:2 | SEQ5193 | 2.E-07 | 2.1 | FTD | ZMIZ1-AS1:33 | SEQ4236 | 2.E-04 | 0.5 |
| FTD | lnc-MRPL48-1:2 | SEQ5193 | 3.E-04 | 1.6 | miAD | ZMIZ1-AS1:33 | SEQ4236 | 1.E-02 | 0.7 |
| DLB | lnc-MRPL48-1:2 | SEQ5193 | 4.E-04 | 1.7 | All AD | ZMIZ1-AS1:33 | SEQ4236 | 3.E-02 | 0.7 |
| All AD | lnc-MRPL48-1:2 | SEQ5193 | 4.E-02 | 1.1 | miAD | ZNF436-AS1:9 | SEQ4235 | 1.E-02 | 0.6 |
| DLB | lnc-MRPL48-1:3 | SEQ4932 | 8.E-04 | 1.4 | All AD | ZNF436-AS1:9 | SEQ4235 | 3.E-02 | 0.7 |
| DLB | lnc-MRPL58-2:2 | SEQ5615 | 2.E-04 | 1.4 | DLB | ZNF460-AS1:2 | SEQ3955 | 7.E-04 | 1.7 |
| FTD | lnc-MRPS14-1:6 | SEQ2452 | 2.E-04 | 0.7 | msAD | ZNF460-AS1:2 | SEQ3955 | 3.E-02 | 1.3 |
| DLB | lnc-MRPS25-5:2 | SEQ5123 | 6.E-04 | 1.5 | All AD | ZNF460-AS1:2 | SEQ3955 | 4.E-02 | 1.2 |
| MCI | lnc-MRPS5-2:2 | SEQ4304 | 9.E-05 | 2.1 | FTD | ZSCAN16-AS1:12 | SEQ4808 | 1.E-03 | 0.7 |

To further identify lncRNAs differentially expressed in AD patients, whole blood (Paxgene RNA tube) expression in AD patients were compared with non-AD subject groups. 136 lncRNAs were differentially expressed in whole blood (Paxgene RNA tube) of AD patient groups (mild AD+moderate-to-severe AD groups) when compared to non-AD subject groups (either DLB+ FTD groups or DLB+FTD+HC groups), with statistical significance (p value <0.05, Wilcoxon test) and a fold change FC≤0.80 or ≥1.20. The 136 lncRNAs are shown in Table 11.

TABLE 11

136 whole blood (Paxgene RNA tube) lncRNAs differentially expressed in AD patient groups (mild AD + moderate-to-severe AD groups) when compared to non-AD subject groups (either DLB + FTD groups or DLB + FTD + HC groups).

| Group compared to AD | lncRNA | SEQ | p-value | FC | Group compared to AD | lncRNA | SEQ | p-value | FC |
|---|---|---|---|---|---|---|---|---|---|
| NAD | ARRDC3-AS1:3 | SEQ 6042 | 8E-04 | 0.8 | NAD + HC | lnc-LRRC37A3-5:8 | SEQ 3442 | 4E-03 | 0.8 |
| NAD + HC | ARRDC3-AS1:3 | SEQ 6042 | 3E-03 | 0.8 | NAD | lnc-LRRC47-4:4 | SEQ 6118 | 4E-04 | 0.7 |
| NAD + HC | CARS-AS1:1 | SEQ 6047 | 4E-03 | 0.8 | NAD | lnc-MARS-1:1 | SEQ 6068 | 3E-04 | 0.8 |
| NAD | CELF2-AS1:2 | SEQ 6134 | 2E-05 | 0.5 | NAD + HC | lnc-MARS-1:1 | SEQ 6068 | 3E-04 | 0.8 |
| NAD + HC | CFLAR-AS1:21 | SEQ 6090 | 2E-03 | 0.8 | NAD + HC | lnc-NDUFB3-2:1 | SEQ 6043 | 2E-03 | 0.8 |
| NAD + HC | CFLAR-AS1:8 | SEQ 6080 | 2E-03 | 0.8 | NAD | lnc-NPTX1-2:4 | SEQ 6117 | 1E-04 | 0.6 |
| NAD + HC | CSNK1G2-AS1:2 | SEQ 6094 | 2E-03 | 0.8 | NAD + HC | lnc-NPTX1-2:4 | SEQ 6117 | 5E-04 | 0.7 |
| NAD | DLEU2:21 | SEQ 6064 | 7E-05 | 0.7 | NAD | lnc-OR4F29-7:1 | SEQ 6119 | 6E-04 | 0.6 |
| NAD + HC | DLEU2:21 | SEQ 6064 | 1E-03 | 0.8 | NAD + HC | lnc-OR4F29-7:1 | SEQ 6119 | 3E-03 | 0.7 |
| NAD | FAM157C:5 | SEQ 6125 | 2E-04 | 0.6 | NAD | lnc-OTOL 1-5:1 | SEQ 6019 | 8E-05 | 2.3 |
| NAD + HC | FAM157C:5 | SEQ 6125 | 3E-04 | 0.7 | NAD + HC | lnc-OTOL1-5:1 | SEQ 6019 | 2E-04 | 1.9 |
| NAD | FAM198B-AS1:2 | SEQ 6051 | 3E-05 | 0.7 | NAD | lnc-PBX2-1:1 | SEQ 6081 | 3E-04 | 0.7 |
| NAD + HC | FAM198B-AS1:2 | SEQ 6051 | 1E-03 | 0.8 | NAD + HC | lnc-PBX2-1:1 | SEQ 6081 | 3E-04 | 0.8 |
| NAD + HC | ITGB2-AS1:6 | SEQ 6097 | 4E-03 | 0.7 | NAD | lnc-PBX2-1:2 | SEQ 6077 | 3E-04 | 0.7 |
| NAD | JPX:34 | SEQ 6017 | 3E-04 | 2.7 | NAD + HC | lnc-PBX2-1:2 | SEQ 6077 | 4E-04 | 0.8 |
| NAD + HC | LCMT1-AS1:9 | SEQ 2883 | 4E-03 | 0.7 | NAD + HC | lnc-PGAM1-4:1 | SEQ 6066 | 3E-03 | 0.8 |
| NAD | LINC00324:3 | SEQ 6113 | 3E-04 | 0.7 | NAD + HC | lnc-PLCD3-4:8 | SEQ 6112 | 3E-03 | 0.7 |
| NAD | LINC00861:2 | SEQ 6132 | 7E-04 | 0.6 | NAD | lnc-PLCG2-6:1 | SEQ 6095 | 7E-04 | 0.7 |
| NAD + HC | LINC01000:3 | SEQ 6093 | 1E-03 | 0.8 | NAD + HC | lnc-PLEKHG3-1:1 | SEQ 6056 | 3E-03 | 0.8 |
| NAD + HC | LINC01001:1 | SEQ 6128 | 2E-03 | 0.6 | NAD | lnc-RMDN2-11:1 | SEQ 6067 | 2E-04 | 0.7 |
| NAD + HC | LINC01814:2 | SEQ 6071 | 2E-03 | 0.8 | NAD + HC | lnc-RMDN2-11:1 | SEQ 6067 | 2E-03 | 0.8 |
| NAD | lnc-ALDH1A2-9:1 | SEQ 6031 | 4E-04 | 1.5 | NAD | lnc-RNF19A-8:2 | SEQ 6085 | 7E-04 | 0.8 |
| NAD | lnc-ANXA2R-1:25 | SEQ 6121 | 3E-06 | 0.6 | NAD | lnc-ROM1-7:2 | SEQ 6015 | 9E-06 | 3.8 |
| NAD + HC | lnc-ANXA2R-1:25 | SEQ 6121 | 2E-05 | 0.7 | NAD + HC | lnc-ROM1-7:2 | SEQ 6015 | 3E-04 | 2.9 |
| NAD | lnc-ARFGEF2-6:1 | SEQ 6083 | 4E-04 | 0.7 | NAD | lnc-RPEL1-2:1 | SEQ 6102 | 5E-04 | 0.7 |
| NAD + HC | lnc-ARFGEF2-6:1 | SEQ 6083 | 2E-03 | 0.8 | NAD + HC | lnc-RPEL 1-2:1 | SEQ 6102 | 6E-04 | 0.7 |
| NAD | lnc-ATG2A-2:1 | SEQ 6087 | 5E-04 | 0.8 | NAD + HC | lnc-RPLP0-4:4 | SEQ 6060 | 2E-03 | 0.8 |
| NAD | lnc-ATP6V1G3-6:1 | SEQ 6079 | 6E-04 | 0.8 | NAD | lnc-SAG-4:1 | SEQ 6114 | 6E-04 | 0.7 |
| NAD + HC | lnc-B3GNTL1-2:2 | SEQ 6040 | 4E-03 | 0.8 | NAD | lnc-SAMD11-12:2 | SEQ 6021 | 2E-04 | 2.0 |
| NAD | lnc-BCL2L11-6:5 | SEQ 6101 | 2E-04 | 0.7 | NAD + HC | lnc-SAMD11-12:2 | SEQ 6021 | 1E-03 | 1.7 |
| NAD + HC | lnc-BCL2L11-6:5 | SEQ 6101 | 2E-03 | 0.7 | NAD | lnc-SAMD11-15:1 | SEQ 6030 | 4E-04 | 1.5 |
| NAD | lnc-BRD3-7:1 | SEQ 6108 | 4E-05 | 0.6 | NAD + HC | lnc-SAMD11-15:1 | SEQ 6030 | 9E-04 | 1.4 |
| NAD + HC | lnc-BRD3-7:1 | SEQ 6108 | 2E-04 | 0.7 | NAD + HC | lnc-SBDS-19:2 | SEQ 2509 | 3E-03 | 1.5 |
| NAD | lnc-C1QTNF3-AMACR-2:5 | SEQ 6027 | 4E-04 | 1.6 | NAD + HC | lnc-SETD9-6:1 | SEQ 6091 | 1E-03 | 0.8 |
| NAD | lnc-C5orf56-4:1 | SEQ 6082 | 1E-04 | 0.7 | NAD | lnc-SETDB1-1:1 | SEQ 6115 | 4E-04 | 0.7 |
| NAD + HC | lnc-C5orf56-4:1 | SEQ 6082 | 3E-04 | 0.8 | NAD + HC | lnc-SETDB1-1:1 | SEQ 6115 | 6E-04 | 0.7 |

TABLE 11-continued 136 whole blood (Paxgene RNA tube) lncRNAs differentially expressed in AD patient groups (mild AD + moderate-to-severe AD groups) when compared to non-AD subject groups (either DLB + FTD groups or DLB + FTD + HC groups).

| Group compared to AD | lncRNA | SEQ | p-value | FC | Group compared to AD | lncRNA | SEQ | p-value | FC |
|---|---|---|---|---|---|---|---|---|---|
| NAD | lnc-CACNA1B-1:2 | SEQ 6120 | 3E−04 | 0.6 | NAD | lnc-SHC3-5:3 | SEQ 3102 | 6E−04 | 1.9 |
| NAD + HC | lnc-CACNA1B-1:2 | SEQ 6120 | 1E−03 | 0.7 | NAD | lnc-SLC29A4-1:2 | SEQ 6052 | 5E−04 | 0.8 |
| NAD | lnc-CACNA1B-1:4 | SEQ 6122 | 3E−04 | 0.6 | NAD + HC | lnc-SLC29A4-1:2 | SEQ 6052 | 2E−03 | 0.8 |
| NAD + HC | lnc-CACNA1B-1:4 | SEQ 6122 | 1E−03 | 0.7 | NAD | lnc-SLC35F5-3:9 | SEQ 6022 | 7E−04 | 1.9 |
| NAD + HC | lnc-CAND2-2:5 | SEQ 3083 | 2E−03 | 0.8 | NAD + HC | lnc-SLC35F5-3:9 | SEQ 6022 | 1E−03 | 1.7 |
| NAD + HC | lnc-CAND2-2:6 | SEQ 3084 | 2E−03 | 0.8 | NAD | lnc-SLC5A10-3:2 | SEQ 6133 | 3E−04 | 0.5 |
| NAD | lnc-CATSPER3-2:10 | SEQ 6104 | 5E−04 | 0.7 | NAD | lnc-SNX11-10:2 | SEQ 6024 | 5E−04 | 1.8 |
| NAD | lnc-CDC42BPB-4:1 | SEQ 3357 | 3E−04 | 0.8 | NAD + HC | lnc-SNX11-10:2 | SEQ 6024 | 8E−04 | 1.7 |
| NAD | lnc-CDC42BPB-4:4 | SEQ 6050 | 3E−04 | 0.8 | NAD | lnc-SPATA32-2:12 | SEQ 6109 | 1E−04 | 0.7 |
| NAD + HC | lnc-CDC42BPB-4:4 | SEQ 6050 | 2E−03 | 0.8 | NAD + HC | lnc-SPATA32-2:12 | SEQ 6109 | 1E−04 | 0.7 |
| NAD | lnc-CDHR4-5:2 | SEQ 6089 | 5E−04 | 0.8 | NAD + HC | lnc-STX4-1:4 | SEQ 6075 | 3E−03 | 0.8 |
| NAD | lnc-CDIPT-1:1 | SEQ 6048 | 5E−04 | 0.7 | NAD | lnc-SYNPO-6:1 | SEQ 6123 | 1E−04 | 0.7 |
| NAD + HC | lnc-CDIPT-1:1 | SEQ 6048 | 4E−03 | 0.8 | NAD | lnc-SYT2-4:1 | SEQ 6107 | 2E−04 | 0.7 |
| NAD + HC | lnc-CDIPT-1:5 | SEQ 6028 | 5E−04 | 1.5 | NAD | lnc-TARDBP-5:3 | SEQ 6131 | 5E−04 | 0.6 |
| NAD | lnc-CDIPT-1:5 | SEQ 6028 | 7E−04 | 1.6 | NAD | lnc-TCF19-1:103 | SEQ 6130 | 6E−04 | 0.6 |
| NAD + HC | lnc-CEBPB-13:13 | SEQ 6070 | 3E−03 | 0.8 | NAD | lnc-THTPA-2:29 | SEQ 6016 | 8E−05 | 2.7 |
| NAD + HC | lnc-CEBPG-4:1 | SEQ 6069 | 2E−03 | 0.8 | NAD + HC | lnc-THTPA-2:29 | SEQ 6016 | 2E−04 | 2.2 |
| NAD | lnc-CEL-4:1 | SEQ 6032 | 7E−04 | 1.5 | NAD + HC | lnc-TLE3-6:8 | SEQ 6035 | 3E−03 | 1.3 |
| NAD + HC | lnc-CHIC1-2:1 | SEQ 6026 | 1E−03 | 1.7 | NAD + HC | lnc-TMEM150A-4:2 | SEQ 6046 | 4E−03 | 0.8 |
| NAD + HC | lnc-CLLU1-2:6 | SEQ 3284 | 1E−04 | 12 | NAD + HC | lnc-TMEM181-1:1 | SEQ 6084 | 2E−03 | 0.8 |
| NAD | lnc-CLLU1-2:6 | SEQ 3284 | 2E−04 | 18 | NAD | lnc-TREM2-1:1 | SEQ 6029 | 1E−04 | 1.5 |
| NAD + HC | lnc-CNTRL-6:31 | SEQ 6023 | 3E−03 | 1.8 | NAD | lnc-TRMT61B-5:6 | SEQ 6103 | 9E−05 | 0.7 |
| NAD + HC | lnc-CTXN1-6:1 | SEQ 3096 | 3E−03 | 0.8 | NAD + HC | lnc-TRMT61B-5:6 | SEQ 6103 | 2E−04 | 0.7 |
| NAD | lnc-DDX39A-4:1 | SEQ 6045 | 3E−04 | 0.8 | NAD | lnc-UGT2B28-1:2 | SEQ 1001 | 4E−04 | 1.8 |
| NAD + HC | lnc-DDX39A-4:1 | SEQ 6045 | 3E−03 | 0.8 | NAD + HC | lnc-UGT2B28-1:2 | SEQ 1001 | 2E−03 | 1.7 |
| NAD | lnc-DDX49-1:1 | SEQ 2759 | 3E−04 | 0.8 | NAD | lnc-UNC93B1-1:8 | SEQ 6092 | 6E−05 | 0.8 |
| NAD + HC | lnc-DDX49-1:1 | SEQ 2759 | 3E−03 | 0.9 | NAD + HC | lnc-WASHC3-2:3 | SEQ 6073 | 3E−03 | 0.8 |
| NAD | lnc-DEPTOR-2:1 | SEQ 6037 | 4E−04 | 1.3 | NAD | lnc-WDR81-6:1 | SEQ 6055 | 8E−04 | 0.7 |
| NAD | lnc-DGKE-7:1 | SEQ 6062 | 3E−04 | 0.7 | NAD + HC | lnc-WDR81-6:1 | SEQ 6055 | 3E−03 | 0.8 |
| NAD + HC | lnc-DGKE-7:1 | SEQ 6062 | 4E−03 | 0.8 | NAD + HC | lnc-WSB1-1:1 | SEQ 6054 | 2E−03 | 0.8 |
| NAD + HC | lnc-DHRS7B-1:10 | SEQ 6041 | 1E−03 | 0.8 | NAD + HC | lnc-ZFP57-21:6 | SEQ 6099 | 3E−03 | 0.7 |
| NAD | lnc-EIF4H-1:1 | SEQ 6053 | 1E−04 | 0.7 | NAD | lnc-ZNF705B-1:6 | SEQ 6086 | 7E−04 | 0.7 |
| NAD + HC | lnc-EIF4H-1:1 | SEQ 6053 | 8E−04 | 0.8 | NAD + HC | lnc-ZNF705B-1:6 | SEQ 6086 | 3E−03 | 0.8 |
| NAD | lnc-EPHB1-1:1 | SEQ 6129 | 1E−04 | 0.6 | NAD | lnc-ZRANB1-7:1 | SEQ 6039 | 6E−04 | 0.8 |
| NAD + HC | lnc-FANCI-5:3 | SEQ 6044 | 3E−03 | 0.8 | NAD + HC | lnc-ZRANB1-7:1 | SEQ 6039 | 2E−03 | 0.8 |
| NAD | lnc-FKBP6-4:1 | SEQ 3394 | 8E−04 | 0.8 | NAD + HC | MALAT1:17 | SEQ 6076 | 2E−03 | 0.8 |
| NAD + HC | lnc-FKBP6-4:1 | SEQ 3394 | 3E−03 | 0.8 | NAD + HC | MIR22HG:36 | SEQ 6038 | 2E−03 | 0.9 |
| NAD + HC | lnc-GABBR1-1:1 | SEQ 6036 | 2E−03 | 1.3 | NAD + HC | MIR4435-2HG:29 | SEQ 6074 | 4E−03 | 0.8 |
| NAD | lnc-GINS2-2:6 | SEQ 6096 | 2E−04 | 0.7 | NAD | MME-AS1:1 | SEQ 6106 | 1E−04 | 0.6 |
| NAD + HC | lnc-GINS2-2:6 | SEQ 6096 | 4E−03 | 0.7 | NAD + HC | MME-AS1:1 | SEQ 6106 | 2E−03 | 0.7 |
| NAD + HC | lnc-GPR20-3:6 | SEQ 6105 | 3E−03 | 0.7 | NAD | NALT1:14 | SEQ 6127 | 7E−04 | 0.7 |
| NAD + HC | lnc-GPR68-1:1 | SEQ 6088 | 2E−03 | 0.8 | NAD | NUTM2A-AS1:16 | SEQ 6110 | 2E−04 | 0.6 |
| NAD | lnc-GTPBP1-4:1 | SEQ 6072 | 3E−04 | 0.7 | NAD + HC | NUTM2A-AS1:16 | SEQ 6110 | 1E−03 | 0.7 |
| NAD + HC | lnc-GTPBP1-4:1 | SEQ 6072 | 6E−04 | 0.8 | NAD + HC | PCBP1-AS1:170 | SEQ 6098 | 4E−03 | 0.7 |
| NAD | lnc-HLA-B-2:12 | SEQ 6116 | 4E−06 | 0.6 | NAD + HC | PCBP1-AS1:27 | SEQ 6100 | 3E−03 | 0.7 |
| NAD + HC | lnc-HLA-B-2:12 | SEQ 6116 | 9E−05 | 0.7 | NAD + HC | RARA-AS1:2 | SEQ 6049 | 2E−03 | 0.8 |
| NAD + HC | lnc-HYAL3-1:1 | SEQ 6065 | 8E−04 | 0.8 | NAD | SNHG10:11 | SEQ 6078 | 3E−04 | 0.8 |
| NAD | lnc-IL10-1:1 | SEQ 6126 | 3E−04 | 0.7 | NAD | SNHG22:6 | SEQ 6034 | 7E−04 | 1.4 |
| NAD | lnc-IL31RA-2:1 | SEQ 2557 | 8E−04 | 0.7 | NAD + HC | SNHG7:16 | SEQ 6124 | 4E−04 | 0.7 |
| NAD | lnc-INSM2-8:1 | SEQ 6033 | 4E−04 | 1.4 | NAD | SNHG7:16 | SEQ 6124 | 4E−04 | 0.6 |
| NAD + HC | lnc-IRF1-2:5 | SEQ 6058 | 4E−03 | 0.8 | NAD + HC | TCONS_00011974 | SEQ 1218 | 3E−03 | 0.8 |
| NAD | lnc-ISYNA1-2:1 | SEQ 6063 | 3E−04 | 0.8 | NAD | TCONS_00017370 | SEQ 1271 | 4E−05 | 103 |
| NAD + HC | lnc-ISYNA1-2:1 | SEQ 6063 | 2E−03 | 0.8 | NAD + HC | TCONS_00017370 | SEQ 1271 | 3E−03 | 66 |
| NAD + HC | lnc-KIAA1551-3:1 | SEQ 6061 | 2E−03 | 0.8 | NAD + HC | TCONS_00017373 | SEQ 1274 | 2E−03 | 1.5 |
| NAD | lnc-KLHDC7B-5:2 | SEQ 6111 | 7E−04 | 0.7 | NAD | XIST:27 | SEQ 6020 | 4E−04 | 2.1 |
| NAD + HC | lnc-LAX1-4:1 | SEQ 6059 | 4E−03 | 0.8 | NAD + HC | XIST:27 | SEQ 6020 | 1E−03 | 1.8 |
| NAD | lnc-LGALS2-1:2 | SEQ 6057 | 3E−04 | 0.8 | NAD + HC | XIST:47 | SEQ 6025 | 3E−03 | 1.7 |
| NAD + HC | lnc-LGALS2-1:2 | SEQ 6057 | 2E−03 | 0.8 | NAD | ZNF529-AS1:19 | SEQ 6018 | 3E−05 | 2.4 |

Brain-enriched lncRNAs: Out of the 10122 lncRNAs sequenced by the invention in the AD and control brains and having an expression level >5 CPM (median), 860 lncRNAs showed an expression level 2-fold higher in the brain as compared to peripheral organs lung, ovary, colon, prostate, breast, liver, bladder, kidney, skin, heart, muscle. The 860 lncRNAs are shown in Table 12.

TABLE 12

860 brain-enriched lncRNAs with an expression level in the brain at least 2-fold higher than that in 12 peripheral organs.

| lncRNA | SEQ | Ratio Br/org |
|---|---|---|
| TCONS_00005325 | SEQ1141 | 7.7E+01 |
| TCONS_00035021 | SEQ1566 | 4.0E+00 |
| TCONS_00035024 | SEQ1571 | 1.9E+01 |
| TCONS_00035022 | SEQ1567 | 4.6E+32 |
| TCONS_00012059 | SEQ1200 | 1.2E+03 |
| TCONS_00045364 | SEQ1785 | 3.7E+00 |
| TCONS_00050012 | SEQ1801 | 6.7E+02 |
| TCONS_00035023 | SEQ1568 | 6.9E+04 |
| TCONS_00012060 | SEQ1201 | 5.6E+02 |
| TCONS_00035090 | SEQ1564 | 4.8E+00 |
| TCONS_00035091 | SEQ1565 | 1.3E+01 |
| TCONS_00050014 | SEQ1803 | 1.2E+03 |
| TCONS_00035094 | SEQ1573 | 2.7E+01 |
| TCONS_00035092 | SEQ1569 | 3.4E+02 |
| TCONS_00035093 | SEQ1570 | 4.5E+00 |
| TCONS_00012009 | SEQ1185 | 3.2E+01 |
| TCONS_00045125 | SEQ1790 | 1.1E+01 |
| TCONS_00024864 | SEQ1388 | 5.0E+01 |
| lnc-SP110-8:2 | SEQ6135 | 9.6E+02 |
| MEG3:21 | SEQ6136 | 2.0E+02 |
| lnc-CCDC150-6:1 | SEQ6137 | 1.8E+02 |
| lnc-ZNF45-2:1 | SEQ6138 | 1.7E+02 |
| NUTM2B-AS1:31 | SEQ6139 | 1.5E+02 |
| lnc-HMBS-1:1 | SEQ6140 | 1.2E+02 |
| TMEM5-AS1:2 | SEQ6141 | 9.4E+01 |
| lnc-ZNF583-4:2 | SEQ6142 | 9.2E+01 |
| lnc-LYRM2-2:1 | SEQ6143 | 6.5E+01 |
| lnc-TBX2-4:2 | SEQ6144 | 6.5E+01 |
| lnc-NAA50-3:1 | SEQ2266 | 6.1E+01 |
| lnc-HINFP-1:1 | SEQ6145 | 5.9E+01 |
| MIR4458HG:7 | SEQ6146 | 4.8E+01 |
| lnc-SLC25A44-1:2 | SEQ6147 | 4.4E+01 |
| lnc-SEPT5-1:4 | SEQ6148 | 4.2E+01 |
| lnc-UBE4A-1:1 | SEQ6149 | 4.1E+01 |
| lnc-RP11-334E6.3.1-2:1 | SEQ6150 | 4.0E+01 |
| lnc-GBP5-2:6 | SEQ6151 | 4.0E+01 |
| lnc-FAM49B-5:1 | SEQ6152 | 4.0E+01 |
| STXBP5-AS1:2 | SEQ6153 | 4.0E+01 |
| lnc-ROBO3-2:2 | SEQ6154 | 3.9E+01 |
| lnc-ZNF91-4:4 | SEQ6155 | 3.9E+01 |
| lnc-ATRNL1-1:1 | SEQ6156 | 3.7E+01 |
| lnc-MAPK8IP1-3:1 | SEQ6157 | 3.5E+01 |
| LINC01024:12 | SEQ6158 | 3.4E+01 |
| lnc-CSNK2A2-2:2 | SEQ6159 | 3.2E+01 |
| lnc-LPL-4:2 | SEQ6160 | 3.1E+01 |
| lnc-TBL1XR1-17:1 | SEQ2374 | 3.1E+01 |
| lnc-POM121L2-2:1 | SEQ2133 | 2.8E+01 |
| lnc-MBOAT2-5:1 | SEQ6161 | 2.8E+01 |
| lnc-CDC27-7:1 | SEQ6162 | 2.7E+01 |
| lnc-RP11-345P4.5.1-1:1 | SEQ6163 | 2.7E+01 |
| lnc-PNPLA8-2:8 | SEQ6164 | 2.5E+01 |
| lnc-CYP20A1-1:3 | SEQ6165 | 2.5E+01 |
| lnc-CTD-2117L12.1.1-4:4 | SEQ6166 | 2.5E+01 |
| lnc-KNG1-2:3 | SEQ6167 | 2.4E+01 |
| lnc-SNAP25-3:1 | SEQ6168 | 2.4E+01 |
| UBA6-AS1:10 | SEQ6169 | 2.3E+01 |
| EIF3J-AS1:2 | SEQ6170 | 2.3E+01 |
| SLC25A25-AS1:16 | SEQ6171 | 2.2E+01 |
| lnc-UQCRH-1:3 | SEQ6172 | 2.1E+01 |
| lnc-DLX1-2:5 | SEQ6173 | 2.0E+01 |
| SUCLG2-AS1:5 | SEQ6174 | 2.0E+01 |
| lnc-ARSG-1:1 | SEQ6175 | 1.8E+01 |
| lnc-COX17-2:2 | SEQ6176 | 1.8E+01 |
| lnc-TRIM26-2:8 | SEQ6177 | 1.8E+01 |
| lnc-RAB27A-1:4 | SEQ6178 | 1.8E+01 |
| TP73-AS1:23 | SEQ6179 | 1.8E+01 |
| lnc-VPREB1-7:6 | SEQ6180 | 1.7E+01 |
| RNF219-AS1:4 | SEQ6181 | 1.7E+01 |
| lnc-BRAF-2:1 | SEQ6182 | 1.7E+01 |
| lnc-TPTE2-4:1 | SEQ2431 | 1.5E+01 |
| MYLK-AS1:1 | SEQ6183 | 1.5E+01 |
| lnc-UQCRH-1:1 | SEQ6184 | 1.5E+01 |
| lnc-GPR39-9:1 | SEQ2704 | 1.4E+01 |
| lnc-TRIM26-2:24 | SEQ6185 | 1.4E+01 |
| lnc-EPHA4-4:1 | SEQ6186 | 1.4E+01 |
| lnc-LSM5-2:1 | SEQ6187 | 1.4E+01 |
| lnc-MLST8-2:6 | SEQ6188 | 1.4E+01 |
| NCBP2-AS2:1 | SEQ6189 | 1.3E+01 |
| LIMD1-AS1:3 | SEQ6190 | 1.3E+01 |
| PINK1-AS:1 | SEQ2712 | 1.3E+01 |
| lnc-BRWD1-2:2 | SEQ6191 | 1.3E+01 |
| lnc-FAM200B-1:5 | SEQ6192 | 1.3E+01 |
| lnc-ARL6IP4-1:10 | SEQ6193 | 1.3E+01 |
| lnc-TMEM189-UBE2V1-4:5 | SEQ6194 | 1.3E+01 |
| lnc-ARL16-2:2 | SEQ6195 | 1.3E+01 |
| lnc-NAGA-2:1 | SEQ6196 | 1.3E+01 |
| lnc-LPCAT1-3:23 | SEQ6197 | 1.3E+01 |
| lnc-NEDD8-MDP1-1:1 | SEQ6198 | 1.2E+01 |
| LIFR-AS1:3 | SEQ6199 | 1.2E+01 |
| lnc-NEK3-1:8 | SEQ6200 | 1.2E+01 |
| lnc-KCNE4-7:1 | SEQ2466 | 1.2E+01 |
| lnc-FAM200B-1:11 | SEQ6201 | 1.2E+01 |
| lnc-CDC42SE2-1:10 | SEQ2613 | 1.2E+01 |
| lnc-TM9SF2-8:1 | SEQ6202 | 1.2E+01 |
| MIR4458HG:6 | SEQ6203 | 1.2E+01 |
| lnc-DCTN3-1:3 | SEQ6204 | 1.1E+01 |
| lnc-PAPLN-3:1 | SEQ6205 | 1.1E+01 |
| lnc-RP11-1035H13.3.1-1:3 | SEQ6206 | 1.1E+01 |
| lnc-NDUFS1-2:2 | SEQ6207 | 1.1E+01 |
| LINC00630:8 | SEQ6208 | 1.1E+01 |
| lnc-ZNF449-3:5 | SEQ2420 | 1.1E+01 |
| lnc-ZNF449-3:4 | SEQ2421 | 1.1E+01 |
| PEG3-AS1:1 | SEQ2398 | 1.1E+01 |
| lnc-XRRA1-1:3 | SEQ6209 | 1.0E+01 |
| lnc-USP13-5:1 | SEQ6210 | 1.0E+01 |
| lnc-FAM104A-2:1 | SEQ2542 | 1.0E+01 |
| lnc-CPO-2:1 | SEQ6211 | 1.0E+01 |
| lnc-KBTBD6-2:1 | SEQ2349 | 1.0E+01 |
| lnc-GPC2-2:7 | SEQ6212 | 9.7E+00 |
| lnc-POLK-3:1 | SEQ6213 | 9.6E+00 |
| lnc-INO80B-1:2 | SEQ6214 | 9.6E+00 |
| lnc-ZSCAN10-3:1 | SEQ6215 | 9.4E+00 |
| lnc-RASA1-13:5 | SEQ6216 | 9.4E+00 |
| lnc-PRMT5-1:2 | SEQ6217 | 9.4E+00 |
| lnc-CPOX-1:1 | SEQ6218 | 9.4E+00 |
| lnc-VEPH1-2:1 | SEQ6219 | 9.3E+00 |
| lnc-RPAIN-2:1 | SEQ6220 | 9.3E+00 |
| lnc-SNX20-5:3 | SEQ2643 | 9.3E+00 |
| RNF219-AS1:16 | SEQ4990 | 9.2E+00 |
| lnc-C9orf123-8:2 | SEQ6221 | 9.1E+00 |
| lnc-SLC5A2-1:4 | SEQ2622 | 9.1E+00 |
| lnc-GDPD4-7:1 | SEQ6223 | 9.0E+00 |
| lnc-PRKD2-2:1 | SEQ6224 | 9.0E+00 |
| lnc-C18orf54-3:4 | SEQ6225 | 9.0E+00 |
| lnc-AGPHD1-1:6 | SEQ6226 | 9.0E+00 |
| lnc-NPR3-3:5 | SEQ6227 | 8.9E+00 |
| lnc-CBWD5-2:8 | SEQ6228 | 8.9E+00 |
| lnc-NUDT3-1:2 | SEQ6229 | 8.8E+00 |
| lnc-VSTM5-1:13 | SEQ2419 | 8.7E+00 |
| LINC00630:12 | SEQ6230 | 8.7E+00 |
| lnc-SLMO2-3:1 | SEQ6231 | 8.7E+00 |
| lnc-DPH5-2:7 | SEQ6232 | 8.6E+00 |
| lnc-SCN4B-2:3 | SEQ6233 | 8.5E+00 |
| lnc-NDUFA6-1:1 | SEQ6234 | 8.5E+00 |
| RAB11B-AS1:1 | SEQ6235 | 8.5E+00 |
| lnc-LRRC37A2-2:3 | SEQ6236 | 8.4E+00 |
| lnc-PAQR7-1:1 | SEQ6237 | 8.3E+00 |
| lnc-POLR2I-1:2 | SEQ6238 | 8.3E+00 |

TABLE 12-continued 860 brain-enriched lncRNAs with an expression level in the brain at least 2-fold higher than that in 12 peripheral organs.

| lncRNA | SEQ | Ratio Br/org |
|---|---|---|
| lnc-H2AFZ-1:4 | SEQ6239 | 8.2E+00 |
| SVIL-AS1:4 | SEQ6240 | 8.1E+00 |
| lnc-DCUN1D3-1:5 | SEQ6241 | 8.1E+00 |
| lnc-PRR4-1:2 | SEQ6242 | 8.0E+00 |
| MAGI2-AS3:13 | SEQ6243 | 8.0E+00 |
| lnc-FANCM-8:3 | SEQ2291 | 7.9E+00 |
| lnc-CRLF1-2:1 | SEQ6244 | 7.8E+00 |
| lnc-PPP4C-1:1 | SEQ6245 | 7.7E+00 |
| lnc-RNF187-2:2 | SEQ6246 | 7.6E+00 |
| lnc-ATAT1-4:1 | SEQ6247 | 7.5E+00 |
| lnc-AP2M1-2:1 | SEQ6248 | 7.5E+00 |
| lnc-MARCH7-1:3 | SEQ6249 | 7.5E+00 |
| lnc-ZNF518B-2:4 | SEQ5239 | 7.5E+00 |
| lnc-OTP-4:1 | SEQ6250 | 7.4E+00 |
| EPB41L4A-AS1:4 | SEQ6251 | 7.4E+00 |
| lnc-ATAD5-3:22 | SEQ6252 | 7.4E+00 |
| NDUFA6-AS1:4 | SEQ6253 | 7.4E+00 |
| lnc-RGPD1-6:1 | SEQ6254 | 7.4E+00 |
| lnc-DLG2-3:2 | SEQ6255 | 7.3E+00 |
| lnc-PSMA3-1:5 | SEQ6256 | 7.3E+00 |
| lnc-GRIN2A-1:2 | SEQ6257 | 7.0E+00 |
| lnc-KNG1-2:6 | SEQ6258 | 7.0E+00 |
| lnc-AMN1-1:2 | SEQ6259 | 7.0E+00 |
| lnc-MTMR4-2:1 | SEQ6260 | 7.0E+00 |
| lnc-PRTFDC1-3:1 | SEQ6261 | 6.9E+00 |
| lnc-PRKAR1A-2:1 | SEQ6262 | 6.9E+00 |
| lnc-ANKRD56-5:1 | SEQ6263 | 6.9E+00 |
| lnc-GJC2-2:2 | SEQ6264 | 6.9E+00 |
| lnc-CDKL3-3:1 | SEQ6265 | 6.9E+00 |
| MYCBP2-AS1:10 | SEQ6266 | 6.8E+00 |
| lnc-POM121L2-2:8 | SEQ6267 | 6.8E+00 |
| lnc-IQUB-2:6 | SEQ6268 | 6.7E+00 |
| lnc-ARMC9-2:2 | SEQ6269 | 6.7E+00 |
| lnc-DBF4-3:1 | SEQ6270 | 6.7E+00 |
| lnc-SOCS6-10:1 | SEQ2214 | 6.6E+00 |
| lnc-AF131216.6.1-2:2 | SEQ6271 | 6.5E+00 |
| lnc-CLEC2D-8:7 | SEQ3369 | 6.5E+00 |
| lnc-UROS-2:4 | SEQ6272 | 6.5E+00 |
| lnc-EDC4-1:2 | SEQ6273 | 6.5E+00 |
| lnc-ESCO2-1:2 | SEQ6274 | 6.5E+00 |
| OTUD6B-AS1:3 | SEQ6275 | 6.4E+00 |
| lnc-SREBF1-1:1 | SEQ6276 | 6.4E+00 |
| lnc-DLG5-4:1 | SEQ6277 | 6.4E+00 |
| lnc-GNGT1-4:1 | SEQ6278 | 6.4E+00 |
| lnc-PRDX2-1:1 | SEQ6279 | 6.4E+00 |
| lnc-MBOAT4-5:1 | SEQ6280 | 6.3E+00 |
| lnc-RBM25-5:2 | SEQ6281 | 6.2E+00 |
| LINC-PINT:9 | SEQ6282 | 6.2E+00 |
| lnc-RP11-478C19.2.1-2:7 | SEQ6283 | 6.2E+00 |
| lnc-APOPT1-1:1 | SEQ6284 | 6.1E+00 |
| lnc-ZBTB17-4:1 | SEQ6285 | 6.1E+00 |
| lnc-PRKAB2-5:1 | SEQ6286 | 6.1E+00 |
| lnc-TMEM154-4:2 | SEQ6287 | 6.1E+00 |
| GLIDR:2 | SEQ6288 | 6.1E+00 |
| lnc-ZNF664-2:16 | SEQ6289 | 6.0E+00 |
| lnc-MLL3-1:2 | SEQ6290 | 6.0E+00 |
| lnc-MRPL48-4:1 | SEQ6291 | 6.0E+00 |
| lnc-TMEM232-7:1 | SEQ6292 | 6.0E+00 |
| lnc-BRCC3-4:1 | SEQ6293 | 6.0E+00 |
| lnc-PKD2L1-6:1 | SEQ6294 | 5.9E+00 |
| UBA6-AS1:2 | SEQ6295 | 5.9E+00 |
| lnc-SESN3-2:2 | SEQ6296 | 5.9E+00 |
| lnc-SGIP1-3:1 | SEQ6297 | 5.9E+00 |
| SNHG3:2 | SEQ6298 | 5.8E+00 |
| lnc-GABBR1-1:1 | SEQ6036 | 5.7E+00 |
| lnc-EXD1-1:1 | SEQ6299 | 5.7E+00 |
| lnc-VPREB1-7:1 | SEQ6300 | 5.7E+00 |
| lnc-PPFIA4-1:1 | SEQ2325 | 5.7E+00 |
| lnc-C2orf63-3:1 | SEQ6301 | 5.7E+00 |
| TP73-AS1:21 | SEQ6302 | 5.7E+00 |
| lnc-FAM200B-1:3 | SEQ6303 | 5.6E+00 |
| lnc-FAM210A-1:1 | SEQ6304 | 5.6E+00 |
| lnc-FAM153A-3:4 | SEQ6305 | 5.6E+00 |
| lnc-PCGF5-5:4 | SEQ6306 | 5.6E+00 |
| BCDIN3D-AS1:1 | SEQ6307 | 5.5E+00 |
| lnc-KIAA1704-3:1 | SEQ6308 | 5.5E+00 |
| lnc-C5orf13-1:3 | SEQ6309 | 5.5E+00 |
| lnc-RGR-3:4 | SEQ6310 | 5.5E+00 |
| lnc-RPGRIP1L-1:2 | SEQ6311 | 5.5E+00 |
| lnc-FAM120AOS-3:6 | SEQ6312 | 5.5E+00 |
| lnc-DYNC1LI2-2:2 | SEQ6313 | 5.5E+00 |
| lnc-GPS2-1:1 | SEQ6314 | 5.5E+00 |
| PRKCQ-AS1:11 | SEQ4800 | 5.4E+00 |
| lnc-ZAR1L-2:1 | SEQ6315 | 5.4E+00 |
| lnc-TRIOBP-1:3 | SEQ6316 | 5.4E+00 |
| lnc-RNPEP-3:1 | SEQ6317 | 5.4E+00 |
| lnc-FOXD4L6-2:6 | SEQ6318 | 5.4E+00 |
| lnc-FAM150B-5:3 | SEQ6319 | 5.4E+00 |
| LINC00662:21 | SEQ6320 | 5.4E+00 |
| lnc-PNLIPRP1-1:2 | SEQ2540 | 5.3E+00 |
| CARS-AS1:2 | SEQ6321 | 5.3E+00 |
| lnc-FBXO3-3:2 | SEQ6322 | 5.2E+00 |
| lnc-XRCC5-3:1 | SEQ2326 | 5.2E+00 |
| lnc-AIPL1-6:1 | SEQ6323 | 5.2E+00 |
| lnc-AF131215.2.1-1:3 | SEQ6324 | 5.1E+00 |
| lnc-MC5R-6:1 | SEQ6325 | 5.1E+00 |
| lnc-DNAJC17-1:1 | SEQ6326 | 5.1E+00 |
| HEIH: 11 | SEQ6327 | 5.1E+00 |
| MIR100HG:17 | SEQ6328 | 5.1E+00 |
| lnc-TMEM232-4:6 | SEQ6329 | 5.1E+00 |
| lnc-TMEM99-5:3 | SEQ6330 | 5.0E+00 |
| lnc-AC005609.1-3:7 | SEQ6331 | 5.0E+00 |
| lnc-SPAG16-5:1 | SEQ6332 | 5.0E+00 |
| lnc-CYP19A1-2:1 | SEQ6333 | 4.9E+00 |
| lnc-TYSND1-1:6 | SEQ6334 | 4.9E+00 |
| lnc-CDT1-1:1 | SEQ2708 | 4.9E+00 |
| lnc-C16orf61-3:7 | SEQ6335 | 4.9E+00 |
| lnc-IFI27L2-3:2 | SEQ6336 | 4.9E+00 |
| lnc-CLDN25-5:1 | SEQ6337 | 4.9E+00 |
| lnc-UNC80-1:1 | SEQ2219 | 4.9E+00 |
| lnc-PRKAA1-2:1 | SEQ6338 | 4.8E+00 |
| lnc-RPRML-3:24 | SEQ6339 | 4.8E+00 |
| SNHG16:11 | SEQ6340 | 4.8E+00 |
| lnc-MRFAP1-2:1 | SEQ6341 | 4.8E+00 |
| lnc-CERK-2:1 | SEQ6342 | 4.8E+00 |
| lnc-RAB11A-2:1 | SEQ6343 | 4.8E+00 |
| lnc-NETO2-1:1 | SEQ6344 | 4.8E+00 |
| lnc-LYN-9:4 | SEQ6345 | 4.8E+00 |
| lnc-GATC.1-2:1 | SEQ6346 | 4.8E+00 |
| lnc-PTMS-1:3 | SEQ6347 | 4.7E+00 |
| lnc-SOD1-4:4 | SEQ6348 | 4.7E+00 |
| lnc-HMGA1-2:9 | SEQ6349 | 4.7E+00 |
| lnc-ZNF518B-2:3 | SEQ6350 | 4.7E+00 |
| lnc-RAP1GAP2-5:1 | SEQ6351 | 4.7E+00 |
| lnc-CCNB2-2:1 | SEQ6352 | 4.6E+00 |
| lnc-LIN7A-3:1 | SEQ3437 | 4.6E+00 |
| lnc-UBE2B-2:1 | SEQ2253 | 4.6E+00 |
| lnc-MBP-13:10 | SEQ6353 | 4.6E+00 |
| lnc-RAP1GAP2-6:2 | SEQ6354 | 4.6E+00 |
| lnc-NEDD8-MDP1-1:3 | SEQ6355 | 4.6E+00 |
| lnc-MFSD4-3:3 | SEQ6356 | 4.6E+00 |
| lnc-PKIA-4:1 | SEQ6357 | 4.5E+00 |
| lnc-NRBP2-2:1 | SEQ6358 | 4.5E+00 |
| TP53TG1:8 | SEQ6359 | 4.5E+00 |
| BCDIN3D-AS1:6 | SEQ6360 | 4.5E+00 |
| BCDIN3D-AS1:2 | SEQ6361 | 4.5E+00 |
| lnc-MMADHC-11:1 | SEQ6362 | 4.5E+00 |
| lnc-RNF123-1:1 | SEQ4013 | 4.5E+00 |
| lnc-PRPF18-1:1 | SEQ6363 | 4.5E+00 |
| lnc-ZNF91-4:19 | SEQ6364 | 4.5E+00 |
| lnc-SATB1-8:6 | SEQ6365 | 4.4E+00 |
| lnc-FGD4-4:1 | SEQ6366 | 4.4E+00 |
| lnc-PALLD-7:1 | SEQ6367 | 4.4E+00 |
| lnc-KIAA1841-3:1 | SEQ6368 | 4.4E+00 |
| lnc-AARSD1-2:6 | SEQ6369 | 4.4E+00 |
| lnc-TRIM26-2:6 | SEQ6370 | 4.4E+00 |
| OTUD6B-AS1:8 | SEQ6371 | 4.4E+00 |
| lnc-TRIM26-2:13 | SEQ6372 | 4.4E+00 |

TABLE 12-continued 860 brain-enriched lncRNAs with an expression level in the brain at least 2-fold higher than that in 12 peripheral organs.

| lncRNA | SEQ | Ratio Br/org |
|---|---|---|
| lnc-RGPD3-5:2 | SEQ6373 | 4.4E+00 |
| lnc-ENSA-1:2 | SEQ6374 | 4.4E+00 |
| LINC01278:3 | SEQ6375 | 4.4E+00 |
| lnc-SUGP1-1:1 | SEQ6376 | 4.3E+00 |
| lnc-ORMDL2-1:17 | SEQ6377 | 4.3E+00 |
| lnc-ZNF397-7:1 | SEQ6378 | 4.3E+00 |
| lnc-TUBA1C-1:3 | SEQ6379 | 4.3E+00 |
| lnc-RERE-4:2 | SEQ6380 | 4.3E+00 |
| lnc-PDE7A-3:1 | SEQ6381 | 4.3E+00 |
| lnc-UROS-2:3 | SEQ6382 | 4.2E+00 |
| lnc-SRP19-1:4 | SEQ6383 | 4.2E+00 |
| ZNF571-AS1:12 | SEQ6384 | 4.2E+00 |
| ZNF571-AS1:13 | SEQ6385 | 4.2E+00 |
| lnc-MOB4-1:1 | SEQ6386 | 4.2E+00 |
| lnc-FMR1NB-4:3 | SEQ6387 | 4.2E+00 |
| lnc-NOL11-3:1 | SEQ6388 | 4.2E+00 |
| lnc-SMN1-1:2 | SEQ6389 | 4.2E+00 |
| lnc-POLR3GL-3:2 | SEQ6390 | 4.2E+00 |
| lnc-PRPF39-2:1 | SEQ6391 | 4.2E+00 |
| PAXIP1-AS1:7 | SEQ6392 | 4.2E+00 |
| lnc-ACOT12-8:2 | SEQ6393 | 4.1E+00 |
| lnc-ZNF582-3:2 | SEQ6394 | 4.1E+00 |
| lnc-CPVL-2:1 | SEQ6395 | 4.1E+00 |
| lnc-TARSL2-2:1 | SEQ6396 | 4.1E+00 |
| lnc-THRAP3-1:1 | SEQ6397 | 4.1E+00 |
| lnc-CCNB1-1:2 | SEQ6398 | 4.1E+00 |
| lnc-TIRAP-2:3 | SEQ6399 | 4.1E+00 |
| lnc-ZNF583-4:3 | SEQ6400 | 4.1E+00 |
| lnc-FAM200B-1:9 | SEQ6401 | 4.0E+00 |
| lnc-ANKUB1-2:2 | SEQ6402 | 4.0E+00 |
| lnc-NKAIN3-3:4 | SEQ6403 | 4.0E+00 |
| lnc-SNURF-1:10 | SEQ6404 | 4.0E+00 |
| MEG3:11 | SEQ6405 | 4.0E+00 |
| lnc-GSPT2-4:1 | SEQ6406 | 4.0E+00 |
| PTOV1-AS1:4 | SEQ6407 | 3.9E+00 |
| lnc-ZZZ3-1:1 | SEQ6408 | 3.9E+00 |
| lnc-CHRNA5-4:2 | SEQ6409 | 3.9E+00 |
| LINC01024:6 | SEQ6410 | 3.9E+00 |
| PAXIP1-AS1:1 | SEQ6411 | 3.9E+00 |
| lnc-CTDSP2-2:11 | SEQ6412 | 3.9E+00 |
| lnc-ITGAL-2:2 | SEQ6413 | 3.9E+00 |
| lnc-MACROD2-2:1 | SEQ6414 | 3.9E+00 |
| lnc-RABGAP1L-1:1 | SEQ6415 | 3.9E+00 |
| lnc-CEP192-2:3 | SEQ6416 | 3.9E+00 |
| lnc-PRR18-1:1 | SEQ6417 | 3.9E+00 |
| lnc-CTD-2228K2.5.1-1:2 | SEQ6418 | 3.9E+00 |
| lnc-ARSG-1:2 | SEQ6419 | 3.8E+00 |
| SNHG8:11 | SEQ6420 | 3.8E+00 |
| lnc-AL592284.1-1:19 | SEQ6421 | 3.8E+00 |
| lnc-C1QL3-1:1 | SEQ6422 | 3.8E+00 |
| lnc-HELLS-2:1 | SEQ6423 | 3.8E+00 |
| lnc-STXBP4-1:1 | SEQ6424 | 3.8E+00 |
| lnc-DOM3Z-3:6 | SEQ6425 | 3.8E+00 |
| lnc-EML6-5:3 | SEQ6426 | 3.8E+00 |
| lnc-CLK4-2:2 | SEQ6427 | 3.8E+00 |
| lnc-AC084851.1-9:1 | SEQ6428 | 3.8E+00 |
| lnc-POM121L2-2:2 | SEQ2341 | 3.8E+00 |
| PAXBP1-AS1:4 | SEQ6429 | 3.8E+00 |
| PAXBP1-AS1:3 | SEQ6430 | 3.8E+00 |
| TRAF3IP2-AS1:4 | SEQ6431 | 3.8E+00 |
| lnc-KAZALD1-2:3 | SEQ6432 | 3.8E+00 |
| lnc-AL669831.1-3:33 | SEQ6433 | 3.8E+00 |
| lnc-SLC6A18-2:2 | SEQ6434 | 3.8E+00 |
| lnc-VPS72-2:2 | SEQ6435 | 3.8E+00 |
| LINC01278:1 | SEQ6436 | 3.7E+00 |
| lnc-BDH1-5:3 | SEQ6437 | 3.7E+00 |
| NPTN-IT1:2 | SEQ6438 | 3.7E+00 |
| lnc-DAXX-2:1 | SEQ6439 | 3.7E+00 |
| lnc-UBE2E3-2:12 | SEQ6440 | 3.7E+00 |
| lnc-MINOS1-2:2 | SEQ6441 | 3.7E+00 |
| lnc-POM121C-1:3 | SEQ6442 | 3.7E+00 |
| WAC-AS1:2 | SEQ6443 | 3.7E+00 |
| lnc-RGPD8-1:1 | SEQ6444 | 3.7E+00 |
| lnc-SLC4A5-5:4 | SEQ6445 | 3.7E+00 |
| lnc-GABBR1-1:2 | SEQ2290 | 3.7E+00 |
| lnc-AC006465.3.1-1:13 | SEQ6446 | 3.7E+00 |
| lnc-TRAPPC11-4:1 | SEQ6447 | 3.7E+00 |
| lnc-UROS-2:1 | SEQ6448 | 3.7E+00 |
| CD27-AS1:5 | SEQ6449 | 3.7E+00 |
| lnc-LXN-1:3 | SEQ6450 | 3.7E+00 |
| lnc-RASL11B-10:1 | SEQ6451 | 3.6E+00 |
| lnc-DLG2-3:1 | SEQ6452 | 3.6E+00 |
| lnc-NECAP1-1:2 | SEQ6453 | 3.6E+00 |
| lnc-EDEM1-1:1 | SEQ6454 | 3.6E+00 |
| lnc-STX2-8:1 | SEQ6455 | 3.6E+00 |
| lnc-SLC35F5-14:11 | SEQ6456 | 3.6E+00 |
| lnc-EPB41L5-1:1 | SEQ6457 | 3.6E+00 |
| lnc-LAMTOR1-1:1 | SEQ6458 | 3.6E+00 |
| lnc-KBTBD2-2:2 | SEQ6459 | 3.5E+00 |
| lnc-ARC-1:5 | SEQ6460 | 3.5E+00 |
| lnc-SON-3:2 | SEQ6461 | 3.5E+00 |
| lnc-CCNL2-3:2 | SEQ6462 | 3.5E+00 |
| lnc-RP11-1035H13.3.1-1:2 | SEQ6463 | 3.5E+00 |
| lnc-LPCAT1-3:13 | SEQ6464 | 3.5E+00 |
| lnc-RP11-96020.4.1-1:1 | SEQ6465 | 3.5E+00 |
| lnc-THAP4-3:2 | SEQ6466 | 3.5E+00 |
| lnc-SFXN5-1:4 | SEQ6467 | 3.5E+00 |
| lnc-GOLT1B-1:3 | SEQ6468 | 3.5E+00 |
| lnc-SUGT1-3:1 | SEQ0131 | 3.5E+00 |
| ATP6VOE2-AS1:5 | SEQ6469 | 3.5E+00 |
| lnc-FAM71E1-1:1 | SEQ6470 | 3.4E+00 |
| lnc-ZNF8-4:3 | SEQ6471 | 3.4E+00 |
| LINC00936:2 | SEQ6472 | 3.4E+00 |
| DANCR:2 | SEQ6473 | 3.4E+00 |
| lnc-DDX31-3:1 | SEQ6474 | 3.4E+00 |
| lnc-TKT-1:9 | SEQ6475 | 3.4E+00 |
| lnc-EFCAB8-1:2 | SEQ6476 | 3.4E+00 |
| lnc-RSPH10B2-1:3 | SEQ2580 | 3.4E+00 |
| lnc-NTRK1-4:1 | SEQ6477 | 3.4E+00 |
| lnc-RPL3-2:3 | SEQ6478 | 3.4E+00 |
| lnc-CCL28-2:1 | SEQ6479 | 3.4E+00 |
| lnc-ARHGEF35-2:1 | SEQ6480 | 3.4E+00 |
| lnc-IL12RB2-3:1 | SEQ6481 | 3.4E+00 |
| lnc-BDH1-5:2 | SEQ6482 | 3.4E+00 |
| lnc-TRIM38-1:1 | SEQ6483 | 3.4E+00 |
| lnc-ATPAF2-2:5 | SEQ6484 | 3.4E+00 |
| lnc-HIGD1C-1:5 | SEQ6485 | 3.4E+00 |
| lnc-RP11-645C24.1.1-3:8 | SEQ6486 | 3.3E+00 |
| lnc-TCTA-1:1 | SEQ4966 | 3.3E+00 |
| MAPKAPK5-AS1:8 | SEQ6487 | 3.3E+00 |
| lnc-TMSB10-1:1 | SEQ6488 | 3.3E+00 |
| lnc-AES-1:3 | SEQ6489 | 3.3E+00 |
| lnc-GNAI2-1:12 | SEQ6490 | 3.3E+00 |
| lnc-ATP6V1C1-9:4 | SEQ3802 | 3.3E+00 |
| lnc-GLTSCR2-2:6 | SEQ6491 | 3.3E+00 |
| lnc-IL9R-1:6 | SEQ6492 | 3.3E+00 |
| lnc-ZEB2-1:9 | SEQ6493 | 3.3E+00 |
| lnc-AL669831.1-3:10 | SEQ6494 | 3.3E+00 |
| lnc-GRIK2-5:1 | SEQ6495 | 3.3E+00 |
| lnc-OTP-5:1 | SEQ6496 | 3.3E+00 |
| lnc-ST6GALNAC6-1:4 | SEQ6497 | 3.3E+00 |
| lnc-BLZF1-2:4 | SEQ6498 | 3.3E+00 |
| lnc-AL669831.1-3:4 | SEQ6499 | 3.2E+00 |
| lnc-CNR2-1:7 | SEQ6500 | 3.2E+00 |
| lnc-SRPRB-1:1 | SEQ2427 | 3.2E+00 |
| lnc-NETO2-4:1 | SEQ6501 | 3.2E+00 |
| lnc-RP11-796G6.2.1-4:7 | SEQ6502 | 3.2E+00 |
| lnc-SLC25A16-1:1 | SEQ6503 | 3.2E+00 |
| lnc-FAM165B-1:2 | SEQ6504 | 3.2E+00 |
| lnc-NUTF2-1:1 | SEQ6505 | 3.2E+00 |
| lnc-CTDSP2-2:9 | SEQ6506 | 3.2E+00 |
| lnc-HNRNPA1L2-2:4 | SEQ6507 | 3.2E+00 |
| lnc-NDUFA7-1:2 | SEQ6508 | 3.2E+00 |
| lnc-TRAPPC6B-3:1 | SEQ6509 | 3.2E+00 |
| TCONS_00062327 | SEQ2005 | 7.4E+23 |
| TCONS_00062311 | SEQ1996 | 1.9E+05 |
| TCONS_00033704 | SEQ1562 | 2.8E+03 |
| TCONS_00036143 | SEQ1611 | 9.6E+01 |

TABLE 12-continued 860 brain-enriched lncRNAs with an expression level in the brain at least 2-fold higher than that in 12 peripheral organs.

| lncRNA | SEQ | Ratio Br/org |
|---|---|---|
| TCONS_00045398 | SEQ1789 | 7.7E+01 |
| TCONS_00033666 | SEQ1553 | 3.9E+01 |
| TCONS_00021559 | SEQ1333 | 3.3E+01 |
| TCONS_00026547 | SEQ1410 | 2.6E+01 |
| TCONS_00055516 | SEQ1902 | 2.4E+01 |
| TCONS_00062422 | SEQ2040 | 2.4E+01 |
| TCONS_00024800 | SEQ1391 | 2.0E+01 |
| TCONS_00021416 | SEQ1328 | 1.9E+01 |
| TCONS_00014326 | SEQ1225 | 1.3E+01 |
| TCONS_00045346 | SEQ1781 | 9.0E+00 |
| TCONS_00021544 | SEQ1320 | 9.0E+00 |
| TCONS_00023115 | SEQ1352 | 7.6E+00 |
| TCONS_00014261 | SEQ1249 | 6.3E+00 |
| lnc-NKX1-2-2:1 | SEQ6510 | 3.2E+00 |
| lnc-HSDL1-1:1 | SEQ6511 | 3.2E+00 |
| lnc-FAM115C-1:1 | SEQ6512 | 3.2E+00 |
| lnc-AARSD1-2:7 | SEQ6513 | 3.2E+00 |
| LINC00969:38 | SEQ6514 | 3.2E+00 |
| lnc-VPREB1-7:13 | SEQ6515 | 3.2E+00 |
| lnc-MYO15A-1:1 | SEQ6516 | 3.2E+00 |
| lnc-SNURF-1:22 | SEQ6517 | 3.2E+00 |
| lnc-ZNF415-2:9 | SEQ6518 | 3.2E+00 |
| lnc-KNG1-2:5 | SEQ6519 | 3.2E+00 |
| LINC00641:4 | SEQ6520 | 3.1E+00 |
| lnc-KCND3-3:1 | SEQ6521 | 3.1E+00 |
| lnc-XPOT-2:1 | SEQ6522 | 3.1E+00 |
| lnc-ARIH2-2:6 | SEQ6523 | 3.1E+00 |
| lnc-GNGT1-1:3 | SEQ6524 | 3.1E+00 |
| lnc-CEPT1-1:6 | SEQ6525 | 3.1E+00 |
| lnc-SLC25A4-1:1 | SEQ6526 | 3.1E+00 |
| lnc-AGAP9-2:2 | SEQ6527 | 3.1E+00 |
| lnc-DLG5-4:2 | SEQ6528 | 3.1E+00 |
| lnc-PPHLN1-1:2 | SEQ6529 | 3.1E+00 |
| lnc-RBM25-2:1 | SEQ6530 | 3.1E+00 |
| lnc-USH2A-4:1 | SEQ6531 | 3.1E+00 |
| lnc-ENC1-5:1 | SEQ2244 | 3.1E+00 |
| lnc-FAM106A-2:18 | SEQ6532 | 3.1E+00 |
| lnc-METTL17-1:2 | SEQ6533 | 3.1E+00 |
| lnc-TMEM178-1:19 | SEQ6534 | 3.1E+00 |
| lnc-CHRNA5-4:7 | SEQ6535 | 3.1E+00 |
| lnc-C1orf200-9:1 | SEQ6536 | 3.1E+00 |
| lnc-HEXA-3:1 | SEQ6537 | 3.1E+00 |
| lnc-PKHD1L1-2:7 | SEQ6538 | 3.1E+00 |
| lnc-GALNT5-4:1 | SEQ6539 | 3.0E+00 |
| lnc-TOB1-4:1 | SEQ5647 | 3.0E+00 |
| lnc-ZNF238-7:1 | SEQ6540 | 3.0E+00 |
| lnc-KCNMB4-4:3 | SEQ6541 | 3.0E+00 |
| lnc-BRWD1-1:1 | SEQ6542 | 3.0E+00 |
| lnc-DYNLL1-1:1 | SEQ6543 | 3.0E+00 |
| lnc-TMF1-2:1 | SEQ6544 | 3.0E+00 |
| lnc-HSPBP1-1:1 | SEQ6545 | 3.0E+00 |
| TTC28-AS1:33 | SEQ6546 | 3.0E+00 |
| lnc-SLC8A1-1:1 | SEQ6547 | 3.0E+00 |
| lnc-HMGA1-2:4 | SEQ3415 | 3.0E+00 |
| lnc-TH1L-5:6 | SEQ6548 | 3.0E+00 |
| lnc-RGS9-1:5 | SEQ6549 | 3.0E+00 |
| lnc-SERINC1-3:1 | SEQ5720 | 3.0E+00 |
| lnc-SMARCA5-6:4 | SEQ6550 | 3.0E+00 |
| lnc-RGS9-1:1 | SEQ6551 | 3.0E+00 |
| LINC01420:2 | SEQ6552 | 3.0E+00 |
| lnc-AC007401.2.1-2:1 | SEQ6553 | 3.0E+00 |
| lnc-BX255923.1-8:3 | SEQ6554 | 3.0E+00 |
| NR2F1-AS1:15 | SEQ6555 | 3.0E+00 |
| lnc-AC138969.4.1-1:1 | SEQ6556 | 3.0E+00 |
| lnc-CYP26C1-1:1 | SEQ6557 | 3.0E+00 |
| lnc-TCEA1-3:1 | SEQ6558 | 3.0E+00 |
| lnc-CSNK1D-2:6 | SEQ6559 | 2.9E+00 |
| lnc-DNAL1-1:1 | SEQ2480 | 2.9E+00 |
| lnc-MLNR-2:2 | SEQ6560 | 2.9E+00 |
| lnc-THEMIS-6:1 | SEQ6561 | 2.9E+00 |
| lnc-DAPL1-3:1 | SEQ6562 | 2.9E+00 |
| lnc-ARL15-7:1 | SEQ6563 | 2.9E+00 |
| lnc-CDKL2-2:1 | SEQ6564 | 2.9E+00 |
| lnc-UBLCP1-3:3 | SEQ6565 | 2.9E+00 |
| lnc-VEZF1-1:6 | SEQ6566 | 2.9E+00 |
| SNHG4:19 | SEQ6567 | 2.9E+00 |
| lnc-TANK-3:1 | SEQ6568 | 2.9E+00 |
| ATP6VOE2-AS1:1 | SEQ4643 | 2.9E+00 |
| lnc-SP3-10:1 | SEQ6569 | 2.9E+00 |
| lnc-SNURF-1:8 | SEQ6570 | 2.9E+00 |
| lnc-AZIN1-1:5 | SEQ6571 | 2.9E+00 |
| lnc-CHMP1A-4:6 | SEQ6572 | 2.9E+00 |
| GAS5:40 | SEQ6573 | 2.9E+00 |
| lnc-BCO2-2:3 | SEQ6574 | 2.9E+00 |
| lnc-POC1B-GALNT4-3:1 | SEQ6575 | 2.9E+00 |
| lnc-TPD52-3:12 | SEQ6576 | 2.9E+00 |
| lnc-FAM27B-12:3 | SEQ6577 | 2.9E+00 |
| lnc-STARD9-1:1 | SEQ6578 | 2.9E+00 |
| lnc-IKBIP-1:1 | SEQ4407 | 2.9E+00 |
| lnc-MBOAT4-2:1 | SEQ2592 | 2.9E+00 |
| lnc-ATP6V1E1-2:2 | SEQ6579 | 2.9E+00 |
| lnc-SPINK9-2:2 | SEQ6580 | 2.9E+00 |
| lnc-SHC4-3:1 | SEQ6581 | 2.9E+00 |
| lnc-GATSL1-4:4 | SEQ6582 | 2.9E+00 |
| lnc-DNAJC16-1:2 | SEQ4625 | 2.8E+00 |
| lnc-SLC39A6-3:1 | SEQ6583 | 2.8E+00 |
| lnc-POU5F1-10:2 | SEQ6584 | 2.8E+00 |
| lnc-NMD3-1:1 | SEQ2364 | 2.8E+00 |
| lnc-FGD4-5:1 | SEQ6585 | 2.8E+00 |
| lnc-RAD54B-2:3 | SEQ6586 | 2.8E+00 |
| LINC01355:4 | SEQ6587 | 2.8E+00 |
| lnc-IMPDH1-3:3 | SEQ6588 | 2.8E+00 |
| lnc-TMEM88B-3:8 | SEQ6589 | 2.8E+00 |
| EIF3J-AS1:4 | SEQ6590 | 2.8E+00 |
| lnc-PRR11-3:1 | SEQ6591 | 2.8E+00 |
| lnc-ZNF880-1:1 | SEQ6592 | 2.8E+00 |
| lnc-SLC4A5-3:1 | SEQ6593 | 2.8E+00 |
| NR2F1-AS1:27 | SEQ6594 | 2.8E+00 |
| lnc-STARD4-4:2 | SEQ6595 | 2.8E+00 |
| lnc-GUSB-15:1 | SEQ6596 | 2.8E+00 |
| SNHG21:15 | SEQ6597 | 2.8E+00 |
| lnc-CSNK2A2-2:1 | SEQ6598 | 2.8E+00 |
| lnc-PON3-2:1 | SEQ6599 | 2.8E+00 |
| lnc-C14orf132-1:5 | SEQ6600 | 2.8E+00 |
| lnc-RNASEK-1:4 | SEQ6601 | 2.7E+00 |
| lnc-NR2C2-1:1 | SEQ2751 | 2.7E+00 |
| lnc-PNP-1:1 | SEQ6602 | 2.7E+00 |
| lnc-CWH43-3:4 | SEQ6603 | 2.7E+00 |
| lnc-CLSTN2-1:1 | SEQ6604 | 2.7E+00 |
| lnc-SLC9A5-2:1 | SEQ6605 | 2.7E+00 |
| lnc-C1orf185-5:1 | SEQ6606 | 2.7E+00 |
| lnc-TMEM167A-4:5 | SEQ6607 | 2.7E+00 |
| lnc-TSC22D2-1:2 | SEQ6608 | 2.7E+00 |
| lnc-TULP4-1:1 | SEQ6609 | 2.7E+00 |
| lnc-SYNE2-4:1 | SEQ2308 | 2.7E+00 |
| lnc-RPRML-3:20 | SEQ6610 | 2.7E+00 |
| PSMD5-AS1:5 | SEQ6611 | 2.7E+00 |
| lnc-R3HDM1-1:2 | SEQ6612 | 2.7E+00 |
| PCBP1-AS1:183 | SEQ6613 | 2.7E+00 |
| lnc-PHLDB2-2:3 | SEQ6614 | 2.7E+00 |
| LINC00339:21 | SEQ6615 | 2.7E+00 |
| lnc-POLR1B-2:1 | SEQ6616 | 2.7E+00 |
| lnc-MOCOS-3:10 | SEQ6617 | 2.7E+00 |
| lnc-CSTF3-2:1 | SEQ6618 | 2.7E+00 |
| lnc-SEPT5-1:2 | SEQ6619 | 2.7E+00 |
| NFYC-AS1:2 | SEQ6620 | 2.7E+00 |
| lnc-PABPC1L-2:1 | SEQ6621 | 2.7E+00 |
| lnc-DUS4L-2:4 | SEQ6622 | 2.7E+00 |
| CKMT2-AS1:6 | SEQ6623 | 2.7E+00 |
| MIF-AS1:7 | SEQ3858 | 2.7E+00 |
| lnc-TBR1-1:1 | SEQ6624 | 2.7E+00 |
| lnc-NFAT5-2:1 | SEQ6625 | 2.7E+00 |
| lnc-NLRP3-1:5 | SEQ6626 | 2.7E+00 |
| lnc-SLC25A39-2:1 | SEQ5393 | 2.7E+00 |
| lnc-PPHLN1-1:1 | SEQ6627 | 2.7E+00 |
| lnc-CTC-554D6.1.1-2:1 | SEQ6628 | 2.7E+00 |
| lnc-DDIT3-2:1 | SEQ6629 | 2.7E+00 |
| lnc-ABCD2-4:1 | SEQ2216 | 2.6E+00 |

TABLE 12-continued 860 brain-enriched lncRNAs with an expression level in the brain at least 2-fold higher than that in 12 peripheral organs.

| lncRNA | SEQ | Ratio Br/org |
|---|---|---|
| lnc-BMF-3:4 | SEQ6630 | 2.6E+00 |
| lnc-CXXC11-8:6 | SEQ6631 | 2.6E+00 |
| lnc-PSMC1-2:2 | SEQ6632 | 2.6E+00 |
| lnc-AC008394.1-7:1 | SEQ6633 | 2.6E+00 |
| lnc-TNFRSF14-5:3 | SEQ6634 | 2.6E+00 |
| lnc-FER-8:1 | SEQ6635 | 2.6E+00 |
| lnc-ELN-2:2 | SEQ6636 | 2.6E+00 |
| lnc-PSMA7-1:1 | SEQ5951 | 2.6E+00 |
| lnc-TTYH2-1:4 | SEQ6637 | 2.6E+00 |
| lnc-RPL36A-1:4 | SEQ6638 | 2.6E+00 |
| lnc-WSB1-5:1 | SEQ6639 | 2.6E+00 |
| lnc-SLC25A38-2:1 | SEQ6640 | 2.6E+00 |
| lnc-LEPREL4-1:3 | SEQ6641 | 2.6E+00 |
| lnc-B4GALT2-1:2 | SEQ6642 | 2.6E+00 |
| lnc-AL049840.1-3:1 | SEQ6643 | 2.6E+00 |
| lnc-SUMF2-10:1 | SEQ6644 | 2.6E+00 |
| lnc-EIF1AD-1:1 | SEQ2653 | 2.6E+00 |
| lnc-NUDT16L1-2:1 | SEQ6645 | 2.6E+00 |
| lnc-TMEM180-2:1 | SEQ6646 | 2.6E+00 |
| lnc-PPIL2-1:2 | SEQ6647 | 2.6E+00 |
| lnc-ERAS-4:1 | SEQ6648 | 2.6E+00 |
| lnc-USP34-1:10 | SEQ3127 | 2.6E+00 |
| lnc-EIF4G1-1:1 | SEQ6649 | 2.6E+00 |
| lnc-GPRIN2-2:1 | SEQ2453 | 2.6E+00 |
| DICER1-AS1:9 | SEQ6650 | 2.6E+00 |
| lnc-C10orf40-5:1 | SEQ6651 | 2.6E+00 |
| lnc-BCAT1-2:1 | SEQ6652 | 2.6E+00 |
| lnc-RP11-96020.4.1-1:4 | SEQ6653 | 2.5E+00 |
| lnc-RP11-1012A1.4.1-1:5 | SEQ6654 | 2.5E+00 |
| lnc-RP11-632K20.1.1-1:1 | SEQ6655 | 2.5E+00 |
| lnc-BDH2-2:1 | SEQ6656 | 2.5E+00 |
| lnc-CDO1-1:7 | SEQ6657 | 2.5E+00 |
| lnc-GDI1-1:1 | SEQ4743 | 2.5E+00 |
| lnc-SSBP2-5:9 | SEQ6658 | 2.5E+00 |
| CERS6-AS1:3 | SEQ6659 | 2.5E+00 |
| lnc-ABCA3-2:1 | SEQ6660 | 2.5E+00 |
| SNHG1:25 | SEQ6661 | 2.5E+00 |
| lnc-MLLT6-1:1 | SEQ6662 | 2.5E+00 |
| lnc-OTOA-2:1 | SEQ6663 | 2.5E+00 |
| lnc-CDK2AP1-1:1 | SEQ6664 | 2.5E+00 |
| lnc-CDK2AP1-1:7 | SEQ6665 | 2.5E+00 |
| LINC00963:8 | SEQ6666 | 2.5E+00 |
| lnc-C3orf25-2:7 | SEQ6667 | 2.5E+00 |
| LINC00894:9 | SEQ6668 | 2.5E+00 |
| lnc-CCDC68-4:1 | SEQ6669 | 2.5E+00 |
| lnc-S100A13-2:7 | SEQ6670 | 2.5E+00 |
| lnc-EFHB-5:1 | SEQ6671 | 2.5E+00 |
| lnc-AC073263.1-3:1 | SEQ6672 | 2.5E+00 |
| LINC00623:8 | SEQ6673 | 2.5E+00 |
| lnc-ZNF33B-4:11 | SEQ6674 | 2.5E+00 |
| LINC01278:2 | SEQ6675 | 2.5E+00 |
| lnc-PLAT-4:1 | SEQ6676 | 2.5E+00 |
| lnc-STXBP3-1:2 | SEQ6677 | 2.5E+00 |
| CERS6-AS1:4 | SEQ6678 | 2.5E+00 |
| CERS6-AS1:5 | SEQ6679 | 2.5E+00 |
| TMEM254-AS1:1 | SEQ6680 | 2.5E+00 |
| lnc-EPB41L3-3:1 | SEQ6681 | 2.5E+00 |
| lnc-XRCC5-1:3 | SEQ6682 | 2.5E+00 |
| lnc-CCAR1-4:1 | SEQ6683 | 2.5E+00 |
| lnc-SNX2-1:2 | SEQ4824 | 2.5E+00 |
| lnc-GALNTL1-5:5 | SEQ6684 | 2.5E+00 |
| lnc-FAM200B-1:16 | SEQ6685 | 2.4E+00 |
| EAF1-AS1:14 | SEQ6686 | 2.4E+00 |
| lnc-SLC16A9-6:2 | SEQ6687 | 2.4E+00 |
| lnc-GNA13-2:9 | SEQ6688 | 2.4E+00 |
| lnc-GALT-1:9 | SEQ6689 | 2.4E+00 |
| lnc-ATP6V0A1-1:2 | SEQ6690 | 2.4E+00 |
| lnc-CCNB1IP1-1:1 | SEQ6691 | 2.4E+00 |
| lnc-C11orf58-2:3 | SEQ6692 | 2.4E+00 |
| lnc-ST7L-3:10 | SEQ6693 | 2.4E+00 |
| lnc-DHX33-2:1 | SEQ6694 | 2.4E+00 |
| lnc-AC011551.1-1:1 | SEQ6695 | 2.4E+00 |
| lnc-SP9-4:2 | SEQ6696 | 2.4E+00 |
| lnc-C11orf31-1:1 | SEQ6697 | 2.4E+00 |
| lnc-AL669831.1-11:3 | SEQ6698 | 2.4E+00 |
| lnc-NINL-2:1 | SEQ6699 | 2.4E+00 |
| OIP5-AS1:25 | SEQ5168 | 2.4E+00 |
| lnc-KIAA1383-7:2 | SEQ6700 | 2.4E+00 |
| lnc-APBA1-1:2 | SEQ6701 | 2.4E+00 |
| NIPBL-AS1:3 | SEQ6702 | 2.4E+00 |
| lnc-MRPL30-2:4 | SEQ6703 | 2.4E+00 |
| lnc-RWDD2B-4:2 | SEQ6704 | 2.4E+00 |
| lnc-RASL11B-9:1 | SEQ6705 | 2.4E+00 |
| lnc-TBC1D5-2:1 | SEQ6706 | 2.4E+00 |
| lnc-CEP152-1:1 | SEQ6707 | 2.4E+00 |
| lnc-CCDC144NL-7:1 | SEQ6708 | 2.4E+00 |
| lnc-PLCE1-3:1 | SEQ6709 | 2.4E+00 |
| lnc-CENPV-2:1 | SEQ2516 | 2.4E+00 |
| lnc-ZNF397-4:1 | SEQ4775 | 2.4E+00 |
| lnc-WDR41-1:1 | SEQ6710 | 2.4E+00 |
| lnc-AC112715.2.1-7:1 | SEQ6711 | 2.4E+00 |
| lnc-PHAX-2:1 | SEQ6712 | 2.4E+00 |
| lnc-BMI1-3:3 | SEQ6713 | 2.4E+00 |
| lnc-NAV3-5:5 | SEQ6714 | 2.4E+00 |
| lnc-FAM156A-2:1 | SEQ3387 | 2.4E+00 |
| lnc-CAND1-3:2 | SEQ6715 | 2.4E+00 |
| lnc-DAPL1-6:2 | SEQ6716 | 2.4E+00 |
| lnc-ENAH-2:3 | SEQ6717 | 2.4E+00 |
| lnc-PLSCR3-1:1 | SEQ6718 | 2.4E+00 |
| lnc-HMBS-1:4 | SEQ6719 | 2.4E+00 |
| lnc-RAPSN-1:1 | SEQ6720 | 2.4E+00 |
| lnc-MATR3-3:2 | SEQ6721 | 2.4E+00 |
| lnc-GLB1L-1:1 | SEQ6722 | 2.4E+00 |
| lnc-CLEC18B-7:5 | SEQ2353 | 2.4E+00 |
| LINC-PINT:2 | SEQ6723 | 2.4E+00 |
| lnc-MRPS36-2:1 | SEQ6724 | 2.4E+00 |
| lnc-RNF187-2:1 | SEQ6725 | 2.3E+00 |
| lnc-PEX19-4:1 | SEQ6726 | 2.3E+00 |
| lnc-SNURF-1:44 | SEQ6727 | 2.3E+00 |
| lnc-RNF43-2:2 | SEQ6728 | 2.3E+00 |
| lnc-AF131216.6.1-2:1 | SEQ6729 | 2.3E+00 |
| lnc-SCFD2-4:1 | SEQ6730 | 2.3E+00 |
| CD27-AS1:4 | SEQ6731 | 2.3E+00 |
| lnc-ENSA-1:1 | SEQ6732 | 2.3E+00 |
| lnc-RP11-439E19.8.1-2:1 | SEQ6733 | 2.3E+00 |
| lnc-OGFRL1-4:1 | SEQ6734 | 2.3E+00 |
| lnc-C12orf10-1:3 | SEQ6735 | 2.3E+00 |
| lnc-HIBADH-5:1 | SEQ3962 | 2.3E+00 |
| CRHR1-IT1:8 | SEQ6736 | 2.3E+00 |
| lnc-BRAF-3:2 | SEQ6737 | 2.3E+00 |
| lnc-SIRT2-1:2 | SEQ6738 | 2.3E+00 |
| lnc-RAB27A-1:2 | SEQ6739 | 2.3E+00 |
| lnc-SNRNP35-1:2 | SEQ6740 | 2.3E+00 |
| MSC-AS1:2 | SEQ6741 | 2.3E+00 |
| lnc-WSB2-1:1 | SEQ6742 | 2.3E+00 |
| lnc-ISCU-2:1 | SEQ6743 | 2.3E+00 |
| lnc-KIAA0564-2:1 | SEQ6744 | 2.3E+00 |
| CRHR1-IT1:9 | SEQ6745 | 2.3E+00 |
| lnc-DRD5-23:2 | SEQ5314 | 2.3E+00 |
| lnc-CHST10-2:1 | SEQ6746 | 2.3E+00 |
| lnc-GJC2-2:9 | SEQ6747 | 2.3E+00 |
| LINC01578:14 | SEQ6748 | 2.3E+00 |
| lnc-ERN1-3:1 | SEQ6749 | 2.3E+00 |
| lnc-GRIA4-2:1 | SEQ6750 | 2.3E+00 |
| lnc-GMNN-3:1 | SEQ6751 | 2.3E+00 |
| PRKCQ-AS1:9 | SEQ6752 | 2.3E+00 |
| lnc-VOPP1-5:1 | SEQ6753 | 2.3E+00 |
| lnc-FAM53B-1:1 | SEQ6754 | 2.3E+00 |
| lnc-C12orf10-1:2 | SEQ6755 | 2.3E+00 |
| lnc-ERICH1-19:8 | SEQ6756 | 2.3E+00 |
| lnc-PALLD-8:1 | SEQ2633 | 2.3E+00 |
| lnc-POLD3-1:1 | SEQ6757 | 2.3E+00 |
| lnc-ELAC1-1:1 | SEQ6758 | 2.3E+00 |
| lnc-RAB4A-2:2 | SEQ6759 | 2.3E+00 |
| lnc-VEZT-2:2 | SEQ6760 | 2.3E+00 |
| lnc-C6orf228-4:1 | SEQ6761 | 2.3E+00 |
| LINC00294:2 | SEQ6762 | 2.3E+00 |
| lnc-LRRC8E-2:1 | SEQ6763 | 2.3E+00 |

TABLE 12-continued 860 brain-enriched lncRNAs with an expression level in the brain at least 2-fold higher than that in 12 peripheral organs.

| lncRNA | SEQ | Ratio Br/org |
|---|---|---|
| RNF139-AS1:1 | SEQ6764 | 2.2E+00 |
| lnc-PRSS1-6:3 | SEQ6765 | 2.2E+00 |
| lnc-SLC9A7-1:2 | SEQ6766 | 2.2E+00 |
| lnc-UBXN6-1:3 | SEQ6767 | 2.2E+00 |
| lnc-ALG1-2:1 | SEQ6768 | 2.2E+00 |
| lnc-AES-1:1 | SEQ6769 | 2.2E+00 |
| lnc-PLAGL2-4:1 | SEQ6770 | 2.2E+00 |
| GMDS-AS1:44 | SEQ6771 | 2.2E+00 |
| lnc-PABPC4-1:3 | SEQ6772 | 2.2E+00 |
| LINC00294:1 | SEQ6773 | 2.2E+00 |
| USP46-AS1:4 | SEQ6774 | 2.2E+00 |
| lnc-GLTPD1-1:1 | SEQ6775 | 2.2E+00 |
| lnc-HEBP2-1:1 | SEQ6776 | 2.2E+00 |
| lnc-VSTM5-1:12 | SEQ6777 | 2.2E+00 |
| lnc-ZNF595-1:1 | SEQ6778 | 2.2E+00 |
| lnc-URGCP-2:8 | SEQ5108 | 2.2E+00 |
| lnc-SERGEF-3:2 | SEQ6779 | 2.2E+00 |
| lnc-APBB2-2:4 | SEQ6780 | 2.2E+00 |
| lnc-C19orf71-1:1 | SEQ6781 | 2.2E+00 |
| lnc-VEZF1-1:3 | SEQ6782 | 2.2E+00 |
| lnc-COMMD1-1:1 | SEQ2294 | 2.2E+00 |
| lnc-SECISBP2L-3:1 | SEQ6783 | 2.2E+00 |
| lnc-TAOK3-1:5 | SEQ6784 | 2.2E+00 |
| lnc-RWDD1-1:1 | SEQ6785 | 2.2E+00 |
| lnc-TDRKH-1:1 | SEQ6786 | 2.2E+00 |
| lnc-SNAPIN-2:2 | SEQ6787 | 2.2E+00 |
| lnc-C1orf132-1:7 | SEQ6788 | 2.2E+00 |
| lnc-ARVCF-4:8 | SEQ6789 | 2.2E+00 |
| lnc-COLEC10-1:4 | SEQ6790 | 2.2E+00 |
| lnc-CCNL2-3:1 | SEQ6791 | 2.2E+00 |
| lnc-BCL7B-1:5 | SEQ6792 | 2.2E+00 |
| lnc-METTL2B-3:16 | SEQ6793 | 2.2E+00 |
| lnc-FAM72B-12:1 | SEQ6794 | 2.2E+00 |
| lnc-SLC39A3-2:1 | SEQ6795 | 2.2E+00 |
| lnc-MSH3-2:1 | SEQ6796 | 2.2E+00 |
| lnc-OTP-4:2 | SEQ6797 | 2.2E+00 |
| lnc-SNURF-9:1 | SEQ6798 | 2.2E+00 |
| lnc-DCHS2-1:1 | SEQ6799 | 2.1E+00 |
| EIF3J-AS1:3 | SEQ6800 | 2.1E+00 |
| lnc-VPREB1-7:14 | SEQ6801 | 2.1E+00 |
| lnc-CLASP2-3:1 | SEQ6802 | 2.1E+00 |
| lnc-BICD1-1:1 | SEQ2413 | 2.1E+00 |
| lnc-NIPA1-1:3 | SEQ6803 | 2.1E+00 |
| lnc-MBTPS1-1:1 | SEQ6804 | 2.1E+00 |
| lnc-SLC35G3-1:4 | SEQ6805 | 2.1E+00 |
| lnc-STK16-4:1 | SEQ6806 | 2.1E+00 |
| TTC28-AS1:2 | SEQ6807 | 2.1E+00 |
| lnc-ECE1-2:2 | SEQ6808 | 2.1E+00 |
| lnc-DNA2-1:1 | SEQ6809 | 2.1E+00 |
| lnc-TCF3-2:2 | SEQ6810 | 2.1E+00 |
| lnc-POLR21-1:1 | SEQ6811 | 2.1E+00 |
| lnc-GRM1-1:4 | SEQ6812 | 2.1E+00 |
| lnc-ADAMTS18-1:1 | SEQ6813 | 2.1E+00 |
| lnc-CCDC56-2:1 | SEQ6814 | 2.1E+00 |
| lnc-SLC30A10-7:1 | SEQ6815 | 2.1E+00 |
| lnc-AL627171.1-1:1 | SEQ6816 | 2.1E+00 |
| lnc-ARL6IP4-1:6 | SEQ6817 | 2.1E+00 |
| lnc-DNAJC5-1:3 | SEQ5372 | 2.1E+00 |
| lnc-SMYD5-1:4 | SEQ6818 | 2.1E+00 |
| lnc-NAP1L5-3:1 | SEQ6819 | 2.1E+00 |
| lnc-APBA2-1:8 | SEQ6820 | 2.1E+00 |
| lnc-WTAP-2:2 | SEQ6821 | 2.1E+00 |
| MIF-AS1:8 | SEQ2383 | 2.1E+00 |
| lnc-NCAPD3-2:1 | SEQ6822 | 2.1E+00 |
| lnc-ZBTB8OS-3:1 | SEQ6823 | 2.1E+00 |
| lnc-EXTL3-6:7 | SEQ6824 | 2.1E+00 |
| lnc-MKKS-4:1 | SEQ6825 | 2.1E+00 |
| lnc-CWH43-3:1 | SEQ6826 | 2.1E+00 |
| lnc-FAM75A4-3:3 | SEQ6827 | 2.1E+00 |
| lnc-PKHD1L1-2:11 | SEQ6828 | 2.1E+00 |
| lnc-TUBB3-3:1 | SEQ6829 | 2.1E+00 |
| lnc-ARHGAP15-2:3 | SEQ2483 | 2.1E+00 |
| lnc-NAB1-2:2 | SEQ6830 | 2.1E+00 |
| lnc-KCNT1-6:1 | SEQ2699 | 2.1E+00 |
| lnc-GRSF1-1:1 | SEQ4817 | 2.1E+00 |
| lnc-LYRM7-3:1 | SEQ6831 | 2.1E+00 |
| lnc-RNF111-2:1 | SEQ6832 | 2.1E+00 |
| lnc-DCTN5-1:2 | SEQ6833 | 2.1E+00 |
| lnc-C3orf38-3:3 | SEQ6834 | 2.1E+00 |
| lnc-PXDC1-12:3 | SEQ4641 | 2.1E+00 |
| lnc-EGLN2-1:1 | SEQ6835 | 2.1E+00 |
| lnc-GRID2IP-1:2 | SEQ6836 | 2.1E+00 |
| lnc-RP11-977G19.10.1-1:3 | SEQ6837 | 2.1E+00 |
| lnc-THAP4-4:1 | SEQ6838 | 2.1E+00 |
| lnc-AL139333.1-1:1 | SEQ6839 | 2.1E+00 |
| lnc-UXS1-4:7 | SEQ6840 | 2.1E+00 |
| lnc-ZNF746-3:4 | SEQ6841 | 2.1E+00 |
| lnc-FAM213A-1:1 | SEQ6842 | 2.1E+00 |
| lnc-RP11-219B4.5.1-2:1 | SEQ6843 | 2.1E+00 |
| lnc-PRR3-1:2 | SEQ6844 | 2.1E+00 |
| lnc-IL17RC-3:3 | SEQ6845 | 2.1E+00 |
| lnc-C11orf48-1:2 | SEQ6846 | 2.1E+00 |
| lnc-FRG1B-2:3 | SEQ6847 | 2.1E+00 |
| lnc-SNAP47-2:1 | SEQ5143 | 2.1E+00 |
| lnc-AKT3-6:1 | SEQ6848 | 2.1E+00 |
| lnc-ITGB3BP-5:5 | SEQ6849 | 2.1E+00 |
| lnc-AL049840.1-2:1 | SEQ6850 | 2.1E+00 |
| lnc-HIGD1C-1:7 | SEQ6851 | 2.0E+00 |
| lnc-CNP-1:1 | SEQ3058 | 2.0E+00 |
| lnc-PRPF31-2:1 | SEQ6852 | 2.0E+00 |
| lnc-BX255923.1-5:1 | SEQ6853 | 2.0E+00 |
| lnc-GUCY1A2-1:1 | SEQ6854 | 2.0E+00 |
| LINC00674:12 | SEQ6855 | 2.0E+00 |
| lnc-ARMCX6-3:1 | SEQ6856 | 2.0E+00 |
| lnc-ODF4-4:1 | SEQ6857 | 2.0E+00 |
| lnc-DDX19B-2:1 | SEQ6858 | 2.0E+00 |
| lnc-CLNS1A-3:1 | SEQ6859 | 2.0E+00 |
| lnc-PPIL1-2:2 | SEQ6860 | 2.0E+00 |
| lnc-PSMA3-1:1 | SEQ6861 | 2.0E+00 |
| lnc-TCEANC2-2:2 | SEQ6862 | 2.0E+00 |
| LINCO1123:5 | SEQ6863 | 2.0E+00 |
| lnc-CLPB-1:1 | SEQ6864 | 2.0E+00 |
| lnc-RNMT-1:1 | SEQ6865 | 2.0E+00 |
| lnc-CUEDC1-2:1 | SEQ6866 | 2.0E+00 |
| lnc-NAB1-2:3 | SEQ6867 | 2.0E+00 |
| lnc-MUC5B-1:1 | SEQ5724 | 2.0E+00 |
| lnc-BDH1-5:9 | SEQ6868 | 2.0E+00 |
| lnc-CTDSP2-2:6 | SEQ6869 | 2.0E+00 |
| lnc-LRRC40-3:1 | SEQ6870 | 2.0E+00 |
| lnc-C5orf32-3:1 | SEQ6871 | 2.0E+00 |
| lnc-RPP38-5:1 | SEQ5046 | 2.0E+00 |
| lnc-JAG1-6:1 | SEQ2547 | 2.0E+00 |
| lnc-FGF14-1:1 | SEQ6872 | 2.0E+00 |
| lnc-ZNF8-4:1 | SEQ6873 | 2.0E+00 |
| lnc-CPLX1-2:11 | SEQ6874 | 2.0E+00 |
| lnc-KRT80-3:1 | SEQ3433 | 2.0E+00 |
| lnc-CPSF3-2:1 | SEQ6875 | 2.0E+00 |
| lnc-PROKR2-1:1 | SEQ6876 | 2.0E+00 |
| lnc-POLD1-2:1 | SEQ6877 | 2.0E+00 |
| lnc-C16orf52-1:1 | SEQ6878 | 2.0E+00 |

The correlation between 31 lncRNAs identified in the invention and neurocognitive MMSE (Mini-Mental State Examination) test or cerebrospinal fluid CSF biomarkers Abeta and Tau or phosphorylated tau or age were examined. The result is shown in Table 13.

TABLE 13

Correlation between blood lncRNAs and neurocognitive MMSE test or cerebrospinal fluid CSF biomarkers Abeta and Tau or phosphorylated tau or age.

|  |  | ab42 n=70 | tau 70 | ptau 70 | MMSE 84 | age 137 |
|---|---|---|---|---|---|---|
| ab42 | r | 1.000 | −0.207 | −.322* | 0.067 | 0.044 |
| tau | r | −0.207 | 1.000 | .853* | 0.028 | 0.117 |
| FTX_19 | r | .266* | 0.000 | −0.076 | −0.032 | −0.093 |
| LEF1_AS1_1 | r | −0.121 | 0.013 | −0.016 | 0.089 | −.364** |
| lnc_ADAD1_3_1 | r | .302* | 0.031 | −0.050 | −0.089 | −0.124 |
| lnc_ANKRD36_1_4 | r | −0.053 | −0.191 | −0.138 | 0.035 | −.222** |
| lnc_ATP6AP2_13_1 | r | −0.218 | 0.113 | 0.196 | −.216* | 0.151 |
| lnc_CA6_8_1 | r | 0.003 | −0.067 | −0.030 | .220* | −0.133 |
| lnc_CA6_8_2 | r | 0.080 | 0.035 | 0.047 | .351** | −0.082 |
| lnc_CDIPT_2_1 | r | −0.058 | −0.086 | 0.051 | .255* | −0.073 |
| lnc_CGREF1_2_1 | r | .494** | −0.089 | −0.177 | −0.099 | −0.156 |
| lnc_EVX1_15_1 | r | .255* | 0.005 | −0.027 | 0.193 | −0.078 |
| lnc_IL31RA_1_1 | r | 0.231 | −0.053 | −0.077 | 0.164 | −.360* |
| lnc_KIF14_1_2 | r | 259* | 0.075 | −0.021 | 0.035 | −0.015 |
| lnc_NEMF_1_4 | r | −.325* | 0.089 | 0.168 | 0.096 | .213* |
| lnc_NID1_4_4 | r | .305* | 0.118 | 0.053 | 0.038 | −0.130 |
| lnc_OCM_3_4 | r | 0.088 | −0.087 | −0.128 | 0.206 | −.308** |
| lnc_PCP4L1_3_2 | r | .342* | 0.072 | −0.035 | −0.015 | −0.167 |
| lnc_PDGFA_6_2 | r | −.290* | 0.130 | 0.204 | 0.103 | .179* |
| lnc_SLC35E3_8_2 | r | .386** | 0.002 | −0.069 | −0.084 | −0.106 |
| lnc_SOCS6_10_1 | r | .321** | −0.135 | −0.209 | −0.160 | −0.069 |
| lnc_STX10_2_1 | r | −.276** | 0.141 | 0.218 | 0.079 | −0.002 |
| lnc_UQCC3_2_1 | r | −.356** | −0.003 | 0.086 | 0.161 | 0.114 |
| lnc_USP47_2_1 | r | .2377** | −0.047 | −0.042 | 0.210 | −0.080 |
| lnc_ZCCHC13_4_1 | r | 329** | 0.081 | −0.019 | −0.043 | −0.120 |
| lnc_ZNF516_14_1 | r | .270** | 0.025 | −0.060 | −0.003 | −0.097 |
| MYLK_AS1_13 | r | .419** | −0.031 | −0.183 | 0.031 | −.247** |
| OIP5_AS1_36 | r | .316** | −0.075 | −0.110 | 0.079 | −.227** |
| PCBP1_AS1_302 | r | .251* | 0.048 | −0.058 | −0.152 | 0.026 |
| TCONS_00017372 | r | −.306* | 0.083 | 0.118 | 0.038 | .182* |
| TTC21B_AS1_2 | r | 0.193 | 0.005 | 0.027 | −0.001 | .194* |
| lnc-FOXD4L5-16:1 | r | −.341* | 0.120 | 0.174 | 0.100 | 0.059 |
| lnc-ZC3H12B-11:1 | r | .302* | −0.094 | −0.227 | −0.045 | −.235** |

In all lncRNAs examined, except ANKRD36-1-4, the correlation with age still remained significant for subject groups after adjusting with age by generalized linear model, indicating that the differential expression of selected lncRNAs when comparing subject groups is not due simply to an age effect but to the disease effect, highlighting their relevance for diagnosis and/or therapeutic applications for the respective dementia types.

To further select the best candidates of lncRNAs, fold change (FC) and AUC were calculated for each lncRNA and for each tested condition. lncRNA candidates were selected when differential expression was determined based on an appropriate fold-change (FC) such as a FC >1.2 (or <0.8) and/or an appropriate AUC such as AUC >0.65 (or <0.35) when comparing two groups. Random Forest algorithm (Breimann 2001, Breiman and Cutler 2001) was used to build the model and also to select the top ranked lncRNAs. A predictive model based on the combination of the list of top ranked candidates comprising at least 2 lncRNAs enables to predict the disease with an accuracy of ≥65% and up to 100%.

The predictive modelling based on the random forest algorithm to discriminate between mild cognitive impairment (MCI) patient and healthy control populations when using the total of the 844 lncRNAs measurable in whole blood samples and having an AUC ≥0.8 (or ≤0.2) described in the Table 11 enabled to show that the AUC in function of the number of lncRNAs reached a plateau with the following 2 lncRNAs. These 2 lncRNAs were used to construct the model. The results show that this lncRNA signature enabled a discrimination between the 2 populations (Mild cognitive impairment patient and healthy control populations) with an AUC value=1, an accuracy=100%, sensitivity=100% and specificity=100%.

| lncRNA | Rank |
|---|---|
| TCONS_00035093 | 1 |
| lnc-OCM-3:4 | 2 |

The predictive modelling based on the random forest algorithm to discriminate between mild AD patient and healthy control populations when using the total of the 500 lncRNAs measurable in whole blood and having an AUC ≥0.7 (or ≤0.3) described in the Table 11, enabled to show that the AUC in function of the number of lncRNAs reached a plateau with the following 7 lncRNAs. These 7 lncRNAs were used to construct the model. The results show that this lncRNA signature enabled a discrimination between the 2 populations (mild AD patient and healthy control populations) with an AUC value=0.954, an accuracy=91%, sensitivity=90% and specificity=91%.

| lncRNA | Rank |
|---|---|
| lnc-KIF14-1:2 | 1 |
| PCBP1-AS1:302 | 2 |
| lnc-CA6-8:1 | 3 |
| NEAT1:22 | 4 |

| lncRNA | Rank |
|---|---|
| lnc-CA6-8:2 | 5 |
| STARD7-AS1:5 | 6 |
| lnc-IL31RA-1:1 | 7 |

The predictive modelling based on the random forest algorithm to discriminate between moderate-to-severe AD patient and healthy control populations when using the total of the 605 lncRNAs measurable in whole blood and having an AUC ≥0.65 (or ≤0.35) described in the Table 11, enabled to show that the AUC in function of the number of lncRNAs reached a plateau with the following 6 lncRNAs. These 6 lncRNAs were used to construct the model. The results show that this lncRNA signature enabled a discrimination between the 2 populations (moderate to severe AD patient and healthy control populations) with an AUC value=0.922, an accuracy=83%, sensitivity=70% and specificity=91%.

| lncRNA | Rank |
|---|---|
| lnc-CA6-8:2 | 1 |
| lnc-ANKRD36-1:4 | 2 |
| lnc-ATP6AP2-13:1 | 3 |
| lnc-SOCS6-10:1 | 4 |
| lnc-CDIPT-2:1 | 5 |
| lnc-USP47-2:1 | 6 |

The predictive modelling based on the random forest algorithm to discriminate between all AD patient (mild+ moderate-to-severe) and healthy control populations when using the total of the 1124 lncRNAs measurable in whole blood and having an AUC ≥0.65 (or ≤0.35) described in the Table 11, enabled to show that the AUC in function of the number of lncRNAs reached a plateau with the following 7 lncRNAs. These 7 lncRNAs were used to construct the model. The results show that this lncRNA signature enabled a discrimination between the 2 populations (AD patient and healthy control populations) with an AUC value=0.954, an accuracy=91%, sensitivity=88% and specificity=92%.

| lncRNA | Rank |
|---|---|
| lnc-CA6-8:2 | 1 |
| lnc-CA6-8:1 | 2 |
| RBM26-AS1:1 | 3 |
| PCBP1-AS1:302 | 4 |
| MIR181A2HG:1 | 5 |
| TTC21B-AS1:2 | 6 |
| lnc-SOCS6-10:1 | 7 |

The predictive modelling based on the random forest algorithm to discriminate between dementia with Levy bodies patient and healthy control populations when using the total of the 1352 lncRNAs measurable in whole blood and having an AUC ≥0.8 (or ≤0.2) described in the Table 11, enabled to show that the AUC in function of the number of lncRNA reached a plateau with the following 2 lncRNAs. These 2 lncRNAs were used to construct the model. The results show that this lncRNA signature enabled a discrimination between the 2 populations (Dementia with Levy bodies patient and healthy control populations) with an AUC value=1, an accuracy=100%, sensitivity=100% and specificity=100%.

| lncRNA | Rank |
|---|---|
| lnc-OCM-3:4 | 1 |
| lnc-SLC35E3-8:1 | 2 |

The predictive modelling based on the random forest algorithm to discriminate between frontotemporal dementia patient and healthy control populations when using the total of the 1041 lncRNAs measurable in whole blood and having an AUC ≥0.8 (or ≤0.2) described in the Table 4, enabled to show that the AUC in function of the number of lncRNA reached a plateau with the following 3 lncRNAs. These 3 lncRNAs were used to construct the model. The results show that this lncRNA signature enabled a discrimination between the 2 populations (Frontotemporal dementia patient and healthy control populations) with an AUC value=1, an accuracy=100%, sensitivity=100% and specificity=100%.

| lncRNA | Rank |
|---|---|
| lnc-ZCCHC13-4:1 | 1 |
| PCBP1-AS1:302 | 2 |
| lnc-NEMF-1:4 | 3 |

The predictive modelling based on the random forest algorithm to discriminate between All AD patients' population and NAD (FTD+DLB) patients populations when using the total of the 6 lncRNAs measurable in whole blood and having an AUC ≥0.65 (or ≤0.35) described in the Tables 11, 12, enabled to show that the AUC in function of the number of lncRNA reached a plateau with the following 6 lncRNAs. These X6 lncRNAs were used to construct the model. The results show that this lncRNA signature enabled a discrimination between the 2 populations (AD populations and population suffering other dementia types) with an AUC value=0,804, an accuracy=79%, sensitivity=56% and specificity=91%.

| lncRNA | rank |
|---|---|
| lnc-STAT3-1:2 | 1 |
| lnc-NEMF-1:4 | 2 |
| lnc-EPN2-3:2 | 3 |
| lnc-SLC25A39-2:1 | 4 |
| lnc-ARF6-1:1 | 5 |
| lnc-CCNYL1-2:1 | 6 |

The predictive modelling based on the random forest algorithm to discriminate between All AD patients' population and DLB, FTD patients+healthy control populations when using the total of the 5 lncRNAs measurable in whole blood and having an AUC ≥0.65 (or ≤0.35) described in the Table 4, enabled to show that the AUC in function of the number of lncRNAs reached a plateau with the following 5 lncRNAs. These 5 lncRNAs were used to construct the model. The results show that this lncRNA signature enabled a discrimination between the 2 populations (AD population and population either suffering other dementia type or having normal cognitive status) with an AUC value=0,811, an accuracy=72%, sensitivity=61% and specificity=81%.

| lncRNA | rank |
| --- | --- |
| ANKRD44-IT1:1 | 1 |
| APOBEC3B-AS1:2 | 2 |
| ADAMTSL4-AS1:2 | 3 |
| AGAP2-AS1:2 | 4 |
| A1BG-AS1:14 | 5 |

As for diagnosis, for differential diagnosis, several other lncRNAs panels were identified such as those listed below comprising at least 3 lncRNAs from Tables 11, 12 and enabling to detect each dementia type specifically:

| Panel Example 1 | Panel Example 2 | Panel Example 3 | Panel Example 4 |
| --- | --- | --- | --- |
| LEF1-AS1:1 | lnc-CGREF1-2:1 | TCONS_00011994 | OIP5-AS1:36 |
| PCBP1-AS1:302 | PSMB8-AS1:14 | lnc-EVX1-15:1 | MYLK-AS1:13 |
| lnc-CA6-8:2 | lnc-STX10-2:1 | lnc-REC8-2:1 | lnc-PCP4L1-3:2 |
| | lnc-TCFL5-6:1 | | |
| | ZC3H12B-11:1 | | |

The signature of the following 11 top ranked lncRNAs expressed in whole blood (Paxgene RNA samples) enabled an excellent discrimination between HC group and all other groups (MCI, all AD, DLB, FTD) with AUC=0.963, accuracy=93.4%, sensitivity=65% and specificity=98.3%.

| lncRNA | Rank |
| --- | --- |
| PCBP1-AS1:302 | 1 |
| STARD7-AS1:5 | 2 |
| lnc-NID1-4:4 | 3 |
| RBM26-AS1:1 | 4 |
| LEF1-AS1:1 | 5 |
| lnc-CA6-8:1 | 6 |
| lnc-CA6-8:2 | 7 |
| lnc-OCM-3:4 | 8 |
| lnc-AFG1L-7:1 | 9 |
| lnc-LASP1-5:1 | 10 |
| lnc-GCGR-1:2 | 11 |

The signature of the following 7 top ranked lncRNAs expressed in whole blood (Paxgene RNA samples) enabled an excellent discrimination between HC group and patients with mild AD, with with accuracy=90.7%, sensitivity=90% and specificity=91.2%.

| lncRNA | Rank |
| --- | --- |
| lnc-KIF14-1:2 | 1 |
| PCBP1-AS1:302 | 2 |
| lnc-CA6-8:1 | 3 |
| NEAT1:22 | 4 |
| lnc-CA6-8:2 | 5 |
| STARD7-AS1:5 | 6 |
| lnc-IL31RA-1:1 | 7 |

The signature of the following 7 top ranked lncRNAs expressed in whole blood (Paxgene RNA samples) enabled an excellent discrimination between HC group and patients with moderate to severe AD with accuracy=83.3%, sensitivity=70% and specificity=91.2%.

| | |
| --- | --- |
| lnc-CA6-8:2 | 1 |
| lnc-ANKRD36-1:4 | 2 |
| lnc-ATP6AP2-13:1 | 3 |
| lnc-SOCS6-10:1 | 4 |
| lnc-CDIPT-2:1 | 5 |
| lnc-USP47-2:1 | 6 |
| lnc-UXS1-3:1 | 7 |

The signature of the following 3 top ranked lncRNAs expressed in whole blood (Paxgene RNA samples) enabled an excellent discrimination between HC group and patients with dementia with Lewy bodies with accuracy=100%, sensitivity=100% and specificity=100%.

| | |
| --- | --- |
| lnc-OCM-3:4 | 1 |
| lnc-SLC35E3-8:1 | 2 |
| LINC-PINT:11 | 3 |

The signature of the following 2 top ranked lncRNAs expressed in whole blood (Paxgene RNA samples) enabled an excellent discrimination between HC group and patients with frontotemporal dementia with accuracy=100%, sensitivity=100% and specificity=100%.

| | |
| --- | --- |
| lnc-ZCCHC13-4:1 | 1 |
| PCBP1-AS1:302 | 2 |

The signature of the following 5 top ranked lncRNAs expressed in whole blood (Paxgene RNA samples) enabled an excellent discrimination between AD patients (with mild AD patients and moderate-to severe AD) and non-AD dementia group (FTD+DLB) with accuracy=76.5%, sensitivity=55.9% and specificity=86.8%.

| lncRNA | rank |
| --- | --- |
| lnc-JUNB-1:1 | 1 |
| lnc-RARB-4:1 | 2 |
| lnc-ZNF284-1:1 | 3 |
| TCONS_00035093 | 4 |
| lnc-TELO2-3:3 | 5 |

The signature of the following 5 top ranked lncRNAs expressed in whole blood (Paxgene RNA samples) enabled an excellent discrimination between AD patients (with mild AD patients and moderate-to severe AD) and non-AD dementia group (FTD+DLB) with accuracy=82.4%, sensitivity=61.8% and specificity=92.6%.

| lncRNA | Rank |
| --- | --- |
| lnc-CGREF1-2:1 | 1 |
| PSMB8-AS1:14 | 2 |
| lnc-STX10-2:1 | 3 |
| lnc-TCFL5-6:1 | 4 |
| lnc-ZC3H12B-11:1 | 5 |

Material and Methods

To identify lncRNAs in brain, serum, plasma, whole blood or other samples of human subjects, total RNA was first extracted and sequencing libraries were prepared by removal of ribosomic RNA (RiboZero TruSeq library preparation kit, Illumina Inc. San Diego, USA) and sequenced on Illumina NextSeq500 with 2×75 bp read length.

lncRNAs were also measured by qPCR using specific primers. For this, total RNA was first extracted, reverse transcription and real time PCR using specific primers were performed. Using FiMAP (also called Quantamatrix QMAP platform and also a new fully automatized version QMX), a proprietary platform based on hybridization of PCR products on coated microdiscs with complementary oligonucleotide coupled to detection probes. Total RNA was extracted followed by reverse transcription and PCR step allowing multiplexing of several targets using specific primers to the lncRNAs.

To show the efficacy of FiMAP as a multiplexed platform capable to quantify lncRNAs, plasma samples have been tested using NGS, qPCR, Celemics and FiMAP. Most of the lncRNAs showed that they are well quantified since the dilutions of the input RNAs are concentration dependent manner measured on QMAP, and that for lncRNA 20321 very equivalent results were obtained when using the reference qPCR method. Quantification was therefore performed on the FiMAP platform using coded microdiscs specific of each lncRNA.

Patient Population and Samples

Brain tissue biopsies: postmortem brain medio-temporal cortex tissue samples and the blood samples other than from the below-mentioned prospective studies, as well peripheral organ biopsies: lung, ovary, colon, prostate, breast, liver, bladder, kidney, skin, heart, muscle) were from diverse European hospitals and Firalis biobanks.

Body fluid samples: Body fluid samples were from healthy volunteers (HV), donors at the "Etablissement Français du Sang" (EFS) of Mulhouse, France, and from cognitively intact healthy control subjects and from patients with mild cognitive impairment or with different stages of Alzheimer's disease (AD) or with other dementia types recruited, according to the protocols of European hospitals accepted by country ethic committees, and in the Amoneta Diagnostics sponsored prospective studies registered to the Agence Nationale de Sécurité du Médicament et des Produits de Santé (ANSM) such as under the ID RCB: 2015-A00118-41 on Jan. 22, 2015, the ID RCB: 2016-A200227-44 on Feb. 4, 2016. Whole blood samples were collected in Paxgene RNA tubes. Serum or plasma samples were prepared from blood samples collected in lithium-heparin tubes or EDTA tubes and CSF, urine, saliva and tears were collected using polypropylene tubes.

Results shown in tables and drawings from the invention are those obtained in 10 postmortem brain samples (5AD, 5 HC), 24 serum samples (12 AD and 12 HC), 12 plasma samples (6 AD and 6 HC) and 139 samples from the following subject groups:

| Subject Group | Gender | | |
|---|---|---|---|
| | Male | Female | Total |
| HC | 6 | 14 | 20 |
| MCI | 8 | 7 | 15 |
| Mild AD | 15 | 19 | 34 |
| Mod-SevAD | 11 | 23 | 34 |
| DLB | 5 | 10 | 15 |
| FTD | 2 | 17 | 19 |
| Other diseases | 2 | 0 | 2 |
| Total | 49 | 90 | 139 |

Method for lncRNAs
Samples Sequencing

Ribonucleic acid (RNA) extraction is performed starting from 1.5 ml of serum, using Norgen Serum/plasma extraction and RNA Clean-Up and Concentration Micro-Elute Kits according to the manufacturer's instructions. Sequencing libraries are prepared from the total amount of extracted RNA, using the Illumina TruSeq stranded total RNA library preparation kit combined with the human/mouse/rat RiboZero rRNA removal kit (Illumina Inc. San Diego, USA, C). All steps are performed with the low-throughput protocol and according to the manufacturer's instructions, with no fragmentation step. Briefly, cytoplasmic ribosomal RNA (rRNA) are hybridized to biotinylated target-specific oligos and removed using streptavidin coated magnetic beads. rRNA depleted RNA samples are then reverse transcribed into complementary deoxyribonucleic acid (cDNA). To ensure strand specificity, single stranded cDNA is first synthetized using Super-Script II reverse transcriptase (Invitrogen) and random primers in the presence of Actinomycin D, and then converted to double stranded cDNA with the second strand marking mix that incorporates dUTP in place of dTTP. Resulting blunt ended cDNA are purified using AMPure XP magnetic beads. After a 3'end adenylation step, Illumina's adapters ligation is performed. So, obtained singled indexed libraries are washed twice using AMPure XP beads to remove excess adapters and enriched by PCR (15 cycles). PCR products are purified with a final AMPure XP beads wash and sequencing ready libraries are eluted in 30 µl of resuspension buffer.

For quality control, 1 µl of each library is run on the Agilent Technologies 2100 Bioanalyzer using a DNA 1000 chip according to the manufacturer's recommendations. Absence of adapter dimers is checked and the average library size is determined by a region table. Libraries are quantified on Qubit 2.0 using Qubit dsDNA High Sensitivity assay kit (Invitrogen). Library size previously determined on the Bioanalyzer is used to calculate molar concentrations from mass concentrations. All libraries are sequenced with the Illumina NextSeq500 (2×75 bp).

Bioinformatic Analysis
lncRNA Based on the *Homo sapiens* hg38 Genome

RNA-seq data analysis is performed using Partek Flow (Partek Inc., St Louis, MO, USA build 6). The pre-alignment QA/QC module of Partek Flow is used to visualize the read quality of the FASTQ files. All reads are examined. The raw FASTQ files are trimmed at the 3' end in function of their quality score (Phred score). The parameters used are an end minimum quality level of 30 and a minimum trimmed read length of 50. Unaligned reads are mapped using the *Homo sapiens* hg38 genome. This mapping is done using the software STAR version 2.5.3 (Dobin A. et al., 2013). STAR: ultrafast universal RNA-seq aligner. Bioinforma. Oxf. Engl. 29, 15-21). The default parameters are used. The post-alignment QC module of Partek Flow was used to visualize the average base quality score per position as well as the mapping quality per alignment. The mapped reads were quantified using the GTF file with the patented lncRNA annotation for quantification using the Partek Expectation/Maximization (E/M) algorithm (Xing Y. et al, 2006). An expectation-maximization algorithm for probabilistic reconstructions of full-length isoforms from splice graphs. Nucleic Acids Res. 34, 3150-3160). The default parameters are used. The transcripts where their medians are under the median read density in intergenic regions are discarded for the next steps of the analysis. The transcript counts were normalized by CPM (counts per million). Only transcripts showing high expression (CPM ≥5) in at least half the samples of one group are considered.

Novel lncRNAs Discovery

The novel discovery was performed by using UCIncR pipeline version 1.1.1 (Sun Z. et al., Scientific Reports, 7 (1): 14196, 2017). In this pipeline, StringTie version 1.3.4d (Pertea M. et al., Nat Biotechnol, 33 (3): 290-295, 2015) was used for the reconstruction.

The "cuffcompare" program version 2.2.1 (C. Trapnell et al., 'Nat Protoc, 7 (3): 562-578, 2012) was used to compare the assembled transcripts to the reference annotated GTF file (Gencode 27 and LNCipedia 5) and to generate a new GTF file with all transcripts from 9 samples for further analysis.

Filtering was done on Transfrag class codes generated by cuffcompare, transcript length, number of exons and protein coding potential. Firstly, the transcripts with code 'i', 'j', 'o', 'u', 'x' and '.' were extracted, all of which could potentially include novel lncRNAs. The 'i' category, for example, could contain the lncRNAs entirely within the intron of known genes. Similarly, the 'j' category could be long non-coding isoforms of known genes. The 'o' category could include novel lncRNAs having generic exonic overlap with known transcripts. The 'u' category could be long intergenic non-coding RNAs (lincRNAs). The 'x' category could contain novel lncRNAs on the opposite strand of reference genes. The '.' category may be sequences with multiple classifications. Following this, only the transcripts with a length of ≥200 nt and with at least 2 exons were kept for the next step. CPAT (Coding-Potential Assessment Tool, L. Wang L., et al., Nucleic Acids Res, 41 (6): e74,2013.) is used for the evaluation the non-coding potential. The transcripts with CPAT score <0.3 were considered as non-coding. A new GTF file was generated with the final list of selected novel lncRNAs.

Fastq files of GSE45326 were downloaded from ArrayExpress [9]. The dataset includes RNA-seq data of 12 normal human tissues. The paired-end sequencing was performed on ribominus total RNA library. Reads alignment was performed as described before. The quantification was done with the novel lncRNA annotation using the Partek E/M algorithm.

Statistical Analysis and Predictive Modelling

To determine differentially expressed lncRNA, a statistical analysis is performed using Wilcoxon Mann-Whitney parametric test to compare 2 groups of subjects. A lncRNA with a p value≤0.05 is considered as differentially expressed. Anova test is used for comparison of more than 2 subject groups.

In order to build classification models for the 2 classifications, the Classification for MicroArrays (CMA) package of R (Slawski M, Daumer M, Boulesteix A L. CMA: a comprehensive Bioconductor package for supervised classification with high dimensional data. BMC Bioinformatics 2008, 9:439) with a leave-one-out cross-validation has been used.

The algorithms used for this predictive modelling are (a) random forest, (b) linear discriminant analysis and (c) naïve Bayes (Breiman L. Random forests. Machine Learning, 45 (1): 5-32, 2001).

The rank of the RNA candidate in a model was calculated by the mean rank of 10 candidates' selections (per CV-fold). Per model (and RNA selection method) the AUC was plotted as a function of the number of RNAs in the model. The optimal number of RNAs per model was determined graphically. ROC curves and confusion matrices were generated to assess the predictive performance of our models. The values of AUC, accuracy, sensitivity, specificity, positive and negative predictive values are reported.

Additional Method for Quantification of lncRNA

Total RNA Extraction

Total RNA was extracted using Paxgene Blood RNA kit (Qiagen, France) and Serum/Plasma mini kit (Norgen Biotek, Canada) respectively, according to manufacturer's instructions. RNA quality was examined on an Agilent 2100 Bioanalyzer with the RNA 6000 Nano Kits (Agilent, France). RNA quantity was measured on Qubit 3.0 fluorometer using RNA High sensitivity kit (Fisher Scientific, France).

cDNA Synthesis

Reverse transcription was performed using high capacity cDNA reverse transcription kit (Fisher scientific, France) according to the manufacturer instructions.

qPCR Quantification lncRNA were preamplified before qPCR. Preamplification reactions were prepared using Applied Biosystems preamplification master mix with 0.1× (100 nM) of each of the primers pairs corresponding to the lncRNAs. 16 preamplification cycles were performed as preconized by the furnisher (50° C. 2 minutes, 96° C. 10 minutes, 40 cycles at 95° C. for 15 seconds and 60° C. for 1 minute). Quantitative PCR of biological samples was done in 10 µl total volume with 1 µl of preamplification product diluted 1/20 in TE buffer, 5 µl of 2× Soadvanced SYBR green PCR master mix (Biorad, USA) and 250 nM of each primer. Cycling conditions were 95° C. for 5-10 min followed by 40 cycles of 95° C. for 10-30 sec and 60° C. 30-60 sec. A melting curve analysis (60° C. to 99° C.) was performed after the thermal profile to ensure specificity in the amplification. Relative expression level was determined against a standard curve realized on a 5 log scale using CFX maestro Software (Biorad, USA).

QUANTAMATRIX FIMAP Quantification lncRNAs of interest were also quantified using the FIMAP/QMAP platform developed by Quantamatrix (South Korea). Briefly, lncRNAs were amplified by PCR using primers with the same sequences as for qPCR that were chemically modified. Forward primers were phosphorylated in 5' and Reverse primers biotinylated in 5'. Multiplexed PCR reactions were performed on Biorad T100 thermocycler in 20 µl reactions containing 2 µl of lncRNA cDNA, 250 nM of each primers and 10 µl of 2× One Taq Hot Start 2× master Mix (New England Biolabs, USA) with the following conditions: 30 seconds at 94° C., 25 cycles of 30s at 94° C., 1 min at 60° C. and 1 min at 68° C., followed by a final extension at 68° C. for 5 minutes. PCR products were then digested with 25 U of lambda exonuclease for 30 minutes at 37° C. to eliminate the phosphorylated strand and keep only the biotinylated ones. So digested products were quantified on QMAP using coded silica microdisks coated with oligos complementary to the RNAs of interest (one code per target oligo). Briefly, biotinylated PCR products were incubated with the coated microdisks in a 96 well plate, and hybridized products revealed by addition of a fluorescent streptavidin conjugate, SAPE (Prozyme, Denmark) after washing steps. Plates were imaged on QMAP that takes 2 images per spot: one dark image to quantify the fluorescence and 1 white light image to read the microdisks codes. Each target relative expression is then calculated by QMAP software by assigning fluorescence signal to each target according to the associated microdisk code.

lncRNAs were also measured by qPCR using specific primers. For this, total RNA was first extracted, reverse transcription and real time PCR using specific primers were performed. Using FiMAP (also called Quantamatrix QMAP platform and also a new fully automatized version QMX), a proprietary platform based on hybridization of PCR products on coated microdiscs with complementary oligonucleotide coupled to detection probes. Total RNA was extracted followed by reverse transcription and PCR step allowing multiplexing of several targets using specific primers to the lncRNAs.

To show the efficacy of FiMAP as a multiplexed platform capable to quantify lncRNAs, plasma samples have been tested using NGS, qPCR, Celemics and FiMAP. Most of the lncRNAs showed that they are well quantified on the QMAP and quantitative with dilutions linearity in function of the input RNAs concentration on a dose dependent manner measured on QMAP with very equivalent results obtained when using the reference qPCR method as for the known reference lncRNA 20321.

Quantification performed on the FiMAP platform using coded microdiscs specific of each lncRNA was appropriate for multiplexing testing platform.

Celemics Description

Celemics is based on a targeted sequencing approach using capture probes of 120 nucleotides that hybridize with the selected lncRNAs with magnetics beads. The capture step is performed following library preparation describe above. Briefly, 100 ng of library DNA is used in a volume of 3.4 µl mixed with 5.6 µl of Block Mix. Then, 7 µL of the Capture Library and 13 µL of the Hybridization Buffer is mixed with 9 µl of the DNA library preparation and incubated 24 h at 65° C. After the incubation, 50 µl of Dynabeads Myone Steptavidin T1 are mixed with 200 µl of wash buffer #1 and added to the hybridization mixture. After removal of supernatant under magnetic condition, 500 µl of wash buffer #2 is added and removed using separator and wash 3 to 6 time with wash buffer #3 and then add 30 µl of nuclease free water for elution. Library is then amplified using PCR mixing on beads Captured DNA (15 µl), PCR post capture primer (5 µl), KAPA Library Amplification Mix (25 µl) and nuclease free water (5 µl) for 16 cycles and sample are purified of using AMPure XP beads prior sequencing. All libraries are sequenced with the Illumina NextSeq500 (2×75 bp).

Results

Profiling 127,802 transcripts based on LNCipedia v5.2 was performed on serum samples from patients suffering of Alzheimer disease and cognitively intact healthy subjects using total-RNAseq technology. Above 127,802 transcripts, 19867 lncRNAs were identified with expression level of over 10 CPM in at least half the samples of one group.

Out of 19867 serum lncRNAs, a list of 1008 lncRNAs useful for diagnosis of Alzheimer disease was selected based on the statistical significance (p value <0.05, Wilcoxon test). Random Forest algorithm was used for the classification model. From this, several sets of 2-20 lncRNAs with high predictive value were identified. The sets of selected 2-20 lncRNAs provide an AUC ranged from 0.7 and up to 1 with an accuracy, sensitivity and specificity ranged from 0.7 to 1.

A total of 1091 novel lncRNAs were further identified using transcript reconstruction in the human postmortem mediotemporal brain tissue of 5 AD cases and 10 HC cases from deep-sequencing experiments. Profiling these novel 1091 novel lncRNAs was performed on same brain area, the mediotemporal cortex from the group of human AD brains and the group of healthy control brains using total-RNAseq technology. Out of these 1091 novel brain transcripts, 26 showed deficient expression and 16 showed overexpression level in AD brains as compared to HC brains (P<0.05).

Profiling of a total of 128 893 comprising the 1091 novel lncRNAs and 127,802 transcripts based on LNCipedia v5.2 was performed using total-RNAseq technology on brain cortex (mediotemporal) from 5 AD cases and 5 healthy controls, and on plasma samples from 12 subjects, 6 patients suffering Alzheimer and 6 healthy controls as well as on whole blood (Paxgene RNA tubes) samples from 137 subjects included in 5 groups: patients suffering of MCI, mild AD, moderate-to-severe AD, DLB or, FTD and cognitively intact healthy control subjects.

Out of the 128 893 transcripts sequenced in each biological sample type from all patient and HC groups, lncRNAs were identified based on their threshold expression level (median over 5 count per million (CPM) in at least half the samples of at least one subject group studied). 10122 brain lncRNAs, 3774 plasma lncRNAs and 9367 whole blood lncRNAs were retained for statistical analysis. The results show:

1—Brain lncRNAs panels: Out of the 10122 brain lncRNAs sequenced in the brains and having an expression level >5 CPM:

We confirmed on all brains tested, the expression in the brain of the 1091 novel lncRNAs (Table 7) never described before, which represent novel therapeutic and diagnostic targets for brain disorders including cognitive disorders.

We identified 860 brain-enriched lncRNAs (Table 12) that exhibit at least 2-fold higher expression level in the brain as compared to all other peripheral organs studied (lung, ovary, colon, prostate, breast, liver, bladder, kidney, skin, heart, muscle). These 860 lncRNAs represent novel therapeutic and/or diagnosis targets for brain disorders including cognitive disorders.

We identified 1202 lncRNAs (Table 8) comprising 42 novel lncRNAs, showing a statistically significant differential expression when comparing AD brains to HC brains: These 1202 lncRNAs represent therapeutic and/or diagnosis candidates specifically for cognitive disorders in particular Alzheimer 2—Plasma lncRNAs panels: Out of the retained 3714 plasma lncRNAs, we identified 410 plasma lncRNAs (Table 9) that showed a statistically significant differential expression (p<0.05, Wilcoxon test) when comparing AD plasma samples to HC plasma samples: These 410 lncRNAs represent novel panel of biomarkers useful for diagnosis and for therapeutic response monitoring applications of cognitive disorders in particular MCI and Alzheimer.

3—Blood lncRNA panels: Out of the retained blood 9367 lncRNAs, we identified 2982 blood lncRNAs (Tables 10, 11) that showed statistically significant differential expression in at least one of the subject groups studied (HC, MCI, mild AD, Moderate-to-severe AD, all AD, DLB, FTD) (p value<0.05 using Anova test comparing all groups and a p value <0.05 when using the Wilcoxon test to compare the HC group and one of the patient population groups studied). Further, we applied additional criteria such as fold change <0.8 or >1.2 and AUC >0.65 or <0.35 to select the 2847 lncRNAs and 136 lncRNAs listed in Tables 10 and 11. These 2982 blood lncRNAs represent novel biomarker(s) and biomarker signature(s) useful for diagnosis, differential diagnosis and for therapeutic response monitoring applications of cognitive disorders in particular MCI and Alzheimer as MCI, mild AD, moderate-to-severe AD, DLB and FTD and other cognitive disorders.

'-Circulating lncRNAs panels (common-to brain and present in peripheral body fluids): Out of the 10122 lncRNAs sequenced in the brains, the following numbers were identified as circulating lncRNAs in body fluids:

2096 circulating lncRNAs in plasma: Out of these 2096 lncRNAs, a panel of 46 lncRNAs showed a differential expression in plasma samples of AD patients group as compared to HC subject group with statistical significance (p<0.05, Wilcoxon test) and having all an AUC value >0.8 or <0.2. Out of these 46 differentially expressed circulating lncRNAs, 17 have an AUC value >0.9, 4 candidates have AUC value=1 thus fully discriminating AD patients from healthy control subjects.

4902 lncRNAs detected in blood samples (Pax RNA tube) and thus identified as a novel panel of lncRNAs measurable in the peripheral body fluid. Out of these 4902 lncRNAs, a panel of 310 lncRNAs showed a differential expression in blood samples of at least one of the 5 patients groups studies (MCI, mild AD, moderate-to-severe AD, DLB or FTD patients) as compared to HC subject group with statistical significance (p<0.05, Wilcoxon test) and represent good candidates for diagnosis and therapeutic applications for cognitive disorders.-5054 lncRNAs circulating lncRNAs in serum. Out of these 5054 lncRNAs, 43 lncRNAs are differentially expressed in serum of AD group as compared to healthy group with statistical significance (p<0.05, Wilcoxon test). Thus, the invention also relates to any common brain/plasma and/or common brain/blood and/or brain/serum lncRNAs and/or brain-enriched lncRNA circulating in plasma, blood, serum or in any other non-invasive peripheral body fluid detected using the methods of the invention for use for therapeutic and diagnosis applications of any brain disorders where such circulating lncRNAs are altered.

In particular the invention relates to the panels of lncRNAs listed in tables 1-12 for use for therapeutic and diagnosis applications of brain disorders in particular cognitive disorders.

The sequences of lncRNAs disclosed in this disclosure are shown in the sequence listing included in this application.

SEQUENCE LISTING

The patent contains a lengthy sequence listing. A copy of the sequence listing is available in electronic form from the USPTO web site (https://seqdata.uspto.gov/?pageRequest=docDetail&DocID=US12344895B2). An electronic copy of the sequence listing will also be available from the USPTO upon request and payment of the fee set forth in 37 CFR 1.19(b)(3).

The invention claimed is:

1. A method of detecting the levels of expression of lncRNAs in a lncRNA signature in a subject, comprising:
   (a) isolating a biological sample from the subject, wherein the biological sample is selected from blood, plasma, or serum;
   (b) detecting the levels of expression of lncRNAs in a lncRNA signature in a biological sample from said subject;
   wherein the lncRNA signature comprises the 2 lncRNA of TCONS_00035093 and lnc-OCM-3:4, wherein the lncRNA of TCONS 00035093 consists of the nucleotide sequence SEQ ID NO: 1570 and the lncRNA of lnc-OCM-3:4 consist of the nucleotide sequence SEQ ID NO: 5076.

2. A method for treating a subject suffering from Alzheimer disease, said method comprising:
   (i) performing the method of claim 1;
   (ii) comparing the level of expression of lncRNAs of TCONS 00035093 and lnc-OCM-3:4 in the sample to the level of expression of TCONS 00035093 and lnc-OCM-3:4 in a reference sample, wherein the reference sample is a sample from a normal, healthy subject;
   (iii) identifying the subject as having Alzheimer's disease based on detecting a decreased level of TCONS_00035093 and lnc-OCM-3:4 in the sample as compared to that in a reference sample; and
   (iv) administering a treatment to the subject identified as having Alzheimer's disease in step (iii), wherein the treatment is selected from cholinesterase inhibitors, NMDA receptor antagonists, beta-secretase inhibitors, anti-beta-amyloid monoclonal antibodies, modulators of kinases or phosphatases that regulate tau phosphorylation status and anti-tau antibodies.

3. The method of claim 2, wherein the treatment is selected from donepezil, rivastigmine, galantamine, and memantine.

* * * * *